US011945843B2

(12) United States Patent
Donohue et al.

(10) Patent No.: US 11,945,843 B2
(45) Date of Patent: Apr. 2, 2024

(54) CONTROL OF COLEOPTERAN PESTS USING RNA MOLECULES

(71) Applicant: Syngenta Participations AG, Basel (CH)

(72) Inventors: Kevin L. Donohue, Research Triangle Park, NC (US); Yann Naudet, Ghent (BE); Pascale Feldmann, Ghent (BE); Lies Degrave, Ghent (BE); Isabelle Maillet, Ghent (BE)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/321,904

(22) PCT Filed: Aug. 1, 2017

(86) PCT No.: PCT/US2017/044825
§ 371 (c)(1),
(2) Date: Jan. 30, 2019

(87) PCT Pub. No.: WO2018/026770
PCT Pub. Date: Feb. 8, 2018

(65) Prior Publication Data

US 2019/0185526 A1 Jun. 20, 2019

Related U.S. Application Data

(60) Provisional application No. 62/371,259, filed on Aug. 5, 2016.

(51) Int. Cl.

| | |
|---|---|
| ***C07K 14/42*** | (2006.01) |
| ***C07K 14/325*** | (2006.01) |
| ***C07K 16/18*** | (2006.01) |
| ***C12N 9/42*** | (2006.01) |
| ***C12N 15/82*** | (2006.01) |

(52) U.S. Cl.
CPC ............ *C07K 14/42* (2013.01); *C07K 14/325* (2013.01); *C07K 16/18* (2013.01); *C12N 9/2442* (2013.01); *C12N 15/8218* (2013.01); *C12N 15/8286* (2013.01); *C12Y 302/01014* (2013.01); *Y02A 40/146* (2018.01)

(58) Field of Classification Search
CPC ...................................................... C07K 14/42
USPC .......................................................... 800/279
See application file for complete search history.

(56) References Cited

U.S. PATENT DOCUMENTS

| | | | |
|---|---|---|---|
| 7,943,819 B2 | 5/2011 | Baum et al. | |
| 8,759,611 B2 | 6/2014 | Baum et al. | |
| 9,238,822 B2 | 1/2016 | Baum et al. | |
| 9,388,409 B2 | 7/2016 | Boukharov et al. | |
| 9,695,439 B2 | 4/2017 | Baum et al. | |
| 9,657,293 B2 | 5/2017 | Donohue et al. | |
| 2006/0021087 A1 | 1/2006 | Baum et al. | |
| 2007/0124836 A1* | 5/2007 | Baum | C07K 14/43536 800/279 |
| 2009/0298787 A1 | 12/2009 | Raemaekers et al. | |
| 2011/0154545 A1 | 6/2011 | Andersen et al. | |
| 2012/0174258 A1 | 7/2012 | Narva et al. | |
| 2012/0174259 A1* | 7/2012 | Narva | A61K 31/7088 800/279 |
| 2014/0230090 A1 | 8/2014 | Avniel et al. | |
| 2014/0275208 A1 | 9/2014 | Hu et al. | |
| 2015/0257389 A1 | 9/2015 | Hu et al. | |
| 2015/0322456 A1* | 11/2015 | Narva | C12N 15/8218 800/279 |
| 2015/0337302 A1 | 11/2015 | Donohue et al. | |
| 2016/0230185 A1* | 8/2016 | Baum | A01N 57/16 |
| 2017/0101651 A1 | 6/2017 | Baum et al. | |
| 2017/0183684 A1 | 6/2017 | Baum et al. | |
| 2017/0283828 A1 | 10/2017 | Baum et al. | |
| 2019/0177736 A1 | 6/2019 | Donohoe et al. | |
| 2019/0292543 A1 | 9/2019 | Crane et al. | |

FOREIGN PATENT DOCUMENTS

| | | | |
|---|---|---|---|
| CN | 105143453 | A | 3/2005 |
| CN | 101310020 | A | 11/2008 |
| RU | 2006103365 | A | 6/2006 |
| RU | 2306339 | C2 | 9/2007 |
| RU | 2321634 | C2 | 4/2008 |
| WO | 0134815 | A1 | 5/2001 |
| WO | 2005019414 | A2 | 3/2005 |
| WO | 2011025860 | A1 | 3/2011 |
| WO | 2012143542 | A1 | 10/2012 |
| WO | 2016060911 | A1 | 4/2016 |
| WO | 2016/174258 | A1 | 6/2016 |
| WO | 2016100517 | A1 | 6/2016 |
| WO | 2016105696 | A1 | 6/2016 |

(Continued)

OTHER PUBLICATIONS

Thomas et al. 2001, The Plant Journal 25(4):417-425.*
International Search Report mailed in International Application No. PCT/US2017/044825 dated Nov. 27, 2017.
Partial European Search Report for EP Application No. 17837508.5 dated Apr. 15, 2020.
Sergio Casas-Tinto et al: "Troponin-I enhances and is required for oncogenic overgrowth", Oncotarget, vol. 7, No. 33, Jul. 15, 2016.
Aartsma-Rus A. et al. Guidelines for Antisense Oligonucleotide Design and Insight Into Splice-modulating Mechanisms, Molecular Therapy, Mar. 2009, vol. 17, No. 3, p. 548-553; cf. p. 548, first paragraph.

(Continued)

*Primary Examiner* — Li Zheng
(74) *Attorney, Agent, or Firm* — BakerHostetler

(57) ABSTRACT

Disclosed are double stranded RNA molecules that are toxic to coleopteran insects. In particular, interfering RNA molecules capable of interfering with pest target genes and that are toxic to the target pest are provided. Further, methods of making and using the interfering RNA, for example in transgenic plants or as the active ingredient in a composition, to confer protection from insect damage are disclosed.

21 Claims, No Drawings

Specification includes a Sequence Listing.

(56) References Cited

FOREIGN PATENT DOCUMENTS

| | | | |
|---|---|---|---|
| WO | 2016138106 | A1 | 9/2016 |
| WO | 2017066041 | A2 | 4/2017 |
| WO | 2018026770 | A1 | 2/2018 |
| WO | 2018026774 | A1 | 2/2018 |

OTHER PUBLICATIONS

Alves A.P. et al., "Rna Interference As A Method For Target-Site Screening In The Western Corn Rootworm, Diabrotica Virgifera Virgifera" Journal Of Insect Science, 2010.

Capelle K. et al: "The involvement of clathrin-mediated endocytosis and two SID transmembrane proteins in double-stranded RNA uptake in the Colorado potato beetle midgut", 2016, Insect Molecular Biology, XP55932561.

Vidal Oscar Marino et al: "Negative Regulation Of *Drosophila* JAK-STAT Signalling By Endocytic Trafficking", 2010, Journal Of Cell Science, XP55932583A.

Wu Ke et al: "Clathrin Heavy Chain Is Important for Viability, Oviposition, Embryogenesis and, Possibly, Systemic RNAi Response in the Predatory Mite Metaseiulus occidentalis", 2014, Plos One, XP55932566.

Wynant N. et al: "Scavenger Receptor-Mediated Endocytosis Facilitates Rna Interference In The Desert Locust, *Schistocerca gregaria*", 2014, Insect Molecular Biology, XP55932569.

Xiao Da et al: "Clathrin-dependent endocytosis plays a predominant role in cellular uptake of double-stranded RNA in the red flour beetle", 2015, Insects Biochemistry And Molecular Biology, XP029586161.

Zenkova M. A. et al. "Imperfectly Matched Nucleic Acid Complexes And Their Biochemical Manifestation", Chemical Achievements, 1993, vol. 62, 4, pp. 414-435.

Office Action of corresponding UA App. No. 201901772 dated Sep. 19, 2022.

Office Action of corresponding RU App. No. 2022 102 484 dated Sep. 8, 2022.

Partial European Search Report of corresponding EP App. No. 22161351.6 dated Sep. 16, 2022.

Rospatent; Office Action with English translation of corresponding Russian App No. 2022 102 484; dated Feb. 3, 2023, 9 pages.

Michal Lapidot, et al., "Genome-Wide Natural Antisense Transcription: Coupling its Regulation to its Different Regulatory Mechanisms", European Molecular Biology Organization Reports, 2006, pp. 1216-1222, vol. 7, No. 12.

Young Ho Kim, et al. "RNA interference: applications and advances in insect toxicology and insect pest management." Pesticide Biochemistry and Physiology 120 (2015): 109-117.

Tao Tang, et al., "RNA Interference and Its Applications on Silencing of Insecticide-resistant Genes in Insects". Cotton Science, 2010, 22(6): 617-624. https://doi.org/10.11963/cs100617.

CNIPA; Office Action with English translation of corresponding Chinese App. No. 201780046979.8; dated Mar. 27, 2023; 27 pages.

Communication Pursuant to Article 94(3) EPC for EP Application No. 17837508.5, dated Dec. 15, 2021.

Argentenian Office Action (and English translation) for Argentenian Patent Application No. 20170102161, dated Nov. 18, 2021.

Thais Barros Rodrigues et al., Management of Insect Pest by RNAI—A New Tool for Crop Protection; RNA Interference, Apr. 6, 2016.

Communication pursuant to Article 94(3) EPC and Annex, for EP Application No. 17837508.5, dated Mar. 2, 2021.

Written Opinion of the International Searching Authority for International Application No. PCT/US2017/044825, dated Nov. 27, 2017.

Russian Office Action and translation for Russian Patent Application No. 2019105135, dated Jul. 12, 2021.

International Preliminary Report on Patentability for Application No. PCT/US2017/044825, dated Mar. 26, 2019.

Provisional Opinion Accompanying the Partial Search Result for EP Application No. 17837508.5, 2020.

Russian Office Action and translation for Russian Patent Application No. 2019105354, dated Feb. 22, 2022.

Chinese Office Action (and English translation) issued in CN 201780048634.6, dated Jan. 6, 2022.

Ivašenko N. I. et al., "Osobennosti sistemnogo zamalčivania gomologičnyh posledovatel"nostej v processe RNK-interferacii (Peculiarities of system silencing of homological sequences in the process of RNA interference), Uspehi sovremennoj biologii, (2009), vol. 129, No. 5, pp. 419-439.

Communication Pursuant to Rule 164(1) EPC enclosing European Partial Search Report for EP Application No. 17837511.9 and accompanying provisional opinion, dated Dec. 17, 2019.

Supplementary European Search Report for European Application No. 17837511.9, dated Mar. 24, 2020.

European Examination Reports for European Patent Application No. 17837511.9, dated Nov. 12, 2020 and Jun. 21, 2021.

Russian Office Action and translation for Russian Patent Application No. 2019105344, dated May 13, 2021.

Lincoln Fishilevich et al., University of Nebraska—RNAi as a management tool for the western corn rootworm, *Diabrotica virgifera* virgifera; Jan. 1, 2016.

Supplementary Partial European Search Report for EP Application No. 17837511.9 dated Dec. 12, 2019.

* cited by examiner

CONTROL OF COLEOPTERAN PESTS USING RNA MOLECULES

RELATED APPLICATION INFORMATION

This application is a 371 of International Application No. PCT/US2017/044825, filed Aug. 1, 2017, which claims priority to U.S. Application No. 62/371,259, filed Aug. 5, 2016, the contents of which are incorporated herein by reference in their entirety.

STATEMENT REGARDING ELECTRONIC SUBMISSION OF A

SEQUENCE LISTING

A Sequence Listing in ASCII text format, submitted under 37 C.F.R. § 1.821, entitled "81018 ST25.txt", 560,179 bytes in size, generated on Aug. 20, 2019 and filed via EFS-Web is provided in lieu of a paper copy. This Sequence Listing is hereby incorporated by reference into the specification for its disclosures.

FIELD OF THE INVENTION

The invention relates generally to the control of pests that cause damage to crop plants by their feeding activities, and more particularly to the control of coleopteran pests by compositions comprising interfering RNA molecules. The invention further relates to the compositions and to methods of using such compositions comprising the interfering RNA molecules.

BACKGROUND

Insect species in the genus *Diabrotica* (corn rootworms and cucumber beetles) are considered some of the most important pests to crop plants. For example, species of corn rootworm, including *Diabrotica virgifera virgifera*, the western corn rootworm (WCR), *D. barberi*, the northern corn rootworm (NCR), *D. undecimpunctata howardi*, the southern corn rootworm (SCR), and *D. virgifera zeae*, the Mexican corn rootworm (MCR), are the most destructive corn pests in North America causing an estimated loss of over $1 billion annually. The western corn rootworm has also invaded Europe and causes an estimated 0.5 billion euros in damage each year. *Diabrotica speciosa* (common names include, among others, leaf beetle, little Brazilian beetle, cucurbit beetle and *chrysanthemum* beetle) is an important pest of corn, soybean and peanuts, in South America.

Most of the damage in corn is caused by larval rootworm feeding. Newly hatched rootworm larvae locate corn roots in the soil and initially begin feeding on the fine root hairs and burrow into root tips of the corn plant. As larvae grow larger, they feed on and tunnel into primary roots. When rootworms are abundant, larval feeding and deterioration of injured roots by root rot pathogens can result in roots being pruned to the base of the stalk. Severe root injury interferes with the roots' ability to transport water and nutrients into the plant, reduces plant growth, and results in reduced grain production. Severe root injury also may result in lodging of corn plants, making mechanical harvest more difficult or impossible. Corn rootworm adults feed primarily on corn silk, pollen, and kernels on exposed ear tips. If corn rootworm adults begin emerging before corn reproductive tissues are present, adults may feed on leaf tissue, scraping away the green surface tissue and leaving a window-pane appearance. Silk feeding by adults can result in pruning of silks at the ear tip, commonly called silk clipping. In field corn, beetle populations may reach a level high enough to cause severe silk clipping during pollen shed, which may interfere with pollination and reduce yield. Thus, unlike lepidopteran pests of corn in which only the larval stages cause damage, both the larval and adult stages of corn rootworm are capable of causing economic damage to corn.

*Diabrotica* insect pests are mainly controlled by intensive applications of chemical pesticides, which may be active against both larval and adult stages, through inhibition of insect growth, prevention of insect feeding or reproduction, or cause death. Good insect control can thus be reached, but these chemicals can sometimes also affect other, beneficial insects. Additional problems occur in areas of high insecticide use where populations of corn rootworm beetles have become resistant to certain insecticides. This has been partially alleviated by various resistance management practices, but there is an increasing need for alternative pest control agents.

Several native Cry proteins from *Bacillus thuringiensis*, or engineered Cry proteins, have been expressed in transgenic crop plants and exploited commercially to control certain lepidopteran and coleopteran insect pests. For example, starting in 2003, transgenic corn hybrids that control corn rootworm by expressing a Cry3Bb1, Cry34Ab1/Cry35Ab1 or modified Cry3A (mCry3A) or Cry3Ab (eCry3.1Ab) protein have been available commercially in the US.

The seed industry, university researchers and the US Environmental Protection Agency have worked together to develop management plans to help mitigate the onset of insect resistance to transgenic plants expressing insecticidal proteins. They are based primarily on a high dose and refuge strategy. A high dose strategy for corn is to use corn hybrids that express high enough levels of an insecticidal protein such as a Cry protein to kill even partially resistant insects. The underlying hypothesis is that killing partially resistant insects and preventing their mating greatly delays the development of resistance. The success of a high dose strategy depends in part on the specific activity of the insecticidal protein to the particular insect species and how much of that insecticidal protein can be expressed in the transgenic corn plant. The higher the specific activity of an insecticidal protein to a pest, the less amount of the insecticidal protein is required to be expressed in a transgenic plant to achieve a high dose strategy. For example, corn hybrids expressing the lepidopteran-active Cry protein, Cry1Ab, are considered high-dose against the primary target pest European corn borer (*Ostrinia nubilalis*). Because Cry1Ab is very toxic to European corn borer larvae with an LC50<10 ng/$cm^2$ (i.e. high specific activity), levels of expression of Cry1Ab that are achievable in transgenic plants easily places such corn hybrids in a high dose category. However, unlike the lepidopteran-active products, current rootworm products are not considered high-dose. The proteins they express are not active against adults and have limited activity against late instar larvae. Therefore, the current transgenic rootworm products allow some rootworm larvae to survive and emerge as adults.

Thus, economic levels of silk clipping by corn rootworm adults may still occur even in portions of fields planted to a transgenic corn rootworm hybrid. For example, densities of western corn rootworm adults may exceed economic levels in portions of fields planted to transgenic corn rootworm hybrids due to immigration of beetles as well as direct emergence of adults from transgenic root systems. There have been many reports that confirm western corn rootworm adult emergence from certain corn transgenic rootworm hybrids (Crowder et al. (2005) J. Econ. Entomol. 98:534-551). Another publication suggests that western corn rootworm adults will exhibit similar feeding behaviors when encountering some transgenic corn plants or non-transgenic corn plants in the field and that it is unlikely that certain insecticidal proteins in transgenic plants will have significant effects on adults that might impact resistance management.

Therefore, identifying alternative insect control agents with new modes of action would be beneficial. Particularly useful would be new insect control agents that may be toxic to multiple life stages of the target insect pest. Such insect control agents may include those that target genetic elements, such as genes that are essential to the growth and survival of a target insect pest.

RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant microRNAs (miRNAs) show extensive base pairing to, and guide cleavage of, their target mRNAs (Jones-Rhoades et al. (2006) *Annu. Rev. Plant Biol.* 57, 19-53; Llave et al. (2002) *Proc. Natl. Acad. Sci. USA* 97, 13401-13406). In other instances, interfering RNAs may bind to target RNA molecules having imperfect complementarity, causing translational repression without mRNA degradation. The majority of the animal miRNAs studied so far appear to function in this manner.

RNAi has been found to be useful for insect control of certain insect pests. RNAi strategies typically employ a synthesized, non-naturally occurring "interfering RNA", or "interfering RNA molecule" which typically comprises at least a RNA fragment against a target gene, a spacer sequence, and a second RNA fragment which is complementary to the first, so that a double-stranded RNA structure can be formed. This non-naturally double-stranded RNA takes advantage of the native RNAi pathways in the insect to trigger down-regulation of target genes that may lead to the cessation of feeding and/or growth and may result in the death of the insect pest.

Although it is known in the literature that RNAi strategies focused on target genes can lead to an insecticidal effect in *Diabrotica* species, it is also known that not every target sequence is successful, and that an insecticidal effect cannot be predicted. The overwhelming majority of sequences complementary to corn rootworm DNAs are not lethal in species of corn rootworm when used as dsRNA or siRNA. For example, Baum et al. ((2007) Nature Biotechnology 25:1322-1326), describe the effects of inhibiting several WCR gene targets by RNAi. These authors reported that the 8 of 26 target genes they tested were not able to provide experimentally significant coleopteran pest mortality, even at a very high iRNA (e.g., dsRNA) concentration of more than 520 ng/$cm^2$. Additionally, target genes against which a dsRNA molecule is known to give a strong RNAi effect in one insect species may not be a good target for different insect species. Whyard et al. ((2009) *Insect Biochemistry and Molecular Biology* 39: 824-832) report nearly 100-fold differences in efficacy when testing conspecific dsRNA molecules against a V-ATPase gene in four different insect species.

There is an ongoing need for compositions containing insecticidal active ingredients, and for methods of using such compositions, for instance for use in crop protection or insect-mediated disease control. Novel compositions are required to overcome the problem of resistance to existing insecticides and/or to help mitigate the development of resistance to existing transgenic plant approaches. Ideally such compositions have a high toxicity and are effective when ingested orally by the target pest and have applicability for use against both the larval and adult stages of the pest insect. Thus any invention which provided compositions in which any of these properties was enhanced would represent a step forward in the art.

SUMMARY

The needs outlined above are met by the invention which, in various embodiments, provides new methods of controlling economically important insect pests. The invention in part comprises a method of inhibiting expression of one or more target genes and proteins in coleopteran insect pests. Specifically, the invention comprises methods of modulating expression of one or more target genes in *Diabrotica* species, such as *Diabrotica virgifera virgifera* (western corn rootworm), *Diabrotica barberi* (northern corn rootworm), *Diabrotica undecimpunctata howardi* (southern corn rootworm), *Diabrotica virgifera zeae* (Mexican corn rootworm), *Diabrotica speciosa* (*chrysanthemum* beetle), and related species, that causes cessation of feeding, growth, development and reproduction, and eventually results in the death of the insect. The method comprises introduction of an interfering RNA molecule comprising a double-stranded RNA (dsRNA) or its modified forms such as small interfering RNA (siRNA) sequences, into cells or into the extracellular environment, such as the midgut, within a pest insect body wherein the dsRNA or siRNA enters the cells and inhibits expression of at least one or more target genes and wherein inhibition of the one or more target genes exerts a deleterious effect upon the pest insect. The interfering RNA molecule is non-naturally occurring. It is specifically contemplated that the methods and compositions of the invention will be useful in limiting or eliminating pest insect infestation in or on any plant by providing one or more compositions comprising interfering RNA molecules comprising dsRNA or siRNA molecules in the diet of the pest. The invention also provides interfering RNA molecules that when delivered to an insect pest inhibits, through a toxic effect, the ability of the insect pest to survive, grow, feed and/or reproduce, or to limit pest related damage or loss to crop plants. Such delivery may be through production of the interfering RNA in a transgenic plant, for example corn, or by topically applying a composition comprising the interfering RNA to a plant or plant seed, such as a corn plant or corn seed. Delivery may further be through contacting the insect with the interfering RNA, such as when the insect feeds on plant material comprising the interfering RNA, either because the plant material is expressing the interfering RNA through a transgenic approach, or because the plant material is coated with a composition comprising the interfering RNA. The interfering RNA may also be provided in an artificial insect diet which the insect then contacts by feeding. The interfering RNA molecule comprises a nucleotide sequence that is complementary to a nucleotide sequence of a mRNA transcribable from a target gene or a portion of a nucleotide sequence of a mRNA transcribable from a target gene of the pest insect and therefore inhibits expression of the target gene, which causes cessation of feeding, growth, development, reproduction and eventually results in death of the pest insect. The invention is further drawn to nucleic acid constructs, nucleic acid molecules and recombinant vectors that comprise or encode at least a fragment of one strand of an interfering RNA molecule of the invention. The invention also provides chimeric nucleic acid molecules comprising an antisense strand of a dsRNA of the interfering RNA operably associated with a plant microRNA precursor molecule. The invention also provides artificial plant microRNA precursors comprising an antisense strand of a dsRNA of an interfering RNA of the invention.

The invention further provides an interfering ribonucleic acid (RNA) molecule wherein the RNA comprises at least one dsRNA wherein the dsRNA is a region of double-stranded RNA comprising annealed complementary strands, one strand of which comprises a sequence of at least 19 contiguous nucleotides which is at least partially complementary to a target nucleotide sequence within a *Diabrotica* spp target gene, and (i) is at least 85% identical to at least a 19 contiguous nucleotide fragment of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; or (ii) comprises at least a 19 contiguous nucleotide fragment of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; or (iii) comprises at least a 19 contiguous nucleotide fragment of a nucleotide sequence encoding an amino acid sequence encoded by SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof, wherein the interfering RNA molecule has insecticidal activity on a coleopteran plant pest. In some embodiments, the interfering molecule may comprise at least two dsRNAs, wherein each dsRNA comprises a sequence of nucleotides which is at least partially complementary to a target nucleotide sequence within the target gene. In further embodiments, each of the dsRNAs may comprise a different sequence of nucleotides which is complementary to a different target nucleotide sequence within the target gene.

The invention further provides compositions comprising one or more interfering RNA molecules comprising two or more of dsRNA molecules, wherein the two or more RNA molecules each comprise a different antisense strand, or comprising two or more nucleic acid constructs or nucleic acid molecules or artificial plant microRNA precursors of the invention.

The invention further provides insecticidal compositions for inhibiting the expression of a Coleopteran insect gene that comprises a dsRNA of the invention and an agriculturally acceptable carrier. In one embodiment, inhibition of the expression of a *Diabrotica* gene described here leads to cessation of feeding and growth and ultimately results in the death of the *Diabrotica* insect.

The invention is further drawn to transgenic plants which produce one or more interfering RNA molecules of the invention that are self-protected from insect feeding damage and to methods of using the plants alone or in combination with other insect control strategies to confer maximal insect control capabilities. Plants and/or plant parts producing one or more interfering RNA molecules of the invention or treated with a composition comprising one or more interfering RNA molecules of the invention are highly resistant to insect pest infestation. For example, economically important coleopteran pests can be controlled by a plant that produces an interfering RNA molecule of the invention or by a plant or plant seed that is treated with a composition comprising an interfering RNA molecule of the invention.

The invention also provides a method of controlling a Coleopteran insect plant pest comprising contacting the Coleopteran insect with a nucleic acid molecule that is or is capable of producing an interfering RNA of the invention for inhibiting expression of a gene in the Coleopteran insect thereby controlling the Coleopteran insect.

In other aspects, the invention provides a method of reducing a *Diabrotica* insect population on a transgenic plant expressing a second insecticidal agent, for example an insecticidal protein, in addition to an interfering RNA of the invention capable of inhibiting expression of an target gene in a *Diabrotica* insect, thereby reducing the *Diabrotica* insect population. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the second insecticidal agent may be derived from sources other than *B. thuringiensis*. The second insecticidal agent can be an agent selected from the group comprising a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporous* insecticidal protein, a *Lysinibacillus sphearicus* insecticidal protein, a *Chromobacterium* spp. insecticidal protein, a *Yersinia* entomophaga insecticidal protein, a *Paenibacillus* popiliae insecticidal protein, a *Clostridium* spp. (such as *C. bifermentans*) insecticidal protein, a *Alcaligenes* ssp. insecticidal protein, a *Pseudomonas* spp. insecticidal protein, and a lignin. In other embodiments, the second agent may be at least one insecticidal protein derived from an insecticidal toxin complex (Tc) from *Photorhabdus, Xenorhabus, Serratia*, or *Yersinia*. In other embodiments, the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In other aspects, the invention provides a method of reducing resistance development in a *Diabrotica* insect population to an interfering RNA of the invention, the method comprising expressing in a transgenic plant fed upon by the *Diabrotica* insect population an interfering RNA of the invention that is capable of inhibiting expression of a target gene in a larval and adult *Diabrotica* insect, thereby reducing resistance development in the *Diabrotica* insect population compared to a *Diabrotica* insect population exposed to an interfering RNA capable of inhibiting expression of a *Diabrotica* gene described herein in only the larval stage or adult stage of a *Diabrotica* insect.

In other aspects, the invention provides a method of reducing the level of a target RNA transcribable from a *Diabrotica* gene described herein in a *Diabrotica* insect comprising contacting the *Diabrotica* insect with a composition comprising an interfering RNA molecule of the invention, wherein the interfering RNA molecule reduces the level of the target RNA in a cell of the *Diabrotica* insect.

In still other aspects, the invention provides a method of conferring *Diabrotica* insect tolerance or Coleopteran plant pest tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, thereby conferring to the plant or part thereof tolerance to the *Diabrotica* insect or Coleopteran plant pest.

In further aspects, the invention provides a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, thereby reducing root damage to the plant fed upon by a *Diabrotica* insect.

In other aspects, the invention provides a method of producing a transgenic plant cell having toxicity to a Coleopteran insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the Coleopteran insect compared to a control plant cell.

In further aspects, the invention provides a method of producing a transgenic plant having enhanced tolerance to Coleopteran insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to Coleopteran insect feeding damage compared to a control plant.

In other aspects, the invention provides a method of enhancing control of a Coleopteran insect population comprising providing a transgenic plant or transgenic seed of the invention and applying to the transgenic plant or the transgenic seed a chemical pesticide that is insecticidal to a Coleopteran insect, thereby enhancing control of the Coleopteran insect population.

In other aspects, the invention provides a method of providing a corn grower with a means of controlling a Coleopteran insect pest population below an economic threshold in a corn crop comprising (a) selling or providing to the grower transgenic corn seed comprising a dsRNA, a nucleic acid molecule, a nucleic acid construct, a chimeric nucleic acid molecule, an artificial plant microRNA precursor molecule and/or a composition of the invention; and (b) advertising to the grower that the transgenic corn seed produces transgenic corn plants capable of controlling a Coleopteran insect pest population.

In another aspect, the invention provides a method of identifying an orthologous target gene for using as a RNAi strategy for the control of a plant pest, said method comprising the steps of: a) producing a primer pair that will amplify a target selected from the group comprising or consisting of SEQ ID NO: 31-90, 397, 398, or a complement thereof; b) amplifying an orthologous target gene from a nucleic acid sample of the plant pest; c) identifying a sequence of an orthologous target gene; d) producing an interfering RNA molecule, wherein the RNA comprises at least one dsRNA, wherein the dsRNA is a region of double-stranded RNA comprising annealed complementary strands, one strand of which comprises a sequence of at least 19 contiguous nucleotides which is at least partially complementary to the orthologous target nucleotide sequence within the target gene; ande) determining if the interfering RNA molecule of step (d) has insecticidal activity on the plant pest. If the interfering RNA has insecticidal activity on the plant pest target gene, an orthologous target gene for using in the control of a plant pest has been identified.

These and other aspects of the invention are set forth in more detail in the description of the invention below.

BRIEF DESCRIPTION OF THE SEQUENCES IN THE SEQUENCE LISTING

SEQ ID NOs: 1-30 are fragments of DNA coding sequences used to synthesize interfering RNA molecules to test for insecticidal activity.

SEQ ID NOs: 31-90 and 397-398 are nucleic acid sequences of primers used to identify target genes from *Diabrotica* spp. for testing for insecticidal activity using a RNAi strategy.

SEQ ID NOs: 91-120 are complete DNA coding sequences of the 30 target genes identified in the RNAi-based screen for insecticidal activity.

SEQ ID NOs: 121-150 are RNA sequences of the fragments of the DNA coding sequences used to synthesize interfering RNA molecules to test for insecticidal activity.

SEQ ID NOs: 151-180 are RNA sequences of the complete DNA coding sequences of the 30 target genes identified in the RNAi-based screen for insecticidal activity.

SEQ ID NOs: 181-210 are complete mRNA sequences, including 5' and 3' UTRs, for the 30 target genes identified in the RNAi-based screen for insecticidal activity.

SEQ ID NOs: 211-240 are antisense RNA sequences of the complete DNA coding sequences of the 30 target genes identified in the RNAi-based screen for insecticidal activity.

SEQ ID NOs: 241-270 are amino acid sequences of the proteins encoded by the 30 target genes identified in the RNAi-based screen for insecticidal activity.

SEQ ID NOs: 271-273 are DNA coding sequences of NCR orthologs of three selected WCR target genes identified in the RNAi-based screen for insecticidal activity (BPA_15366, BPA_71568, and BPA_16830).

SEQ ID NOs: 274-276 are RNA sequences of the DNA coding sequences of the NCR orthologs of three selected WCR target genes identified in the RNAi-based screen for insecticidal activity (BPA_15366, BPA_71568, and BPA_16830).

SEQ ID NOs: 277-279 are DNA coding sequences of SCR orthologs of three selected WCR target genes identified in the RNAi-based screen for insecticidal activity (BPA_15366, BPA_71568, and BPA_16830).

SEQ ID NOs: 280-282 are RNA sequences of the DNA coding sequences of the SCR orthologs of three selected WCR target genes identified in the RNAi-based screen for insecticidal activity (BPA_15366, BPA_71568, and BPA_16830).

SEQ ID NOs: 283-287 and 399-400 are DNA sequences of fragments of the BPA_15366 target gene.

SEQ ID NOs: 288-293 are DNA sequences of fragments of the BPA_71568 target gene.

SEQ ID NOs: 294-297 are DNA sequences of fragments of the BPA_16830 target gene.

SEQ ID NOs: 298-302 and 401-402 are RNA sequences of fragments of the BPA_15366 target gene mRNA.

SEQ ID NOs: 303-308 are RNA sequences of fragments of the BPA_71568 target gene mRNA.

SEQ ID NOs: 309-312 are RNA sequences of fragments of the BPA_16830 target gene mRNA SEQ ID NOs: 313-317 are DNA sequences of fragments of the BPA_15366 target gene.

SEQ ID NOs: 318-322 are DNA sequences of fragments of the BPA_15366 target gene operably linked to GFP DNA sequence.

SEQ ID NOs: 323-344 are DNA sequences of fragments of the BPA_15366 target gene operably linked at the 5' and 3' ends to GFP “filler” DNA sequence.

SEQ ID NOs: 345-349 are RNA sequences of fragments of the BPA_15366 target gene mRNA operably linked to GFP RNA sequence.

SEQS ID NOs: 350-371 are RNA sequences of fragments of the BPA_15366 target gene operably linked at the 5' and 3' ends to GFP “filler” RNA sequence SEQ ID NO: 372 is a nucleic acid sequence of the coding sequence of the BPA_16372 target gene.

SEQ ID NO: 373 is a RNA sequence of SEQ ID NO: 372.

SEQ ID NO: 374 is a mRNA sequence, including 5' and 3' UTRs, of the BPA_16372 target gene.

SEQ ID NO: 375 is an antisense RNA sequences of SEQ ID NO: 372.

SEQ ID NO: 376 is an amino acid sequence of the protein encoded by SEQ ID NO: 372.

SEQ ID NO: 377 is a nucleic acid coding sequence of the NCR ortholog of the BPA_16372 target gene.

SEQ ID NO: 378 is an RNA sequence of SEQ ID NO: 377.

SEQ ID NO: 379 is a nucleic acid coding sequence of the SCR ortholog of the BPA_16372 target gene.

SEQ ID NO: 380 is an RNA sequence of SEQ ID NO: 379.

SEQ ID NOs: 381-388 are DNA sequences of fragments of the BPA_16372 target gene.

SEQ ID NOs: 389-396 are RNA sequences of fragments of the BPA_16372 target gene mRNA.

SEQ ID NO: 403 is a DNA sequence which encodes for a hairpin RNA structure to a target gene.

DETAILED DESCRIPTION

The following is a detailed description of the invention provided to aid those skilled in the art in practicing the invention. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments of the invention will be apparent to those skilled in the art in light of the instant disclosure, which do not depart from the invention. Hence, the following descriptions are intended to illustrate some particular embodiments of the invention, and not to exhaustively specify all permutations, combinations and variations thereof. Those of ordinary skill in the art will recognize that modifications and variations in the embodiments described herein may be made without departing from the spirit or scope of the invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

For clarity, certain terms used in the specification are defined and presented as follows:

As used herein, “a,” “an” or “the” can mean one or more than one. For example, “a cell” can mean a single cell or a multiplicity of cells.

As used herein, “and/or” refers to and encompasses any and all possible combinations of one or more of the associated listed items, as well as the lack of combinations when interpreted in the alternative (or).

Further, the term “about,” as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase “consisting essentially of” means that the scope of a claim is to be interpreted to encompass the specified materials or steps recited in the claim and those that do not materially affect the basic and novel characteristic(s) of the claimed invention. Thus, the term “consisting essentially of” when used in a claim of this invention is not intended to be interpreted to be equivalent to “comprising.” A “coding sequence” is a nucleic acid sequence that is transcribed into RNA such as mRNA, rRNA, tRNA, snRNA, sense RNA or antisense RNA. Preferably the RNA is then translated in an organism to produce a protein.

The terms “sequence similarity” or “sequence identity” of nucleotide or amino acid sequences mean a degree of identity or similarity of two or more sequences and may be determined conventionally by using known software or computer programs such as the Best-Fit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482-489 (1981), to find the best segment of identity or similarity between two sequences. Sequence comparison between two or more polynucleotides or polypeptides is generally performed by comparing portions of the two sequences over a comparison window to identify and compare local regions of sequence similarity. The comparison window is generally from about 20 to 200 contiguous nucleotides. Gap performs global alignments: all of one sequence with all of another similar sequence using the method of Needleman and Wunsch, J. Mol. Biol. 48:443-453 (1970). When using a sequence alignment program such as BestFit to determine the degree of DNA sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

The term "homology" in the context of the invention refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For an amino acid sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, or at least 30% identical, or at least 40% identical, or at least 50% identical, or at least 60% identical, or at least 70% identical, or at least 80% identical, or at least 88% identical, or at least 90% identical, or at least 92% identical, or at least 95% identical, across any substantial region of the molecule (DNA, RNA, or protein molecule).

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a polynucleotide will hybridize to its target sequence to a detectably greater degree than other sequences (e.g., at least 2-fold over background). Stringent conditions are sequence-dependent and will be different in different circumstances. By controlling the stringency of the hybridization and/or washing conditions, target polynucleotides can be identified which are 100% complementary to the probe (homologous probing). Alternatively, stringency conditions can be adjusted to allow some mismatching in sequences so that lower degrees of similarity are detected (heterologous probing). Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Moderate stringency conditions detect sequences that share at least 80% sequence identity. Exemplary moderate stringency conditions include hybridization in 40 to 45% formamide, 1 M NaCl, 1% SDS at 37° C., and a wash in 0.5× to 1×SSC at 55 to 60° C. High stringency conditions detect sequences that share at least 90% sequence identity. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267-284, 1984): Tm=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., eds., Greene Publishing and Wiley-Interscience, New York (1995). Methods of stringent hybridization are known in the art which conditions can be calculated by means known in the art. This is disclosed in Sambrook et al., Molecular Cloning: A Laboratory Manual, 2nd Ed., Cold Spring Harbor Laboratory Press, 1989, Cold Spring Harbor, N.Y. and Current Protocols in Molecular Biology, Ausebel et al, eds., John Wiley and Sons, Inc., 2000. Methods of determining percent sequence identity are known in the art, an example of which is the GCG computer sequence analysis software (GCG, Inc, Madison Wis.).

Nucleic acids that do not hybridize to each other under stringent conditions are still substantially identical if the proteins that they encode are substantially identical (e.g., due to the degeneracy of the genetic code).

A further indication that two nucleic acids or proteins are substantially identical is that the protein encoded by the first nucleic acid is immunologically cross reactive with the protein encoded by the second nucleic acid. Thus, a protein is typically substantially identical to a second protein, for example, where the two proteins differ only by conservative substitutions.

A nucleic acid sequence is "isocoding with" a reference nucleic acid sequence when the nucleic acid sequence encodes a polypeptide having the same amino acid sequence as the polypeptide encoded by the reference nucleic acid sequence.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

As used herein, "dsRNA" or "RNAi" refers to a polyribonucleotide structure formed either by a single self-complementary RNA strand or at least by two complementary RNA strands. The degree of complementary, in other words the % identity, need not necessarily be 100%. Rather, it must be sufficient to allow the formation of a double-stranded structure under the conditions employed. As used herein, the term "fully complementary" means that all the bases of the nucleotide sequence of the dsRNA are complementary to or 'match' the bases of the target nucleotide sequence. The term "at least partially complementary" means that there is less than a 100% match between the bases of the dsRNA and the bases of the target nucleotide sequence. The skilled person will understand that the dsRNA need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the dsRNA and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the dsRNA may comprise 1, 2 or 3 mismatches as compared with the target nucleotide sequence over every length of 24 partially complementary nucleotides. It will be appreciated by the person skilled in the art that the degree of complementarity shared between the dsRNA and the target nucleotide sequence may vary depending on the target gene to be down-regulated or depending on the insect pest species in which gene expression is to be controlled.

It will be appreciated that the dsRNA may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene. The skilled person will be aware of methods of identifying the most suitable target nucleotide sequences within the context of the full-length target gene. For example, multiple dsRNAs targeting different regions of the target gene can be synthesised and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

Preferably, the % identity of a polyribonucleotide is determined by GAP (Needleman and Wunsch, 1970) analysis (GCG program) using the default settings, wherein the query sequence is at least about 21 to about 23 nucleotides in length, and the GAP analysis aligns the two sequences over a region of at least about 21 nucleotides. In another embodiment, the query sequence is at least 150 nucleotides in length, and the GAP analysis aligns the two sequences over a region of at least 150 nucleotides. In a further embodiment, the query sequence is at least 300 nucleotides in length and the GAP analysis aligns the two sequences over a region of at least 300 nucleotides. In yet another embodiment, the query sequence corresponds to the full length of the target RNA, for example mRNA, and the GAP analysis aligns the two sequences over the full length of the target RNA.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand.

RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. It is well-known in the art that small dsRNA of about 19-23 bp in length can be used to trigger gene silencing of a target gene. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 19 to about 23 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to a molecule that is double stranded for its full length, corresponding in size to a full length target RNA molecule. Bolognesi et al (2012, *PLOS One,* 7(10): e47534, herein incorporated by reference) teach that dsRNAs greater than or equal to about 60 bp are required for biological activity in artificial diet bioassays with Southern Corn Rootworm (SCR; *Diabrotica undecimpunctata howardii*).

Mao et al (2007, *Nature Biotechnology,* 35(11): 1307-1313) teach a transgenic plant expressing a dsRNA construct against a target gene (CYP6AE14) of an insect pest (cotton bollworm, *Helicoverpa armigera*). Insects feeding on the transgenic plant have small RNAs of about 19-23 bp in size of the target gene in their midgut, with a corresponding reduction in CYP6AE14 transcripts and protein. This suggests that the small RNAs were efficacious in reducing expression of the target gene in the insect pest. Therefore, small RNAs of about 19 bp, about 20 bp, about 21 bp, about 22 bp, about 23 bp, about 24 bp, about 25 bp, about 26 bp, about 27 bp, about 28 bp, about 29 bp, or about 30 bp may be efficacious in reducing expression of the target gene in an insect pest.

Alternatively, the dsRNA may comprise a target dsRNA of at least 19 base pairs, and the target dsRNA may be within a dsRNA "carrier" or "filler" sequence. For example, Bolognesi et al (2012) show that a 240 bp dsRNA encompassing a target dsRNA, which comprised a 21 bp contiguous sequence with 100% identity to the target sequence, had biological activity in bioassays with Southern Corn Rootworm. The present application exemplifies a similar approach in bioassays with Western Corn Rootworm. The target dsRNA may have a length of at least 19 to about 25 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs. Combined with the carrier dsRNA sequence, the dsRNA of the target sequence and the carrier dsRNA may have a total length of at least about 50 to about 100 base pairs, optionally a sequence of about 100 to about 200 base pairs, optionally a sequence of about 200 to about 500, and optionally a sequence of about 500 to about 1000 or more base pairs.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

The interfering RNAs of the current invention may comprise one dsRNA or multiple dsRNAs, wherein each dsRNA comprises or consists of a sequence of nucleotides which is at least partially complementary to a target nucleotide sequence within the target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single dsRNA i.e. repeats of a dsRNA that binds to a particular target nucleotide sequence within a specific target gene. In another embodiment, the dsRNAs within the interfering RNA comprise or consist of different sequences of nucleotides complementary to different target nucleotide sequences. It should be clear that combinations of multiple copies of the same dsRNA combined with dsRNAs binding to different target nucleotide sequences are within the scope of the current invention.

The dsRNAs may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target gene(s).

In addition to the dsRNA(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyses processing of the interfering RNA within the insect pest cells and thereby enhances the efficacy of the interfering RNA. Structures for enhancing the stability of RNA molecules are well known in the art and are described further in WO2006/046148 as incorporated herein by reference.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions. Alternatively, the interfering RNA may be transcribed from a polynucleotide encoding the same. Thus, provided herein is an isolated polynucleotide encoding any of the interfering RNAs of the current invention.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, *Cell,* 116:281-297 (2004); Zhang et al. *Dev. Biol.* 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. *Genes Dev.* 16:1616-1626 (2002), Park et al. *Curr. Biol.* 12:1484-1495 (2002)) many hundreds have been identified. Furthermore, many plant miRNAs have been shown to be highly conserved across very divergent taxa. (Floyd et al. *Nature* 428:485-486 (2004); Zhang et al. *Plant J.* 46:243-259 (2006)). Many microRNA genes (MIR genes) have been identified and made publicly available in a database (miRBase, available via the world wide web). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. *Proc. Natl. Acad. Sci.* 105:9851-9852 (2008)). Many reviews on microRNA biogenesis and function are available, for example, see, Bartel *Cell* 116:281-297 (2004), Murchison et al. *Curr. Opin. Cell Biol.* 16:223-229 (2004), Dugas et al. *Curr. Opin. Plant Biol.* 7:512-520 (2004) and Kim *Nature Rev. Mol. Cell Biol.* 6:376-385 (2005).

The term "plant microRNA precursor molecule" as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA (mRNA). The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that of a non-native, heterologous miRNA (amiRNA/amiRNA*; e.g. siRNA/siRNA*) that is then processed into the mature miRNA sequence with the siRNA sequence.

In the context of the invention, the term "toxic" used to describe a dsRNA of the invention means that the dsRNA molecules of the invention and combinations of such dsRNA molecules function as orally active insect control agents that have a negative effect on an insect. When a composition of the invention is delivered to the insect, the result is typically death of the insect, or the insect does not feed upon the source that makes the composition available to the insect. Such a composition may be a transgenic plant expressing the dsRNA of the invention.

To "control" or "controlling" insects means to inhibit, through a toxic effect, the ability of one or more insect pests to survive, grow, feed, and/or reproduce, or to limit insect-related damage or loss in crop plants. To "control" insects may or may not mean killing the insects, although it preferably means killing the insects. A composition that controls a target insect has insecticidal activity against the target insect.

To "deliver" or "delivering" a composition or dsRNA means that the composition or dsRNA comes in contact with an insect, resulting in a toxic effect and control of the insect. The composition or dsRNA can be delivered in many recognized ways, e.g., orally by ingestion by the insect via transgenic plant expression, formulated composition(s), sprayable composition(s), a bait matrix, or any other art-recognized toxicant delivery system.

The term "insect" as used herein includes any organism now known or later identified that is classified in the animal kingdom, phylum Arthropoda, class Insecta, including but not limited to insects in the orders Coleoptera (beetles), Lepidoptera (moths, butterflies), Diptera (flies), Protura, Collembola (springtails), Diplura, Microcoryphia (jumping bristletails), Thysanura (bristletails, silverfish), Ephemeroptera (mayflies), Odonata (dragonflies, damselflies), Orthoptera (grasshoppers, crickets, katydids), Phasmatodea (walkingsticks), Grylloblattodea (rock crawlers), Mantophasmatodea, Dermaptera (earwigs), Plecoptera (stoneflies), Embioptera (web spinners), Zoraptera, Isoptera (termites), Mantodea (mantids), Blattodea (cockroaches), Hemiptera (true bugs, cicadas, leafhoppers, aphids, scales), Thysanoptera (*thrips*), Psocoptera (book and bark lice), Phthiraptera (lice; including but not limited to suborders Amblycera, Ischnocera and Anoplura), Neuroptera (lacewings, owlflies, mantispids, antlions), Hymenoptera (bees, ants, wasps), Trichoptera (caddisflies), Siphonaptera (fleas), Mecoptera (scorpion flies), Strepsiptera (twisted-winged parasites), and any combination thereof.

As used herein, a "coleopteran insect" refers to any member of the Coleoptera order, including coleopteran plant pests. Insects in the order Coleoptera include but are not limited to any coleopteran insect now known or later identified including those in suborders Archostemata, Myxophaga, Adephaga and *Polyphaga*, and any combination thereof.

"*Diabrotica*" is a genus of beetles (from the Coleoptera order) commonly referred to as "corn rootworms" or "cucumber beetles." *Diabrotica* insects that are pests of crop plants, include without limitation, *Diabrotica barberi* (northern corn rootworm; NCR), *D. virgifera virgifera* (western corn rootworm; WCR), *D. undecimpunctata howardii* (southern corn rootworm; SCR), *D. virgifera zeae* (Mexican corn rootworm; MCR) and *D. speciosa*. In the context of the invention, the term "corn rootworm" or "cucumber beetle" is interchangeable with the term "*Diabrotica.*"

Other nonlimiting examples of coleopteran insect pests according to the present invention include *Leptinotarsa* spp. such as *L. decemlineata* (Colorado potato beetle); *Chrysomela* spp. such as *C. scripta* (cottonwood leaf beetle); Hypothenemus spp. such as *H. hampei* (coffee berry borer); *Sitophilus* spp. such as *S. zeamais* (maize weevil); *Epitrix* spp. such as *E. hirtipennis* (tobacco flea beetle) and *E. cucumeris* (potato flea beetle); *Phyllotreta* spp. such as *P. cruciferae* (crucifer flea beetle) and *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); and any combination of the foregoing.

A "*Diabrotica* life stage" or "corn rootworm life stage" means the egg, larval, pupal or adult developmental form of a *Diabrotica* species.

"Effective insect-controlling amount" means that concentration of dsRNA that inhibits, through a toxic effect, the ability of insects to survive, grow, feed and/or reproduce, or to limit insect-related damage or loss in crop plants. "Effective insect-controlling amount" may or may not mean a concentration that kills the insects, although it preferably means that it kills the insects.

The term "agrochemically active ingredient" refers to chemicals and/or biological compositions, such as those described herein, which are effective in killing, preventing, or controlling the growth of undesirable pests, such as, plants, insects, mice, microorganism, algae, fungi, bacteria, and the like (such as pesticidally active ingredients). An interfering RNA molecule of the invention is an agrochemically active ingredient.

An "agriculturally acceptable carrier" includes adjuvants, mixers, enhancers, etc. beneficial for application of an active ingredient, such as an interfering RNA molecule of the invention. Suitable carriers should not be phytotoxic to valuable crops, particularly at the concentrations employed in applying the compositions in the presence of crops, and should not react chemically with the compounds of the active ingredient herein, namely an interfering RNA of the invention, or other composition ingredients. Such mixtures can be designed for application directly to crops, or can be concentrates or formulations which are normally diluted with additional carriers and adjuvants before application. They may include inert or active components and can be solids, such as, for example, dusts, granules, water dispersible granules, or wettable powders, or liquids, such as, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like.

For the present invention, an agriculturally acceptable carrier may also include non-pathogenic, attenuated strains of microorganisms, which carry the insect control agent, namely an interfering RNA molecule of the invention. In this case, the microorganisms carrying the interfering RNA may also be referred to as insect control agents. The microorganisms may be engineered to express a nucleotide sequence of a target gene to produce interfering RNA molecules comprising RNA sequences homologous or complementary to RNA sequences typically found within the cells of an insect. Exposure of the insects to the microorganisms result in ingestion of the microorganisms and down-regulation of expression of target genes mediated directly or indirectly by the interfering RNA molecules or fragments or derivatives thereof.

In another embodiment, the interfering RNA molecules may be encapsulated in a synthetic matrix such as a polymer and applied to the surface of a host such as a plant. Ingestion of the host cells by an insect permits delivery of the insect control agents to the insect and results in down-regulation of a target gene in the host.

A composition of the invention, for example a composition comprising an interfering RNA molecule of the invention and an agriculturally acceptable carrier, may be used in conventional agricultural methods. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

"Expression cassette" as used herein means a nucleic acid sequence capable of directing expression of a particular nucleic acid sequence in an appropriate host cell, comprising a promoter operably linked to the nucleic acid sequence of interest which is operably linked to termination signal sequences. It also typically comprises sequences required for proper translation of the nucleic acid sequence. The expression cassette comprising the nucleic acid sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleic acid sequence in the expression cassette may be under the control of, for example, a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding sequence, comprises other, primarily regulatory nucleic acid sequences responsible for the control of the expression, that is to say the transcription and translation, of the coding portion. A gene may also comprise other 5' and 3' untranslated sequences and termination sequences. Further elements that may be present are, for example, introns.

As used herein, the term "grower" means a person or entity that is engaged in agriculture, raising living organisms, such as crop plants, for example corn, for food, feed or raw materials.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Insecticidal" is defined as a toxic biological activity capable of controlling insects, preferably by killing them.

An "isolated" nucleic acid molecule or nucleotide sequence or nucleic acid construct or dsRNA molecule or protein of the invention is generally exists apart from its native environment and is therefore not a product of nature.

An isolated nucleic acid molecule or nucleotide sequence or nucleic acid construct or dsRNA molecule or protein may exist in a purified form or may exist in a non-native environment such as, for example, a recombinant host or host cell such as a transgenic plant or transgenic plant cell.

In the context of the invention, a number in front of the suffix "mer" indicates a specified number of subunits. When applied to RNA or DNA, this specifies the number of bases in the molecule. For example, a 19 nucleotide subsequence of an mRNA having the sequence ACUGGUCGCGUUGCAUGCU is a "19-mer."

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A corn rootworm "transcriptome" is a collection of all or nearly all the ribonucleic acid (RNA) transcripts in a corn rootworm cell.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

The nomenclature used herein for DNA or RNA bases and amino acids is as set forth in 37 C.F.R. § 1.822.

The invention is based on the unexpected discovery that double stranded RNA (dsRNA) or small interfering RNAs (siRNA) designed to target a mRNA transcribable from the *Diabrotica* genes described herein are toxic to the *Diabrotica* insect pest and can be used to control *Diabrotica* or Coleopteran infestation of a plant and impart to a transgenic plant tolerance to a *Diabrotica* or Coleopteran infestation. Thus, in one embodiment, the invention provides a double stranded RNA (dsRNA) molecule comprising a sense strand and an antisense strand, wherein a nucleotide sequence of the antisense strand is complementary to a portion of a mRNA polynucleotide transcribable from a *Diabrotica* insect gene described in the present disclosure, wherein the dsRNA molecule is toxic to a *Diabrotica* insect or Coleopteran plant pest.

It is known in the art that dsRNA molecules that are not perfectly complementary to a target sequence (for example, having only 95% identity to the target gene) are effective to control coleopteran pests (see, for example, Narva et al., U.S. Pat. No. 9,012,722). The invention provides an interfering RNA molecule comprising at least one dsRNA, where the dsRNA is a region of double-stranded RNA comprising annealed at least partially complementary strands. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous nucleotides which is at least partially complementary to a target nucleotide sequence within a *Diabrotica* spp target gene. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof, or (iv) can hybridize under stringent conditions to a polynucleotide selected from the group consisting of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, and the complements thereof, wherein the interfering RNA molecule has insecticidal activity on a coleopteran plant pest.

In some embodiments, the interfering RNA molecule comprises at least two dsRNAs, wherein each dsRNA comprises a sequence of nucleotides which is at least partially complementary to a target nucleotide sequence within the target gene. In some embodiments, each of the dsRNAs comprise a different sequence of nucleotides which is complementary to a different target nucleotide sequence within the target gene. In other embodiments, each of the dsRNAs comprise a different sequence of nucleotides which is complementary to a target nucleotide sequence within two different target genes.

In some embodiments, the interfering RNA molecule comprises a dsRNA that can comprise, consist essentially of or consist of from at least 18 to about 25 consecutive nucleotides (e.g. 18, 19, 20, 21, 22, 23, 24, 25, 26, 27, 28, or 29) to at least about 300 consecutive nucleotides. Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the interfering RNA molecule comprises a dsRNA which comprises an antisense strand that is complementary to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof. In other embodiments, the portion of dsRNA comprises, consists essentially of or consists of at least from 19, 20 or 21 consecutive nucleotides to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof.

In other embodiments, an interfering RNA molecule of the invention comprises a dsRNA which comprises, consists essentially of or consists of any 21-mer subsequence of SEQ ID NO: 181-210 consisting of N to N+20 nucleotides, or any complement thereof. For example, an interfering RNA molecule of the invention comprises a dsRNA which comprises, consist essentially of or consists of any 21-mer subsequence of SEQ ID NO: 181, wherein N is nucleotide 1 to nucleotide 776 of SEQ ID NO: 181, or any complement thereof. In other words, the portion of the mRNA that is targeted comprises any of the 776 21 consecutive nucleotide subsequences (i.e. 21-mers) of SEQ ID NO: 181, or any of their complementing sequences. It will be recognized that these 776 21 consecutive nucleotide subsequences include all possible 21 consecutive nucleotide subsequences from SEQ ID NO: 121 and from SEQ ID NO: 151, and their complements, as SEQ ID NOs 121, 151, and 181 are all to the same target, namely BPA_15366. It will similarly be recognized that all 21-mer subsequences of SEQ ID NO: 181-210, and all complement subsequences thereof, include all possible 21 consecutive nucleotide subsequences of SEQ ID NOs: 121-180, and the complement subsequences thereof.

Similarly, an interfering RNA molecule of the invention comprises a dsRNA which comprises, consist essentially of or consists of any 21-mer subsequence of SEQ ID NO: 182, wherein N is nucleotide 1 to nucleotide 771 of SEQ ID NO: 182, or any complement thereof. Another interfering RNA molecule of the invention comprises a dsRNA which comprises, consist essentially of or consists of any 21-mer subsequence of SEQ ID NO: 183, wherein N is nucleotide 1 to nucleotide 2907 of SEQ ID NO: 183, or any complement thereof. Another interfering RNA molecule of the invention comprises a dsRNA which comprises, consist essentially of or consists of any 21-mer subsequence of SEQ ID NO: 184, wherein N is nucleotide 1 to nucleotide 1600 of SEQ ID NO: 184, or any complement thereof. Another interfering RNA molecule of the invention comprises a dsRNA which comprises, consist essentially of or consists of any 21-mer subsequence of SEQ ID NO: 185, wherein N is nucleotide 1 to nucleotide 2410 of SEQ ID NO: 185, or any complement thereof. Another interfering RNA molecule of the invention comprises a dsRNA which comprises, consist essentially of or consists of any 21-mer subsequence of SEQ ID NO: 186, wherein N is nucleotide 1 to nucleotide 2802 of SEQ ID NO: 186, or any complement thereof. Another interfering RNA molecule of the invention comprises a dsRNA which comprises, consist essentially of or consists of any 21-mer subsequence of SEQ ID NO: 187, wherein N is nucleotide 1 to nucleotide 3681 of SEQ ID NO: 187, or any complement thereof. Another interfering RNA molecule of the invention comprises a dsRNA which comprises, consist essentially of or consists of any 21-mer subsequence of SEQ ID NO: 188, wherein N is nucleotide 1 to nucleotide 651 of SEQ ID NO: 188, or any complement thereof. Another interfering RNA molecule of the invention comprises a dsRNA which comprises, consist essentially of or consists of any 21-mer subsequence of SEQ ID NO: 189, wherein N is nucleotide 1 to nucleotide 673 of SEQ ID NO: 189, or any complement thereof. Another interfering RNA molecule of the invention comprises a dsRNA which comprises, consist essentially of or consists of any 21-mer subsequence of SEQ ID NO: 190, wherein N is nucleotide 1 to nucleotide 2664 of SEQ ID NO: 190, or any complement thereof. Another interfering RNA molecule of the invention comprises a dsRNA which comprises, consist essentially of or consists of any 21-mer subsequence of SEQ ID NO: 191, wherein N is nucleotide 1 to nucleotide 438 of SEQ ID NO: 191, or any complement thereof. Another interfering RNA molecule of the invention comprises a dsRNA which comprises, consist essentially of or consists of any 21-mer subsequence of SEQ ID NO: 192, wherein N is nucleotide 1 to nucleotide 2458 of SEQ ID NO: 192, or any complement thereof. Another interfering RNA molecule of the invention comprises a dsRNA which comprises, consist essentially of or consists of any 21-mer subsequence of SEQ ID NO: 193, wherein N is nucleotide 1 to nucleotide 3254 of SEQ ID NO: 193, or any complement thereof. Another interfering RNA molecule of the invention comprises a dsRNA which comprises, consist essentially of or consists of any 21-mer subsequence of SEQ ID NO: 194, wherein N is nucleotide 1 to nucleotide 3632 of SEQ ID NO: 194, or any complement thereof. Another interfering RNA molecule of the invention comprises a dsRNA which comprises, consist essentially of or consists of any 21-mer subsequence of SEQ ID NO: 195, wherein N is nucleotide 1 to nucleotide 7611 of SEQ ID NO: 195, or any complement thereof. Another interfering RNA molecule of the invention comprises a dsRNA which comprises, consist essentially of or consists of any 21-mer subsequence of SEQ ID NO: 196, wherein N is nucleotide 1 to nucleotide 1008 of SEQ ID NO: 196, or any complement thereof. Another interfering RNA molecule of the invention comprises a dsRNA which comprises, consist essentially of or consists of any 21-mer subsequence of SEQ ID NO: 197, wherein N is nucleotide 1 to nucleotide 2992 of SEQ ID NO: 197, or any complement thereof. Another interfering RNA molecule of the invention comprises a dsRNA which comprises, consist essentially of or consists of any 21-mer subsequence of SEQ ID NO: 198, wherein N is nucleotide 1 to nucleotide 1192 of SEQ ID NO: 198, or any complement thereof. Another interfering RNA molecule of the invention comprises a dsRNA which comprises, consist essentially of or consists of any 21-mer subsequence of SEQ ID NO: 199, wherein N is nucleotide 1 to nucleotide 7626 of SEQ ID NO: 199, or any complement thereof. Another interfering RNA molecule of the invention comprises a dsRNA which comprises, consist essentially of or consists of any 21-mer subsequence of SEQ ID NO: 200, wherein N is nucleotide 1 to nucleotide 2580 of SEQ ID NO: 200, or any complement thereof. Another interfering RNA molecule of the invention comprises a dsRNA which comprises, consist essentially of or consists of any 21-mer subsequence of SEQ ID NO: 201, wherein N is nucleotide 1 to nucleotide 4628 of SEQ ID NO: 201, or any complement thereof. Another interfering RNA molecule of the invention comprises a dsRNA which comprises, consist essentially of or consists of any 21-mer subsequence of SEQ ID NO: 202, wherein N is nucleotide 1 to nucleotide 1557 of SEQ ID NO: 202, or any complement thereof. Another interfering RNA molecule of the invention comprises a dsRNA which comprises, consist essentially of or consists of any 21-mer subsequence of SEQ ID NO: 203, wherein N is nucleotide 1 to nucleotide 1019 of SEQ ID NO: 203, or any complement thereof. Another interfering RNA molecule of the invention comprises a dsRNA which comprises, consist essentially of or consists of any 21-mer subsequence of SEQ ID NO: 204, wherein N is nucleotide 1 to nucleotide 677 of SEQ ID NO: 204, or any complement thereof. Another interfering RNA molecule of the invention comprises a dsRNA which comprises, consist essentially of or consists of any 21-mer subsequence of SEQ ID NO: 205, wherein N is nucleotide 1 to nucleotide 764 of SEQ ID NO: 205, or any complement thereof. Another interfering RNA molecule of the invention comprises a dsRNA which comprises, consist essentially of or consists of any 21-mer subsequence of SEQ ID NO: 206, wherein N is nucleotide 1 to nucleotide 1830 of SEQ ID NO: 206, or any complement thereof. Another interfering RNA molecule of the invention comprises a dsRNA which comprises, consist essentially of or consists of any 21-mer subsequence of SEQ ID NO: 207, wherein N is nucleotide 1 to nucleotide 3225 of SEQ ID NO: 207, or any complement thereof. Another interfering RNA molecule of the invention comprises a dsRNA which comprises, consist essentially of or consists of any 21-mer subsequence of SEQ ID NO: 208, wherein N is nucleotide 1 to nucleotide 1003 of SEQ ID NO: 208, or any complement thereof. Another interfering RNA molecule of the invention comprises a dsRNA which comprises, consist essentially of or consists of any 21-mer subsequence of SEQ ID NO: 209, wherein N is nucleotide 1 to nucleotide 1419 of SEQ ID NO: 209, or any complement thereof. Another interfering RNA molecule of the invention comprises a dsRNA which comprises, consist essentially of or consists of any 21-mer subsequence of SEQ ID NO: 210, wherein N is nucleotide 1 to nucleotide 5206 of SEQ ID NO: 210, or any complement thereof. Another interfering RNA molecule of the invention comprises a dsRNA which comprises, consist essentially of or consists of any 21-mer subsequence of SEQ ID NO: 374, wherein N is nucleotide 1 to nucleotide 7112 of SEQ ID NO: 374, or any complement thereof.

In still other embodiments, the interfering RNA molecule of the invention comprises a dsRNA which comprises, consists essentially of or consists of SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof.

In other embodiments of the interfering RNA molecule of the invention, the nucleotide sequence of the antisense strand of a dsRNA of the invention comprises, consists essentially of or consists of the nucleotide sequence of SEQ ID NO: 211-240 or SEQ ID NO: 375. The nucleotide sequence of the antisense strand of a dsRNA of the invention can have one nucleotide at either the 3' or 5' end deleted or can have up to six nucleotides added at the 3' end, the 5' end or both, in any combination to achieve an antisense strand consisting essentially of any 19-mer, any 20-mer, or any 21-mer nucleotide sequence of SEQ ID NO: 211-240 or SEQ ID NO: 375, as it would be understood that the deletion of the one nucleotide or the addition of up to the six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3' end may be present, which is used to stabilize the siRNA duplex and does not affect the specificity of the siRNA.

In some embodiments of this invention, the antisense strand of the double stranded RNA of the interfering RNA molecule can be fully complementary to the target RNA polynucleotide or the antisense strand can be substantially complementary or partially complementary to the target RNA polynucleotide. The dsRNA of the interfering RNA molecule may comprise a dsRNA which is a region of double-stranded RNA comprising substantially complementary annealed strands, or which is a region of double-stranded RNA comprising fully complementary annealed strands. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allele1*" Acta Pharmacol. Sin.* 29:211-216 (2008); Schwarz et al. "Asymmetry in the assembly of the RNAi enzyme complex" Cell 115:199-208 (2003)).

In some embodiments of this invention, the interfering RNA comprises a dsRNA which comprises a short hairpin RNA (shRNA) molecule. Expression of shRNA in cells is typically accomplished by delivery of plasmids or recombinant vectors, for example in transgenic plants such as transgenic corn.

The invention encompasses a nucleic acid construct comprising an interfering RNA of the invention. The invention further encompasses a nucleic acid molecule encoding at least one interfering molecule of the invention. The invention further encompasses a nucleic acid construct comprising at least one interfering molecule of the invention or comprising a nucleic acid molecule encoding the at least one interfering molecule of the invention. The invention further encompasses a nucleic acid construct wherein the nucleic acid construct is an expression vector. The invention further encompasses a recombinant vector comprising a regulatory sequence operably linked to a nucleotide sequence that encodes an interfering RNA molecule of the invention. A regulatory sequence may refer to a promoter, enhancer, transcription factor binding site, insulator, silencer, or any other DNA element involved in the expression of a gene.

The invention further encompasses chimeric nucleic acid molecules comprising an interfering RNA molecule with an antisense strand of a dsRNA operably linked with a plant microRNA precursor molecule. In some embodiments, the chimeric nucleic acid molecule comprises an antisense strand having the nucleotide sequence of any of the 21-mer subsequences of SEQ ID NOs: 181-210, or any complement thereof, operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA of an interfering RNA molecule of the invention. In other embodiments, the artificial plant microRNA precursor molecule comprises an antisense strand having the nucleotide sequence of any of the 19-mer, 20-mer, or 21-mer subsequences of SEQ ID NOs: 211-240. The use of artificial plant microRNAs to deliver a nucleotide sequence of interest (e.g an artificial miRNA; siRNA/siRNA*) into a plant is known in the art (see, e.g., Schwab et al. 2006. The Plant Cell 18:1121-1133 and Examples section herein). In the invention, the artificial microRNAs are chimeric or hybrid molecules, having a plant microRNA precursor backbone and an insect siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Non-limiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses interfering RNA molecules, nucleic acid constructs, nucleic acid molecules or recombinant vectors comprising at least one strand of a dsRNA of an interfering RNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

In some embodiments, the interfering RNA molecules of the invention have insecticidal activity on a *Diabrotica* insect. In some embodiments the *Diabrotica* insect selected from the group consisting of *Diabrotica barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle), *D. virgifera zeae* (Mexican corn rootworm), *D. beniensis, D. cristata, D. curvipustulata, D. dissimilis, D. elegantula, D. emorsitans, D. graminea, D. hispanolae, D. lemniscata, D. linsleyi, D. milleri, D. nummularis, D. occlusa, D. porracea, D. scutellata, D. tibialis, D. trifasciata* and *D. viridula*. In further embodiments, the *Diabrotica* insect is *D. virgifera virgifera* (western corn rootworm), *D. undecimpunctata howardi* (southern corn rootworm) or *D. barberi* (northen corn rootworm). In some embodiments, the coding sequence of the target gene comprises a sequence selected from the group comprising SEQ ID NO: 91-120 and SEQ ID NO: 372.

In some embodiments, the invention encompasses a composition comprising one or more or two or more of the interfering RNA molecules of the invention. In some embodiments, the interfering RNA molecules are present on the same nucleic acid construct, on different nucleic acid constructs, or any combination thereof. For example, one interfering RNA molecule of the invention may be present on a nucleic acid construct, and a second interfering RNA molecule of the invention may be present on the same nucleic acid construct or on a separate, second nucleic acid construct. The second interfering RNA molecule of the invention may be to the same target gene or to a different target gene.

In some embodiments, the invention encompasses a composition comprising an interfering RNA molecule which comprises at least one dsRNA wherein the dsRNA is a region of double-stranded RNA comprising annealed complementary strands. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous nucleotides which is at least partially complementary to a target nucleotide sequence within a *Diabrotica* spp target gene. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or ae complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO:121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof, or (iv) can hybridize under stringent conditions to a polynucleotide selected from the group consisting of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, and the complements thereof.

In some embodiments, the invention encompasses compositions comprising an interfering RNA molecule comprising two or more dsRNAs, wherein the two or more dsRNAs each comprise a different antisense strand. In some embodiments the invention encompasses compositions comprising at least two more interfering RNA molecules, wherein the two or more interfering RNA molecules each comprise a dsRNA comprising a different antisense strand. The two or more interfering RNAs may be present on the same nucleic acid construct, on different nucleic acid constructs or any combination thereof. In other embodiments, the composition comprises a RNA molecule comprising an antisense strand consisting essentially of a nucleotide sequence comprising at least a 19 contiguous nucleotide fragment of SEQ ID NO: 211-240 or SEQ ID NO: 375, and in some embodiments may further comprise an RNA molecule comprising an antisense strand consisting essentially of a second nucleotide sequence comprising at least a 19 contiguous nucleotide fragment of SEQ ID NO: 211-240 or SEQ ID NO: 375; and in some embodiments may further comprise an RNA molecule comprising an antisense strand consisting essentially of a third nucleotide sequence comprising at least a 19 contiguous nucleotide fragment of SEQ ID NO: 211-240 or SEQ ID NO: 375, and in some embodiments may further comprise an RNA molecule comprising an antisense strand consisting essentially of a fourth nucleotide sequence comprising at least a 19 contiguous nucleotide fragment of SEQ ID NO: 211-240 or SEQ ID NO: 375, and in some embodiments may further comprise an RNA molecule comprising an antisense strand consisting essentially of a fifth nucleotide sequence comprising at least a 19 contiguous nucleotide fragment of SEQ ID NO: 211-240 or SEQ ID NO: 375, and in some embodiments may further comprise an RNA molecule comprising an antisense strand consisting essentially of a sixth nucleotide sequence comprising at least a 19 contiguous nucleotide fragment of SEQ ID NO: 211-240 or SEQ ID NO: 375, and in some embodiments may further comprise an RNA molecule comprising an antisense strand consisting essentially of a seventh nucleotide sequence comprising at least a 19 contiguous nucleotide fragment of SEQ ID NO: 211-240 or SEQ ID NO: 375. In other embodiments, the composition may comprise two or more of the nucleic acid molecules, wherein the two or more nucleic acid molecules each encode a different interfering RNA molecule. In other embodiments, the composition may comprise two or more of the nucleic acid constructs, wherein the two or more nucleic acid constructs each comprise a nucleic acid molecule encoding a different interfering RNA.

In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

In some embodiments, the invention encompasses an insecticidal composition for inhibiting the expression of a *Diabrotica* insect gene described herein, comprising an interfering RNA of the invention and an agriculturally acceptable carrier. In some embodiments, the acceptable agricultural carrier is a transgenic organism expressing an interfering RNA of the invention. In some embodiments the transgenic organism may be a transgenic plant expressing the interfering RNA of the invention that when fed upon by a target Coleopteran plant pest causes the target Coleopteran plant pest to stop feeding, growing or reproducing or causing death of the target Coleopteran plant pest. In other embodiments, the transgenic plant is a transgenic corn plant and the target pest is a *Diabrotica* insect pest. In still other embodiments, the *Diabrotica* insect pest is selected from the group consisting of *Diabrotica barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle), *D. virgifera zeae* (Mexican corn rootworm).

In other embodiments, the transgenic organism is selected from, but not limited to, the group consisting of: yeast, fungi, algae, bacteria, virus or an arthropod expressing the interfering RNA molecule of the invention. In some embodiments, the transgenic organism is a virus, for example an insect baculovirus that expresses an interfering RNA molecule of the invention upon infection of an insect host. Such a baculovirus is likely more virulent against the target insect than the wildtype untransformed baculovirus. In other embodiments the transgenic organism is a transgenic bacterium that is applied to an environment where a target pest occurs or is known to have occurred. In some embodiments, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive interfering RNA molecule for the same purpose.

In some embodiments, an acceptable agricultural carrier is a formulation useful for applying the composition comprising the interfering RNA molecule to a plant or seed. In some embodiments, the interfering RNA molecules are stabilized against degradation because of their double stranded nature and the introduction of Dnase/Rnase inhibitors. For example, dsRNA or siRNA can be stabilized by including thymidine or uridine nucleotide 3' overhangs. The dsRNA or siRNA contained in the compositions of the invention can be chemically synthesized at industrial scale in large amounts. Methods available would be through chemical synthesis or through the use of a biological agent.

In other embodiments the formulation comprises a transfection promoting agent. In other embodiments, the transfection promoting agent is a lipid-containing compound. In further embodiments, the lipid-containing compound is selected from the group consisting of; Lipofectamine, Cellfectin, DMRIE-C, DOTAP and Lipofectin. In another embodiment, the lipid-containing compound is a Tris cationic lipid.

In some embodiments, the formulation further comprises a nucleic acid condensing agent. The nucleic acid condensing agent can be any such compound known in the art. Examples of nucleic acid condensing agents include, but are not limited to, spermidine (N-[3-aminopropyl]-1,4-butanediamine), protamine sulphate, poly-lysine as well as other positively charged peptides. In some embodiments, the nucleic acid condensing agent is spermidine or protamine sulfate.

In still further embodiments, the formulation further comprises buffered sucrose or phosphate buffered saline.

In some embodiments, the invention encompasses transgenic plants, or parts thereof, comprising an interfering RNA molecule, a nucleic acid construct, a chimeric nucleic acid molecule, a artificial plant microRNA precursor molecule and/or a composition of the invention, wherein the transgenic plant has enhanced resistance to a Coleopteran insect or *Diabrotica* insect as compared to a control plant. In other embodiments, the transgenic plant, or part thereof, is a transgenic corn plant, or part thereof. The invention further encompasses transgenic seed of the transgenic plants of the invention, wherein the transgenic seed comprises an interfering RNA molecule, a nucleic acid construct, a chimeric nucleic acid molecule, an artificial plant microRNA precursor molecule and/or a composition of the invention. In some embodiments the transgenic seed is a transgenic corn seed.

Transgenic plants expressing an interfering RNA of the invention are tolerant or resistant to attack by target insect pests. When the insect starts feeding on such a transgenic plant, it also ingests the expressed dsRNA or siRNA. This may deter the insect from further biting into the plant tissue or may even harm or kill the insect. A nucleic acid sequence encoding a dsRNA or siRNA of the invention is inserted into an expression cassette, which is then preferably stably integrated in the genome of the plant. The nucleic acid sequences of the expression cassette introduced into the genome of the plant are heterologous to the plant and non-naturally occurring. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, *papaya*, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees. In further embodiments, the transgenic plant is a transgenic corn plant.

Expression of the interfering RNA molecule in transgenic plants is driven by regulatory sequences comprising promoters that function in plants. The choice of promoter will vary depending on the temporal and spatial requirements for expression, and also depending on the insect target species. Thus, expression of the interfering RNAs of this invention in leaves, in stalks or stems, in ears, in inflorescences (e.g. spikes, panicles, cobs, etc.), in roots, and/or seedlings is contemplated. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the dsRNA or siRNA in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

In some embodiments, tissue-specific/tissue-preferred promoters can be used. Tissue-specific or tissue-preferred expression patterns include, but are not limited to, green tissue specific or preferred, root specific or preferred, stem specific or preferred, and flower specific or preferred. In addition, promoters functional in plastids can be used. In some embodiments of the invention, inducible promoters can be used. In further aspects, the nucleotide sequences of the invention can be operably associated with a promoter that is wound inducible or inducible by pest or pathogen infection (e.g., a insect or nematode plant pest).

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

In some embodiments, a recombinant nucleic acid molecule of the invention can be an "expression cassette." As used herein, "expression cassette" means a recombinant nucleic acid molecule comprising a nucleotide sequence of interest (e.g., the nucleotide sequences of the invention), wherein the nucleotide sequence is operably associated with at least a control sequence (e.g., a promoter). Thus, some embodiments of the invention provide expression cassettes designed to express nucleotides sequences encoding the dsRNAs or siRNAs of the invention. In this manner, for example, one or more plant promoters operably associated with one or more nucleotide sequences of the invention are provided in expression cassettes for expression in a corn plant, plant part and/or plant cell.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

An expression cassette of the invention also can include polynucleotides that encode other desired traits. Such desired traits can be other polynucleotides which confer insect resistance, or which confer nematode resistance, or other agriculturally desirable traits. Such polynucleotides can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a single transgene can comprise multiple expression cassettes, such that multiple expression cassettes are introduced into the genome of a transformed cell at a single genomic location. Alternatively, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

Thus, an expression cassette can include a coding sequence for one or more polypeptides for agronomic traits that primarily are of benefit to a seed company, grower or grain processor. A polypeptide of interest can be any polypeptide encoded by a polynucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construct of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors of the invention may also comprise other selectable marker genes, for example, phosphomannose isomerase (pmi), which provides for positive selection of the transgenic plants as disclosed in U.S. Pat. Nos. 5,767,378 and 5,994,629, herein incorporated by reference, or phosphinotricin acetyltransferase (pat), which provides tolerance to the herbicide phosphinotricin (glufosinate). The choice of selectable marker is not, however, critical to the invention.

In other embodiments, a nucleic acid sequence of the invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) *Proc. Natl. Acad. Sci. USA* 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid sequence of the present invention is inserted into a plastid-targeting vector and transformed into the plastid genome of a desired plant host. Plants homoplastic for plastid genomes containing a nucleic acid sequence of the present invention are obtained, and are preferentially capable of high expression of the nucleic acid sequence.

Transgenic plants or seed comprising an interfering RNA of the invention can also be treated with an insecticide or insecticidal seed coating as described in U.S. Pat. Nos. 5,849,320 and 5,876,739, herein incorporated by reference. Where both the insecticide or insecticidal seed coating and the transgenic plant or seed of the invention are active against the same target insect, for example a Coleopteran pest or a *Diabrotica* target pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of a *Diabrotica* insect population comprising providing a transgenic plant or seed of the invention and applying to the plant or the seed an insecticide or insecticidal seed coating to a transgenic plant or seed of the invention. Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan® (carbofuran), Lanate® (methomyl, metomil, mesomile), Sevin® (carbaryl), Talstar® (bifenthrin), Force® (tefluthrin), Ammo® (cypermethrin), Cymbush® (cypermethrin), Delta Gold® (deltamethrin), Karate® (lambda-cyhalothrin), Ambush® (permethrin), Pounce® (permethrin), Brigade® (bifenthrin), Capture® (bifenthrin), ProShield® (tefluthrin), Warrior® (lambda-cyhalothrin), Dursban® (chlorphyrifos), Fortress® (chlorethoxyfos), Mocap® (ethoprop), Thimet® (phorate), AAstar® (phorate, flucythinate), Rampart® (phorate), Counter® (terbufos), Cygon® (dimethoate), Dicapthon, Regent® (fipronil), Cruiser® (thiamethoxam), Gaucho® (imidacloprid), Prescribe® (imidacloprid), Poncho® (clothianidin) and Aztec® (cyfluthrin, tebupirimphos).

The compositions of the invention can also be combined with other biological control agents to enhance control of a coleopteran insect or a *Diabrotica* insect populations. Thus, the invention provides a method of enhancing control of a Coleopteran insect population or a *Diabrotica* insect population by providing a transgenic plant that produces an interfering RNA of the invention and further comprises a polynucleotide that encodes a second insecticidal agent. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417, a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the transgenic plant may produce an interfering RNA of the invention and a second insecticidal agent which is derived from sources other than *B. thuringiensis*. The second insecticidal agent can be an agent selected from the group comprising a patatin, a protease, a protease inhibitor, a chitinase, a urease, an alpha-amylase inhibitor, a pore-forming protein, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporous* insecticidal protein, a *Lysinibacillus sphearicus* insecticidal protein, a *Chromobacterium* spp. insecticidal protein, a *Yersinia* entomophaga insecticidal protein, a *Paenibacillus popiliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia*, or *Yersinia*. In other embodiments, the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In another embodiment, the transgenic plant and transgenic seed is a corn plant or corn seed. In another embodiment, the transgenic corn plant is provided by crossing a first transgenic corn plant comprising a dsRNA of the invention with a transgenic corn plant comprising a transgenic event selected from the group consisting of MIR604, Event 5307, DAS51922-7, MON863 and MON88017.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to the transgenic plant or seed of the invention, which has activity against coleopteran insects, the treated plant or coated transgenic seed controls both lepidopteran and coleopteran insect pests.

In further embodiments, the invention encompasses a biological sample from a transgenic plant, seed, or parts thereof, of the invention, wherein the sample comprises a nucleic acid that is or encodes at least one strand of a dsRNA of the invention. In other embodiments, the invention encompasses a commodity product derived from a transgenic plant, seed, or parts thereof, of the invention. In some embodiments, the commodity product is selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage, fiber, paper or other food or product produced from plants. In other embodiments, the biological sample or commodity product is toxic to insects. In other embodiments, the transgenic plant is a transgenic corn plant.

The invention further encompasses a method of controlling a coleopteran insect or a *Diabrotica* insect comprising contacting the insect with a nucleic acid molecule that is or is capable of producing an interfering RNA molecule of the invention for inhibiting expression of a target gene in the insect thereby controlling the coleopteran insect or the *Diabrotica* insect. In some embodiments, the target gene comprises a coding sequence (i) having at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 1-30, SEQ ID NO: 91-120, SEQ ID NO: 271-273, SEQ ID NO: 277-279, SEQ ID NO: 283-297, SEQ ID NO: 313-317, SEQ ID NO: 372, 377, 379, SEQ ID NO: 381-388, SEQ ID NO: 399, or SEQ ID NO: 400; (ii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 1-30, SEQ ID NO: 91-120, SEQ ID NO: 271-273, SEQ ID NO: 277-279, SEQ ID NO: 283-297, SEQ ID NO: 313-317, SEQ ID NO: 372, 377, 379, SEQ ID NO: 381-388, SEQ ID NO: 399, or SEQ ID NO: 400; (iii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO: 1-30, SEQ ID NO: 91-120, SEQ ID NO: 271-273, SEQ ID NO: 277-279, SEQ ID NO: 283-297, SEQ ID NO: 313-317, SEQ ID NO: 372, 377, 379, SEQ ID NO: 381-388, SEQ ID NO: 399, or SEQ ID NO: 400, or (iv) can hybridize under stringent conditions to a polynucleotide selected from the group consisting of SEQ ID NO: 1-30, SEQ ID NO: 91-120, SEQ ID NO: 271-273, SEQ ID NO: 277-279, SEQ ID NO: 283-297, SEQ ID NO: 313-317, SEQ ID NO: 372, 377, 379, SEQ ID NO: 381-388, SEQ ID NO: 399, or SEQ ID NO: 400, and the complements thereof. In some embodiments the target gene coding sequence comprises SEQ ID NO: 1-30, SEQ ID NO: 91-120, SEQ ID NO: 271-273, SEQ ID NO: 277-279, SEQ ID NO: 283-297, SEQ ID NO: 313-317, SEQ ID NO: 372, 377, 379, SEQ ID NO: 381-388, SEQ ID NO: 399, or SEQ ID NO: 400. In other embodiments, the interfering RNA molecule of the invention is complementary to a portion of a mRNA polynucleotide transcribable from the *Diabrotica* target genes described herein.

In some embodiments of the method of controlling a coleopteran insect pest or a *Diabrotica* insect pest, the interfering RNA molecule of the invention comprises at least one dsRNA, wherein the dsRNA is a region of double-stranded RNA comprising annealed complementary strands, one strand of which comprises a sequence of at least 19 contiguous nucleotides which (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof, or (iv) can hybridize under stringent conditions to a polynucleotide selected from the group consisting of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, and the complements thereof.

In some embodiments of the method of controlling a coleopteran insect pest or a *Diabrotica* insect pest, the interfering RNA molecule comprises, consists essentially of or consists of from 18, 19, 20 or 21 consecutive nucleotides to at least about 300 consecutive nucleotides of SEQ ID NO: 181-210. In other embodiments, the interfering RNA of the invention comprises, consists essentially of or consists of any 21-mer subsequence of SEQ ID NO: 181-210 consisting of N to N+20 nucleotides, or any complement thereof. For example, an interfering RNA molecule of the invention comprises a dsRNA which comprises, consist essentially of or consists of any 21-mer subsequence of SEQ ID NO: 181, wherein N is nucleotide 1 to nucleotide 776 of SEQ ID NO: 181, or any complement thereof. In other words, the portion of the mRNA that is targeted comprises any of the 776 21 consecutive nucleotide subsequences i.e. 21-mers) of SEQ ID NO: 181, or any of their complementing sequences. It will be recognized that these 776 21 consecutive nucleotide subsequences include all possible 21 consecutive nucleotide subsequences from SEQ ID NO: 121 and from SEQ ID NO: 151, and their complements, as SEQ ID NOs 121, 151, and 181 are all to the same target, namely BPA_15366. It will similarly be recognized that all 21-mer subsequences of SEQ ID NO: 181-210, and all complement subsequences thereof, include all possible 21 consecutive nucleotide subsequences of SEQ ID NOs: 121-180 and SEQ ID NO: 373, and the complement subsequences thereof.

Similarly, an interfering RNA molecule of the invention comprises a dsRNA which comprises, consist essentially of or consists of any 21-mer subsequence of SEQ ID NO: 182, wherein N is nucleotide 1 to nucleotide 771 of SEQ ID NO: 182, or any complement thereof. Another interfering RNA molecule of the invention comprises a dsRNA which comprises, consist essentially of or consists of any 21-mer subsequence of SEQ ID NO: 183, wherein N is nucleotide 1 to nucleotide 2907 of SEQ ID NO: 183, or any complement thereof. Another interfering RNA molecule of the invention comprises a dsRNA which comprises, consist essentially of or consists of any 21-mer subsequence of SEQ ID NO: 184, wherein N is nucleotide 1 to nucleotide 1600 of SEQ ID NO: 184, or any complement thereof. Another interfering RNA molecule of the invention comprises a dsRNA which comprises, consist essentially of or consists of any 21-mer subsequence of SEQ ID NO: 185, wherein N is nucleotide 1 to nucleotide 2410 of SEQ ID NO: 185, or any complement thereof. Another interfering RNA molecule of the invention comprises a dsRNA which comprises, consist essentially of or consists of any 21-mer subsequence of SEQ ID NO: 186, wherein N is nucleotide 1 to nucleotide 2802 of SEQ ID NO: 186, or any complement thereof. Another interfering RNA molecule of the invention comprises a dsRNA which comprises, consist essentially of or consists of any 21-mer subsequence of SEQ ID NO: 187, wherein N is nucleotide 1 to nucleotide 3681 of SEQ ID NO: 187, or any complement thereof. Another interfering RNA molecule of the invention comprises a dsRNA which comprises, consist essentially of or consists of any 21-mer subsequence of SEQ ID NO: 188, wherein N is nucleotide 1 to nucleotide 651 of SEQ ID NO: 188, or any complement thereof. Another interfering RNA molecule of the invention comprises a dsRNA which comprises, consist essentially of or consists of any 21-mer subsequence of SEQ ID NO: 189, wherein N is nucleotide 1 to nucleotide 673 of SEQ ID NO: 189, or any complement thereof. Another interfering RNA molecule of the invention comprises a dsRNA which comprises, consist essentially of or consists of any 21-mer subsequence of SEQ ID NO: 190, wherein N is nucleotide 1 to nucleotide 2664 of SEQ ID NO: 190, or any complement thereof. Another interfering RNA molecule of the invention comprises a dsRNA which comprises, consist essentially of or consists of any 21-mer subsequence of SEQ ID NO: 191, wherein N is nucleotide 1 to nucleotide 438 of SEQ ID NO: 191, or any complement thereof. Another interfering RNA molecule of the invention comprises a dsRNA which comprises, consist essentially of or consists of any 21-mer subsequence of SEQ ID NO: 192, wherein N is nucleotide 1 to nucleotide 2458 of SEQ ID NO: 192, or any complement thereof. Another interfering RNA molecule of the invention comprises a dsRNA which comprises, consist essentially of or consists of any 21-mer subsequence of SEQ ID NO: 193, wherein N is nucleotide 1 to nucleotide 3254 of SEQ ID NO: 193, or any complement thereof. Another interfering RNA molecule of the invention comprises a dsRNA which comprises, consist essentially of or consists of any 21-mer subsequence of SEQ ID NO: 194, wherein N is nucleotide 1 to nucleotide 3632 of SEQ ID NO: 194, or any complement thereof. Another interfering RNA molecule of the invention comprises a dsRNA which comprises, consist essentially of or consists of any 21-mer subsequence of SEQ ID NO: 195, wherein N is nucleotide 1 to nucleotide 7611 of SEQ ID NO: 195, or any complement thereof. Another interfering RNA molecule of the invention comprises a dsRNA which comprises, consist essentially of or consists of any 21-mer subsequence of SEQ ID NO: 196, wherein N is nucleotide 1 to nucleotide 1008 of SEQ ID NO: 196, or any complement thereof. Another interfering RNA molecule of the invention comprises a dsRNA which comprises, consist essentially of or consists of any 21-mer subsequence of SEQ ID NO: 197, wherein N is nucleotide 1 to nucleotide 2992 of SEQ ID NO: 197, or any complement thereof. Another interfering RNA molecule of the invention comprises a dsRNA which comprises, consist essentially of or consists of any 21-mer subsequence of SEQ ID NO: 198, wherein N is nucleotide 1 to nucleotide 1192 of SEQ ID NO: 198, or any complement thereof. Another interfering RNA molecule of the invention comprises a dsRNA which comprises, consist essentially of or consists of any 21-mer subsequence of SEQ ID NO: 199, wherein N is nucleotide 1 to nucleotide 7626 of SEQ ID NO: 199, or any complement thereof. Another interfering RNA molecule of the invention comprises a dsRNA which comprises, consist essentially of or consists of any 21-mer subsequence of SEQ ID NO: 200, wherein N is nucleotide 1 to nucleotide 2580 of SEQ ID NO: 200, or any complement thereof. Another interfering RNA molecule of the invention comprises a dsRNA which comprises, consist essentially of or consists of any 21-mer subsequence of SEQ ID NO: 201, wherein N is nucleotide 1 to nucleotide 4628 of SEQ ID NO: 201, or any complement thereof. Another interfering RNA molecule of the invention comprises a dsRNA which comprises, consist essentially of or consists of any 21-mer subsequence of SEQ ID NO: 202, wherein N is nucleotide 1 to nucleotide 1557 of SEQ ID NO: 202, or any complement thereof. Another interfering RNA molecule of the invention comprises a dsRNA which comprises, consist essentially of or consists of any 21-mer subsequence of SEQ ID NO: 203, wherein N is nucleotide 1 to nucleotide 1019 of SEQ ID NO: 203, or any complement thereof. Another interfering RNA molecule of the invention comprises a dsRNA which comprises, consist essentially of or consists of any 21-mer subsequence of SEQ ID NO: 204, wherein N is nucleotide 1 to nucleotide 677 of SEQ ID NO: 204, or any complement thereof. Another interfering RNA molecule of the invention comprises a dsRNA which comprises, consist essentially of or consists of any 21-mer subsequence of SEQ ID NO: 205, wherein N is nucleotide 1 to nucleotide 764 of SEQ ID NO: 205, or any complement thereof. Another interfering RNA molecule of the invention comprises a dsRNA which comprises, consist essentially of or consists of any 21-mer subsequence of SEQ ID NO: 206, wherein N is nucleotide 1 to nucleotide 1830 of SEQ ID NO: 206, or any complement thereof. Another interfering RNA molecule of the invention comprises a dsRNA which comprises, consist essentially of or consists of any 21-mer subsequence of SEQ ID NO: 207, wherein N is nucleotide 1 to nucleotide 3225 of SEQ ID NO: 207, or any complement thereof. Another interfering RNA molecule of the invention comprises a dsRNA which comprises, consist essentially of or consists of any 21-mer subsequence of SEQ ID NO: 208, wherein N is nucleotide 1 to nucleotide 1003 of SEQ ID NO: 208, or any complement thereof. Another interfering RNA molecule of the invention comprises a dsRNA which comprises, consist essentially of or consists of any 21-mer subsequence of SEQ ID NO: 209, wherein N is nucleotide 1 to nucleotide 1419 of SEQ ID NO: 209, or any complement thereof. Another interfering RNA molecule of the invention comprises a dsRNA which comprises, consist essentially of or consists of any 21-mer subsequence of SEQ ID NO: 210, wherein N is nucleotide 1 to nucleotide 5206 of SEQ ID NO: 210, or any complement thereof. Another interfering RNA molecule of the invention comprises a dsRNA which comprises, consist essentially of or consists of any 21-mer subsequence of SEQ ID NO: 374, wherein N is nucleotide 1 to nucleotide 7112 of SEQ ID NO: 374, or any complement thereof.

In some embodiments of the method of controlling a *Diabrotica* insect pest, the 5 *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle) and *D. virgifera zeae* (Mexican corn rootworm).

In other embodiments of the method of controlling a coleopteran insect pest or a *Diabrotica* insect pest, the contacting comprises (a) planting a transgenic seed capable of producing a transgenic plant that expresses the nucleic acid molecule, wherein the insect feeds on the transgenic plant, or part thereof; or (b) applying a composition comprising the nucleic acid molecule to a seed or plant, or part thereof, wherein the insect feeds on the seed, the plant, or a part thereof. In some embodiments, the transgenic seed and the transgenic plant is a corn seed or a corn plant. In other embodiments the seed or plant is a corn seed or a corn plant.

The invention also encompasses a method of controlling a *Diabrotica* insect comprising contacting the *Diabrotica* insect with a nucleic acid molecule that is or is capable of producing the interfering RNA molecule of the invention for inhibiting expression of a target gene in the *Diabrotica* insect, and also contacting the *Diabrotica* insect with at least a second insecticidal agent for controlling *Diabrotica*, wherein said second insecticidal agent comprises a *B. thuringiensis* insecticidal protein, thereby controlling the *Diabrotica* insect. The invention also encompasses a method for controlling *Diabrotica* insect pests on a plant, comprising topically applying to said plant a pesticide composition comprising an interfering RNA of the invention and at least a second insecticidal agent for controlling *Diabrotica*, wherein said second insecticidal agent does not comprise a *B. thuringiensis* insecticidal protein, and providing said plant in the diet of said *Diabrotica* insect. The invention also encompasses a method wherein the second insecticidal agent comprises a patatin, a protease, a protease inhibitor, a urease, an alpha-amylase inhibitor, a pore-forming protein, a lectin, an engineered antibody or antibody fragment, or a chitinase. The second insecticidal agent may also be a *Bacillus cereus* insecticidal protein, a *Xenorhabdus* spp. insecticidal protein, a *Photorhabdus* spp. insecticidal protein, a *Brevibacillus laterosporous* insecticidal protein, a *Lysinibacillus sphearicus* insecticidal protein, a *Chromobacterium* ssp. insecticidal protein, a *Yersinia* entomophaga insecticidal protein, a *Paenibacillus popiliae* insecticidal protein, or a *Clostridium* spp. insecticidal protein.

The invention also encompasses a method of reducing an adult coleopteran insect population or an adult *Diabrotica* insect population on a transgenic plant expressing a Cry protein, a hybrid Cry protein or modified Cry protein comprising expressing in the transgenic plant a nucleic acid molecule that is or is capable of producing an interfering RNA molecule of the invention capable of inhibiting expression of a target gene as described herein in an adult insect, thereby reducing the adult coleopteran insect population or adult *Diabrotica* insect population.

In some embodiments, the invention encompasses a method of reducing the level of a target mRNA transcribable from a target gene as described herein in a coleopteran insect or a *Diabrotica* insect comprising contacting the insect with a composition comprising the interfering RNA molecule of the invention, wherein the interfering RNA molecule reduces the level of the target mRNA in a cell of the insect. In some embodiments, the interfering RNA of the method comprises at least one dsRNA, wherein the dsRNA is a region of double-stranded RNA comprising annealed complementary strands, one strand of which comprises a sequence of at least 19 contiguous nucleotides which (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 contiguous nucleotide fragment of a nucleotide sequence encoding an amino acid sequence encoded by SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, or a complement thereof, or (iv) can hybridize under stringent conditions to a polynucleotide selected from the group consisting of SEQ ID NO: 121-210, SEQ ID NO: 274-276, SEQ ID NO: 280-282, SEQ ID NO: 298-312, SEQ ID NO: 345-371, SEQ ID NO: 373, 374, 378, 380, 389-396, 399, 400, and the complements thereof, wherein the interfering RNA molecule has insecticidal activity against the target coleopteran insect or a *Diabrotica* insect. In another embodiment, the contacting is achieved by the target insect feeding on the composition. In other embodiments, production of the protein encoded by the target mRNA is reduced. In other embodiments, the target protein comprises an amino acid having at least about 80%, at least about 85%, at least about 90%, at least about 91%, at least about 92%, at least about 93%, at least about 94%, at least about 95%, at least about 96%, at least about 97%, at least about 98% or at least about 99% identity to SEQ ID NO: 241-270 or SEQ ID NO: 376. In other embodiments the target protein comprises SEQ ID NO: 241-270 or SEQ ID NO: 376. In other embodiments, the interfering RNA is contacted with a coleopteran insect or a *Diabrotica* insect through a transgenic organism expressing the interfering RNA. In other embodiments, the transgenic organism is a transgenic plant, a transgenic microorganism, a transgenic bacterium or a transgenic endophyte. In other embodiments, the interfering RNA is contacted with a coleopteran insect or a *Diabrotica* insect by topically applying an interfering RNA in an acceptable agricultural carrier to a plant or plant part on which the insect feeds. In some embodiments, the interfering RNA that reduces the level of a target mRNA transcribable from a target gene described herein is lethal to the coleopteran insect or *Diabrotica* insect. In some embodiments, the *Diabrotica* insect is selected from the group consisting of *D. barberi* (northern corn rootworm), *D. virgifera virgifera* (western corn rootworm), *D. undecimpunctata howardi* (southern corn rootworm), *D. balteata* (banded cucumber beetle), *D. undecimpunctata undecimpunctata* (western spotted cucumber beetle), *D. significata* (3-spotted leaf beetle), *D. speciosa* (*chrysanthemum* beetle) and *D. virgifera zeae* (Mexican corn rootworm).

In some embodiments, the invention encompasses a method of conferring coleopteran insect tolerance or *Diabrotica* insect tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, wherein the dsRNA molecule, nucleic acid construct, chimeric nucleic acid molecule, artificial plant microRNA precursor molecule and/or composition of the invention are toxic to the insect, thereby conferring tolerance of the plant or part thereof to the coleopteran insect or *Diabrotica* insect. In other embodiments, the introducing step is performed by transforming a plant cell and producing the transgenic plant from the transformed plant cell. In still other embodiments, the introducing step is performed by breeding two plants together.

In other embodiments, the invention encompasses a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, wherein the dsRNA, nucleic acid molecule, nucleic acid construct, chimeric nucleic acid molecule, artificial plant microRNA precursor molecule and/or composition of the invention are toxic to the *Diabrotica* insect, thereby reducing root damage to the plant. In other embodiments, the introducing step is performed by transforming a plant cell and producing the transgenic plant from the transformed plant cell. In still other embodiments, the introducing step is performed by breeding two plants together.

In still other embodiments, the invention encompasses a method of producing a transgenic plant cell having toxicity to a coleopteran insect or *Diabrotica* insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the insect compared to a control plant cell. In some embodiments, the invention encompasses a plurality of transgenic plant cells produced by this method. In other embodiments, the plurality of transgenic plant cells is grown under conditions which include natural sunlight. In other embodiments, the introducing step is performed by transforming a plant cell and producing the transgenic plant from the transformed plant cell. In still other embodiments, the introducing step is performed by breeding two plants together.

In some embodiments, the invention encompasses a method of producing a transgenic plant having enhanced tolerance to coleopteran or *Diabrotica* insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to coleopteran or *Diabrotica* insect feeding damage compared to a control plant. In other embodiments, the introducing step is performed by transforming a plant cell and producing the transgenic plant from the transformed plant cell. In still other embodiments, the introducing step is performed by breeding two plants together.

In some embodiments, the invention encompasses a method of providing a corn grower with a means of controlling a coleopteran insect pest population or a *Diabrotica* insect pest population in a corn crop comprising (a) selling or providing to the grower transgenic corn seed that comprises an interfering RNA, a nucleic acid molecule, a nucleic acid construct, a chimeric nucleic acid molecule, an artificial plant microRNA precursor molecule and/or a composition of the invention; and (b) advertising to the grower that the transgenic corn seed produce transgenic corn plants that control a coleopteran or *Diabrotica* pest population.

In some embodiments, the invention encompasses a method of identifying a target gene for using as a RNAi strategy for the control of a plant pest for RNAi in a coleopteran plant pest, said method comprising the steps of a) producing a primer pair with sequences selected from the group comprising or consisting of SEQ ID NO: 31-90, 397, 398, or a complement thereof; b) amplifying an orthologous target from a nucleic acid sample of the plant pest; c) identifying a sequence of an orthologous target gene; d) producing an interfering RNA molecule, wherein the RNA comprises at least one dsRNA, wherein the dsRNA is a region of double-stranded RNA comprising annealed complementary strands, one strand of which comprises a sequence of at least 19 contiguous nucleotides which is at least partially complementary to a target nucleotide sequence within a coleopteran target gene, is obtained; and e) determining if the interfering RNA molecule has insecticidal activity on the plant peast. If the interfering RNA has insecticidal activity on the coleopteran pest, a target gene for using in the control of the plant pest has been identified. In some embodiments, the plant pest is a coleopteran plant pest.

EXAMPLES

The invention will be further described by reference to the following detailed examples. These examples are provided for the purposes of illustration only, and are not intended to be limiting unless otherwise specified.

Example 1. Identification of RNAi Gene Targets in *Diabrotica Virgifera Virgifera*

This example describes the cloning and sequencing of RNAi target genes and coding sequences from *Diabrotica* insects.

*Diabrotica virgifera Virgifera* Pyrosequencing Library Preparation and Sequencing A whole-body neonate *Diabrotica virgifera virgifera* (Western Corn Rootworm (WCR)) transcriptome was sequenced by pyrosequencing on a 454 platform (454 Life Sciences, Branford, CT) essentially according to the manufacturer's instructions. The resulting reads (i.e., short fragments of nucleic acid sequence) were trimmed and assembled into contigs using a MIRA assembler (See, for example, Chevreux et al. 2004. Genome Res. 14:1147-1159, incorporated herein by reference).

Identification of Lead Target Genes from *Diabrotica* Spp.

Assembled contigs were compared via BLAST to known lethal genes and alleles in other organisms, which were identified based on published disclosures including those in the website wormbase (wormbase.org) and Boutros et al (2004, Science 303: 832-835). From this analysis, 4,608 target genes were identified. Each of these target genes is non-redundant and is known to possess an allele(s) which is lethal, or is known to result in lethality when targeted by RNAi, in either *C. elegans, Drosophila*, or both. Therefore, each of these targets were considered essential. It was expected that a significantly large percentage of these target genes would have an insecticidal effect in WCR. Surprisingly, that was not the case.

dsRNAs of the 4,608 targets were produced on an 384 well automated library synthesis platform. All the dsRNA samples tested were designed automatically using Primer3, a primer design tool, to synthetize a dsRNA fragment of around 500-600 bp based on the coding sequence of each target gene. Smaller fragments were designed if the size of the coding sequence did not allow a 500 bp fragment. These samples were screened in a 24-well WCR assay, at one concentration (100 ng dsRNA/$cm^2$, i.e. 190 ng dsRNA/well) with 10 L2 WCR larvae per well. The mortality was scored after 10 days. The cut-off for candidate hits was 69% mortality. Of the 4,608 candidate dsRNA targets, 183 target genes were identified. These results are surprising, as a person skilled in the art would have expected that a greater number of the 4,608 candidate targets would have conferred toxicity in the bioassays.

In a first assay, 7 targets were tested in laboratory bioassays in a 10-fold dilution series starting from 1 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. dsRNA molecules were diluted to appropriate concentration so that 20 μl of solution was added to the surface of the diet in half of the wells of a 48-well plate, with a final overlay concentration of 1 μg, 0.1 μg, 0.01 μg and 0.001 μg per well. One or two WCR larvae were added to each well to have between 24 and 48 replicate larvae per concentration of dsRNA tested. Each 48-well plate was maintained at approximately 26° C. with a 16 hour:8 hour light:dark photoperiod. Mortality was recorded at 1, 2, 3, 4, 6 and 7 d post-infestation. dsRNA designed to target green fluorescent protein (GFP) was used in all bioassays as a negative control and dsRNA designed to target an ubiquitin gene of WCR was used as a positive control. From this assay, BPA_46378 (alpha-snap) was confirmed positive. Four candidates were not confirmed positive.

The other 176 target genes were tested simultaneously in a confirmation screen. dsRNA of the 176 targets, as well as positive and negative control dsRNAs, were produced on an automated library synthesis platform. BPA_46378 was also tested under this screen. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. dsRNA molecules were diluted to appropriate concentration so that 20 μl of solution was added to the surface of the diet in half of the wells of a 48-well plate, with a final overlay concentration of 0.5 μg dsRNA per well. One or two WCR larvae were added to each well to have between 24 and 48 replicate larvae per dsRNA tested. Each 48-well plate was maintained at approximately 26° C. and 16:8 light:dark photoperiod. Mortality was recorded at 7 days after treatment.

The results, shown in Table 1, found 29 dsRNA molecules of the initial 176 dsRNA molecules identified were confirmed to be highly toxic to *Diabrotica virgifera virgifera* (western corn rootworm), in addition to the alpha-snap target which was re-confirmed. SEQ ID NOs: 1-30 are nucleotide sequences of the nucleic acid fragments of each toxic target gene identified in the screen. SEQ ID NOs: 31-90, 397, 398 and complements thereof are nucleotide sequences of the primer pairs used to synthesize the nucleic acid fragments of each target gene identified in the screen. SEQ ID NOs: 91-120 are nucleotide sequences of the full-length coding sequences of each target gene identified by this screen.

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,612,194, which discloses 9,112 sequences. However, as demonstrated here, the ability of any given gene target to confer toxicity through an RNAi approach cannot be predicted, and can only be determined empirically. Similar conclusions have been reached by Narva et al. (U.S. Publication No. 2015/0322456). The present invention identifies 30 target genes which each provide surprising and unexpected superior control of *Diabrotica*.

TABLE 1

Activity of dsRNA against *Diabrotica virgifera virgifera* 7 d after treatment

| Target ID | Putative Dm orthologue | putative gene name or function | SEQ ID NO: | % mortality at d7 (0.5 μg/well) |
|---|---|---|---|---|
| BPA_15366 | CG7178 | troponin | 1 | 96.00 |
| BPA_16909 | CG12051 | actin 42A | 2 | 100.00 |
| BPA_45189 | CG6699 | beta'-coatomer | 3 | 100.00 |
| BPA_71902 | CG32744 | ubiquitin-5E | 4 | 90.91 |

TABLE 1-continued

Activity of dsRNA against *Diabrotica virgifera virgifera* 7 d after treatment

| Target ID | Putative Dm orthologue | putative gene name or function | SEQ ID NO: | % mortality at d7 (0.5 μg/well) |
|---|---|---|---|---|
| BPA_16014 | CG18290 | Actin 87E | 5 | 84.00 |
| BPA_41555 | CG1528 | gamma-coatomer | 6 | 97.14 |
| BPA_71568 | CG3664 | Rab5 | 7 | 100.00 |
| BPA_16830 | NA | unknown function | 8 | 92.00 |
| BPA_15330 | CG5271 | RpS27A | 9 | 85.29 |
| BPA_2526 | CG11415 | tetraspanin | 10 | 97.22 |
| BPA_11606 | CG33865 | histone2A | 11 | 93.94 |
| BPA_12879 | CG1664 | small bristles | 12 | 97.30 |
| BPA_2443 | CG6223 | beta-coatomer | 13 | 93.94 |
| BPA_10976 | CG8385 | ARF1 | 14 | 78.95 |
| BPA_875 | CG3722 | DE-cadherin | 15 | 76.47 |
| BPA_2184 | CG40127 | RNase K | 16 | 75.76 |
| BPA_7931 | CG11027 | ARF102F | 17 | 82.35 |
| BPA_17622 | CG7007 | Vacuolar H[+] ATPase PPA1 | 18 | 70.00 |
| BPA_450 | CG1554 | RNApol II | 19 | 78.05 |
| BPA_46378 | CG6625 | Alpha snap | 20 | 100.00 |
| BPA_71489 | CG3320 | Rab1 | 21 | 85.00 |
| BPA_4800 | CG7269 | helicase | 22 | 69.57 |
| BPA_880 | CG4775 | Tango14 | 23 | 63.64 |
| BPA_15751 | CG12775 | RpL21 | 24 | 65.79 |
| BPA_41770 | CG3948 | zeta-coatomer | 25 | 71.05 |
| BPA_9438 | CG8472 | calmodulin | 26 | 65.63 |
| BPA_16140 | CG7185 | RNA recognition motif domain | 27 | 54.80 |
| BPA_65371 | CG1519 | proteasome alpha | 28 | 52.50 |
| BPA_12351 | CG8186 | Vacuolar H[+] ATPase Vha36-1 | 29 | 42.60 |
| BPA_17046 | CG9311 | myopic | 30 | 47.40 |
| | | GFP repl1 | | 21.21 |
| | | GFP repl2 | | 11.76 |
| | | Dv ubiquitin control repl1 | | 100.00 |
| | | Dv ubiquitin control repl2 | | 100.00 |

Example 2. Activity of dsRNA Against *Diabrotica Virgifera Virgifera*—DRC 4 Concentrations This example describes testing dsRNAs of the invention for biological activity against *Diabrotica virgifera virgifera* (WCR).

The 30 dsRNA molecules described above were tested for toxicity against WCR in laboratory bioassays in a 10-fold dilution series starting from 1 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentration so that 20 μl of solution was added to the surface of the diet in half of the wells of a 48-well plate, with a final overlay concentration of 1 μg, 0.1 μg, 0.01 μg and 0.001 μg per well. One or two WCR larvae were added to each well to have between 24 and 48 replicate larvae per concentration of dsRNA tested. Each 48-well plate was maintained at approximately 26° C. and 16:8 light:dark photoperiod. Mortality was recorded at 1, 2, 3, 4, 6 and 7 d post-infestation. dsRNA designed to target GFP was used as a negative control and dsRNA designed to target an ubiquitin gene of WCR was used as a positive control.

The results, shown in Table 2, show that the 30 dsRNA molecules designed to target mRNA transcribable from WCR genes are toxic to highly toxic to WCR. After correction for the control mortality on the GFP dsRNA, the estimated $LT_{50}$ and $LC_{50}$ were calculated by curve fitting analysis. $LT_{50}$ stands for the lethal time to obtain 50% of mortality in the test insects. $LC_{50}$ stands for the concentration of the dsRNA, which causes the death of 50% of the test insects. In Table 2, the % mortality at day 7 is based on 1 μg dsRNA/well. The $LT_{50}$ is based on using 1 μg dsRNA/day and is measured in days. The $LC_{50}$ was measured in μg dsRNA/well.

TABLE 2

Activity of dsRNA against *Diabrotica virgifera virgifera*, 7 d after treatment

| Target ID | SEQ ID NO: | % mortality at d7 (1 μg/well) | $LT_{50}$ (days) | $LC_{50}$ (μg/well) |
|---|---|---|---|---|
| BPA_15366 | 1 | 97.30 | 2.53 | 0.005 |
| BPA_16909 | 2 | 100.00 | 3.52 | 0.009 |
| BPA_45189 | 3 | 100.00 | 5.14 | 0.005 |
| BPA_71902 | 4 | 88.89 | 3.74 | 0.045 |
| BPA_16014 | 5 | 85.71 | 5.21 | 0.077 |
| BPA_41555 | 6 | 100.00 | 5.14 | <0.001 |
| BPA_71568 | 7 | 97.22 | 5.03 | 0.015 |
| BPA_16830 | 8 | 84.21 | 5.73 | 0.008 |
| BPA_15330 | 9 | 58.33 | 6.98 | 0.858 |
| BPA_2526 | 10 | 97.37 | 5.22 | 0.028 |
| BPA_11606 | 11 | 97.22 | 5.03 | 0.061 |
| BPA_12879 | 12 | 93.55 | 4.85 | 0.009 |
| BPA_2443 | 13 | 100.00 | 4.71 | 0.004 |
| BPA_10976 | 14 | 85.00 | 5.49 | 0.008 |
| BPA_875 | 15 | 94.29 | 4.84 | 0.084 |
| BPA_2184 | 16 | 64.44 | 6.71 | 0.763 |
| BPA_7931 | 17 | 90.32 | 5.38 | 0.081 |
| BPA_17622 | 18 | 70.73 | 6.60 | 0.649 |
| BPA_450 | 19 | 65.71 | 6.57 | 0.256 |
| BPA_46378 | 20 | 100.00 | 5.49 | 0.015 |
| BPA_71489 | 21 | 92.68 | 5.29 | 0.009 |
| BPA_4800 | 22 | 51.35 | NA | NA |
| BPA_880 | 23 | 53.13 | NA | NA |
| BPA_15751 | 24 | 85.29 | 5.74 | 0.058 |
| BPA_41770 | 25 | 62.16 | 6.71 | 0.090 |
| BPA_9438 | 26 | 51.35 | NA | NA |
| BPA_16140 | 27 | 76.67 | 6.56 | 0.201 |
| BPA_65371 | 28 | 34.29 | NA | NA |
| BPA_12351 | 29 | 35.29 | NA | NA |
| BPA_17046 | 30 | 51.43 | NA | NA |
| GFP repl1 | | 15.80 | NA | NA |
| GFP repl2 | | 20.00 | NA | NA |
| Dv ubiquitin | | 97.22 | 3.33 | 0.028 |

Based on these results, a sub-set of targets were prioritized for further investigation. The results of these targets are shown below.

Example 3. Activity of dsRNA Against *Diabrotica Virgifera Virgifera*

This example describes testing of a sub-set of the identified target dsRNAs of the invention for biological activity against *Diabrotica virgifera virgifera* (WCR).

The dsRNA molecules described above were tested for toxicity against WCR in laboratory bioassays in a 3-fold dilution series starting at 0.5 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. dsRNA molecules were diluted to appropriate concentration so that 20 μl of solution was added to the surface of the diet in half of the wells of a 48-well plate, with a final overlay concentration of 0.5 μg, 0.16 μg, 0.05 μg, 0.02 μg, 0.006 μg, 0.002 μg, 0.0007 μg and 0.0002 μg per well. One or two WCR larvae were added to each well to have between 24 and 48 replicate larvae per concentration of dsRNA tested. Each 48-well plate was maintained at approximately 26° C. and 16:8 light:dark photoperiod. Mortality was recorded at 1, 2, 3, 4, 6 and 7 d post-infestation. dsRNA designed to target GFP was used as a negative control and dsRNA designed to target an ubiquitin gene of WCR was used as a positive control.

The results, shown in Table 3, show that the dsRNA molecules designed to target mRNA transcribable from WCR genes are toxic to highly toxic to WCR. After correction for the control mortality on the GFP dsRNA, the estimated $LT_{50}$ and $LC_{50}$ were calculated by curve fitting analysis. $LT_{50}$ stands for the lethal time to obtain 50% of mortality in the test insects. $LC_{50}$ stands for the concentration of the dsRNA, which causes the death of 50% of the test insects. In Table 3, the % mortality at day 7 is based on 0.5 μg dsRNA/well. The $LT_{50}$ is based on using 0.5 μg dsRNA/day and is measured in days. The $LC_{50}$ was measured in μg dsRNA/well. These results confirm the toxicity of the candidate targets.

TABLE 3

Activity of dsRNA against *Diabrotica virgifera virgifera*

| Target ID | SEQ ID NO: | % mortality at d7 (0.5 μg/well) | $LT_{50}$ (days) | $LC_{50}$ (μg/well) |
|---|---|---|---|---|
| BPA_15366 | 1 | 100.0 | 2.6 | 0.0026 |
| BPA_71568 | 7 | 100.0 | 5.0 | 0.0015 |
| BPA_16830 | 8 | 66.7 | 6.5 | 0.0167 |
| GFP | | 22.9 | NA | NA |
| Dv ubiquitin | | 100.0 | 3.7 | 0.0065 |

Example 4. Activity of dsRNA Against *Diabrotica Undecimpunctata Howardi*

This example describes testing dsRNAs of the invention for biological activity against *Diabrotica undecimpunctata howardi* (southern corn rootworm (SCR)).

The dsRNA molecules described above were tested for toxicity against SCR in laboratory bioassays in a 10-fold dilution series starting at 0.5 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentrations so that 20 μl of solution was added to the surface of the diet in each well, with a final overlay concentration series of 8 concentrations going from 0.5 μg/well down to 0.00022 μg/well in steps of 3× dilution. One or two SCR larvae were added to each well to have between 24 and 48 replicate larvae per concentration of dsRNA tested. Each 48-well plate was maintained at approximately 26° C. and 16:8 light:dark photoperiod. Mortality was recorded at 1, 2, 3, 4, 5, 6, 7, 8, 9, 10, and 14 days post-infestation. dsRNA designed to target GFP was used as a negative control and dsRNA designed to target the *Diabrotica virgifera virgifera* (Dv) ubiquitin gene and the *Diabrotica undecimpunctata howardi* (Du) ubiquitin gene were used as positive controls.

After correction for the control mortality on the GFP dsRNA, the estimated $LT_{50}$ and $LC_{50}$ were calculated by curve fitting analysis. $LT_{50}$ stands for the lethal time to obtain 50% of mortality in the test insects. $LC_{50}$ stands for the concentration of the dsRNA, which causes the death of 50% of the test insects. In Table 4, the % mortality at day 14 is based on 0.5 μg dsRNA/well. The $LT_{50}$ is based on using 0.5 μg dsRNA/day and is measured in days. The $LC_{50}$ was measured in μg dsRNA/well. The results, shown in Table 4, show that the dsRNA molecules designed to target mRNA transcribable from *Diabrotica virgifera virgifera* (WCR) genes are also toxic to *Diabrotica undecimpunctata howardi* (SCR). This demonstrates that the targets of the invention are suitable targets for SCR as well, such that dsRNA molecules based on the native SCR mRNAs would be toxic to SCR and other *Diabrotica* spp. as well.

TABLE 4

Activity of dsRNA against *Diabrotica undecimpunctata howardi* 14 d after treatment

| Target ID | SEQ ID NO: | % mortality at d14 (0.5 μg/well) | $LT_{50}$ (days) | $LC_{50}$ (μg/well) |
|---|---|---|---|---|
| BPA_15366 | 1 | 8.33 | NA | NA |
| BPA_71568 | 7 | 97.44 | 7.44 | 0.0062 |
| BPA_16830 | 8 | 94.29 | 8.09 | 0.0556 |
| GFP | | 8.33 | NA | NA |
| Dv ubiquitin | | 97.14 | 6.75 | 0.0123 |
| Du ubiquitin | | 100.00 | 5.57 | 0.0209 |

Example 5. Activity of dsRNA Against *Diabrotica barberi*

This example describes testing dsRNAs of the invention for biological activity against *Diabrotica barberi* (northern corn rootworm (NCR)).

The dsRNA molecules described above were tested for toxicity against NCR in laboratory bioassays. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentration so that 20 μl of solution was added to the surface of the diet in half of the wells of a 48-well plate, with a final overlay concentration of 0.5 μg dsRNA per well. One or two NCR larvae were added to each well to have between 24 and 48 replicate larvae per dsRNA tested. Each 48-well plate was maintained at approximately 26° C. and 16:8 light:dark photoperiod. Mortality was recorded at 7 d post-infestation. dsRNA designed to target GFP was used in all bioassays as a negative control and dsRNA designed to target the *Diabrotica barberi* (Dr) ubiquitin gene was used as positive control.

The results, shown in Table 5, show that the dsRNA molecules designed to target mRNA transcribable from *Diabrotica virgifera virgifera* genes are also toxic to *Diabrotica barberi*. This demonstrates that the targets of the invention are suitable targets for NCR as well, such that dsRNA molecules based on the native NCR mRNAs would be toxic to NCR and other *Diabrotica* spp. as well.

TABLE 5

Activity of dsRNA against *Diabrotica barberi* 7 d after treatment

| target ID | SEQ ID NO: | % mortality at day 9 |
|---|---|---|
| BPA_15366 | 1 | 97.37 |
| BPA_71568 | 7 | 98.00 |

TABLE 5-continued

Activity of dsRNA against *Diabrotica barberi* 7 d after treatment

| target ID | SEQ ID NO: | % mortality at day 9 |
|---|---|---|
| BPA_16830 | 8 | 100.00 |
| GFP repl1 | | 18.75 |
| GFP repl2 | | 22.00 |
| Dr ubiquitin repl1 | | 85.00 |
| Dr ubiquitin repl2 | | 86.00 |

Example 6. Fragment Size Assays in WCR

All dsRNA samples tested in the previous examples were designed automatically using Primer3, a primer design tool, to synthesize a dsRNA fragment of around 500 bp based on the coding sequence of each target gene. Smaller fragments were designed if the size of the coding sequence did not allow a 500 bp fragment.

In the fragment size experiments, different dsRNA fragments were designed based on the complete coding sequence of each target gene. The complete coding sequence was tested as a whole if available and if not greater than 1000 bp. The coding sequence was also divided into fragments, with some overlap of 25-30 bp between subsequent fragments. For each fragment new primers were designed and dsRNA was synthesized on the automated library synthesis platform. Additionally, target BPA_16372, whose synthesized dsRNA molecules were found in a separate screening to have insecticidal activity against WCR, also was tested with different dsRNA fragments. All dsRNA fragments were tested in a WCR bioassay at two different concentrations (0.1 μg dsRNA and 0.01 μg dsRNA per well) and mortality was scored at day 7.

The dsRNA molecules described above were tested for toxicity against *Diabrotica virgifera virgifera* in laboratory bioassays. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentration so that 20 μl of solution was added to the surface of the diet in half of the wells of a 48-well plate, with a final overlay concentration of 0.1 μg dsRNA or 0.01 μg dsRNA per well. One or two *Diabrotica virgifera virgifera* larvae were added to each well to have between 24 and 48 replicate larvae per dsRNA tested. Each 48-well plate was maintained at approximately 26° C. and 16:8 light:dark photoperiod. Mortality was recorded at 7 d post-infestation. dsRNA designed to target GFP was used in all bioassays as a negative control and dsRNA designed to target an ubiquitin gene of *Diabrotica virgifera virgifera* was used as a positive control.

The results, shown in Table 6, show that the dsRNA fragments designed to target mRNA transcribable from *Diabrotica virgifera virgifera* genes are toxic to highly toxic to *Diabrotica virgifera virgifera*.

TABLE 6

Activity of dsRNA sub-fragments against *Diabrotica virgifera virgifera* 7 d after treatment

| Target ID | SEQ ID NO: | Fragment size (bp) | % mortality at d7 0.01 μg | % mortality at d7 0.1 μg |
|---|---|---|---|---|
| BPA_15366_54 | 283 | 633 | 64 | 93 |
| BPA_15366_55 | 284 | 120 | 33 | 89 |
| BPA_15366_56 | 285 | 127 | 32 | 74 |
| BPA_15366_57 | 286 | 137 | 44 | 89 |
| BPA_15366_58 | 399 | 130 | 24 | 91 |
| BPA_15366_5 | 287 | 133 | 47 | 87 |
| BPA_15366_59 | 400 | 119 | 31 | 63 |
| BPA_71568_screen | 288 | 500 | 88 | 97 |
| BPA_71568_1 | 289 | 648 | 42 | 100 |
| BPA_71568_2 | 290 | 188 | 91 | 100 |
| BPA_71568_3 | 291 | 205 | 76 | 95 |
| BPA_71568_4 | 292 | 224 | 84 | 100 |
| BPA_71568_5 | 293 | 196 | 24 | 89 |
| BPA_16830_screen | 294 | 189 | 55 | 85 |
| BPA_16830_1 | 295 | 330 | 41 | 78 |
| BPA_16830_2 | 296 | 197 | 38 | 61 |
| BPA_16830_3 | 297 | 179 | 56 | 86 |
| BPA_16372_2 | 381 | 687 | 53 | 90 |
| BPA_16372_3 | 382 | 693 | 87 | 93 |
| BPA_16372_4 | 383 | 700 | 65 | 97 |
| BPA_16372_5 | 384 | 549 | 43 | 86 |
| BPA_16372_6 | 385 | 677 | 63 | 81 |
| BPA_16372_7 | 386 | 706 | 74 | 94 |
| BPA_16372_8 | 387 | 686 | 42 | 94 |
| BPA_16372_9 | 388 | 565 | 32 | 73 |
| GFP | | | NA | 3 |
| GFP | | | NA | 24 |
| positive control | | | 79 | 100 |
| positive control | | | 57 | 75 |

Example 7. Correlation of Size of dsRNA with Activity Against *Diabrotica Virgifera Virgifera*

This example describes testing dsRNAs of the invention for biological activity against *Diabrotica virgifera virgifera* (WCR).

The example focusses on different 42-46 bp sub-fragments of the BPA_15366_5 dsRNA (SEQ ID NOs: 313-317). DNA encoding the sub-fragments were operably linked to a 89 nt long GFP sequence which acted as “filler” sequence to generate a 133 bp long sequence for testing (SEQ ID NOs: 318-322). Each of SEQ ID NOs: 318-322 was tested for toxicity against WCR in laboratory bioassays in a 10-fold dilution series starting from 1 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentration so that 20 μl of solution was added to the surface of the diet in half of the wells of a 48-well plate, with a final overlay concentration of 1 μg, 0.1 μg, 0.01 μg and 0.001 μg per well. One or two WCR larvae were added to each well to have between 24 and 48 replicate larvae per concentration of dsRNA tested. Each 48-well plate was maintained at approximately 26° C. and 16:8 hr light:dark photoperiod. Mortality was recorded at 1, 2, 3, 4, 5, 6 and 7 d post-infestation. dsRNA designed to target GFP was used as a negative control and dsRNA designed to target the larger 133 nt fragment of the troponin gene of WCR was used as a positive control.

The results, shown in Table 7, show that the five 42-46 bp dsRNA fragments operably linked to the “filler” GFP sequence (encoded by SEQ ID NOs: 318-322) to create a 133 bp sequence are almost as toxic as the 133 bp dsRNA fragment of BPA_15366_5 (encoded by SEQ ID NO: 315). The % mortality at day 7 is based on 1 μg dsRNA/well concentration. After correcting for the control mortality on the GFP dsRNA, the estimated $LT_{50}$ and $LC_{50}$ were calculated by curve fitting analysis. The $LT_{50}$ is based on using 1 μg dsRNA/day and is measured in days. The $LC_{50}$ was measured in μg dsRNA/well.

TABLE 7

Activity of dsRNA against *Diabrotica virgifera virgifera*, 7 d after treatment

| Target ID | SEQ ID NO: | length of active dsRNA fragment (bp) | % mortality at day 7 (1 μg/well) | $LT_{50}$ (days) | $LC_{50}$ (μg/well) |
|---|---|---|---|---|---|
| BPA_15366_5 | 315 | 133 | 100 | 2.1 | 0.078 |
| BPA_15366_13 | 318 | 44 | 89 | 2.62 | 0.079 |
| BPA_15366_14 | 319 | 45 | 72 | 4.77 | 0.069 |
| BPA_15366_15 | 320 | 44 | 90 | 3 | 0.083 |
| BPA_15366_16 | 321 | 42 | 94 | 2.58 | 0.046 |
| BPA_15366_17 | 322 | 46 | 77 | 3.43 | 0.078 |
| GFP | | NA | 18 | NA | NA |

Example 8. Identification of 21Mers with Activity Against *Diabrotica Virgifera Virgifera*

This example describes testing dsRNAs of the invention for biological activity against *Diabrotica virgifera virgifera* (WCR).

The example focusses on different 21mer siRNA's of the active 42 bp dsRNA fragment encoded by BPA_15366_16 (SEQ ID NO: 321). The sub-fragments as described above were embedded in GFP "filler" sequence to a total of 145 bp. Each of the embedded 21mers was tested for toxicity against WCR in laboratory bioassays in a 10-fold dilution series starting from 1 μg dsRNA/well. Bioassays were performed using an RNA-treated artificial diet method. Briefly, molten artificial diet, modified from the diet of Marrone et al. 1985 (J. Econ. Entomol. 78:290-293), was poured into each well of 48-well plates and allowed to solidify. Synthesized dsRNA molecules were diluted to appropriate concentration so that 20 μl of solution was added to the surface of the diet in half of the wells of a 48-well plate, with a final overlay concentration of 1 μg, 0.1 μg, 0.01 μg and 0.001 μg per well. One or two WCR larvae were added to each well to have between 24 and 48 replicate larvae per concentration of dsRNA tested. Each 48-well plate was maintained at approximately 26° C. and 16:8 light:dark photoperiod. Mortality was recorded at 1, 2, 3, 4, 5, 6 and 7 d post-infestation. dsRNA designed to target GFP was used as a negative control and dsRNA designed to target the larger 133 bp fragment of BPA_15366_5 (SEQ ID NO: 287) and the 42 bp fragment of BPA_15366_16 embedded in GFP filler sequence (SEQ ID NO: 321) were used as positive controls.

The results, shown in Table 8, show that most of the embedded 21mer dsRNA fragments designed to target the mRNA transcribable from the WCR BPA_15366 target gene show toxicity against WCR.

TABLE 8

Activity of dsRNA against *Diabrotica virgifera virgifera*, 7 d after treatment

| Target ID | SEQ ID NO: | length of active dsRNA fragment (bp) | % mortality at d7 (1 μg/well) |
|---|---|---|---|
| BPA_15366_5 | 287 | 133 | 100 |
| BPA_15366_16 | 321 | 42 | 97 |
| BPA_15366_18 | 323 | 21 | 9 |
| BPA_15366_19 | 324 | 21 | 29 |
| BPA_15366_20 | 325 | 21 | 46 |
| BPA_15366_21 | 326 | 21 | 42 |
| BPA_15366_22 | 327 | 21 | 25 |
| BPA_15366_23 | 328 | 21 | 61 |
| BPA_15366_24 | 329 | 21 | 62 |
| BPA_15366_25 | 330 | 21 | 49 |
| BPA_15366_26 | 331 | 21 | 52 |
| BPA_15366_27 | 332 | 21 | 55 |
| BPA_15366_28 | 333 | 21 | 69 |
| BPA_15366_29 | 334 | 21 | 58 |
| BPA_15366_30 | 335 | 21 | 58 |
| BPA_15366_31 | 336 | 21 | 51 |
| BPA_15366_32 | 337 | 21 | 77 |
| BPA_15366_33 | 338 | 21 | 67 |
| BPA_15366_34 | 339 | 21 | 63 |
| BPA_15366_35 | 340 | 21 | 77 |
| BPA_15366_36 | 341 | 21 | 64 |
| BPA_15366_37 | 342 | 21 | 57 |
| BPA_15366_28 | 343 | 21 | 83 |
| BPA_15366_39 | 344 | 21 | 56 |
| GFP | | NA | 9 |

Example 9. Expression of an Interfering RNA Molecule Comprising Target dsRNA in Corn Plants This example describes introducing a construct that expresses an interfering RNA molecule into plant cells.

Vector Construction

Expression vectors designed to produce hairpin RNAs (hpRNA) consisted of a cassette containing a promoter, a sense strand, an intron functioning as a loop sequence, an antisense strand, and terminator. Binary vector 23130 comprises an expression cassette comprising a DNA sequence designed to produce a hpRNA targeting a 133 nucleotide fragment of BPA_15366 (SEQ ID NO: 403). Each binary vector also contained a second cassette between the left and right borders, designed to express phosphomannose isomerase (PMI) which provides the ability to metabolize mannose (U.S. Pat. Nos. 5,767,378 and 5,994,629, which are incorporated by reference herein) as a selectable marker during plant transformation. The vectors also contained selectable markers for selection in bacteria.

*Agrobacterium* Mediated Transformation

The resulting plasmid containing the hairpin cassette was transformed into *Agrobacterium tumefaciens* using standard molecular biology techniques known to those skilled in the art. To prepare the Agrobacteria for transformation cells were cultured in liquid YPC media at 28° C. and 220 rpm overnight. The vectors described above are transformed into maize. *Agrobacterium* transformation of immature maize embryos was performed essentially as described in Negrotto et al., 2000, Plant Cell Reports 19: 798-803. For this example, all media constituents are essentially as described in Negrotto et al., supra. However, various media constituents known in the art may be substituted. Following transformation, selection, and regeneration, plants were tested for the presence of the pmi gene and the hairpin dsRNA interfering RNA molecule. Positive plants from the PCR assay were transferred to the greenhouse and allowed to set seed.

Transgenic Maize Insect Assay

Field trials of 7 different transgenic events with positive and negative controls were planted in four locations. There were three replicate plots of each event per location, and each plot had 12 plants. The arrangement of plots was determined using randomized complete block design. Field trials relied on natural populations of corn rootworm. When the maize plants reached the early R2 stage, roots were dug from 5 plants per plot, washed to remove soil, and rated using the node injury scale of 0-3 (Oleson et al., 2005, J. Econ. Entomol. 98: 1-8). Root damage data was analyzed using Least Square Means with the SAS JMP statistical package (JMPSAS Institute 2010). Results are shown in Table 9. The positive control plants comprised event 5307 (WO publication WO 2010/077816, incorporated by reference herein) and also event MIR604 (WO publication WO 2005/103301, incorporated by reference herein). “RDR” is the least square mean of 1.5 inch root feeding rating of all samples evaluated.

TABLE 9

Transgenic maize insect assay

| Plant ID | RDR |
|---|---|
| Negative control | 2.12 |
| Positive control | 0.66 |
| Event 1 | 0.61 |
| Event 2 | 1.33 |
| Event 3 | 0.82 |
| Event 4 | 0.80 |
| Event 5 | 1.29 |
| Event 6 | 1.50 |
| Event 7 | 1.37 |

All events comprising the interfering RNA molecule expressed from the transgene from vector 23130 have enhanced tolerance to insect pests as compared to the non-transgenic control plants. This illustrates that a transgenic plant comprising an interfering RNA molecule of the invention has enhanced resistance to an insect pest as compared to a non-transgenic-control plant.

Example 10. Interfering RNA Molecules with a Second Insecticidal Agent Bioassays This example illustrates the toxicity of interfering RNA molecules of the invention in combination with a second insecticidal agent.

Double stranded RNA molecules were produced against the BPA_15366 target. Additionally, a second insecticidal agent was prepared. Both the RNA and the second insecticidal agent were tested in combination for toxicity against WCR in laboratory bioassays.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and, patent applications are herein incorporated by reference to the same extent as if each individual publication or patent application was specifically and individually indicated to be incorporated by reference.

What is claimed is:

1. An interfering RNA molecule comprising a double-stranded RNA (dsRNA), the dsRNA consisting of annealed complementary strands, one strand of which consists of the nucleotide sequence of SEQ ID NO:390, and the other strand of which consists of the complement of SEQ ID NO:390, wherein the dsRNA has insecticidal activity on a coleopteran plant pest.

2. The interfering RNA molecule of claim 1, wherein said coleopteran plant pest is a *Diabrotica* insect.

3. The interfering RNA molecule of claim 1, wherein the annealed strands are substantially complementary.

4. The interfering RNA molecule of claim 1, wherein the annealed strands are fully complementary.

5. The interfering RNA molecule of claim 2, wherein the *Diabrotica* insect is selected from the group consisting of *D. barberi, D. virgifera, D. undecimpunctata, D. balteata, D undecimpunctata, D significate*, and *D. speciosa.*

6. A nucleic acid molecule encoding the interfering RNA molecule of claim 1.

7. A recombinant vector comprising a regulatory sequence operably linked to a nucleotide sequence that encodes the interfering RNA molecule of claim 1.

8. A transgenic plant, or part thereof, comprising the nucleic acid molecule of claim 6, wherein the transgenic plant has enhanced resistance to a *Diabrotica* insect as compared to a control plant.

9. The transgenic plant, or part thereof, of claim 8, wherein the transgenic plant comprises at least a second insecticidal agent for controlling *Diabrotica* insects.

10. The transgenic plant, or part thereof, of claim 9, wherein the second insecticidal agent is a *Bacillus thuringiensis* insecticidal protein, a *Bacillus cereus* insecticidal protein, a Xenorhabdus spp. insecticidal protein, a *Photorhabdus* spp. insecticidal protein, a *Brevibacillus* laterosporous insecticidal protein, a *Lysinibacillus sphearicus* insecticidal protein, a Chromobacterium spp. insecticidal protein, a *Yersinia* entomophaga insecticidal protein, a *Paenibacillus* popiliae insecticidal protein, a *Clostridium* spp. insecticidal protein, a patatin, a protease, a protease inhibitor, a urease, an alpha-amylase inhibitor, a pore-forming protein, a lectin, an engineered antibody or antibody fragment, or a chitinase.

11. The transgenic plant, or part thereof, of claim 8, wherein the transgenic plant, or part thereof, is a maize plant or part thereof.

12. Transgenic seed of the transgenic plant of claim 11.

13. A commodity product produced from the transgenic plant, or part thereof, of claim 8, wherein the commodity product comprises a detectable amount of said nucleic acid molecule.

14. The commodity product of claim 13, selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage fiber, paper or other food or product produced from plants.

15. A method of controlling a *Diabrotica* insect comprising contacting the *Diabrotica* insect with a nucleic acid molecule that is or is capable of producing the interfering RNA molecule of claim 1 for inhibiting expression of a target gene in the *Diabrotica* insect thereby controlling the *Diabrotica* insect.

16. The method of claim 15, wherein the *Diabrotica* insect is selected from the group consisting of *D. barberi, D. virgifera, D. undecimpunctata, D. balteata, D. undecimpunctata, D. significata*, and *D. speciosa.*

17. The method of claim 16, wherein contacting comprises:

a) planting a transgenic seed capable of producing a transgenic plant that expresses the nucleic acid molecule, wherein the *Diabrotica* insect feeds on the transgenic plant, or part thereof, or b) applying a composition comprising the nucleic acid molecule to a seed or plant, or part thereof, wherein the *Diabrotica* insect feeds on the seed, the plant, or a part thereof.

18. The method of claim 17, wherein the transgenic seed and transgenic plant is a corn seed and a corn plant.

19. A method of controlling a *Diabrotica* insect comprising contacting the *Diabrotica* insect with a nucleic acid molecule that is or is capable of producing the interfering RNA molecule of claim 1 for inhibiting expression of a target gene in the *Diabrotica* insect, and contacting the *Diabrotica* insect with at least a second insecticidal agent for controlling *Diabrotica.*

20. The method of claim 19, wherein said second insecticidal agent comprises a *B. thuringiensis* insecticidal protein, a *Bacillus cereus* insecticidal protein, a *Xenorhabdus* spp. insecticidal protein, a *Photorhabdus* spp. Insecticidal protein, a *Brevibacillus laterosporous* insecticidal protein, a *Lysinibacillus sphearicus* insecticidal protein, a *Chromobacterium* spp. insecticidal protein, a *Yersinia* entomophaga insecticidal protein, a *Paenibacillus* popiliae insecticidal protein, a *Clostridium* spp. insecticidal protein, a patatin, a protease, a protease inhibitor, a urease, an alpha-amylase inhibitor, a pore-forming protein, a lectin, an engineered antibody or antibody fragment, or a chitinase.

21. The interfering RNA molecule of claim 1, wherein the interfering RNA molecule provides at least 87% mortality at 0.01 μg and at least 93% mortality at 0.1 λg after 7 days in western corn rootworm.

* * * * *

SEQUENCE LISTING

```
<160> NUMBER OF SEQ ID NOS: 403

<210> SEQ ID NO 1
<211> LENGTH: 478
<212> TYPE: DNA
<213> ORGANISM: Diabrotica virgifera

<400> SEQUENCE: 1

ggtttcatga cccctgagag aaagaagaaa cttaggttac tgttgagaaa gaaagccgcc      60

gaagaattaa agaaagaaca agaacgcaaa gcagccgaaa ggaggcgtat cattgaagaa     120

aggtgcggta aacccaaact tgtcgatgac gcaaatgaag gcccattaaa acaagtatgt     180

gagggatatc acagacgtat tgtagaccta gaaaataaga aatttgacct cgaaaaagaa     240

gtggaattca gagattttca gatctccgaa ttgaacagcc aagtaaacga ccttagaggc     300

aaattcgtca aaccaacctt gaagaaggta tccaaatacg aaaacaaatt cgccaaactt     360

caaaagaagg cagctgaatt taacttccgt aaccaactca aagttgtcaa gaagaaagaa     420

ttcaccttag aagaagaaga caaagaaaag aaaccagact ggtcaaagaa gggagacg       478


<210> SEQ ID NO 2
<211> LENGTH: 529
<212> TYPE: DNA
<213> ORGANISM: Diabrotica virgifera

<400> SEQUENCE: 2

agaagttgcc gctttagtcg tagacaatgg atccggtatg tgcaaagctg gttttgctgg      60
```

-continued

```
ggatgatgca cctcgtgctg tattcccttc aattgttgga cgcccaagac atcagggtgt    120

gatggtagga atgggacaaa aagattccta tgtaggtgat gaagctcaaa gtaaaagagg    180

tatccttacc ttaaaatacc ccatcgagca cggaatagtc acaaactggg atgatatgga    240

gaaaatttgg catcatacat tctacaatga actcagagta gccccagaag aacaccctgt    300

tctgttgaca gaagctcctc tcaaccccaa ggccaacagg gaaaagatga cacaaataat    360

gtttgaaact ttcaacaccc cagccatgta tgttgccatc caggctgtac tctccttgta    420

tgcatctggt cgtacaactg gtattgtgtt ggattctggt gatggtgtat cccacactgt    480

cccaatctat gaaggttatg ctcttcctca tgcaatcctt cgtttggac               529


<210> SEQ ID NO 3
<211> LENGTH: 592
<212> TYPE: DNA
<213> ORGANISM: Diabrotica virgifera

<400> SEQUENCE: 3

accggccttt gtatgtcttg ggatatgtgc ctaaagacga tagattatac ctcgtagata     60

aagagttgcg cgtagtaagc taccaattac ttctttctgt tcttgaatat caaactgccg    120

tcatgagaag agactttcca acagcagaca gagtacttcc gtccattcct aaggagcaca    180

gaacgagagt ggcacatttc ttagaaaagc aaggcttcaa acagcaagct ttggccgtaa    240

gtacagatcc agagcacaga ttcgagctgg cagtagcatt agaggatctt aatatagcca    300

aaactctagc tcaagaagcg aacagtccgc aaaagtggaa tcaactagca gaattggcag    360

ctgctactaa taatgtaagc gtagccaagg aatgtatgca aaaagcgcaa gattatggag    420

gcttgttgct tcttgctacg agctccggtg atgaaaattt agtccgtact ctaggagaaa    480

cgacacaagc tgaaagcaaa cataacttag catttttgtc acacttgtta gtaggtgatt    540

taaacaaatg tctagacatt cttattaata ccggtagatt gccagaagct gc            592


<210> SEQ ID NO 4
<211> LENGTH: 594
<212> TYPE: DNA
<213> ORGANISM: Diabrotica virgifera

<400> SEQUENCE: 4

gaaagcagtt ggaagatggc cgtactctct cagactacaa cattcaaaaa gagtctaccc     60

tccatttggt acttcgtctt agaggaggta tgcagatttt tgttaaaact ttaactggaa    120

agaccatcac ccttgaagta gaaccttctg ataccatcga aaatgtcaaa gccaaaattc    180

aagacaaaga aggtattcca ccagatcaac aaagattaat ctttgccgga aagcaattgg    240

aagatggtcg tacactctca gactacaaca ttcaaaagga atctaccctc catttggtac    300

ttcgtcttag aggaggtatg caaatctttg taaaaacact cactggtaag accatcaccc    360

tcgaggttga accatcagat accatcgaga atgtcaaagc taaaattcaa gacaaagaag    420

gtattccacc agatcaacag agattaatct tcgctggaaa gcagttggaa gatggccgta    480

ctctctcaga ctacaatatt cagaaagagt ctaccctcca tttggtactt cgtcttagag    540

gaggtatgca aatctttgta aaaactctca ctggtaagac catcaccctc gagg          594


<210> SEQ ID NO 5
<211> LENGTH: 547
<212> TYPE: DNA
<213> ORGANISM: Diabrotica virgifera

<400> SEQUENCE: 5
```

```
taccccattg aacacggaat tatcactaac tgggacgata tggaaaagat ctggcatcac     60

accttctaca atgaacttag agtagccccc gaagaacatc ccattctttt gactgaagct    120

ccacttaacc caaaagccaa cagagaaaag atgactcaaa tcatgtttga aactttcaat    180

acccctgcca tgtatgttgc cattcaagct gtattgtctc tgtacgcttc cggtcgtacc    240

actggtattg tacttgattc tggagatggt gtatcccaca cagtacccat ctatgaaggt    300

tacgctctcc cacacgccat cttgcgtttg gacttggccg gtagagactt gactgactac    360

cttatgaaga tcttaaccga aagaggttac tctttcacca ccacagctga aagagaaata    420

gttcgtgaca tcaaggaaaa attgtgctat gtagctttgg acttcgaaca ggaaatggcc    480

acagcagcca gctccacctc cttagaaaag agttatgaac ttcctgacgg tcaagtcatc    540

accattg                                                              547
```

<210> SEQ ID NO 6
<211> LENGTH: 592
<212> TYPE: DNA
<213> ORGANISM: Diabrotica virgifera

<400> SEQUENCE: 6

```
aggaaaggaa ggacccaaga ccaaacaacc atcgagatac atccgtttta tctacaatcg     60

cgtcatattg gaatgtcctt ctgtaagagc tgctgcagtc tccgccatgg cacaattcgg    120

agcctcttgt cccgatttgt tagaaaatat ccaaatatta ctttcgaggt gtcagatgga    180

ttcagacgat gaagttaggg acagagctac atattatagt aatatactta acaaaaatga    240

taaaagttta tacaacaatt acattttgga ttctttgcag gtttcaattc cttcactaga    300

aagatcgctt agagaataca ttcaaaatcc aactgacgaa ccatttgaca ttaagtccgt    360

acctgtagca gcagtgccaa cagcagaaga acgagaagtt aaaaacaaat ctgaaggact    420

gctagtctct caaggtccag tccgacctcc tccggtgtct agagaagaaa acttcgccga    480

aaaacttagt aacgttccgg gtatacaaca gttaggacct ttgttcaaaa cttccgacgt    540

cgttgaactc actgaatctg aaacagagta ttttgtccgc tgtatcaagc ac            592
```

<210> SEQ ID NO 7
<211> LENGTH: 500
<212> TYPE: DNA
<213> ORGANISM: Diabrotica virgifera

<400> SEQUENCE: 7

```
tactaggcga aagtgccgtc ggtaagtcga gtttggtact gaggttcgtc aaaggacagt     60

tccacgaata ccaggagagt accataggag cagctttcct tacacaaacc atatgcctcg    120

acgatacaac tgttaaattt gaaatttggg acacagcggg tcaagaaagg taccacagtt    180

tagctcctat gtactatagg ggcgcacagg cagctatagt cgtctacgac ataaccaatc    240

aagacacatt cggcagggcg aaaacgtggg tgaaggaact tcaaaggcag gccagtccga    300

cgatcgtgat agctttggcc ggcaacaagc aagatttggc caacaaacgt atggtagaat    360

acgaagaggc gcagacgtat gctgacgaaa acggcttact ttttatggaa acttccgcaa    420

agacggcaat gaacgtcaac gatatatttt tagcaatagc taagaaactg cccaagaatg    480

aacaaaccac aggtcaaggc                                                500
```

<210> SEQ ID NO 8
<211> LENGTH: 189
<212> TYPE: DNA

-continued

<213> ORGANISM: Diabrotica virgifera

<400> SEQUENCE: 8
cgatgaggtt gaaggaagga gaaaaatttt gatggggcga aaaagcatta ccaggacata 60
tcttcgtgga aatgctgttc ctgcgtatgt gataataatc cttgtaggaa ttggtcaaat 120
catcctggga gggatattgt acgttgcatt gaggaagaag atcattgctg cacctgtaac 180
ggcatcata 189

<210> SEQ ID NO 9
<211> LENGTH: 393
<212> TYPE: DNA
<213> ORGANISM: Diabrotica virgifera

<400> SEQUENCE: 9
tgaggtcgag ccctcagata ctatcgaaaa tgtgaaagct aaaatccagg ataaagaagg 60
aattccccca gaccagcaac gtctcatctt cgctggaaaa caactcgaag atggtcgtac 120
cttgtctgac tataatattc aaaaagaatc aacccttcac ttggtgttga gattgagagg 180
aggtgctaag aaacgtaaga agaagaatta ctccaccccc aagaaaaatca agcacaagaa 240 gaagaaggtt aagttagctg tattgaaatt ttataaggtt gacgaaaatg gtaaaatcca 300
ccgattgaga cgtgaatgcc ccgctgaaca atgtggagct ggtgtcttca tggcagccat 360
ggaagacagg cattactgtg gcaagtgcgg tta 393

<210> SEQ ID NO 10
<211> LENGTH: 524
<212> TYPE: DNA
<213> ORGANISM: Diabrotica virgifera

<400> SEQUENCE: 10
tctttgcctt tggctacgat tcgaggaggg cattcaagaa tggctccaga aattggattc 60
agaacaattt tacatcggag tatatgtact tatagtcgct tcactgatcg tcatgattgt 120
gtcctttata ggatgtatta gtgccctgca ggagagtacc atggcccttt tagtgtacat 180
cggcacccaa gtgctcagtt ttatattcgg tttatccggt tcggcggttc ttctggataa 240
cagcgccaga gattcccact tccaaccgag gatccgagag agtatgcgac gtcttatcat 300
gaatgctcat cacgaccaat ccagacaaac actagccatg attcaggaaa atgttggttg 360
ctgcggagct gatggcgcaa cagactacct ctctcttcag cagccccttc caagtcagtg 420
cagagacacc gttactggaa acccattctt ccacggatgt gtagatgaac tcacctggtt 480
cttcgaagaa aaatgtggtt ggatagcagg tttagctatg gcga 524

<210> SEQ ID NO 11
<211> LENGTH: 267
<212> TYPE: DNA
<213> ORGANISM: Diabrotica virgifera

<400> SEQUENCE: 11
tcgtgctggt ttacaatttc ctgtaggtcg tattcatcgt ttattgagaa aaggaaatta 60
tgccgaaaga gttggtgctg gagctcctgt atacttggca gctgttatgg aatatttagc 120
tgctgaagtt ttggaattgg caggaaatgc agctagagat aacaaaaaga cccgtataat 180
tcctagacat ttacaattgg ccataagaaa tgacgaggaa ttgaacaaat tactgtcagg 240
agttaccatc gcccaaggtg gagtatt 267

-continued

<210> SEQ ID NO 12
<211> LENGTH: 558
<212> TYPE: DNA
<213> ORGANISM: Diabrotica virgifera

<400> SEQUENCE: 12
gtgcatgaag ttggatggtg tagatctgcc cccaccaatt agcttcgaca ttgcggaaga 60
gcaaccgtta ccaccttgcc aacagacgtt cttatgtaat ggtgatggag gatccatagt 120
gcgacagttt ctcgagctgt atttcgtaat atatgattca gataataggc agtcccttct 180
tcaggcatat cacgaaaaag ccacattttc aatgacaatg gcctacccgt acggctattc 240
caaagacagt aaaggagtat cgtggttgaa ttggtatgcc accgataata gaaatttatt 300
acgagttcaa gatccagaca gaagaaacaa gttgttaaga cagggacaag ttgctgtagt 360
ttcgttcttg caagatatgc cgcacacgaa gcacgatatt cacagtttta cagtagattt 420
gacagttttt acaccccaga tgttatgttt gacagtggct ggtatgttta aagaattgaa 480
aagtggccac aaagtacctc ctttaagata tttcttcaga acccttgtaa ttgtacctgc 540
tggatcaggt ttttgcat 558

<210> SEQ ID NO 13
<211> LENGTH: 582
<212> TYPE: DNA
<213> ORGANISM: Diabrotica virgifera

<400> SEQUENCE: 13
gattcggagc cctacaatga aatgcaacta aaaatggatt tagaaaaggg tgaggttaaa 60
gtaaaaataa gagcattaga aaaaataatt cacatgattc tggcaggaga aaggttgccg 120
aatggatttc taatgaccat cataagaaac gttttacctt tacaagatca tttggcaaaa 180
aaactattat tgattttctg ggaaatagtt ccaaaaacaa atccagaagg taaactacta 240
caagagatga ttttggtatg tgatgcctat agaaaagatc tgcaacaccc aaatgaattt 300
ttgagaggtt ctacacttcg cttcttgtgc aaactgaagg aaccagaatt gttggaacca 360
ttaatgccca gtattagagc ttgtttggat cataggcaca gctatgtgag gaggaatgct 420
gtactggcaa tttttaccat ttacaaaaat tttgaagccc tcattccaga tgctcctgaa 480
ctgatctcca attatttgga tggtgagcaa gacatgtctt gtaaaagaaa tgcgttttta 540
atgcttcttc atgctgacca agaaagggcg ttgtcgtatt tg 582

<210> SEQ ID NO 14
<211> LENGTH: 458
<212> TYPE: DNA
<213> ORGANISM: Diabrotica virgifera

<400> SEQUENCE: 14
ttggcaaaaa ggaaatgagg atattgatgg taggactcga tgcagctggt aaaaccacaa 60
ttttatataa acttaaatta ggagaaattg taacaactat tccaacaatt ggatttaatg 120
tggagactgt agaatataag aacattagtt ttacagtatg ggatgtaggt ggtcaagata 180
aaattaggcc attgtggaga cactatttcc aaaacacaca aggcctaatt ttcgtagtag 240
acagtaacga cagggaacgt atcactgagg ctaaagatga attaatgcgt atgttggccg 300
aagatgaact tagagatgcc gtacttctca ttttcgccaa caaacaagat ttgcccaatg 360
caatgaacgc tgcagaaatc accgacaaac tcggtctcca ttcactacgc aaccgcaact 420
ggtacattca agctacctgt gcaactagcg gagatggt 458

<210> SEQ ID NO 15
<211> LENGTH: 592
<212> TYPE: DNA
<213> ORGANISM: Diabrotica virgifera

<400> SEQUENCE: 15
ggtcgcgaaa gaacagaaag atttttgac cgtatctgcc gatggatgcg tacaagtaac 60
aaaacctctc gaccgagatc cgcctttcgg tagcccaaca cgacaagtct tcatctatgc 120
tcgtgataat gatggaggca caaattcatt gttggccact gcagaaattg aaattatttt 180
aatagatata aacgataatg ctccctttt aaatgttaca gaaattgttt attatgaaaa 240
ccaggatcca ggttttatag gtaacctaag tgccgatgat tacgatggtc ctgataatgg 300
acctccgttt gcttttcgat tatcagacac tgcttcagat agtattagat cgaaattttc 360
cattatcgga aaccagcttt tcgctttaga aatgtttgat agagaagagc aaaaatatta 420
tgacattgcc attgacatta cagatagtgg agtacctcca ctaacaggaa ctagtattct 480
tagagttata atcggagatg taaatgataa tccagctaca gacggaaaca gcacgatctt 540
tgtgtataag tacgtcaatg ggccagaaaa tttcatggaa atcggacgtg ta 592

<210> SEQ ID NO 16
<211> LENGTH: 214
<212> TYPE: DNA
<213> ORGANISM: Diabrotica virgifera

<400> SEQUENCE: 16
gcatggggta tcatccagtt gggtttcatg ggtgtattct attacattgg ggctgtggct 60
ttagcagaag atattccaga ggttgagttt aagggcgatt tagacaaatt tttatagcgac 120 gtcaacacgg gtttcacaca gaatgcttac aactgctgga ttgctgctct cctatacctg 180
ataacattag cagtatcagc tcaccaattc tggg 214

<210> SEQ ID NO 17
<211> LENGTH: 459
<212> TYPE: DNA
<213> ORGANISM: Diabrotica virgifera

<400> SEQUENCE: 17
tagatgccgc aggtaaaacc acaatcttat acaaattgaa gcttggtgaa atcgtaacta 60
caataccaac catcggcttc aatgtagaaa ccgttgagta caagaatata tctttcacgg 120
tatgggatgt aggtggccag acgagaatca gaaaactctg gagacactat ttcgccaaca 180
ctgatggact catttttgtg gttgattcca acgaccgaga ccgtatcgcg gaagccgaag 240
aagaattgca caatatgtta ggagaggacg atttaagaga ctgcattttg ttaatattcg 300
ccaacaaaca agatttaccg aactcgatgt ccactgctga attgaccgat aagcttaagt 360
tgcacacttt gaagaatagg aggtggtaca tacaagccac atgtgctact caagggaatg 420
gtttgtacga aggactagat tggttgtcga atgaattgg 459

<210> SEQ ID NO 18
<211> LENGTH: 536
<212> TYPE: DNA
<213> ORGANISM: Diabrotica virgifera

<400> SEQUENCE: 18
gctaccctag cgtccactgt aacactgatt tttgccctct actactgcct cacgggaaaa 60
ggagagcaag ttagtttagc atggttattg ttgaatgtgt ctccccacat gtgggcaggt 120

```
ctaggaattg gccttgctgt atcattatca gttgtaggag ctgctgcagg aattcacact    180

acaggagtca gtatcgtagg agctggtgtt aaagccccca gaatcaaaac caaaaattta    240

atttctatta ttttctgtga agctgtggct atctatgggt taattatggc tatagtactc    300

tgtggaagtt ggaagaattt cgatgtagac ctattcaacc tcaaaactca taactttgct    360

caaaaccatt atggatcaca tgttattttt ggatccggtt taactgttgg atttgtaaat    420

ctattatgtg gattttgtgt tggagtagtt ggttctggtg cagccatttc tgatgcagcc    480

aattcatcat tattcgtcaa aattttgatt attgagattt ttggaagtgc cattgg        536


<210> SEQ ID NO 19
<211> LENGTH: 547
<212> TYPE: DNA
<213> ORGANISM: Diabrotica virgifera

<400> SEQUENCE: 19

accttatggg aaagcgtgtg gacttttctg cacgtactgt catcacacca gatcccaatt     60

tacgtatcga ccaagtagga gtgcctagaa gtattgctca aaacatgacg tttccagaaa    120

tcgtcacacc tttcaatttt gacaaaatgt tggaattggt acagagaggt aattctcagt    180

atccaggagc taagtatatc atcagagaca atggagagag gattgattta cgtttccacc    240

caaaaccgtc agatttacat ttgcagtgtg gttataaggt agaaagacac atcagagacg    300

gcgatctagt aatcttcaac cgtcaaccaa ccctccacaa gatgagtatg atgggccaca    360

gagtcaaagt cttaccctgg tcgacgttcc gtatgaatct ctcgtgcacc tctccctaca    420

acgccgattt tgacggcgac gaaatgaacc tccatgtgcc ccaaagtatg gaaactcgag    480

ctgaagtcga aaacctccac atcactccca ggcaaatcat tactccgcaa gctaaccaac    540

ccgtcat                                                              547


<210> SEQ ID NO 20
<211> LENGTH: 564
<212> TYPE: DNA
<213> ORGANISM: Diabrotica virgifera

<400> SEQUENCE: 20

cggatctcta tttgggggat caagtcgtat tgaagatgca gtggaatgtt acacaagagc     60

tgcaaacctt tttaaaatgg ccaagagctg ggatgctgcc ggtaaagcct tttgtgaggc    120

tgctaatttg cattccagaa ctggtgctcg tcatgacgct gccactaatt atatagatgc    180

tgcaaattgt tacaaaaaag ccgatgtatt tgaggctgta aactgcttta taaaagctat    240

agacatttat accgaaatgg gtcgctttac aatggctgca aaacaccatc agactattgc    300

agaaatgtat gagactgatg ctgtggacat cgaaagggct gttcaacact atgaacaggc    360

ggctgattac ttcagaggag aagaaagcaa tgcttccgcc aataagtgtc ttcttaaagt    420

ggctcaatat gcagcccaac ttgaaaacta tgaaaaagca gtgggaattt atcaagaagt    480

ggcttatgca gctctggaaa gctctctttt aaaatacagt gcaaaggaat acttattcag    540

agctgccctt tgtcaccttt gtgt                                           564


<210> SEQ ID NO 21
<211> LENGTH: 564
<212> TYPE: DNA
<213> ORGANISM: Diabrotica virgifera

<400> SEQUENCE: 21
```

tgctgattgg agattcagga gtaggaaaat cttgtcttct actgagattt gcagatgata 60
cctacacaga aagctatatt agtaccattg gcgtagattt taaaatcagg acaatcgatt 120
tagatggaaa gacaattaaa ttgcaaattt gggatacagc aggtcaggaa aggtttagaa 180
cgattacatc aagttattac cgaggagcac atggtattat tgtagtgtac gattgcacag 240
accaagattc attcaataac gttaaacagt ggctcgaaga aatcgaccgt tatgcgtgtg 300
acaatgtaaa caaattactg gtagggaata aaagcgattt gacaactaag aaagttgtcg 360
acttcactac agccaaggag tatgccgacc aattgggtat accatttttg gaaacctcag 420
ctaagaatgc aaccaatgta gaacaggcct ttatgactat ggccgctgaa ataaaaaata 480
gagtaggacc tccatcttct gcggtagacc aaggaaataa ggttaggttc gatcaaagtc 540
gcccagtcga aacaaccaaa tccg 564

<210> SEQ ID NO 22
<211> LENGTH: 502
<212> TYPE: DNA
<213> ORGANISM: Diabrotica virgifera

<400> SEQUENCE: 22
gagctatagt ggactgcggg ttcgaacatc cttcagaagt tcaacatgaa tgtattcctc 60
aagctgtcat tggcatggat attctgtgcc aagctaaatc cggtatggga aaaacggctg 120
tttttgtatt agctacactc caagtaatag atcctacaga aaatgttgta tatgttctcg 180
tcatgtgcca taccagagag ttagccttcc agataagcaa agagtacgaa cgtttcagta 240
aatatatgcc caatattaaa gtaggggtct tctttggtgg cttgcctatc cagaaagatg 300
aggaaacgtt aaaaaataat tgcccgcata tcgttgtggg tactccagga agaattttag 360
cattggtcag atcgaaaaaa cttaatctca aacatctaaa gcattttatt ttggatgaat 420
gtgataaaat gttggagtta ttagacatga gacgtgatgt tcaagaaata tatcgtaaca 480
ctccccacga aaaacaagtc at 502

<210> SEQ ID NO 23
<211> LENGTH: 505
<212> TYPE: DNA
<213> ORGANISM: Diabrotica virgifera

<400> SEQUENCE: 23
tggtagattt ggctaacctc gtatattggt gtttaggtct taatattccg tacgttagtt 60
tctatgatta taaaggtaat ttaaaaaagc atgaagagaa gttgcaacaa attgtagaat 120
ccagaaaatc agagaatatc aacataattt ggcacaccca tgcagaacaa aggcataaaa 180
atggattttt gggtccaaaa atccacgtaa aagtgttaac acacgcggac ggaaagcaaa 240
gtatagtaaa tgttactaaa aaattagctc taaataaaga aaaagacatt agtaaagaaa 300
aaattagtga attactatta aggcagtatg aatttccaga tccagaaatg gctattattt 360
gtggaaagaa actgaacatt tataattatc ctccttggca gttaagactc acagaattct 420
ttaaagtcaa caaagtcaac aacatcacat tcccagtgtt tgtggaaaaa ttggaaaagt 480
acagcaaatg tgaacagagg gtggg 505

<210> SEQ ID NO 24
<211> LENGTH: 410
<212> TYPE: DNA
<213> ORGANISM: Diabrotica virgifera

<400> SEQUENCE: 24
aaccagggat ctatttgccc gcaagtttaa aaaacgtggt gtaattccac tttccacata 60
tttgagagtc tacaaagttg gagatattgt agatatcaag ggtaatggtg cagttcaaaa 120
gggtatgccc cacaaagtgt accatggtaa gacaggacgt gttttcaatg ttactgcaca 180
tgcattaggt gtaattgtaa acaaaagggt tcgaggaaga atcatcccca aaagaatcaa 240
tctccgtatt gaacatgtaa accactccaa gtgtcgtcaa gacttcttgc aaagagtaaa 300
atccaacgaa aagctacgta aagaagctaa agaaaagaac attaaagtag aacttaggag 360
acaacctgcc caacctaggc cagcacatat tgttagcgga aaggttccag 410

<210> SEQ ID NO 25
<211> LENGTH: 467
<212> TYPE: DNA
<213> ORGANISM: Diabrotica virgifera

<400> SEQUENCE: 25
tgatggtaat agagtgctgg ctaaatacta cgataaagat atatttccta cagcaaaaga 60
gcagaaagct tttgagaaaa atttgttcaa taaaactcat agggcagacg cagaaattat 120
catgttggat ggtttaactt gtgtgtatag aagtaatgta gatttattct tttatgttat 180
gggcagttca catgaaaatg agctaatttt aatgagtgtt ttaaattgct tgtatgactc 240
agtaagtcaa atattgaaga aaaatatgca aaaacgagct gtcttggaat cactagatat 300
tgttatgctg gctatggatg aaattgttga tggaggaata attatagatt ctgattcaag 360
ttcagtagta tctagaatag cattaaggac tgatgatatt ccattaggag aacaaactgt 420
agctcaggta ttccaaacgg ccaaagaaca gctgaaatgg tcattgc 467

<210> SEQ ID NO 26
<211> LENGTH: 368
<212> TYPE: DNA
<213> ORGANISM: Diabrotica virgifera

<400> SEQUENCE: 26
caccgaagaa caaattgctg aattcaaaga agctttctca ctattcgata aagatggtga 60
tggtacaatt acgactaaag aattaggaac agtaatgaga tctctaggac aaaatccaac 120
agaggctgaa ttacaggata tgatcaatga agtagatgcc gatggtaacg gcacgatcga 180
tttcccagaa tttttaacga tgatggcacg taaaatgaaa gataccgata gtgaggaaga 240
aattcgtgaa gcattccgag tgttcgacaa agacggcaat ggtttcatct cagcagcaga 300
attgcgccac gtcatgacca acttgggtga aaaattgaca gacgaagaag tcgatgaaat 360
gattcggg 368

<210> SEQ ID NO 27
<211> LENGTH: 430
<212> TYPE: DNA
<213> ORGANISM: Diabrotica virgifera

<400> SEQUENCE: 27
ttcgcacaag atgactttgg tggtgaaaat gttgatctat atgacgatgt aatatccgct 60
cctcctggaa ataatgacaa cccaggtgat tcaaatcatc atgctcctcc tggtgctggt 120
gaagatggtg gaggtaattt tgttgggtca ggaggagcac ccaataatat aaattcttct 180
ggaagaagac atcagctgta tgttggaaat ctgacttggt ggacaactga tcaagatata 240
gaaaatgcag tgcatgatat aggggtaacc gacttccatg aagttaagtt ttttgaacac 300

```
agagcaaatg gtcaatccaa gggattctgt gtcatatctt tgggatctga gggaagcatg    360

agactctgcc tggaactcct atctaaaaaa gagatcaatg gccaaaatcc ccttgttacc    420

cttcccacaa                                                           430
```

<210> SEQ ID NO 28
<211> LENGTH: 505
<212> TYPE: DNA
<213> ORGANISM: Diabrotica virgifera

<400> SEQUENCE: 28

```
taggaatggc attttcaggc ttaatagctg atgcaaggca aatcgttgag attgctagaa     60

aagaagcatc aaattataga catcaatatg gttcaaatat tcctcttaaa tacctaaatg    120

atagagtaag catgtacatg catgcataca ctttatacag tgctgttaga ccatttggtt    180

gcagtgtcat cttggccagt tatgaagata gtgacccatc tatgtatctg attgatccat    240

ctggagttag ctatggatac tttggatgtg ctacaggtaa agcaaaacag tctgcaaaga    300

ctgaaataga aaaattgaag atggggaatc taacatgcaa agaacttgtt aaagaagcag    360

ccaaaatcat ttatttggtc catgatgagc tgaaggataa gaattttgaa ctggaacttt    420

catgggtatg caaagatacg aatggtttac ataccaaagt gcctgaatca gtgtttgctg    480

atgcagaaaa agctgccaaa caagc                                          505
```

<210> SEQ ID NO 29
<211> LENGTH: 548
<212> TYPE: DNA
<213> ORGANISM: Diabrotica virgifera

<400> SEQUENCE: 29

```
tccatctaga ggagcccaaa tgatgatgaa atccaggcta aagggagccc aaaagggaca     60

tagtttatta aagaagaaag ctgatgcttt acaaatgaga tttagaatga ttttgaacaa    120

aattattgag accaaaactc tcatgggtga agtaatgaaa gaagctgcct tttctttagc    180

tgaagcaaag tttgcaactg gtgacttcaa tcaagttgtt cttcaaaatg tcaccaaggc    240

tcaaataaaa ataagaacta agaaagacaa cgttgctggt gttactttac cagtgtttga    300

atgctaccaa gatggtacag atacatatga gttggctggt ttggctaggg gaggtcaaca    360

attgacaaaa ctcaagaaga attatcaaag tgctgttaaa ctgttggttg aattagcctc    420

tttgcaaact tcttttgtaa ctcttgatga tgtaatcaaa ataacaaaca gaagagtcaa    480

tgccattgaa catgttatca ttccaagaat agagcgtact ttggcttaca tcatatccga    540

actggacg                                                             548
```

<210> SEQ ID NO 30
<211> LENGTH: 521
<212> TYPE: DNA
<213> ORGANISM: Diabrotica virgifera

<400> SEQUENCE: 30

```
gatctggaag cgctagttgc aaaagtagac gaaatgagaa cccaaagagc catgctatgg     60

gctcaacttc gagaatctat tcaccaagac gatattacaa gttcccttgt aacgaaacaa    120

ccaaatcagt cgctggaaca gctgttccag caagaacttc aaaagcatca aaatctgatt    180

tcgttgattg aacaaaacac ctcggcacaa gaaaacatta agagcgcctt agtcgattct    240

tacgcttacg ctgtaaattc aagaaaatac atccaagata tactccaaaa gagaaccaca    300

accataacgt cactgatagc atcgttcgac tcttacgaag acttattggc aaaagctaac    360
```

aaagggatag agttttactc aaaacttgaa acgaacgtat ccaagttact gcaaagaata 420
aggagtacct gcaaagttca acaagaagag cgagatcaga tgatgtcgac tgcgcaagtg 480
cctcaatggg agagtcatac gtcacttgcc gctcctaaac t 521

<210> SEQ ID NO 31
<211> LENGTH: 20
<212> TYPE: DNA
<213> ORGANISM: Diabrotica virgifera

<400> SEQUENCE: 31
ggtttcatga cccctgagag 20

<210> SEQ ID NO 32
<211> LENGTH: 20
<212> TYPE: DNA
<213> ORGANISM: Diabrotica virgifera

<400> SEQUENCE: 32
cgtctccctt ctttgaccag 20

<210> SEQ ID NO 33
<211> LENGTH: 20
<212> TYPE: DNA
<213> ORGANISM: Diabrotica virgifera

<400> SEQUENCE: 33
agaagttgcc gctttagtcg 20

<210> SEQ ID NO 34
<211> LENGTH: 20
<212> TYPE: DNA
<213> ORGANISM: Diabrotica virgifera

<400> SEQUENCE: 34
gtccaaacga aggattgcat 20

<210> SEQ ID NO 35
<211> LENGTH: 20
<212> TYPE: DNA
<213> ORGANISM: Diabrotica virgifera

<400> SEQUENCE: 35
accggccttt gtatgtcttg 20

<210> SEQ ID NO 36
<211> LENGTH: 20
<212> TYPE: DNA
<213> ORGANISM: Diabrotica virgifera

<400> SEQUENCE: 36
gcagcttctg gcaatctacc 20

<210> SEQ ID NO 37
<211> LENGTH: 20
<212> TYPE: DNA
<213> ORGANISM: Diabrotica virgifera

<400> SEQUENCE: 37
gaaagcagtt ggaagatggc 20

<210> SEQ ID NO 38

<211> LENGTH: 20
<212> TYPE: DNA
<213> ORGANISM: Diabrotica virgifera

<400> SEQUENCE: 38
cctcgagggt gatggtctta 20

<210> SEQ ID NO 39
<211> LENGTH: 20
<212> TYPE: DNA
<213> ORGANISM: Diabrotica virgifera

<400> SEQUENCE: 39
taccccattg aacacggaat 20

<210> SEQ ID NO 40
<211> LENGTH: 20
<212> TYPE: DNA
<213> ORGANISM: Diabrotica virgifera

<400> SEQUENCE: 40
caatggtgat gacttgaccg 20

<210> SEQ ID NO 41
<211> LENGTH: 20
<212> TYPE: DNA
<213> ORGANISM: Diabrotica virgifera

<400> SEQUENCE: 41
aggaaaggaa ggacccaaga 20

<210> SEQ ID NO 42
<211> LENGTH: 20
<212> TYPE: DNA
<213> ORGANISM: Diabrotica virgifera

<400> SEQUENCE: 42
gtgcttgata cagcggacaa 20

<210> SEQ ID NO 43
<211> LENGTH: 20
<212> TYPE: DNA
<213> ORGANISM: Diabrotica virgifera

<400> SEQUENCE: 43
tactaggcga aagtgccgtc 20

<210> SEQ ID NO 44
<211> LENGTH: 20
<212> TYPE: DNA
<213> ORGANISM: Diabrotica virgifera

<400> SEQUENCE: 44
gccttgacct gtggtttgtt 20

<210> SEQ ID NO 45
<211> LENGTH: 20
<212> TYPE: DNA
<213> ORGANISM: Diabrotica virgifera

<400> SEQUENCE: 45
cgatgaggtt gaaggaagga 20

<210> SEQ ID NO 46
<211> LENGTH: 20
<212> TYPE: DNA
<213> ORGANISM: Diabrotica virgifera

<400> SEQUENCE: 46
tatgatgccg ttacaggtgc 20

<210> SEQ ID NO 47
<211> LENGTH: 20
<212> TYPE: DNA
<213> ORGANISM: Diabrotica virgifera

<400> SEQUENCE: 47
tgaggtcgag ccctcagata 20

<210> SEQ ID NO 48
<211> LENGTH: 20
<212> TYPE: DNA
<213> ORGANISM: Diabrotica virgifera

<400> SEQUENCE: 48
taaccgcact tgccacagta 20

<210> SEQ ID NO 49
<211> LENGTH: 20
<212> TYPE: DNA
<213> ORGANISM: Diabrotica virgifera

<400> SEQUENCE: 49
tctttgcctt tggctacgat 20

<210> SEQ ID NO 50
<211> LENGTH: 20
<212> TYPE: DNA
<213> ORGANISM: Diabrotica virgifera

<400> SEQUENCE: 50
tcgccatagc taaacctgct 20

<210> SEQ ID NO 51
<211> LENGTH: 21
<212> TYPE: DNA
<213> ORGANISM: Diabrotica virgifera

<400> SEQUENCE: 51
tcgtgctggt ttacaatttc c 21

<210> SEQ ID NO 52
<211> LENGTH: 20
<212> TYPE: DNA
<213> ORGANISM: Diabrotica virgifera

<400> SEQUENCE: 52
aatactccac cttgggcgat 20

<210> SEQ ID NO 53
<211> LENGTH: 20
<212> TYPE: DNA
<213> ORGANISM: Diabrotica virgifera

<400> SEQUENCE: 53
gtgcatgaag ttggatggtg 20

<210> SEQ ID NO 54
<211> LENGTH: 20
<212> TYPE: DNA
<213> ORGANISM: Diabrotica virgifera

<400> SEQUENCE: 54
atgcaaaaac ctgatccagc 20

<210> SEQ ID NO 55
<211> LENGTH: 20
<212> TYPE: DNA
<213> ORGANISM: Diabrotica virgifera

<400> SEQUENCE: 55
gattcggagc cctacaatga 20

<210> SEQ ID NO 56
<211> LENGTH: 20
<212> TYPE: DNA
<213> ORGANISM: Diabrotica virgifera

<400> SEQUENCE: 56
caaatacgac aacgcccttt 20

<210> SEQ ID NO 57
<211> LENGTH: 20
<212> TYPE: DNA
<213> ORGANISM: Diabrotica virgifera

<400> SEQUENCE: 57
ttggcaaaaa ggaaatgagg 20

<210> SEQ ID NO 58
<211> LENGTH: 20
<212> TYPE: DNA
<213> ORGANISM: Diabrotica virgifera

<400> SEQUENCE: 58
accatctccg ctagttgcac 20

<210> SEQ ID NO 59
<211> LENGTH: 20
<212> TYPE: DNA
<213> ORGANISM: Diabrotica virgifera

<400> SEQUENCE: 59
ggtcgcgaaa gaacagaaag 20

<210> SEQ ID NO 60
<211> LENGTH: 20
<212> TYPE: DNA
<213> ORGANISM: Diabrotica virgifera

<400> SEQUENCE: 60
tacacgtccg atttccatga 20

<210> SEQ ID NO 61
<211> LENGTH: 20
<212> TYPE: DNA
<213> ORGANISM: Diabrotica virgifera

<400> SEQUENCE: 61
gcatggggta tcatccagtt 20

<210> SEQ ID NO 62
<211> LENGTH: 20
<212> TYPE: DNA
<213> ORGANISM: Diabrotica virgifera

<400> SEQUENCE: 62
cccagaattg gtgagctgat 20

<210> SEQ ID NO 63
<211> LENGTH: 20
<212> TYPE: DNA
<213> ORGANISM: Diabrotica virgifera

<400> SEQUENCE: 63
tagatgccgc aggtaaaacc 20

<210> SEQ ID NO 64
<211> LENGTH: 20
<212> TYPE: DNA
<213> ORGANISM: Diabrotica virgifera

<400> SEQUENCE: 64
ccaattcatt cgacaaccaa 20

<210> SEQ ID NO 65
<211> LENGTH: 20
<212> TYPE: DNA
<213> ORGANISM: Diabrotica virgifera

<400> SEQUENCE: 65
gctaccctag cgtccactgt 20

<210> SEQ ID NO 66
<211> LENGTH: 20
<212> TYPE: DNA
<213> ORGANISM: Diabrotica virgifera

<400> SEQUENCE: 66
ccaatggcac ttccaaaaat 20

<210> SEQ ID NO 67
<211> LENGTH: 20
<212> TYPE: DNA
<213> ORGANISM: Diabrotica virgifera

<400> SEQUENCE: 67
accttatggg aaagcgtgtg 20

<210> SEQ ID NO 68
<211> LENGTH: 20
<212> TYPE: DNA
<213> ORGANISM: Diabrotica virgifera

<400> SEQUENCE: 68
atgacgggtt ggttagcttg 20

<210> SEQ ID NO 69
<211> LENGTH: 20
<212> TYPE: DNA
<213> ORGANISM: Diabrotica virgifera

<400> SEQUENCE: 69
cggatctcta tttgggggat 20

<210> SEQ ID NO 70
<211> LENGTH: 20
<212> TYPE: DNA
<213> ORGANISM: Diabrotica virgifera

<400> SEQUENCE: 70
acacaaaggt gacaaagggc 20

<210> SEQ ID NO 71
<211> LENGTH: 21
<212> TYPE: DNA
<213> ORGANISM: Diabrotica virgifera

<400> SEQUENCE: 71
tgctgattgg agattcagga g 21

<210> SEQ ID NO 72
<211> LENGTH: 20
<212> TYPE: DNA
<213> ORGANISM: Diabrotica virgifera

<400> SEQUENCE: 72
cggatttggt tgtttcgact 20

<210> SEQ ID NO 73
<211> LENGTH: 20
<212> TYPE: DNA
<213> ORGANISM: Diabrotica virgifera

<400> SEQUENCE: 73
gagctatagt ggactgcggg 20

<210> SEQ ID NO 74
<211> LENGTH: 20
<212> TYPE: DNA
<213> ORGANISM: Diabrotica virgifera

<400> SEQUENCE: 74
atgacttgtt tttcgtgggg 20

<210> SEQ ID NO 75
<211> LENGTH: 21
<212> TYPE: DNA
<213> ORGANISM: Diabrotica virgifera

<400> SEQUENCE: 75
tggtagattt ggctaacctc g 21

<210> SEQ ID NO 76
<211> LENGTH: 20
<212> TYPE: DNA
<213> ORGANISM: Diabrotica virgifera

<400> SEQUENCE: 76
cccaccctct gttcacattt 20

<210> SEQ ID NO 77
<211> LENGTH: 20
<212> TYPE: DNA
<213> ORGANISM: Diabrotica virgifera

<400> SEQUENCE: 77
aaccagggat ctatttgccc 20

<210> SEQ ID NO 78
<211> LENGTH: 20
<212> TYPE: DNA
<213> ORGANISM: Diabrotica virgifera

<400> SEQUENCE: 78
ctggaacctt tccgctaaca 20

<210> SEQ ID NO 79
<211> LENGTH: 22
<212> TYPE: DNA
<213> ORGANISM: Diabrotica virgifera

<400> SEQUENCE: 79
tgatggtaat agagtgctgg ct 22

<210> SEQ ID NO 80
<211> LENGTH: 21
<212> TYPE: DNA
<213> ORGANISM: Diabrotica virgifera

<400> SEQUENCE: 80
gcaatgacca tttcagctgt t 21

<210> SEQ ID NO 81
<211> LENGTH: 20
<212> TYPE: DNA
<213> ORGANISM: Diabrotica virgifera

<400> SEQUENCE: 81
caccgaagaa caaattgctg 20

<210> SEQ ID NO 82
<211> LENGTH: 20
<212> TYPE: DNA
<213> ORGANISM: Diabrotica virgifera

<400> SEQUENCE: 82
cccgaatcat ttcatcgact 20

<210> SEQ ID NO 83
<211> LENGTH: 20
<212> TYPE: DNA
<213> ORGANISM: Diabrotica virgifera

<400> SEQUENCE: 83
ttcgcacaag atgactttgg 20

<210> SEQ ID NO 84
<211> LENGTH: 20
<212> TYPE: DNA
<213> ORGANISM: Diabrotica virgifera

<400> SEQUENCE: 84
ttgtgggaag ggtaacaagg 20

<210> SEQ ID NO 85
<211> LENGTH: 20
<212> TYPE: DNA
<213> ORGANISM: Diabrotica virgifera

<400> SEQUENCE: 85
taggaatggc attttcaggc 20

<210> SEQ ID NO 86
<211> LENGTH: 20
<212> TYPE: DNA
<213> ORGANISM: Diabrotica virgifera

<400> SEQUENCE: 86
gcttgtttgg cagctttttc 20

<210> SEQ ID NO 87
<211> LENGTH: 20
<212> TYPE: DNA
<213> ORGANISM: Diabrotica virgifera

<400> SEQUENCE: 87
tccatctaga ggagcccaaa 20

<210> SEQ ID NO 88
<211> LENGTH: 20
<212> TYPE: DNA
<213> ORGANISM: Diabrotica virgifera

<400> SEQUENCE: 88
cgtccagttc ggatatgatg 20

<210> SEQ ID NO 89
<211> LENGTH: 20
<212> TYPE: DNA
<213> ORGANISM: Diabrotica virgifera

<400> SEQUENCE: 89
gatctggaag cgctagttgc 20

<210> SEQ ID NO 90
<211> LENGTH: 20
<212> TYPE: DNA
<213> ORGANISM: Diabrotica virgifera

<400> SEQUENCE: 90
agtttaggag cggcaagtga 20

<210> SEQ ID NO 91
<211> LENGTH: 633
<212> TYPE: DNA
<213> ORGANISM: Diabrotica virgifera

<400> SEQUENCE: 91
atggcggacg atgagagaaa gaaactggag gaggaaaaga agaggaaaca ggccgaaatt 60
gaacgcaaaa gggccgaggt cagggctcgt atggaagagg cctcaaaagc caagaaggcc 120
aagaaaggtt tcatgacccc tgagagaaag aagaaactta ggttactgtt gagaaagaaa 180
gccgccgaag aattaaagaa agaacaagaa cgcaaagcag ccgaaaggag gcgtatcatt 240
gaagaaaggt gcggtaaacc caaacttgtc gatgacgcaa atgaaggccc attaaaacaa 300
gtatgtgagg gatatcacag acgtattgta gacctagaaa ataagaaatt tgacctcgaa 360
aaagaagtgg aattcagaga ttttcagatc tccgaattga acagccaagt aaacgacctt 420
agaggcaaat tcgtcaaacc aaccttgaag aaggtatcca aatacgaaaa caaattcgcc 480
aaacttcaaa agaaggcagc tgaatttaac ttccgtaacc aactcaaagt tgtcaagaag 540

```
aaagaattca ccttagaaga agaagacaaa gaaaagaaac cagactggtc aaagaaggga    600

gacgaaaaga aggtacaaga ggctgaagca tga                                 633
```

<210> SEQ ID NO 92
<211> LENGTH: 603
<212> TYPE: DNA
<213> ORGANISM: Diabrotica virgifera

<400> SEQUENCE: 92

```
atgtgtgaag aagaagttgc cgctttagtc gtagacaatg gatccggtat gtgcaaagct     60

ggttttgctg ggatgatgc acctcgtgct gtattccctt caattgttgg acgcccaaga    120

catcagggtg tgatggtagg aatgggacaa aaagattcct atgtaggtga tgaagctcaa    180

agtaaaagag gtatccttac cttaaaatac cccatcgagc acggaatagt cacaaactgg    240

gatgatatgg agaaaatttg gcatcataca ttctacaatg aactcagagt agccccagaa    300

gaacaccctg ttctgttgac agaagctcct ctcaacccca aggccaacag ggaaaagatg    360

acacaaataa tgtttgaaac tttcaacacc ccagccatgt atgttgccat ccaggctgta    420

ctctccttgt atgcatctgg tcgtacaact ggtattgtgt tggattctgg tgatggtgta    480

tcccacactg tcccaatcta tgaaggttat gctcttcctc atgcaatcct tcgtttggac    540

ttagctggta gagacttgac tgattacctc atgaaaattt tgactgaacg tggctactct    600

ttc                                                                  603
```

<210> SEQ ID NO 93
<211> LENGTH: 2742
<212> TYPE: DNA
<213> ORGANISM: Diabrotica virgifera

<400> SEQUENCE: 93

```
atgccacttc gattagatat aaaaagaaag ctaacagctc gctcagaccg ggtaaaatgt     60

gtggatcttc accctacaga accttggatg ctgtgttctc tttacagcgg aaatataaac    120

gtttggaaca ccgaaaatca gcaactggtt aagacttttg aagtatgtga tgtacctgtt    180

cggacagcta agtttttgcc caggaagaac tggatagtca gtgggtctga tgatatgcag    240

attcgagttt tcaattacaa taccttagat cgggtacatt cttttgaggc tcattcggat    300

tatgtgagat gtattgtcgt acaccctaca caaccttata tattaacaag tagtgatgat    360

atgcttatca agctttggaa ttgggaaaaa gcatgggctt gtcagcaagt tttcgaagga    420

cacactcatt atattatgca aatcgccata aatccaaaag acaacaacac atttgccagt    480

gcatccctag atagaacatt gaaagtatgg caattgggag cgtccacagc gaatttcaca    540

ctagaaggtc atgagaaagg cgttaactgt gtggactatt atcacggtgg agataaacct    600

tatttaatct caggcgctga tgatagatta gtaaaaatct gggattatca aaacaaaact    660

tgtgttcaaa ctttggaagg acatgctcaa aatgtaaccg ctgcatgttt ccatccagaa    720

cttcctgtag ctcttactgg aagtgaagat ggtactgtca gagtgtggca tgccaacacc    780

cataggttag aaagtagctt aaattatggc tttgaaagag tatggactat tttctgccta    840

aagggatcca ataacgtggc attgggttat gatgaaggta gcattttggt taaagttggt    900

agagaagaac cagctgttag tatggatgcc agtggaggca aaattatttg ggccagacac    960

tctgaacttc aacaggcaaa tctcaaggcg ttagctgaag gtgcggaaat aagagatgga   1020

gaacgccttc cagtttctgt aaaagatatg ggtgcttgcg agatataccc tcagacaatt   1080
```

```
caacacaatc ccaatggccg ttttgttgtt gtctgtgggg atggagaata cataatctac   1140
acagcaatgg ctttaagaaa caaagcgttt ggtagcgcac aagaatttgt gtgggctcaa   1200
gattccagcg aatatgccat cagagaatcc ggatctacta tcagaatttt taagaatttc   1260
aaagagaaga agaattttaa gtccgatttt ggagctgaag gtatatacgg tggatacctt   1320
ttgggagtca aatcggtttc tggtttgact ttctatgatt gggaaactct cgatttagtc   1380
agaagaatcg agatacaacc aaaagcagtt tactggtcag atagtggtaa attagtatgt   1440
ttggccacag aagatagcta ctttattctt tcttatgatt ctgatgaagt tcaaaaagcc   1500
agagataaca atcaggttgc ggatgatgga gtagaatcgg ctttcaatct tctaggtgaa   1560
ataaacgaat cagtgcgaac tggtctctgg gtaggcgact gttttatcta cacgaattct   1620
gttaatcgta tcaactactt cgttggaggt gaactggtta caattgctca tttggaccgg   1680
cctttgtatg tcttgggata tgtgcctaaa gacgatagat tatacctcgt agataaagag   1740
ttgcgcgtag taagctacca attacttctt tctgttcttg aatatcaaac tgccgtcatg   1800
agaagagact ttccaacagc agacagagta cttccgtcca ttcctaagga gcacagaacg   1860
agagtggcac atttcttaga aaagcaaggc ttcaaacagc aagctttggc cgtaagtaca   1920
gatccagagc acagattcga gctggcagta gcattagagg atcttaatat agccaaaact   1980
ctagctcaag aagcgaacag tccgcaaaag tggaatcaac tagcagaatt ggcagctgct   2040
actaataatg taagcgtagc caaggaatgt atgcaaaaag cgcaagatta tggaggcttg   2100
ttgcttcttg ctacgagctc cggtgatgaa aatttagtcc gtactctagg agaaacgaca   2160
caagctgaaa gcaaacataa cttagcattt ttgtcacact tgttagtagg tgatttaaac   2220
aaatgtctag acattcttat taataccggt agattgccag aagctgcatt tttcgccaga   2280
tcttaccttc ctgataagat tacagaagtc gtggaactgt ggaagactca gttatcttca   2340
gtcaatcaaa aagctggaca gagccttgcc gatcctaaaa actacgaaaa tctgttccct   2400
ggtttacaag aggcggtggt agctcagaaa tttttggaac agcagaataa aggtttagcg   2460
cccgcaagag ttgccaccac cattcctcct aatcacgaca ggaatgttgt agccgaagtt   2520
caagcacaat cgaaacacga tgtaccatca tttagttctt cgtttatttc atcagaaata   2580
gaagcacaaa caaggagttc tgctaaacct gaagaatctt caaacattat acagctggac   2640
caagatgacg acgatatcga tttagatttg gacggtgtaa atatcgatga gaacattgac   2700
acgacggata tcaacatcga tgatgatttg ctgagtgatt ga                      2742
```

<210> SEQ ID NO 94
<211> LENGTH: 1146
<212> TYPE: DNA
<213> ORGANISM: Diabrotica virgifera

<400> SEQUENCE: 94

```
atgcagatct ttgtaaaaac actcactggt aaaaccatca ccctcgaggt tgaaccatca     60
gataccatcg agaatgtcaa agctaaaatt caagacaaag aaggtattcc accagatcaa    120
cagagattaa tctttgctgg aaagcagtta gaagatggcc gtactctctc agactacaac    180
attcagaaag aatctacact acacttagtg cttcgtctta gaggaggtat gcacatcttt    240
gtaaaaactc tcactggtaa gaccatcacc cttgaggttg aaccatcaga taccatcgag    300
aatgtcaaag ctaaaattca agacaaagaa ggtattccac cagatcaaca gagattaatc    360
tttgctggaa agcagttgga agatggccgt actctctcag actacaacat tcaaaaagag    420
tctaccctcc atttggtact tcgtcttaga ggaggtatgc agatttttgt taaaacttta    480
```

```
actggaaaga ccatcaccct tgaagtagaa ccttctgata ccatcgaaaa tgtcaaagcc    540

aaaattcaag acaaagaagg tattccacca gatcaacaaa gattaatctt tgccggaaag    600

caattggaag atggtcgtac actctcagac tacaacattc aaaaggaatc taccctccat    660

ttggtacttc gtcttagagg aggtatgcaa atctttgtaa aaacactcac tggtaagacc    720

atcaccctcg aggttgaacc atcagatacc atcgagaatg tcaaagctaa aattcaagac    780

aaagaaggta ttccaccaga tcaacagaga ttaatcttcg ctggaaagca gttggaagat    840

ggccgtactc tctcagacta caatattcag aaagagtcta ccctccattt ggtacttcgt    900

cttagaggag gtatgcaaat ctttgtaaaa actctcactg gtaagaccat caccctcgag    960

gttgaaccat cagataccat cgagaatgtc aaagctaaaa ttcaagacaa agaaggtatt   1020

ccaccagatc aacaaagatt aatctttgcc ggaaagcagt tggaagatgg ccgtactctc   1080

tcagactaca acattcaaaa agagtctacc cttcacttgg tacttcgttt aagaggagga   1140

aattaa                                                              1146
```

<210> SEQ ID NO 95
<211> LENGTH: 1131
<212> TYPE: DNA
<213> ORGANISM: Diabrotica virgifera

<400> SEQUENCE: 95

```
atgtgtgacg acgatgtagc ggctcttgtc gtcgacaatg gctccggaat gtgcaaagcc     60

ggtttcgccg gtgatgacgc ccctcgtgct gtctttccat ccatcgtagg tcgtcccaga    120

caccaaggtg tcatggtggg tatgggtcaa aaagactcct acgtaggaga cgaagcccaa    180

agcaaaagag gtatcctcac cttaaaatac cccattgaac acggaattat cactaactgg    240

gacgatatgg aaaagatctg gcatcacacc ttctacaatg aacttagagt agcccccgaa    300

gaacatccca ttcttttgac tgaagctcca cttaacccaa aagccaacag agaaaagatg    360

actcaaatca tgtttgaaac tttcaatacc cctgccatgt atgttgccat tcaagctgta    420

ttgtctctgt acgcttccgg tcgtaccact ggtattgtac ttgattctgg agatggtgta    480

tcccacacag tacccatcta tgaaggttac gctctcccac acgccatctt gcgtttggac    540

ttggccggta gagacttgac tgactacctt atgaagatct taaccgaaag aggttactct    600

ttcaccacca cagctgaaag agaaatagtt cgtgacatca aggaaaaatt gtgctatgta    660

gctttggact tcgaacagga aatggccaca gcagccagct ccacctcctt agaaaagagt    720

tatgaacttc ctgacggtca agtcatcacc attggtaatg aaaggttccg ttgccctgaa    780

gctctcttcc aaccttcctt cttgggtatg gaatcttgcg gtatccacga aactgtctac    840

aactccatca tgaagtgcga tgtcgacatc cgtaaagact tgtacgccaa cactgtcctt    900

tctggaggta ccacaatgta ccctggtatt gccgatcgta tgcaaaagga aatcactgcc    960

ttggctccat caaccatcaa aatcaagatc atcgctcccc cagaaagaaa gtactccgtt   1020

tggatcggtg gctccatctt ggcctccctc tccaccttcc aacagatgtg gatctccaaa   1080

caagaatacg acgaatccgg ccctggaatt gttcaccgca aatgcttcta a            1131
```

<210> SEQ ID NO 96
<211> LENGTH: 2640
<212> TYPE: DNA
<213> ORGANISM: Diabrotica virgifera

<400> SEQUENCE: 96

-continued

```
atgggtactt ttaaaagaga tactcatgat gaggacgggg gatcaagtgc ttttcaaaat     60
ctggagaaaa ctactgtttt gcaggaagct agagttttta atgaaactag tgtaaatcca    120
agaaaatgta caccgatact aacaaaactg ttgtacttat tgaaccaggg tgaaacttta    180
agtgccaaag aggccacaga tgttttcttt gccatgacca aactgttcca atcaaaagat    240
gtaatattga gaaggatggt ttatttggga attaaagaac tcagttctgt tgctgatgat    300
gtcattattg taacatccag tcttacaaaa gatatgactg gtaaagaaga catgtacaga    360
gcagctgcta taagagcatt atgcagtatt actgatgcta ctatgcttca agctatagaa    420
cgttatatga agcaagctat tgtagataga aacgcagctg tcagttcagc agcactaatt    480
agttcattac atatgagcaa attagctcca gatgtagtaa aaagatgggt aaatgaagct    540
caggaagcag taaatagtga taatgcaatg gtacagtatc acgcattagg tcttctatac    600
catattagga agactgataa gctagcagtg acaaaattga tttccaagct gaattcaatg    660
ggtttaaaga gcccttatgc tttgtgtatg ttgataagaa tcactgcaaa acttttagaa    720
gaagaggacc aagagtcact cctcaactcc ccatatacaa taatatttac aatgggctta    780
aggaacaaat ctgaaatggt ggtgtatgaa gctgcacatg ccatggttaa cctgaagttc    840
acgagtagta atgtgctagc acccgctata agtgttctac aactattttg tggatctcct    900
aaagccacac tcagatttgc tgctgttaga actttaaatc aagtggccac cacccaccct    960
gcgtcagtga cagcttgtaa tttggatcta gaaaatttga ttactgatcc taataggtca   1020
attgctacac tggccattac tactcttttg aaaacaggtg ccgaatcttc tgttgacaga   1080
ctaatgaaac aaatcgctac ttttgtatct gaaatcagtg atgaatttaa agtggttgtc   1140
attcaggcaa ttaaggtatt agctttgaaa tttccaagga aacatagcac gcttatgaat   1200
ttcctatccg ccatgttaag agatgaggga ggtttagaat ataaagcatc catagcagat   1260
accattataa ccctaatcga agataatccc gaagctaaag aatctggttt ggcgcatctt   1320
tgcgagttca ttgaagactg tgaacatgtt tctttggctg tgagaatctt gcatttgtta   1380
ggaaaggaag gacccaagac caaacaacca tcgagataca tccgttttat ctacaatcgc   1440
gtcatattgg aatgtccttc tgtaagagct gctgcagtct ccgccatggc acaattcgga   1500
gcctcttgtc ccgatttgtt agaaaatatc caaatattac tttcgaggtg tcagatggat   1560
tcagacgatg aagttaggga cagagctaca tattatagta atatacttaa caaaaatgat   1620
aaaagtttat acaacaatta cattttggat tctttgcagg tttcaattcc ttcactagaa   1680
agatcgctta gagaatacat tcaaaatcca actgacgaac catttgacat taagtccgta   1740
cctgtagcag cagtgccaac agcagaagaa cgagaagtta aaaacaaatc tgaaggactg   1800
ctagtctctc aaggtccagt ccgacctcct ccggtgtcta gagaagaaaa cttcgccgaa   1860
aaacttagta acgttccggg tatacaacag ttaggacctt tgttcaaaac ttccgacgtc   1920
gttgaactca ctgaatctga aacagagtat tttgtccgct gtatcaagca ctgtttcaaa   1980
catcacatcg tcctccaatt cgattgtctg aataccttgc cagaccagct tttagaaaac   2040
gttagagtgg agatagacgc cggtgaaacc ttcgaaattt tggcagaaat accttgtgaa   2100
aagttgcact ataacgaaac cggtaccaca tatgtagtag ttaagttgcc tgatgatgat   2160
ctccccaact ctgttggtac gtgtggagcc gtgttgaagt tcttagtgaa agattgtgat   2220
ccatcaacgg gaataccaga ttctgatgag ggttacgatg atgaatatac actggaagac   2280
atcgaaataa cattagggga ccaaattcaa aaagtaagca aagtaaattg ggctgcagcc   2340
tgggaagaag ctgcagctac ttatgtagaa aaagaggata catactcctt gaccatcaat   2400
```

acgctaagtg gcgctgttaa gaatattatt cagttcttgg gattacagcc tgcggaaagg 2460
actgacagag taccggaggg taaatctacg cacacattac ttcttgctgg tgtattcagg 2520
ggaggtattg acatactagt aagagcgaaa ctagctttgg gcgaatgtgt tacgatgcaa 2580
ctaacagtca ggtcgccaga tcctgacgtt gctgagctta taacttcaac tgtaggttaa 2640

<210> SEQ ID NO 97
<211> LENGTH: 651
<212> TYPE: DNA
<213> ORGANISM: Diabrotica virgifera

<400> SEQUENCE: 97
atggcggcaa acagaactgg acctgctcag agaccaaatg gcgctaccca aggaaagata 60
tgtcagttca aactggtcct actaggcgaa agtgccgtcg gtaagtcgag tttggtactg 120
aggttcgtca aaggacagtt ccacgaatac caggagagta ccataggagc agctttcctt 180
acacaaacca tatgcctcga cgatacaact gttaaatttg aaatttggga cacagcgggt 240
caagaaaggt accacagttt agctcctatg tactataggg gcgcacaggc agctatagtc 300
gtctacgaca taaccaatca agacacattc ggcagggcga aaacgtgggt gaaggaactt 360
caaaggcagg ccagtccgac gatcgtgata gctttggccg gcaacaagca agatttggcc 420
aacaaacgta tggtagaata cgaagaggcg cagacgtatg ctgacgaaaa cggcttactt 480
tttatggaaa cttccgcaaa gacggcaatg aacgtcaacg atatattttt agcaatagct 540
aagaaactgc ccaagaatga acaaaccaca ggtcaaggcg gcagtgccca aggcaggcgg 600
ctagcggagg gcgattcggg cgccaaggca cccggaaatt gttgcaagtg a 651

<210> SEQ ID NO 98
<211> LENGTH: 279
<212> TYPE: DNA
<213> ORGANISM: Diabrotica virgifera

<400> SEQUENCE: 98
atgaagtttt taagatcgac agtgtgctac attgccatct tggcaattct ctttaccctc 60
tgtgccgatg aggttgaagg aaggagaaaa attttgatgg ggcgaaaaag cattaccagg 120
acatatcttc gtggaaatgc tgttcctgcg tatgtgataa taatccttgt aggaattggt 180
caaatcatcc tgggagggat attgtacgtt gcattgagga agaagatcat tgctgcacct 240
gtaacggcat catatgcagt ggctagacaa gaaccataa 279

<210> SEQ ID NO 99
<211> LENGTH: 474
<212> TYPE: DNA
<213> ORGANISM: Diabrotica virgifera

<400> SEQUENCE: 99
atgcagatct tcgttaaaac cttaacgggt aagaccatca ctcttgaggt cgagccctca 60
gatactatcg aaaatgtgaa agctaaaatc caggataaag aaggaattcc cccagaccag 120
caacgtctca tcttcgctgg aaaacaactc gaagatggtc gtaccttgtc tgactataat 180
attcaaaaag aatcaaccct tcacttggtg ttgagattga gaggaggtgc taagaaacgt 240
aagaagaaga attactccac ccccaagaaa atcaagcaca agaagaagaa ggttaagtta 300
gctgtattga aattttataa ggttgacgaa aatggtaaaa tccaccgatt gagacgtgaa 360
tgccccgctg aacaatgtgg agctggtgtc ttcatggcag ccatggaaga caggcattac 420
tgtggcaagt gcggttacac tcttgtcttc tccaaaccag gagatgagaa atag 474

<210> SEQ ID NO 100
<211> LENGTH: 747
<212> TYPE: DNA
<213> ORGANISM: Diabrotica virgifera

<400> SEQUENCE: 100
atgatgtcca aagcagacac acaggaagat gcctccttcg ccaaattgga aaatcagatt 60
gctatcatca aatacgtaat actctttacc aacgttttgc aatgggctct cggtgcagca 120
atcttcgctc tttgcctttg gctacgattc gaggagggca ttcaagaatg gctccagaaa 180
ttggattcag aacaatttta catcggagta tatgtactta tagtcgcttc actgatcgtc 240
atgattgtgt cctttatagg atgtattagt gccctgcagg agagtaccat ggccctttta 300
gtgtacatcg gcacccaagt gctcagtttt atattcggtt tatccggttc ggcggttctt 360
ctggataaca gcgccagaga ttcccacttc caaccgagga tccgagagag tatgcgacgt 420
cttatcatga atgctcatca cgaccaatcc agacaaacac tagccatgat tcaggaaaat 480
gttggttgct gcggagctga tggcgcaaca gactacctct ctcttcagca gccccttcca 540
agtcagtgca gagacaccgt tactggaaac ccattcttcc acggatgtgt agatgaactc 600
acctggttct tcgaagaaaa atgtggttgg atagcaggtt tagctatggc gatatgcatg 660
attaacgtcc ttagtattgt tttatctacg gtactcatcc aggcattgaa aaaagaagaa 720
gaagcatccg attcatacag gagatag 747

<210> SEQ ID NO 101
<211> LENGTH: 375
<212> TYPE: DNA
<213> ORGANISM: Diabrotica virgifera

<400> SEQUENCE: 101
atgtctggac gtggcaaggg aggcaaagta aagggaaaag caaagtcccg atcaaatcgt 60
gctggtttac aatttcctgt aggtcgtatt catcgtttat tgagaaaagg aaattatgcc 120
gaaagagttg gtgctggagc tcctgtatac ttggcagctg ttatggaata tttagctgct 180
gaagttttgg aattggcagg aaatgcagct agagataaca aaaagacccg tataattcct 240
agacatttac aattggccat aagaaatgac gaggaattga acaaattact gtcaggagtt 300
accatcgccc aaggtggagt attgcctaat atacaagcag tactgttacc taaaaaaact 360
gaaaagaaag cttaa 375

<210> SEQ ID NO 102
<211> LENGTH: 864
<212> TYPE: DNA
<213> ORGANISM: Diabrotica virgifera

<400> SEQUENCE: 102
atgaagttgg atggtgtaga tctgccccca ccaattagct tcgacattgc ggaagagcaa 60
ccgttaccac cttgccaaca gacgttctta tgtaatggtg atggaggatc catagtgcga 120
cagtttctcg agctgtattt cgtaatatat gattcagata ataggcagtc ccttcttcag 180
gcatatcacg aaaaagccac attttcaatg acaatggcct acccgtacgg ctattccaaa 240
gacagtaaag gagtatcgtg gttgaattgg tatgccaccg ataatagaaa tttattacga 300
gttcaagatc cagacagaag aaacaagttg ttaagacagg gacaagttgc tgtagtttcg 360
ttcttgcaag atatgccgca cacgaagcac gatattcaca gttttacagt agatttgaca 420

-continued

```
gtttttacac cccagatgtt atgtttgaca gtggctggta tgtttaaaga attgaaaagt    480

ggccacaaag tacctccttt aagatatttc ttcagaaccc ttgtaattgt acctgctgga    540

tcaggttttt gcatagcaaa tgaagaactt cacatatcca atgcaactcc ggaccaagca    600

aaagatgctt tcaagaccac cgttaatgta gctccggcac cagcccctgt gattacctct    660

cctggaccca gtataccaca acccgctgtg ccagatgatg ctacaaaaca agaaatggta    720

aaacagatgt ccgcagtatc cggaatgaat ctcgagtggt cgctacagtg tctcgaagaa    780

acacaatggg actaccagaa agccataatg gtattccaaa atttaaacgc acaaggtgtt    840

gtaccacaag cagcatttat taaa                                           864
```

<210> SEQ ID NO 103
<211> LENGTH: 2868
<212> TYPE: DNA
<213> ORGANISM: Diabrotica virgifera

<400> SEQUENCE: 103

```
atgactgcgg tagaacaacc ttgttacaca ctaataaact tgccaacaga ttcggagccc     60

tacaatgaaa tgcaactaaa aatggattta gaaaagggtg aggttaaagt aaaaaataaga   120

gcattagaaa aaataattca catgattctg gcaggagaaa ggttgccgaa tggatttcta    180

atgaccatca taagaaacgt tttaccttta caagatcatt tggcaaaaaa actattattg    240

attttctggg aaatagttcc aaaaacaaat ccagaaggta aactactaca agagatgatt    300

ttggtatgtg atgcctatag aaaagatctg caacacccaa atgaattttt gagaggttct    360

acacttcgct tcttgtgcaa actgaaggaa ccagaattgt tggaaccatt aatgcccagt    420

attagagctt gtttggatca taggcacagc tatgtgagga ggaatgctgt actggcaatt    480

tttaccattt acaaaaattt tgaagccctc attccagatg ctcctgaact gatctccaat    540

tatttggatg gtgagcaaga catgtcttgt aaaagaaatg cgtttttaat gcttcttcat    600

gctgaccaag aaagggcgtt gtcgtatttg gcatcatgtt tagatcaagt aaattcattt    660

ggagatattc tacaactggt catcgttgag ttgatatata aggtgtgtca ttccaatcct    720

gcggaaagat ctagatttat tagatgtata tataacttgt tgaactcaag cagtcctgct    780

gtcaggtacg aagctgcagg aactttagtc accctctcca gtgccccgac tgccgttaaa    840

gctgctgcta gctgttacat tgagttaatt atcaaagaaa gtgacaacaa tgtaaaactc    900

atcgttttgg acaggctgat agcacttaag gagcttccta atcacgaaag aattctgcag    960

gatttagtta tggacatact gagagtactc tctgctcctg acttagaagt ccgcaagaag   1020

actttaagtc tagcccttga attagtctct tcacggaaca tagaagaaat ggtattagta   1080

ttaacaaagg aagtgagtaa aacggtagac agtgaacatg aggatacagg aaagtacagg   1140

caattgttag taaggactct acattcgtgt tccattaagt tcccagatat cgcacgtagt   1200

gttataccag tcttgattga atttttatcc gataataatg aactggctgc cacagatgta   1260

ttgctgttct taagggaagc catacagaag tttaaagaat tgcaaccgtt aattattgag   1320

aaactcatcg aaactttcaa agacattaaa ttggtcaaag tccatagagc agcaatttgg   1380

attttgggag aatacgcgag tactgcttcc gatatagaag ttatcgttgg agaaattaac   1440

agattgttgg gtgaaggatc cctcgttgaa gctgagcaga agttaatagc aggagatacg   1500

gaagagaatg ctcctgcacc tgctgcaggc gccaccactt tagttacttc cgatggaaca   1560

tatgctaccc aatcagcttt caacactgtc agccaaacca ctaaagaagc acgacctcct   1620
```

ctaagacaat acctcatgga tggtgatttt ttcatcggag cctctttggc atctacatta 1680
accaaactgt ctttgcggta tgaggacctc acctctcctg ctgctagcaa tggattcaat 1740
gccaaaatta tgcttattat ggctggaatt cttcacttgg gaaaatcagg acttcccaca 1800
aaatcaataa ccaacgacga taaagaccac attctgttct gtttacgagt cctatctgat 1860
cgttctccaa tcattgttga aattttcaaa aaattgtgcc gctcggcact aaatgagatg 1920
cttctagcta aggaatcggt agaagcgatc tcgcaaaaga gcaaagaaaa aaacaagcgt 1980
acgattcaaa ctgacgacgc tataagcttc ctgcaattag agacagataa aagtggagag 2040
ctaggagaaa acgtattcga gatgtcgctg tcacaagctt tagtaggagg tcgaacggga 2100
ggtggcgaat cagtattaag ttccaataaa ttagataaaa tcacacaact gactggtttt 2160
tccgatccag tttattccga agcatacgtt cacgtgaatc agtacgatat cgtgcttgat 2220
gtcttaatcg taaaccaaac taacgatact ttacaaaact gcacgctaga gctggctact 2280
ttaggcgatt tgaagttggt agagaagcca caacctgtcg tattggcgcc caaagacttt 2340
tgcaacatta aagctaacgt gaaagtggcc tcaactgaaa acggaattat atttggcaac 2400
attgtgtatg atgtcatagg agcggggtca gataggaatg ttgtagtttt gaatgatata 2460
cacatagata taatggacta tatagtgcct gctagttgta cagatagcga gtttatgaga 2520
atgtgggcgg aatttgaatg ggaaaataag gtaaccgtta acacacccct cacggaactt 2580
tcagaatacc tcgaacatct actcaaaagc acaaatttga aatgtttaac atcagaaaaa 2640
gctctgagcg ggcagtgtgg ttttatggca gccaatttat atgcaaaatc catttttgga 2700
gaagacgctt tggccaactt aagtatagag aaacctttta ataaacccga tgcgccagta 2760
agcggtcata ttagaataag ggccaaaagt cagggcatgg ccttaagttt aggagacaaa 2820
gtcaatatga cacagaagag cacacaacat aaagtagtag ctgcataa 2868

<210> SEQ ID NO 104
<211> LENGTH: 549
<212> TYPE: DNA
<213> ORGANISM: Diabrotica virgifera

<400> SEQUENCE: 104
atgggtaatg tgtttgcaaa tttattcaaa ggcctctttg gcaaaaagga aatgaggata 60
ttgatggtag gactcgatgc agctggtaaa accacaattt tatataaact taaattagga 120
gaaattgtaa caactattcc aacaattgga tttaatgtgg agactgtaga atataagaac 180
attagtttta cagtatggga tgtaggtggt caagataaaa ttaggccatt gtggagacac 240
tatttccaaa acacacaagg cctaattttc gtagtagaca gtaacgacag ggaacgtatc 300
actgaggcta aagatgaatt aatgcgtatg ttggccgaag atgaacttag agatgccgta 360
cttctcattt tcgccaacaa acaagatttg cccaatgcaa tgaacgctgc agaaatcacc 420
gacaaactcg gtctccattc actacgcaac cgcaactggt acattcaagc tacctgtgca 480
actagcggag atggtctcta tgaaggtctg gactggttgt ccaatcaatt aaagaacgcc 540
aatcgctag 549

<210> SEQ ID NO 105
<211> LENGTH: 4425
<212> TYPE: DNA
<213> ORGANISM: Diabrotica virgifera

<400> SEQUENCE: 105
atgggacggt tgcactgttt attttgtatt ttcctatgtt ttaccgtcat caacacgcag 60

```
acaacgaata tacatggatt ctcggaaaat tccgtggata catttctatc acctcatggg    120
aaaagtgcaa aattcgtgca ccaaaatcac aaacccaaaa ttgaaaattg tcagaactac    180
aaaccctcgg tgaaagaaga acagccaggc ggaacgtacg taacaacggt taccgctatc    240
gatgacgatc ctagggaggg aggaggaaca attagttaca aactaattca tagagaagga    300
gaacatgttt tatttgacat agacaacgtt actggtgttt tgacaactat ccagccattt    360
gatcgggatg aaccagtaag gcagaaggaa ctttatgtaa ccgtacaagc ttcagacaac    420
ggcaggccac cattagcaga tgtctgtaca tttacagtta ccattaccga cattaatgat    480
aatgcgccac agcttgataa actgaaatac gatgcacaag tttctgaaga tttaaaagta    540
ggaagtgaag tgatgagagt tttgcttac gacattgatg atggggaaaa ttcaagatta    600
tcgtataact tttcaaacga aaatgctcaa ttcacccagt atttcaggat agatcgagat    660
actggcgttg tgtatttaaa ggaagcttta acagacaaaa agaatactag atttaacagt    720
gctgtttatg tagccgataa tggcgttaac gatcaagaag gccaaaaaga ttcaaccgct    780
aagatatcta taacagtagt agggtctgat aaacagcctc ccagatttac tcaaaaaatg    840
cctgatggaa tcttggagat ccccgaagat tttaaagact tttctaaaca tattgtcaca    900
gtcgaagcaa cgtccaacat tgcggatcca caacttgctt ttgaattggt gaagggaaag    960
acatatcaaa ccaataaaga ccaaacgttt cttttggagg cagaaggaaa taaagcgcac   1020
ataaagctag tgcgtccact ggattatgaa acagtaacgg aatatactct aactattcga   1080
gtaaaaaaca aagatttaat ggattcttcc ataaatatac caattaaagt attagatgtt   1140
aatgatgaaa ttcctaattt ccttgaattt cttaaaggta gtgtcgtgga aaatgacaag   1200
ccaggtgcac aagcgattca agtaagagca atcgataaag acggaactgc tgctaacaac   1260
attgtgagct atgaactcgt tgacaataca gatttgtttg caataaaccg atctacggga   1320
gtaattacgt cgagagtgga gtttgatcgt gaaactgtac ctctatatca cgtaaacgtt   1380
aaagcttatg ataactctcc gtctgctttg tataacacga cattgcctaa cattgtaatt   1440
cagacattcc aaatcagtat agaagatcaa aatgacaaca aacctgtatt tactcatcca   1500
atttatcagt tcagtaatat tactgagctt gctgataaat cgagtattgt tggtgaagtc   1560
aaagctttag ataatgacac ggcttcagtt ataagttata gtattacaaa tggaaatatt   1620
gacgatgcgt ttatgattga aaattctacc ggcagaataa gagttaatgg aaaactggat   1680
tacgagaaaa tcgaacaata caacttaacc gttcgcgcat ttgatggggc atttgaagat   1740
tttgcaattg ttttaatttc catacttaat gaaaatgacg aacctccagt ttttgacgac   1800
tatatcagag aaattcaaat taaagaggaa gaacctatga tatccggatg cgttgttaga   1860
gtgactgctc atgatccaga tattaaagac aggcatgctg atcaacacat agtatatgag   1920
gtcgcgaaag aacagaaaga ttttttgacc gtatctgccg atggatgcgt acaagtaaca   1980
aaacctctcg accgagatcc gcctttcggt agcccaacac gacaagtctt catctatgct   2040
cgtgataatg atggaggcac aaattcattg ttggccactg cagaaattga aattatttta   2100
atagatataa acgataatgc tccccttttta aatgttacag aaattgttta ttatgaaaac   2160
caggatccag gttttatagg taacctaagt gccgatgatt acgatggtcc tgataatgga   2220
cctccgtttg cttttcgatt atcagacact gcttcagata gtattagatc gaaattttcc   2280
attatcggaa accagctttt cgctttagaa atgtttgata gagaagagca aaaatattat   2340
gacattgcca ttgacattac agatagtgga gtacctccac taacaggaac tagtattctt   2400
```

```
agagttataa tcggagatgt aaatgataat ccagctacag acggaaacag cacgatcttt   2460

gtgtataagt acgtcaatgg gccagaaaat ttcatggaaa tcggacgtgt atatgttaca   2520

gacctagacg attgggattt aaatgacaaa gtctttgttc aagaagataa ctttgatgaa   2580

tttgtgttaa accagcataa caacggtatg attctgatga aaccaacaac ggctgaggga   2640

acttatgagg ttcattacag ggtcactgaa acccatgaac ccacaataca cgaacataca   2700

gttaatgcaa tagtcacgat tacagttaaa gtacttccag aggaagcggt tgtaaaatca   2760

ggatcaattc gattgagagg aacaactaag gaagaattca tagaaaattc attgaatgga   2820

aagagcaaaa gagacatatt acaccaagaa ctctccaaaa tattaaatac atctttagcg   2880

aatgttgatg tatttactgt tttaaattca ccccaccaga atagttcgtt tgtggatgtt   2940

cgattttctg ctcatggatc tccatattat gctccagaga aactcgaaaa caaagttaca   3000

gatcatcaaa tggagcttga acaaaaatta gatgtggaat tctacatgat caacgtaaac   3060

gagtgcctta acgaaacaac gtgtggagct gaaaactcat gtacgaacaa attaaacata   3120

acacgagaac cagctgtagt gtttactaac agaacatcct ttgtcggtgt aaatgcattt   3180

attgatcctg tgtgtgccgc tttaccaaga gatgttatgg aatgtttcaa cggaggcgtc   3240

cttatcgaaa acacagcgtg taattgtcct gcaggatttg aaggaccaca ttgtgaaatc   3300

ctagctatag gatttacagg aactggttgg gctatgtatc catcctttga cgctacaaac   3360

aggactgaga ttatactgca tattttatca caaactgata atggtttgat attttacaat   3420

ggacctttaa atataagaca aacttctttg tctaaagatt atatatcatt agaacttaaa   3480

gacggatatc cattacttca aatttgcacc ggctcaagca ctcaagaaat ttatctgaaa   3540

gagcgcattc acaaattgag cgatggatcg ttacacaaaa taaaaatagg atctggattt   3600

gacgatatat ccctggaagt agacgactgt ggaacaacgt gttcaatttg gactaataaa   3660

ctacataaag gtgttatccg agcaaatggc ccccttcaac tgggaggtat gaaaaacaga   3720

ttcaccgatc aagaattcaa acgaatttgg gaccatttgc caccgactgc cacccgtttc   3780

tctggttgta ttagaaattt gacgtataat gaattttact acaacctcgg tgcaccttct   3840

gatgcattcc aagcgtatcc cgactgtaac tatgcagtga tgcaagctgt gactttcggt   3900

atcgactcca atttcttggt tgctattctg gtttgtgtag caattttgat aattcttctt   3960

ctggcagtag ttgtacatag acgtaaacac gacaacttta acgaaaaaga aatcgatgat   4020

actcgcgaaa acattatcaa ctacgaagat gaaggtggcg gcgaatgtga caccaactac   4080

gacctgtctg ttttccatca gaacaacatt gtggacgaaa aaccattgat gagagacaac   4140

cccgatgtac ctgcagatat aagtggcttt ttagataaca agaaagacaa ctgtgataaa   4200

gaccccgata atttgcctta tgacgacgtt cgccattatg cctacgaggg agacggaaat   4260

agcaccggat ccttatcttc tctcgcttca tgtacggacg aaggagattt aaagttcaac   4320

tacttatcaa gttttggacc cagattcaga aagttagccg acatgtatgg agaagatcca   4380

agcgatgaag actcacacga tggaaacgaa gaatcctggt gctag                 4425
```

<210> SEQ ID NO 106
<211> LENGTH: 291
<212> TYPE: DNA
<213> ORGANISM: Diabrotica virgifera

<400> SEQUENCE: 106

```
atgcctttct gtggtcccaa attgtccctc tgcggcctga ttatcagtgc atggggtatc     60

atccagttgg gtttcatggg tgtattctat tacattgggg ctgtggcttt agcagaagat    120
```

attccagagg ttgagtttaa gggcgattta gacaaatttt atagcgacgt caacacgggt 180
ttcacacaga atgcttacaa ctgctggatt gctgctctcc tatacctgat aacattagca 240
gtatcagctc accaattctg ggccaacaac agatcatcat tgaacgtcta a 291

<210> SEQ ID NO 107
<211> LENGTH: 540
<212> TYPE: DNA
<213> ORGANISM: Diabrotica virgifera

<400> SEQUENCE: 107
atgggtctta ccatatcagc agtgtttaat aggttgttta gtaaaaagcc tatgagaatt 60
ttaatggtag gattagatgc cgcaggtaaa accacaatct tatacaaatt gaagcttggt 120
gaaatcgtaa ctacaatacc aaccatcggc ttcaatgtag aaaccgttga gtacaagaat 180
atatctttca cggtatggga tgtaggtggc cagacgagaa tcagaaaact ctggagacac 240
tatttcgcca acactgatgg actcattttt gtggttgatt ccaacgaccg agaccgtatc 300
gcggaagccg aagaagaatt gcacaatatg ttaggagagg acgatttaag agactgcatt 360
ttgttaatat tcgccaacaa acaagattta ccgaactcga tgtccactgc tgaattgacc 420
gataagctta agttgcacac tttgaagaat aggaggtggt acatacaagc cacatgtgct 480
actcaaggga atggtttgta cgaaggacta gattggttgt cgaatgaatt ggccaagtga 540

<210> SEQ ID NO 108
<211> LENGTH: 618
<212> TYPE: DNA
<213> ORGANISM: Diabrotica virgifera

<400> SEQUENCE: 108
atgcggtaca ctttgagtta catcggtgct accctagcgt ccactgtaac actgattttt 60
gccctctact actgcctcac gggaaaagga gagcaagtta gtttagcatg gttattgttg 120
aatgtgtctc cccacatgtg ggcaggtcta ggaattggcc ttgctgtatc attatcagtt 180
gtaggagctg ctgcaggaat tcacactaca ggagtcagta tcgtaggagc tggtgttaaa 240
gcccccagaa tcaaaaccaa aaatttaatt tctattattt tctgtgaagc tgtggctatc 300
tatgggttaa ttatggctat agtactctgt ggaagttgga agaatttcga tgtagaccta 360
ttcaacctca aaactcataa ctttgctcaa aaccattatg gatcacatgt tatttttgga 420
tccggtttaa ctgttggatt tgtaaatcta ttatgtggat tttgtgttgg agtagttggt 480
tctggtgcag ccatttctga tgcagccaat tcatcattat tcgtcaaaat tttgattatt 540
gagatttttg gaagtgccat tggtctcttc ggtctgattg ttggagtata cttgacgtca 600
agaggctcta tggtttaa 618

<210> SEQ ID NO 109
<211> LENGTH: 5694
<212> TYPE: DNA
<213> ORGANISM: Diabrotica virgifera

<400> SEQUENCE: 109
atggctacca acgatagtaa agctccgttg aggacagtta aaagagtgca atttggaata 60
cttagtccag atgaaattag acgaatgtca gtcacagaag gggcatccg cttcccagaa 120 accatggaag caggccgccc caaactatgc ggtcttatgg accccagaca aggtgtcata 180
gacagaagct caagatgcca gacatgtgcc ggaaatatga cagaatgtcc tggacatttc 240

-continued

```
ggacatatcg agctggcaaa accagttttc cacgtaggat tcgtaacaaa aacaataaag    300
atcttgagat gcgtttgctt cttttgcagt aaattattag tcagtccaaa taatccgaaa    360
attaaagaag ttgtaatgaa atcaaaggga cagccacgta aaagattagc tttcgtttat    420
gatctgtgta aaggtaaaaa tatttgtgaa ggtggagatg aaatggatgt gggtaaagaa    480
agcgaagatc ccaataaaaa agcaggccat ggtggttgtg gtcgatatca accaaatatc    540
agacgtgccg gtttagattt aacagcagaa tggaaacacg tcaatgaaga cacacaagaa    600
aagaaaatcg cactatctgc cgaacgtgtc tgggaaatcc taaaacatat cacagatgaa    660
gaatgtttca ttcttggtat ggatcccaaa tttgctagac cagattggat gatagtaacg    720
gtacttcctg ttcctcccct agcagtacga cctgctgtag ttatgcacgg atctgcaagg    780
aatcaggatg atatcactca caaattggcc gacattatca aggcgaataa cgaattacag    840
aagaacgagt ctgcaggtgc agccgctcat ataatcacag aaaatattaa gatgttgcaa    900
tttcacgtcg ccactttagt tgacaacgat atgccgggaa tgccgagagc aatgcaaaaa    960
tctggaaaac ccctaaaagc tatcaaagct cggctgaaag gtaaagaagg aaggattcga   1020
ggtaacctta tgggaaagcg tgtggacttt tctgcacgta ctgtcatcac accagatccc   1080
aatttacgta tcgaccaagt aggagtgcct agaagtattg ctcaaaacat gacgtttcca   1140
gaaatcgtca cacctttcaa ttttgacaaa atgttggaat tggtacagag aggtaattct   1200
cagtatccag gagctaagta tatcatcaga gacaatggag agaggattga tttacgtttc   1260
cacccaaaac cgtcagattt acatttgcag tgtggttata aggtagaaag acacatcaga   1320
gacggcgatc tagtaatctt caaccgtcaa ccaaccctcc acaagatgag tatgatgggc   1380
cacagagtca aagtcttacc ctggtcgacg ttccgtatga atctctcgtg cacctctccc   1440
tacaacgccg attttgacgg cgacgaaatg aacctccatg tgccccaaag tatggaaact   1500
cgagctgaag tcgaaaacct ccacatcact cccaggcaaa tcattactcc gcaagctaac   1560
caacccgtca tgggtattgt acaagatacg ttgacagctg ttaggaagat gacaaaaagg   1620
gatgtattca tcgagaagga acaaatgatg aatatattga tgttcttgcc aatttgggat   1680
ggtaaaatgc cccgtccagc catcctcaaa cccaaaccgt tgtggacagg aaaacagata   1740
ttttccctga tcattcctgg caatgtaaat atgatacgta cccattctac gcatccagac   1800
gacgaggacg acggtcccta taaatggata tcgccaggag atacgaaagt tatggtagaa   1860
catggagaat tggtcatggg tatattgtgt aagaaaagtc ttggaacatc agcaggttcc   1920
ctgctgcata tttgtatgtt ggaattagga cacgaagtgt gtggtagatt ttatggtaac   1980
attcaaactg taatcaacaa ctggttgttg ttagaaggtc acagcatcgg tattggagac   2040
accattgccg atcctcagac ttacacagaa attcagagag ccatcaggaa agccaaagaa   2100
gatgtaatag aagtcatcca gaaagctcac aacatggaac tggaaccgac tcccggtaat   2160
acgttgcgtc agactttcga aaatcaagta aacagaattc taaacgacgc tcgtgacaaa   2220
actggtggtt ccgctaagaa atctttgact gaatacaata acctaaaggc tatggtcgta   2280
tcgggatcca agggatccaa cattaatatt tcccaggtta ttgcttgcgt gggtcaacag   2340
aacgtagaag gtaaacgtat tccatttggc ttcagaaaac gcacgttgcc gcacttcatc   2400
aaggacgatt acggtcctga atccagaggt ttcgtagaaa attcgtatct tgccggtctc   2460
actccttcgg agttctattt ccacgctatg ggaggtcgtg aaggtcttat cgatactgct   2520
gtaaaaactg ccgaaactgg ttacatccag cgtcgtctga tcaaggctat ggagagtgta   2580
atggtacact acgacggtac cgtaagaaat tctgtaggac aacttatcca gttgagatac   2640
```

-continued

```
ggtgaggacg gactctgtgg agagatggta gagtttcaat atttagcaac ggtcaaatta   2700
agtaacaagg cgtttgagag aaaattcaga tttgatccga gtaatgaaag gtatttgaga   2760
agagttttca atgaagaagt tatcaagcaa ctgatgggtt caggggaagt catttccgaa   2820
cttgagagag aatgggaaca actccagaaa gacagagaag ccttaagaca aatcttccct   2880
agcggagaat ccaaagtagt actcccctgt aatttacaac gtatgatctg gaatgtacaa   2940
aaaattttcc acataaacaa acgagccccg acagacctgt ccccgttaag agttatccaa   3000
ggcgttcgag aattactcag gaaatgcgtc atcgtagctg gcgaggatcg tctgtccaaa   3060
caagccaacg aaaacgcaac gttactcttc cagtgtctag tcagatcgac cctctgcacc   3120
aaatgcgttt ctgaagaatt caggctcagc accgaagcct tcgagtggtt gataggagaa   3180
atcgagacga ggttccaaca agcccaagcc aatcctggag aaatggtggg cgctctggcc   3240
gcgcagtcac tgggagaacc cgctactcag atgacactga acactttcca ttttgctggt   3300
gtatcctcca agaacgtaac cctgggtgta cctagattaa aggaaattat taatatttcc   3360
aagaaaccca aggctccatc tctaaccgtg tttttaactg gtgcggctgc tagagatgcg   3420
gaaaaagcga agaatgtgtt atgcagactt gaacacacca ctcttcgtaa agtaaccgcc   3480
aacaccgcca tctattacga tcctgaccca caaaataccg tcattcctga ggatcaggag   3540
ttcgttaacg tctactatga aatgcccgat ttcgatccta cccgtatatc gccgtggttg   3600
cttcgtatcg aactggacag aaagagaatg acagataaga aactaactat ggaacaaatt   3660
gctgaaaaga tcaacgctgg gttcggggac gatttgaatt gtattttcaa cgacgacaat   3720
gctgaaaagt tggtgctgcg tatcagaatc atgaacagcg acgatggaaa attcggagaa   3780
ggtgctgatg aggacgtaga caaaatggat gacgacatgt tttgagatg catcgaagcg   3840
aacatgctga gcgatatgac cttgcaaggt atagaagcga tttccaaggt atacatgcac   3900
ttgccacaga ctgactcgaa aaaaaggatc gtcatcactg aaacaggcga atttaaggcc   3960
atcgcagaat ggctattgga aactgacggt accagcatga tgaaagtact gtcagaaaga   4020
gacgtcgatc cggtcaggac gttttctaac gacatttgtg aaatattttc ggtacttggt   4080
atcgaggctg tgcgtaagtc tgtagagaag gaaatgaacg ctgtcctttc gttctacggt   4140
ctgtatgtaa actatcgcca tcttgccttg ctttgtgacg taatgacagc caaaggtcac   4200
ttaatggcca tcacccgtca cggtatcaac agacaagaca ctggagctct gatgaggtgt   4260
tccttcgagg aaactgtaga tgtattgatg gacgctgcca gtcatgcgga ggtcgaccca   4320
atgagaggag tatctgaaaa cattatcctc ggtcaactac caagaatggg cacaggctgc   4380
ttcgatcttt tgctggacgc cgaaaaatgt aaaatgggaa ttgccatacc tcaagcgcac   4440
agcagcgatc taatggcttc aggaatgttc tttggattag ccgctacacc cagcagtatg   4500
agtccaggtg gtgctatgac cccatggaat caagcagcta caccatacgt tggcagtatc   4560
tggtctccac agaatttaat gggcagtgga atgacaccag gtggtgccgc tttctcccca   4620
tcagctgcgt cagatgcatc aggaatgtca ccagcttatg gcggttggtc accaacacca   4680
caatctcctg caatgtcgcc atatatggct tctccacatg gacaatcgcc ttcctacagt   4740
ccatcaagtc cagcgttcca acctacttca ccatccatga cgccgacctc tcctggatat   4800
tctcccagtt ctcctggtta ttcacctacc agtctcaatt acagtccaac gagtcccagt   4860
tattcaccca cttctcagag ttactcccca acctcaccta gttactcacc gacttctcca   4920
aattattcac ctacttcccc aagctacagt ccaacatccc ctaactattc accaacatct   4980
```

```
cccaactatt cacccacttc acctagttat ccttcaactt cgccaggtta cagccccact   5040
tcacgcagct actcacccac atctcctagt tactcaggaa cttcgccctc ttattcacca   5100
acttcgccaa gttactcccc tacttctcct agttattcgc cgtcgtctcc taattactct   5160
cccacttctc caaattacag tcccacttct cctaattact caccgtcctc tcctaggtac   5220
acgcccggtt ctcctagttt ttccccaagt tcgaacagtt actctcccac atctcctcaa   5280
tattctccaa catctccaag ttattcgcct tcttcgccca aatattcacc aacttccccc   5340
aattattcgc caacatctcc atcattttct ggaggaagtc cacaatattc acccacatca   5400
ccgaaatact ctccaacctc gcccaattac actctgtcga gtccgcagca cactccaaca   5460
ggtagcagtc gatattcacc gtcaacttcg agttattctc ctaattcgcc caattattca   5520
ccgacgtctc cacaatactc catccacagt acaaaatatt cccctgcaag tcctacattc   5580
acacccacca gtcctagttt ctctcccgct tcacccgcat attcgcctca acctatgtat   5640
tcaccttctt ctcctaatta ttctcccact agtcccagtc aagacactga ctaa         5694
```

<210> SEQ ID NO 110
<211> LENGTH: 876
<212> TYPE: DNA
<213> ORGANISM: Diabrotica virgifera

<400> SEQUENCE: 110

```
atgtcgtcaa atattcaaaa ggcccagcag ttgatggcgg atgcagaaaa gaaagtaaca     60
tctcgaggtt tcttcggatc tctatttggg ggatcaagtc gtattgaaga tgcagtggaa    120
tgttacacaa gagctgcaaa ccttttttaaa atggccaaga gctgggatgc tgccggtaaa    180
gccttttgtg aggctgctaa tttgcattcc agaactggtg ctcgtcatga cgctgccact    240
aattatatag atgctgcaaa ttgttacaaa aaagccgatg tatttgaggc tgtaaactgc    300
tttataaaag ctatagacat ttataccgaa atgggtcgct ttacaatggc tgcaaaacac    360
catcagacta ttgcagaaat gtatgagact gatgctgtgg acatcgaaag ggctgttcaa    420
cactatgaac aggcggctga ttacttcaga ggagaagaaa gcaatgcttc cgccaataag    480
tgtcttctta aagtggctca atatgcagcc caacttgaaa actatgaaaa agcagtggga    540
atttatcaag aagtggctta tgcagctctg gaaagctctc ttttaaaata cagtgcaaag    600
gaatacttat tcagagctgc cctttgtcac ctttgtgttg atgtactcaa tgcacaacat    660
gctatagaaa gctatatttc aaggtatccc gcatttcaag attcccgtga atacaaactt    720
ttgaaaaccc tcatagaaaa catcgaagag caaaacgtag atggatatac agaagccgtc    780
aaagattacg attcaatttc tcgtcttgat cagtggtata ctacaattct tttacgtatt    840
aagaaacaag taagcgaaag ccctgactta cgttaa                              876
```

<210> SEQ ID NO 111
<211> LENGTH: 609
<212> TYPE: DNA
<213> ORGANISM: Diabrotica virgifera

<400> SEQUENCE: 111

```
atgaatcccg agtatgatta tttattcaaa cttctgctga ttggagattc aggagtagga     60
aaatcttgtc ttctactgag atttgcagat gatacctaca cagaaagcta tattagtacc    120
attggcgtag attttaaaat caggacaatc gatttagatg gaaagacaat taaattgcaa    180
atttgggata cagcaggtca ggaaaggttt agaacgatta catcaagtta ttaccgagga    240
gcacatggta ttattgtagt gtacgattgc acagaccaag attcattcaa taacgttaaa    300
```

cagtggctcg aagaaatcga ccgttatgcg tgtgacaatg taaacaaatt actggtaggg 360
aataaaagcg atttgacaac taagaaagtt gtcgacttca ctacagccaa ggagtatgcc 420
gaccaattgg gtataccatt tttggaaacc tcagctaaga atgcaaccaa tgtagaacag 480
gcctttatga ctatggccgc tgaaataaaa aatagagtag gacctccatc ttctgcggta 540
gaccaaggaa ataaggttag gttcgatcaa agtcgcccag tcgaaacaac caaatccggt 600
tgctgctga 609

<210> SEQ ID NO 112
<211> LENGTH: 789
<212> TYPE: DNA
<213> ORGANISM: Diabrotica virgifera

<400> SEQUENCE: 112
atggcagacg ctgatgatct attagattat gaagatgagg aacagacaga acaaaccgca 60
actgaaacgg caactacaga ggtacagaaa aagggtgtca agggcacata tgtatcaata 120
cacagttctg ggtttagaga ttttctgtta aaaccagcaa ttctcagagc tatagtggac 180
tgcgggttcg aacatccttc agaagttcaa catgaatgta ttcctcaagc tgtcattggc 240
atggatattc tgtgccaagc taaatccggt atgggaaaaa cggctgtttt tgtattagct 300
acactccaag taatagatcc tacagaaaat gttgtatatg ttctcgtcat gtgccatacc 360
agagagttag ccttccagat aagcaaagag tacgaacgtt tcagtaaata tatgcccaat 420
attaaagtag gggtcttctt tggtggcttg cctatccaga aagatgagga aacgttaaaa 480
aataattgcc cgcatatcgt tgtgggtact ccaggaagaa ttttagcatt ggtcagatcg 540
aaaaaactta atctcaaaca tctaaagcat tttattttgg atgaatgtga taaaatgttg 600
gagttattag acatgagacg tgatgttcaa gaaatatatc gtaacactcc ccacgaaaaa 660
caagtcatga tgttcagtgc caccttaagt aaagaaatta gaccagtttg caagaaattt 720
atgcaagatg taattcaaaa ttcttataat acacaatttt gtaatgacgc acccactcgc 780
aatgtttga 789

<210> SEQ ID NO 113
<211> LENGTH: 738
<212> TYPE: DNA
<213> ORGANISM: Diabrotica virgifera

<400> SEQUENCE: 113
atgccggtca ttgatggtta taaagtactt tacattttat tacacagttt atatacaatt 60
tttgaaaata tttggaggac tcttttattt atttatcaaa attgtataag ggttataaac 120
cctgaatcta cattcgatga tgctgaccag ttaaagaaaa gactgtctag actaacaaaa 180
aagcctcaac atttaactat cattattggt gtggaagaat attcattggt agatttggct 240
aacctcgtat attggtgttt aggtcttaat attccgtacg ttagtttcta tgattataaa 300
ggtaatttaa aaaagcatga agagaagttg caacaaattg tagaatccag aaaatcagag 360
aatatcaaca taatttggca cacccatgca gaacaaaggc ataaaaatgg atttttgggt 420
ccaaaaatcc acgtaaaagt gttaacacac gcggacggaa agcaaagtat agtaaatgtt 480
actaaaaaat tagctctaaa taaagaaaaa gacattagta aagaaaaaat tagtgaatta 540
ctattaaggc agtatgaatt tccagatcca gaaatggcta ttatttgtgg aaagaaactg 600
aacatttata attatcctcc ttggcagtta agactcacag aattctttaa agtcaacaaa 660

```
gtcaacaaca tcacattccc agtgtttgtg gaaaaattgg aaaagtacag caaatgtgaa    720

cagagggtgg gaaaataa                                                  738


<210> SEQ ID NO 114
<211> LENGTH: 480
<212> TYPE: DNA
<213> ORGANISM: Diabrotica virgifera

<400> SEQUENCE: 114

atgaccaact ctaaaggtta ccgccgagga accagggatc tatttgcccg caagtttaaa     60

aaacgtggtg taattccact ttccacatat ttgagagtct acaaagttgg agatattgta    120

gatatcaagg gtaatggtgc agttcaaaag ggtatgcccc acaaagtgta ccatggtaag    180

acaggacgtg ttttcaatgt tactgcacat gcattaggtg taattgtaaa caaaagggtt    240

cgaggaagaa tcatccccaa aagaatcaat ctccgtattg aacatgtaaa ccactccaag    300

tgtcgtcaag acttcttgca aagagtaaaa tccaacgaaa agctacgtaa agaagctaaa    360

gaaaagaaca ttaaagtaga acttaggaga caacctgccc aacctaggcc agcacatatt    420

gttagcggaa aggttccagc acaggtgctt gctcctatcc catatgaatt cattgcttag    480


<210> SEQ ID NO 115
<211> LENGTH: 537
<212> TYPE: DNA
<213> ORGANISM: Diabrotica virgifera

<400> SEQUENCE: 115

atggaaggaa tactactgga accaacattg tataccataa aaggtattgc tatattggac     60

tatgatggta atagagtgct ggctaaatac tacgataaag atatatttcc tacagcaaaa    120

gagcagaaag cttttgagaa aaatttgttc aataaaactc atagggcaga cgcagaaatt    180

atcatgttgg atggtttaac ttgtgtgtat agaagtaatg tagatttatt cttttatgtt    240

atgggcagtt cacatgaaaa tgagctaatt ttaatgagtg ttttaaattg cttgtatgac    300

tcagtaagtc aaatattgaa gaaaaatatg caaaaacgag ctgtcttgga atcactagat    360

attgttatgc tggctatgga tgaaattgtt gatggaggaa taattataga ttctgattca    420

agttcagtag tatctagaat agcattaagg actgatgata ttccattagg agaacaaact    480

gtagctcagg tattccaaac ggccaaagaa cagctgaaat ggtcattgct gaaataa       537


<210> SEQ ID NO 116
<211> LENGTH: 450
<212> TYPE: DNA
<213> ORGANISM: Diabrotica virgifera

<400> SEQUENCE: 116

atggctgacc aactcaccga agaacaaatt gctgaattca aagaagcttt ctcactattc     60

gataaagatg gtgatggtac aattacgact aaagaattag gaacagtaat gagatctcta    120

ggacaaaatc caacagaggc tgaattacag gatatgatca atgaagtaga tgccgatggt    180

aacggcacga tcgatttccc agaattttta acgatgatgg cacgtaaaat gaaagatacc    240

gatagtgagg aagaaattcg tgaagcattc cgagtgttcg acaaagacgg caatggtttc    300

atctcagcag cagaattgcg ccacgtcatg accaacttgg gtgaaaaatt gacagacgaa    360

gaagtcgatg aaatgattcg ggaggccgat atcgatggtg atggtcaagt caattacgaa    420

gagttcgtca ccatgatgac ttcaaagtga                                     450
```

<210> SEQ ID NO 117
<211> LENGTH: 2013
<212> TYPE: DNA
<213> ORGANISM: Diabrotica virgifera

<400> SEQUENCE: 117
atgatgcaag caaacaatcg agtcccacct ataaagttgg aaaacgatat agatctttac 60
gccgatgata tcgaggattt cgcacaagat gactttggtg gtgaaaatgt tgatctatat 120
gacgatgtaa tatccgctcc tcctggaaat aatgacaacc caggtgattc aaatcatcat 180
gctcctcctg gtgctggtga agatggtgga ggtaattttg ttgggtcagg aggagcaccc 240
aataatataa attcttctgg aagaagacat cagctgtatg ttggaaatct gacttggtgg 300
acaactgatc aagatataga aaatgcagtg catgatatag ggtaaccga cttccatgaa 360 gttaagtttt ttgaacacag agcaaatggt caatccaagg gattctgtgt catatctttg 420
ggatctgagg gaagcatgag actctgcctg gaactcctat ctaaaaaaga gatcaatggc 480
caaaatcccc ttgttaccct tcccacaaaa caagctctta gtaactttga aagtcagtct 540
aaaacacgcc cttctcctac taataattct aactcacgtc ctccccatcc taataataat 600
gttcattcag gtcctatgca gaattatgga ggtagaatgc ctatgaaccc ttccatgcgt 660
cccatgcccc caggtatgca aggtgctcca agaatgcagg gtccacctgg atttaatgga 720
ccaccaaaca tgaatcagca accccccagg ttccaaggta atccacaatg gaatggacct 780
agacctaatg gtcctgggcc caatatggga atgagaccca tggggccacc tcatggacaa 840
caagggcccc caagaccacc aatgcaggga ccaccgcagc aaggtcctcc aagaggaatg 900
ccgccacaag gtccaccgca gatgcgtcca gaatggaatc gaccaccaat gcaacaaggg 960
taccctcaag gcccgccgca tatgcaagga cctaacatgg gtccaagagg tccaccccaa 1020
atgggaccac ccggggcgcc tcaacagcaa ggaccagctc cgcacgtaaa tccagcattc 1080
tttcaacaag gaggaggacc accgccccca atgcaacaca tgcctggacc agggcccgtc 1140
atgcctcctc aaggaccccc gcaaggtcca ccacacggac ccgttggacc tccacacggc 1200
ccaccattgg gtccagcgaa tgttccgcct catggaccac ctcacggata tggtccacct 1260
gcagcgatgc cacagccgcc atacggtggc ccacctccag accaccgcgc tgagattcct 1320
cagttaacag agcaagagtt tgaggatata atgtcccgga atagaacagt ttccagttcg 1380
gcgattgggc gggccgtatc cgacgccgca gctggagaat ttgcaagcgc cattgagact 1440
ttggttactg ctatttcact catcaaacaa tccaaagtgg ctaacgacga tcgttgcaag 1500
atccttataa gttcgctgca agatactttg cgtggtgtcg aagacaaaag ctacagctcc 1560
agccgcagag accggtcaag atccagggac agatcacata gaagaactag aagagaacga 1620
tcctcgtcac ggtacagaga cagaagcaga gagagggagc gtgaacgcga tagagatcgt 1680
gatcgtgaac gtgacagata ttatgataga tacagcgaaa gagaaagaga ccgagatcgt 1740
tcaagaagca gagaaagaac agaaagggat agagaacgag attatagaga ccgggaaccc 1800
gaagagacag ataaagaaaa atctaaagta tccagagtct caagatcaag aaacaaatct 1860
ccggaacctg tcgaacctag cagcgaggta ccgaaatcat cccgctatta tgaggatagg 1920
tatcgggaac gagagagaga aggtcgacga gagagcgatc gcgaaagaga aagagataga 1980
agaggggaag acagccatag gtctcgacac tag 2013

<210> SEQ ID NO 118
<211> LENGTH: 765
<212> TYPE: DNA

-continued

<213> ORGANISM: Diabrotica virgifera

<400> SEQUENCE: 118
atgagttcta ttggaactgg gtacgattta tcagcttccc aattctctcc tgatggaaga 60
gtatttcaag ttgaatatgc aatgaaagca gttgaaaata gtggcaccgt aataggcctc 120
cgaggtacag atggcattgt attggctgct gaaaagctca ttatgtcaaa attgcatgaa 180
ccaagtacaa ataaacgaat tttcaacatt gataaacaca taggaatggc attttcaggc 240
ttaatagctg atgcaaggca aatcgttgag attgctagaa aagaagcatc aaattataga 300
catcaatatg gttcaaatat tcctcttaaa tacctaaatg atagagtaag catgtacatg 360
catgcataca ctttatacag tgctgttaga ccatttggtt gcagtgtcat cttggccagt 420
tatgaagata gtgacccatc tatgtatctg attgatccat ctggagttag ctatggatac 480
tttggatgtg ctacaggtaa agcaaaacag tctgcaaaga ctgaaataga aaaattgaag 540
atggggaatc taacatgcaa agaacttgtt aaagaagcag ccaaaatcat ttatttggtc 600
catgatgagc tgaaggataa gaattttgaa ctggaacttt catgggtatg caaagatacg 660
aatggtttac ataccaaagt gcctgaatca gtgtttgctg atgcagaaaa agctgccaaa 720
caagcaatgg aagcagattc agaatcagat acagaagata tgtaa 765

<210> SEQ ID NO 119
<211> LENGTH: 744
<212> TYPE: DNA
<213> ORGANISM: Diabrotica virgifera

<400> SEQUENCE: 119
atggcttcaa aagacagatt gatgattttt ccatctagag gagcccaaat gatgatgaaa 60
tccaggctaa agggagccca aaagggacat agtttattaa agaagaaagc tgatgcttta 120
caaatgagat ttagaatgat tttgaacaaa attattgaga ccaaaactct catgggtgaa 180
gtaatgaaag aagctgcctt ttctttagct gaagcaaagt ttgcaactgg tgacttcaat 240
caagttgttc ttcaaaatgt caccaaggct caaataaaaa taagaactaa gaaagacaac 300
gttgctggtg ttactttacc agtgtttgaa tgctaccaag atggtacaga tacatatgag 360
ttggctggtt tggctagggg aggtcaacaa ttgacaaaac tcaagaagaa ttatcaaagt 420
gctgttaaac tgttggttga attagcctct ttgcaaactt cttttgtaac tcttgatgat 480
gtaatcaaaa taacaaacag aagagtcaat gccattgaac atgttatcat tccaagaata 540
gagcgtactt tggcttacat catatccgaa ctggacgagt tagaaagaga ggagttctat 600
agattaaaga agatccagga caaaaagaag atcagcagag caaaggccga gaaacaaaaa 660
caagctcttc tccaagctgg gctacttaaa gagtcccagg caaacatgct tttggatgag 720
ggcgatgaag atctactttt ctag 744

<210> SEQ ID NO 120
<211> LENGTH: 4818
<212> TYPE: DNA
<213> ORGANISM: Diabrotica virgifera

<400> SEQUENCE: 120
atggaggcgg ctcccaagtt accgatgctc tcgttcgagt taaatacttg tacagagaac 60
gtccactttg gcccccagtt aaaacagtat attgctgctt tttatggtga agatccagaa 120
tcctacatta cagaaatcag caatcttgaa tccttaagat cagctgcagt tcgaccatca 180
acggatgtaa atggtgtaca actgttgaaa aagtatttct gtcagcttcg ttttctcaaa 240

-continued

```
tctaggtttc ccatggaaga gaatcaagat gctgcagttc tattttcatg gaaaaataat    300
gaattagaca taacttcaac atccagtgat atcagatatg aattaatggt aataatgtat    360
aacattggag ccttacacac ttttcttgga gccaacgact caagaaacaa tccggatggt    420
atgaaaatgg catgtactca ttttcaatgt gctgcatggg cttttcaaaa cgtaaaagaa    480
aagtaccacc aattcatatc aaacatctca ttggtagaac tggttcattt ttttcaacaa    540
gtctgtttag ctcaggctca ggagtgtata ttagagaaga gcatgtttga caataggaaa    600
cctaccatca ttgcaaaagt tgctatccaa gtctacagtt attacagaca gtctttacgt    660
gtcttggaat cagtaaatga agcctacttt agggataaaa cctacaagga gtggatgaaa    720
tatcttcaat tcaagctgac ctactacaaa tgcatctcgt tcctattcca agggcaacaa    780
gctgaggaac aacagaaaat gggagaaagg gttgcattct atcaagctgc atgtgaacag    840
ctggacgagg caaagaaaat tgctgctaca ttaaaaaacc aacaccacca gcaagaaata    900
aatgagggac tagcattcac tactgatgtg gttgaaggta aaagaaaagc agctaaaaat    960
gaaaatgagt tcatctacca tgaatcagtg cctgataaag accaattgcc agaggttaag   1020
ggtgcttcat tagtcaaagg aataccattc agtataaatg atatagaagt ttcaggacca   1080
gatattttct cccgattggt cccaatggag gcacacgaag cagcttcctt gtacagcgag   1140
aagaaagctc agagattaag acagatcggg gaacttattg aaaataaaga tcaaacattg   1200
gctgaattta tgtcgtcaat gcagctagat ctattgacca agatgcacca ggctactgga   1260
ataccgcagg agttgattga tagagcagcg gctctatctg ctaaacctaa cgccattcaa   1320
gatcttataa gtgctatggg aaagctatct aatatatacc aagacgttga agcaagtttg   1380
aatgagattg attctttatt aaaggccgaa gaacaaagtg aacaaaagta ccaagaaacg   1440
attggtaaaa gaccaccgag cattttagct acagatttaa ctagggaagc ggcaaaatac   1500
agggaggctc atactaaagc gaacgactca aaccaaactt tacacagggc gatgatggct   1560
cacgtggcta atctgaaaat actccaacaa ccgctaaagc agctgcaaca tcagctgccc   1620
tttgtcgagt ttccaaatcc aaatatcgac gaaaaatctt tgaaagatct ggaagcgcta   1680
gttgcaaaag tagacgaaat gagaacccaa agagccatgc tatgggctca acttcgagaa   1740
tctattcacc aagacgatat tacaagttcc cttgtaacga aacaaccaaa tcagtcgctg   1800
gaacagctgt tccagcaaga acttcaaaag catcaaaatc tgatttcgtt gattgaacaa   1860
aacacctcgg cacaagaaaa cattaagagc gccttagtcg attcttacgc ttacgctgta   1920
aattcaagaa aatacatcca agatatactc caaaagagaa ccacaaccat aacgtcactg   1980
atagcatcgt tcgactctta cgaagactta ttggcaaaag ctaacaaagg gatagagttt   2040
tactcaaaac ttgaaacgaa cgtatccaag ttactgcaaa gaataaggag tacctgcaaa   2100
gttcaacaag aagagcgaga tcagatgatg tcgactgcgc aagtgcctca atgggagagt   2160
catacgtcac ttgccgctcc taaactgaaa gattacttgg actccaggaa gaagagtgct   2220
gcgtattcgg agccgagtgt tcaaccacaa cagccaactt taagttactc agctgctatg   2280
gatctgcctc ctggtattag gccgactcca gttggatcag aaataacgga tgtaccgaaa   2340
aatattcaag gtgaaccaca aggttatatt ccatataatt accaacaacc ttctgttcct   2400
gcctcacaga atattgatga agagactatt aaaaaaatga acgcattgat gccaggtgct   2460
aagacgtcag tgcctagtca gtacggatac agcaactaca ttccaccaac ataccctcaa   2520
agtgcgtacc aaccaggtaa tcagtcttac ggaaaagaaa ctccagatat taactcaccg   2580
```

-continued

```
tacgaccctaccaaggcgtt cacggctact actaacgctt atcgttcggt gcagagctcc   2640
tcaactcaag gatacgtacc gtacgcagaa tctaacgttt cgaatgttga cagagttgga   2700
tatcctagca ggtatcagta ccaacaagta cctgagatag ctactactcc agctgatccc   2760
aatattaatg cgtactaccc acatgggtac tcaccgagcc agaatttacc gaatgctaat   2820
actcaacata ttaccggcca actgaagtac cattcggtgg agtacgcttc ttctgtgccg   2880
aacaacatca attataacag ctctacctac tcgtcgccgc tttctaatat gtctagtacc   2940
aattcctcaa atcctagtaa cttgaataat tcttacgagt actactatga cccgaatacc   3000
agtagtggtg cagtaccgaa tgcttcaaag cctcaacagt cgagcgccag ctctgcaaac   3060
ccgagtaccg ctatgaacaa ctacaattat tactacaata caagtaccag cggtagtgta   3120
gcagcggata cttcaaaaat acaacaacaa caacagtacc caggtactca gatgagtcaa   3180
gcgcagtact atcccgccaa tgccagttat tactcaacca gtacttacaa taccaacgtc   3240
caaggtggta ccaatccctc gtacgcaact ggacaaacat ataatcaagt gacaccagtg   3300
acctctcaaa atgtttctca aaattacaac tttaaccaag ttggttctgg agcaggacac   3360
cagcatcagt actactcgtc cgctaacgcc gcagtaccat cccaacaagc tgtaaataac   3420
agttcattac caaactacgg atacgatcag tattacggca acaactataa ttccagtcaa   3480
ccgagtacct acagcgcaaa ccaagcacct cctgcagcac aagctgctcc aagtaatatt   3540
cctgctgcca ccaaatcctc ctctaatgtg gatctgctca gtggcttgga cttcagcata   3600
agccaagctc ctctagtgcc tcaacaaaac attacgataa aaccccaaga aaaggaaaca   3660
aaaccaccgg ctgtttcttc tgaaaccaaa aaccaagatc caacaccagt aaccacgccc   3720
aaacaaccca ctggaccaga agtaaagcgc ttgtacgtca aatcctgcc gagcaaaccc    3780
ttaaacaacg atgatgtgaa gaaattgttc ggccaagagc tggacaggta tgagaagttc   3840
gtggagacct tgacccacaa aactttgagc ggtccgacca ctctggatat taaatggaag   3900
gagatccaag accagcagga ttgcgagccg cagaagaaga tcatttccgt cgctagatgt   3960
tatcctatga agaataggtt cccggatatc ttgccttacg acttttccag ggtggagttg   4020
tgcgatagta aagatgatta tatcaacgct tcatacatta aggatatctc gccatatgct   4080
ccgtcattta ttgttacaca agtgccgttg tcttcaactg ttggtgatat gtggacgatg   4140
attagagaac aacaggtcga actgatcctc tgtttggtaa acgacaatga gatcggtgaa   4200
gatatttact ggcccaaaga aaaaggcagt agtcttaaca tacttaacat ggtcataacg   4260
ttgcaaaacg ttatagttaa gtctcattgg actgaaagac tgatagcgat aaacttacct   4320
gaaaaacggg agtcccgtgt gataatgcat ctacaattta catcgtggcc tggcagcttg   4380
tttccaacaa atcctgaacc gttcgtcagc tacaccttgg aatccatcaa cctataccaa   4440
caacagaaga ccaacaccca tccggtggtg gtccattgtt catctggcat aggaagaagc   4500
ggcctgctct gtttactgac agctgctatg ttcgatgctg ccaacaatgc taactcgata   4560
ccagatctta cagctttgag tatcaagttg tccaattgca ggaagaatat tctcagagat   4620
cgagagcatt tgaagtttgg ttacgaaagt tttttggcgt atattaggca tatagtttgt   4680
gaagataaag ccagaaagaa actgaacgag atccagccca aggttaagga ggaaccactg   4740
gaaccacctg tcatagttcc agaaccaaat atagatcctt taagtacttt agacccattt   4800
tgggctagta aaagataa                                                4818
```

<210> SEQ ID NO 121
<211> LENGTH: 478

<212> TYPE: RNA
<213> ORGANISM: Diabrotica virgifera

<400> SEQUENCE: 121
gguuucauga ccccugagag aaagaagaaa cuuagguuac uguugagaaa gaaagccgcc 60
gaagaauuaa agaaagaaca agaacgcaaa gcagccgaaa ggaggcguau cauugaagaa 120
aggugcggua aacccaaacu ugucgaugac gcaaaugaag gcccauuaaa acaaguaugu 180
gagggauauc acagacguau uguagaccua gaaaauaaga aauuugaccu cgaaaaagaa 240
guggaauuca gagauuuuca gaucuccgaa uugaacagcc aaguaaacga ccuuagaggc 300
aaauucguca aaccaaccuu gaagaaggua uccaaauacg aaaacaaauu cgccaaacuu 360
caaaagaagg cagcugaauu uaacuuccgu aaccaacuca aaguugucaa gaagaaagaa 420
uucaccuuag aagaagaaga caaagaaaag aaaccagacu ggucaaagaa gggagacg 478

<210> SEQ ID NO 122
<211> LENGTH: 529
<212> TYPE: RNA
<213> ORGANISM: Diabrotica virgifera

<400> SEQUENCE: 122
agaaguugcc gcuuuagucg uagacaaugg auccgguaug ugcaaagcug guuuugcugg 60
ggaugaugca ccucgugcug uauucccuuc aauuguugga cgcccaagac aucagggugu 120
gaugguagga augggacaaa aagauuccua uguaggugau gaagcucaaa guaaaagagg 180
uauccuuacc uuaaaauacc ccaucgagca cggaauaguc acaaacuggg augauaugga 240
gaaaauuugg caucauacau ucuacaauga acucagagua gccccagaag aacacccugu 300
ucuguugaca gaagcuccuc ucaaccccaa ggccaacagg gaaaagauga cacaaauaau 360
guuugaaacu uucaacaccc cagccaugua uguugccauc caggcuguac ucuccuugua 420
ugcaucuggu cguacaacug guauuguguu ggauucuggu gaugguguau cccacacugu 480
cccaaucuau gaagguuaug cucuucccuca ugcaauccuu cguuuggac 529

<210> SEQ ID NO 123
<211> LENGTH: 592
<212> TYPE: RNA
<213> ORGANISM: Diabrotica virgifera

<400> SEQUENCE: 123
accggccuuu guaugucuug ggauaugugc cuaaagacga uagauuauac cucguagaua 60
aagaguugcg cguaguaagc uaccaauuac uucuuucugu ucuugaauau caaacugccg 120
ucaugagaag agacuuucca acagcagaca gaguacuucc guccauuccu aaggagcaca 180
gaacgagagu ggcacauuuc uuagaaaagc aaggcuucaa acagcaagcu uuggccguaa 240
guacagaucc agagcacaga uucgagcugg caguagcauu agaggaucuu aauauagcca 300
aaacucuagc ucaagaagcg aacaguccgc aaaaguggaa ucaacuagca gaauuggcag 360
cugcuacuaa uaauguaagc guagccaagg aauguaugca aaaagcgcaa gauuauggag 420
gcuuguugcu ucuugcuacg agcuccggug augaaaauuu aguccguacu cuaggagaaa 480
cgacacaagc ugaaagcaaa cauaacuuag cauuuuuguc acacuuguua guaggugauu 540
uaaacaaaug ucuagacauu cuuauuaaua ccgguagauu gccagaagcu gc 592

<210> SEQ ID NO 124
<211> LENGTH: 594
<212> TYPE: RNA

<213> ORGANISM: Diabrotica virgifera

<400> SEQUENCE: 124
gaaagcaguu ggaagauggc cguacucucu cagacuacaa cauucaaaaa gagucuaccc 60
uccauuuggu acuucgucuu agaggaggua ugcagauuuu uguuaaaacu uuaacuggaa 120
agaccaucac ccuugaagua gaaccuucug auaccaucga aaaugucaaa gccaaaauuc 180
aagacaaaga agguauucca ccagaucaac aaagauuaau cuuugccgga aagcaauugg 240
aagauggucg uacacucuca gacuacaaca uucaaaagga aucuacccuc cauuugguac 300
uucgucuuag aggagguaug caaaucuuug uaaaaacacu cacugguaag accaucaccc 360
ucgagguuga accaucagau accaucgaga augucaaagc uaaaauucaa gacaaagaag 420
guauuccacc agaucaacag agauuaaucu ucgcuggaaa gcaguuggaa gauggccgua 480
cucucucaga cuacaauauu cagaaagagu cuacccucca uuugguacuu cgucuuagag 540
gagguaugca aaucuuugua aaaacucuca cugguaagac caucacccuc gagg 594

<210> SEQ ID NO 125
<211> LENGTH: 547
<212> TYPE: RNA
<213> ORGANISM: Diabrotica virgifera

<400> SEQUENCE: 125
uaccccauug aacacggaau uaucacuaac ugggacgaua uggaaaagau cuggcaucac 60
accuucuaca augaacuuag aguagccccc gaagaacauc ccauucuuuu gacugaagcu 120
ccacuuaacc caaaagccaa cagagaaaag augacucaaa ucauguuuga aacuuucaau 180
accccugcca uguauguugc cauucaagcu guauugucuc uguacgcuuc cggucguacc 240
acugguauug uacuugauuc uggagauggu guaucccaca caguacccau cuaugaaggu 300
uacgcucucc cacacgccau cuugcguuug gacuuggccg guagagacuu gacugacuac 360
cuuaugaaga ucuuaaccga aagagguuac ucuuucacca ccacagcuga aagagaaaua 420
guucgugaca ucaaggaaaa auugugcuau guagcuuugg acuucgaaca ggaaauggcc 480
acagcagcca gcuccaccuc cuuagaaaag aguuaugaac uuccugacgg ucaagucauc 540
accauug 547

<210> SEQ ID NO 126
<211> LENGTH: 592
<212> TYPE: RNA
<213> ORGANISM: Diabrotica virgifera

<400> SEQUENCE: 126
aggaaaggaa ggacccaaga ccaaacaacc aucgagauac auccguuuua ucuacaaucg 60
cgucauauug gaauguccuu cuguaagagc ugcugcaguc uccgccaugg cacaauucgg 120
agccucuugu cccgauuugu uagaaaauau ccaaauauua cuuucgaggu gucagaugga 180
uucagacgau gaaguuaggg acagagcuac auauuauagu aauauacuua acaaaaauga 240
uaaaaguuua uacaacaauu acauuuugga uucuuugcag guuucaauuc cuucacuaga 300
aagaucgcuu agagaauaca uucaaaaucc aacugacgaa ccauuugaca uuaaguccgu 360
accuguagca gcagugccaa cagcagaaga acgagaaguu aaaaacaaau cugaaggacu 420
gcuagucucu caagguccag uccgaccucc uccggugucu agagaagaaa acuucgccga 480
aaaacuuagu aacguuccgg guauacaaca guuaggaccu uuguucaaaa cuuccgacgu 540
cguugaacuc acugaaucug aaacagagua uuuuguccgc uguaucaagc ac 592

<210> SEQ ID NO 127
<211> LENGTH: 500
<212> TYPE: RNA
<213> ORGANISM: Diabrotica virgifera

<400> SEQUENCE: 127
uacuaggcga aagugccguc gguaagucga guuugguacu gagguucguc aaaggacagu 60
uccacgaaua ccaggagagu accauaggag cagcuuuccu uacacaaacc auaugccucg 120
acgauacaac uguuaaauuu gaaauuuggg acacagcggg ucaagaaagg uaccacaguu 180
uagcuccuau guacuauagg ggcgcacagg cagcuauagu cgucuacgac auaaccaauc 240
aagacacauu cggcagggcg aaaacguggg ugaaggaacu ucaaaggcag gccaguccga 300
cgaucgugau agcuuuggcc ggcaacaagc aagauuuggc caacaaacgu augguagaau 360
acgaagaggc gcagacguau gcugacgaaa acggcuuacu uuuuauggaa acuuccgcaa 420
agacggcaau gaacgucaac gauauauuuu uagcaauagc uaagaaacug cccaagaaug 480
aacaaaccac aggucaaggc 500

<210> SEQ ID NO 128
<211> LENGTH: 189
<212> TYPE: RNA
<213> ORGANISM: Diabrotica virgifera

<400> SEQUENCE: 128
cgaugagguu gaaggaagga gaaaaauuuu gaugggggcga aaaagcauua ccaggacaua 60
ucuucgugga aaugcuguuc cugcguaugu gauaauaauc cuuguaggaa uuggucaaau 120
cauccuggga gggauauugu acguugcauu gaggaagaag aucauugcug caccuguaac 180
ggcaucaua 189

<210> SEQ ID NO 129
<211> LENGTH: 393
<212> TYPE: RNA
<213> ORGANISM: Diabrotica virgifera

<400> SEQUENCE: 129
ugaggucgag cccucagaua cuaucgaaaa ugugaaagcu aaaauccagg auaaagaagg 60 aauucccccca gaccagcaac gucucaucuu cgcuggaaaa caacucgaag auggucguac 120
cuugucugac uauaauauuc aaaaagaauc aacccuucac uuggugguga gauugagagg 180
aggugcuaag aaacguaaga agaagaauua cuccaccccc aagaaaauca agcacaagaa 240
gaagaagguu aaguuagcug uauugaaauu uuauaagguu gacgaaaaug guaaaaucca 300
ccgauugaga cgugaaugcc ccgcugaaca auguggagcu ggugucuuca uggcagccau 360
ggaagacagg cauuacugug gcaagugcgg uua 393

<210> SEQ ID NO 130
<211> LENGTH: 524
<212> TYPE: RNA
<213> ORGANISM: Diabrotica virgifera

<400> SEQUENCE: 130
ucuuugccuu uggcuacgau ucgaggaggg cauucaagaa uggcuccaga aauuggauuc 60
agaacaauuu uacaucggag uauauguacu uauagucgcu ucacugaucg ucaugauugu 120
guccuuuaua ggauguauua gugcccugca ggagaguacc auggcccuuu uaguguacau 180
cggcacccaa gugcucaguu uuauauucgg uuuauccggu ucggcgguuc uucuggauaa 240
cagcgccaga gauucccacu uccaaccgag gauccgagag aguaugcgac gucuuaucau 300
gaaugcucau cacgaccaau ccagacaaac acuagccaug auucaggaaa auguugguug 360
cugcggagcu gauggcgcaa cagacuaccu cucucuucag cagccccuuc caagucagug 420
cagagacacc guuacuggaa acccauucuu ccacggaugu guagaugaac ucaccugguu 480
cuucgaagaa aaaugugguu ggauagcagg uuuagcuaug gcga 524

<210> SEQ ID NO 131
<211> LENGTH: 267
<212> TYPE: RNA
<213> ORGANISM: Diabrotica virgifera

<400> SEQUENCE: 131
ucgugcuggu uuacaauuuc cuguaggucg uauucaucgu uuauugagaa aaggaaauua 60
ugccgaaaga guuggugcug gagcuccugu auacuuggca gcuguuaugg aauauuuagc 120
ugcugaaguu uuggaauugg caggaaaugc agcuagagau aacaaaaaga cccguauaau 180
uccuagacau uuacaauugg ccauaagaaa ugacgaggaa uugaacaaau uacugucagg 240
aguuaccauc gcccaaggug gaguauu 267

<210> SEQ ID NO 132
<211> LENGTH: 558
<212> TYPE: RNA
<213> ORGANISM: Diabrotica virgifera

<400> SEQUENCE: 132
gugcaugaag uuggauggug uagaucugcc cccaccaauu agcuucgaca uugcggaaga 60
gcaaccguua ccaccuugcc aacagacguu cuuauguaau ggugauggag gauccauagu 120
gcgacaguuu cucgagcugu auuucguaau auaugauuca gauaauaggc agucccuucu 180
ucaggcauau cacgaaaaag ccacauuuuc aaugacaaug gccuacccgu acggcuauuc 240
caaagacagu aaaggaguau cgugguugaa uugguaugcc accgauaaua gaaauuuauu 300
acgaguucaa gauccagaca gaagaaacaa guuguuaaga cagggacaag uugcuguagu 360
uucguucuug caagauaugc cgcacacgaa gcacgauauu cacaguuuua caguagauuu 420
gacaguuuuu acaccccaga uguuauguuu gacaguggcu gguauguuua aagaauugaa 480
aaguggccac aaaguaccuc cuuuaagaua uuucuucaga acccuuguaa uuguaccugc 540
uggaucaggu uuuugcau 558

<210> SEQ ID NO 133
<211> LENGTH: 582
<212> TYPE: RNA
<213> ORGANISM: Diabrotica virgifera

<400> SEQUENCE: 133
gauucggagc ccuacaauga aaugcaacua aaaauggauu uagaaaaggg ugagguuaaa 60
guaaaaauaa gagcauuaga aaaaauaauu cacaugauuc uggcaggaga aagguugccg 120
aauggauuuc uaaugaccau cauaagaaac guuuuaccuu uacaagauca uuuggcaaaa 180
aaacuauuau ugauuuucug ggaaauaguu ccaaaaacaa auccagaagg uaaacuacua 240
caagagauga uuuugguaug ugaugccuau agaaaagauc ugcaacaccc aaaugaauuu 300
uugagagguu cuacacuucg cuucuugugc aaacugaagg aaccagaauu guuggaacca 360
uuaaugccca guauuagagc uuguuuggau cauaggcaca gcuaugugag gaggaaugcu 420
guacuggcaa uuuuuaccau uuacaaaaau uuugaagccc ucauuccaga ugcuccugaa 480
cugaucucca auuauuugga uggugagcaa gacaugucuu guaaaagaaa ugcguuuuua 540
augcuucuuc augcugacca agaaagggcg uugucguauu ug 582

<210> SEQ ID NO 134
<211> LENGTH: 458
<212> TYPE: RNA
<213> ORGANISM: Diabrotica virgifera

<400> SEQUENCE: 134
uuggcaaaaa ggaaaugagg auauugaugg uaggacucga ugcagcuggu aaaaccacaa 60
uuuuauauaa acuuaaauua ggagaaauug uaacaacuau uccaacaauu ggauuuaaug 120
uggagacugu agaauauaag aacauuaguu uuacaguaug ggauguaggu ggucaagaua 180
aaauuaggcc auuguggaga cacuauuucc aaaacacaca aggccuaauu uucguaguag 240
acaguaacga cagggaacgu aucacugagg cuaaagauga auuaaugcgu auguuggccg 300
aagaugaacu uagagaugcc guacuucuca uuuucgccaa caaacaagau uugcccaaug 360
caaugaacgc ugcagaaauc accgacaaac ucggucucca uucacuacgc aaccgcaacu 420
gguacauuca agcuaccugu gcaacuagcg gagauggu 458

<210> SEQ ID NO 135
<211> LENGTH: 592
<212> TYPE: RNA
<213> ORGANISM: Diabrotica virgifera

<400> SEQUENCE: 135
ggucgcgaaa gaacagaaag auuuuuugac cguaucugcc gauggaugcg uacaaguaac 60
aaaaccucuc gaccgagauc cgccuuucgg uagcccaaca cgacaagucu ucaucuaugc 120
ucgugauaau gauggaggca caaauucauu guuggccacu gcagaaauug aaauuauuuu 180
aauagauaua aacgauaaug cucccuuuuu aaauguuaca gaaauuguuu auuaugaaaa 240
ccaggaucca gguuuuauag guaaccuaag ugccgaugau uacgaugguc cugauaaugg 300
accuccguuu gcuuuucgau uaucagacac ugcuucagau aguauuagau cgaaauuuuc 360
cauuaucgga aaccagcuuu ucgcuuuaga aauguuugau agagaagagc aaaaauauua 420
ugacauugcc auugacauua cagauagugg aguaccucca cuaacaggaa cuaguauucu 480
uagaguuaua aucggagaug uaaaugauaa uccagcuaca gacggaaaca gcacgaucuu 540
uguguauaag uacgucaaug ggccagaaaa uuucauggaa aucggacgug ua 592

<210> SEQ ID NO 136
<211> LENGTH: 214
<212> TYPE: RNA
<213> ORGANISM: Diabrotica virgifera

<400> SEQUENCE: 136
gcauggggua ucauccaguu ggguuucaug ggguguauucu auuacauugg ggcuguggcu 60
uuagcagaag auauuccaga gguugaguuu aagggcgauu uagacaaauu uuauagcgac 120
gucaacacgg guuucacaca gaaugcuuac aacugcugga uugcugcucu ccuauaccug 180
auaacauuag caguaucagc ucaccaauuc uggg 214

<210> SEQ ID NO 137
<211> LENGTH: 459
<212> TYPE: RNA

<213> ORGANISM: Diabrotica virgifera

<400> SEQUENCE: 137
uagaugccgc agguaaaacc acaaucuuau acaaauugaa gcuuggugaa aucguaacua 60
caauaccaac caucggcuuc aauguagaaa ccguugagua caagaauaua ucuuucacgg 120
uaugggaugu agguggccag acgagaauca gaaaacucug gagacacuau uucgccaaca 180
cugauggacu cauuuuugug guugauucca acgaccgaga ccguaucgcg gaagccgaag 240
aagaauugca caauauguua ggagaggacg auuuaagaga cugcauuuug uuaauauucg 300
ccaacaaaca agauuuaccg aacucgaugu ccacugcuga auugaccgau aagcuuaagu 360
ugcacacuuu gaagaauagg aggugguaca uacaagccac augugcuacu caagggaaug 420
guuuguacga aggacuagau ugguugucga augaauugg 459

<210> SEQ ID NO 138
<211> LENGTH: 536
<212> TYPE: RNA
<213> ORGANISM: Diabrotica virgifera

<400> SEQUENCE: 138
gcuacccuag cguccacugu aacacugauu uuugcccucu acuacugccu cacgggaaaa 60
ggagagcaag uuaguuuagc augguuauug uugaaugugu cuccccacau gugggcaggu 120
cuaggaauug gccuugcugu aucauuauca guuguaggag cugcugcagg aauucacacu 180
acaggaguca guaucguagg agcuggugu aaagccccca gaaucaaaac caaaaauuua 240
auuucuauua uuuucuguga agcuguggcu aucuaugggu uaauuauggc uauaguacuc 300
uguggaaguu ggaagaauuu cgauguagac cuauucaacc ucaaaacuca uaacuuugcu 360
caaaaccauu auggaucaca uguuauuuuu ggauccgguu uaacuguugg auuuguaaau 420
cuauuaugug gauuuugugu uggaguaguu gguucuggug cagccauuuc ugaugcagcc 480
aauucaucau uauucgucaa aauuuugauu auugagauuu uuggaagugc cauugg 536

<210> SEQ ID NO 139
<211> LENGTH: 547
<212> TYPE: RNA
<213> ORGANISM: Diabrotica virgifera

<400> SEQUENCE: 139
accuuauggg aaagcgugug gacuuuucug cacguacugu caucacacca gaucccaauu 60
uacguaucga ccaaguagga gugccuagaa guauugcuca aaacaugacg uuuccagaaa 120
ucgucacacc uuucaauuuu gacaaaaugu uggaauuggu acagagaggu aauucucagu 180
auccaggagc uaaguauauc aucagagaca auggagagag gauugauuua cguuuccacc 240
caaaaccguc agauuuacau uugcagugug guuauaaggu agaaagacac aucagagacg 300
gcgaucuagu aaucuucaac cgucaaccaa cccuccacaa gaugaguaug augggccaca 360
gagucaaagu cuuacccugg ucgacguucc guaugaaucu cucgugcacc ucucccuaca 420
acgccgauuu ugacggcgac gaaaugaacc uccaugugcc ccaaaguaug gaaacucgag 480
cugaagucga aaaccuccac aucacuccca ggcaaaucau uacuccgcaa gcuaaccaac 540
ccgucau 547

<210> SEQ ID NO 140
<211> LENGTH: 564
<212> TYPE: RNA
<213> ORGANISM: Diabrotica virgifera

<400> SEQUENCE: 140
cggaucucua uuugggggau caagucguau ugaagaugca guggaauguu acacaagagc 60
ugcaaaccuu uuuaaaaugg ccaagagcug ggaugcugcc gguaaagccu uuugugaggc 120
ugcuaauuug cauuccagaa cuggugcucg ucaugacgcu gccacuaauu auauagaugc 180
ugcaaauugu uacaaaaaag ccgauguauu ugaggcugua aacugcuuua uaaaagcuau 240
agacauuuau accgaaaugg gucgcuuuac aauggcugca aaacaccauc agacuauugc 300
agaaauguau gagacugaug cuguggacau cgaaagggcu guucaacacu augaacaggc 360
ggcugauuac uucagaggag aagaaagcaa ugcuucccgcc aauaagguguc uucuuaaagu 420 ggcucaauau gcagcccaac uugaaaacua ugaaaaagca gugggaauuu aucaagaagu 480
ggcuuaugca gcucuggaaa gcucucuuuu aaaauacagu gcaaaggaau acuuauucag 540
agcugcccuu ugucaccuuu gugu 564

<210> SEQ ID NO 141
<211> LENGTH: 564
<212> TYPE: RNA
<213> ORGANISM: Diabrotica virgifera

<400> SEQUENCE: 141
ugcugauugg agauucagga guaggaaaau cuugucuucu acugagauuu gcagaugaua 60
ccuacacaga aagcuauauu aguaccauug gcguagauuu uaaaaucagg acaaucgauu 120
uagauggaaa gacaauuaaa uugcaaauuu gggauacagc aggucaggaa agguuuagaa 180
cgauuacauc aaguuauuac cgaggagcac augguauuau uguagugual gauugcacag 240 accaagauuc auucaauaac guuaaacagu ggcucgaaga aaucgaccgu uaugcgugug 300
acaauguaaa caaauuacug guagggaaua aaagcgauuu gacaacuaag aaaguugucg 360
acuucacuac agccaaggag uaugccgacc aauuggguau accauuuuug gaaaccucag 420
cuaagaaugc aaccaaugua gaacaggccu uuaugacuau ggccgcugaa auaaaaaaua 480
gaguaggacc uccaucuucu gcgguagacc aaggaaauaa gguuagguuc gaucaaaguc 540
gcccagucga aacaaccaaa uccg 564

<210> SEQ ID NO 142
<211> LENGTH: 502
<212> TYPE: RNA
<213> ORGANISM: Diabrotica virgifera

<400> SEQUENCE: 142
gagcuauagu ggacugcggg uucgaacauc cuucagaagu ucaacaugaa uguauuccuc 60
aagcugucau uggcauggau auucugugcc aagcuaaauc cgguauggga aaaacggcug 120
uuuuuguauu agcuacacuc caaguaauag auccuacaga aaauguugua uauguucucg 180
ucaugugcca uaccagagag uuagccuucc agauaagcaa agaguacgaa cguuucagua 240
aauauaugcc caauauuaaa guaggggucu ucuuuggugg cuugccuauc cagaaagaug 300
aggaaacguu aaaaaaauaau ugcccgcaua ucguuguggg uacuccagga agaauuuuag 360
cauuggucag aucgaaaaaa cuuaaucuca aacaucuaaa gcauuuuauu uuggaugaau 420
gugauaaaau guuggaguua uuagacauga gacgugaugu ucaagaaaua uaucguaaca 480
cuccccacga aaaacaaguc au 502

<210> SEQ ID NO 143

<211> LENGTH: 505
<212> TYPE: RNA
<213> ORGANISM: Diabrotica virgifera

<400> SEQUENCE: 143
ugguagauuu ggcuaaccuc guauauuggu guuuaggucu uaauauuccg uacguuaguu 60
ucuaugauua uaaagguaau uuaaaaaagc augaagagaa guugcaacaa auuguagaau 120
ccagaaaauc agagaauauc aacauaauuu ggcacaccca ugcagaacaa aggcauaaaa 180
auggauuuuu ggguccaaaa auccacguaa aaguguuaac acacgcggac ggaaagcaaa 240
guauaguaaa uguuacuaaa aaauuagcuc uaaauaaaga aaaagacauu aguaaagaaa 300
aaauuaguga auuacuauua aggcaguaug aauuuccaga uccagaaaug gcuauuauuu 360
guggaaagaa acugaacauu uauaauuauc cuccuuggca guuaagacuc acagaauucu 420
uuaaagucaa caaagucaac aacaucacau ucccaguguu uguggaaaaa uuggaaaagu 480
acagcaaaug ugaacagagg guggg 505

<210> SEQ ID NO 144
<211> LENGTH: 410
<212> TYPE: RNA
<213> ORGANISM: Diabrotica virgifera

<400> SEQUENCE: 144
aaccagggau cuauuugccc gcaaguuuaa aaaacguggu guaauuccac uuuccacaua 60
uuugagaguc uacaaaguug gagauauugu agauaucaag gguaauggug caguucaaaa 120
ggguaugccc cacaaagugu accaugguaa gacaggacgu guuuucaaug uuacugcaca 180
ugcauuaggu guaauuguaa acaaaagggu ucgaggaaga aucaucccca aaagaaucaa 240
ucuccguauu gaacauguaa accacuccaa gugucgucaa gacuucuugc aaagaguaaa 300
auccaacgaa aagcuacgua aagaagcuaa agaaaagaac auuaaaguag aacuuaggag 360
acaaccugcc caaccuaggc cagcacauau uguuagcgga aagguuccag 410

<210> SEQ ID NO 145
<211> LENGTH: 467
<212> TYPE: RNA
<213> ORGANISM: Diabrotica virgifera

<400> SEQUENCE: 145
ugaugguaau agagugcugg cuaaauacua cgauaaagau auauuuccua cagcaaaaga 60
gcagaaagcu uuugagaaaa auuuguucaa uaaaacucau agggcagacg cagaaauuau 120
cauguuggau gguuuaacuu guguguauag aaguaaugua gauuuauucu uuuauguuau 180
gggcaguuca caugaaaaug agcuaauuuu aaugaguguu uuaaauugcu uguaugacuc 240
aguaagucaa auauugaaga aaaauaugca aaaacgagcu gucuuggaau cacuagauau 300
uguuaugcug gcuauggaug aaauuguuga uggaggaaua auuauagauu cugauucaag 360
uucaguagua ucuagaauag cauuaaggac ugaugauauu ccauuaggag aacaaacugu 420
agcucaggua uuccaaacgg ccaaagaaca gcugaaaugg ucauugc 467

<210> SEQ ID NO 146
<211> LENGTH: 368
<212> TYPE: RNA
<213> ORGANISM: Diabrotica virgifera

<400> SEQUENCE: 146
caccgaagaa caaauugcug aauucaaaga agcuuucuca cuauucgaua aagaugguga 60
ugguacaauu acgacuaaag aauuaggaac aguaaugaga ucucuaggac aaaauccaac 120
agaggcugaa uuacaggaua ugaucaauga aguagaugcc gaugguaacg gcacgaucga 180
uuucccagaa uuuuuaacga ugauggcacg uaaaaugaaa gauaccgaua gugaggaaga 240
aauucgugaa gcauuccgag uguucgacaa agacggcaau gguuucaucu cagcagcaga 300
auugcgccac gucaugacca acuuggguga aaaauugaca gacgaagaag ucgaugaaau 360
gauucggg 368

<210> SEQ ID NO 147
<211> LENGTH: 430
<212> TYPE: RNA
<213> ORGANISM: Diabrotica virgifera

<400> SEQUENCE: 147
uucgcacaag augacuuugg uggugaaaau guugaucuau augacgaugu aauauccgcu 60
ccuccuggaa auaaugacaa cccaggugau ucaaaucauc augcuccucc uggugcuggu 120
gaagauggug gagguaauuu uguuggguca ggaggagcac ccaauaauau aaauucuucu 180
ggaagaagac aucagcugua uguuggaaau cugacuuggu ggacaacuga ucaagauaua 240
gaaaaugcag ugcaugauau aggggguaacc gacuuccaug aaguuaaguu uuuugaacac 300
agagcaaaug gucaauccaa gggauucugu gucauaucuu ugggaucuga gggaagcaug 360
agacucugcc uggaacuccu aucuaaaaaa gagaucaaug gccaaaaucc ccuuguuacc 420
cuucccacaa 430

<210> SEQ ID NO 148
<211> LENGTH: 505
<212> TYPE: RNA
<213> ORGANISM: Diabrotica virgifera

<400> SEQUENCE: 148
uaggaauggc auuuucaggc uuaauagcug augcaaggca aaucguugag auugcuagaa 60
aagaagcauc aaauuauaga caucaauaug guucaaauau uccucuuaaa uaccuaaaug 120
auagaguaag cauguacaug caugcauaca cuuuauacag ugcuguuaga ccauuugguu 180
gcagugucau cuuggccagu uaugaagaua gugacccauc uauguaucug auugauccau 240
cuggaguuag cuauggauac uuuggaugug cuacagguaa agcaaaacag ucugcaaaga 300
cugaaauaga aaaauugaag augggggaauc uaacaugcaa agaacuuguu aaagaagcag 360
ccaaaaucau uuauuugguc caugaugagc ugaaggauaa gaauuuugaa cuggaacuuu 420 caugggguaug caaagauacg aaugguuuac auaccaaagu gccugaauca guguuugcug 480
augcagaaaa agcugccaaa caagc 505

<210> SEQ ID NO 149
<211> LENGTH: 548
<212> TYPE: RNA
<213> ORGANISM: Diabrotica virgifera

<400> SEQUENCE: 149
uccaucuaga ggagcccaaa ugaugaugaa auccaggcua aagggagccc aaaagggaca 60
uaguuuauua aagaagaaag cugaugcuuu acaaaugaga uuuagaauga uuuugaacaa 120
aauuauugag accaaaacuc ucaugggguga aguaaugaaa gaagcugccu uuucuuuagc 180
ugaagcaaag uuugcaacug gugacuucaa ucaaguuguu cuucaaaaug ucaccaaggc 240

-continued

```
ucaaauaaaa auaagaacua agaaagacaa cguugcuggu guuacuuuac caguguuuga    300

augcuaccaa gaugguacag auacauauga guuggcuggu uuggcuaggg gaggucaaca    360

auugacaaaa cucaagaaga auuaucaaag ugcuguuaaa cuguugguug aauuagccuc    420

uuugcaaacu ucuuuuguaa cucuugauga uguaaucaaa auaacaaaca gaagagucaa    480

ugccauugaa cauguuauca uuccaagaau agagcguacu uuggcuuaca ucauauccga    540

acuggacg                                                             548
```

<210> SEQ ID NO 150
<211> LENGTH: 521
<212> TYPE: RNA
<213> ORGANISM: Diabrotica virgifera

<400> SEQUENCE: 150

```
gaucuggaag cgcuaguugc aaaaguagac gaaaugagaa cccaaagagc caugcuaugg     60

gcucaacuuc gagaaucuau ucaccaagac gauauuacaa guucccuugu aacgaaacaa    120

ccaaaucagu cgcuggaaca gcuguuccag caagaacuuc aaaagcauca aaaucugauu    180

ucguugauug aacaaaacac cucggcacaa gaaaacauua agagcgccuu agucgauucu    240

uacgcuuacg cuguaaauuc aagaaaauac auccaagaua uacuccaaaa gagaaccaca    300

accauaacgu cacugauagc aucguucgac ucuuacgaag acuuauuggc aaaagcuaac    360

aaagggauag aguuuuacuc aaaacuugaa acgaacguau ccaaguuacu gcaaagaaua    420

aggaguaccu gcaaaguuca acaagaagag cgagaucaga ugaugucgac ugcgcaagug    480

ccucaauggg agagucauac gucacuugcc gcuccuaaac u                        521
```

<210> SEQ ID NO 151
<211> LENGTH: 633
<212> TYPE: RNA
<213> ORGANISM: Diabrotica virgifera

<400> SEQUENCE: 151

```
auggcggacg augagagaaa gaaacuggag gaggaaaaga agaggaaaca ggccgaaauu     60

gaacgcaaaa gggccgaggu cagggcucgu auggaagagg ccucaaaagc caagaaggcc    120

aagaaagguu ucaugacccc ugagagaaag aagaaacuua gguuacuguu gagaaagaaa    180

gccgccgaag aauuaaagaa agaacaagaa cgcaaagcag ccgaaaggag gcguaucauu    240

gaagaaaggu gcgguaaacc caaacuuguc gaugacgcaa augaaggccc auuaaaacaa    300

guaugugagg gauaucacag acguauugua gaccuagaaa auaagaaauu ugaccucgaa    360

aaagaagugg aauucagaga uuuucagauc uccgaauuga acagccaagu aaacgaccuu    420

agaggcaaau ucgucaaacc aaccuugaag aagguaucca aauacgaaaa caaauucgcc    480

aaacuucaaa agaaggcagc ugaauuuaac uuccguaacc aacucaaagu ugucaagaag    540

aaagaauuca ccuuagaaga agaagacaaa gaaaagaaac cagacugguc aaagaaggga    600

gacgaaaaga agguacaaga ggcugaagca uga                                 633
```

<210> SEQ ID NO 152
<211> LENGTH: 603
<212> TYPE: RNA
<213> ORGANISM: Diabrotica virgifera

<400> SEQUENCE: 152

```
augugugaag aagaaguugc cgcuuuaguc guagacaaug gauccgguau gugcaaagcu     60

gguuuugcug gggaugaugc accucgugcu guauucccuu caauuguugg acgcccaaga    120
```

caucagggug ugaugguagg aaugggacaa aaagauuccu auguagguga ugaagcucaa 180
aguaaaagag guauccuuac cuuaaaauac cccaucgagc acggaauagu cacaaacugg 240
gaugauaugg agaaaauuug gcaucauaca uucuacaaug aacucagagu agccccagaa 300
gaacacccug uucuguugac agaagcuccu cucaacccca aggccaacag ggaaaagaug 360
acacaaauaa uguuugaaac uuucaacacc ccagccaugu auguugccau ccaggcugua 420
cucuccuugu augcaucugg ucguacaacu gguauugugu uggauucugg ugauggugua 480
ucccacacug ucccaaucua ugaagguuau gcucuuccuc augcaauccu ucguuuggac 540
uuagcuggua gagacuugac ugauuaccuc augaaaauuu ugacugaacg uggcuacucu 600
uuc 603

<210> SEQ ID NO 153
<211> LENGTH: 2742
<212> TYPE: RNA
<213> ORGANISM: Diabrotica virgifera

<400> SEQUENCE: 153
augccacuuc gauuagauau aaaaagaaag cuaacagcuc gcucagaccg gguaaaaugu 60
guggaucuuc acccuacaga accuuggaug cuguguucuc uuuacagcgg aaauauaaac 120
guuuggaaca ccgaaaauca gcaacugguu aagacuuuug aaguauguga uguaccuguu 180
cggacagcua aguuuuugcc caggaagaac uggauaguca gugggucuga ugauaugcag 240
auucgaguuu ucaauuacaa uaccuuagau cggguacauu cuuuugaggc ucauucggau 300
uaugugagau guauugucgu acacccuaca caaccuuaua uauuaacaag uagugaugau 360
augcuuauca agcuuuggaa uugggaaaaa gcaugggcuu gucagcaagu uuucgaagga 420
cacacucauu auauuaugca aaucgccaua aauccaaaag acaacaacac auuugccagu 480
gcaucccuag auagaacauu gaaaguaugg caauugggag cguccacagc gaauuucaca 540
cuagaagguc augagaaagg cguuaacugu guggacuauu aucacggugg agauaaaccu 600
uauuuaaucu caggcgcuga ugauagauua guaaaaaucu gggauuauca aaacaaaacu 660
uguguucaaa cuuuggaagg acaugcucaa aauguaaccg cugcauguuu ccauccagaa 720
cuuccuguag cucuuacugg aagugaagau gguacuguca gaguguggca ugccaacacc 780
cauagguuag aaaguagcuu aaauuauggc uuugaaagag uauggacuau uuucugccua 840
aagggaucca auaacguggc auuggguuau gaugaaggua gcauuuuggu uaaaguuggu 900
agagaagaac cagcuguuag uauggaugcc aguggaggca aaauuauuug ggccagacac 960
ucugaacuuc aacaggcaaa ucucaaggcg uuagcugaag gugcggaaau aagagaugga 1020
gaacgccuuc caguuucugu aaaagauaug ggugcuugcg agauauaccc ucagacaauu 1080
caacacaauc ccaauggccg uuuuguuguu gucugugggg auggagaaua cauaaucuac 1140
acagcaaugg cuuuaagaaa caaagcguuu gguagcgcac aagaauuugu gugggcucaa 1200
gauuccagcg aauaugccau cagagaaucc ggaucuacua ucagaauuuu uaagaauuuc 1260
aaagagaaga agaauuuuaa guccgauuuu ggagcugaag guauauacgg uggauaccuu 1320
uugggaguca aaucgguuuc ugguuugacu uucuaugauu gggaaacucu cgauuuaguc 1380
agaagaaucg agauacaacc aaaagcaguu uacuggucag auaguggua auuaguaugu 1440 uuggccacag aagauagcua cuuuauucuu ucuuaugauu cugaugaagu ucaaaaagcc 1500
agagauaaca aucagguugc ggaugaugga guagaaucgg cuuucaaucu ucuaggugaa 1560
auaaacgaau cagugcgaac uggucucugg guaggcgacu guuuuaucua cacgaauucu 1620
guuaaucgua ucaacuacuu cguuggaggu gaacugguua caauugcuca uuuggaccgg 1680
ccuuuguaug ucuugggaua ugugccuaaa gacgauagau uauaccucgu agauaaagag 1740
uugcgcguag uaagcuacca auuacuucuu ucuguucuug aauaucaaac ugccgucaug 1800
agaagagacu uuccaacagc agacagagua cuuccgucca uuccuaagga gcacagaacg 1860
agaguggcac auuucuuaga aaagcaaggc uucaaacagc aagcuuuggc cguaaguaca 1920
gauccagagc acagauucga gcuggcagua gcauuagagg aucuuaauau agccaaaacu 1980
cuagcucaag aagcgaacag uccgcaaaag uggaaucaac uagcagaauu ggcagcugcu 2040
acuaauaaug uaagcguagc caaggaaugu augcaaaaag cgcaagauua uggaggcuug 2100
uugcuucuug cuacgagcuc cggugaugaa aauuuagucc guacucuagg agaaacgaca 2160
caagcugaaa gcaaacauaa cuuagcauuu uugucacacu uguuaguagg ugauuuaaac 2220
aaaugucuag acauucuuau uaauaccggu agauugccag aagcugcauu uuucgccaga 2280
ucuuaccuuc cugauaagau uacagaaguc guggaacugu ggaagacuca guuaucuuca 2340
gucaaucaaa aagcuggaca gagccuugcc gauccuaaaa acuacgaaaa ucuguucccu 2400
gguuuacaag aggcggugga agcucagaaa uuuuuggaac agcagaauaa agguuuagcg 2460
cccgcaagag uugccaccac cauuccuccu aaucacgaca ggaauguugu agccgaaguu 2520
caagcacaau cgaaacacga uguaccauca uuuaguucuu cguuuauuuc aucagaaaua 2580
gaagcacaaa caaggaguuc ugcuaaaccu gaagaaucuu caaacauuau acagcuggac 2640
caagaugacg acgauaucga uuuagauuug gacgguguaa auaucgauga gaacauugac 2700
acgacggaua ucaacaucga ugaugauuug cugagugauu ga 2742

<210> SEQ ID NO 154
<211> LENGTH: 1146
<212> TYPE: RNA
<213> ORGANISM: Diabrotica virgifera

<400> SEQUENCE: 154
augcagaucu uuguaaaaac acucacuggu aaaaccauca cccucgaggu ugaaccauca 60
gauaccaucg agaaugucaa agcuaaaauu caagacaaag aagguauucc accagaucaa 120
cagagauuaa ucuuugcugg aaagcaguua gaagauggcc guacucucuc agacuacaac 180
auucagaaag aaucuacacu acacuuagug cuucgucuua gaggagguau gcacaucuuu 240
guaaaaacuc ucacugguaa gaccaucacc cuugagguug aaccaucaga uaccaucgag 300
aaugucaaag cuaaaauuca agacaaagaa gguauuccac cagaucaaca gagauuaauc 360
uuugcuggaa agcaguugga agauggccgu acucucucag acuacaacau ucaaaaagag 420
ucuacccucc auuugguacu ucgucuuaga ggagguaugc agauuuuugu uaaaacuuua 480
acuggaaaga ccaucacccu ugaaguagaa ccuucugaua ccaucgaaaa ugucaaagcc 540
aaaauucaag acaaagaagg uauuccacca gaucaacaaa gauuaaucuu ugccggaaag 600
caauuggaag auggucguac acucucagac uacaacauuc aaaaggaauc uacccuccau 660
uugguacuuc gucuuagagg agguaugcaa aucuuuguaa aaacacucac ugguaagacc 720
aucacccucg agguugaacc aucagauacc aucgagaaug ucaaagcuaa aauucaagac 780
aaagaaggua uuccaccaga ucaacagaga uuaaucuucg cuggaaagca guuggaagau 840
ggccguacuc ucucagacua caauauucag aaagagucua cccuccauuu gguacuucgu 900
cuuagaggag guaugcaaau cuuuguaaaa acucucacug guaagaccau cacccucgag 960

```
guugaaccau cagauaccau cgagaauguc aaagcuaaaa uucaagacaa agaagguauu   1020

ccaccagauc aacaaagauu aaucuuugcc ggaaagcagu uggaagaugg ccguacucuc   1080

ucagacuaca acauucaaaa agagucuacc cuucacuugg uacuucguuu aagaggagga   1140

aauuaa                                                              1146
```

<210> SEQ ID NO 155
<211> LENGTH: 1131
<212> TYPE: RNA
<213> ORGANISM: Diabrotica virgifera

<400> SEQUENCE: 155

```
augugugacg acgauguagc ggcucuuguc gucgacaaug gcuccggaau gugcaaagcc     60

gguuucgccg gugaugacgc cccucgugcu gucuuuccau ccaucguagg ucgucccaga    120

caccaaggug ucaugguggg uaugggucaa aaagacuccu acguaggaga cgaagcccaa    180

agcaaaagag guauccucac cuuaaaauac cccauugaac acggaauuau cacuaacugg    240

gacgauaugg aaaagaucug gcaucacacc uucuacaaug aacuuagagu agcccccgaa    300

gaacauccca uucuuuugac ugaagcucca cuuaacccaa aagccaacag agaaaagaug    360

acucaaauca uguuugaaac uuucaauacc ccugccaugu auguugccau ucaagcugua    420

uugucucugu acgcuuccgg ucguaccacu gguauuguac uugauucugg agauggugua    480

ucccacacag uacccaucua ugaagguuac gcucuccccac acgccaucuu gcguuuggac    540

uuggccggua gagacuugac ugacuaccuu augaagaucu uaaccgaaag agguuacucu    600

uucaccacca cagcugaaag agaaauaguu cgugacauca aggaaaaauu gugcuaugua    660

gcuuuggacu ucgaacagga aauggccaca gcagccagcu ccaccuccuu agaaaagagu    720

uaugaacuuc cugacgguca agucaucacc auugguaaug aaagguuccg uugcccugaa    780

gcucucuucc aaccuuccuu cuuggguaug gaaucuugcg guauccacga aacugucuac    840

aacuccauca ugaagugcga ugucgacauc cguaaagacu uguacgccaa cacuguccuu    900

ucuggaggua ccacaaugua cccugguauu gccgaucgua ugcaaaagga aaucacugcc    960

uuggcuccau caaccaucaa aaucaagauc aucgcucccc cagaaagaaa guacuccguu   1020

uggaucggug gcuccaucuu ggccucccuc uccaccuucc aacagaugug gaucuccaaa   1080

caagaauacg acgaauccgg cccuggaauu guucaccgca aaugcuucua a            1131
```

<210> SEQ ID NO 156
<211> LENGTH: 2640
<212> TYPE: RNA
<213> ORGANISM: Diabrotica virgifera

<400> SEQUENCE: 156

```
auggguacuu uuaaaagaga uacucaugau gaggacgggg gaucaagugc uuuucaaaau     60

cuggagaaaa cuacuguuuu gcaggaagcu agaguuuuua augaaacuag uguaaaucca    120

agaaaaugua caccgauacu aacaaaacug uuguacuuau ugaaccaggg ugaaacuuua    180

agugccaaag aggccacaga uguuuucuuu gccaugacca aacuguucca aucaaaagau    240

guaauauuga gaaggauggu uuauuuggga auuaaagaac ucaguucugu ugcugaugau    300

gucauuauug uaacauccag ucuuacaaaa gauaugacug guaaagaaga cauguacaga    360

gcagcugcua uaagagcauu augcaguauu acugaugcua cuaugcuuca agcuauagaa    420

cguuauauga agcaagcuau uguagauaga aacgcagcug ucaguucagc agcacuaauu    480
```

-continued

```
aguucauuac auaugagcaa auuagcucca gauguaguaa aaagaugggu aaaugaagcu    540
caggaagcag uaaauaguga uaaugcaaug guacaguauc acgcauuagg ucuucuauac    600
cauauuagga agacugauaa gcuagcagug acaaaauuga uuuccaagcu gaauucaaug    660
gguuuaaaga gcccuuaugc uuuguguaug uugauaagaa ucacugcaaa acuuuuagaa    720
gaagaggacc aagagucacu ccucaacucc ccauauacaa uaauauuuac aaugggcuua    780
aggaacaaau cugaaauggu gguguaugaa gcugcacaug ccaugguuaa ccugaaguuc    840
acgaguagua augugcuagc acccgcuaua aguguucuac aacuauuuug uggaucuccu    900
aaagccacac ucagauuugc ugcuguuaga acuuuaaauc aaguggccac cacccacccu    960
gcgucaguga cagcuuguaa uuuggaucua gaaaauuuga uuacugaucc uaauagguca   1020
auugcuacac uggccauuac uacucuuuug aaaacaggug ccgaaucuuc uguugacaga   1080
cuaaugaaac aaaucgcuac uuuuguaucu gaaaucagug augaauuuaa agugguuguc   1140
auucaggcaa uuaagguauu agcuuugaaa uuuccaagga aacauagcac gcuuaugaau   1200
uuccuauccg ccauguuaag agaugaggga gguuuagaau auaaagcauc cauagcagau   1260
accauuauaa cccuaaucga agauaauccc gaagcuaaag aaucugguuu ggcgcaucuu   1320
ugcgaguuca uugaagacug ugaacauguu ucuuuggcug ugagaaucuu gcauuuguua   1380
ggaaaggaag gacccaagac caaacaacca ucgagauaca uccguuuuau cuacaaucgc   1440
gucauauugg aauguccuuc uguaagagcu gcugcagucu ccgccauggc acaauucgga   1500
gccucuuguc ccgauuuguu agaaaauauc caaauauuac uuucgaggug ucagauggau   1560
ucagacgaug aaguuaggga cagagcuaca uauuauagua auauacuuaa caaaaaugau   1620
aaaaguuuau acaacaauua cauuuuggau ucuuugcagg uuucaauucc uucacuagaa   1680
agaucgcuua gagaauacau ucaaaaucca acugacgaac cauuugacau uaaguccgua   1740
ccuguagcag cagugccaac agcagaagaa cgagaaguua aaaacaaauc ugaaggacug   1800
cuagucucuc aagguccagu ccgaccuccu ccggugucua gagaagaaaa cuucgccgaa   1860
aaacuuagua acguuccggg uauacaacag uuaggaccuu uguucaaaac uuccgacguc   1920
guugaacuca cugaaucuga aacagaguau uuuguccgcu guaucaagca cuguuucaaa   1980
caucacaucg uccuccaauu cgauugucug aauaccuugc cagaccagcu uuuagaaaac   2040
guuagagugg agauagacgc cggugaaacc uucgaaauuu uggcagaaau accuugugaa   2100
aaguugcacu auaacgaaac cgguaccaca uauguaguag uuaaguugcc ugaugaugau   2160
cuccccaacu cuguugguac guguggagcc guguugaagu ucuuagugaa agauugugau   2220
ccaucaacgg gaauaccaga uucugaugag gguuacgaug augaauauac acuggaagac   2280
aucgaaauaa cauuagggga ccaaauucaa aaaguaagca aaguaaauug ggcugcagcc   2340
ugggaagaag cugcagcuac uuauguagaa aaagaggaua cauacuccuu gaccaucaau   2400
acgcuaagug gcgcuguuaa gaauauuauu caguucuugg gauuacagcc ugcggaaagg   2460
acugacagag uaccggaggg uaaaucuacg cacacauuac uucuugcugg uguauucagg   2520
ggagguauug acauacuagu aagagcgaaa cuagcuuugg gcgaaugugu uacgaugcaa   2580
cuaacaguca ggucgccaga uccugacguu gcugagcuua uaacuucaac uguagguuaa   2640
```

<210> SEQ ID NO 157
<211> LENGTH: 651
<212> TYPE: RNA
<213> ORGANISM: Diabrotica virgifera

<400> SEQUENCE: 157
auggcggcaa acagaacugg accugcucag agaccaaaug gcgcuaccca aggaaagaua 60
ugucaguuca aacugguccu acuaggcgaa agugccgucg guaagucgag uuugguacug 120
agguucguca aaggacaguu ccacgaauac caggagagua ccauaggagc agcuuuccuu 180
acacaaacca uaugccucga cgauacaacu guuaaauuug aaauuuggga cacagcgggu 240
caagaaaggu accacaguuu agcuccuaug uacuauaggg gcgcacaggc agcuauaguc 300
gucuacgaca uaaccaauca agacacauuc ggcagggcga aaacgugggu gaaggaacuu 360
caaaggcagg ccaguccgac gaucgugaua gcuuuggccg gcaacaagca agauuuggcc 420
aacaaacgua ugguagaaua cgaagaggcg cagacguaug cugacgaaaa cggcuuacuu 480
uuuauggaaa cuuccgcaaa gacggcaaug aacgucaacg auauauuuuu agcaauagcu 540
aagaaacugc ccaagaauga acaaaccaca ggucaaggcg gcagugccca aggcaggcgg 600
cuagcggagg gcgauucggg cgccaaggca cccggaaauu guugcaagug a 651

<210> SEQ ID NO 158
<211> LENGTH: 279
<212> TYPE: RNA
<213> ORGANISM: Diabrotica virgifera

<400> SEQUENCE: 158
augaaguuuu uaagaucgac agugugcuac auugccaucu uggcaauucu cuuuacccuc 60
ugugccgaug agguugaagg aaggagaaaa auuuugaugg ggcgaaaaag cauuaccagg 120
acauaucuuc guggaaaugc uguuccugcg uaugugauaa uaauccuugu aggaauuggu 180
caaaucaucc ugggagggau auuguacguu gcauugagga agaagaucau ugcugcaccu 240
guaacggcau cauaugcagu ggcuagacaa gaaccauaa 279

<210> SEQ ID NO 159
<211> LENGTH: 474
<212> TYPE: RNA
<213> ORGANISM: Diabrotica virgifera

<400> SEQUENCE: 159
augcagaucu ucguuaaaac cuuaacgggu aagaccauca cucuugaggu cgagcccuca 60
gauacuaucg aaaaugugaa agcuaaaauc caggauaaag aaggaauucc cccagaccag 120
caacgucuca ucuucgcugg aaaacaacuc gaagaugguc guaccuuguc ugacuauaau 180
auucaaaaag aaucaacccu ucacuuggug uugagauuga gaggaggugc uaagaaacgu 240
aagaagaaga auuacuccac ccccaagaaa aucaagcaca agaagaagaa gguuaaguua 300
gcuguauuga aauuuuauaa gguugacgaa aaugguaaaa uccaccgauu gagacgugaa 360
ugccccgcug aacaaugugg agcuggugu c uucauggcag ccauggaaga caggcauuac 420
uguggcaagu gcgguuacac ucuugucuuc uccaaaccag gagaugagaa auag 474

<210> SEQ ID NO 160
<211> LENGTH: 747
<212> TYPE: RNA
<213> ORGANISM: Diabrotica virgifera

<400> SEQUENCE: 160
augaugucca aagcagacac acaggaagau gccuccuucg ccaaauugga aaaucagauu 60
gcuaucauca aauacguaau acucuuuacc aacguuuugc aaugggcucu cggugcagca 120
aucuucgcuc uuugccuuug gcuacgauuc gaggagggca uucaagaaug gcuccagaaa 180
uuggauucag aacaauuuua caucggagua uauguacuua uagucgcuuc acugaucguc 240
augauugugu ccuuuauagg auguauuagu gcccugcagg agaguaccau ggcccuuuua 300
guguacaucg gcacccaagu gcucaguuuu auauucgguu uauccgguuc ggcgguucuu 360
cuggauaaca gcgccagaga uucccacuuc caaccgagga uccgagagag uaugcgacgu 420
cuuaucauga augcucauca cgaccaaucc agacaaacac uagccaugau ucaggaaaau 480
guugguugcu gcggagcuga uggcgcaaca gacuaccucu cucuucagca gccccuucca 540
agucagugca gagacaccgu uacuggaaac ccauucuucc acggaugugu agaugaacuc 600
accugguucu ucgaagaaaa auguguuggg auagcagguu uagcuauggc gauaugcaug 660
auuaacgucc uuaguauugu uuuaucuacg guacucaucc aggcauugaa aaaagaagaa 720
gaagcauccg auucauacag gagauag 747

<210> SEQ ID NO 161
<211> LENGTH: 375
<212> TYPE: RNA
<213> ORGANISM: Diabrotica virgifera

<400> SEQUENCE: 161
augucuggac guggcaaggg aggcaaagua aagggaaaag caaagucccg aucaaaucgu 60
gcugguuuac aauuuccugu aggucguauu caucguuuau ugagaaaagg aaauuaugcc 120
gaaagaguug gugcuggagc uccuguauac uuggcagcug uuauggaaua uuuagcugcu 180
gaaguuuugg aauuggcagg aaaugcagcu agagauaaca aaaagacccg uauaauuccu 240
agacauuuac aauuggccau aagaaaugac gaggaauuga acaaauuacu gucaggaguu 300
accaucgccc aagguggagu auugccuaau auacaagcag uacuguuacc uaaaaaaacu 360
gaaaagaaag cuuaa 375

<210> SEQ ID NO 162
<211> LENGTH: 864
<212> TYPE: RNA
<213> ORGANISM: Diabrotica virgifera

<400> SEQUENCE: 162
augaaguugg augguguaga ucugccccca ccaauuagcu ucgacauugc ggaagagcaa 60
ccguuaccac cuugccaaca gacguucuua uguaauggug auggaggauc cauagugcga 120
caguuucucg agcuguauuu cguaauauau gauucagaua auaggcaguc ccuucuucag 180
gcauaucacg aaaaagccac auuuucaaug acaauggccu acccguacgg cuauuccaaa 240
gacaguaaag gaguaucgug guugaauugg uaugccaccg auaauagaaa uuuauuacga 300
guucaagauc cagacagaag aaacaaguug uuaagacagg gacaaguugc uguaguuucg 360
uucuugcaag auaugccgca cacgaagcac gauauucaca guuuuacagu agauuugaca 420
guuuuuacac cccagauguu auguuugaca guggcuggua uguuuaaaga auugaaaagu 480
ggccacaaag uaccuccuuu aagauauuuc uucagaaccc uuguaauugu accugcugga 540
ucagguuuuu gcauagcaaa ugaagaacuu cacauaucca augcaacucc ggaccaagca 600
aaagaugcuu ucaagaccac cguuaaugua gcuccggcac cagccccugu gauuaccucu 660
ccuggaccca guauaccaca acccgcugug ccagaugaug cuacaaaaca agaaauggua 720
aaacagaugu ccgcaguauc cggaaugaau cucgaguggu cgcuacagug ucucgaagaa 780
acacaauggg acuaccagaa agccauaaug guauuccaaa auuuaaacgc acaagguguu 840
guaccacaag cagcauuuau uaaa 864

<210> SEQ ID NO 163
<211> LENGTH: 2868
<212> TYPE: RNA
<213> ORGANISM: Diabrotica virgifera

<400> SEQUENCE: 163
augacugcgg uagaacaacc uuguuacaca cuaauaaacu ugccaacaga uucggagccc 60
uacaaugaaa ugcaacuaaa aauggauuua gaaaagggug agguuaaagu aaaaauaaga 120
gcauuagaaa aaauaauuca caugauucug gcaggagaaa gguugccgaa uggauuucua 180
augaccauca uaagaaacgu uuuaccuuua caagaucauu uggcaaaaaa acuauuauug 240
auuuucuggg aaauaguucc aaaaacaaau ccagaaggua aacuacuaca agagaugauu 300
uugguaugug augccuauag aaaagaucug caacacccaa augaauuuuu gagagguucu 360
acacuucgcu ucuugugcaa acugaaggaa ccagaauugu uggaaccauu aaugcccagu 420
auuagagcuu guuuggauca uaggcacagc uaugugagga ggaaugcugu acuggcaauu 480
uuuaccauuu acaaaaauuu ugaagcccuc auuccagaug cuccugaacu gaucuccaau 540
uauuuggaug gugagcaaga caugucuugu aaaagaaaug cguuuuuaau gcuucuucau 600
gcugaccaag aaagggcguu gucguauuug gcaucauguu uagaucaagu aaauucauuu 660
ggagauauuc uacaacuggu caucguugag uugauauaua aggugugucu uuccaauccu 720
gcggaaagau cuagauuuau uagauguaua uauaacuugu ugaacucaag caguccugcu 780
gucagguacg aagcugcagg aacuuuaguc acccucucca gugccccgac ugccguuaaa 840
gcugcugcua gcuguuacau ugaguuaauu aucaaagaaa gugacaacaa uguaaaacuc 900
aucguuuugg acaggcugau agcacuuaag gagcuuccua aucacgaaag aauucugcag 960
gauuuaguua uggacauacu gagaguacuc ucugcuccug acuuagaagu ccgcaagaag 1020
acuuuaaguc uagcccuuga auuagucucu ucacggaaca uagaagaaau gguauuagua 1080
uuaacaaagg aagugaguaa aacgguagac agugaacaug aggauacagg aaaguacagg 1140
caauuguuag uaaggacucu acauucgugu uccauuaagu ucccagauau cgcacguagu 1200
guuauaccag ucuugauuga auuuuuaucc gauaauaaug aacuggcugc cacagaugua 1260
uugcuguucu uaagggaagc cauacagaag uuuaaagaau ugcaaccguu aauuauugag 1320
aaacucaucg aaacuuucaa agacauuaaa uuggucaaag uccauagagc agcaauuugg 1380
auuuugggag aauacgcgag uacugcuucc gauauagaag uuaucguugg agaaauuaac 1440
agauuguugg gugaaggauc ccucguugaa gcugagcaga aguuaauagc aggagauacg 1500
gaagagaaug cuccugcacc ugcugcaggc gccaccacuu uaguuacuuc cgauggaaca 1560
uaugcuaccc aaucagcuuu caacacuguc agccaaacca cuaaagaagc acgaccuccu 1620
cuaagacaau accucaugga uggugauuuu uucaucggag ccucuuuggc aucuacauua 1680
accaaacugu cuuugcggua ugaggaccuc accucuccug cugcuagcaa uggauucaau 1740
gccaaaauua ugcuuauuau ggcuggaauu cuucacuugg gaaaaucagg acuucccaca 1800
aaaucaauaa ccaacgacga uaaagaccac auucuguucu guuuacgagu ccuaucugau 1860
cguucuccaa ucauuguuga aauuuucaaa aaauugugcc gcucggcacu aaaugagaug 1920
cuucuagcua aggaaucggu agaagcgauc ucgcaaaaga gcaaagaaaa aaacaagcgu 1980
acgauucaaa cugacgacgc uauaagcuuc cugcaauuag agacagauaa aaguggagag 2040
cuaggagaaa acguauucga gaugucgcug ucacaagcuu uaguaggagg ucgaacggga 2100

```
ggugggcgaau caguauuaag uuccaauaaa uuagauaaaa ucacacaacu gacugguuuu   2160

uccgauccag uuuauuccga agcauacguu cacgugaauc aguacgauau cgugcuugau   2220

gucuuaaucg uaaaccaaac uaacgauacu uuacaaaacu gcacgcuaga gcuggcuacu   2280

uuaggcgauu ugaaguuggu agagaagcca caaccugucg uauuggcgcc caaagacuuu   2340

ugcaacauua aagcuaacgu gaaaguggcc ucaacugaaa acggaauuau auuuggcaac   2400

auuguguaug augucauagg agcgggguca gauaggaaug uuguaguuuu gaaugauaua   2460

cacauagaua uaauggacua uauagugccu gcuaguugua cagauagcga guuuaugaga   2520

augugggcgg aauuugaaug ggaaaauaag guaaccguua acacaccccu cacggaacuu   2580

ucagaauacc ucgaacaucu acucaaaagc acaaauuuga aauguuuaac aucagaaaaa   2640

gcucugagcg ggcagugugg uuuuauggca gccaauuuau augcaaaauc cauuuuugga   2700

gaagacgcuu uggccaacuu aaguauagag aaaccuuuua auaaacccga ugcgccagua   2760

agcggucaua uuagaauaag ggccaaaagu cagggcaugg ccuuaaguuu aggagacaaa   2820

gucaauauga cacagaagag cacacaacau aaaguaguag cugcauaa                 2868


<210> SEQ ID NO 164
<211> LENGTH: 549
<212> TYPE: RNA
<213> ORGANISM: Diabrotica virgifera

<400> SEQUENCE: 164

augggguaaug uguuugcaaa uuuauucaaa ggccucuuug gcaaaaagga aaugaggaua     60

uugaugguag gacucgaugc agcugguaaa accacaauuu uauauaaacu uaaauuagga    120

gaaauuguaa caacuauucc aacaauugga uuuaaugugg agacuguaga auauaagaac    180

auuaguuuua caguauggga uguaggugu caagauaaaa uuaggccauu guggagacac    240

uauuuccaaa acacacaagg ccuaauuuuc guaguagaca guaacgacag ggaacguauc    300

acugaggcua aagaugaauu aaugcguaug uuggccgaag augaacuuag agaugccgua    360

cuucucauuu ucgccaacaa acaagauuug cccaaugcaa ugaacgcugc agaaaucacc    420

gacaaacucg gucuccauuc acuacgcaac cgcaacuggu acauucaagc uaccugugca    480

acuagcggag auggucucua ugaaggucug gacugguugu ccaaucaauu aaagaacgcc    540

aaucgcuag                                                            549


<210> SEQ ID NO 165
<211> LENGTH: 4425
<212> TYPE: RNA
<213> ORGANISM: Diabrotica virgifera

<400> SEQUENCE: 165

augggacggu ugcacuguuu auuuuguauu uuccuauguu uuaccgucau caacacgcag     60

acaacgaaua uacauggauu cucggaaaau uccguggaua cauuucuauc accucauggg    120

aaaagugcaa aauucgugca ccaaaaucac aaacccaaaa uugaaaauug ucagaacuac    180

aaacccucgg ugaaagaaga acagccaggc ggaacguacg uaacaacggu uaccgcuauc    240

gaugacgauc cuagggaggg aggaggaaca auuaguuaca aacuaauuca uagagaagga    300

gaacauguuu uauuugacau agacaacguu acugguguuu ugacaacuau ccagccauuu    360

gaucgggaug aaccaguaag gcagaaggaa cuuuauguaa ccguacaagc uucagacaac    420

ggcaggccac cauuagcaga ugucuguaca uuuacaguua ccauuaccga cauuaaugau    480

aaugcgccac agcuugauaa acugaaauac gaugcacaag uuucugaaga uuuaaaagua    540
```

```
ggaagugaag ugaugagagu uuuugcuuac gacauugaug auggggaaaa uucaagauua    600
ucguauaacu uuucaaacga aaaugcucaa uucacccagu auuucaggau agaucgagau    660
acuggcguug uguauuuaaa ggaagcuuua acagacaaaa agaauacuag auuuaacagu    720
gcuguuuaug uagccgauaa uggcguuaac gaucaagaag gccaaaaaga uucaaccgcu    780
aagauaucua uaacaguagu agggucugau aaacagccuc ccagauuuac ucaaaaaaug    840
ccugauggaa ucuuggagau ccccgaagau uuuaaagacu uuucuaaaca uauugucaca    900
gucgaagcaa cguccaacau ugcggaucca caacuugcuu uugaauuggu gaagggaaag    960
acauaucaaa ccaauaaaga ccaaacguuu cuuuuggagg cagaaggaaa uaaagcgcac   1020
auaaagcuag ugcguccacu ggauuaugaa acaguaacgg aauauacucu aacuauucga   1080
guaaaaaaca aagauuuaau ggauucuucc auaaauauac caauuaaagu auuagauguu   1140
aaugaugaaa uuccuaauuu ccuugaauuu cuuaaaggua gugucgugga aaaugacaag   1200
ccaggugcac aagcgauuca aguaagagca aucgauaaag acggaacugc ugcuaacaac   1260
auugugagcu augaacucgu ugacaauaca gauuuguuug caauaaaccg aucuacggga   1320
guaauuacgu cgagagugga guuugaucgu gaaacuguac cucuauauca cguaaacguu   1380
aaagcuuaug auaacucucc gucugcuuug uauaacacga cauugccuaa cauuguaauu   1440
cagacauucc aaaucaguau agaagaucaa aaugacaaca aaccuguauu uacucaucca   1500
auuuaucagu ucaguaauau uacugagcuu gcugauaaau cgaguauugu ugguqaaguc   1560
aaagcuuuag auaaugacac ggcuucaguu auaaguuaua guauuacaaa uggaaauauu   1620
gacgaugcgu uuaugauuga aaauucuacc ggcagaauaa gaguuaaugg aaaacuggau   1680
uacgagaaaa ucgaacaaua caacuuaacc guucgcgcau uugaugggc auuugaagau    1740
uuugcaauug uuuuaauuuc cauacuuaau gaaaaugacg aaccuccagu uuuugacgac   1800
uauaucagag aaauucaaau uaaagaggaa gaaccuauga uauccggaug cguuguuaga   1860
gugacugcuc augauccaga uauuaaagac aggcaugcug aucaacacau aguauaugag   1920
gucgcgaaag aacagaaaga uuuuuugacc guaucugccg auggaugcgu acaaguaaca   1980
aaaccucucg accgagaucc gccuuucggu agcccaacac gacaagucuu caucuaugcu   2040
cgugauaaug auggaggcac aaauucauug uuggccacug cagaaauuga aauuauuuua   2100
auagauauaa acgauaaugc ucccuuuuua aauguuacag aaauuguuua uuaugaaaac   2160
caggauccag guuuuauagg uaaccuaagu gccgaugauu acgauggucc ugauaaugga   2220
ccuccguuug cuuuucgauu aucagacacu gcuucagaua guauuagauc gaaauuuucc   2280
auuaucggaa accagcuuuu cgcuuuagaa auguuugaua gagaagagca aaaauauuau   2340
gacauugcca uugacauuac agauagugga guaccuccac uaacaggaac uaguauucuu   2400
agaguuauaa ucggagaugu aaaugauaau ccagcuacag acggaaacag cacgaucuuu   2460
guguauaagu acgucaaugg gccagaaaau uucauggaaa ucggacgugu auauguuaca   2520
gaccuagacg auugggauuu aaaugacaaa gucuuuguuc aagaagauaa cuuugaugaa   2580
uuuguguuaa accagcauaa caacgguaug auucugauga aaccaacaac ggcugaggga   2640
acuuaugagg uucauuacag ggucacugaa acccaugaac ccacaauaca cgaacauaca   2700
guuaaugcaa uagucacgau uacaguuaaa guacuuccag aggaagcggu uguaaaauca   2760
ggaucaauuc gauugagagg aacaacuaag gaagaauuca uagaaaauuc auugaaugga   2820
aagagcaaaa gagacauauu acaccaagaa cucuccaaaa uauuaaauac aucuuuagcg   2880
```

-continued aauguugaug uauuuacugu uuuaaaauuca ccccaccaga auaguucguu uguggauguu 2940
cgauuuucug cucauggauc uccauauuau gcuccagaga aacucgaaaa caaaguuaca 3000
gaucaucaaa uggagcuuga acaaaaauua gauguggaau ucuacaugau caacguaaac 3060
gagugccuua acgaaacaac guguggagcu gaaaacucau guacgaacaa auuaaacaua 3120
acacgagaac cagcuguagu guuuacuaac agaacauccu uugucggugu aaaugcauuu 3180
auugauccug ugugugccgc uuuaccaaga gauguuaugg aauguuucaa cggaggcguc 3240
cuuaucgaaa acacagcgug uaauuguccu gcaggauuug aaggaccaca uugugaaauc 3300
cuagcuauag gauuuacagg aacugguugg gcuauguauc cauccuuuga cgcuacaaac 3360
aggacugaga uuauacugca uauuuuauca caaacugaua augguuugau auuuuacaau 3420
ggaccuuuaa auauaagaca aacuucuuug ucuaaagauu auauaucauu agaacuuaaa 3480
gacggauauc cauuacuuca aauuugcacc ggcucaagca cucaagaaau uuaucugaaa 3540
gagcgcauuc acaaauugag cgauggaucg uuacacaaaa uaaaaauagg aucuggauuu 3600
gacgauauau cccuggaagu agacgacugu ggaacaacgu guucaauuug gacuaauaaa 3660
cuacauaaag guguuauccg agcaaauggc ccccuucaac ugggagguau gaaaaacaga 3720
uucaccgauc aagaauucaa acgaauuugg gaccauuugc caccgacugc cacccguuuc 3780
ucugguugua uuagaaauuu gacguauaau gaauuuuacu acaaccucgg ugcaccuucu 3840
gaugcauucc aagcguaucc cgacuguaac uaugcaguga ugcaagcugu gacuuucggu 3900
aucgacucca auuucuuggu ugcuauucug guuuguguag caauuuugau aauucuucuu 3960
cuggcaguag uuguacauag acguaaacac gacaacuuua acgaaaaaga aaucgaugau 4020
acucgcgaaa acauuaucaa cuacgaagau gaaggugcg gcgaauguga caccaacuac 4080
gaccugucug uuuuccauca gaacaacauu guggacgaaa aaccauugau gagagacaac 4140
cccgauguac cugcagauau aaguggcuuu uuagauaaca agaaagacaa cugugauaaa 4200
gaccccgaua auuugccuua ugacgacguu cgccauuaug ccuacgaggg agacggaaau 4260
agcaccggau ccuuaucuuc ucucgcuuca uguacggacg aaggagauuu aaaguucaac 4320
uacuuaucaa guuuuggacc cagauucaga aaguuagccg acauguaugg agaagaucca 4380
agcgaugaag acucacacga uggaaacgaa gaauccuggu gcuag 4425

<210> SEQ ID NO 166
<211> LENGTH: 291
<212> TYPE: RNA
<213> ORGANISM: Diabrotica virgifera

<400> SEQUENCE: 166
augccuuucu gugguoccaa auugucccuc ugcggccuga uuaucagugc augggguauc 60
auccaguugg guuucauggg uguauucuau uacauugggg cuguggcuuu agcagaagau 120
auuccagagg uugaguuuaa gggcgauuua gacaaauuuu auagcgacgu caacacgggu 180
uucacacaga augcuuacaa cugcuggauu gcugcucucc uauaccugau aacauuagca 240
guaucagcuc accaauucug ggccaacaac agaucaucau ugaacgucua a 291

<210> SEQ ID NO 167
<211> LENGTH: 540
<212> TYPE: RNA
<213> ORGANISM: Diabrotica virgifera

<400> SEQUENCE: 167
augggucuua ccauaucagc aguguuuaau agguuguuua guaaaaagcc uaugagaauu 60
uuaaugguag gauuagaugc cgcagguaaa accacaaucu uauacaaauu gaagcuuggu 120
gaaaucguaa cuacaauacc aaccaucggc uucaauguag aaaccguuga guacaagaau 180
auaucuuuca cgguauggga uguaggugc cagacgagaa ucagaaaacu cuggagacac 240
uauuucgcca acacugaugg acucauuuuu gugguugauu ccaacgaccg agaccguauc 300
gcggaagccg aagaagaauu gcacaauaug uuaggagagg acgauuuaag agacugcauu 360
uuguuaauau ucgccaacaa acaagauuua ccgaacucga uguccacugc ugaauugacc 420
gauaagcuua aguugcacac uuugaagaau aggagguggu acauacaagc cacaugugcu 480
acucaaggga augguuugua cgaaggacua gauugguugu cgaaugaauu ggccaaguga 540

<210> SEQ ID NO 168
<211> LENGTH: 618
<212> TYPE: RNA
<213> ORGANISM: Diabrotica virgifera

<400> SEQUENCE: 168
augcgguaca cuuugaguua caucggugcu acccuagcgu ccacuguaac acugauuuuu 60
gcccucuacu acugccucac gggaaaagga gagcaaguua guuuagcaug guuauuguug 120
aaugugucuc cccacaugug ggcaggucua ggaauuggcc uugcuguauc auuaucaguu 180
guaggagcug cugcaggaau ucacacuaca ggagucagua ucguaggagc ugguguuaaa 240
gcccccagaa ucaaaaccaa aaauuuaauu ucuauuauuu ucugugaagc uguggcuauc 300 uaugguuaa uuauggcuau aguacucugu ggaaguugga agaauuucga uguagaccua 360
uucaaccuca aaacucauaa cuuugcucaa aaccauuaug gaucacaugu uauuuuugga 420
uccgguuuaa cuguuggauu uguaaaucua uuauguggau uuuguguugg aguaguuggu 480
ucuggugcag ccauuucuga ugcagccaau ucaucauuau ucgucaaaau uuugauuauu 540
gagauuuuug gaagugccau uggucucuuc ggucugauug uuggaguaua cuugacguca 600
agaggcucua ugguuuaa 618

<210> SEQ ID NO 169
<211> LENGTH: 5694
<212> TYPE: RNA
<213> ORGANISM: Diabrotica virgifera

<400> SEQUENCE: 169
auggcuacca acgauaguaa agcuccguug aggacaguua aaagagugca auuuggaaua 60
cuuaguccag augaaauuag acgaauguca gucacagaag ggggcauccg cuucccagaa 120
accauggaag caggccgccc caaacuaugc ggucuuaugg accccagaca aggugucaua 180
gacagaagcu caagaugcca gacaugugcc ggaaauauga cagaaugucc uggacauuuc 240
ggacauaucg agcuggcaaa accaguuuuc cacguaggau ucguaacaaa aacaauaaag 300
aucuugagau gcguuugcuu cuuuugcagu aaauuauuag ucaguccaaa uaauccgaaa 360
auuaaagaag uuguaaugaa aucaaaggga cagccacgua aaagauuagc uuucguuuau 420
gaucugugua aagguaaaaa uauuugugaa gguggagaug aaauggaugu ggguaaagaa 480
agcgaagauc ccaauaaaaa agcaggccau ggugguugug gucgauauca accaaauauc 540
agacgugccg guuuagauuu aacagcagaa uggaaacacg ucaaugaaga cacacaagaa 600
aagaaaaucg cacuaucugc cgaacguguc ugggaaaucc uaaaacauau cacagaugaa 660
gaauguuuca uucuugguau ggaucccaaa uuugcuagac cagauuggau gauaguaacg 720

-continued

```
guacuuccug uuccuccccu agcaguacga ccugcuguag uuaugcacgg aucugcaagg    780
aaucaggaug auaucacuca caaauuggcc gacauuauca aggcgaauaa cgaauuacag    840
aagaacgagu cugcaggugc agccgcucau auaaucacag aaaauauuaa gauguugcaa    900
uuucacgucg ccacuuuagu ugacaacgau augccgggaa ugccgagagc aaugcaaaaa    960
ucuggaaaac cccuaaaagc uaucaaagcu cggcugaaag guaaagaagg aaggauucga   1020
gguaaccuua ugggaaagcg uguggacuuu ucugcacgua cugucaucac accagauccc   1080
aauuuacgua ucgaccaagu aggagugccu agaaguauug cucaaaacau gacguuucca   1140
gaaaucguca caccuuucaa uuuugacaaa auguuggaau ugguacagag agguaauucu   1200
caguauccag gagcuaagua uaucaucaga gacaauggag agaggauuga uuuacguuuc   1260
cacccaaaac cgucagauuu acauuugcag uguggguuaua agguagaaag acacaucaga   1320
gacggcgauc uaguaaucuu caaccgucaa ccaacccucc acaagaugag uaugaugggc   1380
cacagaguca aagucuuacc cuggucgacg uuccguauga aucucucgug caccucuccc   1440
uacaacgccg auuuugacgg cgacgaaaug aaccuccaug ugccccaaag uauggaaacu   1500
cgagcugaag ucgaaaaccu ccacaucacu cccaggcaaa ucauuacucc gcaagcuaac   1560
caacccguca uggguauugu acaagauacg uugacagcug uuaggaagau gacaaaaagg   1620
gauguauuca ucgagaagga acaaaugaug aauauauuga uguucuugcc aauuugggau   1680
gguaaaaugc cccguccagc cauccucaaa cccaaaccgu uguggacagg aaaacagaua   1740
uuuucccuga ucauuccugg caauguaaau augauacgua cccauucuac gcauccagac   1800
gacgaggacg acggucccua uaaauggaua ucgccaggag auacgaaagu uaugguagaa   1860
cauggagaau uggucauggg uauauugugu aagaaaaguc uuggaacauc agcagguucc   1920
cugcugcaua uuuguauguu ggaauuagga cacgaagugu gugguagauu uuaugguaac   1980
auucaaacug uaaucaacaa cugguuguug uuagaaggu c acagcaucgg uauuggagac   2040
accauugccg auccucagac uuacacagaa auucagagag ccaucaggaa agccaaagaa   2100
gauguaauag aagucaucca gaaagcucac aacauggaac uggaaccgac ucccgguaau   2160
acguugcguc agacuuucga aaaucaagua aacagaauuc uaaacgacgc ucgugacaaa   2220
acugguggu u ccgcuaagaa aucuuugacu gaauacaaua accuaaaggc uauggucgua   2280
ucgggaucca agggauccaa cauuaauauu ucccagguua uugcuugcgu gggucaacag   2340
aacguagaag guaaacguau uccauuuggc uucagaaaac gcacguugcc gcacuucauc   2400
aaggacgauu acgguccuga auccagaggu uucguagaaa auucguaucu ugccggucuc   2460
acuccuucgg aguucuauuu ccacgcuaug ggaggucgug aaggucuuau cgauacugcu   2520
guaaaaacug ccgaaacugg uuacauccag cgucgucuga ucaaggcuau ggagagugua   2580
augguacacu acgacgguac cguaagaaau ucuguaggac aacuuaucca guugagauac   2640
ggugaggacg gacucugugg agagauggua gaguuucaau auuuagcaac ggucaaauua   2700
aguaacaagg cguuugagag aaaauucaga uuugauccga guaaugaaag guauuugaga   2760
agaguuuuca augaagaagu uaucaagcaa cugaugggu u caggggaagu cauuuccgaa   2820
cuugagagag aaugggaaca acuccagaaa gacagagaag ccuuaagaca aaucuucccu   2880
agcggagaau ccaaaguagu acuccccugu aauuuacaac guaugaucug gaauguacaa   2940
aaaauuuucc acauaaacaa acgagccccg acagaccugu ccccguuaag aguuauccaa   3000
ggcguucgag aauuacucag gaaaugcguc aucguagcug gcgaggaucg ucuguccaaa   3060
caagccaacg aaaacgcaac guuacucuuc cagugucuag ucagaucgac ccucugcacc   3120
```

-continued aaaugcguuu cugaagaauu caggcucagc accgaagccu ucgagugguu gauaggagaa 3180
aucgagacga gguuccaaca agcccaagcc aauccuggag aaaugguggg cgcucuggcc 3240
gcgcagucac ugggagaacc cgcuacucag augacacuga acacuuucca uuuugcuggu 3300
guauccucca agaacguaac ccugggugua ccuagauuaa aggaaauuau uaauauuucc 3360
aagaaaccca aggcuccauc ucuaaccgug uuuuuaacug gugcggcugc uagagaugcg 3420
gaaaaagcga agaauguguu augcagacuu gaacacacca cucuucguaa aguaaccgcc 3480
aacaccgcca ucuauuacga uccugaccca caaaauaccg ucauuccuga ggaucaggag 3540
uucguuaacg ucuacuauga aaugcccgau uucgauccua cccguauauc gccgugguug 3600
cuucguaucg aacuggacag aaagagaaug acagauaaga aacuaacuau ggaacaaauu 3660
gcugaaaaga ucaacgcugg guucggggac gauuugaauu guauuuucaa cgacgacaau 3720
gcugaaaagu uggugcugcg uaucagaauc augaacagcg acgauggaaa auucggagaa 3780
ggugcugaug aggacguaga caaaauggau gacgacaugu uuuugagaug caucgaagcg 3840
aacaugcuga gcgauaugac cuugcaaggu auagaagcga uuuccaaggu auacaugcac 3900
uugccacaga cugacucgaa aaaaaggauc gucaucacug aaacaggcga auuuaaggcc 3960
aucgcagaau ggcuauugga aacugacggu accagcauga ugaaaguacu gucagaaaga 4020
gacgucgauc cggucaggac guuuucuaac gacauuugug aaauauuuuc gguacuuggu 4080
aucgaggcug ugcguaaguc uguagagaag gaaaugaacg cuguccuuuc guucuacggu 4140
cuguauguaa acuaucgcca ucuugccuug cuuugugacg uaaugacagc caaaggucac 4200
uuaauggcca ucacccguca cgguaucaac agacaagaca cuggagcucu gaugaggugu 4260
uccuucgagg aaacuguaga uguauugaug gacgcugcca gucaugcgga ggucgaccca 4320
augagaggag uaucugaaaa cauuaucuc ggucaacuac caagaauggg cacaggcugc 4380
uucgaucuuu ugcuggacgc cgaaaaaugu aaaaugggaa uugccauacc ucaagcgcac 4440
agcagcgauc uaauggcuuc aggaauguuc uuuggauuag ccgcuacacc cagcaguaug 4500
aguccaggug gugcuaugac cccauggaau caagcagcua caccauacgu uggcaguauc 4560
uggucuccac agaauuuaau gggcagugga augacaccag guggugccgc uuucucccca 4620
ucagcugcgu cagaugcauc aggaauguca ccagcuuaug gcgguugguc accaacacca 4680
caaucuccug caaugucgcc auauauggcu ucuccacaug gacaaucgcc uuccuacagu 4740
ccaucaaguc cagcguucca accuacuuca ccauccauga cgccgaccuc uccuggauau 4800
ucucccaguu cuccugguua uucaccuacc agucucaauu acaguccaac gagucccagu 4860
uauucaccca cuucucagag uuacuccca accucaccua guuacucacc gacuucucca 4920
aauuauucac cuacuucccc aagcuacagu ccaacauccc cuaacuauuc accaacaucu 4980
cccaacuauu cacccacuuc accuaguuau ccuucaacuu cgccagguua cagccccacu 5040
ucacgcagcu acucacccac aucuccuagu uacucaggaa cuucgcccuc uuauucacca 5100
acuucgccaa guuacucccc uacuucuccu aguuauucgc cgucgucucc uaauuacucu 5160
cccacuucuc caaauuacag ucccacuucu ccuaauuacu caccguccuc uccuagguac 5220
acgcccgguu cuccuaguuu uuccccaagu ucgaacaguu acucucccac aucuccucaa 5280
uauucuccaa caucuccaag uuauucgccu ucuucgccca aauauucacc aacuuccccc 5340
aauuauucgc caacaucucc aucauuuucu ggaggaaguc cacaauauuc acccacauca 5400
ccgaaauacu cuccaaccuc gcccaauuac acucugucga guccgcagca cacuccaaca 5460
gguagcaguc gauauucacc gucaacuucg aguuauucuc cuaauucgcc caauuauuca 5520
ccgacgucuc cacaauacuc cauccacagu acaaaauauu ccccugcaag uccuacauuc 5580
acacccacca guccuaguuu cucucccgcu ucacccgcau auucgccuca accuauguau 5640
ucaccuucuu cuccuaauua uucucccacu agucccaguc aagacacuga cuaa 5694

<210> SEQ ID NO 170
<211> LENGTH: 876
<212> TYPE: RNA
<213> ORGANISM: Diabrotica virgifera

<400> SEQUENCE: 170
augucgucaa auauucaaaa ggcccagcag uugauggcgg augcagaaaa gaaaguaaca 60
ucucgagguu ucuucggauc ucuauuuggg ggaucaaguc guauugaaga ugcaguggaa 120
uguuacacaa gagcugcaaa ccuuuuuaaa auggccaaga gcugggaugc ugccgguaaa 180
gccuuuugug aggcugcuaa uuugcauucc agaacuggug cucgucauga cgcugccacu 240
aauuauauag augcugcaaa uuguuacaaa aaagccgaug uauuugaggc uguaaacugc 300
uuuauaaaag cuauagacau uuauaccgaa augggucgcu uuacaauggc ugcaaaacac 360
caucagacua uugcagaaau guaugagacu gaugcugugg acaucgaaag ggcuguucaa 420
cacuaugaac aggcggcuga uuacuucaga ggagaagaaa gcaaugcuuc cgccaauaag 480
ugucuucuua aaguggcuca auaugcagcc caacuugaaa acuaugaaaa agcaguggga 540
auuuaucaag aaguggcuua ugcagcucug gaaagcucuc uuuuaaaaua cagugcaaag 600
gaauacuuau ucagagcugc ccuuugucac cuuuguguug auguacucaa ugcacaacau 660
gcuauagaaa gcuauauuuc aagguauccc gcauuucaag auucccguga auacaaacuu 720
uugaaaaccc ucauagaaaa caucgaagag caaaacguag auggauauac agaagccguc 780
aaagauuacg auucaauuuc ucgucuugau cagugguaua cuacaauucu uuuacguauu 840
aagaaacaag uaagcgaaag cccugacuua cguuaa 876

<210> SEQ ID NO 171
<211> LENGTH: 609
<212> TYPE: RNA
<213> ORGANISM: Diabrotica virgifera

<400> SEQUENCE: 171
augaaucccg aguaugauua uuuauucaaa cuucugcuga uuggagauuc aggaguagga 60
aaaucuuguc uucuacugag auuugcagau gauaccuaca cagaaagcua uauuaguacc 120
auuggcguag auuuuaaaau caggacaauc gauuuagaug gaaagacaau uaaauugcaa 180
auuugggaua cagcagguca ggaaagguuu agaacgauua caucaaguua uuaccgagga 240
gcacauggua uuauuguagu guacgauugc acagaccaag auucauucaa uaacguuaaa 300
caguggcucg aagaaaucga ccguuaugcg ugugacaaug uaaacaaauu acugguaggg 360
aauaaaagcg auuugacaac uaagaaaguu gucgacuuca cuacagccaa ggaguaugcc 420
gaccaauugg guauaccauu uuuggaaacc ucagcuaaga augcaaccaa uguagaacag 480
gccuuuauga cuauggccgc ugaaauaaaa aauagaguag gaccuccauc uucugcggua 540
gaccaaggaa auaagguuag guucgaucaa agucgcccag ucgaaacaac caaauccggu 600
ugcugcuga 609

<210> SEQ ID NO 172
<211> LENGTH: 789

<212> TYPE: RNA
<213> ORGANISM: Diabrotica virgifera

<400> SEQUENCE: 172
auggcagacg cugaugaucu auuagauuau gaagaugagg aacagacaga acaaaccgca 60
acugaaacgg caacuacaga gguacagaaa aagggguguca agggcacaua uguaucaaua 120
cacaguucug gguuuagaga uuuucuguua aaaccagcaa uucucagagc uauaguggac 180
ugcggguucg aacauccuuc agaaguucaa caugaaugua uuccucaagc ugucauuggc 240
auggauauuc ugugccaagc uaaauccggu augggaaaaa cggcuguuuu uguauuagcu 300
acacuccaag uaauagaucc uacagaaaau guuguauaug uucucgucau gugccauacc 360
agagaguuag ccuuccagau aagcaaagag uacgaacguu ucaguaaaua uaugcccaau 420
auuaaaguag gggucuucuu ugguggcuug ccuauccaga aagaugagga aacguuaaaa 480
aauaauugcc cgcauaucgu ugugggguacu ccaggaagaa uuuuagcauu ggucagaucg 540
aaaaaacuua aucucaaaca ucuaaagcau uuuauuuugg augaauguga uaaaauguug 600
gaguuauuag acaugagacg ugauguucaa gaaauauauc guaacacucc ccacgaaaaa 660
caagucauga uguucagugc caccuuaagu aaagaaauua gaccaguuug caagaaauuu 720
augcaagaug uaauucaaaa uucuuauaau acacaauuuu guaaugacgc acccacucgc 780
aauguuuga 789

<210> SEQ ID NO 173
<211> LENGTH: 738
<212> TYPE: RNA
<213> ORGANISM: Diabrotica virgifera

<400> SEQUENCE: 173
augccgguca uugaugguua uaaaguacuu uacauuuuau uacacaguuu auauacaauu 60
uuugaaaaua uuuggaggac ucuuuuauuu auuuaucaaa auuguauaag gguuauaaac 120
ccugaaucua cauucgauga ugcugaccag uuaaagaaaa gacugucuag acuaacaaaa 180
aagccucaac auuuaacuau cauuauuggu guggaagaau auucauuggu agauuuggcu 240
aaccucguau auuggguguuu aggucuuaau auuccguacg uuaguuucua ugauuauaaa 300
gguaauuuaa aaaagcauga agagaaguug caacaaauug uagaauccag aaaaucagag 360
aauaucaaca uaauuuggca cacccaugca gaacaaaggc auaaaaaaugg auuuuugggu 420 ccaaaaaucc acguaaaagu guuaacacac gcggacggaa agcaaaguau aguaaauguu 480
acuaaaaaau uagcucuaaa uaaagaaaaa gacauuagua aagaaaaaau uagugaauua 540
cuauuaaggc aguaugaauu uccagaucca gaaauggcua uuauuugugg aaagaaacug 600
aacauuuaua auuauccucc uuggcaguua agacucacag aauucuuuaa agucaacaaa 660
gucaacaaca ucacauuccc aguguuugug gaaaaauugg aaaaguacag caaaugugaa 720
cagagggugg gaaaauaa 738

<210> SEQ ID NO 174
<211> LENGTH: 480
<212> TYPE: RNA
<213> ORGANISM: Diabrotica virgifera

<400> SEQUENCE: 174
augaccaacu cuaaagguua ccgccgagga accagggauc uauuugcccg caaguuuaaa 60
aaacguggug uaauuccacu uuccacauau uugagagucu acaaaguugg agauauugua 120

```
gauaucaagg guaauggugc aguucaaaag gguaugcccc acaaagugua ccaugguaag    180

acaggacgug uuuucaaugu uacugcacau gcauuaggug uaauuguaaa caaaaggguu    240

cgaggaagaa ucauccccaa aagaaucaau cuccguauug aacauguaaa ccacuccaag    300

ugucgucaag acuucuugca aagaguaaaa uccaacgaaa agcuacguaa agaagcuaaa    360

gaaaagaaca uuaaaguaga acuuaggaga caaccugccc aaccuaggcc agcacauauu    420

guuagcggaa agguuccagc acaggugcuu gcuccuaucc cauaugaauu cauugcuuag    480
```

<210> SEQ ID NO 175
<211> LENGTH: 537
<212> TYPE: RNA
<213> ORGANISM: Diabrotica virgifera

<400> SEQUENCE: 175

```
auggaaggaa uacuacugga accaacauug uauaccauaa aagguauugc uauauuggac     60

uaugauggua auagagugcu ggcuaaauac uacgauaaag auauauuucc uacagcaaaa    120

gagcagaaag cuuuugagaa aaauuuguuc aauaaaacuc auagggcaga cgcagaaauu    180

aucauguugg augguuuaac uugugugaau agaaguaaug uagauuuauu cuuuuauguu    240

augggcaguu cacaugaaaa ugagcuaauu uuaaugagug uuuuaaauug cuuguaugac    300

ucaguaaguc aaauauugaa gaaaaauaug caaaaacgag cugucuugga aucacuagau    360

auuguuaugc uggcuaugga ugaaauuguu gauggaggaa uaauuauaga uucugauuca    420

aguucaguag uaucuagaau agcauuaagg acugaugaua uuccauuagg agaacaaacu    480

guagcucagg uauuccaaac ggccaaagaa cagcugaaau ggucauugcu gaaauaa      537
```

<210> SEQ ID NO 176
<211> LENGTH: 450
<212> TYPE: RNA
<213> ORGANISM: Diabrotica virgifera

<400> SEQUENCE: 176

```
auggcugacc aacucaccga agaacaaauu gcugaauuca aagaagcuuu cucacuauuc     60

gauaaagaug gugaugguac aauuacgacu aaagaauuag gaacaguaau gagaucucua    120

ggacaaaauc caacagaggc ugaauuacag gauaugauca augaaguaga ugccgauggu    180

aacggcacga ucgauuuccc agaauuuuua acgaugaugg cacguaaaau gaaagauacc    240

gauagugagg aagaaauucg ugaagcauuc cgaguguucg acaaagacgg caaugguuuc    300

aucucagcag cagaauugcg ccacgucaug accaacuugg gugaaaaauu gacagacgaa    360

gaagucgaug aaaugauucg ggaggccgau aucgauggug auggucaagu caauuacgaa    420

gaguucguca ccaugaugac uucaaaguga                                     450
```

<210> SEQ ID NO 177
<211> LENGTH: 2013
<212> TYPE: RNA
<213> ORGANISM: Diabrotica virgifera

<400> SEQUENCE: 177

```
augaugcaag caaacaaucg agucccaccu auaaaguugg aaaacgauau agaucuuuac     60

gccgaugaua ucgaggauuu cgcacaagau gacuuuggug gugaaaaugu ugaucuauau    120

gacgauguaa uauccgcucc uccuggaaau aaugacaacc caggugauuc aaaucaucau    180

gcuccuccug gugcuggaga agauggugga gguaauuuug uugggucagg aggagcaccc    240

aauaauauaa auucuucugg aagaagacau cagcuguaug uuggaaaucu gacuuggugg    300
```

acaacugauc aagauauaga aaaugcagug caugauauag ggguaaccga cuuccaugaa 360
guuaaguuuu uugaacacag agcaaauggu caauccaagg gauucugugu cauaucuuug 420
ggaucugagg gaagcaugag acucugccug gaacuccuau cuaaaaaaga gaucaauggc 480
caaaaucccc uuguuacccu ucccacaaaa caagcucuua guaacuuuga aagucagucu 540
aaaacacgcc cuucuccuac uaauaauucu aacucacguc cuccccaucc uaauaauaau 600
guucauucag guccuaugca gaauuaugga gguagaaugc cuaugaaccc uuccaugcgu 660
cccaugcccc cagguaugca aggugcucca agaaugcagg guccaccugg auuuaaugga 720
ccaccaaaca ugaaucagca accccccagg uuccaaggua auccacaaug gaauggaccu 780
agaccuaaug guccugggcc caauauggga augagaccca uggggccacc ucauggacaa 840
caagggcccc caagaccacc aaugcaggga ccaccgcagc aagguccucc aagaggaaug 900
ccgccacaag guccaccgca gaugcgucca gaauggaauc gaccaccaau gcaacaaggg 960
uacccucaag gcccgccgca uaugcaagga ccuaacaugg guccaagagg uccaccccaa 1020
augggaccac ccggggcgcc ucaacagcaa ggaccagcuc cgcacguaaa uccagcauuc 1080
uuucaacaag gaggaggacc accgcccccca augcaacaca ugccuggacc agggcccguc 1140
augccuccuc aaggaccccc gcaaggucca ccacacggac ccguuggacc uccacacggc 1200
ccaccauugg guccagcgaa uguuccgccu cauggaccac cucacggaua ugguccaccu 1260
gcagcgaugc cacagccgcc auacggugge ccaccuccag accaccgcgc ugagauuccu 1320
caguuaacag agcaagaguu ugaggauaua augucccgga auagaacagu uuccaguucg 1380
gcgauugggc gggccguauc cgacgccgca gcuggagaau uugcaagcgc cauugagacu 1440
uugguuacug cuauuucacu caucaaacaa uccaaagugg cuaacgacga ucguugcaag 1500
auccuuauaa guucgcugca agauacuuug cguggugucg aagacaaaag cuacagcucc 1560
agccgcagag accggucaag auccagggac agaucacaua gaagaacuag aagagaacga 1620
uccucgucac gguacagaga cagaagcaga gagagggagc gugaacgcga uagagaucgu 1680
gaucgugaac gugacagaua uuaugauaga uacagcgaaa gagaaagaga ccgagaucgu 1740
ucaagaagca gagaaagaac agaaagggau agagaacgag auuauagaga ccgggaaccc 1800
gaagagacag auaaagaaaa aucuaaagua uccagagucu caagaucaag aaacaaaucu 1860
ccggaaccug ucgaaccuag cagcgaggua ccgaaaucau cccgcuauua ugaggauagg 1920
uaucgggaac gagagagaga aggucgacga gagagcgauc gcgaaagaga aagagauaga 1980
agaggggaag acagccauag gucucgacac uag 2013

<210> SEQ ID NO 178
<211> LENGTH: 765
<212> TYPE: RNA
<213> ORGANISM: Diabrotica virgifera

<400> SEQUENCE: 178
augaguucua uuggaacugg guacgauuua ucagcuuccc aauucucucc ugauggaaga 60
guauuucaag uugaauaugc aaugaaagca guugaaaaua guggcaccgu aauaggccuc 120
cgagguacag auggcauugu auuggcugcu gaaaagcuca uuaugucaaa auugcaugaa 180
ccaaguacaa auaaacgaau uuucaacauu gauaaacaca uaggaauggc auuuucaggc 240
uuaauagcug augcaaggca aaucguugag auugcuagaa aagaagcauc aaauuauaga 300
caucaauaug guucaaauau uccucuuaaa uaccuaaaug auagaguaag cauguacaug 360

-continued caugcauaca cuuuauacag ugcuguuaga ccauuugguu gcagugucau cuuggccagu 420
uaugaagaua gugacccauc uauguaucug auugauccau cuggaguuag cuauggauac 480
uuuggaugug cuacagguaa agcaaaacag ucugcaaaga cugaaauaga aaaauugaag 540
auggggaauc uaacaugcaa agaacuuguu aaagaagcag ccaaaaucau uuauuugguc 600
caugaugagc ugaaggauaa gaauuuugaa cuggaacuuu caugguaug caaagauacg 660 aaugguuuac auaccaaagu gccugaauca guguuugcug augcagaaaa agcugccaaa 720
caagcaaugg aagcagauuc agaaucagau acagaagaua uguaa 765

<210> SEQ ID NO 179
<211> LENGTH: 744
<212> TYPE: RNA
<213> ORGANISM: Diabrotica virgifera
<400> SEQUENCE: 179
auggcuucaa aagacagauu gaugauuuuu ccaucuagag gagcccaaau gaugaugaaa 60
uccaggcuaa agggagccca aaagggacau aguuuauuaa agaagaaagc ugaugcuuua 120
caaaugagau uuagaaugau uuugaacaaa auuauugaga ccaaaacucu caugggugaa 180
guaaugaaag aagcugccuu uucuuuagcu gaagcaaagu uugcaacugg ugacuucaau 240
caaguuguuc uucaaaaugu caccaaggcu caaauaaaaa uaagaacuaa gaaagacaac 300
guugcuggug uuacuuuacc aguguuugaa ugcuaccaag augguacaga uacauaugag 360
uuggcugguu uggcuagggg aggucaacaa uugacaaaac ucaagaagaa uuaucaaagu 420
gcuguuaaac uguugguuga auuagccucu uugcaaacuu cuuuuguaac ucuugaugau 480
guaaucaaaa uaacaaacag aagagucaau gccauugaac auguuaucau uccaagaaua 540
gagcguacuu uggcuuacau cauauccgaa cuggacgagu uagaaagaga ggaguucuau 600
agauuaaaga agauccagga caaaaagaag aucagcagag caaaggccga gaaacaaaaa 660
caagcucuuc uccaagcugg gcuacuuaaa gagucccagg caaacaugcu uuuggaugag 720
ggcgaugaag aucuacuuuu cuag 744

<210> SEQ ID NO 180
<211> LENGTH: 4818
<212> TYPE: RNA
<213> ORGANISM: Diabrotica virgifera
<400> SEQUENCE: 180
auggaggcgg cucccaaguu accgaugcuc ucguucgagu uaaauacuug uacagagaac 60
guccacuuug gcccccaguu aaaacaguau auugcugcuu uuuaugguga agauccagaa 120
uccuacauua cagaaaucag caaucuugaa uccuuaagau cagcugcagu ucgaccauca 180
acggauguaa augguguaca acuguugaaa aaguauuucu gucagcuucg uuuucucaaa 240
ucuagguuuc ccauggaaga gaaucaagau gcugcaguuc uauuuucaug gaaaaauaau 300
gaauuagaca uaacuucaac auccagugau aucagauaug aauuaauggu aauaaauguau 360 aacauuggag ccuuacacac uuuucuugga gccaacgacu caagaaacaa uccggauggu 420
augaaaaugg cauguacuca uuuucaaugu gcugcauggg cuuuucaaaa cguaaaagaa 480
aaguaccacc aauucauauc aaacaucuca uugguagaac ugguucauuu uuuucaacaa 540
gucuguuuag cucaggcuca ggaguguaua uuagagaaga gcauguuuga caauaggaaa 600
ccuaccauca uugcaaaagu ugcuauccaa gucuacaguu auuacagaca gucuuuacgu 660
gucuuggaau caguaaauga agccuacuuu agggauaaaa ccuacaagga guggaugaaa 720

-continued uaucuucaau ucaagcugac cuacuacaaa ugcaucucgu ucccuauucca agggcaacaa 780 gcugaggaac aacagaaaau gggagaaagg guugcauucu aucaagcugc augugaacag 840
cuggacgagg caaagaaaau ugcugcuaca uuaaaaaacc aacaccacca gcaagaaaua 900
aaugagggac uagcauucac uacugaugug guugaaggua aaagaaaagc agcuaaaaau 960
gaaaaugagu ucaucuacca ugaaucagug ccugauaaag accaauugcc agagguuaag 1020
ggugcuucau uagucaaagg aauaccauuc aguauaaaug auauagaagu uucaggacca 1080
gauauuuucu cccgauuggu cccaauggag gcacacgaag cagcuucccuu guacagcgag 1140 aagaaagcuc agagauuaag acagaucggg gaacuuauug aaaauaaaga ucaaacauug 1200
gcugaauuua ugucgucaau gcagcuagau cuauugacca agaugcacca ggcuacugga 1260
auaccgcagg aguugauuga uagagcagcg gcucuaucug cuaaaccuaa cgccauucaa 1320
gaucuuauaa gugcuauggg aaagcuaucu aauauauacc aagacguuga agcaaguuug 1380
aaugagauug auucuuuauu aaaggccgaa gaacaaagug aacaaaagua ccaagaaacg 1440
auugguaaaa gaccaccgag cauuuuagcu acagauuuaa cuagggaagc ggcaaaauac 1500
agggaggcuc auacuaaagc gaacgacuca aaccaaacuu uacacagggc gaugauggcu 1560
cacguggcua aucugaaaau acuccaacaa ccgcuaaagc agcugcaaca ucagcugccc 1620
uuugucgagu uuccaaaucc aaauaucgac gaaaaaucuu ugaaagaucu ggaagcgcua 1680
guugcaaaag uagacgaaau gagaacccaa agagccaugc uaugggcuca acuucgagaa 1740
ucuauucacc aagacgauau uacaaguucc cuuguaacga aacaaccaaa ucagucgcug 1800
gaacagcugu uccagcaaga acuucaaaag caucaaaauc ugauuucguu gauugaacaa 1860
aacaccucgg cacaagaaaa cauuaagagc gccuuagucg auucuuacgc uuacgcugua 1920
aauucaagaa aauacaucca agauauacuc caaaagagaa ccacaaccau aacgucacug 1980
auagcaucgu ucgacucuua cgaagacuua uuggcaaaag cuaacaaagg gauagaguuu 2040
uacucaaaac uugaaacgaa cguauccaag uuacugcaaa gaauaaggag uaccugcaaa 2100
guucaacaag aagagcgaga ucagaugaug ucgacugcgc aagugccuca augggagagu 2160
cauacgucac uugccgcucc uaaacugaaa gauuacuugg acuccaggaa gaagagugcu 2220
gcguauucgg agccgagugu ucaaccacaa cagccaacuu uaaguuacuc agcugcuaug 2280
gaucugccuc cugguauuag gccgacucca guuggaucag aaauaacgga uguaccgaaa 2340
aauauucaag gugaaccaca agguuauauu ccauauaauu accaacaacc uucuguuccu 2400
gccucacaga auauugauga agagacuauu aaaaaaauga acgcauugau gccaggugcu 2460
aagacgucag ugccuaguca guacggauac agcaacuaca uuccaccaac auacccucaa 2520
agugcguacc aaccagguaa ucagucuuac ggaaaagaaa cuccagauau uaacucaccg 2580
uacgacccua ccaaggcguu cacggcuacu acuaacgcuu aucguucggu gcagagcucc 2640
ucaacucaag gauacguacc guacgcagaa ucuaacguuu cgaauguuga cagaguugga 2700
uauccuagca gguaucagua ccaacaagua ccugagauag cuacuacucc agcugauccc 2760
aauauuaaug cguacuaccc acaugggguac ucaccgagcc agaauuuacc gaaugcuaau 2820
acucaacaua uuaccggcca acugaaguac cauucggugg aguacgcuuc uucugugccg 2880
aacaacauca auuauaacag cucuaccuac ucgucgccgc uuucuaauau gucuaguacc 2940
aauuccucaa auccuaguaa cuugaauaau ucuuacgagu acuacuauga cccgaauacc 3000
aguaguggug caguaccgaa ugcuucaaag ccucaacagu cgagcgccag cucugcaaac 3060

```
ccgaguaccg cuaugaacaa cuacaauuau uacuacaaua caaguaccag cgguagugua   3120
gcagcggaua cuucaaaaau acaacaacaa caacaguacc cagguacuca gaugagucaa   3180
gcgcaguacu aucccgccaa ugccaguuau uacucaacca guacuuacaa uaccaacguc   3240
caagguggua ccaaucccuc guacgcaacu ggacaaacau auaaucaagu gacaccagug   3300
accucucaaa auguuucuca aaauuacaac uuuaaccaag uugguucugg agcaggacac   3360
cagcaucagu acuacucguc cgcuaacgcc gcaguaccau cccaacaagc uguaaauaac   3420
aguucauuac caaacuacgg auacgaucag uauuacggca acaacuauaa uuccagucaa   3480
ccgaguaccu acagcgcaaa ccaagcaccu ccugcagcac aagcugcucc aaguaauauu   3540
ccugcugcca ccaaauccuc cucuaaugug gaucugcuca guggcuugga cuucagcaua   3600
agccaagcuc cucuagugcc ucaacaaaac auuacgauaa aaccccaaga aaaggaaaca   3660
aaaccaccgg cuguuucuuc ugaaaccaaa aaccaagauc caacaccagu aaccacgccc   3720
aaacaaccca cuggaccaga aguaaagcgc uuguacguca aaauccugcc gagcaaaccc   3780
uuaaacaacg augaugugaa gaaauuguuc ggccaagagc uggacaggua ugagaaguuc   3840
guggagaccu ugacccacaa aacuuugagc gguccgacca cucuggauau uaaauggaag   3900
gagauccaag accagcagga uugcgagccg cagaagaaga ucauuuccgu cgcuagaugu   3960
uauccuauga agaauagguu cccggauauc uugccuuacg acuuuuccag gguggaguug   4020
ugcgauagua aagaugauua uaucaacgcu ucauacauua aggauaucuc gccauaugcu   4080
ccgucauuua uuguuacaca agugccguug ucuucaacug uuggugauau guggacgaug   4140
auuagagaac aacaggucga acugauccuc uguuugguaa acgacaauga gaucggugaa   4200
gauauuuacu ggcccaaaga aaaaggcagu agucuuaaca uacuuaacau ggucauaacg   4260
uugcaaaacg uuauaguuaa gucucauugg acugaaagac ugauagcgau aaacuuaccu   4320
gaaaaacggg agucccgugu gauaaaugcau cuacaauuua caucguggcc uggcagcuug   4380
uuuccaacaa auccugaacc guucgucagc uacaccuugg aauccaucaa ccuauaccaa   4440
caacagaaga ccaacaccca uccggugug guccauuguu caucuggcau aggaagaagc   4500
ggccugcucu guuuacugac agcugcuaug uucgaugcug ccaacaaugc uaacucgaua   4560
ccagaucuua cagcuuugag uaucaaguug uccaauugca ggaagaauau ucucagagau   4620
cgagagcauu ugaaguuugg uuacgaaagu uuuuuggcgu auauuaggca uauaguuugu   4680
gaagauaaag ccagaaagaa acugaacgag auccagccca agguuaagga ggaaccacug   4740
gaaccaccug ucauaguucc agaaccaaau auagauccuu uaaguacuuu agacccauuu   4800
ugggcuagua aaagauaa                                                 4818
```

<210> SEQ ID NO 181
<211> LENGTH: 888
<212> TYPE: RNA
<213> ORGANISM: Diabrotica virgifera

<400> SEQUENCE: 181

```
auggcggacg augagagaaa gaaacuggag gaggaaaaga agaggaaaca ggccgaaauu     60
gaacgcaaaa gggccgaggu cagggcucgu auggaagagg ccucaaaagc caagaaggcc    120
aagaaagguu ucaugacccc ugagagaaag aagaaacuua gguuacuguu gagaaagaaa    180
gccgccgaag aauuaaagaa agaacaagaa cgcaaagcag ccgaaaggag gcguaucauu    240
gaagaaaggu gcgguaaacc caaacuuguc gaugacgcaa augaaggccc auuaaaacaa    300
guaugugagg gauaucacag acguauugua gaccuagaaa auaagaaauu ugaccucgaa    360
```

aaagaagugg aauucagaga uuuucagauc uccgaauuga acagccaagu aaacgaccuu 420
agaggcaaau ucgucaaacc aaccuugaag aagguaucca aauacgaaaa caaauucgcc 480
aaacuucaaa agaaggcagc ugaauuuaac uuccguaacc aacucaaagu ugucaagaag 540
aaagaauuca ccuuagaaga agaagacaaa gaaaagaaac cagacugguc aaagaaggga 600
gacgaaaaga agguacaaga ggcugaagca ugauuuuucu ccuuuguuaa agcccuuuug 660
ucaacaucaa gggauauguc guuauuucga ugaucccauc gugauuucga uaucuuaaau 720
auauuuauuu uauucauuac uuuccagacu aaaagagugu cuguccgcau guauauuauu 780
uguuuaugua uaacuuauua aaaaauguga aguauuguaa aaaaaaaaaa aaaaaaaaaa 840
aaaaaaaaaa aaaaaaaaaa aaaaaaaaga aaaaaaaaaa aaaaaaaa 888

<210> SEQ ID NO 182
<211> LENGTH: 791
<212> TYPE: RNA
<213> ORGANISM: Diabrotica virgifera

<400> SEQUENCE: 182
ccgugaucuc gagcgguuuu uaacagagag ggaaaaugua aucauauaua ugguugaauu 60
cuugaagguu agacuucauu ccagucuugu gauauuuagu gcuuacuugg uacagcaguu 120
ucagugcugu gcuuuagaau aauuuauuuu uuaacauuua uauagaaauc aaauacuaac 180
caaucaacau gugugaagaa gaaguugccg cuuuagucgu agacaaugga uccgguaugu 240
gcaaagcugg uuuugcuggg gaugaugcac cucgugcugu auucccuuca auuguuggac 300
gcccaagaca ucagggugug augguaggaa ugggacaaaa agauuccuau guaggugaug 360
aagcucaaag uaaaagaggu auccuuaccu uaaaauaccc caucgagcac ggaauaguca 420
caaacuggga ugauauggag aaaauuuggc aucauacauu cuacaaugaa cucagaguag 480
ccccagaaga acacccuguu cuguugacag aagcuccucu caaccccaag gccaacaggg 540
aaaagaugac acaaauaaug uuugaaacuu ucaacacccc agccauguau guugccaucc 600
aggcuguacu cuccuuguau gcaucugguc guacaacugg uauuguguug gauucuggug 660
augguguauc ccacacuguc ccaaucuaug aagguuaugc ucuuccucau gcaauccuuc 720
guuuggacuu agcugguaga gacuugacug auuaccucau gaaaauuuug acugaacgug 780
gcuacucuuu c 791

<210> SEQ ID NO 183
<211> LENGTH: 2927
<212> TYPE: RNA
<213> ORGANISM: Diabrotica virgifera

<400> SEQUENCE: 183
uaauuuuuga caguucgaaa auggugaugu guuuauaauu cgugucaauu uagugaaaua 60
gcauucaauu uuuuguauaa gaucucuuca aaaugccacu ucgauuagau auaaaaagaa 120
agcuaacagc ucgcucagac cggguaaaau guguggaucu ucacccuaca gaaccuugga 180
ugcuguguuc ucuuuacagc ggaaauauaa acguuuggaa caccgaaaau cagcaacugg 240
uuaagacuuu ugaaguaugu gauguaccug uucggacagc uaaguuuuug cccaggaaga 300
acuggauagu caguggguc u gaugauaugc agauucgagu uuucaauuac aauaccuuag 360
aucggguaca uucuuuugag gcucauucgg auuaugugag auguauuguc guacacccua 420
cacaaccuua uauauuaaca aguagugaug auaugcuuau caagcuuugg aauugggaaa 480

-continued

```
aagcaugggc uugucagcaa guuuucgaag gacacacuca uuauauuaug caaaucgcca    540
uaaauccaaa agacaacaac acauuugcca gugcaucccu agauagaaca uugaaaguau    600
ggcaauuggg agcguccaca gcgaauuuca cacuagaagg ucaugagaaa ggcguuaacu    660
guguggacua uuaucacggu ggagauaaac cuuauuuaau cucaggcgcu gaugauagau    720
uaguaaaaau cugggauuau caaaacaaaa cuuguguuca aacuuuggaa ggacaugcuc    780
aaaauguaac cgcugcaugu uuccauccag aacuuccugu agcucuuacu ggaagugaag    840
augguacugu cagagugugg caugccaaca cccauagguu agaaaguagc uuaaaauuaug   900
gcuuugaaag aguauggacu auuuucugcc uaaagggauc caauaacgug gcauuggguu    960
augaugaagg uagcauuuug guuaaaguug guagagaaga accagcuguu aguauggaug   1020
ccaguggagg caaaauuauu ugggccagac acucugaacu ucaacaggca aaucucaagg   1080
cguuagcuga aggugcggaa auaagagaug gagaacgccu uccaguuucu guaaaagaua   1140
ugggugcuug cgagauauac ccucagacaa uucaacacaa ucccaauggc cguuuuguug   1200
uugucugugg ggauggagaa uacauaaucu acacagcaau ggcuuuaaga aacaaagcgu   1260
uugguagcgc acaagaauuu gugugggcuc aagauuccag cgaauaugcc aucagagaau   1320
ccggaucuac uaucagaauu uuuaagaauu ucaaagagaa gaagaauuuu aaguccgauu   1380
uuggagcuga agguauauac gguggauacc uuuugggagu caaaucgguu ucugguuuga   1440
cuuucuauga uugggaaacu cucgauuuag ucagaagaau cgagauacaa ccaaaagcag   1500
uuuacugguc agauaguggu aaauuaguau guuuggccac agaagauagc uacuuuauuc   1560
uuucuuauga uucugaugaa guucaaaaag ccagagauaa caaucagguu gcggaugaug   1620
gaguagaauc ggcuuucaau cuucuaggug aaauaaacga aucagugcga acuggucucu   1680
ggguaggcga cuguuuuauc uacacgaauu cuguuaaucg uaucaacuac uucguuggag   1740
gugaacuggu uacaauugcu cauuuggacc ggccuuugua ugucuuggga uaugugccua   1800
aagacgauag auuauaccuc guagauaaag aguugcgcgu aguaagcuac caauuacuuc   1860
uuucuguucu ugaauaucaa acugccguca ugagaagaga cuuuccaaca gcagacagag   1920
uacuuccguc cauuccuaag gagcacagaa cgagaguggc acauuucuua gaaaagcaag   1980
gcuucaaaca gcaagcuuug gccguaagua cagauccaga gcacagauuc gagcuggcag   2040
uagcauuaga ggaucuuaau auagccaaaa cucuagcuca agaagcgaac aguccgcaaa   2100
aguggaauca acuagcagaa uuggcagcug cuacuaauaa uguaagcgua gccaaggaau   2160
guaugcaaaa agcgcaagau uauggaggcu uguugcuucu ugcuacgagc uccggugaug   2220
aaaauuuagu ccguacucua ggagaaacga cacaagcuga aagcaaacau aacuuagcau   2280
uuuugucaca cuuguuagua ggugauuuaa acaaaugucu agacauucuu auuaauaccg   2340
guagauugcc agaagcugca uuuuucgcca gaucuuaccu uccugauaag auuacagaag   2400
ucguggaacu guggaagacu caguuaucuu cagucaauca aaaagcugga cagagccuug   2460
ccgauccuaa aaacuacgaa aaucuguucc cugguuuaca agaggcggug guagcucaga   2520
aauuuuugga acagcagaau aaagguuuag cgcccgcaag aguugccacc accauuccuc   2580
cuaaucacga caggaauguu guagccgaag uucaagcaca aucgaaacac gauguaccau   2640
cauuuaguuc uucguuuauu ucaucagaaa uagaagcaca aacaaggagu ucugcuaaac   2700
cugaagaauc uucaaacauu auacagcugg accaagauga cgacgauauc gauuuagauu   2760
uggacggugu aaauaucgau gagaacauug acacgacgga uaucaacauc gaugaugauu   2820
ugcugagugu uugaaaauaa cuuuuuuacu uuaguauuaa aucuguauau ucauuccuau   2880
```

ucuuaagaaa aucuauauga auuuuaaugu uuuaauaguu aagaaau 2927

<210> SEQ ID NO 184
<211> LENGTH: 1620
<212> TYPE: RNA
<213> ORGANISM: Diabrotica virgifera

<400> SEQUENCE: 184
uucauuucgc cauuuugauu auuucaauuu uagaaaacgu ucaauaagca gggugcaggg 60
ucaagaagua aaguguucua gaaauacaga uuaaauuguu uccuuugugu uauugaaagg 120
caaaaauaaa auaaugcaga ucuuuguaaa aacacucacu gguaaaacca ucacccucga 180
gguugaacca ucagauacca ucgagaaugu caaagcuaaa auucaagaca aagaagguau 240
uccaccagau caacagagau uaaucuuuag aaagcguucg aguucgauaa gcaagcaggu 300
caagaaguaa aguguucuag aaauacagau uaaauuguuu ccuuuguguu auugaaaggc 360
aaaaaucaaa uaaugcagau cuuuguaaaa acacucacug guaaaaccau cacccucgag 420
guugaaccau cagauaccau cgagaauguc aaagcuaaaa uucaagacaa agaagguauu 480
ccaccagauc aacagagauu aaucuuugcu ggaaagcagu uagaagaugg ccguacucuc 540
ucagacuaca acauucagaa agaaucuaca cuacacuuag ugcuucgucu uagaggaggu 600
augcacaucu uuguaaaaac ucucacuggu aagaccauca cccuugaggu ugaaccauca 660
gauaccaucg agaaugucaa agcuaaaauu caagacaaag aagguauucc accagaucaa 720
cagagauuaa ucuuugcugg aaagcaguug gaagauggcc guacucucuc agacuacaac 780
auucaaaaag agucuacccu ccauuuggua cuucgucuua gaggagguau gcagauuuuu 840
guuaaaacuu uaacuggaaa gaccaucacc cuugaaguag aaccuucuga uaccaucgaa 900
aaugucaaag ccaaaauuca agacaaagaa gguauuccac cagaucaaca aagauuaauc 960
uuugccggaa agcaauugga agauggucgu acacucucag acuacaacau ucaaaaggaa 1020
ucuacccucc auuugguacu ucgucuuaga ggagguaugc aaaucuuugu aaaaacacuc 1080
acugguaaga ccaucacccu cgagguugaa ccaucagaua ccaucgagaa ugucaaagcu 1140
aaaauucaag acaaagaagg uauuccacca gaucaacaga gauuaaucuu cgcuggaaag 1200
caguuggaag auggccguac ucucucagac uacaauauuc agaaagaguc uacccuccau 1260
uugguacuuc gucuuagagg agguaugcaa aucuuuguaa aaacucucac ugguaagacc 1320
aucacccucg agguugaacc aucagauacc aucgagaaug ucaaagcuaa aauucaagac 1380
aaagaaggua uuccaccaga ucaacaaaga uuaaucuuug ccggaaagca guuggaagau 1440
ggccguacuc ucucagacua caacauucaa aaagagucua cccuucacuu gguacuucgu 1500
uuaagaggag gaaauuaaua ugguugaaau uaagcacauu uuuauauuuu caauaaauaa 1560
auuauaaauu auuaaaaaaa aaaaaaaaaa aaaaaaaaaa aaaaaaaaaa aaaaaaaaaa 1620

<210> SEQ ID NO 185
<211> LENGTH: 2430
<212> TYPE: RNA
<213> ORGANISM: Diabrotica virgifera

<400> SEQUENCE: 185
cucgaaacaa augacuguga augaaaagcc cuauagcaac agcaacaaca aauauuugaa 60
uuuucgguaa auaacguuua ugaaaaauaa uaauaauuuu aauuguuaca uaagacacau 120
aagaguacau aagauuguau uauggaagaa cgagauuuag uuucuaauag acgcagauca 180

-continued

```
uugcauaacu auggcgaaga gaaaccuguu ugucgaaaau uuccggauaa ugaugaacaa    240
aauuuccaau auccuccaga uuauauccac aaaguaaaua cagaaacgga aaaauggaau    300
gcucaccuca guaacaucuu agucgaccaa cagagguaca aagaaaaaau acgugaacuu    360
aaaacuguag uguacaauga aaacguuuug ucacaugauc agcaggaauu uuuaaaaucu    420
auagacuuua auacauacuu gagacaaacu gaaauauuuu guaaaaaggu gcauuuagcc    480
gcagaacuau acaguuucaa uaaaagugaa aaauaucaag aguuacagaa aaccauugaa    540
cauguucaag aaaucauuga uaguaaacug aagacauuua aaggucgcug uaccaccaaa    600
ccaaaaaacc auaaaucaug ugugacgacg auguagcggc ucuugucguc gacaauggcu    660
ccggaaugug caaagccggu uucgccggug augacgcccc ucgugcuguc uuuccaucca    720
ucguaggucg ucccagacac caagguguca uggugggaau gggucaaaaa gacuccuacg    780
uaggagacga agcccaaagc aaaagaggua uccucaccuu aaaauacccc auugaacacg    840
gaauuaucac uaacugggac gauauggaaa agaucuggca ucacaccuuc uacaaugaac    900
uuagaguagc ccccgaagaa caucccauuc uuuugacuga agcuccacuu aacccaaaag    960
ccaacagaga aaagaugacu caaaucaugu uugaaacuuu caauaccccu gccauguaug   1020
uugccauuca agcuguauug ucucuguacg cuuccggucg uaccacuggu auuguacuug   1080
auucuggaga ugguguaucc cacacaguac ccaucuauga agguuacgcu cucccacacg   1140
ccaucuugcg uuuggacuug gccgguagag acuugacuga cuaccuuaug aagaucuuaa   1200
ccgaaagagg uuacucuuuc accaccacag cugaaagaga aauaguucgu gacaucaagg   1260
aaaaauugug cuauguagcu uuggacuucg aacaggaaau ggccacagca gccagcucca   1320
ccuccuuaga aaagaguuau gaacuuccug acggucaagu caucaccauu gguaaugaaa   1380
gguuccguug cccugaagcu cucuuccaac cuuccuucuu ggguauggaa ucuugcggua   1440
uccacgaaac ugucuacaac uccaucauga agugcgaugu cgacauccgu aaagacuugu   1500
acgccaacac uguccuuucu ggagguacca caauguaccc ugguauugcc gaucguaugc   1560
aaaaggaaau cacugccuug gcuccaucaa ccaucaaaau caagaucauc gcucccccag   1620
aaagaaagua cuccguuugg aucgguggcu ccaucuuggc cuccccuccc accuuccaac   1680
agauguggau cuccaaacaa gaauacgacg aauccggccc uggaauuguu caccgcaaau   1740
gcuucuaaac uacuuuauau auuuaucgua uacauauuaa guacaauacu gagaguugga   1800
gcaugaaugu auguuuuuau uuaugguuau auauaugaug acuuguugau auuguaacaa   1860
uaaaauucauu uuguauuacu cugguaauau uuuauuuaug agaacaacca gauugaaguc   1920
guaaagagcc aauaacaacc ugaagauauc aauugucaau ugcuacugag uaauaguuug   1980
agguacuuag cuccagcucc uuuucacacg aaaguaagaa guaucugagc gagaauacau   2040
ucuguauugu acuuuuuaaa uaugcgacuu uuguaacauc aauuucauug uaaaauauca   2100
ucaucauugu uuuuauggac cuacgugaca guaggagaca ccugacaaga cuucuuuucc   2160
ugcuguguau acgcaccuuu acaaacaucc ugcuggccua auuguagucc uguaagggac   2220
auccuuuguu gggcauggag uuuguuugug ggaauuguau ugacuacuau uauauaccua   2280
cuuuuauuau uaaggcauuu gaaaucguaa acuaaaauug guuguuuaua uuuuauauga   2340
guauuuuuag uaguagauaa gauuucaauu gcaaaacuac cuauguaugu auucauuaga   2400
aauaaauucu uauuccaaaa uaaaguuuug                                    2430
```

<210> SEQ ID NO 186
<211> LENGTH: 2822

<212> TYPE: RNA
<213> ORGANISM: Diabrotica virgifera

<400> SEQUENCE: 186
guuuauuuug gucgucggcu gaugugacgu guaaagaaau uaaaucaaau uauuuuaaag 60
uuuuuaaauu aaaaugggua cuuuuaaaag agauacucau gaugaggacg ggggaucaag 120
ugcuuuucaa aaucuggaga aaacuacugu uuugcaggaa gcuagaguuu uuaaugaaac 180
uaguguaaau ccaagaaaau guacaccgau acuaacaaaa cuguuguacu uauugaacca 240
gggugaaacu uuaagugcca aagaggccac agauguuuuc uuugccauga ccaaacuguu 300
ccaaucaaaa gauguaauau ugagaaggau gguuuauuug ggaauuaaag aacucaguuc 360
uguugcugau gaugucauua uuguaacauc cagucuuaca aaagauauga cugguaaaga 420
agacauguac agagcagcug cuauaagagc auuaugcagu auuacugaug cuacuaugcu 480
ucaagcuaua gaacguuaua ugaagcaagc uauuguagau agaaacgcag cugucaguuc 540
agcagcacua auuaguucau uacauaugag caaauuagcu ccagauguag uaaaaagaug 600
gguaaaugaa gcucaggaag caguaaauag ugauaaugca augguacagu aucacgcauu 660
aggucuucua uaccauauua ggaagacuga uaagcuagca gugacaaaau ugauuuccaa 720
gcugaauuca augggguuaa agagcccuua ugcuuugugu auguugauaa gaaucacugc 780
aaaacuuuua gaagaagagg accaagaguc acuccucaac uccccauaua caauaauauu 840
uacaaugggc uuaaggaaca aaucugaaau gguggugtau gaagcugcac augccauggu 900
uaaccugaag uucacgagua guaaugugcu agcacccgcu auaaguguuc uacaacuauu 960
uuguggaucu ccuaaagcca cacucagauu ugcugcuguu agaacuuuaa aucaagugge 1020 caccacccac ccugcgucag ugacagcuug uaauuuggau cuagaaaauu ugauuacuga 1080
uccuaauagg ucaauugcua cacuggccau uacuacucuu uugaaaacag gugccgaauc 1140
uucuguugac agacuaauga aacaaaucgc uacuuuugua ucugaaauca gugaugaauu 1200
uaaagugguu gucauucagg caauuaaggu auuagcuuug aaauuuccaa ggaaacauag 1260
cacgcuuaug aauuuccuau ccgccauguu aagagaugag ggagguuuag aauauaaagc 1320
auccauagca gauaccauua uaacccuaau cgaagauaau cccgaagcua aagaaucugg 1380
uuuggcgcau cuuugcgagu ucauugaaga cugugaacau guuucuuugg cugugagaau 1440
cuugcauuug uuaggaaagg aaggacccaa gaccaaacaa ccaucgagau acauccguuu 1500
uaucuacaau cgcgucauau uggaaugucc uucuguaaga gcugcugcag ucuccgccau 1560
ggcacaauuc ggagccucuu gucccgauuu guuagaaaau auccaaauau uacuuucgag 1620
gugucagaug gauucagacg augaaguuag ggacagagcu acauauuaua guaauauacu 1680
uaacaaaaau gauaaaaguu uauacaacaa uuacauuuug gauucuuugc agguuucaau 1740
uccuucacua gaaagaucgc uuagagaaua cauucaaaau ccaacugacg aaccauuuga 1800
cauuaagucc guaccuguag cagcagugcc aacagcagaa gaacgagaag uuaaaaacaa 1860
aucugaagga cugcuagucu cucaaggucc aguccgaccu ccuccggugu cuagagaaga 1920
aaacuucgcc gaaaaacuua guaacguucc ggguauacaa caguuaggac cuuuguucaa 1980
aacuuccgac gucguugaac ucacugaauc ugaaacagag uauuuugucc gcuguaucaa 2040
gcacuguuuc aaacaucaca ucguccucca auucgauugu cugaauaccu ugccagacca 2100
gcuuuuagaa aacguuagag uggagauaga cgccggugaa accuucgaaa uuuuggcaga 2160
aauaccuugu gaaaaguugc acuauaacga aaccgguacc acauauguag uaguuaaguu 2220
gccugaugau gaucucccca acucuguugg uacgugugga gccguguuga aguucuuagu 2280
gaaagauugu gauccaucaa cgggaauacc agauucugau gaggguuacg augaugaaua 2340
uacacuggaa gacaucgaaa uaacauuagg ggaccaaauu caaaaaguaa gcaaaguaaa 2400
uugggcugca gccugggaag aagcugcagc uacuuaugua gaaaaagagg auacauacuc 2460
cuugaccauc aauacgcuaa guggcgcugu uaagaauauu auucaguucu ugggauuaca 2520
gccugcggaa aggacugaca gaguaccgga ggguaaaucu acgcacacau uacuucuugc 2580
ugguguauuc aggggaggua uugacauacu aguaagagcg aaacuagcuu ugggcgaaug 2640
uguuacgaug caacuaacag ucaggucgcc agauccugac guugcugagc uuauaacuuc 2700
aacuguaggu uaaguuuaaa ggcuacguua augauuauau uguauuacaa uuuuuccaua 2760
uguauaaaua uuuugauuua uuuaaauuuu auuagaaauu aaacaauuuu aaguaaaaaa 2820
aa 2822

<210> SEQ ID NO 187
<211> LENGTH: 3701
<212> TYPE: RNA
<213> ORGANISM: Diabrotica virgifera

<400> SEQUENCE: 187
gucguuuagu agaaguguca uuuuugucug cucucguuuu caucuuuugu guauaaaauu 60
ggugcuaagg uagauaaacu auauucgaau aggcguuuuu augucgcaag aaaguguuuu 120
guauauuugu gauacgugau cucguagagg gaguccagaa auucauaauu uauaguuaag 180
uaaaaaaugg cggcaaacag aacuggaccu gcucagagac caaauggcgc uacccaagga 240
aagauauguc aguucaaacu gguccuacua ggcgaaagug ccgucgguaa gucgaguuug 300
guacugaggu ucgucaaagg acaguuccac gaauaccagg agaguaccau aggagcagcu 360
uuccuuacac aaaccauaug ccucgacgau acaacuguua aauuugaaau uugggacaca 420
gcggguucaag aaagguacca caguuuagcu ccuauguacu auaggggcgc acaggcagcu 480
auagucgucu acgacauaac caaucaagac acauucggca gggcgaaaac gugggugaag 540
gaacuucaaa ggcaggccag uccgacgauc gugauagcuu uggccggcaa caagcaagau 600
uuggccaaca aacguauggu agaauacgaa gaggcgcaga cguaugcuga cgaaaacggc 660
uuacuuuuua uggaaacuuc cgcaaagacg gcaaugaacg ucaacgauau auuuuuagca 720
auagcuaaga aacugcccaa gaaugaacaa accacagguc aaggcggcag ugcccaaggc 780
aggcggcuag cggagggcga uucgggcgcc aaggcacccg gaaauuguug caagugaugg 840
uauacgccug caggucgagu guuguuauua aaccgucacg agaaaggacu ggcaagugca 900
gcggcacucu agugauaucu auguguaaua aagguccuuc uauuaacaaa aaaaaauuaa 960
uaaaaaaaua uauuaaacuu cauauacacu gucacauauu ccauuuagau gaugaaaaac 1020
aaaagagcag aagcauuuug gucucuaacg gucauguuga guuggaaugu cucguggggc 1080
auuuaaauuu gugauaauug uaccuauauu uuguuuuuuu uauauauaua auuaauauau 1140
cugacagugu aaguuaagcg uaaacuguuu auaucgaucg uauuagcagc accaauuaaa 1200
aaaauaaaua aaauugaaga ucuuuuuuau uguuuuugua auuuuaacuc uuuggggaag 1260
guuacaaaag aauugauaac guuguguuga aaacauugca uuauaauaaa guaauuccac 1320
ccacuuacga auuauuuuga aaggagaauc aaaaaugugu caauugucac cugucaucuu 1380
augaugacac ucuaugagag ugggggcaau ugcagcgcgc gcauacuauu cagucuagcu 1440
ucauuauguc aauuaaaugu cgauguuuaa aauuucaucg auuaguuuga caguucccaa 1500

```
augaaaaaac aguuacuucc gcauaaaaau guauugcuuc aaaacuuacu uucaguggca   1560
uuucaguggg uuuuagccau cuuauggaga guggucuaac acacuuucua gguacagcug   1620
ugguuuuuaa aaggaaauau aaugaaucgc uuuuguuuuc gaaauuuaca uugggaaucc   1680
cuuaguguccc uuauauuugc ccuacagagu uucauuuaaa cugaaauugg guaauuuaca   1740
uagaccuaaa gcuuucacgu cuauauagcc uaauuagacc acaaaauuga cuugcuuuac   1800
gugaaaugua ugaaccauuc aaacauauuu auaugacaac aauauaauau aauacaauau   1860
aauauaaaua acugacaaca uuuaaaauua gaauuuuuac ccacaauuuu ucucugccau   1920
gugucaucua guacaagaag uauggcaauu uagcccuacu ccucuuauug uacauuucuu   1980
guaauuccuc auuuucuuuu ucaauuacuu cgaucuuuua aacuuaaauc accaaguuua   2040
uuugcaauau uguucuugaa gucuauaguu ugaauuccuu caauauauuu guaauguuuu   2100
ucuucagugu caauccuugc auuccaugaa agaacacgaa aaagaugcag cacuuuauuu   2160
guccauauuc cugcuacaua guuauuuuuc gauuaacaca uucacugcca gcguauagua   2220
aacuggcacu uuacuauacg cuaaacaaaa auuuggccuu gcagauuuuc cuaaaacacg   2280
uagcagcuac gccacugaau ggacuuagga cccccuaucg uuucgcuggu ugcaauaguc   2340
cgguaacuag agaagcaauu auuauauaaa aguaaauuua aauaauugua uuuugcuugc   2400
aguacugcau uuuaauaauu aguuuucuuu acuacauaca auuguuaccu uuuaauaaca   2460
uaaucuaaau cuuacuuuuu uuuuuuuauu uuuuugggcu auggccuuga caauuaucca   2520
guaaccagga cuaauauaau uggccaauau aauuaaaagu gcgaauaaua guacagagcg   2580
uagaaauagg ggucgcuuug ccgaacuugc acggucccaa uaguaaacug gcacuuuacu   2640
auacgcuaaa caaaaauuug gccuugcaua uuuuccuaaa acacguagca gcuacgccac   2700
ugaauggacu uaggaccccc uaucguuucg cugguugcaa uaguccggua acuagagaca   2760
aaagugggguc auuuugcaca cuucauauaa uucucguuuu cuguacuuca cgaguauuuu   2820
uuuugucgga uauguauuga auaguaucgg ugacaacaca cugcccugcg ugacaccccu   2880
uucaaaaccu augugggaac aauauguauc uuuagagaac uuuuuguacc cuuccccuaa   2940
aaacuaaaua uuuuuucacu uagugcaauu uuaauauuag ucucaccuua uuucuagaau   3000
acggucgguc uaaauguaua aucucaacuu ucagcuuaua cuucgaaaac cgagaaguau   3060
aaacuguaag aauauuuaac guuauaugua uuuuauuagg auaaugauug uugaaaguau   3120
guuucccaac acguguaagu uacauuucgu acucuuucca uuuuuauuac aaaaaaaaau   3180
guuuauuuag auaaacuguu gcggaacaua cuuucucgau gcaugacuga aaagaacguu   3240
aacauuuaua cguauuuguu uuuauuuugu gucugaugug acaacccaga ucuuagcgaa   3300
agcguagagg acaaaagaug aguuuuuaag uuucccauug aacuuuuucc guccuuaaau   3360
caaauacaac aacuauucac uuaaguuuuc uaaacauuuu ugcuaauaug ggccccugca   3420
ccauucccga cuuaacaguc uucauuuguu uuuauuaggu uuguucguag uacgauccaa   3480
acgaucggca accguugcca accauuagac gcaugcgcag uuaacaguga gugaucguag   3540
acuacgaaca cgcaugcguc ugaugguugg caacgguugc ugaucguucu acgaacaaac   3600
cuauuauaaa ccgccucuuu uguagguaaa guaaaccuua uaaucauuuu ccgagucuac   3660
aauuucugua ggacaucaag cauuguaaag uuuaaugaaa u                       3701
```

<210> SEQ ID NO 188
<211> LENGTH: 671
<212> TYPE: RNA

<213> ORGANISM: Diabrotica virgifera

<400> SEQUENCE: 188
cugcgauaua gguguguauu ucagcuggaa uuuguaauga aaaaaacgua gaaauauaua 60
cuacaaugaa guuuuuaaga ucgacagugu gcuacauugc caucuuggca auucucuuua 120
cccucugugc cgaugagguu gaaggaagga gaaaaauuuu gaugggggcga aaaagcauua 180 ccaggacaua ucuucgugga aaugcuguuc cugcguaugu gauaauaauc cuuguaggaa 240
uuggucaaau cauccuggga gggauauugu acguugcauu gaggaagaag aucauugcug 300
caccuguaac ggcaucauau gcaguggcua gacaagaacc auaaaauuua uuugucuaga 360
auauuauuuu cuaaauaugc aucuuuuuua aauuauuguc uacguaaaua auaagucuag 420
aaauauauaa aaauuguaua aaaucaugua ccuauauuuu ucaauuuuua uaaaaaacaa 480
cccgaaauuu aauauuuuac ugaauuaaca uuaucauuuc uaucuacacu caccggcaca 540
aaauuccguc acccaaaauu uuugauuaag cuugacaauu uauaacuaua uuauuugugc 600
uccgauuuuc aacuucaugu ugugcaucag uuuguaggua cauguauuga uauuguuugg 660
uauuauuccg g 671

<210> SEQ ID NO 189
<211> LENGTH: 693
<212> TYPE: RNA
<213> ORGANISM: Diabrotica virgifera

<400> SEQUENCE: 189
guagucggua uguauuugaa uuuaucuuaa uuuguuuaau auuaguaguu aaauauuaaa 60
cuauaguuag aaguuguuau auaguggacc aguaguugac uccccaaaau gcagaucuuc 120
guuaaaaccu uaacggguaa gaccaucacu cuugaggucg agcccucaga uacuaucgaa 180
aaugugaaag cuaaaaucca ggauaaagaa ggaauucccc cagaccagca acgucucauc 240
uucgcuggaa aacaacucga agauggucgu accuugucug acuauaauau ucaaaaagaa 300
ucaacccuuc acuuggugu u gagauugaga ggaggugcua agaaacguaa gaagaagaau 360
uacuccaccc ccaagaaaau caagcacaag aagaagaagg uuaaguuagc uguauugaaa 420
uuuuauaagg uugacgaaaa ugguaaaauc caccgauuga gacgugaaug ccccgcugaa 480
caauguggag cugguguc uu cauggcagcc auggaagaca ggcauuacug uggcaagugc 540
gguuacacuc uugucuucuc caaaccagga gaugagaaau agauauaugu ccuuguauau 600
uguuuaagaa aaaaauagaa aaaccuuugu uuauuugaau aaaauauucg aggaagaaaa 660
aaaaaaaaaa aaaaaaaaaa aaaaaaaaaa aaa 693

<210> SEQ ID NO 190
<211> LENGTH: 2684
<212> TYPE: RNA
<213> ORGANISM: Diabrotica virgifera

<400> SEQUENCE: 190
gaauuuaauu ucaaagauuu auguucagua agcuuuguuu caaagugcgg uacuaucggu 60
uucauuuuau aucucuuuau aacggugucg cgaguuuucu ugugaaaaau gauguccaaa 120
gcagacacac aggaagaugc cuccuucgcc aaauuggaaa aucagauugc uaucaucaaa 180
uacguaauac ucuuuaccaa cguuuugcaa ugggcucucg gugcagcaau cuucgcucuu 240
ugccuuuggc uacgauucga ggagggcauu caagaauggc uccagaaauu ggauucagaa 300
caauuuuaca ucggaguaua uguacuuaua gucgcuucac ugaucgucau gauuguguce 360

```
uuuauaggau guauuagugc ccugcaggag aguaccaugg cccuuuuagu guacaucggc    420
acccaagugc ucaguuuuau auucgguuua uccgguucgg cgguucuucu ggauaacagc    480
gccagagauu cccacuucca accgaggauc cgagagagua ugcgacgucu uaucaugaau    540
gcucaucacg accaauccag acaaacacua gccaugauuc aggaaaaugu ugguugcugc    600
ggagcugaug gcgcaacaga cuaccucucu cuucagcagc cccuuccaag ucagugcaga    660
gacaccguua cuggaaaccc auucuuccac ggauguguag augaacucac cugguucuuc    720
gaagaaaaau gugguuggau agcagguuua gcuauggcga uaugcaugau uaacguccuu    780
aguauuguuu uaucuacggu acucauccag gcauugaaaa aagaagaaga agcauccgau    840
ucauacagga gauagauuua gugagauaga gauauaaugu aguaauuaga auuuaaugua    900
ucuucaacua aauuacuuuu ucuuuagaga uauaccugaa auuguaaaga acaggaaaau    960
uaaauaagaa ccaaaaacua aagugaacca acaauaauug aacauuccaa aauacacuuu   1020
uuuuguuaag uuaacuaaac gacauaaauu uuucauuuuu uaaguuuuuu auuguuuuuu   1080
uuaguauuau aauuuggaua agguguuuuu auauuaagug uguaauuaua aaguuuuuuu   1140
auaggacgga accuaaauua uauagaauca uacaauaaac uauugucugc uuauugaauu   1200
uggaaaauaa acauuuggua uauauuaaaa auaauaauau augucuuaau gaggaacuaa   1260
ugaaaacguc uauacauuuu ugaauuuaau accaacagau auuguaauua uuaauuuuaa   1320
uuaaucaacu ccaagucaac aucuggaaag caauagaaau uaaaguaauu aacuaacuag   1380
uaacauucua gcaaccugua cauguggu ug uauuacucug uuuugacauu gacaaaacua   1440
gcuuugugau caguuaucuc uagcaguaau aaacucuagc uguauuuugu uuuauauauu   1500
uguccaaaga auugguuuau uuuaaagcaa auauaauggu uuaacccagg ggugggcaaa   1560
cuuuuuuugg uaagggccau aaaauauuuu ugaucuauua ccgagagccg caauauuugu   1620
uaccuuaaca uauucgaauu uuuaacuuuu uacuaauuuu guuuacgugu guuggggggg   1680
ggggaugguu aaauuaaaua aacacaaaua aacauauuca guacgauuca aagauuauuc   1740
aaaaaaauuu aaaaccaaau auugaaaaau aagccaacgg uggcaaauuu uuacaggcag   1800
cucuaagaaa aaauggauuu ugcaguagau caaugcauau gaaacaaaaa auucaaaaau   1860
auguuauuag cuuaugaguu ucucgaggua acgcuguuga guuuuuuagu uuuaacgauu   1920
uuugaguuuu ugauaucacu caaaauacca gucaaaauaa ggaaauuuuu guaaaaagug   1980
ugaaaaucaa cauauuuauu auuguuaacc aaaacauauc ucgauagagu uacuucacga   2040
agugaccaaa gaaaaucuau gaaaaauuuu agguggagcu gucaaguagg uaguuuuuga   2100
guuacaaugu ccaccgccuu ugaaaaaagc aguuuugaga aaaacgcauu ugguuugaca   2160
acuuuuauuu cccuuuguuu uuugucuguc aaaucguaaa gugauguacg ccggaauaug   2220
uuuuugaauc guagaguaau uuauaaaaga gacgagaaca gcuguuguac guuucucccu   2280
acgcucaggc uacugcaaag cgagucgaag guagggauau uaaacaugcu uuacuuccgg   2340
uaauuuuacu ccagucaagc ugaaaauuuu agagaguagu cuugaaguuu auuuauuuau   2400
uuauuuaugu acuuucauuu aaaauauaaa aaaaaaucaa acauuuaaaa caaaaaaaau   2460
uuucaaaccg uaacccuccc cucuaaacag cauucgcauu uaauuaagca ugguauuucc   2520
cucaaauaua uguguaucua uauauuuauu uauuuuuauu uuaucucuga accuauuucu   2580
uuuuccuuaa uauuguucug aagcuauuug cuuguaacau cuuaugcaau uuacuguuuu   2640
guuugagaau gggccacagu uugaguuuga aauuaaauuu auuu                    2684
```

<210> SEQ ID NO 191
<211> LENGTH: 458
<212> TYPE: RNA
<213> ORGANISM: Diabrotica virgifera

<400> SEQUENCE: 191
gcuugaucuu caagguagaa caacgcaagu agaaaucuaa aacaugucug gacguggcaa 60
gggaggcaaa guaaagggaa aagcaaaguc ccgaucaaau cgugcugguu uacaauuucc 120
uguaggucgu auucaucguu uauugagaaa aggaaauuau gccgaaagag uuggugcugg 180
agcuccugua uacuuggcag cuguuaugga auauuuagcu gcugaaguuu uggaauuggc 240
aggaaaugca gcuagagaua acaaaaagac ccguauaauu ccuagacauu uacaauuggc 300
cauaagaaau gacgaggaau ugaacaaauu acugucagga guuaccaucg cccaaggugg 360
aguauugccu aauauacaag caguacuguu accuaaaaaa acugaaaaga aagcuuaaga 420
guuaguauuc cuuuuuaucc aacccggccc uuuucagg 458

<210> SEQ ID NO 192
<211> LENGTH: 2478
<212> TYPE: RNA
<213> ORGANISM: Diabrotica virgifera

<400> SEQUENCE: 192
acuagguaaa uauaccuugu auauuugucu auuaacggua uuauuuauau uauuuuaaag 60
ugcgcaugcg uguugugaca guuuauccaa uuuucuuaca auuucaggua cccucgaacg 120
caacuaaugu ucuuuuagau uguuagccag auuucacaca auacgugguc acgucaggcc 180
gccguauuca guuuuugauu ucaaacaaac ugacugcugu cugcauaaaa auccaaaaaa 240
ucuuuugcca auauuguugu gacauuuuau uacguauacu cguaaaggcg uaauaaucaa 300
cuugaaauug caauaaaacu aaaagcuaaa uaacgauuuu ucuaguaaua ucugucauac 360
gaauuugaau acuggaaaua gaugaaauua guaucguauu uuuucuuaaa uuuugucacc 420
caugaauuaa aagcuucaga gucaaauuag auacauuaau uuguaaugca gaaauuuaac 480
uguaacuucc ugucauggaa cuugauuuug auauuugaug guacuuucuu ucuauuguua 540
cugauaaaag auuaccaauu aaaaaauaua auguucauug uauucacaug auguauuaca 600
uuuguuggua cucuuuugcg acaauuucga ccaauguaca uuuagauuuu gagcuuuaca 660
gcaauggaac ugaaauuaac guucaagaua ucaauacaaa uaaaaagcuc aaaaucucug 720
gacgauaaga acacuuucau cacaugccaa ugcuugcuua acuuuuuuaa auuaaauuuu 780
uuuguuaaaa ucaaugcagu aaaaguuuuu uauguaagau aucucucccu aguguggaga 840
uaaacuaagg cauauagaau augacaguag uuauauucua uacaaaaaaa auuaaguauc 900
cauguggugg ggguaaaugu augaggguca acaggaucga uacugucugu guauuaaaua 960
aucuaugcuc uuagcgaaug uucccagguu aguguuaugu aaucgugggc cucaucggcc 1020
ucaacacuuu uuuuugucua cagugaagua agaaagcggu uuccaaagug caugaaguug 1080
gaugguguag aucugccccc accaauuagc uucgacauug cggaagagca accguuacca 1140
ccuugccaac agacguucuu auguaauggu gauggaggau ccauagugcg acaguuucuc 1200
gagcuguauu ucguaauaua ugauucagau aauaggcagu cccuucuuca ggcauaucac 1260
gaaaaagcca cauuuucaau gacaauggcc uacccguacg gcuauuccaa agacaguaaa 1320
ggaguaucgu gguugaauug guaugccacc gauaauagaa auuuauuacg aguucaagau 1380
ccagacagaa gaaacaaguu guuaagacag ggacaaguug cuguaguuuc guucuugcaa 1440
gauaugccgc acacgaagca cgauauucac aguuuuacag uagauuugac aguuuuuaca 1500
ccccagaugu uauguuugac aguggcuggu auguuuaaag aauugaaaag uggccacaaa 1560
guaccuccuu uaagauauuu cuucagaacc cuuguaauug uaccugcugg aucagguuuu 1620
ugcauagcaa augaagaacu ucacauaucc aaugcaacuc cggaccaagc aaaagaugcu 1680
uucaagacca ccguuaaugu agcuccggca ccagccccug ugauuaccuc uccuggaccc 1740
aguauaccac aacccgcugu gccagaugau gcuacaaaac aagaaauggu aaaacagaug 1800
uccgcaguau ccggaaugaa ucucgagugg ucgcuacagu gucucgaaga aacacaaugg 1860
gacuaccaga aagccauaau gguauuccaa aauuuaaacg cacaaggugu uguaccacaa 1920
gcagcauuua uuaaaugaua cgaagauuau guuaacuuug guuaauuaau ugacaguuag 1980
uuauaucuug gcaaauguaa auaguaucuu aaauuauagc uaauuuuuag uuuuauuauu 2040
guuuaaggua auguuaguuu aagaugucga auuuuaaguu uguuacauac gaaaaucaaa 2100
ucgaaaaaau guuaauaguc ccuuagaaau accgguagcc cuuaucuuag aagaaaggug 2160
guagauuuua aauaaaaacu ggguuacuuc acaaaaaaau gucuauuuua auuaguugau 2220
cucgauaacu uaauaugauu auauaaauac uggccuaacc uaacaaaucg gacugaaacu 2280
uuuaauauua ccuaaacaag caagauccau uuagacuaaa guuugaaguu uuggaauugu 2340
auugaaauuu gaacauuaca uaaacgguua auuuuauaug agaacuucuu agacaauaau 2400
acuaauuaac uauuuucaau gggaaauaag ccacaauuuu accaaaaaaa ugauuuuauu 2460
aacguuucga cgcccaag 2478

<210> SEQ ID NO 193
<211> LENGTH: 3274
<212> TYPE: RNA
<213> ORGANISM: Diabrotica virgifera

<400> SEQUENCE: 193
caaaacguca acaaucugac acgucuguaa uguuuagccu gacuuuugag uaaaauuacc 60
gaaaaacaua auuaaaauug auuuauuaag aguacauaau aacguacgaa aaugacugcg 120
guagaacaac cuuguuacac acuaauaaac uugccaacag auucggagcc cuacaaugaa 180
augcaacuaa aaauggauuu agaaaagggu gagguuaaag uaaaaauaag agcauuagaa 240
aaaauaauuc acaugauucu ggcaggagaa agguugccga auggauuucu aaugaccauc 300
auaagaaacg uuuuaccuuu acaagaucau uuggcaaaaa aacuauuauu gauuuucugg 360
gaaauaguuc caaaaacaaa uccagaaggu aaacuacuac aagagaugau uuugguaugu 420
gaugccuaua gaaaagaucu gcaacaccca aaugaauuuu ugagagguuc uacacuucgc 480
uucuugugca aacugaagga accagaauug uuggaaccau uaaugcccag uauuagagcu 540
uguuuggauc auaggcacag cuaugugagg aggaaugcug uacuggcaau uuuuaccauu 600
uacaaaaauu uugaagcccu cauuccagau gcuccugaac ugaucuccaa uuauuuggau 660
ggugagcaag acaugucuug uaaaagaaau gcguuuuuaa ugcuucuuca ugcugaccaa 720
gaaagggcgu ugucguauuu ggcaucaugu uuagaucaag uaaauucauu uggagauauu 780
cuacaacugg ucaucguuga guugauauau aaggugugug auuccaaucc ugcggaaaga 840
ucuagauuua uuagauguau auauaacuug uugaacucaa gcaguccugc ugucagguac 900
gaagcugcag gaacuuuagu cacccucucc agugccccga cugccguuaa agcugcugcu 960
agcuguuaca uugaguuaau uaucaaagaa agugacaaca auguaaaacu caucguuuug 1020

-continued

```
gacaggcuga uagcacuuaa ggagcuuccu aaucacgaaa gaauucugca ggauuuaguu   1080
auggacauac ugagaguacu cucugcuccu gacuuagaag uccgcaagaa gacuuuaagu   1140
cuagcccuug aauuagucuc uucacggaac auagaagaaa ugguauuagu auuaacaaag   1200
gaagugagua aaacgguaga cagugaacau gaggauacag gaaaguacag gcaauuguua   1260
guaaggacuc uacauucgug uuccauuaag uucccagaua ucgcacguag uguuauacca   1320
gucuugauug aauuuuuauc cgauaauaau gaacuggcug ccacagaugu auugcuguuc   1380
uuaagggaag ccauacagaa guuuaaagaa uugcaaccgu uaauuauuga gaaacucauc   1440
gaaacuuuca aagacauuaa auuggucaaa guccauagag cagcaauuug gauuuuggga   1500
gaauacgcga guacugcuuc cgauauagaa guuaucguug gagaaauuaa cagauuguug   1560
ggugaaggau cccucguuga agcugagcag aaguuaauag caggagauac ggaagagaau   1620
gcuccugcac cugcugcagg cgccaccacu uuaguuacuu ccgauggaac auaugcuacc   1680
caaucagcuu ucaacacugu cagccaaacc acuaaagaag cacgaccucc ucuaagacaa   1740
uaccucaugg augguggauuu uuucaucgga gccucuuugg caucuacauu aaccaaacug   1800
ucuuugcggu augaggaccu caccucuccu gcugcuagca auggauucaa ugccaaaauu   1860
augcuuauua uggcuggaau ucuucacuug ggaaaaucag gacuucccac aaaaucaaua   1920
accaacgacg auaaagacca cauucuguuc uguuuacgag uccuaucuga ucguucucca   1980
aucauuguug aaauuuucaa aaaauugugc cgcucggcac uaaaugagau gcuucuagcu   2040
aaggaaucgg uagaagcgau cucgcaaaag agcaaagaaa aaaacaagcg uacgauucaa   2100
acugacgacg cuauaagcuu ccugcaauua gagacagaua aaaguggaga gcuaggagaa   2160
aacguauucg agaugucgcu gucacaagcu uuaguaggag gucgaacggg agguggcgaa   2220
ucaguauuaa guuccaauaa auuagauaaa aucacacaac ugacugguuu uuccgaucca   2280
guuuauuccg aagcauacgu ucacgugaau caguacgaua ucgugcuuga ugucuuaaauc  2340
guaaaccaaa cuaacgauac uuuacaaaac ugcacgcuag agcuggcuac uuuaggcgau   2400
uugaaguugg uagagaagcc acaaccuguc guauuggcgc ccaaagacuu uugcaacauu   2460
aaagcuaacg ugaaaguggc cucaacugaa aacggaauua uauuuggcaa cauuguguau   2520
gaugucauag gagcggggguc agauaggaau guuguaguuu ugaaugauau acacauagau  2580
auaauggacu auauagugcc ugcuaguugu acagauagcg aguuuaugag aaugugggcg   2640
gaauuugaau gggaaaauaa gguaaccguu aacacacccc ucacggaacu uucagaauac   2700
cucgaacauc uacucaaaag cacaaauuug aaauguuuaa caucagaaaa agcucugagc   2760
gggcagugug guuuuauggc agccaauuua uaugcaaaau ccauuuuugg agaagacgcu   2820
uuggccaacu uaaguauaga gaaaccuuuu aauaaacccg augcgccagu aagcggucau   2880
auuagaauaa gggccaaaag ucagggcaug gccuuaaguu uaggagacaa agucaauaug   2940
acacagaaga gcacacaaca uaaaguagua gcugcauaaa uaaaaacguu uuuuucuguu   3000
ucaacccuuu ucuucauuuu aaaucauauu cuguaauuua auuaauuuaa uaucauauua   3060
cugguuacac auuguuagau uauaaauauc uuuuaaagaa uaaaauuuau uuagcuuuua   3120
caaagagcgg aaagcaaucu uuaucuucuu cuaauaagau caacaucaag uuuucuggaa   3180
aauauaauau auaaauuaaa gauguuuagc auuuauuagu gaaauacaug gcuuacuauu   3240
uugaugacaa agucagugua auauagaaaa gcag                                3274
```

<210> SEQ ID NO 194
<211> LENGTH: 3652

<212> TYPE: RNA
<213> ORGANISM: Diabrotica virgifera

<400> SEQUENCE: 194
gguagaugau gaugacccua auaaugaaaa caacucaagu cuucuuuuua aaaacugcaa 60
aaaagaaccc uacggagucc accucugaau uagguccaaa ucuuugaaca aaacuccuug 120
cuucgucuga aagagaaguu ccgagccauc cagguucucc uaaaguuaaa ucugguugga 180
cuaauuccaa gaaauuaaaa cuuuuuaaag cccaagcuac aaugccuucg uucucagaua 240
ggguuauagu acauguacug uagaccauga uuccaccugg cuucaauaau uuugcugcau 300
uuucaaacag uuuucuuugu aauggaacga augacuugau cucguuuucu gacgaccuau 360
uggccaguug uggucuuuuc ccaagaacac uacacggugc aucuaaaagu auuuugucga 420
acgauugggg ugcgaauggu ggaccgucua uaacauuuuu ggaacuuaaa guaucugaaa 480
uuauugcagu agaaucagcu ugaaaacuau acacuuuggc gccgaaaucc ucacagcguu 540
uuugaaguug ggcaaccuuc uuuggaguuu ugucuauggc uauuaauauu cccuuauucu 600
gcauuagcuc ugcuauauga guaguuuuau ucccaggaga agcacacaua ucaaguacua 660
caucaccagg uuugggauua agauuaugaa cacauacaau agaugguaua uuuuguagua 720
aaauaucucc gacugguaau aaacuuucgc uuaucgguac acauccugaa auuguuucug 780
uuacuucuac agcaauacca cugggcgcaa uauuaucagu ugcaaacaac uggugccucu 840
gcaucuuaac uaucccauuu ccaaugaaua uuuugaaguc gucuucauau auuuucugaa 900
gucccuuuuu acacuuuuuu gcaacaucgg cguaaaauacu aacguuuucg uuuaucugac 960
aaccugaaac cauuccuaau acuccugggg caaauauaug agcaccccga agaauugcug 1020
cagcacaauc agugucuacu auaauuucuu uaucaaacuu uuuaaagccu gcuggacaau 1080
uuaaacuguc aauuauuauc acauugguaa aagagggaug uauguaaaca uuuggugdau 1140
cauuacaauu uucugcaaaa uagguuuuua auaccuuuaa aacuuuggca guauuuguuu 1200
uuauuguauu uacucuuauc gaaguuauuu uuggugcaga acauaaccau ugcuguauuu 1260
uuaauaauuc uucauuugaa accgauguuu uuguuuuggu gacacuaucg ucaagaaaua 1320
aauucguuau uaauuuauug uugaacguug ucuuaaacgg ggaauuaggg uaaaccaucu 1380
uaaccuuuaa gauaauuuaa aaucaacgua aaauaauucu guaaacaaaa uuaaagucac 1440
aaaacgugca uacuugauag guuagaaguu gaugacuaaa aacuaaaagg ucacguguca 1500
ugcgccaacc aaugcgacac gcugguuccc aagacguggc augagcuacg auucucuuuc 1560
aaguccgcca uauugacauu cgacaacuuu uuugggagga cagguggaaug uuauagcguu 1620 uuucaaagug uaagguguuu auuuucaaaa aguuuauaaa auaagcaauc acuaugggua 1680
auguguuugc aaauuuauuc aaaggccucu uuggcaaaaa ggaaaugagg auauugaugg 1740
uaggacucga ugcagcuggu aaaaccacaa uuuuauauaa acuuaaauua ggagaaauug 1800
uaacaacuau uccaacaauu ggauuuaaug uggagacugu agaauauaag aacauuaguu 1860
uuacaguaug ggauguaggu ggucaagaua aaauuaggcc auuguggaga cacuauuucc 1920
aaaacacaca aggccuaauu uucguaguag acaguaacga cagggaacgu aucacugagg 1980
cuaaagauga auuaaugcgu auguuggccg aagaugaacu uagagaugcc guacuucuca 2040
uuuucgccaa caaacaagau uugcccaaug caaugaacgc ugcagaaauc accgacaaac 2100
ucggucucca uucacuacgc aaccgcaacu gguacauuca agcuaccugu gcaacuagcg 2160
gagauggucu cuaugaaggu cuggacuggu uguccaauca auuaaagaac gccaaucgcu 2220
agaacauagg aaaagagagg agugcgcaaa aaagugugcg agugcagaug guuuuuuucu 2280
uguacucuug ucgugucuac uaccucgcgc gcgcgcgaaa cguuucguau accauauguu 2340
gcaauuuuug uguccgaugg ggaaauucgu cauguuucac uuuggggguu auaaaauugg 2400
cuguuggcga caaguggugu augaggugaa uccgaaaaua guuuuaggca auauaucaua 2460
ugaaucucag cuuucuuuag guugagaguu guuuuuguag uaaaagaacc uuaaacaucc 2520
uucauuggcg auuuauuauu uuuuaacugc augaaaaucu uaguuuuaau guuuuuauau 2580
aacacuuuua gauuguacua acuuuuaaca uuccacaaau uucucauaaa auugugauau 2640
cuuuucuaau accucuuaua ucaaugaacu uauuuuugca ggccaaaaua uuuucuuaga 2700
aaguaauuuu guaucaucua uaaaaauuua auuuugggaa uucaauuaaa gacuuuaacu 2760
ggcaaauuuu aaaauguuac aagguucuag ucacguauuu agucuggacu ugcacuuuau 2820
agcacuuguc gcagaaagca ucuaaccccc aaacacguau ggugaugucc uauuugcaga 2880
aaaugcacua uaauauacga uaguaauuau uuauuguccu cuuucuggug aaaacaggcu 2940
uuuuguaaca uauauuuuuu auuguuugua auagguuaaa auguacagua gacacuuaua 3000
uuuaaaauaa auauuauuuu uuaucuauca auccuuuuug uaacauaugg uaaggcuguu 3060
cguauuuaaa aaauaaaaca agaacauguu uuugaaaagu uuugggcacg gcucaaguau 3120
uuuauuguuu aaauuuaaga ugaaguacga augggcgcgc ccgaauccga caagauauug 3180
uauagccccg uauucguugu caaaccaacg ggucuugcuc ugguaguuaa uuucggcguu 3240
agaguucaag aaggaaguag auuuuuuuau acuuauagua aauauauuau gggauauuua 3300
aagacuggcc gauuggcuua ccagacuuac gucccgcaga ucuuaaccgg cgaugaguau 3360
ucgagguuug uuucugguca gauucgggca cgucguacug uacauaaaau acuuuuguuu 3420
acuucucaaa uuuguaacuc aguuguggau acuuugaggc guaauuuuau uuugacaaac 3480
uguggauuua agguuacauu auaagugauu uauuuaaaga aauauguuuu ugauuuaucg 3540
uggacauucc cuguuuguca gcuguauuau caaauaaauu uauacuauua aaaaaaaaaa 3600
aaaaaaaaaa aaaaaaaaaa aaaaaaaaaa aaaaaaaaaa aaaaaaaaaa aa 3652

<210> SEQ ID NO 195
<211> LENGTH: 7631
<212> TYPE: RNA
<213> ORGANISM: Diabrotica virgifera

<400> SEQUENCE: 195
cuucacuuuu acggguaaac gugcggaagg uacguuccaa guucgaaccu agcgcuugau 60
guucugugua cacucuguac aauuaaaaug gcuuccaagu ucuuugugag uuaacuuugu 120
uaggugcauu uuaguaaauu ucugaauugg guuguuaaau uuagaguguu agugcauagu 180
aacuauuaaa uaguggccuu aaaaagugcu cuuaaugagg auuauaauaa gaaaaacgaa 240
cuuuuaacaa gaacaacgag uguccauucu aauguuauua caaguagcua cuaaaaauau 300
ugcaaaaaaa acuuucggua acuaaaaugg gacgguugca cuguuuauuu uguauuuucc 360
uauguuuuac cgucaucaac acgcagacaa cgaauauaca uggauucucg gaaaauuccg 420
uggauacauu ucuaucaccu caugggaaaa gugcaaaauu cgugcaccaa aaucacaaac 480
ccaaaauuga aaauugucag aacuacaaac ccucggugaa agaagaacag ccaggcggaa 540
cguacguaac aacgguuacc gcuaucgaug acgauccuag ggagggagga ggaacaauua 600
guuacaaacu aauucauaga gaaggagaac auguuuuauu ugacauagac aacguuacug 660
guguuuugac aacuauccag ccauuugauc gggaugaacc aguaaggcag aaggaacuuu 720

```
auguaaccgu acaagcuuca gacaacggca ggccaccauu agcagauguc uguacauuua    780
caguuaccau uaccgacauu aaugauaaug cgccacagcu ugauaaacug aaauacgaug    840
cacaaguuuc ugaagauuua aaaguaggaa gugaagugau gagaguuuuu gcuuacgaca    900
uugaugaugg ggaaaauuca agauuaucgu auaacuuuuc aaacgaaaau gcucaauuca    960
cccaguauuu caggauagau cgagauacug gcguugugua uuuaaaggaa gcuuuaacag   1020
acaaaaagaa uacuagauuu aacagugcug uuuauguagc cgauaauggc guuaacgauc   1080
aagaaggcca aaaagauuca accgcuaaga uaucuauaac aguaguaggg ucugauaaac   1140
agccucccag auuuacucaa aaaaugccug auggaaucuu ggagaucccc gaagauuuua   1200
aagacuuuuc uaaacauauu gucacagucg aagcaacguc caacauugcg gauccacaac   1260
uugcuuuuga auuggugaag ggaaagacau aucaaaccaa uaaagaccaa acguuucuuu   1320
uggaggcaga aggaaauaaa gcgcacauaa agcuagugcg uccacuggau uaugaaacag   1380
uaacggaaua uacucuaacu auucgaguaa aaaacaaaga uuuaauggau ucuuccauaa   1440
auauaccaau uaaaguauua gauguuaaug augaaauucc uaauuuccuu gaauuucuua   1500
aagguagugu cguggaaaau gacaagccag gugcacaagc gauucaagua agagcaaucg   1560
auaaagacgg aacugcugcu aacaacauug ugagcuauga acucguugac aauacagauu   1620
uguuugcaau aaaccgaucu acgggaguaa uuacgucgag aguggaguuu gaucgugaaa   1680
cuguaccucu auaucacgua aacguuaaag cuuaugauaa cucuccgucu gcuuuguaua   1740
acacgacauu gccuaacauu guaauucaga cauuccaaau caguauagaa gaucaaaaug   1800
acaacaaacc uguauuuacu cauccaauuu aucaguucag uaauauuacu gagcuugcug   1860
auaaaucgag uauuguuggu gaagucaaag cuuuagauaa ugacacggcu ucaguuauaa   1920
guuauaguau uacaaaugga aauauugacg augcguuuau gauugaaaau ucuaccggca   1980
gaauaaagagu uaauggaaaa cuggauuacg agaaaaucga acaauacaac uuaaccguuc   2040
gcgcauuuga uggggcauuu gaagauuuug caauuguuuu aauuuccaua cuuaaugaaa   2100
augacgaacc uccaguuuuu gacgacuaua ucagagaaau ucaaauuaaa gaggaagaac   2160
cuaugauauc cggaugcguu guuagaguga cugcucauga uccagauauu aaagacaggc   2220
augcugauca acacauagua uaugaggucg cgaaagaaca gaaagauuuu uugaccguau   2280
cugccgaugg augcguacaa guaacaaaac cucucgaccg agauccgccu uucgguagcc   2340
caacacgaca agucuucauc uaugcucgug auaaugaugg aggcacaaau ucauuguugg   2400
ccacugcaga aauugaaauu auuuuaauag auauaaacga uaaugcuccc uuuuuaaaug   2460
uuacagaaau uguuuauuau gaaaaccagg auccagguuu uauagguaac cuaagugccg   2520
augauuacga ugguccugau aauggaccuc cguuugcuuu ucgauuauca gacacugcuu   2580
cagauaguau uagaucgaaa uuuuccauua ucggaaacca gcuuuucgcu uuagaaaugu   2640
uugauagaga agagcaaaaa uauuaugaca uugccauuga cauuacagau aguggaguac   2700
cuccacuaac aggaacuagu auucuuagag uuauaaucgg agauguaaau gauaauccag   2760
cuacagacgg aaacagcacg aucuuugugu auaaguacgu caaugggcca gaaaauuuca   2820
uggaaaucgg acguguauau guuacagacc uagacgauug ggauuuaaau gacaaagucu   2880
uuguucaaga agauaacuuu gaugaauuug uguuaaacca gcauaacaac gguaugauuc   2940
ugaugaaacc aacaacggcu gagggaacuu augagguuca uuacagggucacugaaaccc   3000
augaacccac aauacacgaa cauacaguua augcaauagu cacgauuaca guuaaaguac   3060
```

-continued

```
uuccagagga agcgguugua aaaucaggau caauucgauu gagaggaaca acuaaggaag   3120
aauucauaga aaauucauug aauggaaaga gcaaaagaga cauauuacac caagaacucu   3180
ccaaaauauu aaauacaucu uuagcgaaug uugauguauu uacuguuuua aauucacccc   3240
accagaauag uucguuugug gauguucgau uuucugcuca uggaucucca uauuaugcuc   3300
cagagaaacu cgaaaacaaa guuacagauc aucaaaugga gcuugaacaa aaauuagaug   3360
uggaauucua caugaucaac guaaacgagu gccuuaacga aacaacgugu ggagcugaaa   3420
acucauguac gaacaaauua aacauaacac gagaaccagc uguaguguuu acuaacagaa   3480
cauccuuugu cgguguaaau gcauuuauug auccugugug ugccgcuuua ccaagagaug   3540
uuauggaaug uuucaacgga ggcguccuua ucgaaaacac agcguguaau uguccugcag   3600
gauuugaagg accacauugu gaaauccuag cuauaggauu uacaggaacu gguugggcua   3660
uguauccauc cuuugacgcu acaaacagga cugagauuau acugcauauu uuaucacaaa   3720
cugauaaugg uuugauauuu uacaauggac cuuuaaauau aagacaaacu ucuuugucua   3780
aagauuauau aucauuagaa cuuaaagacg gauauccauu acuucaaauu ugcaccggcu   3840
caagcacuca agaaauuuau cugaaagagc gcauucacaa auugagcgau ggaucguuac   3900
acaaaauaaa aauaggaucu ggauuugacg auauaucccu ggaaguagac gacuguggaa   3960
caacguguuc aauuuggacu aauaaacuac auaaaggugu uauccgagca aauggccccc   4020
uucaacuggg agguaugaaa aacagauuca ccgaucaaga auucaaacga auuugggacc   4080
auuugccacc gacugccacc cguuucucug guuguauuag aaauuugacg uauaaugaau   4140
uuuacuacaa ccucggugca ccuucugaug cauuccaagc guaucccgac uguaacuaug   4200
cagugaugca agcugugacu uucgguaucg acuccaauuu cuugguugcu auucugguuu   4260
guguagcaau uuugauaauu cuucuucugg caguaguugu acauagacgu aaacacgaca   4320
acuuuaacga aaaagaaauc gaugauacuc gcgaaaacau uaucaacuac gaagaugaag   4380
guggcggcga augugacacc aacuacgacc ugucuguuuu ccaucagaac aacauugugg   4440
acgaaaaacc auugaugaga gacaaccccg auguaccugc agauauaagu ggcuuuuuag   4500
auaacaagaa agacaacugu gauaaagacc ccgauaauuu gccuuaugac gacguucgcc   4560
auuaugccua cgagggagac ggaaauagca ccggauccuu aucuucucuc gcuucaugua   4620
cggacgaagg agauuuaaag uucaacuacu uaucaaguuu uggacccaga uucagaaagu   4680
uagccgacau guauggagaa gauccaagcg augaagacuc acacgaugga aacgaagaau   4740
ccuggugcua gacuaaauuc caugacuccu uagaaaguga cauuuuugua cuuaaauucu   4800
uuuauguuaa ccaaagauug cgaaauuuuu uggaauggaa cugaacaaac uuguacauau   4860
uuuugaaaaa ggauguuuca acuguuugca auacaagaau uguuacguau gcguuucaaa   4920
acauauauuu acauguaacc guucuuguau uguaaauauu uuuauacuau cuuuauacug   4980
acacuuagau aauguuaucu auuaaguggc aagcaguuug guuaagaaua acuuugaguc   5040
uucuauccca agguacugug auuugaacaa aguuagaaua agcaacuucc auaccaucaa   5100
uccacuucau uuuauucaac auacugguuu uccgaaacua aagaagcagc cuaauacaua   5160
gaguucaaua acuuuuauua aacaauccgu auuaggugca cauauucauc gcgcacaagu   5220
acauauugug gaacuguaca cugacgagga acaaauauuc aauaagaauc uuuaaagcga   5280
aaaauauuga aauacacgau cagauuuaac auauuauugu cuagcucaaa agaaaauaau   5340
uuuuaucuug acaauagaca uuuuucauau auaagcuagu agauuuauau caaaaucuau   5400
aaaaaaagug gcuuaaaagu uucuuugauu uuugcgauuc ucuugaauga cuucaguauu   5460
```

```
uuuuacaaaa uuauaagacu guuaaucguu uaagcuggca gcaugguaag auacguaugu   5520

gaaaacuugu auauuuuaca aaauaacuga aaauuaguau guugcgaaaa acaaauggaa   5580

acaaauauac agugaauguc gaauaguauu gucaaaauua aagucauaau uuuuaaagau   5640

uguccaaacu agguuguuga uguauguuaa ucucugaaug ccauccuuua gccaucauug   5700

uguauaucag cuguuuccuu uugcaguuug ugugguacuc cugaauguac ggaauaauca   5760

cauaguuuuc acgaucuuuu acuuuucuuu ucugcagcua auuacagggu gguuguuccc   5820

uuaucaauau ugaaauucuu auauaaucag uuuuuccaga cuuagaaaag uuaaaaaaac   5880

agcaucauau cccugcuaug uuuauucuuc guuguaagga cacucuaauu auuuccaauu   5940

agagaucuca agauguuaug uuuacuagca gguauugaac gaaaacaaua auaaaagcaa   6000

accgaguaau caacaauagu uacaauaccu acaauuuacu augccuucgu agcuuauauu   6060

ggagagauga guggaauuuc ucaauaggcg cauauacaca uaauaauaag acacauauuc   6120

aaauugguug gugguuaaau agcucaaaaa cgauacaaag gaaacauaua gguaacaaca   6180

aaauacaagg uaaaaauaga gguacuuaca aucaggacgc uccaacgaag ucacuauuuu   6240

acgucuuuac acucgaaucg ucugaaugca ucucuuuccu uauguccucg ggguagaauc   6300

uugcaccuca agugguugaa aguuccuuuc uucgucacau guggauuucg cuaauaugcg   6360

aacaaggaac aacacaggcg ucaaaaagga auaugauuuc gaacuauuua aaacaaucaa   6420

aucaauuuau cggaauucca acacaagauu uauaucagca uuucaguagu aaucucacca   6480

uauuccaaau uugucuuuuu guauccaucu uauuuugucu uuaucuuacu uuauauuguu   6540

uuguuuauuu uuuauuuauc uguauccuua ucuuuuucuc uuugacuauc acagcaaauu   6600

uuuguaauuu ggauuuacaa uuaguuauga cuuuaaugaa aacaauacuu accaucucuu   6660

uccuuaaauc gugcgauaua auuuaucaac aauguaguau cauaccacaa caaugucuaa   6720

uaugaaacau acgagaggcc uuaugcauau gccuuaacac guuuaggcac aaauaccaau   6780

aaaaaccuua cacgguucgg caauaaaaug agagaaccgc uauuuuauau acacgcauuu   6840

uuucuauuuu uauuaggauu uuguuaguuu uguuauuacu uaguauaaau uuaggauagu   6900

uauuuuguau uuuuauucuc acguagggcu cagucgacgu agucguuuga auaacauuuu   6960

auuuaaaacu gcagguuuga gaauagccau ucauuggugc cguauuuaaa aaaagauuuu   7020

aaauguuucu uuacuggaua uaucgaaaua caguuuuuuc uuuacguaag gcaguuagau   7080

uauuaaaaua gucuugugaa agcguauagc ucagauguuu uuacaauaua guuucuaaau   7140

uagucuuaaa aggcaacuau ucuuauugca auauuuccca agcuaaauuc acucgagacu   7200

uuggacucau aaauauacaa ugacugaguu cuacuugauu uccguuucau ugacuauuua   7260

auauuuauuu uuacaagucu ugaugaaaau uuggaaauac augauaucaa agcaauuuau   7320

aaucguaauu aggcuaauag uauccuaagg ugauaguauu uccugauuuu caucaauuau   7380

auauauauau uaguaucaca aaauacaguc uguagagacc cgugucauag auaaccuaac   7440

cuuccauugu uacacaucuu guuaacaagu cgauuugaag uggugccggu ugugaagaug   7500

cguaucuuga uguuccacgg cuaaaaucgg uucguucaca aaagcuuuua uauauuuuuu   7560

auuuacuuuu cuucuuaaau guccggcuug aauuuucaag auccagugcu gguacacagg   7620

agggcgcgac g                                                        7631
```

<210> SEQ ID NO 196
<211> LENGTH: 1028
<212> TYPE: RNA

<213> ORGANISM: Diabrotica virgifera

<400> SEQUENCE: 196
gucagugcug ugugcuguca cugucacuac ucuaguguca cgauuuuuua gcccugaaau 60
ugucagauua ucacaugaca uuuugagaaa acuaaauuag uaagugaaca cgaauuuagu 120
ucaaaaugcc uuucugugguu cccaaauugu cccucugcgg ccugauuauc agugcauggg 180
guaucaucca guuggguuuc augggugugau ucuauuacau uggggcugug gcuuuagcag 240
aagauauucc agagguugag uuuaagggcg auuuagacaa auuuuauagc gacgucaaca 300
cggguuucac acagaaugcu uacaacugcu ggauugcugc ucuccuauac cugauaacau 360
uagcaguauc agcucaccaa uucugggcca acaacagauc aucauugaac gucuaagaau 420
cuuuuaauuu gcuuuuguau auauuuauuu acauuccuuc uccagcugua gauuuuaaau 480
guauagaccc ucaaauacuu cagaguacca auuuuucugu uaaacuuagc ggacucguac 540
accaaagcaa uauccaaacg caacaugaaa cacucaacau cccauaaaua ucagagguua 600
uguaucccuu gaacgcgcuu aaaacuaccu aggaguccuc gaacuuuguu caccgacgca 660
augcggauaa ggaucaucca ccgaaaacca gaugcgacac ucagugcaua uuaucuuucc 720
acaguguaug uuuauaugcga uuucgauagg guauugcuuu gguguacgag uccgcuuagg 780
ucagucaaug uagcauguug uuguuuuuaa aguuuucauu gguacuaaaa cuuuuguuca 840
ccaacguagu auuauaaaaa ucauaguaau auaaauaacg cugcaauguu augaaucuua 900
ccaaauuauu uuaugguucu guuguauuag ugauuugaau uuaaaaauug uacacauuua 960
cuaugaaaua aauugauuua uuguuaaaaa aaaaaaaaaa aaaaaaaaaa aaaaaaaaaa 1020
aaaaaaaa 1028

<210> SEQ ID NO 197
<211> LENGTH: 3012
<212> TYPE: RNA
<213> ORGANISM: Diabrotica virgifera

<400> SEQUENCE: 197
auuuauggua cacaucacua aaguauuaau caccacacuu uauaaauuca aauuuuuaga 60
guuggaaucu acaaaguuag ugauaauuag aaccauugug gcauucagaa acggucuaaa 120
cuuucaaugu uagcaaccuu uuguauauag cuacaauacc gauauaacag ugaacugaaa 180
aacucuagug uagugauaca aagcauuuac caugggucuu accauaucag caguguuuaa 240
uagguuguuu aguaaaaagc cuaugagaau uuuaauggua ggauuagaug ccgcagguaa 300
aaccacaauc uuauacaaau ugaagcuugg ugaaaucgua acuacaauac caaccaucgg 360
cuucaaugua gaaaccguug aguacaagaa uauaucuuuc acgguauggg auguaggugg 420
ccagacgaga aucagaaaac ucuggagaca cuauuucgcc aacacugaug gacucauuuu 480
ugugguugau uccaacgacc gagaccguau cgcggaagcc gaagaagaau ugcacaauau 540
guuaggagag gacgauuuaa gagacugcau uuuguuaaua uucgccaaca aacaagauuu 600
accgaacucg auguccacug cugaauugac cgauaagcuu aaguugcaca cuuugaagaa 660
uaggaggugg uacauacaag ccacaugugc uacucaaggg aaugguuugu acgaaggacu 720
agauugguug ucgaaugaau uggccaagug aauagguaga uguugugaag aguagcuuuu 780
auauuuuuua uugauaaugu aaaauccugu uuuauuugcc ucaguuuggu agaauucaua 840
caauauugcu ucuauguuga uaacuuuaua uguuucuauc auuaaaauau ggauaauuuu 900
auccaaaauc uagcuaaacc acuauauaac gcguuggcug uguuacgaga caaauagacc 960
ucguauuaua cuaacaguug gcucugucga cuauguugua auacacugug gcauuacugg 1020
acauauaugc cucguaaagc acucaaugcg ggcuuauaaa uaucucuaaa ugcagccaaa 1080
guauuaaucu uagcuuuaac ucuugauauu uuucaggauu uguguauaau uuauugaaag 1140
uuuaguuaaa uauuacauuu uucuucgauu uuguucauuu aggcaaucuc acauuauuua 1200
uauguaacau guuauugaau cauacccgcc auagccaauu auauacccgc cauagucuaa 1260
uuucagagau uauuuuuuug uuuuauugac gugaguacau uuuuuaagaa auucguuuca 1320
acauuuuugu cucuccucua uucauucauu cauuaaagcc ggauuuacau auacaaguac 1380
uuggauccga gauaucagua gaacugcgaa uuuuuacauu aaauaccagu gauucaaagg 1440
aaauauucau uauaucugca auagcuucau augcauuauu uauuuuguug auaucacaau 1500
auuccuugag uuuacauucc acaaacauuc aaaugaucag uaaaaacuaa uaaacugucc 1560
caucuguucu ccagacaauc uuaguuccac uuuuuuuuuu auuuguaaau uacaugugcu 1620
cuuguauugc uacuugguuu guguucaacu uccauccaug cucguaucca aguaacaaga 1680
ggcccugaga aggcguuuau acuucugaca ugcacucuga guagaguaac ucgaauucaa 1740
guacuuguaa gggcgacuuu agaguuacaa ucccuaggga uuauaucuaa ugccauggug 1800
uucaaaaucc uaugcuuagg ugagguggau uauuccuuug ugucauguau aguuuccugu 1860
augucuuugc ugcuguugug acucuuuuuc auuucuuccu guccuugcac cgaaauuucg 1920
agucuuguuu ugaauuuaau aguauuuugu auuuugacaa cgaaacccga uuugggcuuc 1980
gaaacguuaa uaaauucauu uuuuaguaaa auuguggcuu auuucccaua aaaaauacgu 2040
aauuguuuug aauuauuugc ucaaucuuau caauuguuac auuuacauau uuuuuauuug 2100
ggucgauuuu cuuuguuuau ucacaaaauu guuauaaccu gucugagaaa ucuuucaaau 2160
guuuuuuuac auuuccauua uucaauauua cacaauaucu cuauugggaa cgugcuuagu 2220
uuaucucuau uaggaagacu aguuuuaaaa acuaaaaaug uuuucuucga uaguaaaaua 2280
aacaaccagu guuuaacauc uuugccacau uuaaagauau uuauaacacu acguugggug 2340
cgucaugagg cauauauguc ccgaauaccc ccauuugcca cuguguuacg acacaguuga 2400
cguagccaag cguuagugua guacgaggug ucccguaaca cagccaagau guuaacaaua 2460
aacauaaaca aaauacaauu uugugcuacu aucuaaauaa gaugucaaug aguuauagaa 2520
caaagaauau uguaugaauc uauucgacca uaucauaaac ugacuuuuuc auguaguaaa 2580
caacguuucu gcaacuccuu cuucugugaa uucacuuuuu guucuaccua gauuuaaaua 2640
uuuauauaaa uaaguuuccu auuauauacu acaguggaac cucgauaacu cggauuaaac 2700
gggaccgcgg ccgauccggg uuaucgaaaa uccggguuag ccggagaaua uaguaaaaau 2760
uaauaaauaa ccuccauuau aauuacaaaa acaugaaaca cauaugcaca guacacaucu 2820
aaauuacgua uaguuguaua gaguguagag uuuuguucau uucuugguaa aaaacucagu 2880
cauacuguag agauguaccg acaccauaau augguagguc uggauccugc guacaaaaaa 2940
aaauugauaa auagcaagcc gaaaauuugu uguuagcuug ggggugucua gucggacaga 3000
cauugauaua ug 3012

<210> SEQ ID NO 198
<211> LENGTH: 1212
<212> TYPE: RNA
<213> ORGANISM: Diabrotica virgifera

<400> SEQUENCE: 198
caacacugcu aucugggcug uugcacuaau cauaugggguu gguuguuagu ucacuuuuuu 60
cuacaguacc augugucacu agcauaauac ucaaaaaauu aauauuuaau uuugugaacu 120
uaguuaacau cauuuugaaa aaugcgguac acuuugaguu acaucggugc uacccuagcg 180
uccacuguaa cacugauuuu ugcccucuac uacugccuca cgggaaaagg agagcaaguu 240
aguuuagcau gguuauuguu gaaugugucu ccccacaugu gggcaggucu aggaauuggc 300
cuugcuguau cauuaucagu uguaggagcu gcugcaggaa uucacacuac aggagucagu 360
aucguaggag cugguguuaa agcccccaga aucaaaacca aaaauuuaau uucuauuauu 420
uucugugaag cuguggcuau cuaugggguua auuauggcua uaguacucug uggaaguugg 480
aagaauuucg auguagaccu auucaaccuc aaaacucaua acuuugcuca aaaccauuau 540
ggaucacaug uuauuuuugg auccgguuua acuguuggau uuguaaaucu auuaugugga 600
uuuuguguug gaguaguugg uucuggugca gccauuucug augcagccaa uucaucauua 660
uucgucaaaa uuuugauuau ugagauuuuu ggaagugcca uuggucucuu cggucugauu 720
guuggaguau acuugacguc aagaggcucu augguuuaaa uguucaguaa augaacauga 780
aaaauaaaau gaauaauuug uuaaaagugu gugugaugaa gauacaacua uuuucacuag 840
uuuacgcccc aaaauauuuc auugugguuu uugaacaaua uuuaaaaucc auucuaaauu 900
aaaauucuuc aaauaauugu ugaaaacaga uucaaggguc uuuaaucagu guauauaaua 960
guauuaaaua aauauuccac uaauuuuguu aaucauuguu aaacauugua uaguuacaaa 1020
agaaauuuuu aauuuagaau aauaugcuug uacagcaugu agucccacua guauuaguau 1080
uuaaaaacug uauuaaaaau ugucuuuucu augucuaaua aaauuacaga cgauuuuguu 1140
aaauuuuaau acagaucuaa aaaaaaaaaa aaaaaaaaaa aaaaaaaaaa aaaaaaaaaa 1200
aaaaaaaaaa aa 1212

<210> SEQ ID NO 199
<211> LENGTH: 7646
<212> TYPE: RNA
<213> ORGANISM: Diabrotica virgifera

<400> SEQUENCE: 199
cggauuucgg agaguucgau ucguugucga gccuucaaaa uggcuaccaa cgauaguaaa 60
gcuccguuga ggacaguuaa aagagugcaa uuuggaauac uuaguccaga ugaaauuaga 120
cgaaugucag ucacagaagg gggcauccgc uucccagaaa ccauggaagc aggccgcccc 180
aaacuaugcg gucuuaugga ccccagacaa ggugucauag acagaagcuc aagaugccag 240
acaugugccg gaaauaugac agaaugnccu ggacauuucg gacauaucga gcuggcaaaa 300
ccaguuuucc acguaggauu cguaacaaaa acaauaaaga ucuugagaug cguuugcuuc 360
uuuugcagua aauuauuagu caguccaaau aauccgaaaa uuaaagaagu uguaaugaaa 420
ucaaagggac agccacguaa aagauuagcu uucguuuaug aucuguguaa agguaaaaau 480
auuugugaag guggagauga aauggaugug gguaaagaaa gcgaagaucc caauaaaaaa 540
gcaggccaug gugguugugg ucgauaucaa ccaaauauca gacgugccgg uuuagauuua 600
acagcagaau ggaaacacgu caaugaagac acacaagaaa agaaaaucgc acuaucugcc 660
gaacgugucu gggaaauccu aaaacauauc acagaugaag aauguuucau ucuugguaug 720
gaucccaaau uugcuagacc agauuggaug auaguaacgg uacuuccugu ucccuccccua 780 gcaguacgac cugcuguagu uaugcacgga ucugcaagga aucaggauga uaucacucac 840
aaauuggccg acauuaucaa ggcgaauaac gaauuacaga agaacgaguc ugcaggugca 900

-continued

```
gccgcucaua uaaucacaga aaauauuaag auguugcaau uucacgucgc cacuuuaguu    960
gacaacgaua ugccgggaau gccgagagca augcaaaaau cuggaaaacc ccuaaaagcu   1020
aucaaagcuc ggcugaaagg uaaagaagga aggauucgag guaaccuuau gggaaagcgu   1080
guggacuuuu cugcacguac ugucaucaca ccagaucccc auuuacguau cgaccaagua   1140
ggagugccua gaaguauugc ucaaaacaug acguuuccag aaaucgucac accuuucaau   1200
uuugacaaaa uguuggaauu gguacagaga gguaauucuc aguauccagg agcuaaguau   1260
aucaucagag acaauggaga gaggauugau uuacguuucc acccaaaacc gucagauuua   1320
cauuugcagu gugguuauaa gguagaaaga cacaucagag acggcgaucu aguaaucuuc   1380
aaccgucaac caacccucca caagaugagu augaugggcc acagagucaa agucuuaccc   1440
uggucgacgu uccguaugaa ucucucgugc accucucccu acaacgccga uuuugacggc   1500
gacgaaauga accuccaugu gccccaaagu auggaaacuc gagcugaagu cgaaaaccuc   1560
cacaucacuc ccaggcaaau cauuacuccg caagcuaacc aacccgucau ggguauugua   1620
caagauacgu ugacagcugu uaggaagaug acaaaaaggg auguauucau cgagaaggaa   1680
caaaugauga auauauugau guucuugcca auuugggaug guaaaaugcc ccguccagcc   1740
auccucaaac ccaaaccguu guggacagga aaacagauau uuucccugau cauuccuggc   1800
aauguaaaua ugauacguac ccauucuacg cauccagacg acgaggacga cgguccuau    1860
aaauggauau cgccaggaga uacgaaaguu augguagaac auggagaauu ggucauggguu  1920
auauugugua agaaaagucu uggaacauca gcagguuccc ugcugcauau uuguauguug   1980
gaauuaggac acgaagugug ugguagauuu uaugguaaca uucaaacugu aaucaacaac   2040
ugguuguugu uagaagguca cagcaucggu auuggagaca ccauugccga uccucagacu   2100
uacacagaaa uucagagagc caucaggaaa gccaaagaag auguaauaga agucauccag   2160
aaagcucaca acauggaacu ggaaccgacu cccgguaaua cguugcguca gacuuucgaa   2220
aaucaaguaa acagaauucu aaacgacgcu cgugacaaaa cuggugguuc cgcuaagaaa   2280
ucuuugacug aauacaauaa ccuaaaggcu auggucguau cgggauccaa gggauccaac   2340
auuaauauuu cccagguuau ugcuugcgug ggucaacaga acguagaagg uaaacguauu   2400
ccauuuggcu ucagaaaacg cacguugccg cacuucauca aggacgauua cgguccugaa   2460
uccagagguu ucguagaaaa uucguaucuu gccggucuca cuccuucgga guucuauuuc   2520
cacgcuaugg gaggucguga aggucuuauc gauacugcug uaaaaacugc cgaaacuggu   2580
uacauccagc gucgucugau caaggcuaug gagaguguaa ugguacacua cgacgguacc   2640
guaagaaauu cuguaggaca acuuauccag uugagauacg gugaggacgg acucugugga   2700
gagaugguag aguuucaaua uuuagcaacg gucaaauuaa guaacaaggc guuugagaga   2760
aaauucagau uugauccgag uaaugaaagg uauuugagaa gaguuuucaa ugaagaaguu   2820
aucaagcaac ugauggguuc aggggaaguc auuuccgaac uugagagaga augggaacaa   2880
cuccagaaag acagagaagc cuuaagacaa aucuucccua gcggagaauc caaaguagua   2940
cuccccugua auuuacaacg uaugaucugg aauguacaaa aaauuuucca cauaaacaaa   3000
cgagccccga cagaccuguc cccguuaaga guuauccaag gcguucgaga auuacucagg   3060
aaaugcguca ucguagcugg cgaggaucgu cuguccaaac aagccaacga aaacgcaacg   3120
uuacucuucc agugucuagu cagaucgacc cucugcacca aaugcguuuc ugaagaauuc   3180
aggcucagca ccgaagccuu cgagugguug auaggagaaa ucgagacgag guuccaacaa   3240
```

-continued gcccaagcca auccuggaga aauggugggc gcucuggccg cgcagucacu gggagaaccc 3300
gcuacucaga ugacacugaa cacuuuccau uuugcuggug uauccuccaa gaacguaacc 3360 cugggguguac cuagauuaaa ggaaauuauu aauauuucca agaaacccaa ggcuccaucu 3420
cuaaccgugu uuuuaacugg ugcggcugcu agagaugcgg aaaaagcgaa gaauguguua 3480
ugcagacuug aacacaccac ucuucguaaa guaaccgcca acaccgccau cuauuacgau 3540
ccugacccac aaaauaccgu cauuccugag gaucaggagu ucguuaacgu cuacuaugaa 3600
augcccgauu ucgauccuac ccguauaucg ccgugguugc uucguaucga acuggacaga 3660
aagagaauga cagauaagaa acuaacuaug gaacaaauug cugaaaagau caacgcuggg 3720
uucggggacg auuugaauug uauuuucaac gacgacaaug cugaaaaguu ggugcugcgu 3780
aucagaauca ugaacagcga cgauggaaaa uucggagaag gugcugauga ggacguagac 3840
aaaauggaug acgacauguu uuugagaugc aucgaagcga acaugcugag cgauaugacc 3900
uugcaaggua uagaagcgau uuccaaggua uacaugcacu ugccacagac ugacucgaaa 3960
aaaaggaucg ucaucacuga aacaggcgaa uuuaaggcca ucgcagaaug gcuauuggaa 4020
acugacggua ccagcaugau gaaaguacug ucagaaagag acgucgaucc ggucaggacg 4080
uuuucuaacg acauuuguga aauauuuucg guacuuggua ucgaggcugu gcguaagucu 4140
guagagaagg aaaugaacgc uguccuuucg uucuacgguc uguauguaaa cuaucgccau 4200
cuugccuugc uuugugacgu aaugacagcc aaaggucacu uaauggccau cacccgucac 4260
gguaucaaca gacaagacac uggagcucug augaggugu u ccuucgagga aacuguagau 4320
guauugaugg acgcugccag ucaugcggag gucgacccaa ugagaggagu aucugaaaac 4380
auuauccucg gucaacuacc aagaaugggc acaggcugcu ucgaucuuuu gcuggacgcc 4440
gaaaaaugua aaaugggaau ugccauaccu caagcgcaca gcagcgaucu aauggcuuca 4500
ggaauguucu uuggauuagc cgcuacaccc agcaguauga guccaggugg ugcuaugacc 4560
ccauggaauc aagcagcuac accauacguu ggcaguaucu ggucuccaca gaauuuaaug 4620
ggcaguggaa ugacaccagg uggugccgcu uucuccccau cagcugcguc agaugcauca 4680
ggaaugucac cagcuuaugg cgguugguca ccaacaccac aaucuccugc aaugucgcca 4740
uauauggcuu cuccacaugg acaaucgccu uccuacaguc caucaagucc agcguuccaa 4800
ccuacuucac cauccaugac gccgaccucu ccuggauauu cucccaguuc uccugguuau 4860
ucaccuacca gucucaauua caguccaacg agucccaguu auucacccac uucucagagu 4920
uacuccccaa ccucaccuag uuacucaccg acuucuccaa auuauucacc uacuuccccca 4980 agcuacaguc caacaucccc uaacuauuca ccaacaucuc ccaacuauuc acccacuuca 5040
ccuaguuauc cuucaacuuc gccagguuac agccccacuu cacgcagcua cucacccaca 5100
ucuccuaguu acucaggaac uucgcccucu uauucaccaa cuucgccaag uuacuccccu 5160
acuucuccua guuauucgcc gucgucuccu aauuacucuc ccacuucucc aaauuacagu 5220
cccacuucuc cuaauuacuc accguccucu ccuagguaca cgcccgguuc uccuaguuuu 5280
uccccaaguu cgaacaguua cucucccaca ucuccucaau auucuccaac aucuccaagu 5340
uauucgccuu cuucgcccaa auauucacca acuucccccca auuauucgcc aacaucucca 5400
ucauuuucug gaggaagucc acaauauuca cccacaucac cgaaauacuc uccaaccucg 5460
cccaauuaca cucugucgag uccgcagcac acuccaacag guagcagucg auauucaccg 5520
ucaacuucga guuauucucc uaauucgccc aauuauucac cgacgucucc acaauacucc 5580
auccacagua caaaauauuc cccugcaagu ccuacauuca cacccaccag uccuaguuuc 5640 ucuccccgcuu cacccgcaua uucgccucaa ccuauguauu caccuucuuc uccuaauuau 5700
ucucccacua gucccaguca agacacugac uaaauauaau cauaagauug uagugguuag 5760
uuguauuuua uacauagauu uuaauucaga auuuaauauu auuuuuuacu auuuaccagg 5820
gacauuuuua aaguuguaaa aacacuuaca uuuguuccaa cggauuuuug cacaaacgua 5880
acgaaguuaa aucaaaacau uacaacugaa acauacgucg guauguacug ucaaugugau 5940
cauuaggaaa uggcuauuau cccggaggac guauuuuaua aaguuauuuu auugaagugu 6000
uugaucuuuu uucacuauug aggagauuua uggacucaac auuaaacagc uugaacauca 6060
uaccgacuac uacuaauaua aagauaaaua uagaacggua agaaauagau uaaaaaaaaa 6120
uacaauaagu uaaacaguaa ucuuaaaaau aaacaaauaa guuuccguuc cgacagaacu 6180
auagccagau ucuuguagua uaaugaaaau uuguagguua aaaauauuac uugucacauu 6240
agcuuaaaaa uaaauaauua ccggaaguaa ucaaauaaga gagcaacagu uagucguucu 6300
aacaauuagg uuugaaaaua aaaauuauaa ugaaauauac aaagacuaaa aguuuaaaua 6360
auaugaaaac cauuuuuaac ccuccguuag ucgcuaucgg ugucacacac cgacgacaga 6420
auuauucauu cgggauuuac aaaauaacug uuuuuuucua uaccacuuuc uguaccucuu 6480
ccuaucaacu aaccucgugu uaguauacau ucuuaccuac uuggguacag uugugcgagu 6540
uuuauagcua uuuucggugc aagacuccgu agcgacuaac ggugugguua uuacuuuauu 6600
ggcguaacuu gcaguucagg uaaagauuua gcaucuuauu auugcauuuu aucgguaagu 6660
uuuggucaaa uuuuauuuau agauguccuu ugaagccgaa cgaaaacguu uguuggaauu 6720
augggaaaug guuccuagcg aauauuuuua uauuacaaau aacaauaugu uuauuguuau 6780
acuaggguuu uucauuuuau aucugucguu uuucaaugaa gcauuuucaa aaauauuuuu 6840
uagucauucc uauacacaau auaaaauauu uguaugaauu uuauagcaau aacuuuuuuu 6900
uuuaaauugu cggucucuga caccguagcg acucuugaug cuccguuuau ccuagcgacu 6960 aacgggggguu aaugugaauu uaucacaagc acaaagcaca uagauaaaac caaaccuaua 7020
aguuacuucu aauacaaaau aauuaaaugg uuuugaaguc auaaucucgc caguuuugug 7080
aagaauuauu aaggaccaga caggucuuca agucgugccg uuuucugucu gcuugucucu 7140
gcaauaaauc uuaaacgaaa aguccuaaug auuuaaaacu uaauauuaug uauauuugua 7200
cauaggauau uuacgaucca aggaagaaca aaggaauuug gugucaaugg gucaaaguuu 7260
accaaaaaaa guuacugaua auuccgauua gaaaggacgu agagccuuuu accaucaguu 7320
agagguuaga gguucggcaa aggcuuuugu uacuuuacau aauucuguca gguccuuugg 7380
uacucauuau acaaaagcuu uuaauuuugc accuuucacu uccuuccacu aauucgguac 7440
cacggacuau cgaaggacca aauauaauuu uuuaacauac cuaaagcccu ugccgaaugu 7500
cuaaccgaag auucaauauu ucacauccca ucuggaguuc ucuguaacuu ugagaugauu 7560
uuuaaucuau ugacgcgaaa uucaauaguu uucuuggacc aaaaggacgc uguguaccaa 7620
guuucaugac uuuuccugaa agaguu 7646

<210> SEQ ID NO 200
<211> LENGTH: 2600
<212> TYPE: RNA
<213> ORGANISM: Diabrotica virgifera

<400> SEQUENCE: 200
guugacauug acagugggga caccuauucu ggcaauugga auuaauuugu caauaucauu 60

-continued

```
uuuugucgug aaauugugug uuguaggaga aaguaauauu auuaaaaaau gucgucaaau    120
auucaaaagg cccagcaguu gauggcggau gcagaaaaga aaguaacauc ucgagguuuc    180
uucggaucuc uauuuggggg aucaagucgu auugaagaug caguggaaug uuacacaaga    240
gcugcaaacc uuuuuaaaau ggccaagagc ugggaugcug ccgguaaagc cuuuugugag    300
gcugcuaauu ugcauuccag aacuggugcu cgucaugacg cugccacuaa uuauauagau    360
gcugcaaauu guuacaaaaa agccgaugua uuugaggcug uaaacugcuu uauaaaagcu    420
auagacauuu auaccgaaau gggucgcuuu acaauggcug caaaacacca ucagacuauu    480
gcagaaaugu augagacuga ugcuguggac aucgaaaggg cuguucaaca cuaugaacag    540
gcggcugauu acuucagagg agaagaaagc aaugcuuccg ccaauaagug ucuucuuaaa    600
guggcucaau augcagccca acuugaaaac uaugaaaaag cagugggaau uuaucaagaa    660
guggcuuaug cagcucugga aagcucucuu uuaaaauaca gugcaaagga auacuuauuc    720
agagcugccc uuugucaccu uuguguugau guacucaaug cacaacaugc uauagaaagc    780
uauauuucaa gguaucccgc auuucaagau ucccgugaau acaaacuuuu gaaaacccuc    840
auagaaaaca ucgaagagca aaacguagau ggauauacag aagccgucaa agauuacgau    900
ucaauuucuc gucuugauca gugguauacu acaauucuuu uacguauuaa gaaacaagua    960
agcgaaagcc cugacuuacg uuaagacgua uuuagaaauu ucuuauuaau auuucuuuaa   1020
guguuauuua agagacccau aguuuauuua uuguuggauu auuauuugag uaugucggua   1080
uacaugaagu gauuuaaccu ucauauagca uuuuuaaaua uggaagcgau acauuuaaca   1140
uucauuuuuu acaaaaaaaa uuaguauagc auuuugcaau uuaugguuuc uaaggauaaa   1200
guuaucaaau gagcaaauuc acuuaaguuc uaacauguuc gauaguauaa uaagauuaac   1260
gauacuuuua acgauauauc uguauaaaua uucaaugaaa auacguaagu auuaagcaau   1320
uaccaacuaa uauuauuauu ugcucauuua gguucucauu uuucaauuuu ugaaauuguu   1380
auucuugcua uuagaguaaa aagacuuaac aauaacaguu gguacuacaa uugcuuacua   1440
uauuagcagg caaaucuugg uuaucacaac accaucuuau aucagacuuu agaaacagcu   1500
uguaaaauua uauauaauga gcacuguuau auugauucuu uuaaauauuu ucucaucauc   1560
uaaaggugcg aacugacuug agcauuuuuc uccgaacgaa cugaaugagc agagcgugcu   1620
guagcaaauu gcucuagucu cuagucagua cguguucacg agcaaaauuc ugcugaacug   1680
aauuuucgga ggagugucgg uaaucguuga aagaucaaaa gcuaucauuu guucuuuugu   1740
gcucaauagc uacagacauu uaguguauuu gguguguucc gauugauuua uaugagcccu   1800
uuucuguagu auguaaucca aucaucauaa ucauucaacu cggaucuauc cacugcugga   1860
uguaggucuc ccucagucug uuccauguau uucuguuuug ugcuguuugc auccaauuuu   1920
ugucgagccg uuuuauguca ucagaccauc uuguuggcgg augaccucua cuucgauauu   1980
cuuguuguca ugguauccag uguauuauuc gcugugucca uuuguuauuc gacauucuag   2040
cuaugugucc agcccaguuc cacuuuaggg ucauaauuau uucuauagca ucugucacuc   2100
cuguucuucg ucuuauuucc uuguuuguaa uucgaucccu acgagaaaug uguaauauug   2160
agcguuccau ggcucuuugg guaacacaaa uuuuauuucu uacuuuguug guuauuguua   2220
aaguuucugc accauaugua aguacuggca acacacacug aucaaagacu uuccuuuuga   2280
gacauacaua uguguaaucc aauacacggg caauauuauc auaaaauaua gaaaaugaug   2340
cauggauauu aauagcugaa guaggaugua ccuccaaaga agcaaagaaa aagucauauu   2400
uauaugaauc uccugucgcu auuaaccaca aaguaacagu uaagcgaucu cgaagagaua   2460
```

uauauuauac cuuuucgaaa uguuuugcaa uuguaggacc uacuauaguc cgucccaucu 2520
ugacuuuaca guauggggag caggggcggu gcaguccuua ugagaguuuu uagcgcggug 2580
augccgauuu uaccaaaaac 2600

<210> SEQ ID NO 201
<211> LENGTH: 4648
<212> TYPE: RNA
<213> ORGANISM: Diabrotica virgifera

<400> SEQUENCE: 201
uuggcaauac gucuaauacg ucagucaaau gaaucaaguu guugggauug ggauuuaaca 60
aauacgucgu ucuaaauuuc uaaaacugca uacaaaaaau ccuuaaaaaa cuagugaaga 120
uuacuaaagu gcaauagaua caaaaacaau auuuuuacgu auucaccaua auaauauaaa 180
cguagaaaau gaaucccgag uaugauuauu uauucaaacu ucugcugauu ggagauucag 240
gaguaggaaa aucuugucuu cuacugagau uugcagauga uaccuacaca gaaagcuaua 300
uuaguaccau uggcguagau uuuaaaauca ggacaaucga uuuagaugga aagacaauua 360
aauugcaaau uugggauaca gcaggucagg aaagguuuag aacgauuaca ucaaguuauu 420
accgaggagc acaugguauu auuguagugu acgauugcac agaccaagau ucauucaaua 480
acguuaaaca guggcucgaa gaaaucgacc guuaugcgug ugacaaugua aacaaauuac 540
ugguagggaa uaaaagcgau uugacaacua agaaaguugu cgacuucacu acagccaagg 600
aguaugccga ccaauugggu auaccauuuu uggaaaccuc agcuaagaau gcaaccaaug 660
uagaacaggc cuuuaugacu auggccgcug aaauaaaaaa uagaguagga ccuccaucuu 720
cugcgguaga ccaaggaaau aagguuaggu ucgaucaaag ucgcccaguc gaaacaacca 780
aauccgguug cugcugaaaa uauuuaguuc ucuuugguug aagguggguca cucaugucau 840 cucuuuugua cgguagcagc gcuacaguua cucuuauucu aguaauaucc gucuguaugu 900
auaguuauuu uaaaguuuuu gauuugauuu ucacuuuaga uuuuuuuuuc aaaaauauag 960
aaaacaccaa uaucucuuag ccuaaucuua acucccuuag auaaauaugu aauuaacaaa 1020
aauauuuaua aaaccauuuu uacuaaacua uuaguccaca guauaucguu ccuuuucaaa 1080
aaugauuaca aaagucuuaa aaaugguuuu aauuguuucg uuuaaacgag ucuaccacuu 1140
uaugaaaaau uucagaaaga uuauacguua aaauaaaaua aauuauuuuu gucggacaaa 1200
aaagaggggc aaacacccgc aagaugucac ucuagcgcgg uacaguuuug uuaauuuauu 1260
aguccacagu auaucguucc uuuucaaaaa ugauuacaaa agucuuaaaa augguuuuaa 1320
uuguuucguu uaaacgaguc uaccacuuua ugaaaaauuu cagaaagauu auacguugaa 1380
auaaaaugaa uuauuuuugu cggacaaaaa agaggggcaa acacccgcaa gaugucacuc 1440
uagcgcggua caguuuuguu aauuacaaaa cucauaauuu ucaauugaaa guauugauaa 1500
uuacuaaaua uuguggaucu cuuguccgac agauuugcag ccucguuucu uuagugggac 1560
agcggaaaua uguuaauuau gguagguuau gguuugcggu uacaaaaguc auaauuuuaa 1620
uuuuuuaacg uucaaacugu ucaaaaagua auuguccgac aaaaaaauug uucgacgcaa 1680
acuuauaaca aaaacaguga cagucuacuu guguuugucg guauaaucgc aaauuaccua 1740
ccucuaguau agaugcuuag ucuaguaauu agucuguucc gcucugcgga auugaguaaa 1800
uggaauuaau uaaaaauaag uguaaacuau gaacaauaau auauuuauuu gugucgauaa 1860
aaagacgugu uuugcucgaa agggugugu guugacgcac cgcaucuauc ccgacgcccg 1920

-continued

```
cuggggugug acugccgacg ggagguugua aaucgacccg ugguuaugua ucgacugacg   1980
cuguggcuga aaaaaaccac aaacgcuaau auguuuguac uucuaacauc uggccagaaa   2040
agcgauaaau uacuacaucu guaguuuuaa gaaacgucuu cgaaugcauu uccaugcauu   2100
gacauggaau cugauaaggu aauuaauuca uggggaauuc aguuuguuaa acugaacaca   2160
ccaaaaauau gguuagggau acauuucguu ucguaaaacu ucuuagcauc ugguuuguau   2220
auuaaaugug aauuuauaug accguuuuga gaaaugauau uaaaaaauaa aauuagcaaa   2280
aauaguaauu aaagcguguc gccacaaguc uauguuuaca uucgguuucu auacauuuuc   2340
ugacguucua gacgucacua gacauaaaac uaaacagugc aacaaguaaa ggguccaggg   2400
cuauguuagc ucaauuuauc uaguacugug gcgguugcag uaaaaaaagu uuugaaauua   2460
auuugucgga cuggcuaucu gauacccaau uuuugucgga cauugcucua uuuggauaaa   2520
gaacccucca aucuaucacu uucguguucg aaauuuuaua aucgcaaucu gcauaauugu   2580
uaauuauuaa cauauuuacg uuguucgacu aaagagggga ggcugcgaau uugucugaca   2640
agagaucaac aaucuaguaa uuaauuauua auaaacuaaa agugguuagu ucccuggguu   2700
ggcuguauac cauguaguua aaaaacucua aacauguagu aaaaccacuu cuauauaaaa   2760
gguauaugua cugaaauuuu aaaaaucccg auggauugaa uaaacuaggu ucauucagaa   2820
cguuuucgga ccugucaguc caucaucagu gaauucauau auacuugcgc uaacuagucc   2880
cagaaccaaa caaugguugu acuuauaaau caaucuacau uauaguguua uguauuugga   2940
aaggcuaagc gccgauguuc ugauggacug auagguccga aaacguucug aaugaaccua   3000
uuuuauuuaa uucauuggga uuuuuaaaau uguaguaaau auaccuuuua cacagaagug   3060
guuuuauuuc auguuuuuug uccgacgaaa auaauuuauu uuauucuaac gcguaauuuu   3120
uugauuaaaa uuaaaaauua uaguuuugca aucucaaaac aaccgcgcua gagcuacagg   3180
uuuaaaagga agucaucaaa accauuuuua agacuuuugu aaucauuuuu gaaaaacgac   3240
gauauacugu ggacuacaua uaugagauca uuagaacgag aaagauauac ucaucgacug   3300
uuaauuuugu auuguuuuua guauaccuuu cucuguuuua uaaauccaga ucaugauaga   3360
uugacguuag aaauuauugu ucgcuuuuca aacguguauu agcagaauuu uggcaaauua   3420
aauauaaaaa uucgagaucc uuuauaaaaa gguauauuua aaauucccua aguaaggguu   3480
auauuaagua acagaacguu uucggauuaa aaaauccacc aucaguguua caaaaaaaaa   3540
auagcaugcc ugaggcaccg aaauguuacg gguaaaaacc cuuuaaaugu ugacaguugu   3600
ugucuuauac uaugauguug cuaauauucc uggauauuac ccagggcaac acaggacucu   3660
ucccacgugg uugaaauuug agaauuucaa ucacgaauuu gacacuucca aaauacguaa   3720
aguuuccac aucuuuaauc ugcauguugu gaauaguaaa uagagugucg uuccuugcau   3780
ugguucucau ggacuugauu uuacuaauau uaauuuucaa aucuauuuua uuggcuucag   3840
uggaaaguga auuuugaaaa aaaaucugcu aaaaauaguu uaaaaaauau uuuuuuuuag   3900
uugugacacu auacagauaa aauaacgaaa aauuuacgaa auaauauuua ucaaaagugg   3960
cucuugcagu acagaauaua auaucauuau uauuaucuag uuaauagacu cguacuuuuu   4020
aacgauguaa cuuuaaaaac aauuaacaac guuaaaaaaa uacugcaaaa aggaagauaa   4080
auaagugaua aaugugucac uuuucuugag cacuacgcag auuguuugga auaaagcuau   4140
cacguauuau acuguguaaa cuccacaaac gacacuuuau acacaucuua gaugaacaaa   4200
ugccuggcac aagucgauau gugacacugu uuauguucgg ugcaccguca guuuugguua   4260
aucauuagug ucagcuaacg aaaauacuuu aacuauaaac uugacacuuu uugagauaag   4320
```

```
auuuuguagu uuuauuaaac uguuggugca auaaaaccgu uuuuaaaauu uuuugaguug   4380

ugacacuauu ugagcggagg ugcgacaugu ggaaaauauu uacaauuauu ucauauauca   4440

cuuguucuau acaauaaaaa aacgucauuu cuaacaugau uuuuagugau uucuguuggu   4500

ccaaaacaau uuauuauauu auccauauau acuuguuauu uuuuauguaa ugauuuuucu   4560

uauucgcuac acauuaacgu cauuuuuugu uuauaucaaa uaaaaaguaa uauuguaagu   4620

aauaugugau uguaaaucuu ggucaaua                                      4648
```

<210> SEQ ID NO 202
<211> LENGTH: 1577
<212> TYPE: RNA
<213> ORGANISM: Diabrotica virgifera

<400> SEQUENCE: 202

```
agaaaacaag cgguuuauuu gccgccauuu ugacaagcuu acguaccuac auuuuuaauu     60

cguuguuuua uuuuuaguuu ucaauaauac ucuaaaaaau ggcagacgcu gaugaucuau    120

uagauuauga agaugaggaa cagacagaac aaaccgcaac ugaaacggca acuacagagg    180

uacagaaaaa gggugucaag ggcacauaug uaucaauaca caguucuggg uuuagagauu    240

uucuguuaaa accagcaauu cucagagcua uaguggacug cggguucgaa cauccuucag    300

aaguucaaca ugaauguauu ccucaagcug ucauuggcau ggauauucug ugccaagcua    360

aauccgguau gggaaaaacg gcuguuuuug uauuagcuac acuccaagua auagauccua    420

cagaaaaugu uguauauguu cucgucaugu gccauaccag agaguuagcc uuccagauaa    480

gcaaagagua cgaacguuuc aguaaauaua ugcccaauau uaaaguaggg gucuucuuug    540

guggcuugcc uauccagaaa gaugaggaaa cguuaaaaaa uaauugcccg cauaucguug    600

uggguacucc aggaagaauu uuagcauugg ucagaucgaa aaaacuuaau cucaaacauc    660

uaaagcauuu uauuuuggau gaaugugaua aaauguugga guuauuagac augagacgug    720

auguucaaga aauauaucgu aacacucccc acgaaaaaca agucaugaug uucagugcca    780

ccuuaaguaa agaaauuaga ccaguuugca agaaauuuau gcaagaugua auucaaaauu    840

cuuauaauac acaauuuugu aaugacgcac ccacucgcaa uguuugaaaa guucuaauuc    900

aaaauacggg ccaaaguuuu auuaaaucga aucauuuaaa agaugagggu guuggguuua    960

aaucauuagc gcauuguagc ccaacgagua ggcagggggug ggccgggcca agaagaggac   1020

acuauacagg auuuucuaaa uuuccguaaa ggguuccgcg accacauuuu cggccgagcu   1080

acaauguaga aaaauuuaca cacccuccaa guccaauaga auuaaugggg uuaauguuug   1140

aaguaccgau ggaguucuuu guugauuuau uuagaagagu auuuuuggau aauuguucag   1200

agaucauuuc aauggugaug cagcgaugau gggaugcgag auaucaacug acuguaugua   1260

cgauggauuc agucaagacu ccugagccuc guaacugcag acuauuucau uauuuuauua   1320

acuaaaguaa uaauugaguu uuuuaucgcc ucaauuauua uuucaaauaa uuuauauaaa   1380

gauuuagaaa acuaugauuu uguugauggu uauauuuaac ugucggugag uauuuucauu   1440

cacaaaagug uguguguuau ugcguugccg cuccugaaau aucuagaggc caccuaucga   1500

uggaucaaga guaaacuacc uuuauaguuc auaacauuua aauuagaaug auauaauugc   1560

acauuaaaac auaauua                                                  1577
```

<210> SEQ ID NO 203
<211> LENGTH: 1039
<212> TYPE: RNA

<213> ORGANISM: Diabrotica virgifera

<400> SEQUENCE: 203
gcaucugguc ugcccgcaua agcuuguugg aacugccagu gaguacacag ugauguucac 60
agggaagaca gugaacggug agguguggag uaaugagaau caugaguuuc aucaggugcu 120
aaugcaacuu ccaacaaaaa cagauuuuuu ucguaaaaug ugaacguguu agucagucaa 180
aauagcauca aaaugccggu cauugauggu uauaaaguac uuuacauuuu auuacacagu 240
uuauauacaa uuuuugaaaa uauuuggagg acucuuuuau uuauuuauca aaauuguaua 300
aggguuauaa acccugaauc uacauucgau gaugcugacc aguuaaagaa aagacugucu 360
agacuaacaa aaaagccuca acauuuaacu aucauuauug guguggaaga auauucauug 420
guagauuugg cuaaccucgu auauuggugu uuaggucuua auauuccgua cguuaguuuc 480
uaugauuaua aagguaauuu aaaaaagcau gaagagaagu ugcaacaaau uguagaaucc 540
agaaaaucag agaauaucaa cauaauuugg cacacccaug cagaacaaag gcauaaaaau 600
ggauuuuugg guccaaaaau ccacguaaaa guguuaacac acgcggacgg aaagcaaagu 660
auaguaaaug uuacuaaaaa auuagcucua aauaaagaaa aagacauuag uaaagaaaaa 720
auuagugaau uacuauuaag gcaguaugaa uuuccagauc cagaaauggc uauuauuugu 780
ggaaagaaac ugaacauuua uaauuauccu ccuuggcagu uaagacucac agaauucuuu 840
aaagucaaca aagucaacaa caucacauuc ccaguguuug uggaaaaauu ggaaaaguac 900
agcaaaugug aacagagggu gggaaaauaa uuguuuuaua aaaaacuguu uuuguuuugg 960
uuaucuuuau uauuaagaaa aaaaaaaaaa aaaaaaaaaa aaaaaaaaaa aaaaaaaaaa 1020
aaaaagaaca gagggugggg 1039

<210> SEQ ID NO 204
<211> LENGTH: 697
<212> TYPE: RNA
<213> ORGANISM: Diabrotica virgifera

<400> SEQUENCE: 204
cucgaauaaa cgccacaucc aaacaagagu ugacguugac agcgacauuu ccuccgccau 60
uuccuuuuac uguguuucuu aggauuugga agguacaaaa ugaccaacuc uaaagguuac 120
cgccgaggaa ccagggaucu auuugcccgc aaguuuaaaa aacguggugu aauuccacuu 180
uccacauauu ugagagucua caaaguugga gauauuguag auaucaaggg uaaauggugca 240 guucaaaagg guaugcccca caaaguguac caugguaaga caggacgugu uuucaauguu 300
acugcacaug cauuaggugu aauuguaaac aaaagggguuc gaggaagaau cauccccaaa 360
agaaucaauc uccguauuga acauguaaac cacuccaagu gucgucaaga cuucuugcaa 420
agaguaaaau ccaacgaaaa gcuacguaaa gaagcuaaag aaaagaacau uaaaguagaa 480
cuuaggagac aaccugccca accuaggcca gcacauauug uuagcggaaa gguuccagca 540
caggugcuug cuccuauccc auaugaauuc auugcuuagg uuuguuuauc uuaaaauaaa 600
auccuuuaua uaauaaaaaa aaaaaaaaaa aaaaaaaaaa aaaaaaaaaa aaaaaaaaaa 660
aaaaaaaaaa aaaaaaaaaa aaaaaaaaaa aaaaaaa 697

<210> SEQ ID NO 205
<211> LENGTH: 784
<212> TYPE: RNA
<213> ORGANISM: Diabrotica virgifera

<400> SEQUENCE: 205
cugacuucaa uuaaauggcc ucugucaaug ucagaguaaa ugucaaagug uaaaaaauaa 60
aaaaaguaac aacacaacag auuuuauuaa guuguagacg uguaauuuuu guaaauuuau 120
ucuaagccau uauuaauuaa aguaauacua aaauggaagg aauacuacug gaaccaacau 180
uguauaccau aaaagguauu gcuauauugg acuaugaugg uaauagagug cuggcuaaau 240
acuacgauaa agauauauuu ccuacagcaa aagagcagaa agcuuuugag aaaaauuugu 300
ucaauaaaac ucauagggca gacgcagaaa uuaucauguu ggaugguuua acuugugugu 360
auagaaguaa uguagauuua uucuuuuaug uuaugggcag uucacaugaa aaugagcuaa 420
uuuuaaugag uguuuuaaau ugcuuguaug acucaguaag ucaaauauug aagaaaaaua 480
ugcaaaaacg agcugucuug gaaucacuag auauuguuau gcuggcuaug gaugaaauug 540
uugauggagg aauaauuaua gauucugauu caaguucagu aguaucuaga auagcauuaa 600
ggacugauga uauuccauua ggagaacaaa cuguagcuca gguauuccaa acggccaaag 660
aacagcugaa auggucauug cugaaauaaa gugcguauuu uaaaacaagg uaaucgguau 720
uuauuucaug uacaauuuaa uuauuaagug uaaauaaauu uuuucuguuu aaagaugaaa 780
aaaa 784

<210> SEQ ID NO 206
<211> LENGTH: 1850
<212> TYPE: RNA
<213> ORGANISM: Diabrotica virgifera

<400> SEQUENCE: 206
guuugacgca uugcagguac aagccuacca aucacaaaca cacauuguac gaguagacgu 60
uguaaacaag ccgcacccga uguucaaacu ugacauaaca uacgccacgu caacuagauc 120
gcccaacacu acacaauuuc ccucacgaaa aaccaccgca uccaacacag uuuaaaauug 180
uacagcgaaa auaccaucuu caauaguuug uaaagcuggg aaaacaaaua ggaaaauuua 240
aacguuucgu guguuggcgu aggaauauuu cuaccgguuu cugucauugc cgcacuauug 300
cgcuuuggug guuucgcagc agcaguuccc cccucucuuc ucuuacgucg auccuaaaca 360
aaacgagaaa agacaguugg cuggugcacu uugacgagag gcguuguuag uuacuucguu 420
gugucgacau uuuucuguuu aguguaccga uuaaucuuca aauauuacaa uggcugacca 480
acucaccgaa gaacaaauug cugaauucaa agaagcuuuc ucacuauucg auaaagaugg 540
ugaugguaca auuacgacua aagaauuagg aacaguaaug agaucucuag gacaaaaucc 600
aacagaggcu gaauuacagg auaugaucaa ugaaguagau gccgauggua acggcacgau 660
cgauuuccca gaauuuuuaa cgaugauggc acguaaaaug aaagauaccg auagugagga 720
agaaauucgu gaagcauucc gaguguucga caaagacggc aaugguuuca ucucagcagc 780
agaauugcgc cacgucauga ccaacuuggg ugaaaaauug acagacgaag aagucgauga 840
aaugauucgg gaggccgaua ucgaugguga uggucaaguc aauuacgaag aguucgucac 900
caugaugacu ucaaagugag gaaaccagag uugcauuuuc agcuuuccau uguuucaucc 960
cggcucauug ucuacauuuu ucaacaccuc gaacuuuuug cuuuguggcc ggguccacua 1020
aagugaauaa cuuaaccguu auuugauuua caagacaaau uuaauuaaua aauauauuua 1080
uaaauuaaua uaauugugua aauuuuugua auauauuugu uuuucuuucg caggagucgu 1140
uggcgagauc uagucgcugg cgauucuugu acuguaucaa auucugugcu acaugucuag 1200
uugaaguuua aaaagaguua caaagucaca aaguaugaaa acacguauau auaaugaaga 1260

```
uaaaaaaauc guucuauuug auguuaguuu aggggauaca gcauuagaca cuuucaauuu   1320

uuuucauacu uugugaugua aauuacaucu gaucugugca cuuacuauau aguauguauc   1380

cccuuuuuug acauguucau ucauuuuucc ccuuucuugu acuguaggu uuacauuuuu   1440

agucuaggau uugaauuugc uggaaaguaa gcacauuuuu auugucaucc ugugaugcgu   1500

auggaaaugu uaauauuuuu uggcucuuac uguaucacag gaaauggucu uuagaaauug   1560

aucgaaauuu uuuacaacaa aaauuuuauu cuaauuucuu aagaccacuc ccuuucuuau   1620

uguaagauuu cguuuuuauu caagccuguu aauuuuuuua uuuauucuua cuauuuaaga   1680

uccaguaacg cauccguuac aaugugaaau uauuagaugu uuaaauuuga aauaaaugug   1740

acuaaaauau uuuccuguga cuuacuggua cccaauauau uauuacuaua aaguuuuuau   1800

guuagaauuu uuuucuuuau uuaaaauaaa auauuugaau uaaaaaaaaa              1850
```

<210> SEQ ID NO 207
<211> LENGTH: 3245
<212> TYPE: RNA
<213> ORGANISM: Diabrotica virgifera

<400> SEQUENCE: 207

```
cagcgccauu uuaguauuua gcucugaaga uugaguuuuu acuuccguga aaaauuuuua     60

cgaguuuuua uugucaucgu uauaauauuu ucgacaacug caguucugua uauagucggu    120

uugaaaaucu uaaagaaaau aaugagggua ugaauuuaaa cgugcuccaa uauuagcgcu    180

uagcguguau uugccggugu auuguguuca acgucaccau caaccaugau gcaagcaaac    240

aaucgagucc caccuauaaa guuggaaaac gauauagauc uuuacgccga ugauaucgag    300

gauuucgcac aagaugacuu ugguggugaa aauguugauc uauaugacga uguaauaucc    360

gcuccuccug gaaauaauga caacccaggu gauucaaauc aucaugcucc uccuggugcu    420

ggugaagaug guggagguaa uuuuguuggg ucaggaggag cacccaauaa uauaaauucu    480

ucuggaagaa gacaucagcu guauguugga aaucugacuu gguggacaac ugaucaagau    540

auagaaaaug cagugcauga uauaggggua accgacuucc augaaguuaa guuuuuugaa    600

cacagagcaa auggucaauc caagggauuc ugugucauau cuuugggauc ugagggaagc    660

augagacucu gccuggaacu ccuaucuaaa aaagagauca auggccaaaa uccccuuguu    720

acccuuccca caaaacaagc ucuuaguaac uuugaaaguc agucuaaaac acgcccuucu    780

ccuacuaaua auucuaacuc acguccuccc cauccuaaua auaauguuca uucaggaccu    840

augcagaauu auggagguag aaugccuaug aacccuucca ugcgucccau gcccccaggu    900

augcaaggug cuccaagaau gcagggucca ccuggauuua auggaccacc aaacaugaau    960

cagcaacccc ccagguucca agguaaucca caauggaaug gaccuagacc uaauggaccu   1020

gggcccaaua ugggaaugag acccaugggg ccaccucaug gacaacaagg gcccccaaga   1080

ccaccaaugc agggaccacc gcagcaaggu ccuccaagag gaaugccgcc acaaggucca   1140

ccgcagaugc guccagaaug gaaucgacca ccaaugcaac aaggguaccc ucaaggcccg   1200

ccgcauaugc aaggaccuaa caugggucca agagguccac cccaaauggg accacccggg   1260

gcgccucaac agcaaggacc agcuccgcac guaaauccag cauucuuuca acaaggagga   1320

ggaccaccgc ccccaaugca acacaugccu ggaccagggc ccgucaugcc uccucaagga   1380

cccccgcaag guccaccaca cggacccguu ggaccuccac acggcccacc auuggucca    1440

gcgaauguuc cgccucaugg accaccucac ggauaugguc caccugcagc gaugccacag   1500

ccgccauacg guggcccacc uccagaccac cgcgcugaga uuccucaguu aacagagcaa   1560
```

gaguuugagg auauaauguc ccggaauaga acaguuucca guucggcgau ugggcgggcc 1620
guauccgacg ccgcagcugg agaauuugca agcgccauug agacuuuggu uacugcuauu 1680
ucacucauca aacaauccaa aguggcuaac gacgaucguu gcaagauccu uauaaguucg 1740
cugcaagaua cuuugcgugg ugucgaagac aaaagcuaca gcuccagccg cagagaccgg 1800
ucaagaucca gggacagauc acauagaaga acuagaagag aacgauccuc gucacgguac 1860
agagacagaa gcagagagag ggagcgugaa cgcgauagag aucgugaucg ugaacgugac 1920
agauauuaug auagauacag cgaaagagaa agagaccgag aucguucaag aagcagagaa 1980
agaacagaaa gggauagaga acgagauuau agagaccggg aacccgaaga gacagauaaa 2040
gaaaaaucua aaguauccag agucucaaga ucaagaaaca aaucuccgga accugucgaa 2100
ccuagcagcg agguaccgaa aucaucccgc uauuaugagg auagguaucg ggaacgagag 2160
agagaagguc gacgagagag cgaucgcgaa agagaaagag auagaagagg ggaagacagc 2220
cauaggucuc gacacuagca uauaguuagc gguucacaga aacaacaaca aacaaguuau 2280
aguuggaguu caaacaaaga uuaucguguu uaauuuagag auagguuaua auaugugaug 2340
uuacuuuaca uaaauuuaaa cagguuccga auguguaagu uaaaagagca aaggaaacau 2400
ucacuaacuc auauuuugcu acuuguuuca uuuugcaaug gaacuucugg cuaucuuaaa 2460
uguauucaua aaaaggauaa aaaacauuua ccuguuuauu guuguauuaa guaaaucauu 2520
gacuauaaua uugcgauaaa uguuagauau uuuacuucau gggguuauac uuuugaugua 2580
aaaguuucac auauuuagcu uuaagcaaac gugacuuacu augaauauaa uaaauuaugu 2640
aagaacaaaa uuaaguaaug aauauaccac auaauucuuc aacuaaugag uuacuaugua 2700
caguauauuc uucuuacuau uucuucaguu uucuccugga guagcaaaac uuguuuuugu 2760
aaaaugaauu uauuguuuag gcugugcuau auuaacacug ggucgucuau uaaucuguua 2820
aaaaacaguu uuugagagaa uucuguucuu uauaaaaaau uacaggaggg ugaugaaagg 2880
cuuuauuguu acgugcaugu ugguaaaucg ggaugcuucu aaaugauaaa uaacuuuagg 2940
caacuuguug uuucugugag cuguauuuuu ucacauuuuu auguaaucau acauaaguaa 3000
aucauguaac guauaguuga uaaguacaau auagauggaa aucaaguuuu guuuuugugu 3060
guaguauaug gauuuaaaac auguaucuuu uaauaagaug auguuucaac auacaaugaa 3120
uaauuugugu aauaaauuga auacuauuca acaugaauug ucaaauucuu acaaaaaauc 3180
augauaauuu gaaggcaauu gaccaugaac uacucacaau gcaucuaaau gugaguguau 3240
ccucc 3245

<210> SEQ ID NO 208
<211> LENGTH: 1023
<212> TYPE: RNA
<213> ORGANISM: Diabrotica virgifera

<400> SEQUENCE: 208
gucgucaguc gucaacauca auuucaaguu ucaagaaaaa gcaaaucacu acgacuugcc 60
ggauuuugua guaguguuaa uuuuguauua aaaaaucaaa augaguucua uuggaacugg 120
guacgauuua ucagcuuccc aauucucucc ugauggaaga guauuucaag uugaauaugc 180
aaugaaagca guugaaaaua guggcaccgu aauaggccuc cgagguacag auggcauugu 240
auuggcugcu gaaaagcuca uuaugucaaa auugcaugaa ccaaguacaa auaaacgaau 300
uuucaacauu gauaaacaca uaggaauggc auuuucaggc uuaauagcug augcaaggca 360

```
aaucguugag auugcuagaa aagaagcauc aaauuauaga caucaauaug guucaaauau    420
uccucuuaaa uaccuaaaug auagaguaag cauguacaug caugcauaca cuuuauacag    480
ugcuguuaga ccauuugguu gcagugucau cuuggccagu uaugaagaua gugacccauc    540
uauguaucug auugauccau cuggaguuag cuauggauac uuuggaugug cuacagguaa    600
agcaaaacag ucugcaaaga cugaaauaga aaaauugaag auggggaauc uaacaugcaa    660
agaacuuguu aaagaagcag ccaaaaucau uuauuugguc caugaugagc ugaaggauaa    720
gaauuuugaa cuggaacuuu caugggguaug caaagauacg aaugguuuac auaccaaagu    780
gccugaauca guguuugcug augcagaaaa agcugccaaa caagcaaugg aagcagauuc    840
agaaucagau acagaagaua uguaauaacu acauuuaguu uuuaauauuu cgcugauggu    900
ggcuguucuu acaauauuuc guguguuaug uucauauauu auguaaauacu gugagaauuu    960
ccauuucaag gauagguuua uaacuuuuuu uucuaauaaa uacauaacuu uaaaaaaaaa   1020
aaa                                                                 1023
```

<210> SEQ ID NO 209
<211> LENGTH: 1439
<212> TYPE: RNA
<213> ORGANISM: Diabrotica virgifera

<400> SEQUENCE: 209

```
aaagugucag gugcuguugg ugucagcuga cuuuuuacuu uuuguuccag uccuauauuc     60
aacacacuuu ggauauuaaa uauuuuauuc uaaaucucaa gaauggcuuc aaaagacaga    120
uugaugauuu uuccaucuag aggagcccaa augaugauga aauccaggcu aaagggagcc    180
caaaagggac auaguuuauu aaagaagaaa gcugaugcuu uacaaaugag auuuagaaug    240
auuuugaaca aaauuauuga gaccaaaacu cucaugggug aaguaaugaa agaagcugcc    300
uuuucuuuag cugaagcaaa guuugcaacu ggugacuuca aucaaguugu ucuucaaaau    360
gucaccaagg cucaaauaaa aauaagaacu aagaaagaca acguugcugg uguuacuuua    420
ccaguguuug aaugcuacca agaugguaca gauacauaug aguuggcugg uuuggcuagg    480
ggaggucaac aauugacaaa acucaagaag aauuaucaaa gugcuguuaa acuguugguu    540
gaauuagccu cuuugcaaac uucuuuugua acucuugaug auguaaucaa aauaacaaac    600
agaagaguca augccauuga acauguuauc auuccaagaa uagagcguac uuuggcuuac    660
aucauauccg aacuggacga guuagaaaga gaggaguucu auagauuaaa gaagauccag    720
gacaaaaaga agaucagcag agcaaaggcc gagaaacaaa aacaagcucu ucuccaagcu    780
gggcuacuua aagaguccca ggcaaacaug cuuuuggaug agggcgauga agaucuacuu    840
uucuagaaca ucaaacagcc ugaagugugg uucuguacau augaauaaau auauaacgcu    900
aacuuguuuu uagacgguaa cuguuuauuu uucgcauuaa uuaauacauu uuuaagauau    960
aucuuuauuu uuaacugguu uuuauucuua ugccuugcaa uaguaaaaga uauacgaacc   1020
cggauauuuc cuauauaaau aacuuccuac uuuuuauuaa cuccaguuuu uaggauuuua   1080
auacaauauu caacacaucg ugcaauagaa uuugaaguga auauuacuug cgaaaauuaa   1140
aaagguacca aauauuuuuc uuaauauuga acguauauuc cagaauagua uuauaaaagu   1200
uuugauugaa auucuuguac gugacacuau gaacuuguag auuuuagaga aagcagcuuu   1260
ucaauggaaa augcuuuauu gauauggaca cuagauaaug uaaauacuug uuaauauacu   1320
uugaacagau aaaauaguuu auucguuuua aauucuuuaa aacucuaaau uguuuuucau   1380
caaauguaua cauggccugu aaauuguugg uuagaaauaa aacucuguuc aaaaaaaaa    1439
```

<210> SEQ ID NO 210
<211> LENGTH: 5226
<212> TYPE: RNA
<213> ORGANISM: Diabrotica virgifera

<400> SEQUENCE: 210
gcgauugcgu cugcugaaug cacccauagu auugugguga cugugacagg ugacagucgg 60
agucgacagu gaaguacaaa ucaaaaucau ucccuauuug ucaaacaaaa augaaauuac 120
guguauuauu auuuacccaa guaacuuuuu aauaauuuaa gccgauuauu gcacuguuag 180
uacguaugua caccacaaau aaccaauaua uucuuuguuu cccaugauaa cacaguucua 240
auuucacugu uagaugcaug uuacauguuu uuaguggaau cauuacugga uaaaguccuc 300
ucccauaauu aaauaaauac uuaaaaaaug gaggcggcuc ccaaguuacc gaugcucucg 360
uucgaguuaa auacuuguac agagaacguc cacuuuggcc cccaguuaaa acaguauauu 420
gcugcuuuuu auggugaaga uccagaaucc uacauuacag aaaucagcaa ucuugaaucc 480
uuaagaucag cugcaguucg accaucaacg gauguaaaug guguacaacu guugaaaaag 540
uauuucuguc agcuucguuu ucucaaaucu agguuuccca uggaagagaa ucaagaugcu 600
gcaguucuau uuucauggaa aaauaaugaa uuagacauaa cuucaacauc cagugauauc 660
agauaugaau uaaugguaau aauguauaac auuggagccu uacacacuuu ucuuggagcc 720
aacgacucaa gaaacaaucc ggaugguaug aaaauggcau guacucauuu ucaaugugcu 780
gcaugggcuu uucaaaacgu aaaagaaaag uaccaccaau ucauaucaaa caucucauug 840
guagaacugg uucauuuuuu ucaacaaguc uguuuagcuc aggcucagga guguauauua 900
gagaagagca uguuugacaa uaggaaaccu accaucauug caaaaguugc uauccaaguc 960
uacaguuauu acagacaguc uuuacguguc uuggaaucag uaaaugaagc cuacuuuagg 1020
gauaaaaccu acaaggagug gaugaaauau cuucaauuca agcugaccua cuacaaaugc 1080
aucucguucc uauuccaagg gcaacaagcu gaggaacaac agaaaauggg agaaaggguu 1140
gcauucuauc aagcugcaug ugaacagcug gacgaggcaa agaaaauugc ugcuacauua 1200
aaaaaccaac accaccagca agaaauaaau gagggacuag cauucacuac ugaugugguu 1260
gaagguaaaa gaaaagcagc uaaaaaugaa aaugaguuca ucuaccauga aucagugccu 1320
gauaaagacc aauugccaga gguuaagggu gcuucauuag ucaaaggaau accauucagu 1380 auaaaaugaua uagaaguuuc aggaccagau auuuucuccc gauugguccc aauggaggca 1440
cacgaagcag cuuccuugua cagcgagaag aaagcucaga gauuaagaca gaucggggaa 1500
cuuauugaaa auaaagauca aacauuggcu gaauuuaugu cgucaaugca gcuagaucua 1560
uugaccaaga ugcaccaggc uacuggaaua ccgcaggagu ugauugauag agcagcggcu 1620
cuaucugcua aaccuaacgc cauucaagau cuuuauaagug cuaugggaaa gcuaucuaau 1680
auauaccaag acguugaagc aaguuugaau gagauugauu cuuuauuaaa ggccgaagaa 1740
caaagugaac aaaaguacca agaaacgauu gguaaaagac caccgagcau uuuagcuaca 1800
gauuuaacua gggaagcggc aaaauacagg gaggcucaua cuaaagcgaa cgacucaaac 1860
caaacuuuac acagggcgau gauggcucac guggcuaauc ugaaaauacu ccaacaaccg 1920
cuaaagcagc ugcaacauca gcugcccuuu gucgaguuuc caaauccaaa uaucgacgaa 1980
aaaucuuuga aagaucugga agcgcuaguu gcaaaaguag acgaaaugag aacccaaaga 2040
gccaugcuau gggcucaacu ucgagaaucu auucaccaag acgauauuac aaguucccuu 2100

-continued

```
guaacgaaac aaccaaauca gucgcuggaa cagcuguucc agcaagaacu ucaaaagcau   2160
caaaaucuga uuucguugau ugaacaaaac accucggcac aagaaaacau uaagagcgcc   2220
uuagucgauu cuuacgcuua cgcuguaaau ucaagaaaau acauccaaga uauacuccaa   2280
aagagaacca caaccauaac gucacugaua gcaucguucg acucuuacga agacuuauug   2340
gcaaaagcua acaaagggau agaguuuuac ucaaaacuug aaacgaacgu auccaaguua   2400
cugcaaagaa uaaggaguac cugcaaaguu caacaagaag agcgagauca gaugaugucg   2460
acugcgcaag ugccucaaug ggagagucau acgucacuug ccgcuccuaa acugaaagau   2520
uacuuggacu ccaggaagaa gagugcugcg uauucggagc cgaguguuca accacaacag   2580
ccaacuuuaa guuacucagc ugcuauggau cugccuccug guauuaggcc gacuccaguu   2640
ggaucagaaa uaacggaugu accgaaaaau auucaaggug aaccacaagg uuauauucca   2700
uauaauuacc aacaaccuuc uguuccugcc ucacagaaua uugaugaaga gacuauuaaa   2760
aaaaugaacg cauugaugcc aggugcuaag acgucagugc cuagucagua cggauacagc   2820
aacuacauuc caccaacaua cccucaaagu gcguaccaac cagguaauca gucuuacgga   2880
aaagaaacuc cagauauuaa cucaccguac gacccuacca aggcguucac ggcuacuacu   2940
aacgcuuauc guucggugca gagcuccuca acucaaggau acguaccgua cgcagaaucu   3000
aacguuucga auguugacag aguuggauau ccuagcaggu aucaguacca acaaguaccu   3060
gagauagcua cuacuccagc ugaucccaau auuaaugcgu acuacccaca uggguacuca   3120
ccgagccaga auuuaccgaa ugcuaauacu caacauauua ccggccaacu gaaguaccau   3180
ucgguggagu acgcuucuuc ugugccgaac aacaucaauu auaacagcuc uaccuacucg   3240
ucgccgcuuu cuaauauguc uaguaccaau uccucaaauc cuaguaacuu gaauaauucu   3300
uacgaguacu acuaugaccc gaauaccagu aguggugcag uaccgaaugc uucaaagccu   3360
caacagucga gcgccagcuc ugcaaacccg aguaccgcua ugaacaacua caauuauuac   3420
uacaauacaa guaccagcgg uaguguagca gcggauacuu caaaaauaca acaacaacaa   3480
caguacccag guacucagau gagucaagcg caguacuauc ccgccaaugc caguuauuac   3540
ucaaccagua cuuacaauac caacguccaa ggugguacca aucccucgua cgcaacugga   3600
caaacauaua aucaagugac accagugacc ucucaaaaug uuucucaaaa uuacaacuuu   3660
aaccaaguug guucuggagc aggacaccag caucaguacu acucguccgc uaacgccgca   3720
guaccauccc aacaagcugu aaauaacagu ucauuaccaa acuacggaua cgaucaguau   3780
uacggcaaca acuauaauuc cagucaaccg aguaccuaca gcgcaaacca agcaccuccu   3840
gcagcacaag cugcuccaag uaauauuccu gcugccacca aauccuccuc uaauguggau   3900
cugcucagug gcuuggacuu cagcauaagc caagcuccuc uagugccuca acaaaacauu   3960
acgauaaaac cccaagaaaa ggaaacaaaa ccaccggcug uuucuucuga aaccaaaaac   4020
caagauccaa caccaguaac cacgcccaaa caacccacug gaccagaagu aaagcgcuug   4080
uacgucaaaa uccugccgag caaacccuua aacaacgaug augugaagaa auuguucggc   4140
caagagcugg acagguauga gaaguucgug gagaccuuga cccacaaaac uuugagcggu   4200
ccgaccacuc uggauauuaa auggaaggag auccaagacc agcaggauug cgagccgcag   4260
aagaagauca uuuccgucgc uagauguuau ccuaugaaga auagguuccc ggauaucuug   4320
ccuuacgacu uuuccagggu ggaguugugc gauaguaaag augauuauau caacgcuuca   4380
uacauuaagg auaucucgcc auaugcuccg ucauuuauug uuacacaagu gccguuguuc   4440
ucaacuguug gugauaugug gacgaugauu agagaacaac aggucgaacu gauccucugu   4500
```

uugguaaacg acaaugagau cgguggaagau auuuacuggc ccaaagaaaa aggcaguagu 4560
cuuaacauac uuaacauggu cauaacguug caaaacguua uaguuaaguc ucauuggacu 4620
gaaagacuga uagcgauaaa cuuaccugaa aaacgggagu cccgugugau aaugcaucua 4680
caauuuacau cguggccugg cagcuuguuu ccaacaaauc cugaaccguu cgucagcuac 4740
accuuggaau ccaucaaccu auaccaacaa cagaagacca acacccaucc gguggugguc 4800
cauuguucau cuggcauagg aagaagcggc cugcucuguu uacugacagc ugcuauguuc 4860
gaugcugcca acaaugcuaa cucgauacca gaucuuacag cuuugaguau caaguugucc 4920
aauugcagga agaauauucu cagagaucga gagcauuuga aguuugguua cgaaaguuuu 4980
uuggcguaua uuaggcauau aguuugugaa gauaaagcca gaaagaaacu gaacgagauc 5040
cagcccaagg uuaaggagga accacuggaa ccaccuguca uaguuccaga accaaauaua 5100
gauccuuuaa guacuuuaga cccauuuugg gcuaguaaaa gauaagcuuu acauaguaaa 5160
uauuuauaca augauguauu auuauuuuga auguuaucua caccuucauu aauauuaaau 5220
ucccug 5226

<210> SEQ ID NO 211
<211> LENGTH: 633
<212> TYPE: RNA
<213> ORGANISM: Diabrotica virgifera

<400> SEQUENCE: 211
uaccgccugc uacucucuuu cuuugaccuc cuccuuuucu ucuccuuugu ccggcuuuaa 60
cuugcguuuu cccggcucca gucccgagca uaccuucucc ggaguuuucg guucuuccgg 120
uucuuuccaa aguacugggg acucucuuuc uucuuugaau ccaaugacaa cucuuucuuu 180
cggcggcuuc uuaauuucuu ucuuguucuu gcguuucguc ggcuuuccuc cgcauaguaa 240
cuucuuucca cgccauuugg guuugaacag cuacugcguu uacuuccggg uaauuuuguu 300
cauacacucc cuauaguguc ugcauaaacau cuggaucuuu uauucuuuaa acuggagcuu 360
uuucuucacc uuaagucucu aaaagucuag aggcuuaacu ugucgguuca uuugcuggaa 420
ucuccguuua agcaguuugg uuggaacuuc uuccauaggu uuaugcuuuu guuuaagcgg 480
uuugaaguuu ucuuccgucg acuuaaauug aaggcauugg uugaguuuca acaguucuuc 540
uuucuuaagu ggaaucuucu ucuucuguuu cuuuucuuug gucugaccag uuucuucccu 600
cugcuuuucu uccauguucu ccgacuucgu acu 633

<210> SEQ ID NO 212
<211> LENGTH: 603
<212> TYPE: RNA
<213> ORGANISM: Diabrotica virgifera

<400> SEQUENCE: 212
uacacacuuc uucuucaacg gcgaaaucag caucuguuac cuaggccaua cacguuucga 60
ccaaaacgac cccuacuacg uggagcacga cauaagggaa guuaacaacc ugcggguucu 120
guagucccac acuaccaucc uuacccuguu uuucuaagga uacauccacu acuucgaguu 180
ucauuuucuc cauaggaaug gaauuuuaug ggguagcucg ugccuuauca guguuugacc 240
cuacuauacc ucuuuuaaac cguaguaugu aagauguuac uugagucuca ucggggucuu 300
cuugugggac aagacaacug ucuucgagga gaguuggggu uccgguuguc ccuuuucuac 360
uguguuuauu acaaacuuug aaaguugugg ggucgguaca uacaacggua gguccgacau 420
gagaggaaca uacguagacc agcauguuga ccauaacaca accuaagacc acuaccacau 480
agggugugac aggguuagau acuuccaaua cgagaaggag uacguuagga agcaaaccug 540
aaucgaccau cucugaacug acuaauggag uacuuuuaaa acugacuugc accgaugaga 600
aag 603

<210> SEQ ID NO 213
<211> LENGTH: 2742
<212> TYPE: RNA
<213> ORGANISM: Diabrotica virgifera

<400> SEQUENCE: 213
uacggugaag cuaaucuaua uuuuucuuuc gauugucgag cgagucuggc ccauuuuaca 60
caccuagaag ugggaugucu uggaaccuac gacacaagag aaaugucgcc uuuauauuug 120
caaaccuugu ggcuuuuagu cguugaccaa uucugaaaac uucauacacu acauggacaa 180
gccugucgau ucaaaaacgg guccuucuug accuaucagu cacccagacu acuauacguc 240
uaagcucaaa aguuaauguu auggaaucua gcccauguaa gaaaacuccg aguaagccua 300
auacacucua cauaacagca ugugggaugu guuggaauau auaauuguuc aucacuacua 360
uacgaauagu ucgaaaccuu aacccuuuuu cguacccgaa cagucguuca aaagcuuccu 420
gugugaguaa uauaauacgu uuagcgguau uuagguuuuc uguuguugug uaaacgguca 480
cguagggauc uaucuuguaa cuuucauacc guuaacccuc gcaggugucg cuuaaagugu 540
gaucuuccag uacucuuucc gcaauugaca caccugauaa uagugccacc ucuauuugga 600
auaaauuaga guccgcgacu acuaucuaau cauuuuuaga cccuaauagu uuuguuuuga 660
acacaaguuu gaaaccuucc uguacgaguu uuacauuggc gacguacaaa gguaggucuu 720
gaaggacauc gagaaugacc uucacuucua ccaugacagu cucacaccgu acgguugugg 780
guauccaauc uuucaucgaa uuuaauaccg aaacuuucuc auaccugaua aaagacggau 840
uucccuaggu uauugcaccg uaacccaaua cuacuuccau cguaaaacca auuucaacca 900
ucucuucuug gucgacaauc auaccuacgg ucaccuccgu uuuaauaaac ccggucugug 960
agacuugaag uuguccguuu agaguuccgc aaucgacuuc cacgccuuua uucucuaccu 1020
cuugcggaag gucaaagaca uuuucuauac ccacgaacgc ucuauauggg agucuguuaa 1080
guuguguuag gguuaccggc aaaacaacaa cagacacccc uaccucuuau guauuagaug 1140
ugucguuacc gaaauucuuu guuucgcaaa ccaucgcgug uucuuaaaca cacccgaguu 1200
cuaaggucgc uuauacggua gucucuuagg ccuagaugau agucuuaaaa auucuuaaag 1260
uuucucuucu ucuuaaaauu caggcuaaaa ccucgacuuc cauauaugcc accuauggaa 1320
aacccucagu uuagccaaag accaaacuga aagauacuaa cccuuugaga gcuaaaucag 1380
ucuucuuagc ucuauguugg uuuucgucaa augaccaguc uaucaccauu uaaucauaca 1440 aaccggugucc uucuaucgau gaaauaagaa agaauacuaa gacuacuuca aguuuuucgg 1500
ucucuauugu uaguccaacg ccuacuaccu caucuuagcc gaaaguuaga agauccacuu 1560
uauuugcuua gucacgcuug accagagacc cauccgcuga caaaauagau gugcuuaaga 1620
caauuagcau aguugaugaa gcaaccucca cuugaccaau guuaacgagu aaaccuggcc 1680
ggaaacauac agaacccuau acacggauuu cugcuaucua auauggagca ucuauuucuc 1740
aacgcgcauc auucgauggu uaaugaagaa agacaagaac uuauaguuug acggcaguac 1800
ucuucucuga aagguugucg ucugucucau gaaggcaggu aaggauuccu cgugucuugc 1860
ucucaccgug uaaagaaucu uuucguuccg aaguuugucg uucgaaaccg gcauucaugu 1920
cuaggucucg ugucuaagcu cgaccgucau cguaaucucc uagaauuaua ucgguuuuga 1980
gaucgaguuc uucgcuuguc aggcguuuuc accuuaguug aucgucuuaa ccgucgacga 2040
ugauuauuac auucgcaucg guuccuuaca uacguuuuuc gcguucuaau accuccgaac 2100
aacgaagaac gaugcucgag gccacuacuu uuaaaucagg caugagaucc ucuuugcugu 2160
guucgacuuu cguuuguauu gaaucguaaa aacaguguga acaaucaucc acuaaauuug 2220
uuuacagauc uguaagaaua auuauggcca ucuaacgguc uucgacguaa aaagcggucu 2280
agaauggaag gacuauucua augucuucag caccuugaca ccuucugagu caauagaagu 2340
caguuaguuu uucgaccugu cucggaacgg cuaggauuuu ugaugcuuuu agacaaggga 2400
ccaaauguuc uccgccacca ucgagucuuu aaaaaccuug ucgucuuauu uccaaaucgc 2460
gggcguucuc aacgguggug guaaggagga uuagugcugu ccuuacaaca ucggcuucaa 2520
guucguguua gcuuugugcu acaugguagu aaaucaagaa gcaaauaaag uagucuuuau 2580
cuucguguuu guuccucaag acgauuugga cuucuuagaa guuuguaaua ugucgaccug 2640
guucuacugc ugcuauagcu aaaucuaaac cugccacauu uauagcuacu cuuguaacug 2700
ugcugccuau aguuguagcu acuacuaaac gacucacuaa cu 2742

<210> SEQ ID NO 214
<211> LENGTH: 1173
<212> TYPE: RNA
<213> ORGANISM: Diabrotica virgifera

<400> SEQUENCE: 214
cacaauaacu uuccguuuuu aguuuauuac gucuagaaac auuuuuguga gugaccauuu 60
ugguaguggg agcuccaacu ugguagucua ugguagcucu uacaguuucg auuuuaaguu 120
cuguuucuuc cauaaggugg ucuaguuguc ucuaauuaga aacgaccuuu cgucaaucuu 180
cuaccggcau gagagagucu gauguuguaa gucuuucuua gaugugaugu gaaucacgaa 240
gcagaaucuc cuccauacgu guagaaacau uuuugagagu gaccauucug guaguggggaa 300 cuccaacuug guagucuaug guagcucuua caguuucgau uuuaaguucu guuucuucca 360
uaaggugguc uaguugucuc uaauuagaaa cgaccuuucg ucaaccuucu accggcauga 420
gagagucuga uguuguaagu uuuucucaga ugggagguaa accaugaagc agaaucuccu 480
ccauacgucu aaaaacaauu uugaaauuga ccuuucuggu agugggaacu ucaucuugga 540
agacuauggu agcuuuuaca guuucgguuu uaaguucugu uucuuccaua agguggucua 600
guuguuucua auuagaaacg gccuuucguu aaccuucuac cagcauguga gagucugaug 660
uuguaaguuu uccuuagaug ggagguaaac caugaagcag aaucuccucc auacguuuag 720
aaacauuuuu gugagugacc auucugguag ugggagcucc aacuugguag ucuaugguag 780
cucuuacagu uucgauuuua aguucuguuu cuuccauaag guggucuagu ugucucuaau 840
uagaagcgac cuuucgucaa ccuucuaccg gcaugagaga gucugauguu auaagucuuu 900
cucagauggg agguaaacca ugaagcagaa ucuccuccau acguuuagaa acauuuuuga 960
gagugaccau ucugguagug ggagcuccaa cuugguaguc uaugguagcu cuuacaguuu 1020
cgauuuuaag uucuguuucu uccauaaggu ggucuaguug uuucuaauua gaaacggccu 1080
uucgucaacc uucuaccggc augagagagu cugauguugu aaguuuuucu cagaugggaa 1140
gugaaccaug aagcaaauuc uccuccuuua auu 1173

<210> SEQ ID NO 215

<211> LENGTH: 1131
<212> TYPE: RNA
<213> ORGANISM: Diabrotica virgifera

<400> SEQUENCE: 215
uacacacugc ugcuacaucg ccgagaacag cagcuguuac cgaggccuua cacguuucgg 60
ccaaagcggc cacuacugcg gggagcacga cagaaaggua gguagcaucc agcagggucu 120
gugguuccac aguaccaccc auacccaguu uuucugagga ugcauccucu gcuucggguu 180
ucguuuucuc cauaggagug gaauuuuaug ggguaacuug ugccuuaaua gugauugacc 240
cugcuauacc uuuucuagac cguagugugg aagauguuac uugaaucuca ucgggggcuu 300
cuuguagggu aagaaaacug acuucgaggu gaauuggguu uucgguuguc ucuuuucuac 360
ugaguuuagu acaaacuuug aaaguuaugg ggacgguaca uacaacggua aguucgacau 420
aacagagaca ugcgaaggcc agcaugguga ccauaaacaug aacuaagacc ucuaccacau 480 agggugug uc augguagau acuuccaaug cgagagggug ugcgguagaa cgcaaaccug 540
aaccggccau cucugaacug acugauggaa uacuucuaga auuggcuuuc uccaaugaga 600
aagugguggu gucgacuuuc ucuuuaucaa gcacuguagu uccuuuuuaa cacgauacau 660
cgaaaccuga agcuuguccu uuaccggugu cgucggucga gguggaggaa ucuuuucuca 720
auacuugaag gacugccagu ucaguagugg uaaccauuac uuuccaaggc aacgggacuu 780
cgagagaagg uuggaaggaa gaacccauac cuuagaacgc cauaggugcu uugacagaug 840
uugagguagu acuucacgcu acagcuguag gcauuucuga acaugcgguu gugacaggaa 900
agaccuccau gguguuacau gggaccauaa cggcuagcau acguuuuccu uuagugacgg 960
aaccgaggua guugguaguu uuaguucuag uagcgagggg gucuuucuuu caugaggcaa 1020
accuagccac cgagguagaa ccggagggag agguggaagg uugucuacac cuagagguuu 1080
guucuuaugc ugcuuaggcc gggaccuuaa caaguggcgu uuacgaagau u 1131

<210> SEQ ID NO 216
<211> LENGTH: 2640
<212> TYPE: RNA
<213> ORGANISM: Diabrotica virgifera

<400> SEQUENCE: 216
uacccaugaa aauuuucucu augaguacua cuccugcccc cuaguucacg aaaaguuuua 60
gaccucuuuu gaugacaaaa cguccuucga ucucaaaaau uacuuugauc acauuuaggu 120
ucuuuuacau guggcuauga uuguuuugac aacaugaaua acuugguccc acuuugaaau 180
ucacgguuuc uccggugucu acaaaagaaa cgguacuggu uugacaaggu uaguuuucua 240
cauuauaacu cuuccuacca aauaaacccu uaauuucuug agucaagaca acgacuacua 300
caguaauaac auuguagguc agaauguuuu cuauacugac cauuucuucu guacaugucu 360
cgucgacgau auucucguaa uacgucauaa ugacuacgau gauacgaagu ucgauaucuu 420
gcaauauacu ucguucgaua acaucuaucu uugcgucgac agucaagucg ucgugauuaa 480
ucaaguaaug uauacucguu uaaucgaggu cuacaucauu uuucuaccca uuuacuucga 540
guccuucguc auuuaucacu auuacguuac caugucauag ugcguaaucc agaagauaug 600
guauaauccu ucugacuauu cgaucgucac uguuuuaacu aaagguucga cuuaaguuac 660
ccaaauuucu cgggaauacg aaacacauac aacuauucuu agugacguuu ugaaaaucuu 720
cuucuccugg uucucaguga ggaguugagg gguauauguu auuauaaaug uuacccgaau 780
uccuuguuua gacuuuacca ccacauacuu cgacguguac gguaccaauu ggacuucaag 840

-continued

```
ugcucaucau uacacgaucg ugggcgauau ucacaagaug uugauaaaac accuagagga    900
uuucggugug agucuaaacg acgacaaucu ugaaauuuag uucaccggug gugggugga    960
cgcagucacu gucgaacauu aaaccuagau cuuuuaaacu aaugacuagg auuauccagu   1020
uaacgaugug accgguaaug augagaaaac uuuuguccac ggcuuagaag acaacugucu   1080
gauuacuuug uuuagcgaug aaaacauaga cuuuagucac uacuuaaauu ucaccaacag   1140
uaaguccguu aauuccauaa ucgaaacuuu aaagguuccu uuguaucgug cgaauacuua   1200
aaggauaggc gguacaauuc ucuacucccu ccaaaucuua uauuucguag guaucgucua   1260
ugguaauauu gggauuagcu ucuauuaggg cuucgauuuc uuagaccaaa ccgcguagaa   1320
acgcucaagu aacuucugac acuuguacaa agaaaccgac acucuuagaa cguaaacaau   1380
ccuuuccuuc cuggguucug guuuguuggu agcucuaugu aggcaaaaua gauguuagcg   1440
caguauaacc uuacaggaag acauucucga cgacgucaga ggcgguaccg uguuaagccu   1500
cggagaacag ggcuaaacaa ucuuuuauag guuuauaaug aaagcuccac agucuaccua   1560
agucugcuac uucaaucccu gucucgaugu auaauaucau uauaugaauu guuuuuacua   1620
uuuucaaaua uguuguuaau guaaaaccua agaaacgucc aaaguuaagg aagugaucuu   1680
ucuagcgaau cucuuaugua aguuuuaggu ugacugcuug guaaacugua auucaggcau   1740
ggacaucguc gucacgguug ucgucuucuu gcucuucaau uuuuguuuag acuuccugac   1800
gaucagagag uuccagguca ggcuggagga ggccacagau cucuucuuuu gaagcggcuu   1860
uuugaaucau ugcaaggccc auauguuguc aauccuggaa acaaguuuug aaggcugcag   1920
caacuugagu gacuuagacu uugucucaua aaacaggcga cauaguucgu gacaaaguuu   1980
guaguguagc aggagguuaa gcuaacagac uuauggaacg gucuggucga aaaucuuuug   2040
caaucucacc ucuaucugcg gccacuuugg aagcuuuaaa accgucuuua uggaacacuu   2100
uucaacguga uauugcuuug gccauggugu auacaucauc aauucaacgg acuacuacua   2160
gagggguuga gacaaccaug cacaccucgg cacaacuuca agaaucacuu ucuaacacua   2220
gguaguugcc cuuauggucu aagacuacuc ccaaugcuac uacuuauaug ugaccuucug   2280
uagcuuuauu guaaucccu gguuuaaguu uuucauucgu uucauuuaac ccgacgucgg   2340
acccuucuuc gacgucgaug aauacaucuu uuucuccuau guaugaggaa cugguaguua   2400
ugcgauucac cgcgacaauu cuuauaauaa gucaagaacc cuaaugucgg acgccuuucc   2460
ugacugucuc auggccuccc auuuagaugc guguguaaug aagaacgacc acauaagucc   2520
ccuccauaac uguaugauca uucucgcuuu gaucgaaacc cgcuuacaca augcuacguu   2580
gauugucagu ccagcggucu aggacugcaa cgacucgaau auugaaguug acauccaauu   2640
```

<210> SEQ ID NO 217
<211> LENGTH: 651
<212> TYPE: RNA
<213> ORGANISM: Diabrotica virgifera

<400> SEQUENCE: 217

```
uaccgccguu ugucuugacc uggacgaguc ucugguuuac cgcgaugggu uccuuucuau     60
acagucaagu uugaccagga ugauccgcuu ucacggcagc cauucagcuc aaaccaugac    120
uccaagcagu uuccugucaa ggugcuuaug guccucucau gguauccucg ucgaaaggaa    180
uguguuuggu auacggagcu gcuauguuga caauuuaaac uuuaaacccu gugucgccca    240
guucuuucca uggugucaaa ucgaggauac augauauccc cgcguguccg ucgauaucag    300
```

-continued

```
cagaugcugu auugguuagu ucuguguaag ccgucccgcu uuugcaccca cuuccuugaa    360

guuuccgucc ggucaggcug cuagcacuau cgaaaccggc cguuguucgu ucuaaaccgg    420

uuguuugcau accaucuuau gcuucuccgc gucugcauac gacugcuuuu gccgaaugaa    480

aaauaccuuu gaaggcguuu cugccguuac uugcaguugc uauauaaaaa ucguuaucga    540

uucuuugacg gguucuuacu uguuuggugu ccaguuccgc cgucacgggu uccguccgcc    600

gaucgccucc cgcuaagccc gcgguuccgu gggccuuuaa caacguucac u             651


<210> SEQ ID NO 218
<211> LENGTH: 279
<212> TYPE: RNA
<213> ORGANISM: Diabrotica virgifera

<400> SEQUENCE: 218

uacuucaaaa auucuagcug ucacacgaug uaacgguaga accguuaaga gaaaugggag     60

acacggcuac uccaacuucc uuccucuuuu uaaaacuacc ccgcuuuuuc guaauggucc    120

uguauagaag caccuuuacg acaaggacgc auacacuauu auuaggaaca uccuuaacca    180

guuuaguagg acccucccua uaacaugcaa cguaacuccu ucuucuagua acgacgugga    240

cauugccgua guauacguca ccgaucuguu cuugguauu                           279


<210> SEQ ID NO 219
<211> LENGTH: 474
<212> TYPE: RNA
<213> ORGANISM: Diabrotica virgifera

<400> SEQUENCE: 219

uacgucuaga agcaauuuug gaauugccca uucugguagu gagaacucca gcucgggagu     60

cuaugauagc uuuuacacuu ucgauuuuag guccuauuuc uuccuuaagg gggucugguc    120

guugcagagu agaagcgacc uuuuguugag cuucuaccag cauggaacag acugauauua    180

uaaguuuuuc uuaguuggga agugaaccac aacucuaacu cuccuccacg auucuuugca    240

uucuucuucu uaaugaggug gggguucuuu uaguucgugu ucuucuucuu ccaauucaau    300

cgacauaacu uuaaaaauau ccaacugcuu uuaccauuuu agguggcuaa cucugcacuu    360

acggggcgac uuguuacacc ucgaccacag aaguaccguc gguaccuucu guccguaaug    420

acaccguuca cgccaaugug agaacagaag agguuugguc cucuacucuu uauc          474


<210> SEQ ID NO 220
<211> LENGTH: 747
<212> TYPE: RNA
<213> ORGANISM: Diabrotica virgifera

<400> SEQUENCE: 220

uacuacaggu uucgucugug uguccuucua cggaggaagc gguuuaaccu uuuagucuaa     60

cgauaguagu uuaugcauua ugagaaaugg uugcaaaacg uuacccgaga gccacgucgu    120

uagaagcgag aaacggaaac cgaugcuaag cuccucccgu aaguucuuac cgaggucuuu    180

aaccuaaguc uuguuaaaau guagccucau auacaugaau aucagcgaag ugacuagcag    240

uacuaacaca ggaaauaucc uacauaauca cgggacgucc ucucauggua ccgggaaaau    300

cacauguagc cgugggguuca cgagucaaaa uauaagccaa auaggccaag ccgccaagaa    360

gaccuauugu cgcggucucu aagggugaag guuggcuccu aggcucucuc auacgcugca    420

gaauaguacu uacgaguagu gcugguuagg ucuguuugug aucgguacua aguccuuuua    480

caaccaacga cgccucgacu accgcguugu cugauggaga gagaagucgu cggggaaggu    540
```

ucagucacgu cucuguggca augaccuuug gguaagaagg ugccuacaca ucuacuugag 600
uggaccaaga agcuucuuuu uacaccaacc uaucguccaa aucgauaccg cuauacguac 660
uaauugcagg aaucauaaca aaauagaugc caugaguagg uccguaacuu uuuucuucuu 720
cuucguaggc uaaguauguc cucuauc 747

<210> SEQ ID NO 221
<211> LENGTH: 375
<212> TYPE: RNA
<213> ORGANISM: Diabrotica virgifera

<400> SEQUENCE: 221
uacagaccug caccguuccc uccguuucau uucccuuuuc guuucagggc uaguuuagca 60
cgaccaaaug uuaaaggaca uccagcauaa guagcaaaua acucuuuucc uuuaauacgg 120
cuuucucaac cacgaccucg aggacauaug aaccgucgac aauaccuuau aaaucgacga 180
cuucaaaacc uuaaccgucc uuuacgucga ucucuauugu uuuucugggc auauuaagga 240
ucuguaaaug uuaaccggua uucuuuacug cuccuuaacu uguuuaauga caguccucaa 300
ugguagcggg uuccaccuca uaacggauua uauguucguc augacaaugg auuuuuuuga 360
cuuuucuuuc gaauu 375

<210> SEQ ID NO 222
<211> LENGTH: 864
<212> TYPE: RNA
<213> ORGANISM: Diabrotica virgifera

<400> SEQUENCE: 222
uacuucaacc uaccacaucu agacgggggu gguuaaucga agcuguaacg ccuucucguu 60
ggcaauggug gaacgguugu cugcaagaau acauuaccac uaccuccuag guaucacgcu 120
gucaaagagc ucgacauaaa gcauuauaua cuaagucuau uauccgucag ggaagaaguc 180
cguauagugc uuuuucggug uaaaaguuac uguuaccgga ugggcaugcc gauaagguuu 240
cugucauuuc cucauagcac caacuuaacc auacggugge uauuaucuuu aaauaaugcu 300
caaguucuag gucugucuuc uuuguucaac aauucugucc cuguucaacg acaucaaagc 360
aagaacguuc uauacggcgu gugcuucgug cuauaagugu caaaauguca ucuaaacugu 420
caaaaaugug gggucuacaa uacaaacugu caccgaccau acaaauuucu uaacuuuuca 480
ccgguguuuc auggaggaaa uucuauaaag aagucuuggg aacauuaaca uggacgaccu 540
aguccaaaaa cguaucguuu acuucuugaa guguauaggu uacguugagg ccugguucgu 600
uuucuacgaa aguucuggug gcaauuacau cgaggccgug gucggggaca cuaauggaga 660
ggaccugggu cauauggugu ugggcgacac ggucuacuac gauguuuugu ucuuuaccau 720
uuugucuaca ggcgucauag gccuuacuua gagcucacca gcgaugucac agagcuucuu 780
uguguuaccc ugauggucuu ucgguauuac cauaagguuu uaaauuugcg uguuccacaa 840
caugguguuc gucguaaaua auuu 864

<210> SEQ ID NO 223
<211> LENGTH: 2868
<212> TYPE: RNA
<213> ORGANISM: Diabrotica virgifera

<400> SEQUENCE: 223
uacugacgcc aucuuguugg aacaaugugu gauuauuuga acgguugucu aagccucggg 60

-continued

```
auguuacuuu acguugauuu uuaccuaaau cuuuucccac uccaauuuca uuuuuauucu    120
cguaaucuuu uuuauuaagu guacuaagac cguccucuuu ccaacggcuu accuaaagau    180
uacugguagu auucuuugca aaauggaaau guucuaguaa accguuuuuu ugauaauaac    240
uaaaagaccc uuuaucaagg uuuuuguuua ggucuuccau uugaugaugu ucucuacuaa    300
aaccauacac uacggauauc uuuucuagac guugugggguu uacuuaaaaa cucuccaaga    360
ugugaagcga agaacacguu ugacuuccuu ggucuuaaca accuugguaa uuacggguca    420
uaaucucgaa caaaccuagu auccgugucg auacacuccu ccuuacgaca ugaccguuaa    480
aaaugguaaa uguuuuuaaa acuucgggag uaaggucuac gaggacuuga cuagagguua    540
auaaaccuac cacucguucu guacagaaca uuuucuuuac gcaaaaauua cgaagaagua    600
cgacugguuc uuucccgcaa cagcauaaac cguaguacaa aucuaguuca uuuaaguaaa    660
ccucuauaag auguugacca guagcaacuc aacuauauau uccacacagu aagguuagga    720
cgccuuucua gaucuaaaua aucuacauau auauugaaca acuugaguuc gucaggacga    780
caguccaugc uucgacgucc uugaaaucag ugggagaggu cacggggcug acggcaauuu    840
cgacgacgau cgacaaugua acucaauuaa uaguuucuuu cacuguuguu acauuuugag    900
uagcaaaacc uguccgacua ucgugaauuc cucgaaggau uagugcuuuc uuaagacguc    960
cuaaaucaau accuguauga cucucaugag agacgaggac ugaaucuuca ggcguucuuc   1020
ugaaauucag aucgggaacu uaaucagaga agugccuugu aucuucuuua ccauaaucau   1080
aauuguuucc uucacucauu uugccaucug ucacuuguac ucccuauguccc uuucaugucc   1140
guuaacaauc auuccugaga uguaagcaca agguaauuca agggucuaua gcgugcauca   1200
caauaugguc agaacuaacu uaaaaauagg cuauuauuac uugaccgacg gugucuacau   1260
aacgacaaga auucccuucg guaugucuuc aaauuucuua acguuggcaa uuaauaacuc   1320
uuugaguagc uuugaaaguu ucuguaauuu aaccaguuuc agguaucucg ucguuaaacc   1380
uaaaacccuc uuaugcgcuc augacgaagg cuauaucuuc aauagcaacc ucuuuaauug   1440
ucuaacaacc cacuuccuag ggagcaacuu cgacucgucu ucaauuaucg uccucuaugc   1500
cuucucuuac gaggacgugg acgacguccg cgguggugaa aucaaugaag gcuaccuugu   1560
auacgauggg uuagucgaaa guugugacag ucgguuuggu gauuucuucg ugcuggagga   1620
gauucuguua uggaguaccu accacuaaaa aaguagccuc ggagaaaccg uagauguaau   1680
ugguuugaca gaaacgccau acuccuggag uggagaggac gacgaucguu accuaaguua   1740
cgguuuuaau acgaauaaua ccgaccuuaa gaagugaacc cuuuuagucc ugaagggugu   1800
uuuaguuauu gguugcugcu auuucuggug uaagacaaga caaaugcuca ggauagacua   1860
gcaagagguu aguaacaacu uuaaaaguuu uuuaacacgg cgagccguga uuuacucuac   1920
gaagaucgau ucccuuagcca ucuucgcuag agcguuuucu cguuucuuuu uuuguucgca   1980
ugcuaaguuu gacugcugcg auauucgaag gacguuaauc ucugucuauu uucaccucuc   2040
gauccucuuu ugcauaagcu cuacagcgac aguguucgaa aucauccucc agcuugcccu   2100
ccaccgcuua gucauaauuc aagguuauuu aaucuauuuu aguguguuga cugaccaaaa   2160
aggcuagguc aaauaaggcu ucguaugcaa gugcacuuag ucaugcuaua gcacgaacua   2220
cagaauuagc auuugguuug auugcuauga aauguuuuga cgugcgaucu cgaccgauga   2280
aauccgcuaa acuucaacca ucucuucggu guuggacagc auaaccgcgg guuucugaaa   2340
acguuguaau uucgauugca cuuucaccgg aguugacuuu ugccuuaaua uaaaccguug   2400
uaacacauac uacaguaucc ucgccccagu cuauccuuac aacaucaaaa cuuacuauau   2460
```

guguaucuau auuaccugau auaucacgga cgaucaacau gucuaucgcu caaauacucu 2520
uacacccgcc uuaaacuuac ccuuuuauuc cauuggcaau ugugugggga gugccuugaa 2580
agucuuaugg agcuuguaga ugaguuucg uguuuaaacu uuacaaauug uagucuuuuu 2640
cgagacucgc ccgucacacc aaaauaccgu cgguuaaaua uacguuuuag guaaaaaccu 2700
cuucugcgaa accgguugaa uucauaucuc uuuggaaaau uauuugggcu acgcggucau 2760
ucgccaguau aaucuuauuc ccgguuuuca gucccguacc ggaauucaaa uccucuguuu 2820
caguuauacu gugucuucuc guguguugua uuucaucauc gacguauu 2868

<210> SEQ ID NO 224
<211> LENGTH: 549
<212> TYPE: RNA
<213> ORGANISM: Diabrotica virgifera

<400> SEQUENCE: 224
uacccauuac acaaacguuu aaauaaguuu ccggagaaac cguuuuuccu uuacuccuau 60
aacuaccauc cugagcuacg ucgaccauuu ugguguuaaa auauauuuga auuuaauccu 120
cuuuaacauu guugauaagg uuguuaaccu aaauuacacc ucugacaucu uauauucuug 180
uaaucaaaau gucauacccu acauccacca guucuauuuu aauccgguaa caccucugug 240
auaaagguuu uguguguucc ggauuaaaag caucaucugu cauugcuguc ccuugcauag 300
ugacuccgau uucuacuuaa uuacgcauac aaccggcuuc uacuugaauc ucuacggcau 360
gaagaguaaa agcgguuguu uguucuaaac ggguuacguu acuugcgacg ucuuuagugg 420
cuguuugagc cagagguaag ugaugcguug gcguugacca uguaaguucg auggacacgu 480
ugaucgccuc uaccagagau acuuccagac cugaccaaca gguuaguuaa uuucuugcgg 540
uuagcgauc 549

<210> SEQ ID NO 225
<211> LENGTH: 4425
<212> TYPE: RNA
<213> ORGANISM: Diabrotica virgifera

<400> SEQUENCE: 225
uacccugcca acgugacaaa uaaaacauaa aaggauacaa aauggcagua guugugcguc 60
uguugcuuau auguaccuaa gagccuuuua aggcaccuau guaaagauag uggaguaccc 120
uuuucacguu uuaagcacgu gguuuuagug uuuggguuuu aacuuuuaac agucuugaug 180
uuugggagcc acuuucuucu ugucgguccg ccuugcaugc auuguugcca auggcgauag 240
cuacugcuag gaucccuccc uccuccuugu uaaucaaugu uugauuaagu aucucuuccu 300
cuuguacaaa auaaacugua ucuguugcaa ugaccacaaa acuguugaua ggucgguaaa 360
cuagcccuac uuggucauuc cgucuuccuu gaaauacauu ggcauguucg aagucuguug 420
ccguccggug guaaucgucu acagacaugu aaaugucaau gguaauggcu guaauuacua 480
uuacgcggug ucgaacuauu ugacuuuaug cuacguguuc aaagacuucu aaauuuucau 540
ccuucacuuc acuacucuca aaaacgaaug cuguaacuac uaccccuuuu aaguucuaau 600
agcauauuga aaaguuugcu uuuacgaguu aaguggguca uaaaguccua ucuagcucua 660
ugaccgcaac acauaaauuu ccuucgaaau ugucuguuuu ucuuaugauc uaaauuguca 720
cgacaaauac aucggcuauu accgcaauug cuaguucuuc cgguuuuucu aaguuggcga 780
uucuauagau auugucauca ucccagacua uuugucggag ggucuaaaug aguuuuuuac 840

-continued

```
ggacuaccuu agaaccucua ggggcuucua aaauuucuga aaagauuugu auaacagugu    900
cagcuucguu gcagguugua acgccuaggu guugaacgaa aacuuaacca cuucccuuuc    960
uguauaguuu gguuauuucu gguuugcaaa gaaaaccucc gucuuccuuu auuucgcgug   1020
uauuucgauc acgcagguga ccuaauacuu ugucauugcc uuauaugaga uugauaagcu   1080
cauuuuuugu uucuaaauua ccuaagaagg uauuuauaug guuaauuuca uaaucuacaa   1140
uuacuacuuu aaggauuaaa ggaacuuaaa gaauuuccau cacagcaccu uuuacuguuc   1200
gguccacgug uucgcuaagu ucauucucgu uagcuauuuc ugccuugacg acgauuguug   1260
uaacacucga uacuugagca acuguuaugu cuaaacaaac guuauuuggc uagaugcccu   1320
cauuaaugca gcucucaccu caaacuagca cuuugacaug gagauauagu gcauuugcaa   1380
uuucgaauac uauugagagg cagacgaaac auauugugcu guaacggauu guaacauuaa   1440
gucuguaagg uuuagucaua ucuucuaguu uuacuguugu uuggacauaa augaguaggu   1500
uaaauaguca agucauuaua augacucgaa cgacuauuua gcucauaaca accacuucag   1560
uuucgaaauc uauuacugug ccgaagucaa uauucaauau cauaauguuu accuuuauaa   1620
cugcuacgca aauacuaacu uuuaagaugg ccgucuuauu cucaauuacc uuuugaccua   1680
augcucuuuu agcuuguuau guugaauugg caagcgcgua aacuaccccg uaaacuucua   1740
aaacguuaac aaaauuaaag guaugaauua cuuuuacugc uuggagguca aaaacugcug   1800
auauagucuc uuuaaguuua auuucuccuu cuuggauacu auaggccuac gcaacaaucu   1860
cacugacgag uacuaggucu auaauuucug uccguacgac uaguugugua ucauauacuc   1920
cagcgcuuuc uugucuuucu aaaaaacugg cauagacggc uaccuacgca uguucauugu   1980
uuuggagagc uggcucuagg cggaaagcca ucggguugug cuguucagaa guagauacga   2040
gcacuauuac uaccuccgug uuuaaguaac aaccggugac gucuuuaacu uuaauaaaau   2100
uaucuauauu ugcuauuacg agggaaaaau uuacaauguc uuuaacaaau aauacuuuug   2160
guccuagguc caaaauaucc auuggauuca cggcuacuaa ugcuaccagg acuauuaccu   2220
ggaggcaaac gaaaagcuaa uagucuguga cgaagucuau cauaaucuag cuuuaaaagg   2280
uaauagccuu uggucgaaaa gcgaaaucuu uacaaacuau cucuucucgu uuuuauaaua   2340
cuguaacggu aacuguaaug ucuaucaccu cauggaggug auuguccuug aucauaagaa   2400
ucucaauauu agccucuaca uuuacuauua ggucgauguc ugccuuuguc gugcuagaaa   2460
cacauauuca ugcaguuacc cggucuuuua aaguaccuuu agccugcaca uauacaaugu   2520
cuggaucugc uaacccuaaa uuuacuguuu cagaaacaag uucuucuauu gaaacuacuu   2580
aaacacaauu uggucguauu guugccauac uaagacuacu uugguuguug ccgacucccu   2640
ugaauacucc aaguaauguc ccagugacuu uggguacuug gguguuaugu gcuuguaugu   2700
caauuacguu aucagugcua augucaauuu caugaagguc ucuuucgcca acauuuuagu   2760
ccuaguuaag cuaacucucc uuguugauuc cuucuuaagu aucuuuuaag uaacuuaccu   2820
uucucguuuu cucuguauaa ugugguucuu gagagguuuu auaauuuaug uagaaaucgc   2880
uuacaacuac auaaaugaca aaauuuaagu gggguggucu uaucaagcaa acaccuacaa   2940
gcuaaaagac gaguaccuag agguauaaua cgaggucucu uugagcuuuu guuucaaugu   3000
cuaguaguuu accucgaacu uguuuuuaau cuacaccuua agauguacua guugcauuug   3060
cucacggaau ugcuuuguug cacaccucga cuuuugagua caugcuuguu uaauuuguau   3120
ugugcucuug gucgacauca caaaugauug ucuuguagga aacagccaca uuuacguaaa   3180
uaacuaggac acacacggcg aaaugguucu cuacaauacc uuacaaaguu gccuccgcag   3240
```

gaauagcuuu ugugucgcac auuaacagga cguccuaaac uuccuggugu aacacuuuag 3300
gaucgauauc cuaaaugucc uugaccaacc cgauacauag guaggaaacu gcgauguuug 3360
uccugacucu aauaugacgu auaaaauagu guuugacuau uaccaaacua uaaaauguua 3420
ccuggaaauu uauauucugu uugaagaaac agauuucuaa uauauaguaa ucuugaauuu 3480
cugccuauag guaaugaagu uuaaacgugg ccgaguucgu gaguucuuua aauagacuuu 3540
cucgcguaag uguuuaacuc gcuaccuagc aauguguuuu auuuuuaucc uagaccuaaa 3600
cugcuauaua gggaccuuca ucugcugaca ccuuguugca caaguuaaac cugauuauuu 3660
gauguauuuc cacaauaggc ucguuuaccg ggggaaguug acccuccaua cuuuuugucu 3720
aaguggcuag uucuuaaguu ugcuuaaacc cugguaaacg guggcugacg gugggcaaag 3780
agaccaacau aaucuuuaaa cugcauauua cuuaaaauga uguuggagcc acguggaaga 3840
cuacguaagg uucgcauagg gcugacauug auacgucacu acguucgaca cugaaagcca 3900
uagcugaggu uaaagaacca acgauaagac caaacacauc guuaaaacua uuaagaagaa 3960
gaccgucauc aacauguauc ugcauuugug cuguugaaau ugcuuuuucu uuagcuacua 4020
ugagcgcuuu uguaauaguu gaugcuucua cuuccaccgc cgcuuacacu gugguugaug 4080
cuggacagac aaaagguagu cuuguuguaa caccugcuuu uugguaacua cucucuguug 4140
gggcuacaug gacgucuaua uucaccgaaa aaucuauugu ucuuucuguu gacacuauuu 4200
cuggggcuau uaaacggaau acugcugcaa gcgguaauac ggaugcuccc ucugccuuua 4260
ucguggccua ggaauagaag agagcgaagu acaugccugc uuccucuaaa uuucaaguug 4320
augaauaguu caaaaccugg gucuaagucu uucaaucggc uguacauacc ucuucuaggu 4380
ucgcuacuuc ugagugugcu accuuugcuu cuuaggacca cgauc 4425

<210> SEQ ID NO 226
<211> LENGTH: 291
<212> TYPE: RNA
<213> ORGANISM: Diabrotica virgifera

<400> SEQUENCE: 226
uacggaaaga caccaggguu uaacagggag acgccggacu aauagucacg uaccccauag 60
uaggucaacc caaaguaccc acauaagaua auguaacccc gacaccgaaa ucgucuucua 120
uaaggucucc aacucaaauu cccgcuaaau cuguuuaaaa uaucgcugca guugugccca 180
aagugugucu uacgaauguu gacgaccuaa cgacgagagg auauggacua uuguaaucgu 240
cauagucgag ugguuaagac ccgguuguug ucuaguagua acuugcagau u 291

<210> SEQ ID NO 227
<211> LENGTH: 540
<212> TYPE: RNA
<213> ORGANISM: Diabrotica virgifera

<400> SEQUENCE: 227
uacccagaau gguauagucg ucacaaauua uccaacaaau cauuuuucgg auacucuuaa 60
aauuaccauc cuaaucuacg gcguccauuu uggugpuuaga auauguuuaa cuucgaacca 120
cuuuagcauu gauguuaugg uugguagccg aaguuacauc uuuggcaacu cauguucuua 180
uauagaaagu gccauacccu acauccaccg gucugcucuu agucuuuuga gaccucugug 240
auaaagcggu ugugacuacc ugaguaaaaa caccaacuaa gguugcuggc ucuggcauag 300
cgccuucggc uucuucuuaa cguguuauac aauccucucc ugcuaaauuc ucugacguaa 360
aacaauuaua agcgguuguu uguucuaaau ggcuugagcu acaggugacg acuuaacugg 420
cuauucgaau ucaacgugug aaacuucuua uccuccacca uguauguucg guguacacga 480
ugaguucccu uaccaaacau gcuuccugau cuaaccaaca gcuuacuuaa ccgguucacu 540

<210> SEQ ID NO 228
<211> LENGTH: 618
<212> TYPE: RNA
<213> ORGANISM: Diabrotica virgifera

<400> SEQUENCE: 228
uacgccaugu gaaacucaau guagccacga ugggaucgca ggugacauug ugacuaaaaa 60
cgggagauga ugacggagug cccuuuuccu cucguucaau caaaucguac caauaacaac 120
uuacacagag ggguguacac ccguccagau ccuuaaccgg aacgacauag uaauagucaa 180
cauccucgac gacguccuua agugugaugu ccucagucau agcauccucg accacaauuu 240
cgggggucuu aguuuugguu uuuaaauuaa agauaauaaa agacacuucg acaccgauag 300
auacccaauu aauaccgaua ucaugagaca ccuucaaccu ucuuaaagcu acaucuggau 360
aaguuggagu uuugaguauu gaaacgaguu uugguaauac cuaguguaca auaaaaaccu 420
aggccaaauu gacaaccuaa acauuuagau aauacaccua aaacacaacc ucaucaacca 480
agaccacguc gguaaagacu acgucgguua aguaguaaua agcaguuuua aaacuaauaa 540
cucuaaaaac cuucacggua accagagaag ccagacuaac aaccucauau gaacugcagu 600
ucuccgagau accaaauu 618

<210> SEQ ID NO 229
<211> LENGTH: 5694
<212> TYPE: RNA
<213> ORGANISM: Diabrotica virgifera

<400> SEQUENCE: 229
uaccgauggu ugcuaucauu ucgaggcaac uccugucaau uuucucacgu uaaaccuuau 60
gaaucagguc uacuuuaauc ugcuuacagu cagugucuuc ccccguaggc gaagggucuu 120
ugguaccuuc guccggcggg guuugauacg ccagaauacc uggggucugu uccacaguau 180
cugucuucga guucuacggu cuguacacgg ccuuuauacu gucuuacagg accuguaaag 240
ccuguauagc ucgaccguuu uggucaaaag gugcauccua agcauuguuu uuguuauuuc 300
uagaacucua cgcaaacgaa gaaaacguca uuuaauaauc agucagguuu auuaggcuuu 360
uaauuucuuc aacauuacuu uaguuucccu gucggugcau uuucuaaucg aaagcaaaua 420
cuagacacau uuccauuuuu auaaacacuu ccaccucuac uuuaccuaca cccauuucuu 480
ucgcuucuag gguuauuuuu ucguccggua ccaccaacac cagcuauagu ugguuuauag 540
ucugcacggc caaaucuaaa uugucgucuu accuuugugc aguuacuucu guguguucuu 600
uucuuuuagc gugauagacg gcuugcacag acccuuuagg auuuuguaua gugucuacuu 660
cuuacaaagu aagaaccaua ccuaggguuu aaacgaucug gucuaaccua cuaucauugc 720
caugaaggac aaggaggggga ucgucaugcu ggacgacauc aauacgugcc uagacguucc 780
uuaguccuac uauagugagu guuuaaccgg cuguaaauagu uccgcuuauu gcuuaaugucc 840 uucuugcuca gacguccacg ucggcgagua uauuagugucc uuuuauaauu cuacaacguu 900
aaagugcagc ggugaaauca acuguugcua uacggcccuu acggcucucg uuacguuuuu 960
agaccuuuug gggauuuucg auaguuucga gccgacuuuc cauuucuucc uuccuaagcu 1020
ccauuggaau acccuuucgc acaccugaaa agacgugcau gacaguagug uggucuaggg 1080

-continued

```
uuaaaugcau agcugguuca uccucacgga ucuucauaac gaguuuugua cugcaaaggu   1140
cuuuagcagu guggaaaguu aaaacuguuu uacaaccuua accaugucuc uccauuaaga   1200
gucauagguc cucgauucau auaguagucu cuguuaccuc ucuccuaacu aaaugcaaag   1260
guggguuuug gcagucuaaa uguaaacguc acaccaauau uccaucuuuc uguguagucu   1320
cugccgcuag aucauuagaa guuggcaguu gguugggagg uguucuacuc auacuacccg   1380
gugucucagu uucagaaugg gaccagcugc aaggcauacu uagagagcac guggagaggg   1440
auguugcggc uaaaacugcc gcugcuuuac uuggagguac acgggguuuc auaccuuuga   1500
gcucgacuuc agcuuuugga gguguaguga ggguccguuu aguaaugagg cguucgauug   1560
guugggcagu acccauaaca uguucuaugc aacugucgac aauccuucua cuguuuuucc   1620
cuacauaagu agcucuuccu uguuuacuac uuauauaacu acaagaacgg uuaaacccua   1680
ccauuuuacg gggcaggucg guaggaguuu ggguuuggca acaccugucc uuuugucuau   1740
aaaagggacu aguaaggacc guuacauuua uacuaugcau ggguaagaug cguaggucug   1800
cugcuccugc ugccagggau auuuaccuau agcgguccuc uaugcuuuca auaccaucuu   1860
guaccucuua accaguaccc auauaacaca uucuuuucag aaccuuguag ucguccaagg   1920
gacgacguau aaacauacaa ccuuaauccu gugcuucaca caccaucuaa aauaccauug   1980
uaaguuugac auuaguuguu gaccaacaac aaucuuccag ugucguagcc auaaccucug   2040
ugguaacggc uaggagucug aaugugucuu uaagucucuc gguaguccuu ucgguuucuu   2100
cuacauuauc uucaguaggu cuuucgagug uuguaccuug accuuggcug agggccauua   2160
ugcaacgcag ucugaaagcu uuuaguucau uugucuuaag auuugcugcg agcacuguuu   2220
ugaccaccaa ggcgauucuu uagaaacuga cuuauguuau uggauuuccg auaccagcau   2280
agcccuaggu ucccuagguu guaauuauaa aggguccaau aacgaacgca cccaguuguc   2340
uugcaucuuc cauuugcaua agguaaaccg aagucuuuug cgugcaacgg cgugaaguag   2400
uuccugcuaa ugccaggacu uaggucucca aagcaucuuu uaagcauaga acggccagag   2460
ugaggaagcc ucaagauaaa ggugcgauac ccuccagcac uuccagaaua gcuaugacga   2520
cauuuuugac ggcuuugacc aauguagguc gcagcagacu aguuccgaua ccucucacau   2580
uaccauguga ugcugccaug gcauucuuua agacauccug uugaauaggu caacucuaug   2640
ccacuccugc cugagacacc ucucuaccau cucaaaguua uaaaucguug ccaguuuaau   2700
ucauuguucc gcaaacucuc uuuuaagucu aaacuaggcu cauuacuuuc cauaaacucu   2760
ucucaaaagu uacuucuuca auaguucguu gacuacccaa gucccuuca guaaaggcuu    2820
gaacucucuc uuacccuugu ugaggucuuu cugucucuuc ggaauucugu uuagaaggga   2880
ucgccucuua gguuucauca ugaggggaca uuaaaauguug cauacuagac cuuacauguu  2940
uuuuaaaagg uguauuuguu ugcucggggc ugucuggaca ggggcaauuc ucaauagguu   3000
ccgcaagcuc uuaaugaguc cuuuacgcag uagcaucgac cgcuccuagc agacagguuu   3060
guucgguugc uuuugcguug caaugagaag gucacagauc agucuagcug ggagacgugg   3120
uuuacgcaaa gacuucuuaa guccgagucg uggcuucgga agcucaccaa cuauccucuu   3180
uagcucugcu ccaagguugu ucggguucgg uuaggaccuc uuuaccaccc gcgagaccgg   3240
cgcgucagug acccucuugg gcgaugaguc uacugugacu ugugaaaggu aaaacgacca   3300
cauaggaggu ucuugcauug ggacccacau ggaucuaauu uccuuuaaua auuauaaagg   3360
uucuuugggu uccgagguag agauuggcac aaaaauugac cacgccgacg aucucuacgc   3420
```

```
cuuuuucgcu ucuuacacaa uacgucugaa cuuguguggu gagaagcauu ucauuggcgg   3480
uuguggcggu agauaaugcu aggacugggu guuuuauggc aguaaggacu ccuaguccuc   3540
aagcaauugc agaugauacu uuacgggcua aagcuaggau gggcauauag cggcaccaac   3600
gaagcauagc uugaccuguc uuucucuuac ugucuauucu uugauugaua ccuuguuuaa   3660
cgacuuuucu aguugcgacc caagccccug cuaaacuuaa cauaaaaguu gcugcuguua   3720
cgacuuuuca accacgacgc auagucuuag uacuugucgc ugcuaccuuu uaagccucuu   3780
ccacgacuac uccugcaucu guuuuaccua cugcuguaca aaaacucuac guagcuucgc   3840
uuguacgacu cgcuauacug gaacguucca uaucuucgcu aaagguucca uauguacgug   3900
aacggugucu gacugagcuu uuuuuccuag caguagugac uuuguccgcu uaaauuccgg   3960
uagcgucuua ccgauaaccu uugacugcca uggucguacu acuuucauga cagucuuucu   4020
cugcagcuag gccaguccug caaaagauug cuguaaacac uuuauaaaag ccaugaacca   4080
uagcuccgac acgcauucag acaucucuuc cuuuacuugc gacaggaaag caagaugcca   4140
gacauacauu ugauagcggu agaacggaac gaaacacugc auuacugucg guuuccagug   4200
aauuaccggu agugggcagu gccauaguug ucuguucugu gaccucgaga cuacuccaca   4260
aggaagcucc uuugacaucu acauaaacuac cugcgacggu caguacgccu ccagcugggu   4320
uacucuccuc auagacuuuu guaauaggag ccaguugaug guucuuaccc guguccgacg   4380
aagcuagaaa acgaccugcg gcuuuuuaca uuuuacccuu aacgguaugg aguucgcgug   4440
ucgucgcuag auuaccgaag uccuuacaag aaaccuaauc ggcgaugugg gucgucauac   4500
ucagguccac cacgauacug ggguaccuua guucgucgau gugguaugca accgucauag   4560
accagaggug ucuuaaauua cccgucaccu uacuguggucc caccacggcg aaagaggggu   4620
agucgacgca gucuacguag uccuuacagu ggucgaauac cgccaaccag ugguuguggu   4680
guuagaggac guuacagcgg uauauaccga agaggguguac cuguuagcgg aaggauguca   4740
gguaguucag gucgcaaggu uggaugaagu gguagguacu gcggcuggag aggaccuaua   4800
agagggucaa gaggaccaau aaguggaugg ucagaguuaa ugucagguug cucaggguca   4860
auaagugggu gaagagucuc aaugaggggu uggaguggau caaugagugg cugaagaggu   4920
uuaauaagug gaugaagggg uucgauguca gguuguaggg gauugauaag ugguuguaga   4980
ggguugauaa gugggugaag uggaucaaua ggaaguugaa gcgguccaau gucgggguga   5040
agugcgucga ugagugggug uagaggauca augaguccuu gaagcgggag aauaaguggu   5100
ugaagcgguu caaugagggg augaagagga ucaauaagcg gcagcagagg auuaaugaga   5160
gggugaagag guuuaauguc agggugaaga ggauuaauga guggcaggag aggauccaug   5220
ugcgggccaa gaggaucaaa aaggggguuca agcuugucaa ugagagggug uagaggaguu   5280
auaagagguu guagagguuc aauaaagcgga agaagcgggu uuauaagugg uugaaggggg   5340
uuaauaagcg guuguagagg uaguaaaaga ccuccuucag guguuauaag ugggguguagu   5400
ggcuuuauga gagguuggag cggguuaaug ugagacagcu caggcgucgu gugagguugu   5460
ccaucgucag cuauaagugg caguugaagc ucaauaagag gauuaagcgg guuaauaagu   5520
ggcugcagag guguuaugag guagguguca uguuuuauaa ggggacguuc aggauguaag   5580
ugugggguggu caggaucaaa gagagggcga agugggcgua uaagcggagu uggauacaua   5640
aguggaagaa gaggauuaau aagaggguga ucagggucag uucugugacu gauu         5694
```

<210> SEQ ID NO 230
<211> LENGTH: 876

<212> TYPE: RNA
<213> ORGANISM: Diabrotica virgifera

<400> SEQUENCE: 230
uacagcaguu uauaaguuuu ccgggucguc aacuaccgcc uacgucuuuu cuuucauugu 60
agagcuccaa agaagccuag agauaaaccc ccuaguucag cauaacuucu acgucaccuu 120
acaauguguu cucgacguuu ggaaaaauuu uaccgguucu cgacccuacg acggccauuu 180
cggaaaacac uccgacgauu aaacguaagg ucuugaccac gagcaguacu gcgacggguga 240 uuaauauauc uacgacguuu aacaauguuu uuucggcuac auaaacuccg acauuugacg 300
aaauauuuuc gauaucugua aauauggcuu uacccagcga aauguuaccg acguuuugug 360
guagucugau aacgucuuua cauacucuga cuacgacacc uguagcuuuc ccgacaaguu 420
gugauacuug uccgccgacu aaugaagucu ccucuucuuu cguuacgaag gcgguuauuc 480
acagaagaau uucaccgagu uauacgucgg guugaacuuu ugauacuuuu ucgucacccu 540
uaaauaguuc uucaccgaau acgucgagac cuuucgagag aaaauuuuau gucacguuuc 600
cuuaugaaua agucucgacg ggaaacagug gaaacacaac uacaugaguu acguguugua 660
cgauaucuuu cgauauaaag uuccauaggg cguaaaguuc uaagggcacu uauguuugaa 720
aacuuuuggg aguaucuuuu guagcuucuc guuuugcauc uaccuauaug ucuucggcag 780
uuucuaaugc uaaguuaaag agcagaacua gucaccauau gauguuaaga aaaugcauaa 840
uucuuuguuc auucgcuuuc gggacugaau gcaauu 876

<210> SEQ ID NO 231
<211> LENGTH: 609
<212> TYPE: RNA
<213> ORGANISM: Diabrotica virgifera

<400> SEQUENCE: 231
uacuuagggc ucauacuaau aaauaaguuu gaagacgacu aaccucuaag uccucauccu 60
uuuagaacag aagaugacuc uaaacgucua cuauggaugu gucuuucgau auaaucaugg 120
uaaccgcauc uaaaauuuua guccuguuag cuaaaucuac cuuucuguua auuuaacguu 180
uaaacccuau gucguccagu ccuuuccaaa ucuugcuaau guaguucaau aauggcuccu 240
cguguaccau aauaacauca caugcuaacg ugucugguuc uaaguaaguu auugcaauuu 300
gucaccgagc uucuuuagcu ggcaauacgc acacuguuac auuuguuuaa ugaccauccc 360
uuauuuucgc uaaacuguug auucuuucaa cagcugaagu gaugucgguu ccucauacgg 420
cugguuaacc cauaugguaa aaaccuuugg agucgauucu uacguugguu acaucuuguc 480
cggaaauacu gauaccggcg acuuuauuuu uuaucucauc cuggagguag aagacgccau 540
cugguuccuu uauuccaauc caagcuaguu ucagcggguc agcuuuguug guuuaggcca 600
acgacgacu 609

<210> SEQ ID NO 232
<211> LENGTH: 789
<212> TYPE: RNA
<213> ORGANISM: Diabrotica virgifera

<400> SEQUENCE: 232
uaccgucugc gacuacuaga uaaucuaaua cuucuacucc uugucugucu uguuuggcgu 60
ugacuuugcc guugaugucu ccaugucuuu uucccacagu ucccguguau acauaguuau 120
gugucaagac ccaaaucucu aaaagacaau uuuggucguu aagagucucg auaucaccug 180
acgcccaagc uuguaggaag ucuucaaguu guacuuacau aaggaguucg acaguaaccg 240
uaccuauaag acacgguucg auuuaggcca uacccuuuuu gccgacaaaa acauaaucga 300
ugugagguuc auuaucuagg augucuuuua caacauauac aagagcagua cacgguaugg 360
ucucucaauc ggaaggucua uucguuucuc augcuugcaa agucauuuau auacggguua 420
uaauuucauc cccagaagaa accaccgaac ggauaggucu uucuacuccu uugcaauuuu 480
uuauuaacgg gcguauagca acacccauga gguccuucuu aaaaucguaa ccagucuagc 540
uuuuuugaau uagaguuugu agauuucgua aaauaaaacc uacuuacacu auuuuacaac 600
cucaauaauc uguacucugc acuacaaguu cuuuauauag cauugugagg ggugcuuuuu 660
guucaguacu acaagucacg guggaauuca uuucuuuaau cuggucaaac guucuuuaaa 720
uacguucuac auuaaguuuu aagaauauua uguguuaaaa cauuacugcg ugggugagcg 780
uuacaaacu 789

<210> SEQ ID NO 233
<211> LENGTH: 738
<212> TYPE: RNA
<213> ORGANISM: Diabrotica virgifera

<400> SEQUENCE: 233
uacggccagu aacuaccaau auuucaugaa auguaaaaua augugucaaa uauauguuaa 60
aaacuuuuau aaaccuccug agaaaauaaa uaaauaguuu uaacauauuc ccaauauuug 120
ggacuuagau guaagcuacu acgacugguc aauuucuuuu cugacagauc ugauuguuuu 180
uucggaguug uaaauugaua guaauaacca caccuucuua uaaguaacca ucuaaaccga 240
uuggagcaua uaaccacaaa uccagaauua uaaggcaugc aaucaaagau acuaauauuu 300
ccauuaaauu uuuucguacu ucucuucaac guuguuuaac aucuuagguc uuuuagucuc 360
uuauaguugu auuaaaccgu gugguacgu cuuguuuccg uauuuuuacc uaaaaaccca 420
gguuuuuagg ugcauuuuca caauugugug cgccugccuu ucguuucaua ucauuuacaa 480
ugauuuuuua aucgagauuu auuucuuuuu cuguaaucau uucuuuuuua aucacuuaau 540
gauaauuccg ucauacuuaa aggucuaggu cuuuaccgau aauaaacacc uuucuuugac 600
uuguaaauau uaauaggagg aaccgucaau ucugaguguc uuaagaaauu ucaguuguuu 660
caguuguugu aguguaaggg ucacaaacac cuuuuuaacc uuuucauguc guuuacacuu 720
gucucccacc cuuuuauu 738

<210> SEQ ID NO 234
<211> LENGTH: 480
<212> TYPE: RNA
<213> ORGANISM: Diabrotica virgifera

<400> SEQUENCE: 234
uacugguuga gauuuccaau ggcggcuccu ugguccuag auaaacgggc guucaaauuu 60
uuugcaccac auuaagguga aagguguaua aacucucaga uguuucaacc ucuauaacau 120
cuauaguucc cauuaccacg ucaaguuuuc ccauacgggg uguuucacau gguaccauuc 180
uguccugcac aaaaguuaca augacgugua cguaauccac auuaacauuu guuuucccaa 240
gcuccuucuu aguaggggu uucuuaguua gaggcauaac uuguacauuu ggugagguuc 300
acagcaguuc ugaagaacgu uucucauuuu agguugcuuu ucgaugcauu ucuucgauuu 360
cuuuucuugu aauuucaucu ugaauccucu guuggacggg uuggauccgg ucguguauaa 420
caaucgccuu uccaaggucg uguccacgaa cgaggauagg guauacuuaa guaacgaauc 480

<210> SEQ ID NO 235
<211> LENGTH: 537
<212> TYPE: RNA
<213> ORGANISM: Diabrotica virgifera

<400> SEQUENCE: 235
uaccuuccuu augaugaccu ugguuguaac auaugguauu uuccauaacg auauaaccug 60
auacuaccau uaucucacga ccgauuuaug augcuauuuc uauauaaagg augucguuuu 120
cucgucuuuc gaaaacucuu uuuaaacaag uuauuuugag uaucccgucu gcgucuuuaa 180
uaguacaacc uaccaaauug aacacacaua ucuucauuac aucuaaauaa gaaaauacaa 240
uacccgucaa guguacuuuu acucgauuaa aauuacucac aaaauuuaac gaacauacug 300
agucauucag uuuauaacuu cuuuuuauac guuuuugcuc gacagaaccu uagugaucua 360
uaacaauacg accgauaccu acuuuaacaa cuaccuccuu auuaauaucu aagacuaagu 420
ucaagucauc auagaucuua ucguaauucc ugacuacuau aagguaaucc ucuuguuuga 480
caucgagucc auaagguuug ccgguuucuu gucgacuuua ccaguaacga cuuuauu 537

<210> SEQ ID NO 236
<211> LENGTH: 450
<212> TYPE: RNA
<213> ORGANISM: Diabrotica virgifera

<400> SEQUENCE: 236
uaccgacugg uugaguggcu ucuuguuuaa cgacuuaagu uucuucgaaa gagugauaag 60
cuauuucuac cacuaccaug uuaaugcuga uuucuuaauc cuugucauua cucuagagau 120
ccuguuuuag guugucuccg acuuaauguc cuauacuagu uacuucaucu acggcuacca 180
uugccgugcu agcuaaaggg ucuuaaaaau ugcuacuacc gugcauuuua cuuucuaugg 240
cuaucacucc uucuuuaagc acuucguaag gcucacaagc uguuucugcc guuaccaaag 300
uagagucguc gucuuaacgc ggugcaguac ugguugaacc cacuuuuuaa cugucugcuu 360
cuucagcuac uuuacuaagc ccuccggcua uagcuaccac uaccaguuca guuaaugcuu 420
cucaagcagu gguacuacug aaguuucacu 450

<210> SEQ ID NO 237
<211> LENGTH: 2013
<212> TYPE: RNA
<213> ORGANISM: Diabrotica virgifera

<400> SEQUENCE: 237
uacuacguuc guuuguuagc ucagggugga uauuucaacc uuuugcuaua ucuagaaaug 60
cggcuacuau agcuccuaaa gcguguucua cugaaaccac cacuuuuaca acuagauaua 120
cugcuacauu auaggcgagg aggaccuuua uuacuguugg guccacuaag uuuaguagua 180
cgaggaggac cacgaccacu ucuaccaccu ccauuaaaac aacccagucc uccucguggg 240
uuauuauauu uaagaagacc uucuucugua gucgacauac aaccuuuaga cugaaccacc 300
uguugacuag uucuauaucu uuuacgucac guacuauauc cccauuggcu gaagguacuu 360
caauucaaaa aacuugugue ucguuuacca guuagguucc cuaagacaca guauagaaac 420
ccuagacucc cuucguacuc ugagacggac cuugaggaua gauuuuuucu cuaguuaccg 480
guuuuagggg aacaauggga agggguuuuu guucgagaau cauugaaacu uucagucaga 540
uuuugugcgg gaagaggaug auuauuaaga uugagugcag gaggguagg auuauuauua 600

```
caaguaaguc caggauacgu cuuaauaccu ccaucuuacg gauacuuggg aagguacgca    660
ggguacgggg guccauacgu uccacgaggu ucuuacgucc cagguggacc uaaauuaccu    720
ggugguuugu acuuagucgu ugggggggucc aagguuccau uagguguuac cuuaccugga    780
ucuggauuac caggacccgg guuauacccu uacucugggu accccggugg aguaccuguu    840
guucccgggg guucuggugg uuacgucccu gguggcgucg uuccaggagg uucuccuuac    900
ggcgguguuc cagguggcgu cuacgcaggu cuuaccuuag cuggugguua cguuguuccc    960
augggaguuc cgggcggcgu auacguuccu ggauuguacc cagguucucc aggugggguu   1020
uacccuggug ggccccgcgg aguugucguu ccuggucgag gcgugcauuu aggucguaag   1080
aaaguuguuc cuccuccugg uggcgggggu uacguugugu acggaccugg ucccgggcag   1140
uacggaggag uuccuggggg cguuccaggu ggugugccug ggcaaccugg aggugugccg   1200
ggugguaacc caggucgcuu acaaggcgga guaccuggug gagugccuau accaggugga   1260
cgucgcuacg gugucggcgg uaugccaccg ggugggaggucc ugguggcgcg acucuaagga   1320
gucaauuguc ucguucucaa acuccuauau uacagggccu uaucuuguca aaggucaagc   1380
cgcuaacccg cccggcauag gcugcggcgu cgaccucuua aacguucgcg guaacucuga   1440
aaccaaugac gauaaaguga guaguuuguu agguuucacc gauugcugcu agcaacguuc   1500
uaggaauauu caagcgacgu ucuaugaaac gcaccacagc uucuguuuuc gaugucgagg   1560
ucggcgucuc uggccaguuc uagguccccug ucuaguguau cuucuugauc uucucuugcu   1620
aggagcagug ccaugucucu gucuucgucu cucucccucg cacuugcgcu aucucuagca   1680
cuagcacuug cacugucuau aauacuaucu augucgcuuu cucuuucucu ggcucuagca   1740
aguucuucgu cucuuucuug ucuuucccua ucucuugcuc uaauaucucu ggcccuuggg   1800
cuucucuguc uauuucuuuu uagauuucau aggucucaga guucuaguuc uuuguuuaga   1860
ggccuuggac agcuuggauc gucgcuccau ggcuuuagua gggcgauaau acuccuaucc   1920
auagcccuug cucucucucu uccagcugcu cucucgcuag cgcuuucucu uucucuaucu   1980
ucuccccuuc ugucgguauc cagagcugug auc                              2013
```

```
<210> SEQ ID NO 238
<211> LENGTH: 765
<212> TYPE: RNA
<213> ORGANISM: Diabrotica virgifera

<400> SEQUENCE: 238

uacucaagau aaccuugacc caugcuaaau agucgaaggg uuaagagagg acuaccuucu     60
cauaaaguuc aacuuauacg uuacuuucgu caacuuuuau caccguggca uuauccggag    120
gcuccauguc uaccguaaca uaaccgacga cuuuucgagu aauacaguuu uaacguacuu    180
gguucauguu uauuugcuua aaaguuguaa cuauuugugu auccuuaccg uaaaaguccg    240
aauuaucgac uacguuccgu uuagcaacuc uaacgaucuu uucuucguag uuuaauaucu    300
guaguuauac caaguuuaua aggagaauuu auggauuuac uaucucauuc guacauguac    360
guacguaugu gaaauauguc acgacaaucu gguaaaccaa cgucacagua gaaccgguca    420
auacuucuau cacuggguag auacauagac uaacuaggua gaccucaauc gauaccuaug    480
aaaccuacac gauguccauu ucguuuuguc agacguuucu gacuuuaucu uuuuaacuuc    540
uaccccuuag auuguacguu ucuugaacaa uuucuucguc gguuuuagua aauaaaccag    600
guacuacucg acuuccuauu cuuaaaacuu gaccuugaaa guacccauac guuucuaugc    660
uuaccaaaug uaugguuuca cggacuuagu cacaaacgac uacgucuuuu ucgacgguuu    720
```

guucguuacc uucgucuaag ucuuagucua ugucuucuau acauu 765

<210> SEQ ID NO 239
<211> LENGTH: 744
<212> TYPE: RNA
<213> ORGANISM: Diabrotica virgifera

<400> SEQUENCE: 239
uaccgaaguu uucugucuaa cuacuaaaaa gguagaucuc cucggguuua cuacuacuuu 60
agguccgauu ucccucgggu uuucccugua ucaaauaauu ucuucuuucg acuacgaaau 120
guuuacucua aaucuuacua aaacuuguuu uaauaacucu gguuuugaga guacccacuu 180
cauuacuuuc uucgacggaa aagaaaucga cuucguuuca aacguugacc acugaaguua 240
guucaacaag aaguuuuaca gugguuccga guuuauuuuu auucuugauu cuuucuguug 300
caacgaccac aaugaaaugg ucacaaacuu acgaugguuc uaccaugucu auguauacuc 360
aaccgaccaa accgaucccc uccaguuguu aacuguuuug aguucuucuu aauaguuuca 420
cgacaauuug acaaccaacu uaaucggaga aacguuugaa gaaaacauug agaacuacua 480
cauuaguuuu auuguuuguc uucucaguua cgguaacuug uacaauagua agguucuuau 540
cucgcaugaa accgaaugua guauaggcuu gaccugcuca aucuuucucu ccucaagaua 600
ucuaauuucu ucuagguccu guuuuucuuc uagucgucuc guuuccggcu cuuuguuuuu 660
guucgagaag agguucgacc cgaugaauuu cucagggucc guuuguacga aaaccuacuc 720
ccgcuacuuc uagaugaaaa gauc 744

<210> SEQ ID NO 240
<211> LENGTH: 4818
<212> TYPE: RNA
<213> ORGANISM: Diabrotica virgifera

<400> SEQUENCE: 240
uaccuccgcc gaggguucaa uggcuacgag agcaagcuca auuuaugaac augucucuug 60
caggugaaac cgggggucaa uuuugucaua uaacgacgaa aaauaccacu ucuaggucuu 120
aggauguaau gucuuuaguc guuagaacuu aggaauucua gucgacguca agcugguagu 180
ugccuacauu uaccacaugu ugacaacuuu uucauaaaga cagucgaagc aaaagaguuu 240
agauccaaag gguaccuucu cuuaguucua cgacgucaag auaaaaguac cuuuuuauua 300
cuuaaucugu auugaaguug uaggucacua uagucuauac uuaauuacca uuauuacaua 360
uuguaaccuc ggaaugugug aaaagaaccu cgguugcuga guucuuuguu aggccuacca 420
uacuuuuacc guacaugagu aaaaguuaca cgacguaccc gaaaaguuuu gcauuuucuu 480
uucauggugg uuaaguauag uuuguagagu aaccaucuug accaaguaaa aaaaguuguu 540
cagacaaauc gaguccgagu ccucacauau aaucucuucu cguacaaacu guuauccuuu 600
ggaugguagu aacguuuuca acgauagguu cagaugucaa uaaugucugu cagaaaugca 660
cagaaccuua gucauuuacu ucggaugaaa ucccuauuuu ggauguuccu caccuacuuu 720
auagaaguua aguucgacug gaugauguuu acguagagca aggauaaggu ucccguuguu 780
cgacuccuug uugucuuuua cccucuuucc caacguaaga uaguucgacg uacacuuguc 840
gaccugcucc guuucuuuua acgacgaugu aauuuuuugg uuguggugu cguucuuuau 900 uuacucccug aucguaagug augacuacac caacuuccau uuucuuuucg ucgauuuuua 960
cuuuuacuca aguagauggu acuuagucac ggacuauuuc ugguuaacgg ucuccaauuc 1020

-continued ccacgaagua aucaguuucc uuaugguaag ucauauuuac uauaucuuca aaguccuggu 1080
cuauaaaaga gggcuaacca ggguuaccuc cgugugcuuc gucgaaggaa caugucgcuc 1140
uucuuucgag ucucuaauuc ugucuagccc cuugaauaac uuuuauuucu aguuuguaac 1200
cgacuuaaau acagcaguua cgucgaucua gauaacuggu ucuacguggu ccgaugaccu 1260
uauggcgucc ucaacuaacu aucucgucgc cgagauagac gauuuggauu gcgguaaguu 1320
cuagaauauu cacgauaccc uuucgauaga uuauauaugg uucugcaacu ucguucaaac 1380
uuacucuaac uaagaaauaa uuuccggcuu cuuguuucac uuguuuucau gguucuuugc 1440
uaaccauuuu cugguggcuc guaaaaucga ugucuaaauu gaucccuucg ccguuuuaug 1500
ucccuccgag uaugauuucg cuugcugagu uugguuugaa augugucccg cuacuaccga 1560
gugcaccgau uagacuuuua ugagguuguu ggcgauuucg ucgacguugu agucgacggg 1620
aaacagcuca aagguuuagg uuuauagcug cuuuuuagaa acuuucuaga ccuucgcgau 1680
caacguuuuc aucugcuuua cucuuggguu ucucgguacg auacccgagu ugaagcucuu 1740
agauaagugg uucugcuaua auguucaagg gaacauugcu uuguugguuu agucagcgac 1800
cuugucgaca aggucguucu ugaaguuuuc guaguuuuag acuaaagcaa cuaacuuguu 1860
uuguggagcc guguucuuuu guaauucucg cggaaucagc uaagaaugcg aaugcgacau 1920
uuaaguucuu uuauguaggu ucuauaugag guuuucucuu gguguuggua uugcagugac 1980
uaucguagca agcugagaau gcuucugaau aaccguuuuc gauuguuucc cuaucucaaa 2040
augaguuuug aacuuugcuu gcauagguuc aaugacguuu cuuauuccuc auggacguuu 2100
caaguuguuc uucucgcucu agucuacuac agcugacgcg uucacggagu uacccucuca 2160
guaugcagug aacggcgagg auuugacuuu cuaaugaacc ugagguccuu cuucucacga 2220
cgcauaagcc ucggcucaca aguuggugu gucgguugaa auucaaugag ucgacgauac 2280
cuagacggag gaccauaauc cggcugaggu caaccuaguc uuuauugccu acauggcuuu 2340
uuauaaguuc cacuuggugu uccaauauaa gguauauuaa ugguuguugg aagacaagga 2400
cggagugucu uauaacuacu ucucugauaa uuuuuuuacu ugcguaacua cgguccacga 2460
uucugcaguc acggaucagu caugccuaug ucguugaugu aaggugguug uaugggaguu 2520
ucacgcaugg uugguccauu agucagaaug ccuuuucuuu gaggucuaua auugaguggc 2580
augcugggau gguuccgcaa gugccgauga ugauugcgaa uagcaagcca cgucucgagg 2640
aguugaguuc cuaugcaugg caugcgucuu agauugcaaa gcuuacaacu gucucaaccu 2700
auaggaucgu ccauagucau gguuguucau ggacucuauc gaugaugagg ucgacuaggg 2760
uuauaauuac gcaugauggg uguacccaug aguggcucgg ucuuaaaugg cuuacgauua 2820
ugaguuguau aauggccggu ugacuucaug guaagccacc ucaugcgaag aagacacggc 2880
uuguuguagu uaauauuguc gagauggaug agcagcggcg aaagauuaua cagaucaugg 2940
uuaaggaguu uaggaucauu gaacuuauua agaaugcuca ugaugauacu gggcuuaugg 3000
ucaucaccac gucauggcuu acgaaguuuc ggaguuguca gcucgcgguc gagacguuug 3060
ggcucauggc gauacuuguu gauguuaaua augauguuau guucaugguc gccaucacau 3120
cgucgccuau gaaguuuuua uguuguuguu guugucaugg guccaugagu cuacucaguu 3180
cgcgucauga uagggcgguu acggucaaua augaguuggu caugaauguu augguugcag 3240
guuccaccau gguuagggag caugcguuga ccuguuugua uauuaguuca cugugguccac 3300 uggagaguuu uacaaagagu uuuaauguug aaauugguuc aaccaagacc ucguccugug 3360
gucguaguca ugaugagcag gcgauugcgg cgucauggua ggguuguucg acauuuauug 3420
ucaaguaaug guuugaugcc uaugcuaguc auaaugccgu uguugauauu aaggucaguu 3480
ggcucaugga ugucgcguuu gguucgugga ggacgucgug uucgacgagg uucauuauaa 3540
ggacgacggu gguuuaggag gagauuacac cuagacgagu caccgaaccu gaagucguau 3600
ucgguucgag gagaucacgg aguuguuuug uaaugcuauu uuggggguucu uuuccuuugu 3660 uuugguggcc gacaaagaag acuuugguuu uugguucuag guugugguca uuggugcggg 3720
uuuguugggu gaccuggucu ucauuucgcg aacaugcagu uuuaggacgg cucguuuggg 3780
aauuuguugc uacuacacuu cuuuaacaag ccgguucucg accuguccau acucuucaag 3840
caccucugga acugggugu uugaaacucg ccaggcuggu gagaccuaua auuuaccuuc 3900
cucuagguuc uggucguccu aacgcucggc gucuucuucu aguaaaggca gcgaucuaca 3960
auaggauacu ucuuauccaa gggccuauag aacggaaugc ugaaaagguc ccaccucaac 4020
acgcuaucau uucuacuaau auaguugcga aguauguaau uccuauagag cgguauacga 4080
ggcaguaaau aacaaugugu ucacggcaac agaaguugac aaccacuaua caccugcuac 4140
uaaucucuug uuguccagcu ugacuaggag acaaaccauu ugcuguuacu cuagccacuu 4200
cuauaaauga ccggguuucu uuuuccguca ucagaauugu augaauugua ccaguauugc 4260
aacguuuugc aauaucaauu cagaguaacc ugacuuucug acuaucgcua uuugaaugga 4320
cuuuuugccc ucagggcaca cuauuacgua gauguuaaau guagcaccgg accgucgaac 4380
aaagguuguu uaggacuugg caagcagucg auguggaacc uuagguaguu ggauaugguu 4440
guugucuucu gguugugggu aggccaccac cagguaacaa guagaccgua uccuucuucg 4500
ccggacgaga caaaugacug ucgacgauac aagcuacgac gguuguuacg auugagcuau 4560
ggucuagaau gucgaaacuc auaguucaac agguuaacgu ccuucuuaua agagucucua 4620
gcucucguaa acuucaaacc aaugcuuuca aaaaaccgca uauaauccgu auaucaaaca 4680
cuucuauuuc ggucuuucuu ugacuugcuc uaggucgggu uccaauuccu ccuuggugac 4740 cuuggugac aguaucaagg ucuugguuua uaucuaggaa auucaugaaa ucuggguaaa 4800
acccgaucau uuucuauu 4818

<210> SEQ ID NO 241
<211> LENGTH: 166
<212> TYPE: PRT
<213> ORGANISM: Diabrotica virgifera

<400> SEQUENCE: 241

Met Thr Pro Glu Arg Lys Lys Lys Leu Arg Leu Leu Leu Arg Lys Lys
1 5 10 15

Ala Ala Glu Glu Leu Lys Lys Glu Gln Glu Arg Lys Ala Ala Glu Arg
20 25 30

Arg Arg Ile Ile Glu Glu Arg Cys Gly Lys Pro Lys Leu Val Asp Asp
35 40 45

Ala Asn Glu Gly Pro Leu Lys Gln Val Cys Glu Gly Tyr His Arg Arg
50 55 60

Ile Val Asp Leu Glu Asn Lys Lys Phe Asp Leu Glu Lys Glu Val Glu
65 70 75 80

Phe Arg Asp Phe Gln Ile Ser Glu Leu Asn Ser Gln Val Asn Asp Leu
85 90 95

Arg Gly Lys Phe Val Lys Pro Thr Leu Lys Lys Val Ser Lys Tyr Glu
100 105 110

Asn Lys Phe Ala Lys Leu Gln Lys Lys Ala Ala Glu Phe Asn Phe Arg

```
        115                 120                 125

Asn Gln Leu Lys Val Val Lys Lys Lys Glu Phe Thr Leu Glu Glu Glu
    130                 135                 140

Asp Lys Glu Lys Lys Pro Asp Trp Ser Lys Lys Gly Asp Glu Lys Lys
145                 150                 155                 160

Val Gln Glu Ala Glu Ala
                165


<210> SEQ ID NO 242
<211> LENGTH: 201
<212> TYPE: PRT
<213> ORGANISM: Diabrotica virgifera

<400> SEQUENCE: 242

Met Cys Glu Glu Glu Val Ala Ala Leu Val Val Asp Asn Gly Ser Gly
1               5                   10                  15

Met Cys Lys Ala Gly Phe Ala Gly Asp Asp Ala Pro Arg Ala Val Phe
            20                  25                  30

Pro Ser Ile Val Gly Arg Pro Arg His Gln Gly Val Met Val Gly Met
        35                  40                  45

Gly Gln Lys Asp Ser Tyr Val Gly Asp Glu Ala Gln Ser Lys Arg Gly
    50                  55                  60

Ile Leu Thr Leu Lys Tyr Pro Ile Glu His Gly Ile Val Thr Asn Trp
65                  70                  75                  80

Asp Asp Met Glu Lys Ile Trp His His Thr Phe Tyr Asn Glu Leu Arg
                85                  90                  95

Val Ala Pro Glu Glu His Pro Val Leu Leu Thr Glu Ala Pro Leu Asn
            100                 105                 110

Pro Lys Ala Asn Arg Glu Lys Met Thr Gln Ile Met Phe Glu Thr Phe
        115                 120                 125

Asn Thr Pro Ala Met Tyr Val Ala Ile Gln Ala Val Leu Ser Leu Tyr
    130                 135                 140

Ala Ser Gly Arg Thr Thr Gly Ile Val Leu Asp Ser Gly Asp Gly Val
145                 150                 155                 160

Ser His Thr Val Pro Ile Tyr Glu Gly Tyr Ala Leu Pro His Ala Ile
                165                 170                 175

Leu Arg Leu Asp Leu Ala Gly Arg Asp Leu Thr Asp Tyr Leu Met Lys
            180                 185                 190

Ile Leu Thr Glu Arg Gly Tyr Ser Phe
        195                 200


<210> SEQ ID NO 243
<211> LENGTH: 913
<212> TYPE: PRT
<213> ORGANISM: Diabrotica virgifera

<400> SEQUENCE: 243

Met Pro Leu Arg Leu Asp Ile Lys Arg Lys Leu Thr Ala Arg Ser Asp
1               5                   10                  15

Arg Val Lys Cys Val Asp Leu His Pro Thr Glu Pro Trp Met Leu Cys
            20                  25                  30

Ser Leu Tyr Ser Gly Asn Ile Asn Val Trp Asn Thr Glu Asn Gln Gln
        35                  40                  45

Leu Val Lys Thr Phe Glu Val Cys Asp Val Pro Val Arg Thr Ala Lys
    50                  55                  60

Phe Leu Pro Arg Lys Asn Trp Ile Val Ser Gly Ser Asp Asp Met Gln
```

```
65                  70                  75                  80

Ile Arg Val Phe Asn Tyr Asn Thr Leu Asp Arg Val His Ser Phe Glu
                85                  90                  95

Ala His Ser Asp Tyr Val Arg Cys Ile Val Val His Pro Thr Gln Pro
            100                 105                 110

Tyr Ile Leu Thr Ser Ser Asp Asp Met Leu Ile Lys Leu Trp Asn Trp
        115                 120                 125

Glu Lys Ala Trp Ala Cys Gln Gln Val Phe Glu Gly His Thr His Tyr
    130                 135                 140

Ile Met Gln Ile Ala Ile Asn Pro Lys Asp Asn Asn Thr Phe Ala Ser
145                 150                 155                 160

Ala Ser Leu Asp Arg Thr Leu Lys Val Trp Gln Leu Gly Ala Ser Thr
                165                 170                 175

Ala Asn Phe Thr Leu Glu Gly His Glu Lys Gly Val Asn Cys Val Asp
            180                 185                 190

Tyr Tyr His Gly Gly Asp Lys Pro Tyr Leu Ile Ser Gly Ala Asp Asp
        195                 200                 205

Arg Leu Val Lys Ile Trp Asp Tyr Gln Asn Lys Thr Cys Val Gln Thr
    210                 215                 220

Leu Glu Gly His Ala Gln Asn Val Thr Ala Ala Cys Phe His Pro Glu
225                 230                 235                 240

Leu Pro Val Ala Leu Thr Gly Ser Glu Asp Gly Thr Val Arg Val Trp
                245                 250                 255

His Ala Asn Thr His Arg Leu Glu Ser Ser Leu Asn Tyr Gly Phe Glu
            260                 265                 270

Arg Val Trp Thr Ile Phe Cys Leu Lys Gly Ser Asn Asn Val Ala Leu
        275                 280                 285

Gly Tyr Asp Glu Gly Ser Ile Leu Val Lys Val Gly Arg Glu Glu Pro
    290                 295                 300

Ala Val Ser Met Asp Ala Ser Gly Gly Lys Ile Ile Trp Ala Arg His
305                 310                 315                 320

Ser Glu Leu Gln Gln Ala Asn Leu Lys Ala Leu Ala Glu Gly Ala Glu
                325                 330                 335

Ile Arg Asp Gly Glu Arg Leu Pro Val Ser Val Lys Asp Met Gly Ala
            340                 345                 350

Cys Glu Ile Tyr Pro Gln Thr Ile Gln His Asn Pro Asn Gly Arg Phe
        355                 360                 365

Val Val Val Cys Gly Asp Gly Glu Tyr Ile Ile Tyr Thr Ala Met Ala
    370                 375                 380

Leu Arg Asn Lys Ala Phe Gly Ser Ala Gln Glu Phe Val Trp Ala Gln
385                 390                 395                 400

Asp Ser Ser Glu Tyr Ala Ile Arg Glu Ser Gly Ser Thr Ile Arg Ile
                405                 410                 415

Phe Lys Asn Phe Lys Glu Lys Lys Asn Phe Lys Ser Asp Phe Gly Ala
            420                 425                 430

Glu Gly Ile Tyr Gly Gly Tyr Leu Leu Gly Val Lys Ser Val Ser Gly
        435                 440                 445

Leu Thr Phe Tyr Asp Trp Glu Thr Leu Asp Leu Val Arg Arg Ile Glu
    450                 455                 460

Ile Gln Pro Lys Ala Val Tyr Trp Ser Asp Ser Gly Lys Leu Val Cys
465                 470                 475                 480

Leu Ala Thr Glu Asp Ser Tyr Phe Ile Leu Ser Tyr Asp Ser Asp Glu
                485                 490                 495
```

-continued

```
Val Gln Lys Ala Arg Asp Asn Asn Gln Val Ala Asp Asp Gly Val Glu
            500                 505                 510

Ser Ala Phe Asn Leu Leu Gly Glu Ile Asn Glu Ser Val Arg Thr Gly
        515                 520                 525

Leu Trp Val Gly Asp Cys Phe Ile Tyr Thr Asn Ser Val Asn Arg Ile
    530                 535                 540

Asn Tyr Phe Val Gly Gly Glu Leu Val Thr Ile Ala His Leu Asp Arg
545                 550                 555                 560

Pro Leu Tyr Val Leu Gly Tyr Val Pro Lys Asp Asp Arg Leu Tyr Leu
                565                 570                 575

Val Asp Lys Glu Leu Arg Val Val Ser Tyr Gln Leu Leu Leu Ser Val
            580                 585                 590

Leu Glu Tyr Gln Thr Ala Val Met Arg Arg Asp Phe Pro Thr Ala Asp
        595                 600                 605

Arg Val Leu Pro Ser Ile Pro Lys Glu His Arg Thr Arg Val Ala His
    610                 615                 620

Phe Leu Glu Lys Gln Gly Phe Lys Gln Gln Ala Leu Ala Val Ser Thr
625                 630                 635                 640

Asp Pro Glu His Arg Phe Glu Leu Ala Val Ala Leu Glu Asp Leu Asn
                645                 650                 655

Ile Ala Lys Thr Leu Ala Gln Glu Ala Asn Ser Pro Gln Lys Trp Asn
            660                 665                 670

Gln Leu Ala Glu Leu Ala Ala Ala Thr Asn Asn Val Ser Val Ala Lys
        675                 680                 685

Glu Cys Met Gln Lys Ala Gln Asp Tyr Gly Gly Leu Leu Leu Leu Ala
    690                 695                 700

Thr Ser Ser Gly Asp Glu Asn Leu Val Arg Thr Leu Gly Glu Thr Thr
705                 710                 715                 720

Gln Ala Glu Ser Lys His Asn Leu Ala Phe Leu Ser His Leu Leu Val
                725                 730                 735

Gly Asp Leu Asn Lys Cys Leu Asp Ile Leu Ile Asn Thr Gly Arg Leu
            740                 745                 750

Pro Glu Ala Ala Phe Phe Ala Arg Ser Tyr Leu Pro Asp Lys Ile Thr
        755                 760                 765

Glu Val Val Glu Leu Trp Lys Thr Gln Leu Ser Ser Val Asn Gln Lys
    770                 775                 780

Ala Gly Gln Ser Leu Ala Asp Pro Lys Asn Tyr Glu Asn Leu Phe Pro
785                 790                 795                 800

Gly Leu Gln Glu Ala Val Val Ala Gln Lys Phe Leu Glu Gln Gln Asn
                805                 810                 815

Lys Gly Leu Ala Pro Ala Arg Val Ala Thr Thr Ile Pro Pro Asn His
            820                 825                 830

Asp Arg Asn Val Val Ala Glu Val Gln Ala Gln Ser Lys His Asp Val
        835                 840                 845

Pro Ser Phe Ser Ser Ser Phe Ile Ser Ser Glu Ile Glu Ala Gln Thr
    850                 855                 860

Arg Ser Ser Ala Lys Pro Glu Glu Ser Ser Asn Ile Ile Gln Leu Asp
865                 870                 875                 880

Gln Asp Asp Asp Asp Ile Asp Leu Asp Leu Asp Gly Val Asn Ile Asp
                885                 890                 895

Glu Asn Ile Asp Thr Thr Asp Ile Asn Ile Asp Asp Asp Leu Leu Ser
            900                 905                 910
```

Asp

<210> SEQ ID NO 244
<211> LENGTH: 381
<212> TYPE: PRT
<213> ORGANISM: Diabrotica virgifera

<400> SEQUENCE: 244

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met His Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ser Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Pro Ser Asp Thr Ile Glu Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ser Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Pro Ser Asp Thr Ile Glu Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ser Asp Tyr Asn Ile Gln Lys Glu
        355                 360                 365
```

-continued

```
Ser Thr Leu His Leu Val Leu Arg Leu Arg Gly Gly Asn
    370                 375                 380
```

<210> SEQ ID NO 245
<211> LENGTH: 376
<212> TYPE: PRT
<213> ORGANISM: Diabrotica virgifera

<400> SEQUENCE: 245

```
Met Cys Asp Asp Asp Val Ala Ala Leu Val Val Asp Asn Gly Ser Gly
1               5                   10                  15

Met Cys Lys Ala Gly Phe Ala Gly Asp Asp Ala Pro Arg Ala Val Phe
            20                  25                  30

Pro Ser Ile Val Gly Arg Pro Arg His Gln Gly Val Met Val Gly Met
        35                  40                  45

Gly Gln Lys Asp Ser Tyr Val Gly Asp Glu Ala Gln Ser Lys Arg Gly
    50                  55                  60

Ile Leu Thr Leu Lys Tyr Pro Ile Glu His Gly Ile Ile Thr Asn Trp
65                  70                  75                  80

Asp Asp Met Glu Lys Ile Trp His His Thr Phe Tyr Asn Glu Leu Arg
                85                  90                  95

Val Ala Pro Glu Glu His Pro Ile Leu Leu Thr Glu Ala Pro Leu Asn
            100                 105                 110

Pro Lys Ala Asn Arg Glu Lys Met Thr Gln Ile Met Phe Glu Thr Phe
        115                 120                 125

Asn Thr Pro Ala Met Tyr Val Ala Ile Gln Ala Val Leu Ser Leu Tyr
    130                 135                 140

Ala Ser Gly Arg Thr Thr Gly Ile Val Leu Asp Ser Gly Asp Gly Val
145                 150                 155                 160

Ser His Thr Val Pro Ile Tyr Glu Gly Tyr Ala Leu Pro His Ala Ile
                165                 170                 175

Leu Arg Leu Asp Leu Ala Gly Arg Asp Leu Thr Asp Tyr Leu Met Lys
            180                 185                 190

Ile Leu Thr Glu Arg Gly Tyr Ser Phe Thr Thr Thr Ala Glu Arg Glu
        195                 200                 205

Ile Val Arg Asp Ile Lys Glu Lys Leu Cys Tyr Val Ala Leu Asp Phe
    210                 215                 220

Glu Gln Glu Met Ala Thr Ala Ala Ser Ser Thr Ser Leu Glu Lys Ser
225                 230                 235                 240

Tyr Glu Leu Pro Asp Gly Gln Val Ile Thr Ile Gly Asn Glu Arg Phe
                245                 250                 255

Arg Cys Pro Glu Ala Leu Phe Gln Pro Ser Phe Leu Gly Met Glu Ser
            260                 265                 270

Cys Gly Ile His Glu Thr Val Tyr Asn Ser Ile Met Lys Cys Asp Val
        275                 280                 285

Asp Ile Arg Lys Asp Leu Tyr Ala Asn Thr Val Leu Ser Gly Gly Thr
    290                 295                 300

Thr Met Tyr Pro Gly Ile Ala Asp Arg Met Gln Lys Glu Ile Thr Ala
305                 310                 315                 320

Leu Ala Pro Ser Thr Ile Lys Ile Lys Ile Ile Ala Pro Pro Glu Arg
                325                 330                 335

Lys Tyr Ser Val Trp Ile Gly Gly Ser Ile Leu Ala Ser Leu Ser Thr
            340                 345                 350

Phe Gln Gln Met Trp Ile Ser Lys Gln Glu Tyr Asp Glu Ser Gly Pro
        355                 360                 365
```

Gly Ile Val His Arg Lys Cys Phe
    370                 375

<210> SEQ ID NO 246
<211> LENGTH: 879
<212> TYPE: PRT
<213> ORGANISM: Diabrotica virgifera

<400> SEQUENCE: 246

```
Met Gly Thr Phe Lys Arg Asp Thr His Asp Glu Asp Gly Gly Ser Ser
1               5                   10                  15

Ala Phe Gln Asn Leu Glu Lys Thr Thr Val Leu Gln Glu Ala Arg Val
            20                  25                  30

Phe Asn Glu Thr Ser Val Asn Pro Arg Lys Cys Thr Pro Ile Leu Thr
        35                  40                  45

Lys Leu Leu Tyr Leu Leu Asn Gln Gly Glu Thr Leu Ser Ala Lys Glu
    50                  55                  60

Ala Thr Asp Val Phe Phe Ala Met Thr Lys Leu Phe Gln Ser Lys Asp
65                  70                  75                  80

Val Ile Leu Arg Arg Met Val Tyr Leu Gly Ile Lys Glu Leu Ser Ser
                85                  90                  95

Val Ala Asp Asp Val Ile Ile Val Thr Ser Ser Leu Thr Lys Asp Met
            100                 105                 110

Thr Gly Lys Glu Asp Met Tyr Arg Ala Ala Ala Ile Arg Ala Leu Cys
        115                 120                 125

Ser Ile Thr Asp Ala Thr Met Leu Gln Ala Ile Glu Arg Tyr Met Lys
    130                 135                 140

Gln Ala Ile Val Asp Arg Asn Ala Ala Val Ser Ser Ala Ala Leu Ile
145                 150                 155                 160

Ser Ser Leu His Met Ser Lys Leu Ala Pro Asp Val Val Lys Arg Trp
                165                 170                 175

Val Asn Glu Ala Gln Glu Ala Val Asn Ser Asp Asn Ala Met Val Gln
            180                 185                 190

Tyr His Ala Leu Gly Leu Leu Tyr His Ile Arg Lys Thr Asp Lys Leu
        195                 200                 205

Ala Val Thr Lys Leu Ile Ser Lys Leu Asn Ser Met Gly Leu Lys Ser
    210                 215                 220

Pro Tyr Ala Leu Cys Met Leu Ile Arg Ile Thr Ala Lys Leu Leu Glu
225                 230                 235                 240

Glu Glu Asp Gln Glu Ser Leu Leu Asn Ser Pro Tyr Thr Ile Ile Phe
                245                 250                 255

Thr Met Gly Leu Arg Asn Lys Ser Glu Met Val Val Tyr Glu Ala Ala
            260                 265                 270

His Ala Met Val Asn Leu Lys Phe Thr Ser Ser Asn Val Leu Ala Pro
        275                 280                 285

Ala Ile Ser Val Leu Gln Leu Phe Cys Gly Ser Pro Lys Ala Thr Leu
    290                 295                 300

Arg Phe Ala Ala Val Arg Thr Leu Asn Gln Val Ala Thr Thr His Pro
305                 310                 315                 320

Ala Ser Val Thr Ala Cys Asn Leu Asp Leu Glu Asn Leu Ile Thr Asp
                325                 330                 335

Pro Asn Arg Ser Ile Ala Thr Leu Ala Ile Thr Thr Leu Leu Lys Thr
            340                 345                 350

Gly Ala Glu Ser Ser Val Asp Arg Leu Met Lys Gln Ile Ala Thr Phe
```

```
        355                 360                 365

Val Ser Glu Ile Ser Asp Glu Phe Lys Val Val Val Ile Gln Ala Ile
    370                 375                 380

Lys Val Leu Ala Leu Lys Phe Pro Arg Lys His Ser Thr Leu Met Asn
385                 390                 395                 400

Phe Leu Ser Ala Met Leu Arg Asp Glu Gly Gly Leu Glu Tyr Lys Ala
                405                 410                 415

Ser Ile Ala Asp Thr Ile Ile Thr Leu Ile Glu Asp Asn Pro Glu Ala
            420                 425                 430

Lys Glu Ser Gly Leu Ala His Leu Cys Glu Phe Ile Glu Asp Cys Glu
        435                 440                 445

His Val Ser Leu Ala Val Arg Ile Leu His Leu Leu Gly Lys Glu Gly
    450                 455                 460

Pro Lys Thr Lys Gln Pro Ser Arg Tyr Ile Arg Phe Ile Tyr Asn Arg
465                 470                 475                 480

Val Ile Leu Glu Cys Pro Ser Val Arg Ala Ala Ala Val Ser Ala Met
                485                 490                 495

Ala Gln Phe Gly Ala Ser Cys Pro Asp Leu Leu Glu Asn Ile Gln Ile
            500                 505                 510

Leu Leu Ser Arg Cys Gln Met Asp Ser Asp Asp Glu Val Arg Asp Arg
        515                 520                 525

Ala Thr Tyr Tyr Ser Asn Ile Leu Asn Lys Asn Asp Lys Ser Leu Tyr
    530                 535                 540

Asn Asn Tyr Ile Leu Asp Ser Leu Gln Val Ser Ile Pro Ser Leu Glu
545                 550                 555                 560

Arg Ser Leu Arg Glu Tyr Ile Gln Asn Pro Thr Asp Glu Pro Phe Asp
                565                 570                 575

Ile Lys Ser Val Pro Val Ala Ala Val Pro Thr Ala Glu Glu Arg Glu
            580                 585                 590

Val Lys Asn Lys Ser Glu Gly Leu Leu Val Ser Gln Gly Pro Val Arg
        595                 600                 605

Pro Pro Pro Val Ser Arg Glu Glu Asn Phe Ala Glu Lys Leu Ser Asn
    610                 615                 620

Val Pro Gly Ile Gln Gln Leu Gly Pro Leu Phe Lys Thr Ser Asp Val
625                 630                 635                 640

Val Glu Leu Thr Glu Ser Glu Thr Glu Tyr Phe Val Arg Cys Ile Lys
                645                 650                 655

His Cys Phe Lys His His Ile Val Leu Gln Phe Asp Cys Leu Asn Thr
            660                 665                 670

Leu Pro Asp Gln Leu Leu Glu Asn Val Arg Val Glu Ile Asp Ala Gly
        675                 680                 685

Glu Thr Phe Glu Ile Leu Ala Glu Ile Pro Cys Glu Lys Leu His Tyr
    690                 695                 700

Asn Glu Thr Gly Thr Thr Tyr Val Val Val Lys Leu Pro Asp Asp Asp
705                 710                 715                 720

Leu Pro Asn Ser Val Gly Thr Cys Gly Ala Val Leu Lys Phe Leu Val
                725                 730                 735

Lys Asp Cys Asp Pro Ser Thr Gly Ile Pro Asp Ser Asp Glu Gly Tyr
            740                 745                 750

Asp Asp Glu Tyr Thr Leu Glu Asp Ile Glu Ile Thr Leu Gly Asp Gln
        755                 760                 765

Ile Gln Lys Val Ser Lys Val Asn Trp Ala Ala Ala Trp Glu Glu Ala
    770                 775                 780
```

Ala Ala Thr Tyr Val Glu Lys Glu Asp Thr Tyr Ser Leu Thr Ile Asn
785 790 795 800

Thr Leu Ser Gly Ala Val Lys Asn Ile Ile Gln Phe Leu Gly Leu Gln
805 810 815

Pro Ala Glu Arg Thr Asp Arg Val Pro Glu Gly Lys Ser Thr His Thr
820 825 830

Leu Leu Leu Ala Gly Val Phe Arg Gly Gly Ile Asp Ile Leu Val Arg
835 840 845

Ala Lys Leu Ala Leu Gly Glu Cys Val Thr Met Gln Leu Thr Val Arg
850 855 860

Ser Pro Asp Pro Asp Val Ala Glu Leu Ile Thr Ser Thr Val Gly
865 870 875

<210> SEQ ID NO 247
<211> LENGTH: 216
<212> TYPE: PRT
<213> ORGANISM: Diabrotica virgifera

<400> SEQUENCE: 247

Met Ala Ala Asn Arg Thr Gly Pro Ala Gln Arg Pro Asn Gly Ala Thr
1 5 10 15

Gln Gly Lys Ile Cys Gln Phe Lys Leu Val Leu Leu Gly Glu Ser Ala
20 25 30

Val Gly Lys Ser Ser Leu Val Leu Arg Phe Val Lys Gly Gln Phe His
35 40 45

Glu Tyr Gln Glu Ser Thr Ile Gly Ala Ala Phe Leu Thr Gln Thr Ile
50 55 60

Cys Leu Asp Asp Thr Thr Val Lys Phe Glu Ile Trp Asp Thr Ala Gly
65 70 75 80

Gln Glu Arg Tyr His Ser Leu Ala Pro Met Tyr Tyr Arg Gly Ala Gln
85 90 95

Ala Ala Ile Val Val Tyr Asp Ile Thr Asn Gln Asp Thr Phe Gly Arg
100 105 110

Ala Lys Thr Trp Val Lys Glu Leu Gln Arg Gln Ala Ser Pro Thr Ile
115 120 125

Val Ile Ala Leu Ala Gly Asn Lys Gln Asp Leu Ala Asn Lys Arg Met
130 135 140

Val Glu Tyr Glu Glu Ala Gln Thr Tyr Ala Asp Glu Asn Gly Leu Leu
145 150 155 160

Phe Met Glu Thr Ser Ala Lys Thr Ala Met Asn Val Asn Asp Ile Phe
165 170 175

Leu Ala Ile Ala Lys Lys Leu Pro Lys Asn Glu Gln Thr Thr Gly Gln
180 185 190

Gly Gly Ser Ala Gln Gly Arg Arg Leu Ala Glu Gly Asp Ser Gly Ala
195 200 205

Lys Ala Pro Gly Asn Cys Cys Lys
210 215

<210> SEQ ID NO 248
<211> LENGTH: 92
<212> TYPE: PRT
<213> ORGANISM: Diabrotica virgifera

<400> SEQUENCE: 248

Met Lys Phe Leu Arg Ser Thr Val Cys Tyr Ile Ala Ile Leu Ala Ile
1 5 10 15

```
Leu Phe Thr Leu Cys Ala Asp Glu Val Glu Gly Arg Arg Lys Ile Leu
            20                  25                  30

Met Gly Arg Lys Ser Ile Thr Arg Thr Tyr Leu Arg Gly Asn Ala Val
        35                  40                  45

Pro Ala Tyr Val Ile Ile Ile Leu Val Gly Ile Gly Gln Ile Ile Leu
    50                  55                  60

Gly Gly Ile Leu Tyr Val Ala Leu Arg Lys Lys Ile Ile Ala Ala Pro
65                  70                  75                  80

Val Thr Ala Ser Tyr Ala Val Ala Arg Gln Glu Pro
                85                  90


<210> SEQ ID NO 249
<211> LENGTH: 157
<212> TYPE: PRT
<213> ORGANISM: Diabrotica virgifera

<400> SEQUENCE: 249

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Lys Lys Arg
65                  70                  75                  80

Lys Lys Lys Asn Tyr Ser Thr Pro Lys Lys Ile Lys His Lys Lys Lys
                85                  90                  95

Lys Val Lys Leu Ala Val Leu Lys Phe Tyr Lys Val Asp Glu Asn Gly
            100                 105                 110

Lys Ile His Arg Leu Arg Arg Glu Cys Pro Ala Glu Gln Cys Gly Ala
        115                 120                 125

Gly Val Phe Met Ala Ala Met Glu Asp Arg His Tyr Cys Gly Lys Cys
    130                 135                 140

Gly Tyr Thr Leu Val Phe Ser Lys Pro Gly Asp Glu Lys
145                 150                 155


<210> SEQ ID NO 250
<211> LENGTH: 248
<212> TYPE: PRT
<213> ORGANISM: Diabrotica virgifera

<400> SEQUENCE: 250

Met Met Ser Lys Ala Asp Thr Gln Glu Asp Ala Ser Phe Ala Lys Leu
1               5                   10                  15

Glu Asn Gln Ile Ala Ile Ile Lys Tyr Val Ile Leu Phe Thr Asn Val
            20                  25                  30

Leu Gln Trp Ala Leu Gly Ala Ala Ile Phe Ala Leu Cys Leu Trp Leu
        35                  40                  45

Arg Phe Glu Glu Gly Ile Gln Glu Trp Leu Gln Lys Leu Asp Ser Glu
    50                  55                  60

Gln Phe Tyr Ile Gly Val Tyr Val Leu Ile Val Ala Ser Leu Ile Val
65                  70                  75                  80

Met Ile Val Ser Phe Ile Gly Cys Ile Ser Ala Leu Gln Glu Ser Thr
                85                  90                  95
```

```
Met Ala Leu Leu Val Tyr Ile Gly Thr Gln Val Leu Ser Phe Ile Phe
            100                 105                 110

Gly Leu Ser Gly Ser Ala Val Leu Leu Asp Asn Ser Ala Arg Asp Ser
        115                 120                 125

His Phe Gln Pro Arg Ile Arg Glu Ser Met Arg Arg Leu Ile Met Asn
    130                 135                 140

Ala His His Asp Gln Ser Arg Gln Thr Leu Ala Met Ile Gln Glu Asn
145                 150                 155                 160

Val Gly Cys Cys Gly Ala Asp Gly Ala Thr Asp Tyr Leu Ser Leu Gln
                165                 170                 175

Gln Pro Leu Pro Ser Gln Cys Arg Asp Thr Val Thr Gly Asn Pro Phe
            180                 185                 190

Phe His Gly Cys Val Asp Glu Leu Thr Trp Phe Phe Glu Glu Lys Cys
        195                 200                 205

Gly Trp Ile Ala Gly Leu Ala Met Ala Ile Cys Met Ile Asn Val Leu
    210                 215                 220

Ser Ile Val Leu Ser Thr Val Leu Ile Gln Ala Leu Lys Lys Glu Glu
225                 230                 235                 240

Glu Ala Ser Asp Ser Tyr Arg Arg
                245
```

<210> SEQ ID NO 251
<211> LENGTH: 124
<212> TYPE: PRT
<213> ORGANISM: Diabrotica virgifera

<400> SEQUENCE: 251

```
Met Ser Gly Arg Gly Lys Gly Gly Lys Val Lys Gly Lys Ala Lys Ser
1               5                   10                  15

Arg Ser Asn Arg Ala Gly Leu Gln Phe Pro Val Gly Arg Ile His Arg
            20                  25                  30

Leu Leu Arg Lys Gly Asn Tyr Ala Glu Arg Val Gly Ala Gly Ala Pro
        35                  40                  45

Val Tyr Leu Ala Ala Val Met Glu Tyr Leu Ala Ala Glu Val Leu Glu
    50                  55                  60

Leu Ala Gly Asn Ala Ala Arg Asp Asn Lys Lys Thr Arg Ile Ile Pro
65                  70                  75                  80

Arg His Leu Gln Leu Ala Ile Arg Asn Asp Glu Glu Leu Asn Lys Leu
                85                  90                  95

Leu Ser Gly Val Thr Ile Ala Gln Gly Gly Val Leu Pro Asn Ile Gln
            100                 105                 110

Ala Val Leu Leu Pro Lys Lys Thr Glu Lys Lys Ala
        115                 120
```

<210> SEQ ID NO 252
<211> LENGTH: 288
<212> TYPE: PRT
<213> ORGANISM: Diabrotica virgifera

<400> SEQUENCE: 252

```
Met Lys Leu Asp Gly Val Asp Leu Pro Pro Pro Ile Ser Phe Asp Ile
1               5                   10                  15

Ala Glu Glu Gln Pro Leu Pro Pro Cys Gln Gln Thr Phe Leu Cys Asn
            20                  25                  30

Gly Asp Gly Gly Ser Ile Val Arg Gln Phe Leu Glu Leu Tyr Phe Val
        35                  40                  45
```

```
Ile Tyr Asp Ser Asp Asn Arg Gln Ser Leu Leu Gln Ala Tyr His Glu
    50                  55                  60

Lys Ala Thr Phe Ser Met Thr Met Ala Tyr Pro Tyr Gly Tyr Ser Lys
65                  70                  75                  80

Asp Ser Lys Gly Val Ser Trp Leu Asn Trp Tyr Ala Thr Asp Asn Arg
                85                  90                  95

Asn Leu Leu Arg Val Gln Asp Pro Asp Arg Arg Asn Lys Leu Leu Arg
            100                 105                 110

Gln Gly Gln Val Ala Val Val Ser Phe Leu Gln Asp Met Pro His Thr
        115                 120                 125

Lys His Asp Ile His Ser Phe Thr Val Asp Leu Thr Val Phe Thr Pro
    130                 135                 140

Gln Met Leu Cys Leu Thr Val Ala Gly Met Phe Lys Glu Leu Lys Ser
145                 150                 155                 160

Gly His Lys Val Pro Pro Leu Arg Tyr Phe Phe Arg Thr Leu Val Ile
                165                 170                 175

Val Pro Ala Gly Ser Gly Phe Cys Ile Ala Asn Glu Glu Leu His Ile
            180                 185                 190

Ser Asn Ala Thr Pro Asp Gln Ala Lys Asp Ala Phe Lys Thr Thr Val
        195                 200                 205

Asn Val Ala Pro Ala Pro Ala Pro Val Ile Thr Ser Pro Gly Pro Ser
    210                 215                 220

Ile Pro Gln Pro Ala Val Pro Asp Asp Ala Thr Lys Gln Glu Met Val
225                 230                 235                 240

Lys Gln Met Ser Ala Val Ser Gly Met Asn Leu Glu Trp Ser Leu Gln
                245                 250                 255

Cys Leu Glu Glu Thr Gln Trp Asp Tyr Gln Lys Ala Ile Met Val Phe
            260                 265                 270

Gln Asn Leu Asn Ala Gln Gly Val Val Pro Gln Ala Ala Phe Ile Lys
        275                 280                 285


<210> SEQ ID NO 253
<211> LENGTH: 955
<212> TYPE: PRT
<213> ORGANISM: Diabrotica virgifera

<400> SEQUENCE: 253

Met Thr Ala Val Glu Gln Pro Cys Tyr Thr Leu Ile Asn Leu Pro Thr
1               5                   10                  15

Asp Ser Glu Pro Tyr Asn Glu Met Gln Leu Lys Met Asp Leu Glu Lys
            20                  25                  30

Gly Glu Val Lys Val Lys Ile Arg Ala Leu Glu Lys Ile Ile His Met
        35                  40                  45

Ile Leu Ala Gly Glu Arg Leu Pro Asn Gly Phe Leu Met Thr Ile Ile
    50                  55                  60

Arg Asn Val Leu Pro Leu Gln Asp His Leu Ala Lys Lys Leu Leu Leu
65                  70                  75                  80

Ile Phe Trp Glu Ile Val Pro Lys Thr Asn Pro Glu Gly Lys Leu Leu
                85                  90                  95

Gln Glu Met Ile Leu Val Cys Asp Ala Tyr Arg Lys Asp Leu Gln His
            100                 105                 110

Pro Asn Glu Phe Leu Arg Gly Ser Thr Leu Arg Phe Leu Cys Lys Leu
        115                 120                 125

Lys Glu Pro Glu Leu Leu Glu Pro Leu Met Pro Ser Ile Arg Ala Cys
```

-continued

```
    130                 135                 140

Leu Asp His Arg His Ser Tyr Val Arg Arg Asn Ala Val Leu Ala Ile
145                 150                 155                 160

Phe Thr Ile Tyr Lys Asn Phe Glu Ala Leu Ile Pro Asp Ala Pro Glu
                165                 170                 175

Leu Ile Ser Asn Tyr Leu Asp Gly Glu Gln Asp Met Ser Cys Lys Arg
            180                 185                 190

Asn Ala Phe Leu Met Leu Leu His Ala Asp Gln Glu Arg Ala Leu Ser
        195                 200                 205

Tyr Leu Ala Ser Cys Leu Asp Gln Val Asn Ser Phe Gly Asp Ile Leu
    210                 215                 220

Gln Leu Val Ile Val Glu Leu Ile Tyr Lys Val Cys His Ser Asn Pro
225                 230                 235                 240

Ala Glu Arg Ser Arg Phe Ile Arg Cys Ile Tyr Asn Leu Leu Asn Ser
                245                 250                 255

Ser Ser Pro Ala Val Arg Tyr Glu Ala Ala Gly Thr Leu Val Thr Leu
            260                 265                 270

Ser Ser Ala Pro Thr Ala Val Lys Ala Ala Ala Ser Cys Tyr Ile Glu
        275                 280                 285

Leu Ile Ile Lys Glu Ser Asp Asn Asn Val Lys Leu Ile Val Leu Asp
    290                 295                 300

Arg Leu Ile Ala Leu Lys Glu Leu Pro Asn His Glu Arg Ile Leu Gln
305                 310                 315                 320

Asp Leu Val Met Asp Ile Leu Arg Val Leu Ser Ala Pro Asp Leu Glu
                325                 330                 335

Val Arg Lys Lys Thr Leu Ser Leu Ala Leu Glu Leu Val Ser Ser Arg
            340                 345                 350

Asn Ile Glu Glu Met Val Leu Val Leu Thr Lys Glu Val Ser Lys Thr
        355                 360                 365

Val Asp Ser Glu His Glu Asp Thr Gly Lys Tyr Arg Gln Leu Leu Val
    370                 375                 380

Arg Thr Leu His Ser Cys Ser Ile Lys Phe Pro Asp Ile Ala Arg Ser
385                 390                 395                 400

Val Ile Pro Val Leu Ile Glu Phe Leu Ser Asp Asn Asn Glu Leu Ala
                405                 410                 415

Ala Thr Asp Val Leu Leu Phe Leu Arg Glu Ala Ile Gln Lys Phe Lys
            420                 425                 430

Glu Leu Gln Pro Leu Ile Ile Glu Lys Leu Ile Glu Thr Phe Lys Asp
        435                 440                 445

Ile Lys Leu Val Lys Val His Arg Ala Ala Ile Trp Ile Leu Gly Glu
    450                 455                 460

Tyr Ala Ser Thr Ala Ser Asp Ile Glu Val Ile Val Gly Glu Ile Asn
465                 470                 475                 480

Arg Leu Leu Gly Glu Gly Ser Leu Val Glu Ala Glu Gln Lys Leu Ile
                485                 490                 495

Ala Gly Asp Thr Glu Glu Asn Ala Pro Ala Pro Ala Ala Gly Ala Thr
            500                 505                 510

Thr Leu Val Thr Ser Asp Gly Thr Tyr Ala Thr Gln Ser Ala Phe Asn
        515                 520                 525

Thr Val Ser Gln Thr Thr Lys Glu Ala Arg Pro Pro Leu Arg Gln Tyr
    530                 535                 540

Leu Met Asp Gly Asp Phe Phe Ile Gly Ala Ser Leu Ala Ser Thr Leu
545                 550                 555                 560
```

```
Thr Lys Leu Ser Leu Arg Tyr Glu Asp Leu Thr Ser Pro Ala Ala Ser
                565                 570                 575

Asn Gly Phe Asn Ala Lys Ile Met Leu Ile Met Ala Gly Ile Leu His
            580                 585                 590

Leu Gly Lys Ser Gly Leu Pro Thr Lys Ser Ile Thr Asn Asp Asp Lys
        595                 600                 605

Asp His Ile Leu Phe Cys Leu Arg Val Leu Ser Asp Arg Ser Pro Ile
    610                 615                 620

Ile Val Glu Ile Phe Lys Lys Leu Cys Arg Ser Ala Leu Asn Glu Met
625                 630                 635                 640

Leu Leu Ala Lys Glu Ser Val Glu Ala Ile Ser Gln Lys Ser Lys Glu
                645                 650                 655

Lys Asn Lys Arg Thr Ile Gln Thr Asp Asp Ala Ile Ser Phe Leu Gln
            660                 665                 670

Leu Glu Thr Asp Lys Ser Gly Glu Leu Gly Glu Asn Val Phe Glu Met
        675                 680                 685

Ser Leu Ser Gln Ala Leu Val Gly Gly Arg Thr Gly Gly Gly Glu Ser
    690                 695                 700

Val Leu Ser Ser Asn Lys Leu Asp Lys Ile Thr Gln Leu Thr Gly Phe
705                 710                 715                 720

Ser Asp Pro Val Tyr Ser Glu Ala Tyr Val His Val Asn Gln Tyr Asp
                725                 730                 735

Ile Val Leu Asp Val Leu Ile Val Asn Gln Thr Asn Asp Thr Leu Gln
            740                 745                 750

Asn Cys Thr Leu Glu Leu Ala Thr Leu Gly Asp Leu Lys Leu Val Glu
        755                 760                 765

Lys Pro Gln Pro Val Val Leu Ala Pro Lys Asp Phe Cys Asn Ile Lys
    770                 775                 780

Ala Asn Val Lys Val Ala Ser Thr Glu Asn Gly Ile Ile Phe Gly Asn
785                 790                 795                 800

Ile Val Tyr Asp Val Ile Gly Ala Gly Ser Asp Arg Asn Val Val Val
                805                 810                 815

Leu Asn Asp Ile His Ile Asp Ile Met Asp Tyr Ile Val Pro Ala Ser
            820                 825                 830

Cys Thr Asp Ser Glu Phe Met Arg Met Trp Ala Glu Phe Glu Trp Glu
        835                 840                 845

Asn Lys Val Thr Val Asn Thr Pro Leu Thr Glu Leu Ser Glu Tyr Leu
    850                 855                 860

Glu His Leu Leu Lys Ser Thr Asn Leu Lys Cys Leu Thr Ser Glu Lys
865                 870                 875                 880

Ala Leu Ser Gly Gln Cys Gly Phe Met Ala Ala Asn Leu Tyr Ala Lys
                885                 890                 895

Ser Ile Phe Gly Glu Asp Ala Leu Ala Asn Leu Ser Ile Glu Lys Pro
            900                 905                 910

Phe Asn Lys Pro Asp Ala Pro Val Ser Gly His Ile Arg Ile Arg Ala
        915                 920                 925

Lys Ser Gln Gly Met Ala Leu Ser Leu Gly Asp Lys Val Asn Met Thr
    930                 935                 940

Gln Lys Ser Thr Gln His Lys Val Val Ala Ala
945                 950                 955
```

<210> SEQ ID NO 254
<211> LENGTH: 447

<212> TYPE: PRT
<213> ORGANISM: Diabrotica virgifera

<400> SEQUENCE: 254

```
Met Val Tyr Pro Asn Ser Pro Phe Lys Thr Thr Phe Asn Asn Lys Leu
1               5                   10                  15

Ile Thr Asn Leu Phe Leu Asp Asp Ser Val Thr Lys Thr Lys Thr Ser
            20                  25                  30

Val Ser Asn Glu Glu Leu Leu Lys Ile Gln Gln Trp Leu Cys Ser Ala
        35                  40                  45

Pro Lys Ile Thr Ser Ile Arg Val Asn Thr Ile Lys Thr Asn Thr Ala
    50                  55                  60

Lys Val Leu Lys Val Leu Lys Thr Tyr Phe Ala Glu Asn Cys Asn Asp
65                  70                  75                  80

Thr Pro Asn Val Tyr Ile His Pro Ser Phe Thr Asn Val Ile Ile Ile
                85                  90                  95

Asp Ser Leu Asn Cys Pro Ala Gly Phe Lys Lys Phe Asp Lys Glu Ile
            100                 105                 110

Ile Val Asp Thr Asp Cys Ala Ala Ala Ile Leu Arg Gly Ala His Ile
        115                 120                 125

Phe Ala Pro Gly Val Leu Gly Met Val Ser Gly Cys Gln Ile Asn Glu
    130                 135                 140

Asn Val Ser Ile Tyr Ala Asp Val Ala Lys Lys Cys Lys Lys Gly Leu
145                 150                 155                 160

Gln Lys Ile Tyr Glu Asp Asp Phe Lys Ile Phe Ile Gly Asn Gly Ile
                165                 170                 175

Val Lys Met Gln Arg His Gln Leu Phe Ala Thr Asp Asn Ile Ala Pro
            180                 185                 190

Ser Gly Ile Ala Val Glu Val Thr Glu Thr Ile Ser Gly Cys Val Pro
        195                 200                 205

Ile Ser Glu Ser Leu Leu Pro Val Gly Asp Ile Leu Leu Gln Asn Ile
    210                 215                 220

Pro Ser Ile Val Cys Val His Asn Leu Asn Pro Lys Pro Gly Asp Val
225                 230                 235                 240

Val Leu Asp Met Cys Ala Ser Pro Gly Asn Lys Thr Thr His Ile Ala
                245                 250                 255

Glu Leu Met Gln Asn Lys Gly Ile Leu Ile Ala Ile Asp Lys Thr Pro
            260                 265                 270

Lys Lys Val Ala Gln Leu Gln Lys Arg Cys Glu Asp Phe Gly Ala Lys
        275                 280                 285

Val Tyr Ser Phe Gln Ala Asp Ser Thr Ala Ile Ile Ser Asp Thr Leu
    290                 295                 300

Ser Ser Lys Asn Val Ile Asp Gly Pro Pro Phe Ala Pro Gln Ser Phe
305                 310                 315                 320

Asp Lys Ile Leu Leu Asp Ala Pro Cys Ser Val Leu Gly Lys Arg Pro
                325                 330                 335

Gln Leu Ala Asn Arg Ser Ser Glu Asn Glu Ile Lys Ser Phe Val Pro
            340                 345                 350

Leu Gln Arg Lys Leu Phe Glu Asn Ala Ala Lys Leu Leu Lys Pro Gly
        355                 360                 365

Gly Ile Met Val Tyr Ser Thr Cys Thr Ile Thr Leu Ser Glu Asn Glu
    370                 375                 380

Gly Ile Val Ala Trp Ala Leu Lys Ser Phe Asn Phe Leu Glu Leu Val
385                 390                 395                 400
```

```
Gln Pro Asp Leu Thr Leu Gly Glu Pro Gly Trp Leu Gly Thr Ser Leu
                405                 410                 415

Ser Asp Glu Ala Arg Ser Phe Val Gln Arg Phe Gly Pro Asn Ser Glu
            420                 425                 430

Val Asp Ser Val Gly Phe Phe Phe Ala Val Phe Lys Lys Lys Thr
        435                 440                 445


<210> SEQ ID NO 255
<211> LENGTH: 1474
<212> TYPE: PRT
<213> ORGANISM: Diabrotica virgifera

<400> SEQUENCE: 255

Met Gly Arg Leu His Cys Leu Phe Cys Ile Phe Leu Cys Phe Thr Val
1               5                   10                  15

Ile Asn Thr Gln Thr Thr Asn Ile His Gly Phe Ser Glu Asn Ser Val
            20                  25                  30

Asp Thr Phe Leu Ser Pro His Gly Lys Ser Ala Lys Phe Val His Gln
        35                  40                  45

Asn His Lys Pro Lys Ile Glu Asn Cys Gln Asn Tyr Lys Pro Ser Val
    50                  55                  60

Lys Glu Glu Gln Pro Gly Gly Thr Tyr Val Thr Thr Val Thr Ala Ile
65                  70                  75                  80

Asp Asp Asp Pro Arg Glu Gly Gly Gly Thr Ile Ser Tyr Lys Leu Ile
                85                  90                  95

His Arg Glu Gly Glu His Val Leu Phe Asp Ile Asp Asn Val Thr Gly
            100                 105                 110

Val Leu Thr Thr Ile Gln Pro Phe Asp Arg Asp Glu Pro Val Arg Gln
        115                 120                 125

Lys Glu Leu Tyr Val Thr Val Gln Ala Ser Asp Asn Gly Arg Pro Pro
    130                 135                 140

Leu Ala Asp Val Cys Thr Phe Thr Val Thr Ile Thr Asp Ile Asn Asp
145                 150                 155                 160

Asn Ala Pro Gln Leu Asp Lys Leu Lys Tyr Asp Ala Gln Val Ser Glu
                165                 170                 175

Asp Leu Lys Val Gly Ser Glu Val Met Arg Val Phe Ala Tyr Asp Ile
            180                 185                 190

Asp Asp Gly Glu Asn Ser Arg Leu Ser Tyr Asn Phe Ser Asn Glu Asn
        195                 200                 205

Ala Gln Phe Thr Gln Tyr Phe Arg Ile Asp Arg Asp Thr Gly Val Val
    210                 215                 220

Tyr Leu Lys Glu Ala Leu Thr Asp Lys Lys Asn Thr Arg Phe Asn Ser
225                 230                 235                 240

Ala Val Tyr Val Ala Asp Asn Gly Val Asn Asp Gln Glu Gly Gln Lys
                245                 250                 255

Asp Ser Thr Ala Lys Ile Ser Ile Thr Val Val Gly Ser Asp Lys Gln
            260                 265                 270

Pro Pro Arg Phe Thr Gln Lys Met Pro Asp Gly Ile Leu Glu Ile Pro
        275                 280                 285

Glu Asp Phe Lys Asp Phe Ser Lys His Ile Val Thr Val Glu Ala Thr
    290                 295                 300

Ser Asn Ile Ala Asp Pro Gln Leu Ala Phe Glu Leu Val Lys Gly Lys
305                 310                 315                 320

Thr Tyr Gln Thr Asn Lys Asp Gln Thr Phe Leu Leu Glu Ala Glu Gly
```

-continued

```
                325                 330                 335

Asn Lys Ala His Ile Lys Leu Val Arg Pro Leu Asp Tyr Glu Thr Val
            340                 345                 350

Thr Glu Tyr Thr Leu Thr Ile Arg Val Lys Asn Lys Asp Leu Met Asp
        355                 360                 365

Ser Ser Ile Asn Ile Pro Ile Lys Val Leu Asp Val Asn Asp Glu Ile
    370                 375                 380

Pro Asn Phe Leu Glu Phe Leu Lys Gly Ser Val Val Glu Asn Asp Lys
385                 390                 395                 400

Pro Gly Ala Gln Ala Ile Gln Val Arg Ala Ile Asp Lys Asp Gly Thr
                405                 410                 415

Ala Ala Asn Asn Ile Val Ser Tyr Glu Leu Val Asp Asn Thr Asp Leu
            420                 425                 430

Phe Ala Ile Asn Arg Ser Thr Gly Val Ile Thr Ser Arg Val Glu Phe
        435                 440                 445

Asp Arg Glu Thr Val Pro Leu Tyr His Val Asn Val Lys Ala Tyr Asp
    450                 455                 460

Asn Ser Pro Ser Ala Leu Tyr Asn Thr Thr Leu Pro Asn Ile Val Ile
465                 470                 475                 480

Gln Thr Phe Gln Ile Ser Ile Glu Asp Gln Asn Asp Asn Lys Pro Val
                485                 490                 495

Phe Thr His Pro Ile Tyr Gln Phe Ser Asn Ile Thr Glu Leu Ala Asp
            500                 505                 510

Lys Ser Ser Ile Val Gly Glu Val Lys Ala Leu Asp Asn Asp Thr Ala
        515                 520                 525

Ser Val Ile Ser Tyr Ser Ile Thr Asn Gly Asn Ile Asp Asp Ala Phe
    530                 535                 540

Met Ile Glu Asn Ser Thr Gly Arg Ile Arg Val Asn Gly Lys Leu Asp
545                 550                 555                 560

Tyr Glu Lys Ile Glu Gln Tyr Asn Leu Thr Val Arg Ala Phe Asp Gly
                565                 570                 575

Ala Phe Glu Asp Phe Ala Ile Val Leu Ile Ser Ile Leu Asn Glu Asn
            580                 585                 590

Asp Glu Pro Pro Val Phe Asp Asp Tyr Ile Arg Glu Ile Gln Ile Lys
        595                 600                 605

Glu Glu Glu Pro Met Ile Ser Gly Cys Val Val Arg Val Thr Ala His
    610                 615                 620

Asp Pro Asp Ile Lys Asp Arg His Ala Asp Gln His Ile Val Tyr Glu
625                 630                 635                 640

Val Ala Lys Glu Gln Lys Asp Phe Leu Thr Val Ser Ala Asp Gly Cys
                645                 650                 655

Val Gln Val Thr Lys Pro Leu Asp Arg Asp Pro Pro Phe Gly Ser Pro
            660                 665                 670

Thr Arg Gln Val Phe Ile Tyr Ala Arg Asp Asn Asp Gly Gly Thr Asn
        675                 680                 685

Ser Leu Leu Ala Thr Ala Glu Ile Glu Ile Ile Leu Ile Asp Ile Asn
    690                 695                 700

Asp Asn Ala Pro Phe Leu Asn Val Thr Glu Ile Val Tyr Tyr Glu Asn
705                 710                 715                 720

Gln Asp Pro Gly Phe Ile Gly Asn Leu Ser Ala Asp Asp Tyr Asp Gly
                725                 730                 735

Pro Asp Asn Gly Pro Pro Phe Ala Phe Arg Leu Ser Asp Thr Ala Ser
            740                 745                 750
```

```
Asp Ser Ile Arg Ser Lys Phe Ser Ile Ile Gly Asn Gln Leu Phe Ala
        755                 760                 765

Leu Glu Met Phe Asp Arg Glu Glu Gln Lys Tyr Tyr Asp Ile Ala Ile
    770                 775                 780

Asp Ile Thr Asp Ser Gly Val Pro Pro Leu Thr Gly Thr Ser Ile Leu
785                 790                 795                 800

Arg Val Ile Ile Gly Asp Val Asn Asp Asn Pro Ala Thr Asp Gly Asn
                805                 810                 815

Ser Thr Ile Phe Val Tyr Lys Tyr Val Asn Gly Pro Glu Asn Phe Met
            820                 825                 830

Glu Ile Gly Arg Val Tyr Val Thr Asp Leu Asp Asp Trp Asp Leu Asn
        835                 840                 845

Asp Lys Val Phe Val Gln Glu Asp Asn Phe Asp Glu Phe Val Leu Asn
    850                 855                 860

Gln His Asn Asn Gly Met Ile Leu Met Lys Pro Thr Thr Ala Glu Gly
865                 870                 875                 880

Thr Tyr Glu Val His Tyr Arg Val Thr Glu Thr His Glu Pro Thr Ile
                885                 890                 895

His Glu His Thr Val Asn Ala Ile Val Thr Ile Thr Val Lys Val Leu
            900                 905                 910

Pro Glu Glu Ala Val Val Lys Ser Gly Ser Ile Arg Leu Arg Gly Thr
        915                 920                 925

Thr Lys Glu Glu Phe Ile Glu Asn Ser Leu Asn Gly Lys Ser Lys Arg
    930                 935                 940

Asp Ile Leu His Gln Glu Leu Ser Lys Ile Leu Asn Thr Ser Leu Ala
945                 950                 955                 960

Asn Val Asp Val Phe Thr Val Leu Asn Ser Pro His Gln Asn Ser Ser
                965                 970                 975

Phe Val Asp Val Arg Phe Ser Ala His Gly Ser Pro Tyr Tyr Ala Pro
            980                 985                 990

Glu Lys Leu Glu Asn Lys Val Thr  Asp His Gln Met Glu  Leu Glu Gln
        995                 1000                 1005

Lys Leu  Asp Val Glu Phe Tyr  Met Ile Asn Val Asn  Glu Cys Leu
    1010                 1015                 1020

Asn Glu  Thr Thr Cys Gly Ala  Glu Asn Ser Cys Thr  Asn Lys Leu
    1025                 1030                 1035

Asn Ile  Thr Arg Glu Pro Ala  Val Val Phe Thr Asn  Arg Thr Ser
    1040                 1045                 1050

Phe Val  Gly Val Asn Ala Phe  Ile Asp Pro Val Cys  Ala Ala Leu
    1055                 1060                 1065

Pro Arg  Asp Val Met Glu Cys  Phe Asn Gly Gly Val  Leu Ile Glu
    1070                 1075                 1080

Asn Thr  Ala Cys Asn Cys Pro  Ala Gly Phe Glu Gly  Pro His Cys
    1085                 1090                 1095

Glu Ile  Leu Ala Ile Gly Phe  Thr Gly Thr Gly Trp  Ala Met Tyr
    1100                 1105                 1110

Pro Ser  Phe Asp Ala Thr Asn  Arg Thr Glu Ile Ile  Leu His Ile
    1115                 1120                 1125

Leu Ser  Gln Thr Asp Asn Gly  Leu Ile Phe Tyr Asn  Gly Pro Leu
    1130                 1135                 1140

Asn Ile  Arg Gln Thr Ser Leu  Ser Lys Asp Tyr Ile  Ser Leu Glu
    1145                 1150                 1155
```

Leu Lys Asp Gly Tyr Pro Leu Leu Gln Ile Cys Thr Gly Ser Ser
1160 1165 1170

Thr Gln Glu Ile Tyr Leu Lys Glu Arg Ile His Lys Leu Ser Asp
1175 1180 1185

Gly Ser Leu His Lys Ile Lys Ile Gly Ser Gly Phe Asp Asp Ile
1190 1195 1200

Ser Leu Glu Val Asp Asp Cys Gly Thr Thr Cys Ser Ile Trp Thr
1205 1210 1215

Asn Lys Leu His Lys Gly Val Ile Arg Ala Asn Gly Pro Leu Gln
1220 1225 1230

Leu Gly Gly Met Lys Asn Arg Phe Thr Asp Gln Glu Phe Lys Arg
1235 1240 1245

Ile Trp Asp His Leu Pro Pro Thr Ala Thr Arg Phe Ser Gly Cys
1250 1255 1260

Ile Arg Asn Leu Thr Tyr Asn Glu Phe Tyr Tyr Asn Leu Gly Ala
1265 1270 1275

Pro Ser Asp Ala Phe Gln Ala Tyr Pro Asp Cys Asn Tyr Ala Val
1280 1285 1290

Met Gln Ala Val Thr Phe Gly Ile Asp Ser Asn Phe Leu Val Ala
1295 1300 1305

Ile Leu Val Cys Val Ala Ile Leu Ile Ile Leu Leu Leu Ala Val
1310 1315 1320

Val Val His Arg Arg Lys His Asp Asn Phe Asn Glu Lys Glu Ile
1325 1330 1335

Asp Asp Thr Arg Glu Asn Ile Ile Asn Tyr Glu Asp Glu Gly Gly
1340 1345 1350

Gly Glu Cys Asp Thr Asn Tyr Asp Leu Ser Val Phe His Gln Asn
1355 1360 1365

Asn Ile Val Asp Glu Lys Pro Leu Met Arg Asp Asn Pro Asp Val
1370 1375 1380

Pro Ala Asp Ile Ser Gly Phe Leu Asp Asn Lys Lys Asp Asn Cys
1385 1390 1395

Asp Lys Asp Pro Asp Asn Leu Pro Tyr Asp Asp Val Arg His Tyr
1400 1405 1410

Ala Tyr Glu Gly Asp Gly Asn Ser Thr Gly Ser Leu Ser Ser Leu
1415 1420 1425

Ala Ser Cys Thr Asp Glu Gly Asp Leu Lys Phe Asn Tyr Leu Ser
1430 1435 1440

Ser Phe Gly Pro Arg Phe Arg Lys Leu Ala Asp Met Tyr Gly Glu
1445 1450 1455

Asp Pro Ser Asp Glu Asp Ser His Asp Gly Asn Glu Glu Ser Trp
1460 1465 1470

Cys

<210> SEQ ID NO 256
<211> LENGTH: 96
<212> TYPE: PRT
<213> ORGANISM: Diabrotica virgifera

<400> SEQUENCE: 256

Met Pro Phe Cys Gly Pro Lys Leu Ser Leu Cys Gly Leu Ile Ile Ser
1 5 10 15

Ala Trp Gly Ile Ile Gln Leu Gly Phe Met Gly Val Phe Tyr Tyr Ile
20 25 30

```
Gly Ala Val Ala Leu Ala Glu Asp Ile Pro Glu Val Glu Phe Lys Gly
        35                  40                  45

Asp Leu Asp Lys Phe Tyr Ser Asp Val Asn Thr Gly Phe Thr Gln Asn
    50                  55                  60

Ala Tyr Asn Cys Trp Ile Ala Ala Leu Leu Tyr Leu Ile Thr Leu Ala
65                  70                  75                  80

Val Ser Ala His Gln Phe Trp Ala Asn Asn Arg Ser Ser Leu Asn Val
                85                  90                  95


<210> SEQ ID NO 257
<211> LENGTH: 179
<212> TYPE: PRT
<213> ORGANISM: Diabrotica virgifera

<400> SEQUENCE: 257

Met Gly Leu Thr Ile Ser Ala Val Phe Asn Arg Leu Phe Ser Lys Lys
1               5                   10                  15

Pro Met Arg Ile Leu Met Val Gly Leu Asp Ala Ala Gly Lys Thr Thr
            20                  25                  30

Ile Leu Tyr Lys Leu Lys Leu Gly Glu Ile Val Thr Thr Ile Pro Thr
        35                  40                  45

Ile Gly Phe Asn Val Glu Thr Val Glu Tyr Lys Asn Ile Ser Phe Thr
    50                  55                  60

Val Trp Asp Val Gly Gly Gln Thr Arg Ile Arg Lys Leu Trp Arg His
65                  70                  75                  80

Tyr Phe Ala Asn Thr Asp Gly Leu Ile Phe Val Val Asp Ser Asn Asp
                85                  90                  95

Arg Asp Arg Ile Ala Glu Ala Glu Glu Glu Leu His Asn Met Leu Gly
            100                 105                 110

Glu Asp Asp Leu Arg Asp Cys Ile Leu Leu Ile Phe Ala Asn Lys Gln
        115                 120                 125

Asp Leu Pro Asn Ser Met Ser Thr Ala Glu Leu Thr Asp Lys Leu Lys
    130                 135                 140

Leu His Thr Leu Lys Asn Arg Arg Trp Tyr Ile Gln Ala Thr Cys Ala
145                 150                 155                 160

Thr Gln Gly Asn Gly Leu Tyr Glu Gly Leu Asp Trp Leu Ser Asn Glu
                165                 170                 175

Leu Ala Lys


<210> SEQ ID NO 258
<211> LENGTH: 205
<212> TYPE: PRT
<213> ORGANISM: Diabrotica virgifera

<400> SEQUENCE: 258

Met Arg Tyr Thr Leu Ser Tyr Ile Gly Ala Thr Leu Ala Ser Thr Val
1               5                   10                  15

Thr Leu Ile Phe Ala Leu Tyr Tyr Cys Leu Thr Gly Lys Gly Glu Gln
            20                  25                  30

Val Ser Leu Ala Trp Leu Leu Leu Asn Val Ser Pro His Met Trp Ala
        35                  40                  45

Gly Leu Gly Ile Gly Leu Ala Val Ser Leu Ser Val Val Gly Ala Ala
    50                  55                  60

Ala Gly Ile His Thr Thr Gly Val Ser Ile Val Gly Ala Gly Val Lys
65                  70                  75                  80

Ala Pro Arg Ile Lys Thr Lys Asn Leu Ile Ser Ile Ile Phe Cys Glu
```

```
                85                  90                  95

Ala Val Ala Ile Tyr Gly Leu Ile Met Ala Ile Val Leu Cys Gly Ser
            100                 105                 110

Trp Lys Asn Phe Asp Val Asp Leu Phe Asn Leu Lys Thr His Asn Phe
        115                 120                 125

Ala Gln Asn His Tyr Gly Ser His Val Ile Phe Gly Ser Gly Leu Thr
    130                 135                 140

Val Gly Phe Val Asn Leu Leu Cys Gly Phe Cys Val Gly Val Val Gly
145                 150                 155                 160

Ser Gly Ala Ala Ile Ser Asp Ala Ala Asn Ser Ser Leu Phe Val Lys
                165                 170                 175

Ile Leu Ile Ile Glu Ile Phe Gly Ser Ala Ile Gly Leu Phe Gly Leu
            180                 185                 190

Ile Val Gly Val Tyr Leu Thr Ser Arg Gly Ser Met Val
        195                 200                 205


<210> SEQ ID NO 259
<211> LENGTH: 1897
<212> TYPE: PRT
<213> ORGANISM: Diabrotica virgifera

<400> SEQUENCE: 259

Met Ala Thr Asn Asp Ser Lys Ala Pro Leu Arg Thr Val Lys Arg Val
1               5                   10                  15

Gln Phe Gly Ile Leu Ser Pro Asp Glu Ile Arg Arg Met Ser Val Thr
            20                  25                  30

Glu Gly Gly Ile Arg Phe Pro Glu Thr Met Glu Ala Gly Arg Pro Lys
        35                  40                  45

Leu Cys Gly Leu Met Asp Pro Arg Gln Gly Val Ile Asp Arg Ser Ser
    50                  55                  60

Arg Cys Gln Thr Cys Ala Gly Asn Met Thr Glu Cys Pro Gly His Phe
65                  70                  75                  80

Gly His Ile Glu Leu Ala Lys Pro Val Phe His Val Gly Phe Val Thr
                85                  90                  95

Lys Thr Ile Lys Ile Leu Arg Cys Val Cys Phe Phe Cys Ser Lys Leu
            100                 105                 110

Leu Val Ser Pro Asn Asn Pro Lys Ile Lys Glu Val Val Met Lys Ser
        115                 120                 125

Lys Gly Gln Pro Arg Lys Arg Leu Ala Phe Val Tyr Asp Leu Cys Lys
    130                 135                 140

Gly Lys Asn Ile Cys Glu Gly Gly Asp Glu Met Asp Val Gly Lys Glu
145                 150                 155                 160

Ser Glu Asp Pro Asn Lys Lys Ala Gly His Gly Gly Cys Gly Arg Tyr
                165                 170                 175

Gln Pro Asn Ile Arg Arg Ala Gly Leu Asp Leu Thr Ala Glu Trp Lys
            180                 185                 190

His Val Asn Glu Asp Thr Gln Glu Lys Lys Ile Ala Leu Ser Ala Glu
        195                 200                 205

Arg Val Trp Glu Ile Leu Lys His Ile Thr Asp Glu Glu Cys Phe Ile
    210                 215                 220

Leu Gly Met Asp Pro Lys Phe Ala Arg Pro Asp Trp Met Ile Val Thr
225                 230                 235                 240

Val Leu Pro Val Pro Pro Leu Ala Val Arg Pro Ala Val Val Met His
                245                 250                 255
```

```
Gly Ser Ala Arg Asn Gln Asp Asp Ile Thr His Lys Leu Ala Asp Ile
            260                 265                 270

Ile Lys Ala Asn Asn Glu Leu Gln Lys Asn Glu Ser Ala Gly Ala Ala
        275                 280                 285

Ala His Ile Ile Thr Glu Asn Ile Lys Met Leu Gln Phe His Val Ala
    290                 295                 300

Thr Leu Val Asp Asn Asp Met Pro Gly Met Pro Arg Ala Met Gln Lys
305                 310                 315                 320

Ser Gly Lys Pro Leu Lys Ala Ile Lys Ala Arg Leu Lys Gly Lys Glu
                325                 330                 335

Gly Arg Ile Arg Gly Asn Leu Met Gly Lys Arg Val Asp Phe Ser Ala
            340                 345                 350

Arg Thr Val Ile Thr Pro Asp Pro Asn Leu Arg Ile Asp Gln Val Gly
        355                 360                 365

Val Pro Arg Ser Ile Ala Gln Asn Met Thr Phe Pro Glu Ile Val Thr
    370                 375                 380

Pro Phe Asn Phe Asp Lys Met Leu Glu Leu Val Gln Arg Gly Asn Ser
385                 390                 395                 400

Gln Tyr Pro Gly Ala Lys Tyr Ile Ile Arg Asp Asn Gly Glu Arg Ile
                405                 410                 415

Asp Leu Arg Phe His Pro Lys Pro Ser Asp Leu His Leu Gln Cys Gly
            420                 425                 430

Tyr Lys Val Glu Arg His Ile Arg Asp Gly Asp Leu Val Ile Phe Asn
        435                 440                 445

Arg Gln Pro Thr Leu His Lys Met Ser Met Met Gly His Arg Val Lys
    450                 455                 460

Val Leu Pro Trp Ser Thr Phe Arg Met Asn Leu Ser Cys Thr Ser Pro
465                 470                 475                 480

Tyr Asn Ala Asp Phe Asp Gly Asp Glu Met Asn Leu His Val Pro Gln
                485                 490                 495

Ser Met Glu Thr Arg Ala Glu Val Glu Asn Leu His Ile Thr Pro Arg
            500                 505                 510

Gln Ile Ile Thr Pro Gln Ala Asn Gln Pro Val Met Gly Ile Val Gln
        515                 520                 525

Asp Thr Leu Thr Ala Val Arg Lys Met Thr Lys Arg Asp Val Phe Ile
    530                 535                 540

Glu Lys Glu Gln Met Met Asn Ile Leu Met Phe Leu Pro Ile Trp Asp
545                 550                 555                 560

Gly Lys Met Pro Arg Pro Ala Ile Leu Lys Pro Lys Pro Leu Trp Thr
                565                 570                 575

Gly Lys Gln Ile Phe Ser Leu Ile Ile Pro Gly Asn Val Asn Met Ile
            580                 585                 590

Arg Thr His Ser Thr His Pro Asp Asp Glu Asp Asp Gly Pro Tyr Lys
        595                 600                 605

Trp Ile Ser Pro Gly Asp Thr Lys Val Met Val Glu His Gly Glu Leu
    610                 615                 620

Val Met Gly Ile Leu Cys Lys Lys Ser Leu Gly Thr Ser Ala Gly Ser
625                 630                 635                 640

Leu Leu His Ile Cys Met Leu Glu Leu Gly His Glu Val Cys Gly Arg
                645                 650                 655

Phe Tyr Gly Asn Ile Gln Thr Val Ile Asn Asn Trp Leu Leu Leu Glu
            660                 665                 670

Gly His Ser Ile Gly Ile Gly Asp Thr Ile Ala Asp Pro Gln Thr Tyr
```

-continued

```
        675                 680                 685

Thr Glu Ile Gln Arg Ala Ile Arg Lys Ala Lys Glu Asp Val Ile Glu
    690                 695                 700

Val Ile Gln Lys Ala His Asn Met Glu Leu Glu Pro Thr Pro Gly Asn
705                 710                 715                 720

Thr Leu Arg Gln Thr Phe Glu Asn Gln Val Asn Arg Ile Leu Asn Asp
                725                 730                 735

Ala Arg Asp Lys Thr Gly Gly Ser Ala Lys Lys Ser Leu Thr Glu Tyr
            740                 745                 750

Asn Asn Leu Lys Ala Met Val Val Ser Gly Ser Lys Gly Ser Asn Ile
        755                 760                 765

Asn Ile Ser Gln Val Ile Ala Cys Val Gly Gln Gln Asn Val Glu Gly
    770                 775                 780

Lys Arg Ile Pro Phe Gly Phe Arg Lys Arg Thr Leu Pro His Phe Ile
785                 790                 795                 800

Lys Asp Asp Tyr Gly Pro Glu Ser Arg Gly Phe Val Glu Asn Ser Tyr
                805                 810                 815

Leu Ala Gly Leu Thr Pro Ser Glu Phe Tyr Phe His Ala Met Gly Gly
            820                 825                 830

Arg Glu Gly Leu Ile Asp Thr Ala Val Lys Thr Ala Glu Thr Gly Tyr
        835                 840                 845

Ile Gln Arg Arg Leu Ile Lys Ala Met Glu Ser Val Met Val His Tyr
    850                 855                 860

Asp Gly Thr Val Arg Asn Ser Val Gly Gln Leu Ile Gln Leu Arg Tyr
865                 870                 875                 880

Gly Glu Asp Gly Leu Cys Gly Glu Met Val Glu Phe Gln Tyr Leu Ala
                885                 890                 895

Thr Val Lys Leu Ser Asn Lys Ala Phe Glu Arg Lys Phe Arg Phe Asp
            900                 905                 910

Pro Ser Asn Glu Arg Tyr Leu Arg Arg Val Phe Asn Glu Glu Val Ile
        915                 920                 925

Lys Gln Leu Met Gly Ser Gly Glu Val Ile Ser Glu Leu Glu Arg Glu
    930                 935                 940

Trp Glu Gln Leu Gln Lys Asp Arg Glu Ala Leu Arg Gln Ile Phe Pro
945                 950                 955                 960

Ser Gly Glu Ser Lys Val Val Leu Pro Cys Asn Leu Gln Arg Met Ile
                965                 970                 975

Trp Asn Val Gln Lys Ile Phe His Ile Asn Lys Arg Ala Pro Thr Asp
            980                 985                 990

Leu Ser Pro Leu Arg Val Ile Gln  Gly Val Arg Glu Leu  Leu Arg Lys
        995                 1000                1005

Cys Val  Ile Val Ala Gly Glu  Asp Arg Leu Ser Lys  Gln Ala Asn
    1010                1015                1020

Glu Asn  Ala Thr Leu Leu Phe  Gln Cys Leu Val Arg  Ser Thr Leu
    1025                1030                1035

Cys Thr  Lys Cys Val Ser Glu  Glu Phe Arg Leu Ser  Thr Glu Ala
    1040                1045                1050

Phe Glu  Trp Leu Ile Gly Glu  Ile Glu Thr Arg Phe  Gln Gln Ala
    1055                1060                1065

Gln Ala  Asn Pro Gly Glu Met  Val Gly Ala Leu Ala  Ala Gln Ser
    1070                1075                1080

Leu Gly  Glu Pro Ala Thr Gln  Met Thr Leu Asn Thr  Phe His Phe
    1085                1090                1095
```

```
Ala Gly  Val Ser Ser Lys Asn  Val Thr Leu Gly Val  Pro Arg Leu
    1100                 1105                 1110

Lys Glu  Ile Ile Asn Ile Ser  Lys Lys Pro Lys Ala  Pro Ser Leu
    1115                 1120                 1125

Thr Val  Phe Leu Thr Gly Ala  Ala Ala Arg Asp Ala  Glu Lys Ala
    1130                 1135                 1140

Lys Asn  Val Leu Cys Arg Leu  Glu His Thr Thr Leu  Arg Lys Val
    1145                 1150                 1155

Thr Ala  Asn Thr Ala Ile Tyr  Tyr Asp Pro Asp Pro  Gln Asn Thr
    1160                 1165                 1170

Val Ile  Pro Glu Asp Gln Glu  Phe Val Asn Val Tyr  Tyr Glu Met
    1175                 1180                 1185

Pro Asp  Phe Asp Pro Thr Arg  Ile Ser Pro Trp Leu  Leu Arg Ile
    1190                 1195                 1200

Glu Leu  Asp Arg Lys Arg Met  Thr Asp Lys Lys Leu  Thr Met Glu
    1205                 1210                 1215

Gln Ile  Ala Glu Lys Ile Asn  Ala Gly Phe Gly Asp  Asp Leu Asn
    1220                 1225                 1230

Cys Ile  Phe Asn Asp Asp Asn  Ala Glu Lys Leu Val  Leu Arg Ile
    1235                 1240                 1245

Arg Ile  Met Asn Ser Asp Asp  Gly Lys Phe Gly Glu  Gly Ala Asp
    1250                 1255                 1260

Glu Asp  Val Asp Lys Met Asp  Asp Asp Met Phe Leu  Arg Cys Ile
    1265                 1270                 1275

Glu Ala  Asn Met Leu Ser Asp  Met Thr Leu Gln Gly  Ile Glu Ala
    1280                 1285                 1290

Ile Ser  Lys Val Tyr Met His  Leu Pro Gln Thr Asp  Ser Lys Lys
    1295                 1300                 1305

Arg Ile  Val Ile Thr Glu Thr  Gly Glu Phe Lys Ala  Ile Ala Glu
    1310                 1315                 1320

Trp Leu  Leu Glu Thr Asp Gly  Thr Ser Met Met Lys  Val Leu Ser
    1325                 1330                 1335

Glu Arg  Asp Val Asp Pro Val  Arg Thr Phe Ser Asn  Asp Ile Cys
    1340                 1345                 1350

Glu Ile  Phe Ser Val Leu Gly  Ile Glu Ala Val Arg  Lys Ser Val
    1355                 1360                 1365

Glu Lys  Glu Met Asn Ala Val  Leu Ser Phe Tyr Gly  Leu Tyr Val
    1370                 1375                 1380

Asn Tyr  Arg His Leu Ala Leu  Leu Cys Asp Val Met  Thr Ala Lys
    1385                 1390                 1395

Gly His  Leu Met Ala Ile Thr  Arg His Gly Ile Asn  Arg Gln Asp
    1400                 1405                 1410

Thr Gly  Ala Leu Met Arg Cys  Ser Phe Glu Glu Thr  Val Asp Val
    1415                 1420                 1425

Leu Met  Asp Ala Ala Ser His  Ala Glu Val Asp Pro  Met Arg Gly
    1430                 1435                 1440

Val Ser  Glu Asn Ile Ile Leu  Gly Gln Leu Pro Arg  Met Gly Thr
    1445                 1450                 1455

Gly Cys  Phe Asp Leu Leu Leu  Asp Ala Glu Lys Cys  Lys Met Gly
    1460                 1465                 1470

Ile Ala  Ile Pro Gln Ala His  Ser Ser Asp Leu Met  Ala Ser Gly
    1475                 1480                 1485
```

-continued

```
Met Phe  Phe Gly Leu Ala Ala  Thr Pro Ser Ser Met  Ser Pro Gly
    1490                 1495                 1500

Gly Ala  Met Thr Pro Trp Asn  Gln Ala Ala Thr Pro  Tyr Val Gly
    1505                 1510                 1515

Ser Ile  Trp Ser Pro Gln Asn  Leu Met Gly Ser Gly  Met Thr Pro
    1520                 1525                 1530

Gly Gly  Ala Ala Phe Ser Pro  Ser Ala Ala Ser Asp  Ala Ser Gly
    1535                 1540                 1545

Met Ser  Pro Ala Tyr Gly Gly  Trp Ser Pro Thr Pro  Gln Ser Pro
    1550                 1555                 1560

Ala Met  Ser Pro Tyr Met Ala  Ser Pro His Gly Gln  Ser Pro Ser
    1565                 1570                 1575

Tyr Ser  Pro Ser Ser Pro Ala  Phe Gln Pro Thr Ser  Pro Ser Met
    1580                 1585                 1590

Thr Pro  Thr Ser Pro Gly Tyr  Ser Pro Ser Ser Pro  Gly Tyr Ser
    1595                 1600                 1605

Pro Thr  Ser Leu Asn Tyr Ser  Pro Thr Ser Pro Ser  Tyr Ser Pro
    1610                 1615                 1620

Thr Ser  Gln Ser Tyr Ser Pro  Thr Ser Pro Ser Tyr  Ser Pro Thr
    1625                 1630                 1635

Ser Pro  Asn Tyr Ser Pro Thr  Ser Pro Ser Tyr Ser  Pro Thr Ser
    1640                 1645                 1650

Pro Asn  Tyr Ser Pro Thr Ser  Pro Asn Tyr Ser Pro  Thr Ser Pro
    1655                 1660                 1665

Ser Tyr  Pro Ser Thr Ser Pro  Gly Tyr Ser Pro Thr  Ser Arg Ser
    1670                 1675                 1680

Tyr Ser  Pro Thr Ser Pro Ser  Tyr Ser Gly Thr Ser  Pro Ser Tyr
    1685                 1690                 1695

Ser Pro  Thr Ser Pro Ser Tyr  Ser Pro Thr Ser Pro  Ser Tyr Ser
    1700                 1705                 1710

Pro Ser  Ser Pro Asn Tyr Ser  Pro Thr Ser Pro Asn  Tyr Ser Pro
    1715                 1720                 1725

Thr Ser  Pro Asn Tyr Ser Pro  Ser Ser Pro Arg Tyr  Thr Pro Gly
    1730                 1735                 1740

Ser Pro  Ser Phe Ser Pro Ser  Ser Asn Ser Tyr Ser  Pro Thr Ser
    1745                 1750                 1755

Pro Gln  Tyr Ser Pro Thr Ser  Pro Ser Tyr Ser Pro  Ser Ser Pro
    1760                 1765                 1770

Lys Tyr  Ser Pro Thr Ser Pro  Asn Tyr Ser Pro Thr  Ser Pro Ser
    1775                 1780                 1785

Phe Ser  Gly Gly Ser Pro Gln  Tyr Ser Pro Thr Ser  Pro Lys Tyr
    1790                 1795                 1800

Ser Pro  Thr Ser Pro Asn Tyr  Thr Leu Ser Ser Pro  Gln His Thr
    1805                 1810                 1815

Pro Thr  Gly Ser Ser Arg Tyr  Ser Pro Ser Thr Ser  Ser Tyr Ser
    1820                 1825                 1830

Pro Asn  Ser Pro Asn Tyr Ser  Pro Thr Ser Pro Gln  Tyr Ser Ile
    1835                 1840                 1845

His Ser  Thr Lys Tyr Ser Pro  Ala Ser Pro Thr Phe  Thr Pro Thr
    1850                 1855                 1860

Ser Pro  Ser Phe Ser Pro Ala  Ser Pro Ala Tyr Ser  Pro Gln Pro
    1865                 1870                 1875

Met Tyr  Ser Pro Ser Ser Pro  Asn Tyr Ser Pro Thr  Ser Pro Ser
```

```
    1880                1885                1890

Gln Asp  Thr Asp
    1895


<210> SEQ ID NO 260
<211> LENGTH: 291
<212> TYPE: PRT
<213> ORGANISM: Diabrotica virgifera

<400> SEQUENCE: 260

Met Ser Ser Asn Ile Gln Lys Ala Gln Gln Leu Met Ala Asp Ala Glu
1               5                   10                  15

Lys Lys Val Thr Ser Arg Gly Phe Phe Gly Ser Leu Phe Gly Gly Ser
            20                  25                  30

Ser Arg Ile Glu Asp Ala Val Glu Cys Tyr Thr Arg Ala Ala Asn Leu
        35                  40                  45

Phe Lys Met Ala Lys Ser Trp Asp Ala Ala Gly Lys Ala Phe Cys Glu
    50                  55                  60

Ala Ala Asn Leu His Ser Arg Thr Gly Ala Arg His Asp Ala Ala Thr
65                  70                  75                  80

Asn Tyr Ile Asp Ala Ala Asn Cys Tyr Lys Lys Ala Asp Val Phe Glu
                85                  90                  95

Ala Val Asn Cys Phe Ile Lys Ala Ile Asp Ile Tyr Thr Glu Met Gly
            100                 105                 110

Arg Phe Thr Met Ala Ala Lys His His Gln Thr Ile Ala Glu Met Tyr
        115                 120                 125

Glu Thr Asp Ala Val Asp Ile Glu Arg Ala Val Gln His Tyr Glu Gln
    130                 135                 140

Ala Ala Asp Tyr Phe Arg Gly Glu Glu Ser Asn Ala Ser Ala Asn Lys
145                 150                 155                 160

Cys Leu Leu Lys Val Ala Gln Tyr Ala Ala Gln Leu Glu Asn Tyr Glu
                165                 170                 175

Lys Ala Val Gly Ile Tyr Gln Glu Val Ala Tyr Ala Ala Leu Glu Ser
            180                 185                 190

Ser Leu Leu Lys Tyr Ser Ala Lys Glu Tyr Leu Phe Arg Ala Ala Leu
        195                 200                 205

Cys His Leu Cys Val Asp Val Leu Asn Ala Gln His Ala Ile Glu Ser
    210                 215                 220

Tyr Ile Ser Arg Tyr Pro Ala Phe Gln Asp Ser Arg Glu Tyr Lys Leu
225                 230                 235                 240

Leu Lys Thr Leu Ile Glu Asn Ile Glu Glu Gln Asn Val Asp Gly Tyr
                245                 250                 255

Thr Glu Ala Val Lys Asp Tyr Asp Ser Ile Ser Arg Leu Asp Gln Trp
            260                 265                 270

Tyr Thr Thr Ile Leu Leu Arg Ile Lys Lys Gln Val Ser Glu Ser Pro
        275                 280                 285

Asp Leu Arg
    290


<210> SEQ ID NO 261
<211> LENGTH: 202
<212> TYPE: PRT
<213> ORGANISM: Diabrotica virgifera

<400> SEQUENCE: 261

Met Asn Pro Glu Tyr Asp Tyr Leu Phe Lys Leu Leu Leu Ile Gly Asp
```

-continued

```
1               5                   10                  15

Ser Gly Val Gly Lys Ser Cys Leu Leu Leu Arg Phe Ala Asp Asp Thr
            20                  25                  30

Tyr Thr Glu Ser Tyr Ile Ser Thr Ile Gly Val Asp Phe Lys Ile Arg
        35                  40                  45

Thr Ile Asp Leu Asp Gly Lys Thr Ile Lys Leu Gln Ile Trp Asp Thr
    50                  55                  60

Ala Gly Gln Glu Arg Phe Arg Thr Ile Thr Ser Ser Tyr Tyr Arg Gly
65                  70                  75                  80

Ala His Gly Ile Ile Val Val Tyr Asp Cys Thr Asp Gln Asp Ser Phe
                85                  90                  95

Asn Asn Val Lys Gln Trp Leu Glu Glu Ile Asp Arg Tyr Ala Cys Asp
            100                 105                 110

Asn Val Asn Lys Leu Leu Val Gly Asn Lys Ser Asp Leu Thr Thr Lys
        115                 120                 125

Lys Val Val Asp Phe Thr Thr Ala Lys Glu Tyr Ala Asp Gln Leu Gly
    130                 135                 140

Ile Pro Phe Leu Glu Thr Ser Ala Lys Asn Ala Thr Asn Val Glu Gln
145                 150                 155                 160

Ala Phe Met Thr Met Ala Ala Glu Ile Lys Asn Arg Val Gly Pro Pro
                165                 170                 175

Ser Ser Ala Val Asp Gln Gly Asn Lys Val Arg Phe Asp Gln Ser Arg
            180                 185                 190

Pro Val Glu Thr Thr Lys Ser Gly Cys Cys
        195                 200


<210> SEQ ID NO 262
<211> LENGTH: 262
<212> TYPE: PRT
<213> ORGANISM: Diabrotica virgifera

<400> SEQUENCE: 262

Met Ala Asp Ala Asp Asp Leu Leu Asp Tyr Glu Asp Glu Glu Gln Thr
1               5                   10                  15

Glu Gln Thr Ala Thr Glu Thr Ala Thr Thr Glu Val Gln Lys Lys Gly
            20                  25                  30

Val Lys Gly Thr Tyr Val Ser Ile His Ser Ser Gly Phe Arg Asp Phe
        35                  40                  45

Leu Leu Lys Pro Ala Ile Leu Arg Ala Ile Val Asp Cys Gly Phe Glu
    50                  55                  60

His Pro Ser Glu Val Gln His Glu Cys Ile Pro Gln Ala Val Ile Gly
65                  70                  75                  80

Met Asp Ile Leu Cys Gln Ala Lys Ser Gly Met Gly Lys Thr Ala Val
                85                  90                  95

Phe Val Leu Ala Thr Leu Gln Val Ile Asp Pro Thr Glu Asn Val Val
            100                 105                 110

Tyr Val Leu Val Met Cys His Thr Arg Glu Leu Ala Phe Gln Ile Ser
        115                 120                 125

Lys Glu Tyr Glu Arg Phe Ser Lys Tyr Met Pro Asn Ile Lys Val Gly
    130                 135                 140

Val Phe Phe Gly Gly Leu Pro Ile Gln Lys Asp Glu Glu Thr Leu Lys
145                 150                 155                 160

Asn Asn Cys Pro His Ile Val Val Gly Thr Pro Gly Arg Ile Leu Ala
                165                 170                 175
```

-continued

```
Leu Val Arg Ser Lys Lys Leu Asn Leu Lys His Leu Lys His Phe Ile
            180                 185                 190

Leu Asp Glu Cys Asp Lys Met Leu Glu Leu Leu Asp Met Arg Arg Asp
        195                 200                 205

Val Gln Glu Ile Tyr Arg Asn Thr Pro His Glu Lys Gln Val Met Met
    210                 215                 220

Phe Ser Ala Thr Leu Ser Lys Glu Ile Arg Pro Val Cys Lys Lys Phe
225                 230                 235                 240

Met Gln Asp Val Ile Gln Asn Ser Tyr Asn Thr Gln Phe Cys Asn Asp
                245                 250                 255

Ala Pro Thr Arg Asn Val
            260


<210> SEQ ID NO 263
<211> LENGTH: 245
<212> TYPE: PRT
<213> ORGANISM: Diabrotica virgifera

<400> SEQUENCE: 263

Met Pro Val Ile Asp Gly Tyr Lys Val Leu Tyr Ile Leu Leu His Ser
1               5                   10                  15

Leu Tyr Thr Ile Phe Glu Asn Ile Trp Arg Thr Leu Leu Phe Ile Tyr
            20                  25                  30

Gln Asn Cys Ile Arg Val Ile Asn Pro Glu Ser Thr Phe Asp Asp Ala
        35                  40                  45

Asp Gln Leu Lys Lys Arg Leu Ser Arg Leu Thr Lys Lys Pro Gln His
    50                  55                  60

Leu Thr Ile Ile Ile Gly Val Glu Glu Tyr Ser Leu Val Asp Leu Ala
65                  70                  75                  80

Asn Leu Val Tyr Trp Cys Leu Gly Leu Asn Ile Pro Tyr Val Ser Phe
                85                  90                  95

Tyr Asp Tyr Lys Gly Asn Leu Lys Lys His Glu Glu Lys Leu Gln Gln
            100                 105                 110

Ile Val Glu Ser Arg Lys Ser Glu Asn Ile Asn Ile Ile Trp His Thr
        115                 120                 125

His Ala Glu Gln Arg His Lys Asn Gly Phe Leu Gly Pro Lys Ile His
    130                 135                 140

Val Lys Val Leu Thr His Ala Asp Gly Lys Gln Ser Ile Val Asn Val
145                 150                 155                 160

Thr Lys Lys Leu Ala Leu Asn Lys Glu Lys Asp Ile Ser Lys Glu Lys
                165                 170                 175

Ile Ser Glu Leu Leu Leu Arg Gln Tyr Glu Phe Pro Asp Pro Glu Met
            180                 185                 190

Ala Ile Ile Cys Gly Lys Lys Leu Asn Ile Tyr Asn Tyr Pro Pro Trp
        195                 200                 205

Gln Leu Arg Leu Thr Glu Phe Phe Lys Val Asn Lys Val Asn Asn Ile
    210                 215                 220

Thr Phe Pro Val Phe Val Glu Lys Leu Glu Lys Tyr Ser Lys Cys Glu
225                 230                 235                 240

Gln Arg Val Gly Lys
                245


<210> SEQ ID NO 264
<211> LENGTH: 159
<212> TYPE: PRT
<213> ORGANISM: Diabrotica virgifera
```

<400> SEQUENCE: 264

Met Thr Asn Ser Lys Gly Tyr Arg Arg Gly Thr Arg Asp Leu Phe Ala
1 5 10 15

Arg Lys Phe Lys Lys Arg Gly Val Ile Pro Leu Ser Thr Tyr Leu Arg
20 25 30

Val Tyr Lys Val Gly Asp Ile Val Asp Ile Lys Gly Asn Gly Ala Val
35 40 45

Gln Lys Gly Met Pro His Lys Val Tyr His Gly Lys Thr Gly Arg Val
50 55 60

Phe Asn Val Thr Ala His Ala Leu Gly Val Ile Val Asn Lys Arg Val
65 70 75 80

Arg Gly Arg Ile Ile Pro Lys Arg Ile Asn Leu Arg Ile Glu His Val
85 90 95

Asn His Ser Lys Cys Arg Gln Asp Phe Leu Gln Arg Val Lys Ser Asn
100 105 110

Glu Lys Leu Arg Lys Glu Ala Lys Glu Lys Asn Ile Lys Val Glu Leu
115 120 125

Arg Arg Gln Pro Ala Gln Pro Arg Pro Ala His Ile Val Ser Gly Lys
130 135 140

Val Pro Ala Gln Val Leu Ala Pro Ile Pro Tyr Glu Phe Ile Ala
145 150 155

<210> SEQ ID NO 265
<211> LENGTH: 178
<212> TYPE: PRT
<213> ORGANISM: Diabrotica virgifera

<400> SEQUENCE: 265

Met Glu Gly Ile Leu Leu Glu Pro Thr Leu Tyr Thr Ile Lys Gly Ile
1 5 10 15

Ala Ile Leu Asp Tyr Asp Gly Asn Arg Val Leu Ala Lys Tyr Tyr Asp
20 25 30

Lys Asp Ile Phe Pro Thr Ala Lys Glu Gln Lys Ala Phe Glu Lys Asn
35 40 45

Leu Phe Asn Lys Thr His Arg Ala Asp Ala Glu Ile Ile Met Leu Asp
50 55 60

Gly Leu Thr Cys Val Tyr Arg Ser Asn Val Asp Leu Phe Phe Tyr Val
65 70 75 80

Met Gly Ser Ser His Glu Asn Glu Leu Ile Leu Met Ser Val Leu Asn
85 90 95

Cys Leu Tyr Asp Ser Val Ser Gln Ile Leu Lys Lys Asn Met Gln Lys
100 105 110

Arg Ala Val Leu Glu Ser Leu Asp Ile Val Met Leu Ala Met Asp Glu
115 120 125

Ile Val Asp Gly Gly Ile Ile Ile Asp Ser Asp Ser Ser Ser Val Val
130 135 140

Ser Arg Ile Ala Leu Arg Thr Asp Asp Ile Pro Leu Gly Glu Gln Thr
145 150 155 160

Val Ala Gln Val Phe Gln Thr Ala Lys Glu Gln Leu Lys Trp Ser Leu
165 170 175

Leu Lys

<210> SEQ ID NO 266
<211> LENGTH: 149

<212> TYPE: PRT
<213> ORGANISM: Diabrotica virgifera

<400> SEQUENCE: 266

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
    50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Phe Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Thr
    130                 135                 140

Met Met Thr Ser Lys
145

<210> SEQ ID NO 267
<211> LENGTH: 670
<212> TYPE: PRT
<213> ORGANISM: Diabrotica virgifera

<400> SEQUENCE: 267

Met Met Gln Ala Asn Asn Arg Val Pro Pro Ile Lys Leu Glu Asn Asp
1               5                   10                  15

Ile Asp Leu Tyr Ala Asp Asp Ile Glu Asp Phe Ala Gln Asp Asp Phe
            20                  25                  30

Gly Gly Glu Asn Val Asp Leu Tyr Asp Asp Val Ile Ser Ala Pro Pro
        35                  40                  45

Gly Asn Asn Asp Asn Pro Gly Asp Ser Asn His His Ala Pro Pro Gly
    50                  55                  60

Ala Gly Glu Asp Gly Gly Gly Asn Phe Val Gly Ser Gly Gly Ala Pro
65                  70                  75                  80

Asn Asn Ile Asn Ser Ser Gly Arg Arg His Gln Leu Tyr Val Gly Asn
                85                  90                  95

Leu Thr Trp Trp Thr Thr Asp Gln Asp Ile Glu Asn Ala Val His Asp
            100                 105                 110

Ile Gly Val Thr Asp Phe His Glu Val Lys Phe Phe Glu His Arg Ala
        115                 120                 125

Asn Gly Gln Ser Lys Gly Phe Cys Val Ile Ser Leu Gly Ser Glu Gly
    130                 135                 140

Ser Met Arg Leu Cys Leu Glu Leu Leu Ser Lys Lys Glu Ile Asn Gly
145                 150                 155                 160

Gln Asn Pro Leu Val Thr Leu Pro Thr Lys Gln Ala Leu Ser Asn Phe
                165                 170                 175

Glu Ser Gln Ser Lys Thr Arg Pro Ser Pro Thr Asn Asn Ser Asn Ser
            180                 185                 190

-continued

```
Arg Pro Pro His Pro Asn Asn Asn Val His Ser Gly Pro Met Gln Asn
        195                 200                 205

Tyr Gly Gly Arg Met Pro Met Asn Pro Ser Met Arg Pro Met Pro Pro
    210                 215                 220

Gly Met Gln Gly Ala Pro Arg Met Gln Gly Pro Pro Gly Phe Asn Gly
225                 230                 235                 240

Pro Pro Asn Met Asn Gln Gln Pro Pro Arg Phe Gln Gly Asn Pro Gln
                245                 250                 255

Trp Asn Gly Pro Arg Pro Asn Gly Pro Gly Pro Asn Met Gly Met Arg
            260                 265                 270

Pro Met Gly Pro Pro His Gly Gln Gln Gly Pro Pro Arg Pro Pro Met
        275                 280                 285

Gln Gly Pro Pro Gln Gln Gly Pro Pro Arg Gly Met Pro Pro Gln Gly
    290                 295                 300

Pro Pro Gln Met Arg Pro Glu Trp Asn Arg Pro Pro Met Gln Gln Gly
305                 310                 315                 320

Tyr Pro Gln Gly Pro Pro His Met Gln Gly Pro Asn Met Gly Pro Arg
                325                 330                 335

Gly Pro Pro Gln Met Gly Pro Pro Gly Ala Pro Gln Gln Gln Gly Pro
            340                 345                 350

Ala Pro His Val Asn Pro Ala Phe Phe Gln Gln Gly Gly Gly Pro Pro
        355                 360                 365

Pro Pro Met Gln His Met Pro Gly Pro Gly Pro Val Met Pro Pro Gln
    370                 375                 380

Gly Pro Pro Gln Gly Pro Pro His Gly Pro Val Gly Pro Pro His Gly
385                 390                 395                 400

Pro Pro Leu Gly Pro Ala Asn Val Pro Pro His Gly Pro Pro His Gly
                405                 410                 415

Tyr Gly Pro Pro Ala Ala Met Pro Gln Pro Pro Tyr Gly Gly Pro Pro
            420                 425                 430

Pro Asp His Arg Ala Glu Ile Pro Gln Leu Thr Glu Gln Glu Phe Glu
        435                 440                 445

Asp Ile Met Ser Arg Asn Arg Thr Val Ser Ser Ser Ala Ile Gly Arg
    450                 455                 460

Ala Val Ser Asp Ala Ala Ala Gly Glu Phe Ala Ser Ala Ile Glu Thr
465                 470                 475                 480

Leu Val Thr Ala Ile Ser Leu Ile Lys Gln Ser Lys Val Ala Asn Asp
                485                 490                 495

Asp Arg Cys Lys Ile Leu Ile Ser Ser Leu Gln Asp Thr Leu Arg Gly
            500                 505                 510

Val Glu Asp Lys Ser Tyr Ser Ser Ser Arg Arg Asp Arg Ser Arg Ser
        515                 520                 525

Arg Asp Arg Ser His Arg Arg Thr Arg Arg Glu Arg Ser Ser Ser Arg
    530                 535                 540

Tyr Arg Asp Arg Ser Arg Glu Arg Glu Arg Glu Arg Asp Arg Asp Arg
545                 550                 555                 560

Asp Arg Glu Arg Asp Arg Tyr Tyr Asp Arg Tyr Ser Glu Arg Glu Arg
                565                 570                 575

Asp Arg Asp Arg Ser Arg Ser Arg Glu Arg Thr Glu Arg Asp Arg Glu
            580                 585                 590

Arg Asp Tyr Arg Asp Arg Glu Pro Glu Glu Thr Asp Lys Glu Lys Ser
        595                 600                 605

Lys Val Ser Arg Val Ser Arg Ser Arg Asn Lys Ser Pro Glu Pro Val
```

```
    610                 615                 620

Glu Pro Ser Ser Glu Val Pro Lys Ser Ser Arg Tyr Tyr Glu Asp Arg
625                 630                 635                 640

Tyr Arg Glu Arg Glu Arg Glu Gly Arg Arg Glu Ser Asp Arg Glu Arg
                645                 650                 655

Glu Arg Asp Arg Arg Gly Glu Asp Ser His Arg Ser Arg His
            660                 665                 670


<210> SEQ ID NO 268
<211> LENGTH: 254
<212> TYPE: PRT
<213> ORGANISM: Diabrotica virgifera

<400> SEQUENCE: 268

Met Ser Ser Ile Gly Thr Gly Tyr Asp Leu Ser Ala Ser Gln Phe Ser
1               5                   10                  15

Pro Asp Gly Arg Val Phe Gln Val Glu Tyr Ala Met Lys Ala Val Glu
            20                  25                  30

Asn Ser Gly Thr Val Ile Gly Leu Arg Gly Thr Asp Gly Ile Val Leu
        35                  40                  45

Ala Ala Glu Lys Leu Ile Met Ser Lys Leu His Glu Pro Ser Thr Asn
    50                  55                  60

Lys Arg Ile Phe Asn Ile Asp Lys His Ile Gly Met Ala Phe Ser Gly
65                  70                  75                  80

Leu Ile Ala Asp Ala Arg Gln Ile Val Glu Ile Ala Arg Lys Glu Ala
                85                  90                  95

Ser Asn Tyr Arg His Gln Tyr Gly Ser Asn Ile Pro Leu Lys Tyr Leu
            100                 105                 110

Asn Asp Arg Val Ser Met Tyr Met His Ala Tyr Thr Leu Tyr Ser Ala
        115                 120                 125

Val Arg Pro Phe Gly Cys Ser Val Ile Leu Ala Ser Tyr Glu Asp Ser
    130                 135                 140

Asp Pro Ser Met Tyr Leu Ile Asp Pro Ser Gly Val Ser Tyr Gly Tyr
145                 150                 155                 160

Phe Gly Cys Ala Thr Gly Lys Ala Lys Gln Ser Ala Lys Thr Glu Ile
                165                 170                 175

Glu Lys Leu Lys Met Gly Asn Leu Thr Cys Lys Glu Leu Val Lys Glu
            180                 185                 190

Ala Ala Lys Ile Ile Tyr Leu Val His Asp Glu Leu Lys Asp Lys Asn
        195                 200                 205

Phe Glu Leu Glu Leu Ser Trp Val Cys Lys Asp Thr Asn Gly Leu His
    210                 215                 220

Thr Lys Val Pro Glu Ser Val Phe Ala Asp Ala Glu Lys Ala Ala Lys
225                 230                 235                 240

Gln Ala Met Glu Ala Asp Ser Glu Ser Asp Thr Glu Asp Met
                245                 250


<210> SEQ ID NO 269
<211> LENGTH: 246
<212> TYPE: PRT
<213> ORGANISM: Diabrotica virgifera

<400> SEQUENCE: 269

Met Ala Ser Lys Asp Arg Leu Met Ile Phe Pro Ser Arg Gly Ala Gln
1               5                   10                  15

Met Met Met Lys Ser Arg Leu Lys Gly Ala Gln Lys Gly His Ser Leu
```

```
            20                  25                  30

Leu Lys Lys Lys Ala Asp Ala Leu Gln Met Arg Phe Arg Met Ile Leu
        35                  40                  45

Asn Lys Ile Ile Glu Thr Lys Thr Leu Met Gly Glu Val Met Lys Glu
    50                  55                  60

Ala Ala Phe Ser Leu Ala Glu Ala Lys Phe Ala Thr Gly Asp Phe Asn
65                  70                  75                  80

Gln Val Val Leu Gln Asn Val Thr Lys Ala Gln Ile Lys Ile Arg Thr
                85                  90                  95

Lys Lys Asp Asn Val Ala Gly Val Thr Leu Pro Val Phe Glu Cys Tyr
            100                 105                 110

Gln Asp Gly Thr Asp Thr Tyr Glu Leu Ala Gly Leu Ala Arg Gly Gly
        115                 120                 125

Gln Gln Leu Thr Lys Leu Lys Lys Asn Tyr Gln Ser Ala Val Lys Leu
    130                 135                 140

Leu Val Glu Leu Ala Ser Leu Gln Thr Ser Phe Val Thr Leu Asp Asp
145                 150                 155                 160

Val Ile Lys Ile Thr Asn Arg Arg Val Asn Ala Ile Glu His Val Ile
                165                 170                 175

Ile Pro Arg Ile Glu Arg Thr Leu Ala Tyr Ile Ile Ser Glu Leu Asp
            180                 185                 190

Glu Leu Glu Arg Glu Glu Phe Tyr Arg Leu Lys Lys Ile Gln Asp Lys
        195                 200                 205

Lys Lys Ile Ser Arg Ala Lys Ala Glu Lys Gln Lys Gln Ala Leu Leu
    210                 215                 220

Gln Ala Gly Leu Leu Lys Glu Ser Gln Ala Asn Met Leu Leu Asp Glu
225                 230                 235                 240

Gly Asp Glu Asp Leu Leu
                245


<210> SEQ ID NO 270
<211> LENGTH: 1605
<212> TYPE: PRT
<213> ORGANISM: Diabrotica virgifera

<400> SEQUENCE: 270

Met Glu Ala Ala Pro Lys Leu Pro Met Leu Ser Phe Glu Leu Asn Thr
1               5                   10                  15

Cys Thr Glu Asn Val His Phe Gly Pro Gln Leu Lys Gln Tyr Ile Ala
            20                  25                  30

Ala Phe Tyr Gly Glu Asp Pro Glu Ser Tyr Ile Thr Glu Ile Ser Asn
        35                  40                  45

Leu Glu Ser Leu Arg Ser Ala Ala Val Arg Pro Ser Thr Asp Val Asn
    50                  55                  60

Gly Val Gln Leu Leu Lys Lys Tyr Phe Cys Gln Leu Arg Phe Leu Lys
65                  70                  75                  80

Ser Arg Phe Pro Met Glu Glu Asn Gln Asp Ala Ala Val Leu Phe Ser
                85                  90                  95

Trp Lys Asn Asn Glu Leu Asp Ile Thr Ser Thr Ser Ser Asp Ile Arg
            100                 105                 110

Tyr Glu Leu Met Val Ile Met Tyr Asn Ile Gly Ala Leu His Thr Phe
        115                 120                 125

Leu Gly Ala Asn Asp Ser Arg Asn Asn Pro Asp Gly Met Lys Met Ala
    130                 135                 140
```

-continued

```
Cys Thr His Phe Gln Cys Ala Ala Trp Ala Phe Gln Asn Val Lys Glu
145                 150                 155                 160

Lys Tyr His Gln Phe Ile Ser Asn Ile Ser Leu Val Glu Leu Val His
                165                 170                 175

Phe Phe Gln Gln Val Cys Leu Ala Gln Ala Gln Glu Cys Ile Leu Glu
            180                 185                 190

Lys Ser Met Phe Asp Asn Arg Lys Pro Thr Ile Ile Ala Lys Val Ala
        195                 200                 205

Ile Gln Val Tyr Ser Tyr Tyr Arg Gln Ser Leu Arg Val Leu Glu Ser
    210                 215                 220

Val Asn Glu Ala Tyr Phe Arg Asp Lys Thr Tyr Lys Glu Trp Met Lys
225                 230                 235                 240

Tyr Leu Gln Phe Lys Leu Thr Tyr Tyr Lys Cys Ile Ser Phe Leu Phe
                245                 250                 255

Gln Gly Gln Gln Ala Glu Glu Gln Gln Lys Met Gly Glu Arg Val Ala
            260                 265                 270

Phe Tyr Gln Ala Ala Cys Glu Gln Leu Asp Glu Ala Lys Lys Ile Ala
        275                 280                 285

Ala Thr Leu Lys Asn Gln His His Gln Gln Glu Ile Asn Glu Gly Leu
    290                 295                 300

Ala Phe Thr Thr Asp Val Val Glu Gly Lys Arg Lys Ala Ala Lys Asn
305                 310                 315                 320

Glu Asn Glu Phe Ile Tyr His Glu Ser Val Pro Asp Lys Asp Gln Leu
                325                 330                 335

Pro Glu Val Lys Gly Ala Ser Leu Val Lys Gly Ile Pro Phe Ser Ile
            340                 345                 350

Asn Asp Ile Glu Val Ser Gly Pro Asp Ile Phe Ser Arg Leu Val Pro
        355                 360                 365

Met Glu Ala His Glu Ala Ala Ser Leu Tyr Ser Glu Lys Lys Ala Gln
    370                 375                 380

Arg Leu Arg Gln Ile Gly Glu Leu Ile Glu Asn Lys Asp Gln Thr Leu
385                 390                 395                 400

Ala Glu Phe Met Ser Ser Met Gln Leu Asp Leu Leu Thr Lys Met His
                405                 410                 415

Gln Ala Thr Gly Ile Pro Gln Glu Leu Ile Asp Arg Ala Ala Ala Leu
            420                 425                 430

Ser Ala Lys Pro Asn Ala Ile Gln Asp Leu Ile Ser Ala Met Gly Lys
        435                 440                 445

Leu Ser Asn Ile Tyr Gln Asp Val Glu Ala Ser Leu Asn Glu Ile Asp
    450                 455                 460

Ser Leu Leu Lys Ala Glu Glu Gln Ser Glu Gln Lys Tyr Gln Glu Thr
465                 470                 475                 480

Ile Gly Lys Arg Pro Pro Ser Ile Leu Ala Thr Asp Leu Thr Arg Glu
                485                 490                 495

Ala Ala Lys Tyr Arg Glu Ala His Thr Lys Ala Asn Asp Ser Asn Gln
            500                 505                 510

Thr Leu His Arg Ala Met Met Ala His Val Ala Asn Leu Lys Ile Leu
        515                 520                 525

Gln Gln Pro Leu Lys Gln Leu Gln His Gln Leu Pro Phe Val Glu Phe
    530                 535                 540

Pro Asn Pro Asn Ile Asp Glu Lys Ser Leu Lys Asp Leu Glu Ala Leu
545                 550                 555                 560

Val Ala Lys Val Asp Glu Met Arg Thr Gln Arg Ala Met Leu Trp Ala
```

-continued

```
                565                 570                 575

Gln Leu Arg Glu Ser Ile His Gln Asp Asp Ile Thr Ser Ser Leu Val
            580                 585                 590

Thr Lys Gln Pro Asn Gln Ser Leu Glu Gln Leu Phe Gln Gln Glu Leu
        595                 600                 605

Gln Lys His Gln Asn Leu Ile Ser Leu Ile Glu Gln Asn Thr Ser Ala
    610                 615                 620

Gln Glu Asn Ile Lys Ser Ala Leu Val Asp Ser Tyr Ala Tyr Ala Val
625                 630                 635                 640

Asn Ser Arg Lys Tyr Ile Gln Asp Ile Leu Gln Lys Arg Thr Thr Thr
                645                 650                 655

Ile Thr Ser Leu Ile Ala Ser Phe Asp Ser Tyr Glu Asp Leu Leu Ala
            660                 665                 670

Lys Ala Asn Lys Gly Ile Glu Phe Tyr Ser Lys Leu Glu Thr Asn Val
        675                 680                 685

Ser Lys Leu Leu Gln Arg Ile Arg Ser Thr Cys Lys Val Gln Gln Glu
    690                 695                 700

Glu Arg Asp Gln Met Met Ser Thr Ala Gln Val Pro Gln Trp Glu Ser
705                 710                 715                 720

His Thr Ser Leu Ala Ala Pro Lys Leu Lys Asp Tyr Leu Asp Ser Arg
                725                 730                 735

Lys Lys Ser Ala Ala Tyr Ser Glu Pro Ser Val Gln Pro Gln Gln Pro
            740                 745                 750

Thr Leu Ser Tyr Ser Ala Ala Met Asp Leu Pro Pro Gly Ile Arg Pro
        755                 760                 765

Thr Pro Val Gly Ser Glu Ile Thr Asp Val Pro Lys Asn Ile Gln Gly
    770                 775                 780

Glu Pro Gln Gly Tyr Ile Pro Tyr Asn Tyr Gln Gln Pro Ser Val Pro
785                 790                 795                 800

Ala Ser Gln Asn Ile Asp Glu Glu Thr Ile Lys Lys Met Asn Ala Leu
                805                 810                 815

Met Pro Gly Ala Lys Thr Ser Val Pro Ser Gln Tyr Gly Tyr Ser Asn
            820                 825                 830

Tyr Ile Pro Pro Thr Tyr Pro Gln Ser Ala Tyr Gln Pro Gly Asn Gln
        835                 840                 845

Ser Tyr Gly Lys Glu Thr Pro Asp Ile Asn Ser Pro Tyr Asp Pro Thr
    850                 855                 860

Lys Ala Phe Thr Ala Thr Thr Asn Ala Tyr Arg Ser Val Gln Ser Ser
865                 870                 875                 880

Ser Thr Gln Gly Tyr Val Pro Tyr Ala Glu Ser Asn Val Ser Asn Val
                885                 890                 895

Asp Arg Val Gly Tyr Pro Ser Arg Tyr Gln Tyr Gln Gln Val Pro Glu
            900                 905                 910

Ile Ala Thr Thr Pro Ala Asp Pro Asn Ile Asn Ala Tyr Tyr Pro His
        915                 920                 925

Gly Tyr Ser Pro Ser Gln Asn Leu Pro Asn Ala Asn Thr Gln His Ile
    930                 935                 940

Thr Gly Gln Leu Lys Tyr His Ser Val Glu Tyr Ala Ser Ser Val Pro
945                 950                 955                 960

Asn Asn Ile Asn Tyr Asn Ser Ser Thr Tyr Ser Ser Pro Leu Ser Asn
                965                 970                 975

Met Ser Ser Thr Asn Ser Ser Asn Pro Ser Asn Leu Asn Asn Ser Tyr
            980                 985                 990
```

Glu Tyr Tyr Tyr Asp Pro Asn Thr Ser Ser Gly Ala Val Pro Asn Ala
995 1000 1005

Ser Lys Pro Gln Gln Ser Ser Ala Ser Ser Ala Asn Pro Ser Thr
1010 1015 1020

Ala Met Asn Asn Tyr Asn Tyr Tyr Tyr Asn Thr Ser Thr Ser Gly
1025 1030 1035

Ser Val Ala Ala Asp Thr Ser Lys Ile Gln Gln Gln Gln Gln Tyr
1040 1045 1050

Pro Gly Thr Gln Met Ser Gln Ala Gln Tyr Tyr Pro Ala Asn Ala
1055 1060 1065

Ser Tyr Tyr Ser Thr Ser Thr Tyr Asn Thr Asn Val Gln Gly Gly
1070 1075 1080

Thr Asn Pro Ser Tyr Ala Thr Gly Gln Thr Tyr Asn Gln Val Thr
1085 1090 1095

Pro Val Thr Ser Gln Asn Val Ser Gln Asn Tyr Asn Phe Asn Gln
1100 1105 1110

Val Gly Ser Gly Ala Gly His Gln His Gln Tyr Tyr Ser Ser Ala
1115 1120 1125

Asn Ala Ala Val Pro Ser Gln Gln Ala Val Asn Asn Ser Ser Leu
1130 1135 1140

Pro Asn Tyr Gly Tyr Asp Gln Tyr Tyr Gly Asn Asn Tyr Asn Ser
1145 1150 1155

Ser Gln Pro Ser Thr Tyr Ser Ala Asn Gln Ala Pro Pro Ala Ala
1160 1165 1170

Gln Ala Ala Pro Ser Asn Ile Pro Ala Ala Thr Lys Ser Ser Ser
1175 1180 1185

Asn Val Asp Leu Leu Ser Gly Leu Asp Phe Ser Ile Ser Gln Ala
1190 1195 1200

Pro Leu Val Pro Gln Gln Asn Ile Thr Ile Lys Pro Gln Glu Lys
1205 1210 1215

Glu Thr Lys Pro Pro Ala Val Ser Ser Glu Thr Lys Asn Gln Asp
1220 1225 1230

Pro Thr Pro Val Thr Thr Pro Lys Gln Pro Thr Gly Pro Glu Val
1235 1240 1245

Lys Arg Leu Tyr Val Lys Ile Leu Pro Ser Lys Pro Leu Asn Asn
1250 1255 1260

Asp Asp Val Lys Lys Leu Phe Gly Gln Glu Leu Asp Arg Tyr Glu
1265 1270 1275

Lys Phe Val Glu Thr Leu Thr His Lys Thr Leu Ser Gly Pro Thr
1280 1285 1290

Thr Leu Asp Ile Lys Trp Lys Glu Ile Gln Asp Gln Gln Asp Cys
1295 1300 1305

Glu Pro Gln Lys Lys Ile Ile Ser Val Ala Arg Cys Tyr Pro Met
1310 1315 1320

Lys Asn Arg Phe Pro Asp Ile Leu Pro Tyr Asp Phe Ser Arg Val
1325 1330 1335

Glu Leu Cys Asp Ser Lys Asp Asp Tyr Ile Asn Ala Ser Tyr Ile
1340 1345 1350

Lys Asp Ile Ser Pro Tyr Ala Pro Ser Phe Ile Val Thr Gln Val
1355 1360 1365

Pro Leu Ser Ser Thr Val Gly Asp Met Trp Thr Met Ile Arg Glu
1370 1375 1380

```
Gln Gln  Val Glu Leu Ile Leu  Cys Leu Val Asn Asp  Asn Glu Ile
    1385                 1390                 1395

Gly Glu  Asp Ile Tyr Trp Pro  Lys Glu Lys Gly Ser  Ser Leu Asn
    1400                 1405                 1410

Ile Leu  Asn Met Val Ile Thr  Leu Gln Asn Val Ile  Val Lys Ser
    1415                 1420                 1425

His Trp  Thr Glu Arg Leu Ile  Ala Ile Asn Leu Pro  Glu Lys Arg
    1430                 1435                 1440

Glu Ser  Arg Val Ile Met His  Leu Gln Phe Thr Ser  Trp Pro Gly
    1445                 1450                 1455

Ser Leu  Phe Pro Thr Asn Pro  Glu Pro Phe Val Ser  Tyr Thr Leu
    1460                 1465                 1470

Glu Ser  Ile Asn Leu Tyr Gln  Gln Gln Lys Thr Asn  Thr His Pro
    1475                 1480                 1485

Val Val  Val His Cys Ser Ser  Gly Ile Gly Arg Ser  Gly Leu Leu
    1490                 1495                 1500

Cys Leu  Leu Thr Ala Ala Met  Phe Asp Ala Ala Asn  Asn Ala Asn
    1505                 1510                 1515

Ser Ile  Pro Asp Leu Thr Ala  Leu Ser Ile Lys Leu  Ser Asn Cys
    1520                 1525                 1530

Arg Lys  Asn Ile Leu Arg Asp  Arg Glu His Leu Lys  Phe Gly Tyr
    1535                 1540                 1545

Glu Ser  Phe Leu Ala Tyr Ile  Arg His Ile Val Cys  Glu Asp Lys
    1550                 1555                 1560

Ala Arg  Lys Lys Leu Asn Glu  Ile Gln Pro Lys Val  Lys Glu Glu
    1565                 1570                 1575

Pro Leu  Glu Pro Pro Val Ile  Val Pro Glu Pro Asn  Ile Asp Pro
    1580                 1585                 1590

Leu Ser  Thr Leu Asp Pro Phe  Trp Ala Ser Lys Arg
    1595                 1600                 1605
```

<210> SEQ ID NO 271
<211> LENGTH: 513
<212> TYPE: DNA
<213> ORGANISM: Diabrotica barberi

<400> SEQUENCE: 271

```
atgaaacctt tcttggcccc tgagagaaag aagaaactta ggttactgtt gagaaagaaa     60

gccgctgaag aattaaagaa agaacaagaa cgcaaagcag ccgaaaggag gcgtattatt    120

gaagaaaggt gcggtaaacc caaacttgtc gacgacgcaa atgaaggctc attaaaacaa    180

gtatgtgagg gatatcacag acgtattgta gacctagaaa ataagaaatt tgacctcgaa    240

aaggaagtgg aattcagaga ttttcagatc tccgaattga acagccaagt aaacgacctt    300

agaggcaaat tcgtcaaacc aaccttgaag aaggtatcca aatacgaaaa caaattcgcc    360

aaacttcaaa agaaggcagc tgaatttaac ttccgtaacc aactcaaagt tgtcaagaag    420

aaagaattca ccttagaaga agaagacaaa gaaaagaaac cagactggtc aaagaaggga    480

gacgaaaaga aggtacaaga ggctgaagca tga                                 513
```

<210> SEQ ID NO 272
<211> LENGTH: 279
<212> TYPE: DNA
<213> ORGANISM: Diabrotica barberi

<400> SEQUENCE: 272
atgaagtttt taaaatcgac agtgtgctac attgccatct tggcaattct ctttaccctc 60
tgtgccgatg aggttgaagg aaggagaaaa attttgatgg ggcgaaaaag cattaccagg 120
acatatcttc gtggaaatgc tgttcctgcg tatgtgataa taatccttgt aggaattggt 180
caaatcatcc ttggagggat attgtacgtg gcattgaaga agaagatcat tgatgcacct 240
gtaacgggat catatgcagt ggctagacaa gaaccataa 279

<210> SEQ ID NO 273
<211> LENGTH: 651
<212> TYPE: DNA
<213> ORGANISM: Diabrotica barberi

<400> SEQUENCE: 273
atggcggcaa acagaactgg acctgctcag agaccaaatg gcgctaccca aggaaagata 60
tgtcagttca aactggtcct actaggcgaa agtgccgtcg gtaagtcgag tttggtactg 120
aggttcgtca aaggacagtt ccacgaatac caggagagta ccataggagc agctttcctt 180
acacaaacca tatgcctcga cgatacaact gttaaatttg aaatttggga cacagcgggt 240
caagaaaggt accacagttt agctcctatg tactataggg gcgcacaggc agctatagtc 300
gtctacgaca taaccaatca agacacattc ggcagggcga aaacgtgggt gaaggaactt 360
caaaggcagg ccagtccgac gatcgtgata gctttggccg gcaacaagca ggatttggcc 420
aacaaacgta tggtagaata cgaagaggcg caaacgtatg ctgacgaaaa cggcttactt 480
tttatggaaa cttccgcaaa gacggcaatg aacgtcaacg atatattttt agcaatagct 540
aagaaactgc ccaagaatga acaaaccaca ggtcaaggcg gcagtgccca aggcaggcgg 600
ctagcggaag gcgattcggg cgccaaggca cccggaaatt gttgcaagtg a 651

<210> SEQ ID NO 274
<211> LENGTH: 513
<212> TYPE: RNA
<213> ORGANISM: Diabrotica barberi

<400> SEQUENCE: 274
augaaaccuu ucuuggcccc ugagagaaag aagaaacuua gguuacuguu gagaaagaaa 60
gccgcugaag aauuaaagaa agaacaagaa cgcaaagcag ccgaaaggag gcguauuauu 120
gaagaaaggu gcgguaaacc caaacuuguc gacgacgcaa augaaggcuc auuaaaacaa 180
guaugugagg gauaucacag acguauugua gaccuagaaa auaagaaauu ugaccucgaa 240
aaggaagugg aauucagaga uuuucagauc uccgaauuga acagccaagu aaacgaccuu 300
agaggcaaau ucgucaaacc aaccuugaag aagguaucca aauacgaaaa caaauucgcc 360
aaacuucaaa agaaggcagc ugaauuuaac uuccguaacc aacucaaagu ugucaagaag 420
aaagaauuca ccuuagaaga agaagacaaa gaaaagaaac cagacugguc aaagaaggga 480
gacgaaaaga agguacaaga ggcugaagca uga 513

<210> SEQ ID NO 275
<211> LENGTH: 279
<212> TYPE: RNA
<213> ORGANISM: Diabrotica barberi

<400> SEQUENCE: 275
augaaguuuu uaaaaucgac agugugcuac auugccaucu uggcaauucu cuuuacccuc 60
ugugccgaug agguugaagg aaggagaaaa auuuugaugg ggcgaaaaag cauuaccagg 120
acauaucuuc guggaaaugc uguuccugcg uaugugauaa uaauccuugu aggaauuggu 180
caaaucaucc uuggagggau auuguacgug gcauugaaga agaagaucau ugaugcaccu 240
guaacgggau cauaugcagu ggcuagacaa gaaccauaa 279

<210> SEQ ID NO 276
<211> LENGTH: 651
<212> TYPE: RNA
<213> ORGANISM: Diabrotica barberi

<400> SEQUENCE: 276
auggcggcaa acagaacugg accugcucag agaccaaaug gcgcuaccca aggaaagaua 60
ugucaguuca aacugguccu acuaggcgaa agugccgucg guaagucgag uuugguacug 120
agguucguca aaggacaguu ccacgaauac caggagagua ccauaggagc agcuuuccuu 180
acacaaacca uaugccucga cgauacaacu guuaaauuug aaauuuggga cacagcgggu 240
caagaaaggu accacaguuu agcuccuaug uacuauaggg gcgcacaggc agcuauaguc 300
gucuacgaca uaaccaauca agacacauuc ggcagggcga aaacgugggu gaaggaacuu 360
caaaggcagg ccaguccgac gaucgugaua gcuuuggccg gcaacaagca ggauuuggcc 420
aacaaacgua ugguagaaua cgaagaggcg caaacguaug cugacgaaaa cggcuuacuu 480
uuuauggaaa cuuccgcaaa gacggcaaug aacgucaacg auauauuuuu agcaauagcu 540
aagaaacugc ccaagaauga acaaaccaca ggucaaggcg gcagugccca aggcaggcgg 600
cuagcggaag gcgauucggg cgccaaggca cccggaaauu guugcaagug a 651

<210> SEQ ID NO 277
<211> LENGTH: 744
<212> TYPE: DNA
<213> ORGANISM: Diabrotica undecimpunctata

<400> SEQUENCE: 277
atggcggacg atgaggaaaa gaagaggaaa caggccgaaa ttgaacgcaa aagggccgag 60
gtcagggctc gtatggaaga ggcctcaaaa gccaagaagg ccaagaaagg tttggcggac 120
gatgagagaa agaaactgga ggaggaaaag aagaggaaac aggccgaaat tgaacgcaaa 180
agggccgagg tcagggctcg tatggaagag gcctcaaaag ccaagaaggc caagaaaggt 240
ttcatgaccc ctgagagaaa gaagaaactt aggttactgt tgagaaagaa agccgctgaa 300
gaattaaaga aagaacaaga acgcaaagca gctgaaagga ggcgtatcat tgaagaaagg 360
tgcggtaaac ccaaacttgt cgatgatgca aatgaagcct cattaaaaca agtatgtgag 420
ggatatcaca gacgtattgt agacctagaa aataagaaat ttgacctcga aaaggaagtg 480
gaattcagag attttcagat ctccgaattg aacagccaag taaacgacct tagaggcaaa 540
ttcgtcaaac caaccttgaa gaaggtatcc aaatacgaaa acaaattcgc caaactccaa 600
aagaaggcag ctgaatttaa cttccgtaac caactcaaag ttgtcaagaa gaaagaattc 660
accttagaag aagaagacaa agaaaagaaa ccagactggt caaagaaggg agacgaaaag 720
aaggtacaag aggctgaagc atga 744

<210> SEQ ID NO 278
<211> LENGTH: 279
<212> TYPE: DNA
<213> ORGANISM: Diabrotica undecimpunctata

<400> SEQUENCE: 278
atgaagtttt taaaatcgac agtgtgctac attgccatct tggcaattct ctttaccctc 60
tgtgccgatg aggttgaagg aaggagaaaa attttgatgg ggcgaaaaag cattaccagg 120
acatatcttc gtggaaatgc tgttcctgcg tatgtgataa taatccttgt aggaattggt 180
caaatcatcc ttggagggat attgtacgtg gcattgaaga agaagatcat tgatgcacct 240
gtaacgggat catatgcagt ggctagacaa gaaccataa 279

<210> SEQ ID NO 279
<211> LENGTH: 651
<212> TYPE: DNA
<213> ORGANISM: Diabrotica undecimpunctata

<400> SEQUENCE: 279
atggcggcaa acagaactgg acctgctcag agaccaaatg gcgctaccca aggaaagata 60
tgccagttca aacttgtcct actaggcgaa agtgccgtcg gtaagtcgag tttggtactg 120
aggtttgtca aaggacagtt ccacgaatac caggagagta ccataggagc agctttcctt 180
acacaaacca tatgcctcga cgatacaacc gttaaatttg aaatttggga cacagcgggt 240
caagaaaggt accacagttt agctcctatg tactataggg gcgcacaggc agctatagtc 300
gtctacgaca taaccaatca agacacattc ggcagggcga aaacgtgggt taaggaactt 360
caaaggcagg cgagtccgac gatcgtgata gctttggccg gcaacaagca ggatttggcc 420
aataaacgta tggtagaata cgaagaggcg caaacgtatg ctgacgaaaa tggcttactt 480
tttatggaaa cttccgcaaa gacggcaatg aacgtcaacg atatattttt agcaatagct 540
aagaaactgc ccaagaatga acaaacaaca ggtcaaggag gcagtgccca aggtaggcgg 600
ctagcagaag gcgattcggg ggccaaggca cctggaaact gttgcaagtg a 651

<210> SEQ ID NO 280
<211> LENGTH: 744
<212> TYPE: RNA
<213> ORGANISM: Diabrotica undecimpunctata

<400> SEQUENCE: 280
auggcggacg augaggaaaa gaagaggaaa caggccgaaa uugaacgcaa aagggccgag 60
gucagggcuc guauggaaga ggccucaaaa gccaagaagg ccaagaaagg uuuggcggac 120
gaugagagaa agaaacugga ggaggaaaag aagaggaaac aggccgaaau ugaacgcaaa 180
agggccgagg ucagggcucg uauggaagag gccucaaaag ccaagaaggc caagaaaggu 240
uucaugaccc cugagagaaa gaagaaacuu agguuacugu ugagaaagaa agccgcugaa 300
gaauuaaaga aagaacaaga acgcaaagca gcugaaagga ggcguaucau ugaagaaagg 360
ugcgguaaac ccaaacuugu cgaugaugca aaugaagccu cauuaaaaca aguaugugag 420
ggauaucaca gacguauugu agaccuagaa aauaagaaau uugaccucga aaaggaagug 480
gaauucagag auuuucagau cuccgaauug aacagccaag uaaacgaccu uagaggcaaa 540
uucgucaaac caaccuugaa gaagguaucc aaauacgaaa acaaauucgc caaacuccaa 600
aagaaggcag cugaauuuaa cuuccguaac caacucaaag uugucaagaa gaaagaauuc 660
accuuagaag aagaagacaa agaaaagaaa ccagacuggu caaagaaggg agacgaaaag 720
aagguacaag aggcugaagc auga 744

<210> SEQ ID NO 281
<211> LENGTH: 279
<212> TYPE: RNA
<213> ORGANISM: Diabrotica undecimpunctata

<400> SEQUENCE: 281

```
augaaguuuu uaaaaucgac agugugcuac auugccaucu uggcaauucu cuuuacccuc     60

ugugccgaug agguugaagg aaggagaaaa auuuugaugg ggcgaaaaag cauuaccagg    120

acauaucuuc guggaaaugc uguuccugcg uaugugauaa uaauccuugu aggaauuggu    180

caaaucaucc uuggagggau auuguacgug gcauugaaga agaagaucau ugaugcaccu    240

guaacgggau cauaugcagu ggcuagacaa gaaccauaa                           279
```

<210> SEQ ID NO 282
<211> LENGTH: 651
<212> TYPE: RNA
<213> ORGANISM: Diabrotica undecimpunctata

<400> SEQUENCE: 282

```
auggcggcaa acagaacugg accugcucag agaccaaaug gcgcuaccca aggaaagaua     60

ugccaguuca aacuuguccu acuaggcgaa agugccgucg guaagucgag uuugguacug    120

agguuuguca aaggacaguu ccacgaauac caggagagua ccauaggagc agcuuuccuu    180

acacaaacca uaugccucga cgauacaacc guuaaauuug aaauuuggga cacagcgggu    240

caagaaaggu accacaguuu agcuccuaug uacuauaggg gcgcacaggc agcuauaguc    300

gucuacgaca uaaccaauca agacacauuc ggcagggcga aaacgugggu uaaggaacuu    360

caaaggcagg cgaguccgac gaucgugaua gcuuuggccg gcaacaagca ggauuuggcc    420

aauaaacgua ugguagaaua cgaagaggcg caaacguaug cugacgaaaa uggcuuacuu    480

uuuauggaaa cuuccgcaaa gacggcaaug aacgucaacg auauauuuuu agcaauagcu    540

aagaaacugc ccaagaauga acaaacaaca ggucaaggag gcagugccca agguaggcgg    600

cuagcagaag gcgauucggg ggccaaggca ccuggaaacu guugcaagug a             651
```

<210> SEQ ID NO 283
<211> LENGTH: 478
<212> TYPE: DNA
<213> ORGANISM: Diabrotica virgifera

<400> SEQUENCE: 283

```
ggtttcatga cccctgagag aaagaagaaa cttaggttac tgttgagaaa gaaagccgcc     60

gaagaattaa agaaagaaca agaacgcaaa gcagccgaaa ggaggcgtat cattgaagaa    120

aggtgcggta aacccaaact tgtcgatgac gcaaatgaag gcccattaaa acaagtatgt    180

gagggatatc acagacgtat tgtagaccta gaaaataaga aatttgacct cgaaaaagaa    240

gtggaattca gagattttca gatctccgaa ttgaacagcc aagtaaacga ccttagaggc    300

aaattcgtca aaccaacctt gaagaaggta tccaaatacg aaaacaaatt cgccaaactt    360

caaaagaagg cagctgaatt taacttccgt aaccaactca aagttgtcaa gaagaaagaa    420

ttcaccttag aagaagaaga caaagaaaag aaaccagact ggtcaaagaa gggagacg      478
```

<210> SEQ ID NO 284
<211> LENGTH: 413
<212> TYPE: DNA
<213> ORGANISM: Diabrotica virgifera

<400> SEQUENCE: 284

```
atggcggacg atgagagaaa gaaactggag gaggaaaaga agaggaaaca ggccgaaatt     60

gaacgcaaaa gggccgaggt cagggctcgt atggaagagg cctcaaaagc caagaaggcc    120

aagaaaggtt tcatgacccc tgagagaaag aagaaactta ggttactgtt gagaaagaaa    180
```

gccgccgaag aattaaagaa agaacaagaa cgcaaagcag ccgaaaggag gcgtatcatt 240
gaagaaaggt gcggtaaacc caaacttgtc gatgacgcaa atgaaggccc attaaaacaa 300
gtatgtgagg gatatcacag acgtattgta gacctagaaa ataagaaatt tgacctcgaa 360
aaagaagtgg aattcagaga ttttcagatc tccgaattga acagccaagt aaa 413

<210> SEQ ID NO 285
<211> LENGTH: 100
<212> TYPE: DNA
<213> ORGANISM: Diabrotica virgifera

<400> SEQUENCE: 285
agatctccga attgaacagc caagtaaacg accttagagg caaattcgtc aaaccaacct 60
tgaagaaggt atccaaatac gaaaacaaat tcgccaaact 100

<210> SEQ ID NO 286
<211> LENGTH: 100
<212> TYPE: DNA
<213> ORGANISM: Diabrotica virgifera

<400> SEQUENCE: 286
tcaaaagaag gcagctgaat ttaacttccg taaccaactc aaagttgtca agaagaaaga 60
attcacctta gaagaagaag acaaagaaaa gaaaccagac 100

<210> SEQ ID NO 287
<211> LENGTH: 133
<212> TYPE: DNA
<213> ORGANISM: Diabrotica virgifera

<400> SEQUENCE: 287
gaccttagag gcaaattcgt caaaccaacc ttgaagaagg tatccaaata cgaaaacaaa 60
ttcgccaaac ttcaaaagaa ggcagctgaa tttaacttcc gtaaccaact caaagttgtc 120
aagaagaaag aat 133

<210> SEQ ID NO 288
<211> LENGTH: 500
<212> TYPE: DNA
<213> ORGANISM: Diabrotica virgifera

<400> SEQUENCE: 288
tactaggcga aagtgccgtc ggtaagtcga gtttggtact gaggttcgtc aaaggacagt 60
tccacgaata ccaggagagt accataggag cagctttcct tacacaaacc atatgcctcg 120
acgatacaac tgttaaattt gaaatttggg acacagcggg tcaagaaagg taccacagtt 180
tagctcctat gtactatagg ggcgcacagg cagctatagt cgtctacgac ataaccaatc 240
aagacacatt cggcagggcg aaaacgtggg tgaaggaact tcaaaggcag gccagtccga 300
cgatcgtgat agctttggcc ggcaacaagc aagatttggc caacaaacgt atggtagaat 360
acgaagaggc gcagacgtat gctgacgaaa acggcttact ttttatggaa acttccgcaa 420
agacggcaat gaacgtcaac gatatatttt tagcaatagc taagaaactg cccaagaatg 480
aacaaaccac aggtcaaggc 500

<210> SEQ ID NO 289
<211> LENGTH: 648
<212> TYPE: DNA
<213> ORGANISM: Diabrotica virgifera

<400> SEQUENCE: 289
atggcggcaa acagaactgg acctgctcag agaccaaatg gcgctaccca aggaaagata 60
tgtcagttca aactggtcct actaggcgaa agtgccgtcg gtaagtcgag tttggtactg 120
aggttcgtca aaggacagtt ccacgaatac caggagagta ccataggagc agctttcctt 180
acacaaacca tatgcctcga cgatacaact gttaaatttg aaatttggga cacagcgggt 240
caagaaaggt accacagttt agctcctatg tactataggg gcgcacaggc agctatagtc 300
gtctacgaca taaccaatca agacacattc ggcagggcga aaacgtgggt gaaggaactt 360
caaaggcagg ccagtccgac gatcgtgata gctttggccg gcaacaagca agatttggcc 420
aacaaacgta tggtagaata cgaagaggcg cagacgtatg ctgacgaaaa cggcttactt 480
tttatggaaa cttccgcaaa gacggcaatg aacgtcaacg atatattttt agcaatagct 540
aagaaactgc ccaagaatga acaaaccaca ggtcaaggcg gcagtgccca aggcaggcgg 600
ctagcggagg gcgattcggg cgccaaggca cccggaaatt gttgcaag 648

<210> SEQ ID NO 290
<211> LENGTH: 188
<212> TYPE: DNA
<213> ORGANISM: Diabrotica virgifera

<400> SEQUENCE: 290
atggcggcaa acagaactgg acctgctcag agaccaaatg gcgctaccca aggaaagata 60
tgtcagttca aactggtcct actaggcgaa agtgccgtcg gtaagtcgag tttggtactg 120
aggttcgtca aaggacagtt ccacgaatac caggagagta ccataggagc agctttcctt 180
acacaaac 188

<210> SEQ ID NO 291
<211> LENGTH: 205
<212> TYPE: DNA
<213> ORGANISM: Diabrotica virgifera

<400> SEQUENCE: 291
ggacagttcc acgaatacca ggagagtacc ataggagcag ctttccttac acaaaccata 60
tgcctcgacg atacaactgt taaatttgaa atttgggaca cagcgggtca agaaaggtac 120
cacagtttag ctcctatgta ctataggggc gcacaggcag ctatagtcgt ctacgacata 180
accaatcaag acacattcgg caggg 205

<210> SEQ ID NO 292
<211> LENGTH: 224
<212> TYPE: DNA
<213> ORGANISM: Diabrotica virgifera

<400> SEQUENCE: 292
gcacaggcag ctatagtcgt ctacgacata accaatcaag acacattcgg cagggcgaaa 60
acgtgggtga aggaacttca aaggcaggcc agtccgacga tcgtgatagc tttggccggc 120
aacaagcaag atttggccaa caaacgtatg gtagaatacg aagaggcgca gacgtatgct 180
gacgaaaacg gcttactttt tatggaaact tccgcaaaga cggc 224

<210> SEQ ID NO 293
<211> LENGTH: 196
<212> TYPE: DNA
<213> ORGANISM: Diabrotica virgifera

<400> SEQUENCE: 293
gacgtatgct gacgaaaacg gcttactttt tatggaaact tccgcaaaga cggcaatgaa 60
cgtcaacgat atatttttag caatagctaa gaaactgccc aagaatgaac aaaccacagg 120
tcaaggcggc agtgcccaag gcaggcggct agcggagggc gattcgggcg ccaaggcacc 180
cggaaattgt tgcaag 196

<210> SEQ ID NO 294
<211> LENGTH: 189
<212> TYPE: DNA
<213> ORGANISM: Diabrotica virgifera

<400> SEQUENCE: 294
cgatgaggtt gaaggaagga gaaaaatttt gatggggcga aaaagcatta ccaggacata 60
tcttcgtgga aatgctgttc ctgcgtatgt gataataatc cttgtaggaa ttggtcaaat 120
catcctggga gggatattgt acgttgcatt gaggaagaag atcattgctg cacctgtaac 180
ggcatcata 189

<210> SEQ ID NO 295
<211> LENGTH: 330
<212> TYPE: DNA
<213> ORGANISM: Diabrotica virgifera

<400> SEQUENCE: 295
gtgtgtattt cagctggaat ttgtaatgaa aaaaacgtag aaatatatac tacaatgaag 60
tttttaagat cgacagtgtg ctacattgcc atcttggcaa ttctctttac cctctgtgcc 120
gatgaggttg aaggaaggag aaaaattttg atggggcgaa aaagcattac caggacatat 180
cttcgtggaa atgctgttcc tgcgtatgtg ataataatcc ttgtaggaat tggtcaaatc 240
atcctgggag ggatattgta cgttgcattg aggaagaaga tcattgctgc acctgtaacg 300
gcatcatatg cagtggctag acaagaacca 330

<210> SEQ ID NO 296
<211> LENGTH: 197
<212> TYPE: DNA
<213> ORGANISM: Diabrotica virgifera

<400> SEQUENCE: 296
gtgtgtattt cagctggaat ttgtaatgaa aaaaacgtag aaatatatac tacaatgaag 60
tttttaagat cgacagtgtg ctacattgcc atcttggcaa ttctctttac cctctgtgcc 120
gatgaggttg aaggaaggag aaaaattttg atggggcgaa aaagcattac caggacatat 180
cttcgtggaa atgctgt 197

<210> SEQ ID NO 297
<211> LENGTH: 179
<212> TYPE: DNA
<213> ORGANISM: Diabrotica virgifera

<400> SEQUENCE: 297
atggggcgaa aaagcattac caggacatat cttcgtggaa atgctgttcc tgcgtatgtg 60
ataataatcc ttgtaggaat tggtcaaatc atcctgggag ggatattgta cgttgcattg 120
aggaagaaga tcattgctgc acctgtaacg gcatcatatg cagtggctag acaagaacc 179

<210> SEQ ID NO 298
<211> LENGTH: 478
<212> TYPE: RNA
<213> ORGANISM: Diabrotica virgifera

<400> SEQUENCE: 298
gguuucauga ccccugagag aaagaagaaa cuuagguuac uguugagaaa gaaagccgcc 60
gaagaauuaa agaaagaaca agaacgcaaa gcagccgaaa ggaggcguau cauugaagaa 120
aggugcggua aacccaaacu ugucgaugac gcaaaugaag gcccauuaaa acaaguaugu 180
gagggauauc acagacguau uguagaccua gaaaauaaga aauuugaccu cgaaaaagaa 240
guggaauuca gagauuuuca gaucuccgaa uugaacagcc aaguaaacga ccuuagaggc 300
aaauucguca aaccaaccuu gaagaaggua uccaaauacg aaaacaaauu cgccaaacuu 360
caaaagaagg cagcugaauu uaacuuccgu aaccaacuca aaguugucaa gaagaaagaa 420
uucaccuuag aagaagaaga caaagaaaag aaaccagacu ggucaaagaa gggagacg 478

<210> SEQ ID NO 299
<211> LENGTH: 413
<212> TYPE: RNA
<213> ORGANISM: Diabrotica virgifera

<400> SEQUENCE: 299
auggcggacg augagagaaa gaaacuggag gaggaaaaga agaggaaaca ggccgaaauu 60
gaacgcaaaa gggccgaggu cagggcucgu auggaagagg ccucaaaagc caagaaggcc 120
aagaaagguu ucaugacccc ugagagaaag aagaaacuua gguuacuguu gagaaagaaa 180
gccgccgaag aauuaaagaa agaacaagaa cgcaaagcag ccgaaaggag gcguaucauu 240
gaagaaaggu gcgguaaacc caaacuuguc gaugacgcaa augaaggccc auuaaaacaa 300
guaugugagg gauaucacag acguauugua gaccuagaaa auaagaaauu ugaccucgaa 360
aaagaagugg aauucagaga uuuucagauc uccgaauuga acagccaagu aaa 413

<210> SEQ ID NO 300
<211> LENGTH: 100
<212> TYPE: RNA
<213> ORGANISM: Diabrotica virgifera

<400> SEQUENCE: 300
agaucuccga auugaacagc caaguaaacg accuuagagg caaauucguc aaaccaaccu 60
ugaagaaggu auccaaauac gaaaacaaau ucgccaaacu 100

<210> SEQ ID NO 301
<211> LENGTH: 100
<212> TYPE: RNA
<213> ORGANISM: Diabrotica virgifera

<400> SEQUENCE: 301
ucaaaagaag gcagcugaau uuaacuuccg uaaccaacuc aaaguuguca agaagaaaga 60
auucaccuua gaagaagaag acaaagaaaa gaaaccagac 100

<210> SEQ ID NO 302
<211> LENGTH: 133
<212> TYPE: RNA
<213> ORGANISM: Diabrotica virgifera

<400> SEQUENCE: 302
gaccuuagag gcaaauucgu caaaccaacc uugaagaagg uauccaaaua cgaaaacaaa 60
uucgccaaac uucaaaagaa ggcagcugaa uuuaacuucc guaaccaacu caaaguuguc 120
aagaagaaag aau 133

<210> SEQ ID NO 303
<211> LENGTH: 500
<212> TYPE: RNA
<213> ORGANISM: Diabrotica virgifera

<400> SEQUENCE: 303
uacuaggcga aagugccguc gguaagucga guuugguacu gagguucguc aaaggacagu 60
uccacgaaua ccaggagagu accauaggag cagcuuuccu uacacaaacc auaugccucg 120
acgauacaac uguuaaauuu gaaauuuggg acacagcggg ucaagaaagg uaccacaguu 180
uagcuccuau guacuauagg ggcgcacagg cagcuauagu cgucuacgac auaaccaauc 240
aagacacauu cggcagggcg aaaacguggg ugaaggaacu ucaaaggcag gccaguccga 300
cgaucgugau agcuuuggcc ggcaacaagc aagauuuggc caacaaacgu augguagaau 360
acgaagaggc gcagacguau gcugacgaaa acggcuuacu uuuuauggaa acuuccgcaa 420
agacggcaau gaacgucaac gauauauuuu uagcaauagc uaagaaacug cccaagaaug 480
aacaaaccac aggucaaggc 500

<210> SEQ ID NO 304
<211> LENGTH: 648
<212> TYPE: RNA
<213> ORGANISM: Diabrotica virgifera

<400> SEQUENCE: 304
auggcggcaa acagaacugg accugcucag agaccaaaug gcgcuaccca aggaaagaua 60
ugucaguuca aacugguccu acuaggcgaa agugccgucg guaagucgag uuugguacug 120
agguucguca aaggacaguu ccacgaauac caggagagua ccauaggagc agcuuuccuu 180
acacaaacca uaugccucga cgauacaacu guuaaauuug aaauuuggga cacagcgggu 240
caagaaaggu accacaguuu agcuccuaug uacuauaggg gcgcacaggc agcuauaguc 300
gucuacgaca uaaccaauca agacacauuc ggcagggcga aaacgugggu gaaggaacuu 360
caaaggcagg ccaguccgac gaucgugaua gcuuuggccg gcaacaagca agauuuggcc 420
aacaaacgua ugguagaaua cgaagaggcg cagacguaug cugacgaaaa cggcuuacuu 480
uuuauggaaa cuuccgcaaa gacggcaaug aacgucaacg auauauuuuu agcaauagcu 540
aagaaacugc ccaagaauga acaaaccaca ggucaaggcg gcagugccca aggcaggcgg 600
cuagcggagg gcgauucggg cgccaaggca cccggaaauu guugcaag 648

<210> SEQ ID NO 305
<211> LENGTH: 188
<212> TYPE: RNA
<213> ORGANISM: Diabrotica virgifera

<400> SEQUENCE: 305
auggcggcaa acagaacugg accugcucag agaccaaaug gcgcuaccca aggaaagaua 60
ugucaguuca aacugguccu acuaggcgaa agugccgucg guaagucgag uuugguacug 120
agguucguca aaggacaguu ccacgaauac caggagagua ccauaggagc agcuuuccuu 180
acacaaac 188

<210> SEQ ID NO 306
<211> LENGTH: 205
<212> TYPE: RNA
<213> ORGANISM: Diabrotica virgifera

<400> SEQUENCE: 306
ggacaguucc acgaauacca ggagaguacc auaggagcag cuuuccuuac acaaaccaua 60
ugccucgacg auacaacugu uaaauuugaa auuugggaca cagcggguca agaaagguac 120
cacaguuuag cuccuaugua cuauaggggc gcacaggcag cuauagucgu cuacgacaua 180
accaaucaag acacauucgg caggg 205

<210> SEQ ID NO 307
<211> LENGTH: 224
<212> TYPE: RNA
<213> ORGANISM: Diabrotica virgifera

<400> SEQUENCE: 307
gcacaggcag cuauagucgu cuacgacaua accaaucaag acacauucgg cagggcgaaa 60
acguggguga aggaacuuca aaggcaggcc aguccgacga ucgugauagc uuuggccggc 120
aacaagcaag auuuggccaa caaacguaug guagaauacg aagaggcgca gacguaugcu 180
gacgaaaacg gcuuacuuuu uauggaaacu uccgcaaaga cggc 224

<210> SEQ ID NO 308
<211> LENGTH: 196
<212> TYPE: RNA
<213> ORGANISM: Diabrotica virgifera

<400> SEQUENCE: 308
gacguaugcu gacgaaaacg gcuuacuuuu uauggaaacu uccgcaaaga cggcaaugaa 60
cgucaacgau auauuuuuag caauagcuaa gaaacugccc aagaaugaac aaaccacagg 120
ucaaggcggc agugcccaag gcaggcggcu agcggagggc gauucgggcg ccaaggcacc 180
cggaaauugu ugcaag 196

<210> SEQ ID NO 309
<211> LENGTH: 189
<212> TYPE: RNA
<213> ORGANISM: Diabrotica virgifera

<400> SEQUENCE: 309
cgaugagguu gaaggaagga gaaaaauuuu gauggggcga aaaagcauua ccaggacaua 60
ucuucgugga aaugcuguuc cugcguaugu gauaauaauc cuuguaggaa uuggucaaau 120
cauccuggga gggauauugu acguugcauu gaggaagaag aucauugcug caccuguaac 180
ggcaucaua 189

<210> SEQ ID NO 310
<211> LENGTH: 330
<212> TYPE: RNA
<213> ORGANISM: Diabrotica virgifera

<400> SEQUENCE: 310
guguguauuu cagcuggaau uuguaaugaa aaaaacguag aaauauauac uacaaugaag 60
uuuuuaagau cgacagugug cuacauugcc aucuuggcaa uucucuuuac ccucugugcc 120
gaugagguug aaggaaggag aaaaauuuug auggggcgaa aaagcauuac caggacauau 180
cuucguggaa augcuguucc ugcguaugug auaauaaucc uuguaggaau uggucaaauc 240
auccugggag ggauauugua cguugcauug aggaagaaga ucauugcugc accuguaacg 300
gcaucauaug caguggcuag acaagaacca 330

<210> SEQ ID NO 311

<211> LENGTH: 197
<212> TYPE: RNA
<213> ORGANISM: Diabrotica virgifera

<400> SEQUENCE: 311
guguguauuu cagcuggaau uuguaaugaa aaaaacguag aaauauauac uacaaugaag 60
uuuuuaagau cgacagugug cuacauugcc aucuuggcaa uucucuuuac ccucugugcc 120
gaugagguug aaggaaggag aaaaauuuug augggcgaa aaagcauuac caggacauau 180
cuucguggaa augcugu 197

<210> SEQ ID NO 312
<211> LENGTH: 179
<212> TYPE: RNA
<213> ORGANISM: Diabrotica virgifera

<400> SEQUENCE: 312
auggggcgaa aaagcauuac caggacauau cuucguggaa augcuguucc ugcguaugug 60
auaauaaucc uuguaggaau uggucaaauc auccugggag ggauauugua cguugcauug 120
aggaagaaga ucauugcugc accuguaacg gcaucauaug caguggcuag acaagaacc 179

<210> SEQ ID NO 313
<211> LENGTH: 44
<212> TYPE: DNA
<213> ORGANISM: Diabrotica virgifera

<400> SEQUENCE: 313
gaccttagag gcaaattcgt caaaccaacc ttgaagaagg tatc 44

<210> SEQ ID NO 314
<211> LENGTH: 45
<212> TYPE: DNA
<213> ORGANISM: Diabrotica virgifera

<400> SEQUENCE: 314
caaatacgaa aacaaattcg ccaaacttca aaagaaggca gctga 45

<210> SEQ ID NO 315
<211> LENGTH: 44
<212> TYPE: DNA
<213> ORGANISM: Diabrotica virgifera

<400> SEQUENCE: 315
atttaacttc cgtaaccaac tcaaagttgt caagaagaaa gaat 44

<210> SEQ ID NO 316
<211> LENGTH: 42
<212> TYPE: DNA
<213> ORGANISM: Diabrotica virgifera

<400> SEQUENCE: 316
accaaccttg aagaaggtat ccaaatacga aaacaaattc gc 42

<210> SEQ ID NO 317
<211> LENGTH: 46
<212> TYPE: DNA
<213> ORGANISM: Diabrotica virgifera

<400> SEQUENCE: 317
caaacttcaa aagaaggcag ctgaatttaa cttccgtaac caactc 46

<210> SEQ ID NO 318
<211> LENGTH: 133
<212> TYPE: DNA
<213> ORGANISM: Diabrotica virgifera

<400> SEQUENCE: 318
gaccttagag gcaaattcgt caaaccaacc ttgaagaagg tatcgacatg gtgagcaagg 60
gcgaggagct gttcaccggg gtggtgccca tcctggtcga gctggacggc gacgtaaacg 120
gccacaagtt cag 133

<210> SEQ ID NO 319
<211> LENGTH: 134
<212> TYPE: DNA
<213> ORGANISM: Diabrotica virgifera

<400> SEQUENCE: 319
caaatacgaa aacaaattcg ccaaacttca aaagaaggca gctgagacat ggtgagcaag 60
ggcgaggagc tgttcaccgg ggtggtgccc atcctggtcg agctggacgg cgacgtaaac 120
ggccacaagt tcag 134

<210> SEQ ID NO 320
<211> LENGTH: 133
<212> TYPE: DNA
<213> ORGANISM: Diabrotica virgifera

<400> SEQUENCE: 320
atttaacttc cgtaaccaac tcaaagttgt caagaagaaa gaatgacatg gtgagcaagg 60
gcgaggagct gttcaccggg gtggtgccca tcctggtcga gctggacggc gacgtaaacg 120
gccacaagtt cag 133

<210> SEQ ID NO 321
<211> LENGTH: 131
<212> TYPE: DNA
<213> ORGANISM: Diabrotica virgifera

<400> SEQUENCE: 321
accaaccttg aagaaggtat ccaaatacga aaacaaattc gcgacatggt gagcaagggc 60
gaggagctgt tcaccggggt ggtgcccatc ctggtcgagc tggacggcga cgtaaacggc 120
cacaagttca g 131

<210> SEQ ID NO 322
<211> LENGTH: 135
<212> TYPE: DNA
<213> ORGANISM: Diabrotica virgifera

<400> SEQUENCE: 322
caaacttcaa aagaaggcag ctgaatttaa cttccgtaac caactcgaca tggtgagcaa 60
gggcgaggag ctgttcaccg ggtggtgcc catcctggtc gagctggacg gcgacgtaaa 120
cggccacaag ttcag 135

<210> SEQ ID NO 323
<211> LENGTH: 145
<212> TYPE: DNA
<213> ORGANISM: Diabrotica virgifera

<400> SEQUENCE: 323
ggatccgaca tggtgagcaa gggcgaggag ctgttcaccg ggtggtgcc catcctggtc 60 gaccaacctt gaagaaggta tcagctggac ggcgacgtaa acggccacaa gttcagcgtg 120
tccggcgagg gcgaggggcg gccgc 145

<210> SEQ ID NO 324
<211> LENGTH: 145
<212> TYPE: DNA
<213> ORGANISM: Diabrotica virgifera

<400> SEQUENCE: 324
ggatccgaca tggtgagcaa gggcgaggag ctgttcaccg gggtggtgcc catcctggtc 60
gccaaccttg aagaaggtat ccagctggac ggcgacgtaa acggccacaa gttcagcgtg 120
tccggcgagg gcgaggggcg gccgc 145

<210> SEQ ID NO 325
<211> LENGTH: 145
<212> TYPE: DNA
<213> ORGANISM: Diabrotica virgifera

<400> SEQUENCE: 325
ggatccgaca tggtgagcaa gggcgaggag ctgttcaccg gggtggtgcc catcctggtc 60
gcaaccttga agaaggtatc caagctggac ggcgacgtaa acggccacaa gttcagcgtg 120
tccggcgagg gcgaggggcg gccgc 145

<210> SEQ ID NO 326
<211> LENGTH: 145
<212> TYPE: DNA
<213> ORGANISM: Diabrotica virgifera

<400> SEQUENCE: 326
ggatccgaca tggtgagcaa gggcgaggag ctgttcaccg gggtggtgcc catcctggtc 60
gaaccttgaa gaaggtatcc aaagctggac ggcgacgtaa acggccacaa gttcagcgtg 120
tccggcgagg gcgaggggcg gccgc 145

<210> SEQ ID NO 327
<211> LENGTH: 145
<212> TYPE: DNA
<213> ORGANISM: Diabrotica virgifera

<400> SEQUENCE: 327
ggatccgaca tggtgagcaa gggcgaggag ctgttcaccg gggtggtgcc catcctggtc 60
gaccttgaag aaggtatcca atagctggac ggcgacgtaa acggccacaa gttcagcgtg 120
tccggcgagg gcgaggggcg gccgc 145

<210> SEQ ID NO 328
<211> LENGTH: 145
<212> TYPE: DNA
<213> ORGANISM: Diabrotica virgifera

<400> SEQUENCE: 328
ggatccgaca tggtgagcaa gggcgaggag ctgttcaccg gggtggtgcc catcctggtc 60
gccttgaaga aggtatccaa taagctggac ggcgacgtaa acggccacaa gttcagcgtg 120
tccggcgagg gcgaggggcg gccgc 145

<210> SEQ ID NO 329
<211> LENGTH: 145
<212> TYPE: DNA
<213> ORGANISM: Diabrotica virgifera

<400> SEQUENCE: 329
ggatccgaca tggtgagcaa gggcgaggag ctgttcaccg gggtggtgcc catcctggtc 60
gcttgaagaa ggtatccaat acagctggac ggcgacgtaa acggccacaa gttcagcgtg 120
tccggcgagg gcgaggggcg gccgc 145

<210> SEQ ID NO 330
<211> LENGTH: 145
<212> TYPE: DNA
<213> ORGANISM: Diabrotica virgifera

<400> SEQUENCE: 330
ggatccgaca tggtgagcaa gggcgaggag ctgttcaccg gggtggtgcc catcctggtc 60
gttgaagaag gtatccaata cgagctggac ggcgacgtaa acggccacaa gttcagcgtg 120
tccggcgagg gcgaggggcg gccgc 145

<210> SEQ ID NO 331
<211> LENGTH: 145
<212> TYPE: DNA
<213> ORGANISM: Diabrotica virgifera

<400> SEQUENCE: 331
ggatccgaca tggtgagcaa gggcgaggag ctgttcaccg gggtggtgcc catcctggtc 60
gtgaagaagg tatccaatac gaagctggac ggcgacgtaa acggccacaa gttcagcgtg 120
tccggcgagg gcgaggggcg gccgc 145

<210> SEQ ID NO 332
<211> LENGTH: 145
<212> TYPE: DNA
<213> ORGANISM: Diabrotica virgifera

<400> SEQUENCE: 332
ggatccgaca tggtgagcaa gggcgaggag ctgttcaccg gggtggtgcc catcctggtc 60
ggaagaaggt atccaatacg aaagctggac ggcgacgtaa acggccacaa gttcagcgtg 120
tccggcgagg gcgaggggcg gccgc 145

<210> SEQ ID NO 333
<211> LENGTH: 145
<212> TYPE: DNA
<213> ORGANISM: Diabrotica virgifera

<400> SEQUENCE: 333
ggatccgaca tggtgagcaa gggcgaggag ctgttcaccg gggtggtgcc catcctggtc 60
gaagaaggta tccaatacga aaagctggac ggcgacgtaa acggccacaa gttcagcgtg 120
tccggcgagg gcgaggggcg gccgc 145

<210> SEQ ID NO 334
<211> LENGTH: 145
<212> TYPE: DNA
<213> ORGANISM: Diabrotica virgifera

<400> SEQUENCE: 334
ggatccgaca tggtgagcaa gggcgaggag ctgttcaccg gggtggtgcc catcctggtc 60
gagaaggtat ccaatacgaa aaagctggac ggcgacgtaa acggccacaa gttcagcgtg 120
tccggcgagg gcgaggggcg gccgc 145

<210> SEQ ID NO 335
<211> LENGTH: 145
<212> TYPE: DNA
<213> ORGANISM: Diabrotica virgifera

<400> SEQUENCE: 335
ggatccgaca tggtgagcaa gggcgaggag ctgttcaccg gggtggtgcc catcctggtc 60
ggaaggtatc caatacgaaa acagctggac ggcgacgtaa acggccacaa gttcagcgtg 120
tccggcgagg gcgaggggcg gccgc 145

<210> SEQ ID NO 336
<211> LENGTH: 145
<212> TYPE: DNA
<213> ORGANISM: Diabrotica virgifera

<400> SEQUENCE: 336
ggatccgaca tggtgagcaa gggcgaggag ctgttcaccg gggtggtgcc catcctggtc 60
gaaggtatcc aatacgaaaa caagctggac ggcgacgtaa acggccacaa gttcagcgtg 120
tccggcgagg gcgaggggcg gccgc 145

<210> SEQ ID NO 337
<211> LENGTH: 145
<212> TYPE: DNA
<213> ORGANISM: Diabrotica virgifera

<400> SEQUENCE: 337
ggatccgaca tggtgagcaa gggcgaggag ctgttcaccg gggtggtgcc catcctggtc 60
gaggtatcca atacgaaaac aaagctggac ggcgacgtaa acggccacaa gttcagcgtg 120
tccggcgagg gcgaggggcg gccgc 145

<210> SEQ ID NO 338
<211> LENGTH: 145
<212> TYPE: DNA
<213> ORGANISM: Diabrotica virgifera

<400> SEQUENCE: 338
ggatccgaca tggtgagcaa gggcgaggag ctgttcaccg gggtggtgcc catcctggtc 60
gggtatccaa tacgaaaaca aaagctggac ggcgacgtaa acggccacaa gttcagcgtg 120
tccggcgagg gcgaggggcg gccgc 145

<210> SEQ ID NO 339
<211> LENGTH: 145
<212> TYPE: DNA
<213> ORGANISM: Diabrotica virgifera

<400> SEQUENCE: 339
ggatccgaca tggtgagcaa gggcgaggag ctgttcaccg gggtggtgcc catcctggtc 60
ggtatccaat acgaaaacaa atagctggac ggcgacgtaa acggccacaa gttcagcgtg 120
tccggcgagg gcgaggggcg gccgc 145

<210> SEQ ID NO 340
<211> LENGTH: 145
<212> TYPE: DNA
<213> ORGANISM: Diabrotica virgifera

<400> SEQUENCE: 340
ggatccgaca tggtgagcaa gggcgaggag ctgttcaccg gggtggtgcc catcctggtc 60
gtatccaata cgaaaacaaa ttagctggac ggcgacgtaa acggccacaa gttcagcgtg 120
tccggcgagg gcgaggggcg gccgc 145

<210> SEQ ID NO 341
<211> LENGTH: 145
<212> TYPE: DNA
<213> ORGANISM: Diabrotica virgifera

<400> SEQUENCE: 341
ggatccgaca tggtgagcaa gggcgaggag ctgttcaccg gggtggtgcc catcctggtc 60
gatccaatac gaaaacaaat tcagctggac ggcgacgtaa acggccacaa gttcagcgtg 120
tccggcgagg gcgaggggcg gccgc 145

<210> SEQ ID NO 342
<211> LENGTH: 145
<212> TYPE: DNA
<213> ORGANISM: Diabrotica virgifera

<400> SEQUENCE: 342
ggatccgaca tggtgagcaa gggcgaggag ctgttcaccg gggtggtgcc catcctggtc 60
gtccaatacg aaaacaaatt cgagctggac ggcgacgtaa acggccacaa gttcagcgtg 120
tccggcgagg gcgaggggcg gccgc 145

<210> SEQ ID NO 343
<211> LENGTH: 145
<212> TYPE: DNA
<213> ORGANISM: Diabrotica virgifera

<400> SEQUENCE: 343
ggatccgaca tggtgagcaa gggcgaggag ctgttcaccg gggtggtgcc catcctggtc 60
gccaaatacg aaaacaaatt cgagctggac ggcgacgtaa acggccacaa gttcagcgtg 120
tccggcgagg gcgaggggcg gccgc 145

<210> SEQ ID NO 344
<211> LENGTH: 145
<212> TYPE: DNA
<213> ORGANISM: Diabrotica virgifera

<400> SEQUENCE: 344
ggatccgaca tggtgagcaa gggcgaggag ctgttcaccg gggtggtgcc catcctggtc 60
gcaaatacga aaacaaattc gcagctggac ggcgacgtaa acggccacaa gttcagcgtg 120
tccggcgagg gcgaggggcg gccgc 145

<210> SEQ ID NO 345
<211> LENGTH: 44
<212> TYPE: RNA
<213> ORGANISM: Diabrotica virgifera

<400> SEQUENCE: 345
gaccuuagag gcaaauucgu caaaccaacc uugaagaagg uauc 44

<210> SEQ ID NO 346
<211> LENGTH: 45
<212> TYPE: RNA
<213> ORGANISM: Diabrotica virgifera

<400> SEQUENCE: 346
caaauacgaa aacaaauucg ccaaacuuca aaagaaggca gcuga 45

<210> SEQ ID NO 347
<211> LENGTH: 44
<212> TYPE: RNA
<213> ORGANISM: Diabrotica virgifera

<400> SEQUENCE: 347
auuuaacuuc cguaaccaac ucaaaguugu caagaagaaa gaau 44

<210> SEQ ID NO 348
<211> LENGTH: 42
<212> TYPE: RNA
<213> ORGANISM: Diabrotica virgifera

<400> SEQUENCE: 348
accaaccuug aagaagguau ccaaauacga aaacaaauuc gc 42

<210> SEQ ID NO 349
<211> LENGTH: 46
<212> TYPE: RNA
<213> ORGANISM: Diabrotica virgifera

<400> SEQUENCE: 349
caaacuucaa aagaaggcag cugaauuuaa cuuccguaac caacuc 46

<210> SEQ ID NO 350
<211> LENGTH: 21
<212> TYPE: RNA
<213> ORGANISM: Diabrotica virgifera

<400> SEQUENCE: 350
accaaccuug aagaagguau c 21

<210> SEQ ID NO 351
<211> LENGTH: 21
<212> TYPE: RNA
<213> ORGANISM: Diabrotica virgifera

<400> SEQUENCE: 351
ccaaccuuga agaagguauc c 21

<210> SEQ ID NO 352
<211> LENGTH: 21
<212> TYPE: RNA
<213> ORGANISM: Diabrotica virgifera

<400> SEQUENCE: 352
caaccuugaa gaagguaucc a 21

<210> SEQ ID NO 353
<211> LENGTH: 21
<212> TYPE: RNA
<213> ORGANISM: Diabrotica virgifera

<400> SEQUENCE: 353
aaccuugaag aagguaucca a 21

<210> SEQ ID NO 354
<211> LENGTH: 21
<212> TYPE: RNA
<213> ORGANISM: Diabrotica virgifera

<400> SEQUENCE: 354
accuugaaga agguauccaa u 21

<210> SEQ ID NO 355
<211> LENGTH: 21
<212> TYPE: RNA
<213> ORGANISM: Diabrotica virgifera

<400> SEQUENCE: 355
ccuugaagaa gguauccaau a 21

<210> SEQ ID NO 356
<211> LENGTH: 21
<212> TYPE: RNA
<213> ORGANISM: Diabrotica virgifera

<400> SEQUENCE: 356
cuugaagaag guauccaaua c 21

<210> SEQ ID NO 357
<211> LENGTH: 21
<212> TYPE: RNA
<213> ORGANISM: Diabrotica virgifera

<400> SEQUENCE: 357
uugaagaagg uauccaauac g 21

<210> SEQ ID NO 358
<211> LENGTH: 21
<212> TYPE: RNA
<213> ORGANISM: Diabrotica virgifera

<400> SEQUENCE: 358
ugaagaaggu auccaauacg a 21

<210> SEQ ID NO 359
<211> LENGTH: 21
<212> TYPE: RNA
<213> ORGANISM: Diabrotica virgifera

<400> SEQUENCE: 359
gaagaaggua uccaauacga a 21

<210> SEQ ID NO 360
<211> LENGTH: 21
<212> TYPE: RNA
<213> ORGANISM: Diabrotica virgifera

<400> SEQUENCE: 360
aagaagguau ccaauacgaa a 21

<210> SEQ ID NO 361
<211> LENGTH: 21
<212> TYPE: RNA
<213> ORGANISM: Diabrotica virgifera

<400> SEQUENCE: 361
agaagguauc caauacgaaa a 21

<210> SEQ ID NO 362
<211> LENGTH: 21
<212> TYPE: RNA
<213> ORGANISM: Diabrotica virgifera

<400> SEQUENCE: 362
gaagguaucc aauacgaaaa c 21

<210> SEQ ID NO 363
<211> LENGTH: 21
<212> TYPE: RNA
<213> ORGANISM: Diabrotica virgifera

<400> SEQUENCE: 363
aagguaucca auacgaaaac a 21

<210> SEQ ID NO 364
<211> LENGTH: 21
<212> TYPE: RNA
<213> ORGANISM: Diabrotica virgifera

<400> SEQUENCE: 364
agguauccaa uacgaaaaca a 21

<210> SEQ ID NO 365
<211> LENGTH: 21
<212> TYPE: RNA
<213> ORGANISM: Diabrotica virgifera

<400> SEQUENCE: 365
gguauccaau acgaaaacaa a 21

<210> SEQ ID NO 366
<211> LENGTH: 21
<212> TYPE: RNA
<213> ORGANISM: Diabrotica virgifera

<400> SEQUENCE: 366
guauccaaua cgaaaacaaa u 21

<210> SEQ ID NO 367
<211> LENGTH: 21
<212> TYPE: RNA
<213> ORGANISM: Diabrotica virgifera

<400> SEQUENCE: 367
uauccaauac gaaaacaaau u 21

<210> SEQ ID NO 368
<211> LENGTH: 21
<212> TYPE: RNA
<213> ORGANISM: Diabrotica virgifera

<400> SEQUENCE: 368
auccaauacg aaaacaaauu c 21

<210> SEQ ID NO 369
<211> LENGTH: 21
<212> TYPE: RNA
<213> ORGANISM: Diabrotica virgifera

<400> SEQUENCE: 369
uccaauacga aaacaaauuc g 21

<210> SEQ ID NO 370
<211> LENGTH: 21
<212> TYPE: RNA
<213> ORGANISM: Diabrotica virgifera

<400> SEQUENCE: 370
ccaaauacga aaacaaauuc g 21

<210> SEQ ID NO 371
<211> LENGTH: 21
<212> TYPE: RNA
<213> ORGANISM: Diabrotica virgifera

<400> SEQUENCE: 371
caaauacgaa aacaaauucg c 21

<210> SEQ ID NO 372
<211> LENGTH: 5055
<212> TYPE: DNA
<213> ORGANISM: Diabrotica virgifera

<400> SEQUENCE: 372
atgacgcagc aactgttacc tatcaagttc caagaacatt tgcagcttac caatgttggt 60
atccatgcta ccaacatcac gttcgccaat ctcaccatgg agagcgacaa gtacatctgc 120
gtgagagaaa aagttggaga gacgtcccaa gtagtcatca tagatatggc cgatacggcc 180
aatcccatca gacgaccaat caccgccgaa agtgctatta tgaatccagc atccaaagtc 240
atcgctctta aaggtaaagc aggcgtagaa acacaaaaaa cccttcaaat attcaacata 300
gaaatgaagt caaaaatgaa agcccacacc atgtctgaag acgtaatttt ctggaaatgg 360
atcagcccca atacgttagc gctagtcact gaaacttcag tgtatcattg gtccatggaa 420
ggtgattcaa ttccacagaa aatgtttgac aggcattctt ctcttaacgg ctgccaaatc 480
atcaactacc gaacagatcc caaacaaaac tggctgctac tggtcggtat tagcgctcag 540
caatctcgcg tcgttggtgc tatgcaactg tactcagtag aaagaaaatg ctcgcagcca 600
atcgaaggtc acgccgcttc tttcgcgacc ttcaaaatgg aaggaaaccc tgaaccatcg 660
actctcttct gttttgcagt gaggacttta caaggaggaa agttacatat tatcgaggtt 720
ggtcaaagtc cagcaggcaa ccaatcgttt cctaaaaaga cagtggatgt tttcttccca 780
cccgaggccc aaaatgattt tcctgtagct atgcaagtgt ccgctaaata cgacgtcatt 840
tacctgatta ccaaatacgg ctatattcat atgtatgaca tcgagagcgg cacctgtatc 900
tacatgaaca gaatatctag tgacacaata ttcgtaaccg caccccacga agctacggga 960
ggaatcattg gtgttaatag aaagggtcaa gtcctatctg tctcggtaga tgaggagagc 1020
attattcgat acatcaacac cgtcttacac aatgctgact tagcgctgcg tctagctacg 1080
agaaacaatc tttcaggagc cgaagaactg tttgttagta aattccagat gttgttccag 1140
aacggacagt acgccgaagc tgctaaagtg gctgccaacg ctccaaaagg aattttaaga 1200
accccagcta caattcaaat gtttcaacaa gtcccgactc aacctggaca aaacagtccc 1260
cttttgcaat atttcggtat acttctagac caagggcaac taaacagata cgaatctttg 1320
gaattgtgta aaccagtttt gttgcaaggt cgcaaacagc ttctagaaaa atggttaaaa 1380
gaggaaaaat tagaatgttc cgaagaatta ggagacctag tcaaacaggc agatcctact 1440
ctggctttat ctgtgtatct tagagctaat gtacctgcaa aagttatcca aagctttgcc 1500
gaaactggcc aattccaaaa gatagtcctc tacgccaaaa aagtgtctta tactcccgac 1560
tatgtattcc tgcttcgcca agtcatgcgc accaatcccg accaaggcgc agcatttgca 1620
gggatgttgg tagcggacga cgaacctttg gccgatatca accaaatcgt ggacattttc 1680

-continued

```
atggagcaaa acatggtgca gcagtgtact gcgttcttgt tggacgcctt aaagaataac   1740
aggcctactg aggggcatct acaaactaga ctattagaaa tgaacctgat gtccgcaccg   1800
caagtagcag acgccattct cggcaacaac atgttcactc actacgaccg gccccacgta   1860
gcccagctct gcgaaaaagc tggtctttta caaagagctc tagaacacta cactgatttg   1920
tatgacatca aacgtgctgt ggtacacacc cacttgcttc cagctgattg gttggttaac   1980
ttcttcggaa ctctcagcgt ggaagacagt ttggagtgct tgagggccat gctgaccgcg   2040
aatattcgac agaatttgca gatttgcgtg cagatcgcta ccaagtacca cgaacaactc   2100
accactaagg ctttgatcga tttgtttgaa ggatttaaga gctatgaggg tttgttctat   2160
ttcctcggct ccatcgtcaa cttctcccaa gaccaagaag tgcacttcaa gtacatccaa   2220
gccgcatgca agactggcca aatcaaagaa gtcgagcgta tctgtaggga atcaaactgc   2280
tacaatcccg aaagagtcaa gaatttcctg aaggaagcca aacttacaga tcagttgccg   2340
ttgattattg tctgtgacag atttgatttc gtccacgact tagtgttgta tctatataga   2400
aattcgctgc agaaatatat cgagatttat gtccagaagg tcaatcccag ccgtttaccg   2460
gttgtggtag gaggtctttt agatgtcgac tgttccgaag acataatcaa aaacctaatt   2520
cttgtcgtca gaggccagtt ctccactgac gaattagtag aagaagtaga aaagaggaac   2580
agattgaaac tgttgttgcc ctggttggag agcagagtac acgaaggatg tgtcgagcca   2640
gctacgcaca atgctttggc caagatctac atcgattcca acaacaatgc cgaaagattc   2700
ttgaaggaaa atcaatggta cgattcccga gttgtgggac gttattgcga aaagcgcgat   2760
ccacatctgg cttgcgttgc ttacgaacga ggccaatgcg acagagaact gatagctgta   2820
tgtaacgaaa actctctatt taagtctgaa gctcgttatt tggtccgtag acgtgacgga   2880
gaattatggg ctgaggtttt gaacgagagc aatccttaca gacgtcagtt gatagaccaa   2940
gtagtgcaaa cagctttaag tgaaacccaa gaccccgaag atatctctgt taccgttaaa   3000
gcattcatga cagctgattt accaaatgag ctcattgaat tgttggaaaa gattgtattg   3060
gatagttctg tgttctccga gcatagaaac cttcaaaatt tgcttatcct aacagcaatc   3120
aaagccgatg ctacaagagt tatggactac atcaaccgct tggataacta cgatgcccct   3180
gatatcgcga atatagccat caacaaccat ctctatgaag aagctttcgc tattttcaag   3240
aaatttgatg tcaacacctc agctattcaa gtattgatcg aacaagtcaa caatctggat   3300
cgtgcttatg aattcgcaga acgttgcaat gaaccggccg tatggagtca gctggccaaa   3360
gcgcaactga accaaggctt agtcaaggaa gcaatcgatt cttacattaa agctgatgat   3420
ccttcagctt ataaggacgt cgttgagacc gcttcgaaaa ataatagctg ggaggactta   3480
gtgcggtatt tgcagatggc aagaaagaag gccagagaga gctacatcga atctgaattg   3540
atttattcgt acgcgaagac cggaagattg gctgatttgg aagaattcat cagtggaccc   3600
aaccatgctg atatccagaa gattggtgat aggtgctttg atgacaagat gtatgatgct   3660
gctaagctac tctacaacaa tgtatccaac ttcgctcgtc tcgctattac tttagtgcat   3720
ctaaaagaat tccagggagc tgttgacagt gctaggaagg ctaatagtac cagaacatgg   3780
aaggaagtgt gttttgcttg cgtcgatgcc gaagaattca gattggctca gatgtgtggt   3840
atgcacatcg tggtacacgc tgatgagttg caagatttga ttaattatta tcaagataga   3900
ggatactttg aagaattaat cggcctattg gaagcagcat tgggcttgga aagggcacac   3960
atgggtatgt tcaccgaatt agcaattttg tattccaaat ataagcccgc caaaatgcgc   4020
gaacatctgg aactcttctg gtctcgagtg aatatcccca aagttcttag ggcagctgaa   4080
```

caagcacatt tgtgggcaga gctagtgttt ttgtatgaca aatatgaaga atatgataac 4140
gctgtgttag ccatgatggc tcatcccacc gaagcttggc gcgaaggtca tttcaaggat 4200
attattacaa aagttgccaa tatcgaactt tattatagag ctattcaatt ttacttggat 4260
tacaaaccgc tgttgttaaa tgaccttttg ttggtgttgg cacccaggat ggatcatact 4320
agggctgttt ctttctttac aaaaacagga cacttacagt tggttaaatc ctatctccgg 4380
tctgtgcaaa atttgaacaa caaagctatc aacgaggccc tcaactctct acttatcgaa 4440
gaagaagact tccagggtct gagaacgtcc atcgacgcct tcgataactt cgacaacatc 4500
ggcttggctc agaaattgga gaagcacgaa ctgacggagt tcagacgcat cgccgcctac 4560
ttgtacaaag gcaacaaccg gtggaagcag agcgtagaac tgtgcaaaaa ggatagacta 4620
tttagagacg ctatggagta cacttctgaa tctagaaatc aagaattggc cgaagagttg 4680
ctggcatggt tcttggatag gaaggcctat gattgttttt cggcatgttt gtatcactgc 4740
tacgacttgt tacggcccga cgttatcctt gaactagcat ggaaacacaa cattatggac 4800
ttcgcaatgc ctttccttat tcaagtaact agagaactga cgacaaaagt agaaaagcta 4860
gaacaatcag atgcccaacg acaaagcgag gctgctgaag aaacgaacaa gccaatgatg 4920
ataccagaac cccaacttat gctaacggct ggccctggca tgggtattcc accccaacag 4980
tatgtacctc cccaaggcta cgcgcagcca ggctacgccc cgcaaatggc ttaccaggga 5040
tacccaggca tgtaa 5055

<210> SEQ ID NO 373
<211> LENGTH: 5055
<212> TYPE: RNA
<213> ORGANISM: Diabrotica virgifera

<400> SEQUENCE: 373
augacgcagc aacuguuacc uaucaaguuc caagaacauu ugcagcuuac caauguuggu 60
auccaugcua ccaacaucac guucgccaau cucaccaugg agagcgacaa guacaucugc 120
gugagagaaa aaguuggaga gacgucccaa guagucauca uagauauggc cgauacggcc 180
aaucccauca gacgaccaau caccgccgaa agugcuauua ugaauccagc auccaaaguc 240
aucgcucuua aagguaaagc aggcguagaa acacaaaaaa cccuucaaau auucaacaua 300
gaaaugaagu caaaaaugaa agcccacacc augucugaag acguaauuuu cuggaaaugg 360
aucagcccca auacguuagc gcuagucacu gaaacuucag uguaucauug guccauggaa 420
ggugauucaa uuccacagaa aauguuugac aggcauucuu cucuuaacgg cugccaaauc 480
aucaacuacc gaacagaucc caaacaaaac uggcugcuac uggucgguau uagcgcucag 540
caaucucgcg ucguuggugc uaugcaacug uacucaguag aaagaaaaug cucgcagcca 600
aucgaagguc acgccgcuuc uuucgcgacc uucaaaaugg aaggaaaccc ugaaccaucg 660
acucucuucu guuuugcagu gaggacuuua caaggaggaa aguuacauau uaucgagguu 720
ggucaaaguc cagcaggcaa ccaaucguuu ccuaaaaaga caguggaugu uuucuuccca 780
cccgaggccc aaaaugauuu uccuguagcu augcaagugu ccgcuaaaua cgacgucauu 840
uaccugauua ccaaauacgg cuauauucau auguaugaca ucgagagcgg caccuguauc 900
uacaugaaca gaauaucuag ugacacaaua uucguaaccg caccccacga agcuacggga 960
ggaaucauug guguuaauag aaagggucaa guccuaucug ucucgguaga ugaggagagc 1020
auuauucgau acaucaacac cgucuuacac aaugcugacu uagcgcugcg ucuagcuacg 1080
agaaacaauc uuucaggagc cgaagaacug uuuguuagua aauuccagau guuguuccag 1140
aacggacagu acgccgaagc ugcuaaagug gcugccaacg cuccaaaagg aauuuuaaga 1200
accccagcua caauucaaau guuucaacaa gucccgacuc aaccuggaca aaacaguccc 1260
cuuuugcaau auuucgguau acuucuagac caagggcaac uaaacagaua cgaaucuuug 1320
gaauugugua aaccaguuuu guugcaaggu cgcaaacagc uucuagaaaa augguuaaaa 1380
gaggaaaaau uagaauguuc cgaagaauua ggagaccuag ucaaacaggc agauccuacu 1440
cuggcuuuau cuguguaucu uagagcuaau guaccugcaa aaguuaucca aagcuuugcc 1500
gaaacuggcc aauuccaaaa gauaguccuc uacgccaaaa aagugucuua uacucccgac 1560
uauguauucc ugcuucgcca agucaugcgc accaaucccg accaaggcgc agcauuugca 1620
gggauguugg uagcggacga cgaaccuuug gccgauauca accaaaucgu ggacauuuuc 1680
auggagcaaa acauggugca gcaguguacu gcguucuugu uggacgccuu aaagaauaac 1740
aggccuacug aggggcaucu acaaacuaga cuauuagaaa ugaaccugau guccgcaccg 1800
caaguagcag acgccauucu cggcaacaac auguucacuc acuacgaccg gccccacgua 1860
gcccagcucu gcgaaaaagc uggucuuuua caaagagcuc uagaacacua cacugauuug 1920
uaugacauca aacgugcugu gguacacacc cacuugcuuc cagcugauug guugguuaac 1980
uucuucggaa cucucagcgu ggaagacagu uuggagugcu ugagggccau gcugaccgcg 2040
aauauucgac agaauuugca gauuugcgug cagaucgcua ccaaguacca cgaacaacuc 2100
accacuaagg cuuugaucga uuuguuugaa ggauuuaaga gcuaugaggg uuuguucuau 2160
uuccucggcu ccaucgucaa cuucucccaa gaccaagaag ugcacuucaa guacauccaa 2220
gccgcaugca agacuggcca aaucaaagaa gucgagcgua ucuguaggga aucaaacugc 2280
uacaaucccg aaagagucaa gaauuuccug aaggaagcca aacuuacaga ucaguugccg 2340
uugauuauug ucugugacag auuugauuuc guccacgacu uaguguugua ucuauauaga 2400
aauucgcugc agaaauauau cgagauuuau guccagaagg ucaaucccag ccguuuaccg 2460
guugugguag gaggucuuuu agaugucgac uguuccgaag acauaaauca aaaccuaauu 2520
cuugucguca gaggccaguu cuccacugac gaauuaguag aagaaguaga aaagaggaac 2580
agauugaaac uguuguugcc cugguuggag agcagaguac acgaaggaug ugucgagcca 2640
gcuacgcaca augcuuuggc caagaucuac aucgauucca acaacaaugc cgaaagauuc 2700
uugaaggaaa aucaauggua cgauucccga guugugggac guuauugcga aaagcgcgau 2760
ccacaucugg cuugcguugc uuacgaacga ggccaaugcg acagagaacu gauagcugua 2820
uguaacgaaa acucucuauu uaagucugaa gcucguuauu ugguccguag acgugacgga 2880
gaauuauggg cugagguuuu gaacgagagc aauccuuaca gacgucaguu gauagaccaa 2940
guagugcaaa cagcuuuaag ugaaacccaa gaccccgaag auaucucugu uaccguuaaa 3000
gcauucauga cagcugauuu accaaaugag cucauugaau uguuggaaaa gauuguauug 3060
gauaguucug uguucuccga gcauagaaac cuucaaaauu ugcuuaucuu aacagcaauc 3120
aaagccgaug cuacaagagu uauggacuac aucaaccgcu uggauaacua cgaugccccu 3180
gauaucgcga auauagccau caacaaccau cucuaugaag aagcuuucgc uauuuucaag 3240
aaauuugaug ucaacaccuc agcuauucaa guauugaucg aacaagucaa caaucuggau 3300
cgugcuuaug aauucgcaga acguugcaau gaaccggccg uauggaguca gcuggccaaa 3360
gcgcaacuga accaaggcuu agucaaggaa gcaaucgauu cuuacauuaa agcugaugau 3420
ccuucagcuu auaaggacgu cguugagacc gcuucgaaaa auaauagcug ggaggacuua 3480
gugcgguauu ugcagauggc aagaaagaag gccagagaga gcuacaucga aucugaauug 3540
auuuauucgu acgcgaagac cggaagauug gcugauuugg aagaauucau caguggaccc 3600
aaccaugcug auauccagaa gauuggugau aggugcuuug augacaagau guaugaugcu 3660
gcuaagcuac ucuacaacaa uguauccaac uucgcucguc ucgcuauuac uuuagugcau 3720
cuaaaagaau uccagggagc uguugacagu gcuaggaagg cuaauaguac cagaacaugg 3780
aaggaagugu guuuugcuug cgucgaugcc gaagaauuca gauuggcuca gauguguggu 3840
augcacaucg ugguacacgc ugaugaguug caagauuuga uuaauuauua ucaagauaga 3900
ggauacuuug aagaauuaau cggccuauug gaagcagcau ugggcuugga aagggcacac 3960 augggguaugu ucaccgaauu agcaauuuug uauuccaaau auaagcccgc caaaaugcgc 4020
gaacaucugg aacucuucug gucucgagug aauaucccca aaguucuuag ggcagcugaa 4080
caagcacauu ugugggcaga gcuaguguuu uuguaugaca aauaugaaga auaugauaac 4140
gcuguguuag ccaugauggc ucaucccacc gaagcuuggc gcgaagguca uuucaaggau 4200
auuauuacaa aaguugccaa uaucgaacuu uauuauagag cuauucaauu uuacuuggau 4260
uacaaaccgc uguuguuaaa ugaccuuuug uuggugguugg cacccaggau ggaucauacu 4320
agggcuguuu cuuucuuuac aaaaacagga cacuuacagu ugguuaaauc cuaucuccgg 4380
ucugugcaaa auuugaacaa caaagcuauc aacgaggccc ucaacucucu acuuaucgaa 4440
gaagaagacu uccagggucu gagaacgucc aucgacgccu ucgauaacuu cgacaacauc 4500
ggcuuggcuc agaaauugga gaagcacgaa cugacggagu ucagacgcau cgccgccuac 4560
uuguacaaag gcaacaaccg guggaagcag agcguagaac ugugcaaaaa ggauagacua 4620
uuuagagacg cuauggagua cacuucugaa ucuagaaauc aagaauuggc cgaagaguug 4680
cuggcauggu ucuuggauag gaaggccuau gauuguuuuu cggcauguuu guaucacugc 4740
uacgacuugu uacggcccga cguuauccuu gaacuagcau ggaaacacaa cauuauggac 4800
uucgcaaugc cuuuccuuau ucaaguaacu agagaacuga cgacaaaagu agaaaagcua 4860
gaacaaucag augcccaacg acaaagcgag gcugcugaag aaacgaacaa gccaaugaug 4920
auaccagaac cccaacuuau gcuaacggcu ggcccuggca uggguauucc accccaacag 4980
uauguaccuc cccaaggcua cgcgcagcca ggcuacgccc cgcaaauggc uuaccaggga 5040
uacccaggca uguaa 5055

<210> SEQ ID NO 374
<211> LENGTH: 7132
<212> TYPE: RNA
<213> ORGANISM: Diabrotica virgifera

<400> SEQUENCE: 374
ccggccugua caaaagggcg acgccauauu agauguuuga uucagcuagc ugucaguuua 60
gugaaaaaau ugucauuuuc cuuaaauuuc cgaaaacguu ucaauaagua aaguggaaag 120
uguuuaaauu uuauuuugug uuuuguugca aagaaaaagc aacaugacgc agcaacuguu 180
accuaucaag uuccaagaac auuugcagcu uaccaauguu gguauccaug cuaccaacau 240
cacguucgcc aaucucacca uggagagcga caaguacauc ugcgugagag aaaaaguugg 300
agagacgucc caaguaguca ucauagauau ggccgauacg gccaaucccca ucagacgacc 360 aaucaccgcc gaaagugcua uuaugaaucc agcauccaaa gucaucgcuc uuaaagguaa 420
agcaggcgua gaaacacaaa aaacccuuca aauauucaac auagaaauga agucaaaaau 480

-continued

```
gaaagcccac accaugucug aagacguaau uuucuggaaa uggaucagcc ccaauacguu    540
agcgcuaguc acugaaacuu caguguauca uugguccaug gaaggugauu caauuccaca    600
gaaaauguuu gacaggcauu cuucucuuaa cggcugccaa aucaucaacu accgaacaga    660
ucccaaacaa aacuggcugc uacuggucgg uauuagcgcu cagcaaucuc gcgucguugg    720
ugcuaugcaa cuguacucag uagaaagaaa augcucgcag ccaaucgaag gucacgccgc    780
uucuuucgcg accuucaaaa uggaaggaaa cccugaacca ucgacucucu ucuguuuugc    840
agugaggacu uuacaaggag gaaaguuaca uauuaucgag guuggucaaa guccagcagg    900
caaccaaucg uuuccuaaaa agacagugga uguuuucuuc ccacccgagg cccaaaauga    960
uuuuccugua gcuaugcaag uguccgcuaa auacgacguc auuuaccuga uuaccaaaua   1020
cggcuauauu cauauguaug acaucgagag cggcaccugu aucuacauga acagaauauc   1080
uagugacaca auauucguaa ccgcaccccca cgaagcuacg ggaggaauca uugguguuaa   1140
uagaaagggu caaguccuau cugucucggu agaugaggag agcauuauuc gauacaucaa   1200
caccgucuua cacaaugcug acuuagcgcu gcgucuagcu acgagaaaca aucuuucagg   1260
agccgaagaa cuguuuguua guaaauucca gauguuguuc cagaacggac aguacgccga   1320
agcugcuaaa guggcugcca acgcuccaaa aggaauuuua agaaccccag cuacaauuca   1380
aauguuucaa caagucccga cucaaccugg acaaaacagu ccccuuuugc aauauuucgg   1440
uauacuucua gaccaagggc aacuaaacag auacgaaucu uuggaauugu guaaaccagu   1500
uuuguugcaa ggucgcaaac agcuucuaga aaaaugguua aaagaggaaa aauuagaaug   1560
uuccgaagaa uuaggagacc uagucaaaca ggcagauccu acucuggcuu uaucugugua   1620
ucuuagagcu aauguaccug caaaaguuau ccaaagcuuu gccgaaacug gccaauucca   1680
aaagauaguc cucuacgcca aaaaaguguc uuauacuccc gacuauguau uccugcuucg   1740
ccaagucaug cgcaccaauc ccgaccaagg cgcagcauuu gcagggaugu ugguagcgga   1800
cgacgaaccu uuggccgaua ucaaccaaau cguggacauu uucauggagc aaaacauggu   1860
gcagcagugu acugcguucu uguuggacgc cuuaaagaau aacaggccua cugaggggca   1920
ucuacaaacu agacuauuag aaaugaaccu gauguccgca ccgcaaguag cagacgccau   1980
ucucggcaac aacauguuca cucacuacga ccggccccac guagcccagc ucugcgaaaa   2040
agcuggucuu uuacaaagag cucuagaaca cuacacugau uuguaugaca ucaaacgugc   2100
ugugguacac acccacuugc uuccagcuga uugguugguu aacuucuucg gaacucucag   2160
cguggaagac aguuuggagu gcuugagggc caugcugacc gcgaauauuc gacagaauuu   2220
gcagauuugc gugcagaucg cuaccaagua ccacgaacaa cucaccacua aggcuuugau   2280
cgauuuguuu gaaggauuua agagcuauga ggguuuguuc uauuuccucg gcuccaucgu   2340
caacuucucc caagaccaag aagugcacuu caaguacauc caagccgcau gcaagacugg   2400
ccaaaucaaa gaagucgagc guaucuguag ggaaucaaac ugcuacaauc ccgaaagagu   2460
caagaauuuc cugaaggaag ccaaacuuac agaucaguug ccguugauua uugucuguga   2520
cagauuugau uucguccacg acuuaguguu guaucuauau agaaauucgc ugcagaaaua   2580
uaucgagauu uauguccaga aggucaaucc cagccguuua ccgguugugg uaggaggucu   2640
uuuagauguc gacuguuccg aagacauaau caaaaaccua auucuugucg ucagaggcca   2700
guucuccacu gacgaauuag uagaagaagu agaaaagagg aacagauuga aacuguuguu   2760
gcccugguug gagagcagag uacacgaagg augugucgag ccagcuacgc acaaugcuuu   2820
ggccaagauc uacaucgauu ccaacaacaa ugccgaaaga uucuugaagg aaaaucaaug   2880
```

guacgauucc cgaguugugg gacguuauug cgaaaagcgc gauccacauc uggcuugcgu 2940
ugcuuacgaa cgaggccaau gcgacagaga acugauagcu guauguaacg aaaacucucu 3000
auuuaagucu gaagcucguu auuugguccg uagacgugac ggagaauuau gggcugaggu 3060
uuugaacgag agcaauccuu acagacguca guugauagac caaguagugc aaacagcuuu 3120
aagugaaacc caagaccccg aagauaucuc uguuaccguu aaagcauuca ugacagcuga 3180
uuuaccaaau gagcucauug aauuguugga aaagauugua uuggauaguu cuguguucuc 3240
cgagcauaga aaccuucaaa auuugcuuau ccuaacagca aucaaagccg augcuacaag 3300
aguuauggac uacaucaacc gcuuggauaa cuacgaugcc ccugauaucg cgaauauagc 3360
caucaacaac caucucuaug aagaagcuuu cgcuauuuuc aagaaauuug augucaacac 3420
cucagcuauu caaguauuga ucgaacaagu caacaaucug gaucgugcuu augaauucgc 3480
agaacguugc aaugaaccgg ccguauggag ucagcuggcc aaagcgcaac ugaaccaagg 3540
cuuagucaag gaagcaaucg auucuuacau uaaagcugau gauccuucag cuuauaagga 3600
cgucguugag accgcuucga aaaauaauag cugggaggac uuagugcggu auuugcagau 3660
ggcaagaaag aaggccagag agagcuacau cgaaucugaa uugauuuauu cguacgcgaa 3720
gaccggaaga uuggcugauu uggaagaauu caucagugga cccaaccaug cugauaucca 3780
gaagauuggu gauaggugcu uugaugacaa gauguaugau gcugcuaagc uacucuacaa 3840
caauguaucc aacuucgcuc gucucgcuau uacuuuagug caucuaaaag aauuccaggg 3900
agcuguugac agugcuagga aggcuaauag uaccagaaca uggaaggaag uguguuuugc 3960
uugcgucgau gccgaagaau ucagauuggc ucagaugugu gguaugcaca ucgugguaca 4020
cgcugaugag uugcaagauu ugauuaauua uuaucaagau agaggauacu uugaagaauu 4080
aaucggccua uuggaagcag cauugggcuu ggaaagggca cacaugggua uguucaccga 4140
auuagcaauu uuguauucca aauauaagcc cgccaaaaug cgcgaacauc uggaacucuu 4200
cuggucucga gugaauaucc ccaaaguucu uagggcagcu gaacaagcac auuugugggc 4260
agagcuagug uuuuuguaug acaaauauga agaauaugau aacgcugugu uagccaugau 4320
ggcucauccc accgaagcuu ggcgcgaagg ucauuucaag gauauuauua caaaaguugc 4380
caauaucgaa cuuuauuaua gagcuauuca auuuuacuug gauuacaaac cgcuguuguu 4440
aaaugaccuu uuguuggugu uggcacccag gauggaucau acuagggcug uuucuuucuu 4500
uacaaaaaca ggacacuuac aguugguuaa auccuaucuc cggucugugc aaaauuugaa 4560
caacaaagcu aucaacgagg cccucaacuc ucuacuuauc gaagaagaag acuuccaggg 4620
ucugagaacg uccaucgacg ccuucgauaa cuucgacaac aucggcuugg cucagaaauu 4680
ggagaagcac gaacugacgg aguucagacg caucgccgcc uacuuguaca aaggcaacaa 4740
ccgguggaag cagagcguag aacugugcaa aaaggauaga cuauuuagag acgcuaugga 4800
guacacuucu gaaucuagaa aucaagaauu ggccgaagag uugcuggcau gguucuugga 4860
uaggaaggcc uaugauuguu uuucggcaug uuuguaucac ugcuacgacu uguuacggcc 4920
cgacguuauc cuugaacuag cauggaaaca caacauuaug gacuucgcaa ugccuuuccu 4980
uauucaagua acuagagaac ugacgacaaa aguagaaaag cuagaacaau cagaugccca 5040
acgacaaagc gaggcugcug aagaaacgaa caagccaaug augauaccag aaccccaacu 5100
uaugcuaacg gcuggcccug gcaugggguau uccaccccaa caguauguac cuccccaagg 5160
cuacgcgcag ccaggcuacg ccccgcaaau ggcuuaccag ggauacccag gcauguaaua 5220
uaaggccccu uuuacagcca acuguauagg aaaguggaau uaguuuucaa guuaaacuga 5280
ggagcuagug cuaaggacaa uagagaaguu auaacuaaaa aaauagcggu uccaauucgu 5340
uucguguauu augaacaacg uuacuuucua aaagaagaag aauauauuga ggaguucguu 5400
uuaaaauuau guacaaguag aaguuuuaau acuugguuaa cuaaaaacgu uacauuuuuu 5460
ugagauuaca aauaacugaa uaauugaaaa uauuacuuac aauuuuaugc gaacugcucg 5520
auaaauuucu caaaaauagc aaaacaaaua auagguuuau ugaaguguua cagaaaauuu 5580
aggcauuucc uuuaaaucaa auaaaauguuu cauuauuugu gugaaaaguu auuuauuaac 5640
auuauucauc uuuugcuaaa aaacaguuga gauuauugca aaauguuauu gcauuuugaa 5700
aguaaagaug uaaauguguu acaaaugauc uauuuguagu uuugucauca uuauguuuug 5760
uuuuuccguc cauuguugag uauauuucuu cauaaauaaa guaucagaug auguuuauau 5820
auaauacaau aauuuuuauu cuuuaaucgc uucaauauuu guuauaaugu cuucaauuuc 5880
aacauauugu uuuuuuuguc guauuggucu uuuuaguguu uccugccacc ucuaaccaau 5940
uauuaggcga uuuuacauga ggauuaagcc uacagauguc aaaauggcgu cauaucuauc 6000
gaaugacaac ugacaguuga agugucauau uuaaauuaug aucauacugu uccgucuuuc 6060
uucgucugua auucuaauuc guucauaacg aucuaccuac ucuuuucauu uuuuuuugug 6120
uaguuauuua ggcauuuuua agucuacgac ugucaaaaua gugucaacug acaaguugga 6180
agugucauac uuaaauuauc accauuuuau ccugacuccc uuugucuuca auuuugauuu 6240
cauaauaauu uuuauuucag ugcccacuug aaccuuuuuu uauaauuuac auaucucaua 6300
gucauuuuua ggcguuuaac uuacaacauu guuuccacac acauuuucca gcuucgauau 6360
caguuauuga uuuacaauaa uuuaaauuug cuccuuuaua caaauguaac aacccaauuc 6420
caacccuuuu auuaauuuuc uuuuuguuuu gauaagauuu auuugcaaca aacaauucua 6480
gcgaaggaag aauuuccaac aaguuaaaaa caaacuuauu ucaauuguca aaccuuuuaa 6540
uuuucuuucg aaaucuugau auuucuuucg cuagaauaau ugccccaaau ugaauuucag 6600
guacuuuccu ucgagucaag aucuggucau aaccccaaaa aagacaguug acgugucgug 6660
ucaugacacu gacguuugaa cacuucaauu gucaguuguc auggaagacc guugguagag 6720
auaaaaugac caaauuuucu guagcacauu auguaagcuu aaagcuuaaa gaauaaaugc 6780
uuaaacaaau ucuaguuaaa uacaaucaau cuuguugaac uguuuguugu aguuuuaauu 6840
cauucgcauc auuuucggac auuaggcuuc guuuugacgg gacacuugau uuacuuuuuc 6900
aguuggagaa uguauauaua uuuuuaugua cuagcacccc acuuuagaau guauauaauc 6960
uaaagaaauu auuuuguuuu ccgagagaau uaucaaugcg uucuuuuguu uguuuucuuu 7020
uuuuuagucc guuuaucauu ccuuuauuua aacauagaua uauguauaug aagugacuau 7080
uuaacuuaua uuauuauaug aauuauauga aagugauucu ucaauguuua au 7132

<210> SEQ ID NO 375
<211> LENGTH: 5055
<212> TYPE: RNA
<213> ORGANISM: Diabrotica virgifera

<400> SEQUENCE: 375
uacugcgucg uugacaaugg auaguucaag guucuuguaa acgucgaaug guuacaacca 60
uagguacgau gguuguagug caagcgguua gagugguacc ucucgcuguu cauguagacg 120
cacucucuuu uucaaccucu cugcaggguu caucaguagu aucuauaccg gcuaugccgg 180
uuaggguagu cugcugguua guggcggcuu ucacgauaau acuuaggucg uagguuucag 240

```
uagcgagaau uuccauuucg uccgcaucuu uguguuuuuu gggaaguuua uaaguuguau    300
cuuuacuuca guuuuuacuu ucgggugugg uacagacuuc ugcauuaaaa gaccuuuacc    360
uagucggggu uaugcaaucg cgaucaguga cuuugaaguc acauaguaac cagguaccuu    420
ccacuaaguu aaggugucuu uuacaaacug uccguaagaa gagaauugcc gacgguuuag    480
uaguugaugg cuugucuagg guuuguuuug accgacgaug accagccaua aucgcgaguc    540
guuagagcgc agcaaccacg auacguugac augagucauc uuucuuuuac gagcgucggu    600
uagcuuccag ugcggcgaag aaagcgcugg aaguuuuacc uuccuuuggg acuugguagc    660
ugagagaaga caaaacguca cuccugaaau guuccuccuu ucaauguaua auagcuccaa    720
ccaguuucag gucguccguu gguuagcaaa ggauuuuucu gucaccuaca aaagaagggu    780
gggcuccggg uuuuacuaaa aggacaucga uacguucaca ggcgauuuau gcugcaguaa    840
auggacuaau gguuuaugcc gauauaagua uacauacugu agcucucgcc guggacauag    900
auguacuugu cuuauagauc acuguguuau aagcauuggc guggggugcu ucgaugcccu    960
ccuuaguaac cacaauuauc uuucccaguu caggauagac agagccaucu acuccucucg   1020
uaauaagcua uguaguugug gcagaaugug uuacgacuga aucgcgacgc agaucgaugc   1080
ucuuuguuag aaaguccucg gcuucuugac aaacaaucau uuaaggucua caacaagguc   1140
uugccuguca ugcggcuucg acgauuucac cgacgguugc gagguuuucc uuaaaaauucu  1200
ugggucgau guuaaguuua caaaguuguu cagggcugag uuggaccugu uuugucaggg   1260
gaaaacguua uaaagccaua ugaagaucug guucccguug auuugucuau gcuuagaaac   1320
cuuaacacau uuggucaaaa caacguucca gcguuugucg aagaucuuuu uaccaauuuu   1380
cuccuuuuua aucuuacaag gcuucuuaau ccucuggauc aguuuguccg ucuaggauga   1440
gaccgaaaua gacacauaga aucucgauua cauggacguu uucaauaggu uucgaaacgg   1500
cuuugaccgg uuaagguuuu cuaucaggag augcgguuuu uucacagaau augagggcug   1560
auacauaagg acgaagcggu ucaguacgcg ugguuagggc ugguuccgcg ucguaaacgu   1620
cccuacaacc aucgccugcu gcuuggaaac cggcuauagu ugguuuagca ccuguaaaag   1680
uaccucguuu uguaccacgu cgucacauga cgcaagaaca accugcggaa uuucuuauug   1740
uccggaugac uccccguaga uguuugaucu gauaaucuuu acuuggacua caggcguggc   1800
guucaucguc ugcgguaaga gccguuguug uacaagugag ugaugcuggc cggggugcau   1860
cgggucgaga cgcuuuuucg accagaaaau guuucucgag aucuugugau gugacuaaac   1920
auacuguagu uugcacgaca ccaugugugg gugaacgaag gucgacuaac caaccaauug   1980
aagaagccuu gagagucgca ccuucuguca aaccucacga acucccggua cgacuggcgc   2040
uuauaagcug ucuuaaacgu cuaaacgcac gucuagcgau gguucauggu gcuuguugag   2100
uggugauucc gaaacuagcu aaacaaacuu ccuaaauucu cgauacuccc aaacaagaua   2160
aaggagccga gguagcaguu gaagaggguu cugguucuuc acgugaaguu cauguagguu   2220
cggcguacgu ucugaccggu uuaguuucuu cagcucgcau agacaucccu uaguuugacg   2280
auguuagggc uuucucaguu cuuaaaggac uuccuucggu uugaaugucu agucaacggc   2340
aacuaauaac agacacuguc uaaacuaaag caggugcuga aucacaacau agauauaucu   2400
uuaagcgacg ucuuuauaua gcucuaaaua caggucuucc aguuagggucc ggcaaauggc  2460
caacaccauc cuccagaaaa ucuacagcug acaaggcuuc uguauuaguu uuuggauuaa   2520
gaacagcagu cuccggucaa gaggugacug cuuaaucauc uucuucaucu uuucuccuug   2580
```

-continued ucuaacuuug acaacaacgg gaccaaccuc ucgucucaug ugcuuccuac acagcucggu 2640
cgaugcgugu uacgaaaccg guucuagaug uagcuaaggu uguuguuacg gcuuucuaag 2700
aacuuccuuu uaguuaccau gcuaagggcu caacacccug caauaacgcu uuucgcgcua 2760
gguguagacc gaacgcaacg aaugcuugcu ccgguuacgc ugucucuuga cuaucgacau 2820
acauugcuuu ugagagauaa auucagacuu cgagcaauaa accaggcauc ugcacugccu 2880
cuuaauaccc gacuccaaaa cuugcucucg uuaggaaugu cugcagucaa cuaucugguu 2940
caucacguuu gucgaaauuc acuuugggul cuggggcuuc uauagagaca auggcaauuu 3000
cguaaguacu gucgacuaaa ugguuuacuc gaguaacuua acaaccuuuu cuaacauaac 3060
cuaucaagac acaagaggcu cguaucuuug gaaguuuuaa acgaauagga uugucguuag 3120
uuucggcuac gauguucuca auaccugaug uaguuggcga accuauugau gcuacgggga 3180
cuauagcgcu uauaucggua guuguuggua gagauacuuc uucgaaagcg auaaaaguuc 3240
uuuaaacuac aguuguggag ucgauaaguu cauaacuagc uuguucaguu guuagaccua 3300
gcacgaauac uuaagcgucu ugcaacguua cuuggccggc auaccucagu cgaccgguuu 3360
cgcguugacu ugguuccgaa ucaguuccuu cguuagcuaa gaauguaauu ucgacuacua 3420
ggaagucgaa uauuccugca gcaacucugg cgaagcuuuu uauuaucgac ccuccugaau 3480
cacgccauaa acgucuaccg uucuuucuuc cggucucucu cgauguagcu uagacuuaac 3540
uaaauaagca ugcgcuucug gccuucuaac cgacuaaacc uucuuaagua gucaccuggg 3600
uugguacgac uauaggucuu cuaaccacua uccacgaaac uacuguucua cauacuacga 3660
cgauucgaug agauguuguu acauagguug aagcgagcag agcgauaaug aaaucacgua 3720
gauuuucuua agguccucg acaacuguca cgauccuucc gauuaucaug gucuuguacc 3780
uuccuucaca caaaacgaac gcagcuacgg cuucuuaagu cuaaccgagu cuacacacca 3840
uacguguagc accaugugcg acuacucaac guucuaaacu aauuaauaau aguucuaucu 3900
ccuaugaaac uucuuaauua gccggauaac cuucgucgua acccgaaccu uucccgugug 3960
uacccauaca aguggcuuaa ucguuaaaac auaagguuua uauucgggcg guuuuacgcg 4020
cuuguagacc uugagaagac cagagcucac uuauaggggu uucaagaauc ccgucgacuu 4080
guucguguaa acacccgucu cgaucacaaa aacauacugu uuauacuucu uauacuauug 4140
cgacacaauc gguacuaccg aguagggugg cuucgaaccg cgcuuccagu aaaguuccua 4200
uaauaauguu uucaacgguu auagcuugaa auaauaucuc gauaaguuaa aaugaaccua 4260
auguuuggcg acaacaauuu acuggaaaac aaccacaacc gugggcucua ccuaguauga 4320
ucccgacaaa gaaagaaaug uuuuuguccu gugaauguca accaauuuag gauagaggcc 4380
agacacguuu uaaacuuguu guuucgauag uugcuccggg aguugagaga ugaauagcuu 4440
cuucuucuga agguccccaga cucuugcagg uagcugcgga agcuauugaa gcuguuguag 4500
ccgaaccgag ucuuuaaccu cuucgugcuu gacugccuca agucugcgua gcggcggaug 4560
aacauguuuc cguuguuggc caccuucguc ucgcaucuug acacguuuuu ccuaucugau 4620
aaaucucugc gauaccucau gugaagacuu agaucuuuag uucuuaaccg gcuucucaac 4680
gaccguacca agaaccuauc cuuccggaua cuaacaaaaa gccguacaaa cauagugacg 4740
augcugaaca augccgggcu gcaauaggaa cuugaucgua ccuuuguguu guaauaccug 4800
aagcguuacg gaaaggaaua aguucauuga ucucuugacu gcuguuuuca ucuuuucgau 4860
cuuguuaguc uacggguugc uguuucgcuc cgacgacuuc uuugcuuguu cgguuacuac 4920
uauggucuug ggguugaaua cgauugccga ccgggaccgu acccauaagg ugggguuguc 4980
auacauggag ggguuccgau gcgcgucggu ccgaugcggg gcguuuaccg aauggucccu 5040 augggucgu acauu 5055

<210> SEQ ID NO 376
<211> LENGTH: 1684
<212> TYPE: PRT
<213> ORGANISM: Diabrotica virgifera

<400> SEQUENCE: 376

Met Thr Gln Gln Leu Leu Pro Ile Lys Phe Gln Glu His Leu Gln Leu
1 5 10 15

Thr Asn Val Gly Ile His Ala Thr Asn Ile Thr Phe Ala Asn Leu Thr
20 25 30

Met Glu Ser Asp Lys Tyr Ile Cys Val Arg Glu Lys Val Gly Glu Thr
35 40 45

Ser Gln Val Val Ile Ile Asp Met Ala Asp Thr Ala Asn Pro Ile Arg
50 55 60

Arg Pro Ile Thr Ala Glu Ser Ala Ile Met Asn Pro Ala Ser Lys Val
65 70 75 80

Ile Ala Leu Lys Gly Lys Ala Gly Val Glu Thr Gln Lys Thr Leu Gln
85 90 95

Ile Phe Asn Ile Glu Met Lys Ser Lys Met Lys Ala His Thr Met Ser
100 105 110

Glu Asp Val Ile Phe Trp Lys Trp Ile Ser Pro Asn Thr Leu Ala Leu
115 120 125

Val Thr Glu Thr Ser Val Tyr His Trp Ser Met Glu Gly Asp Ser Ile
130 135 140

Pro Gln Lys Met Phe Asp Arg His Ser Ser Leu Asn Gly Cys Gln Ile
145 150 155 160

Ile Asn Tyr Arg Thr Asp Pro Lys Gln Asn Trp Leu Leu Leu Val Gly
165 170 175

Ile Ser Ala Gln Gln Ser Arg Val Val Gly Ala Met Gln Leu Tyr Ser
180 185 190

Val Glu Arg Lys Cys Ser Gln Pro Ile Glu Gly His Ala Ala Ser Phe
195 200 205

Ala Thr Phe Lys Met Glu Gly Asn Pro Glu Pro Ser Thr Leu Phe Cys
210 215 220

Phe Ala Val Arg Thr Leu Gln Gly Gly Lys Leu His Ile Ile Glu Val
225 230 235 240

Gly Gln Ser Pro Ala Gly Asn Gln Ser Phe Pro Lys Lys Thr Val Asp
245 250 255

Val Phe Phe Pro Pro Glu Ala Gln Asn Asp Phe Pro Val Ala Met Gln
260 265 270

Val Ser Ala Lys Tyr Asp Val Ile Tyr Leu Ile Thr Lys Tyr Gly Tyr
275 280 285

Ile His Met Tyr Asp Ile Glu Ser Gly Thr Cys Ile Tyr Met Asn Arg
290 295 300

Ile Ser Ser Asp Thr Ile Phe Val Thr Ala Pro His Glu Ala Thr Gly
305 310 315 320

Gly Ile Ile Gly Val Asn Arg Lys Gly Gln Val Leu Ser Val Ser Val
325 330 335

Asp Glu Glu Ser Ile Ile Arg Tyr Ile Asn Thr Val Leu His Asn Ala
340 345 350

```
Asp Leu Ala Leu Arg Leu Ala Thr Arg Asn Asn Leu Ser Gly Ala Glu
        355                 360                 365

Glu Leu Phe Val Ser Lys Phe Gln Met Leu Phe Gln Asn Gly Gln Tyr
    370                 375                 380

Ala Glu Ala Ala Lys Val Ala Ala Asn Ala Pro Lys Gly Ile Leu Arg
385                 390                 395                 400

Thr Pro Ala Thr Ile Gln Met Phe Gln Gln Val Pro Thr Gln Pro Gly
                405                 410                 415

Gln Asn Ser Pro Leu Leu Gln Tyr Phe Gly Ile Leu Leu Asp Gln Gly
            420                 425                 430

Gln Leu Asn Arg Tyr Glu Ser Leu Glu Leu Cys Lys Pro Val Leu Leu
        435                 440                 445

Gln Gly Arg Lys Gln Leu Leu Glu Lys Trp Leu Lys Glu Glu Lys Leu
    450                 455                 460

Glu Cys Ser Glu Glu Leu Gly Asp Leu Val Lys Gln Ala Asp Pro Thr
465                 470                 475                 480

Leu Ala Leu Ser Val Tyr Leu Arg Ala Asn Val Pro Ala Lys Val Ile
                485                 490                 495

Gln Ser Phe Ala Glu Thr Gly Gln Phe Gln Lys Ile Val Leu Tyr Ala
            500                 505                 510

Lys Lys Val Ser Tyr Thr Pro Asp Tyr Val Phe Leu Leu Arg Gln Val
        515                 520                 525

Met Arg Thr Asn Pro Asp Gln Gly Ala Ala Phe Ala Gly Met Leu Val
    530                 535                 540

Ala Asp Asp Glu Pro Leu Ala Asp Ile Asn Gln Ile Val Asp Ile Phe
545                 550                 555                 560

Met Glu Gln Asn Met Val Gln Gln Cys Thr Ala Phe Leu Leu Asp Ala
                565                 570                 575

Leu Lys Asn Asn Arg Pro Thr Glu Gly His Leu Gln Thr Arg Leu Leu
            580                 585                 590

Glu Met Asn Leu Met Ser Ala Pro Gln Val Ala Asp Ala Ile Leu Gly
        595                 600                 605

Asn Asn Met Phe Thr His Tyr Asp Arg Pro His Val Ala Gln Leu Cys
    610                 615                 620

Glu Lys Ala Gly Leu Leu Gln Arg Ala Leu Glu His Tyr Thr Asp Leu
625                 630                 635                 640

Tyr Asp Ile Lys Arg Ala Val Val His Thr His Leu Leu Pro Ala Asp
                645                 650                 655

Trp Leu Val Asn Phe Phe Gly Thr Leu Ser Val Glu Asp Ser Leu Glu
            660                 665                 670

Cys Leu Arg Ala Met Leu Thr Ala Asn Ile Arg Gln Asn Leu Gln Ile
        675                 680                 685

Cys Val Gln Ile Ala Thr Lys Tyr His Glu Gln Leu Thr Thr Lys Ala
    690                 695                 700

Leu Ile Asp Leu Phe Glu Gly Phe Lys Ser Tyr Glu Gly Leu Phe Tyr
705                 710                 715                 720

Phe Leu Gly Ser Ile Val Asn Phe Ser Gln Asp Gln Glu Val His Phe
                725                 730                 735

Lys Tyr Ile Gln Ala Ala Cys Lys Thr Gly Gln Ile Lys Glu Val Glu
            740                 745                 750

Arg Ile Cys Arg Glu Ser Asn Cys Tyr Asn Pro Glu Arg Val Lys Asn
        755                 760                 765

Phe Leu Lys Glu Ala Lys Leu Thr Asp Gln Leu Pro Leu Ile Ile Val
```

770 775 780

Cys Asp Arg Phe Asp Phe Val His Asp Leu Val Leu Tyr Leu Tyr Arg
785 790 795 800

Asn Ser Leu Gln Lys Tyr Ile Glu Ile Tyr Val Gln Lys Val Asn Pro
805 810 815

Ser Arg Leu Pro Val Val Val Gly Gly Leu Leu Asp Val Asp Cys Ser
820 825 830

Glu Asp Ile Ile Lys Asn Leu Ile Leu Val Val Arg Gly Gln Phe Ser
835 840 845

Thr Asp Glu Leu Val Glu Glu Val Glu Lys Arg Asn Arg Leu Lys Leu
850 855 860

Leu Leu Pro Trp Leu Glu Ser Arg Val His Glu Gly Cys Val Glu Pro
865 870 875 880

Ala Thr His Asn Ala Leu Ala Lys Ile Tyr Ile Asp Ser Asn Asn Asn
885 890 895

Ala Glu Arg Phe Leu Lys Glu Asn Gln Trp Tyr Asp Ser Arg Val Val
900 905 910

Gly Arg Tyr Cys Glu Lys Arg Asp Pro His Leu Ala Cys Val Ala Tyr
915 920 925

Glu Arg Gly Gln Cys Asp Arg Glu Leu Ile Ala Val Cys Asn Glu Asn
930 935 940

Ser Leu Phe Lys Ser Glu Ala Arg Tyr Leu Val Arg Arg Arg Asp Gly
945 950 955 960

Glu Leu Trp Ala Glu Val Leu Asn Glu Ser Asn Pro Tyr Arg Arg Gln
965 970 975

Leu Ile Asp Gln Val Val Gln Thr Ala Leu Ser Glu Thr Gln Asp Pro
980 985 990

Glu Asp Ile Ser Val Thr Val Lys Ala Phe Met Thr Ala Asp Leu Pro
995 1000 1005

Asn Glu Leu Ile Glu Leu Leu Glu Lys Ile Val Leu Asp Ser Ser
1010 1015 1020

Val Phe Ser Glu His Arg Asn Leu Gln Asn Leu Leu Ile Leu Thr
1025 1030 1035

Ala Ile Lys Ala Asp Ala Thr Arg Val Met Asp Tyr Ile Asn Arg
1040 1045 1050

Leu Asp Asn Tyr Asp Ala Pro Asp Ile Ala Asn Ile Ala Ile Asn
1055 1060 1065

Asn His Leu Tyr Glu Glu Ala Phe Ala Ile Phe Lys Lys Phe Asp
1070 1075 1080

Val Asn Thr Ser Ala Ile Gln Val Leu Ile Glu Gln Val Asn Asn
1085 1090 1095

Leu Asp Arg Ala Tyr Glu Phe Ala Glu Arg Cys Asn Glu Pro Ala
1100 1105 1110

Val Trp Ser Gln Leu Ala Lys Ala Gln Leu Asn Gln Gly Leu Val
1115 1120 1125

Lys Glu Ala Ile Asp Ser Tyr Ile Lys Ala Asp Asp Pro Ser Ala
1130 1135 1140

Tyr Lys Asp Val Val Glu Thr Ala Ser Lys Asn Asn Ser Trp Glu
1145 1150 1155

Asp Leu Val Arg Tyr Leu Gln Met Ala Arg Lys Lys Ala Arg Glu
1160 1165 1170

Ser Tyr Ile Glu Ser Glu Leu Ile Tyr Ser Tyr Ala Lys Thr Gly
1175 1180 1185

Arg Leu Ala Asp Leu Glu Glu Phe Ile Ser Gly Pro Asn His Ala
1190 1195 1200

Asp Ile Gln Lys Ile Gly Asp Arg Cys Phe Asp Asp Lys Met Tyr
1205 1210 1215

Asp Ala Ala Lys Leu Leu Tyr Asn Asn Val Ser Asn Phe Ala Arg
1220 1225 1230

Leu Ala Ile Thr Leu Val His Leu Lys Glu Phe Gln Gly Ala Val
1235 1240 1245

Asp Ser Ala Arg Lys Ala Asn Ser Thr Arg Thr Trp Lys Glu Val
1250 1255 1260

Cys Phe Ala Cys Val Asp Ala Glu Glu Phe Arg Leu Ala Gln Met
1265 1270 1275

Cys Gly Met His Ile Val Val His Ala Asp Glu Leu Gln Asp Leu
1280 1285 1290

Ile Asn Tyr Tyr Gln Asp Arg Gly Tyr Phe Glu Glu Leu Ile Gly
1295 1300 1305

Leu Leu Glu Ala Ala Leu Gly Leu Glu Arg Ala His Met Gly Met
1310 1315 1320

Phe Thr Glu Leu Ala Ile Leu Tyr Ser Lys Tyr Lys Pro Ala Lys
1325 1330 1335

Met Arg Glu His Leu Glu Leu Phe Trp Ser Arg Val Asn Ile Pro
1340 1345 1350

Lys Val Leu Arg Ala Ala Glu Gln Ala His Leu Trp Ala Glu Leu
1355 1360 1365

Val Phe Leu Tyr Asp Lys Tyr Glu Glu Tyr Asp Asn Ala Val Leu
1370 1375 1380

Ala Met Met Ala His Pro Thr Glu Ala Trp Arg Glu Gly His Phe
1385 1390 1395

Lys Asp Ile Ile Thr Lys Val Ala Asn Ile Glu Leu Tyr Tyr Arg
1400 1405 1410

Ala Ile Gln Phe Tyr Leu Asp Tyr Lys Pro Leu Leu Leu Asn Asp
1415 1420 1425

Leu Leu Leu Val Leu Ala Pro Arg Met Asp His Thr Arg Ala Val
1430 1435 1440

Ser Phe Phe Thr Lys Thr Gly His Leu Gln Leu Val Lys Ser Tyr
1445 1450 1455

Leu Arg Ser Val Gln Asn Leu Asn Asn Lys Ala Ile Asn Glu Ala
1460 1465 1470

Leu Asn Ser Leu Leu Ile Glu Glu Glu Asp Phe Gln Gly Leu Arg
1475 1480 1485

Thr Ser Ile Asp Ala Phe Asp Asn Phe Asp Asn Ile Gly Leu Ala
1490 1495 1500

Gln Lys Leu Glu Lys His Glu Leu Thr Glu Phe Arg Arg Ile Ala
1505 1510 1515

Ala Tyr Leu Tyr Lys Gly Asn Asn Arg Trp Lys Gln Ser Val Glu
1520 1525 1530

Leu Cys Lys Lys Asp Arg Leu Phe Arg Asp Ala Met Glu Tyr Thr
1535 1540 1545

Ser Glu Ser Arg Asn Gln Glu Leu Ala Glu Glu Leu Leu Ala Trp
1550 1555 1560

Phe Leu Asp Arg Lys Ala Tyr Asp Cys Phe Ser Ala Cys Leu Tyr
1565 1570 1575

His Cys Tyr Asp Leu Leu Arg Pro Asp Val Ile Leu Glu Leu Ala
1580 1585 1590

Trp Lys His Asn Ile Met Asp Phe Ala Met Pro Phe Leu Ile Gln
1595 1600 1605

Val Thr Arg Glu Leu Thr Thr Lys Val Glu Lys Leu Glu Gln Ser
1610 1615 1620

Asp Ala Gln Arg Gln Ser Glu Ala Ala Glu Glu Thr Asn Lys Pro
1625 1630 1635

Met Met Ile Pro Glu Pro Gln Leu Met Leu Thr Ala Gly Pro Gly
1640 1645 1650

Met Gly Ile Pro Pro Gln Gln Tyr Val Pro Pro Gln Gly Tyr Ala
1655 1660 1665

Gln Pro Gly Tyr Ala Pro Gln Met Ala Tyr Gln Gly Tyr Pro Gly
1670 1675 1680

Met

<210> SEQ ID NO 377
<211> LENGTH: 2975
<212> TYPE: DNA
<213> ORGANISM: Diabrotica barberi

<400> SEQUENCE: 377
atgcaagtgt ccgctaagta cgacgtcatt tacctgatca ccaaatacgg ctatattcat 60
atgtatgaca tcgagagcgg tacctgtatc tacatattcg taaccgcacc ccacgaagct 120
acaggaggaa tcattggtgt taatagaaaa ggtcaagtcc tatccgtctc cgtagacgag 180
gagagcatca ttcgatacat caacaccgtc ttacacaatg ctgacttagc gctgcgtcta 240
gctacgagaa acaatctttc aggagcagaa gaactgtttg ttagtaaatt ccagatgttg 300
ttccagaatg gacagtatgc cgaagctgcc aaagtggctg ccaacgctcc aaaaggaatt 360
ttaagaaccc cagctacaat tcaaatgttt caacaagtcc cgacccaacc tggacaaaac 420
agtcctcttt tgcaatattt cggtatactt ctagaccaag ggcaattgaa cagatatgaa 480
tctttggaac tgtgtaaacc agttttgttg caaggtcgca aacaacttct agaaaaatgg 540
ttaaaagagg aaaaattaga atgttccgaa gaattaggag acctagtcaa acaggcggat 600
cctactctgg ctttatctgt gtatcttaga gctaatgtac ctgcaaaagt tatccaaagc 660
tttgccgaaa caggccaatt ccaaaagata gtcctctacg ccaaaaaagt gtcttatact 720
cccgactatg tattcctgct tcgccaagtc atgcgcacca atcccgacca aggcgccgca 780
ttcgcaggga tgttggtagc agacgacgaa cctttggcag acatcaacca aatcgtggac 840
attttcatgg aacaaaacat ggtgcaacag tgtactgcgt tcctgttgga cgccttaaag 900
aataacaggc ctactgaggg gcatctacaa actagattat tagaaatgaa cctgatgtct 960
gcaccgcaag tggctgacgc catcctcggc aacaacatgt tcactcacta cgaccggccc 1020
cacgtagccc agctctgcga gaaagctggt cttttacaga gagctctaga acactacact 1080
gacttgtatg acatcaaacg tgctgtggta cacactcact tgcttccagc cgattggttg 1140
gttaacttct tcggaactct gagcgtggaa gatagtttgg agtgcttgag ggccatgttg 1200
acggcgaata ttcggcagaa tttacagatt tgtgtgcaga tcgctactaa gtaccacgaa 1260
caactcacca ctaaggcttt gatcgatttg tttgaaggat ttaagagcta tgagggtttg 1320
ttctatttcc tcggctccat cgtcaacttc tcccaagacc aagaagtgca cttcaagtac 1380
atccaagccg catgcaaaac tggccagatc aaagaagtcg agcgtatttg tagggagtcg 1440

-continued aactgctaca atcccgaaag agtcaagaat ttcctgaagg aagccaaact tacagatcag 1500
ttgccgttga ttattgtctg tgacagattt gatttcgtcc acgacttggt gttgtatcta 1560
tatagaaatt cgctgcagaa atatatcgag atttatgtcc agaaggtcaa tcctagccgt 1620
ttaccggttg tagtaggagg tcttttggat gtcgactgtt ccgaagacat aatcaaaaac 1680
cttattctag tcgtcagagg ccagttctcc actgacgaat tagtagaaga agtagaaaag 1740
agaaacagat tgaaactttt gttgccctgg ttggagagca gagtacacga aggatgtgtc 1800
gaaccagcca cgcacaatgc tttggccaag atctacatcg attccaacaa caatgccgaa 1860
agattcttga aggaaaatca atggtacgat tcccgagttg ttggacgtta ttgcgaaaag 1920
cgcgatccac atctggcttg cgttgcttac gaacgaggcc aatgcgacag agaactgata 1980
gctgtatgta acgaaaactc tctattcaag tcagaagcac gttatttggt ccgtagacgt 2040
gacggagaat tatgggctga ggttttgaac gagagcaatc cttacagacg tcagttgata 2100
gaccaagtag tgcaaacagc tttaagtgaa acccaagacc ccgaagatat atccgttacc 2160
gttaaagcat tcatgacagc tgatttacca aatgaactca ttgaattgct ggaaaagatt 2220
gtgctggata gttctgtatt ctccgagcat agaaaccttc aaaacttgct tatcctaaca 2280
gcaatcaaag ccgatgctac aagagttatg gactacatca accgcttgga taactacgat 2340
gctcctgata tcgccaatat agccatcaac aaccatctct atgaagaagc tttcgctatt 2400
ttcaagaaat ttgatgtcaa cacttctgct attcaagtat taatcgaaca agtcaacaac 2460
ctggatcgtg cttacgaatt cgcagaacgt tgcaatgaac cagccgtatg gagccagctg 2520
gccaaagccc aactaaacca aggcttagtt aaagaagcaa tcgattctta cattaaagct 2580
gatgatcctt cagcatacaa ggacgtcgtt gagaccgctt ctaaaaataa tagttgggag 2640
gacttggtcc ggtatttgca gatggcaaga aagaaggcta gagagagcta catcgaatct 2700
gaattgattt attcgtatgc aaagaccgga agattagctg atttggaaga attcatcagt 2760
ggacccaacc atgctgatat ccagaagatt ggtgataggt gctttgacga caagatgtat 2820
gatgctgcca agctactcta caacaatgta tccaacttcg ctcgtctcgc tattacttta 2880
gtgcatctaa aagaattcca gggagctgtt gacagtgcta ggaaggctaa tagtaccaga 2940
acatggaagg aagtgtgttt tgcttgcgtc gatgc 2975

<210> SEQ ID NO 378
<211> LENGTH: 2975
<212> TYPE: RNA
<213> ORGANISM: Diabrotica barberi

<400> SEQUENCE: 378
augcaagugu ccgcuaagua cgacgucauu uaccugauca ccaaauacgg cuauauucau 60
auguaugaca ucgagagcgg uaccuguauc uacauauucg uaaccgcacc ccacgaagcu 120
acaggaggaa ucauuggugu uaauagaaaa ggucaagucc uauccgucuc cguagacgag 180
gagagcauca uucgauacau caacaccguc uuacacaaug cugacuuagc gcugcgucua 240
gcuacgagaa acaaucuuuc aggagcagaa gaacuguuug uuaguaaauu ccagauguug 300
uuccagaaug gacaguaugc cgaagcugcc aaaguggcug ccaacgcucc aaaaggaauu 360
uuaagaaccc cagcuacaau ucaaauguuu caacaagucc cgacccaacc uggacaaaac 420
aguccucuuu ugcaauauuu cgguauacuu cuagaccaag ggcaauugaa cagauaugaa 480
ucuuuggaac uguguaaacc aguuuuguug caaggucgca aacaacuucu agaaaaaugg 540
uuaaaagagg aaaaauuaga auguuccgaa gaauuaggag accuagucaa acaggcggau 600

```
ccuacucugg cuuuaucugu guaucuuaga gcuaauguac cugcaaaagu uauccaaagc    660
uuugccgaaa caggccaauu ccaaaagaua guccucuacg ccaaaaaagu gucuuauacu    720
cccgacuaug uauuccugcu ucgccaaguc augcgcacca aucccgacca aggcgccgca    780
uucgcaggga uguugguagc agacgacgaa ccuuuggcag acaucaacca aaucguggac    840
auuuucaugg aacaaaacau ggugcaacag uguacugcgu uccuguugga cgccuuaaag    900
aauaacaggc cuacugaggg gcaucuacaa acuagauuau uagaaaugaa ccugaugucu    960
gcaccgcaag uggcugacgc cauccucggc aacaacaugu ucacucacua cgaccggccc   1020
cacguagccc agcucugcga gaaagcuggu cuuuuacaga gagcucuaga acacuacacu   1080
gacuuguaug acaucaaacg ugcuguggua cacacucacu ugcuuccagc cgauugguug   1140
guuaacuucu ucggaacucu gagcguggaa gauaguuugg agugcuugag ggccauguug   1200
acggcgaaua uucggcagaa uuuacagauu ugugugcaga ucgcuacuaa guaccacgaa   1260
caacucacca cuaaggcuuu gaucgauuug uuugaaggau uuaagagcua ugaggguuug   1320
uucuauuucc ucggcuccau cgucaacuuc ucccaagacc aagaagugca cuucaaguac   1380
auccaagccg caugcaaaac uggccagauc aaagaagucg agcguauuug uagggagucg   1440
aacugcuaca aucccgaaag agucaagaau uuccugaagg aagccaaacu uacagaucag   1500
uugccguuga uuauugucug ugacagauuu gauuucgucc acgacuuggu guuguaucua   1560
uauagaaauu cgcugcagaa auauaucgag auuuaugucc agaaggucaa uccuagccgu   1620
uuaccgguug uaguaggagg ucuuuuggau gucgacuguu ccgaagacau aaucaaaaac   1680
cuuauucuag ucgucagagg ccaguucucc acugacgaau uaguagaaga aguagaaaag   1740
agaaacagau ugaaacuuuu guugcccugg uuggagagca gaguacacga aggaugguc    1800
gaaccagcca cgcacaaugc uuuggccaag aucuacaucg auuccaacaa caaugccgaa   1860
agauucuuga aggaaaauca augguacgau ucccgaguug uuggacguua uugcgaaaag   1920
cgcgauccac aucuggcuug cguugcuuac gaacgaggcc aaugcgacag agaacugaua   1980
gcuguaugua acgaaaacuc ucuauucaag ucagaagcac guuauuuggu ccguagacgu   2040
gacggagaau uaugggcuga gguuuugaac gagagcaauc cuuacagacg ucaguugaua   2100
gaccaaguag ugcaaacagc uuuaagugaa acccaagacc ccgaagauau auccguuacc   2160
guuaaagcau ucaugacagc ugauuuacca aaugaacuca uugaauugcu ggaaaagauu   2220
gugcuggaua guucuguauu cuccgagcau agaaaccuuc aaaacuugcu uauccuaaca   2280
gcaaucaaag ccgaugcuac aagaguuaug gacuacauca accgcuugga uaacuacgau   2340
gcuccugaua ucgccaauau agccaucaac aaccaucucu augaagaagc uuucgcuauu   2400
uucaagaaau uugaugucaa cacuucugcu auucaaguau uaaucgaaca agucaacaac   2460
cuggaucgug cuuacgaauu cgcagaacgu ugcaaugaac cagccguaug gagccagcug   2520
gccaaagccc aacuaaacca aggcuuaguu aaagaagcaa ucgauucuua cauuaaagcu   2580
gaugauccuu cagcauacaa ggacgucguu gagaccgcuu cuaaaaauaa uaguugggag   2640
gacuuggucc gguauuugca gauggcaaga aagaaggcua gagagagcua caucgaaucu   2700
gaauugauuu auucguaugc aaagaccgga agauuagcug auuuggaaga auucaucagu   2760
ggacccaacc augcugauau ccagaagauu ggugauaggu gcuuugacga caagauguau   2820
gaugcugcca agcuacucua caacaaugua uccaacuucg cucgucucgc uauuacuuua   2880
gugcaucuaa aagaauucca gggagcuguu gacagugcua ggaaggcuaa uaguaccaga   2940
```

acauggaagg aagugugunu ugcuugcguc gaugc 2975

<210> SEQ ID NO 379
<211> LENGTH: 5055
<212> TYPE: DNA
<213> ORGANISM: Diabrotica undecimpunctata

<400> SEQUENCE: 379
atgacgcagc aactgttacc tatcaagttc caagaacatt tgcagcttac caatgttggt 60
atccatgcta ccaacatcac gttcgccaat ctcaccatgg agagtgacaa gtacatctgc 120
gtgagagaaa aagtcggaga gacgtcccaa gtagtcatca tagatatggc cgacacggcc 180
aatcccatca gacgaccaat caccgccgaa agtgctatta tgaatccagc atccaaagtc 240
attgctctta aaggtaaagc cggcgtagaa acacaaaaaa cacttcaaat atttaacata 300
gaaatgaagt caaaaatgaa agcccacacc atgtccgaag acgtaatttt ctggaaatgg 360
ataagcccca atacgttagc tctagtcacc gagacttcag tgtatcattg gtccatggaa 420
ggtgattcca ctccacagaa aatgttcgac agacactctt ctcttaacgg ctgccaaatc 480
atcaactacc gtacagatcc caaacaaaac tggctgctac ttgtcggtat cagcgctcaa 540
cagtcccgcg tcgttggtgc tatgcaactc tattcagtag aaagaaaatg ctcccagccg 600
atcgaaggac acgccgcttc ttttgccacc ttcaaaatgg aaggaaatcc tgaaccatcg 660
acgctcttct gtttcgcagt gagaacttta cagggaggaa aattgcatat tatcgaggtt 720
ggccaaagtc cagcaggcaa tcaatcgttc cccaaaaaga cagtggacgt tttcttcccg 780
cccgaggccc aaaacgattt tcctgtagcc atgcaagtat cagctaagta cgacgtcatt 840
tacctgatca ccaaatacgg ctacattcat atgtatgata ttgagaccgg cacttgtatc 900
tatatgaaca gaatatccag tgaaaccata ttcgtaaccg caccccacga agctactgga 960
ggaataattg gtgtaaatag aaaaggtcaa gtactatccg tctccgtaga cgaggagagc 1020
atcattcggt acatcaacac cgtcttgcac aatgcagact tagcgctgcg tctagctacg 1080
agaaacaatc tctcaggagc cgaagaactg tttgttagta aatttcagat gttgttccag 1140
aatggacagt acgccgaagc tgccaaagtg gctgccaacg ctccaaaagg aattttaaga 1200
accccagcta caattcaaat gtttcaacaa gtcccgactc aacctggaca aaacagtcct 1260
ctcttacaat atttcggtat acttttagac caaggacaac taaacagata cgaatctttg 1320
gaactatgta aaccagtttt gttgcaaggt cgcaaacagc tgctagaaaa atggttaaaa 1380
gaagaaaaat tagaatgttc cgaggaatta ggagacctag tcaaacaggc agaccctact 1440
ctggctttat ctgtgtatct tagagctaat gtacctgcaa aagttatcca aagctttgct 1500
gaaacaggcc aattccaaaa gatagtcctc tacgccaaaa aagtgtccta tacgcccgac 1560
tatatattcc tgcttcgcca agtcatgcgc accaatcccg accaaggcgc cgcgttcgcc 1620
gggatgttgg tagcagacga agaacctttg gccgacatca accaaatcgt ggacattttc 1680
atggaacaaa acatggtgca gcagtgtact gcgtttttgt tggacgcctt aaagaataac 1740
aggcctactg aggggcatct acaaaccaga ctgttagaaa tgaacctgat gtctgcaccg 1800
caagtggcag acgccattct cggcaacaac atgttcactc actacgaccg gcctcacgta 1860
gcccagctct gcgaaaaagc tggtctttta caaagagctc tggaacacta tactgatttg 1920
tacgatatca aacgtgctgt cgtacacacc cacttgcttc cagctgattg gttggttaac 1980
ttcttcggaa ctctcagcgt ggaagacagt ttggagtgct tgagggccat gctgacggcg 2040
aatattcggc agaatttaca gatttgcgtg cagatcgcta ctaagtacca cgaacaactc 2100
accactaagg ctttgatcga tttgtttgaa gggttcaaga gctatgaggg tttgttctat 2160
ttcctcggct ccatcgtcaa cttctcccaa gaccaagaag tgcacttcaa gtacattcaa 2220
gccgcatgca aaactggcca gatcaaggaa gtggagcgta tttgtaggga atcaaactgc 2280
tacaattccg aaagagtcaa gaatttcctg aaagaagcca aacttacaga tcaattgccg 2340
ttgattattg tctgtgacag atttgatttc gtccacgact tagtgttgta tttatacaga 2400
aactcgctgc agaaatatat cgagatttat gtgcagaaag tcaatcccag ccgtttaccg 2460
gttgtagtag gaggtctttt agatgtcgac tgttccgaag acataatcaa aaacctaatt 2520
ctcgtagtca gaggccaatt ctccactgac gaattagtag aagaagtaga aaagaggaac 2580
agattaaaac tgttgttgcc ctggttagaa agcagagtac acgaaggttg tgtcgaacca 2640
gccacacaca atgctttggc taagatctac atcgattcca acaacaatgc cgaaagattt 2700
ttgaaggaaa atcaatggta cgattcccga gttgtcggac gttattgcga aaagcgcgat 2760
ccacatctgg cttgtgttgc ttacgaacga ggccaatgcg acagagaatt gatagctgta 2820
tgcaacgaaa attctctatt taagtctgaa gcgcgttacc tagtccgtag acgtgacgga 2880
gaattatggg ctgaagtttt gaacgagagc aatcctttca gacgccagtt gatagatcaa 2940
gtagtgcaaa cagctttaag tgaaacccaa gaccctgaag atatttccgt caccgttaaa 3000
gcattcatga cagctgattt accaaatgag ctcattgaat tgctggaaaa gattgtgttg 3060
gataattctg tattctccga gcatagaaac cttcaaaact tgcttatcct tacagcaatc 3120
aaagccgatg ctacaagagt tatggactac atcaaccgct tggacaacta cgatgcccct 3180
gatatcgcga atatagccat caacaaccat ctctacgaag aagctttcgc tattttcaag 3240
aagtttgatg tcaacacctc agctattcaa gtattgatcg aacaagtcaa caatctggat 3300
cgtgcttacg aattcgcaga acgttgcaat gaaccagccg tatggagtca gctggccaaa 3360
gctcaactga accaaggctt agtcaaagaa gcaatcgatt cttacattaa agctgacgat 3420
ccttcggctt acaaggatgt cgtggaaacc gcttcgaaaa ataatagctg ggaggacttg 3480
gtgcggtatt tgcaaatggc aagaaagaag gccagagaga gctacatcga atccgaattg 3540
atttattcgt acgccaagac cggaagattg gctgatttgg aagaattcat cagcgggccc 3600
aaccatgccg atatccagaa gattggtgat aggtgctttg atgacaagat gtatgatgct 3660
gctaagctac tgtacaacaa tgtatccaat ttcgctcgtc tcgctattac tttagttcat 3720
ctaaaagaat tccagggtgc tgttgacagt gctagaaagg ctaacagtac aagaacatgg 3780
aaggaagtgt gttttgcttg tgtcgacgcc gaagaattca gattggctca gatgtgtggt 3840
atgcacatcg tcgtgcacgc tgatgagttg caagacttga ttaattatta ccaggataga 3900
ggatactttg aagaattaat cggcctattg gaagcagcat tgggcttgga aagggcacac 3960
atgggtatgt tcaccgaatt agcaatactg tattccaaat acaagcccgc caaaatgcgc 4020
gaacatctag aactcttctg gtctcgagtg aatatcccca aagttcttag ggcagctgaa 4080
caagcacatt tgtgggctga gctagtgttc ttgtacgaca aatacgaaga atacgataat 4140
gcagtattgg ctatgatggc ccatcctacc gaggcctggc gcgaaggtca tttcaaagat 4200
attattacaa aagtggccaa tatcgaactt tattatagag ctattcaatt ttatctggac 4260
tacaaacccc tgttgttaaa tgaccttttg ttggttttgg cacccagaat ggatcatact 4320
agggctgttt ctttcttcac caaaacagga cacttacagt tggttaaatc ctatctccgt 4380
tctgtgcaaa atttgaacaa caaagctatc aacgaggccc ttaactctct acttattgac 4440

```
gaagaagact tccagggtct gagaacgtcc atcgatgcct tcgataactt cgacaatatc   4500
ggtttggcgc agaaattaga gaaacacgaa ctgaccgaat ttagacgcat cgccgcctac   4560
ttgtacaaag gaaacaaccg gtggaagcag agcgtagaac tgtgcaaaaa ggatagattg   4620
tttagagacg caatggagta cacttctgaa tctagaaatc aagaattggc cgaggagttg   4680
ctagcctggt tcttggatag gcaggcctat gattgttttt cggcatgttt gtatcactgc   4740
tacgacttgt tacgacctga cgttatcctt gaactagcat ggaaacacaa cattatggac   4800
tttgcgatgc ctttccttat tcaagtaact agagaactga cgacaaaagt agaaaagcta   4860
gaacaatccg acgcccaacg acaaagtgag gctgctgaag aaacgaacaa gccaatgatg   4920
ataccagaac cccaacttat gctaacggct ggccctggca tgggtattcc accccaacag   4980
tatgtacctc cccaagctta cgcgcagcca ggctacgcac cgcaaatggc ttaccaggga   5040
tacccaggca tgtaa                                                    5055
```

<210> SEQ ID NO 380
<211> LENGTH: 5055
<212> TYPE: RNA
<213> ORGANISM: Diabrotica undecimpunctata

<400> SEQUENCE: 380

```
augacgcagc aacuguuacc uaucaaguuc caagaacauu ugcagcuuac caauguuggu     60
auccaugcua ccaacaucac guucgccaau cucaccaugg agagugacaa guacaucugc    120
gugagagaaa aagucggaga gacgucccaa guagucauca uagauauggc cgacacggcc    180
aaucccauca gacgaccaau caccgccgaa agugcuauua ugaauccagc auccaaaguc    240
auugcucuua aagguaaagc cggcguagaa acacaaaaaa cacuucaaau auuuaacaua    300
gaaaugaagu caaaaaugaa agcccacacc auguccgaag acguaauuuu cuggaaaugg    360
auaagcccca auacguuagc ucuagucacc gagacuucag uguaucauug guccauggaa    420
ggugauucca cuccacagaa aauguucgac agacacucuu cucuuaacgg cugccaaauc    480
aucaacuacc guacagaucc caaacaaaac uggcugcuac uugucgguau cagcgcucaa    540
cagucccgcg ucguuggugc uaugcaacuc uauucaguag aaagaaaaug cucccagccg    600
aucgaaggac acgccgcuuc uuuugccacc uucaaaaugg aaggaaaucc ugaaccaucg    660
acgcucuucu guuucgcagu gagaacuuua cagggaggaa aauugcauau uaucgagguu    720
ggccaaaguc cagcaggcaa ucaaucguuc cccaaaaaga caguggacgu uuucuucccg    780
cccgaggccc aaaacgauuu uccuguagcc augcaaguau cagcuaagua cgacgucauu    840
uaccugauca ccaaauacgg cuacauucau auguaugaua uugagaccgg cacuuguauc    900
uauaugaaca gaauauccag ugaaaccaua uucguaaccg caccccacga agcuacugga    960
ggaauaauug guguaaauag aaaaggucaa guacuauccg ucuccguaga cgaggagagc   1020
aucauucggu acaucaacac cgucuugcac aaugcagacu uagcgcugcg ucuagcuacg   1080
agaaacaauc ucucaggagc cgaagaacug uuuguuagua aauuucagau guuguuccag   1140
aauggacagu acgccgaagc ugccaaagug gcugccaacg cuccaaaagg aauuuuaaga   1200
accccagcua caauucaaau guuucaacaa gucccgacuc aaccuggaca aaacaguccu   1260
cucuuacaau auuucgguau acuuuuagac caaggacaac uaaacagaua cgaaucuuug   1320
gaacuaugua aaccaguuuu guugcaaggu cgcaaacagc ugcuagaaaa augguuaaaa   1380
gaagaaaaau uagaaauguuc cgaggaauua ggagaccuag ucaaacaggc agacccuacu   1440
cuggcuuuau cuguguaucu uagagcuaau guaccugcaa aaguuaucca aagcuuugcu   1500
```

-continued

```
gaaacaggcc aauuccaaaa gauaguccuc uacgccaaaa aaguguccua uacgcccgac   1560
uauauauucc ugcuucgcca agucaugcgc accaaucccg accaaggcgc cgcguucgcc   1620
gggauguugg uagcagacga agaaccuuug gccgacauca accaaaucgu ggacauuuuc   1680
auggaacaaa acauggugca gcaguguacu gcguuuuugu uggacgccuu aaagaauaac   1740
aggccuacug aggggcaucu acaaaccaga cuguuagaaa ugaaccugau gucugcaccg   1800
caaguggcag acgccauucu cggcaacaac auguucacuc acuacgaccg gccucacgua   1860
gcccagcucu gcgaaaaagc uggucuuuua caaagagcuc uggaacacua uacugauuug   1920
uacgauauca aacgugcugu cguacacacc cacuugcuuc cagcugauug guugguuaac   1980
uucuucggaa cucucagcgu ggaagacagu uuggagugcu ugagggccau gcugacggcg   2040
aauauucggc agaauuuaca gauuugcgug cagaucgcua cuaaguacca cgaacaacuc   2100
accacuaagg cuuugaucga uuuguuugaa ggguucaaga gcuaugaggg uuuguucuau   2160
uuccucggcu ccaucgucaa cuucucccaa gaccaagaag ugcacuucaa guacauucaa   2220
gccgcaugca aaacuggcca gaucaaggaa guggagcgua uuuguaggga aucaaacugc   2280
uacaauuccg aaagagucaa gaauuuccug aaagaagcca aacuuacaga ucaauugccg   2340
uugauuauug ucugugacag auuugauuuc guccacgacu uaguguugua uuuauacaga   2400
aacucgcugc agaaauauau cgagauuuau gugcagaaag ucaaucccag ccguuuaccg   2460
guuguaguag gaggucuuuu agaugucgac uguuccgaag acauaaucaa aaaccuaauu   2520
cucguaguca gaggccaauu cuccacugac gaauuaguag aagaaguaga aaagaggaac   2580
agauuaaaac uguuguugcc cugguuagaa agcagaguac acgaagguug ugucgaacca   2640
gccacacaca augcuuuggc uaagaucuac aucgauucca acaacaaugc cgaaagauuu   2700
uugaaggaaa aucaauggua cgauucccga guugucggac guuauugcga aaagcgcgau   2760
ccacaucugg cuuguguugc uuacgaacga ggccaaugcg acagagaauu gauagcugua   2820
ugcaacgaaa auucucuauu uaagucugaa gcgcguuacc uaguccguag acgugacgga   2880
gaauuauggg cugaaguuuu gaacgagagc aauccuuuca gacgccaguu gauagaucaa   2940
guagugcaaa cagcuuuaag ugaaacccaa gacccugaag auauuuccgu caccguuaaa   3000
gcauucauga cagcugauuu accaaaugag cucauugaau ugcuggaaaa gauuguguug   3060
gauaaaucug uauucuccga gcauagaaac cuucaaaacu ugcuuauccu uacagcaauc   3120
aaagccgaug cuacaagagu uauggacuac aucaaccgcu uggacaacua cgaugccccu   3180
gauaucgcga auauagccau caacaaccau cucuacgaag aagcuuucgc uauuuucaag   3240
aaguuugaug ucaacacecuc agcuauucaa guauugaucg aacaagucaa caaucuggau   3300
cgugcuuacg aauucgcaga acguugcaau gaaccagccg uauggaguca gcuggccaaa   3360
gcucaacuga accaaggcuu agucaaagaa gcaaucgauu cuuacauuaa agcugacgau   3420
ccuucggcuu acaaggaugu cguggaaacc gcuucgaaaa auaauagcug ggaggacuug   3480
gugcgguauu ugcaaauggc aagaaagaag gccagagaga gcuacaucga auccgaauug   3540
auuuauucgu acgccaagac cggaagauug gcugauuugg aagaauucau cagcgggccc   3600
aaccaugccg auauccagaa gauuggugau aggugcuuug augacaagau guaugaugcu   3660
gcuaagcuac uguacaacaa uguauccaau uucgcucguc ucgcuauuac uuuaguucau   3720
cuaaaagaau uccagggugc uguugacagu gcuagaaagg cuaacaguac aagaacaugg   3780
aaggaagugu guuuugcuug ugucgacgcc gaagaauuca gauuggcuca gaugugugu   3840
```

-continued augcacaucg ucgugcacgc ugaugaguug caagacuuga uuaauuauua ccaggauaga 3900
ggauacuuug aagaauuaau cggccuauug gaagcagcau ugggcuugga aagggcacac 3960 augggguaugu ucaccgaauu agcaauacug uauuccaaau acaagcccgc caaaaugcgc 4020
gaacaucuag aacucuucug gucucgagug aauaucccca aaguucuuag ggcagcugaa 4080
caagcacauu ugugggcuga gcuaguguuc uuguacgaca aauacgaaga auacgauaau 4140
gcaguauugg cuaugauggc ccauccuacc gaggccuggc gcgaagguca uuucaaagau 4200
auuauuacaa aaguggccaa uaucgaacuu uauuauagag cuauucaauu uuaucuggac 4260
uacaaacccc uguuguuaaa ugaccuuuug uugguuuugg cacccagaau ggaucauacu 4320
agggcuguuu cuuucuucac caaaacagga cacuuacagu ugguuaaauc cuaucuccgu 4380
ucugugcaaa auuugaacaa caaagcuauc aacgaggccc uuaacucucu acuuauugac 4440
gaagaagacu uccagggucu gagaacgucc aucgaugccu ucgauaacuu cgacaauauc 4500
gguuuggcgc agaaauuaga gaaacacgaa cugaccgaau uuagacgcau cgccgccuac 4560
uuguacaaag gaaacaaccg guggaagcag agcguagaac ugugcaaaaa ggauagauug 4620
uuuagagacg caauggagua cacuucugaa ucuagaaauc aagaauuggc cgaggaguug 4680
cuagccuggu ucuuggauag gcaggccuau gauuguuuuu cggcauguuu guaucacugc 4740
uacgacuugu uacgaccuga cguuauccuu gaacuagcau ggaaacacaa cauuauggac 4800
uuugcgaugc cuuuccuuau ucaaguaacu agagaacuga cgacaaaagu agaaaagcua 4860
gaacaauccg acgcccaacg acaaagugag gcugcugaag aaacgaacaa gccaaugaug 4920
auaccagaac cccaacuuau gcuaacggcu ggcccuggca ugggguauucc accccaacag 4980 uauguaccuc cccaagcuua cgcgcagcca ggcuacgcac cgcaaauggc uuaccaggga 5040
uacccaggca uguaa 5055

<210> SEQ ID NO 381
<211> LENGTH: 687
<212> TYPE: DNA
<213> ORGANISM: Diabrotica virgifera

<400> SEQUENCE: 381
atgacgcagc aactgttacc tatcaagttc caagaacatt tgcagcttac caatgttggt 60
atccatgcta ccaacatcac gttcgccaat ctcaccatgg agagcgacaa gtacatctgc 120
gtgagagaaa aagttggaga gacgtcccaa gtagtcatca tagatatggc cgatacggcc 180
aatcccatca gacgaccaat caccgccgaa agtgctatta tgaatccagc atccaaagtc 240
atcgctctta aaggtaaagc aggcgtagaa acacaaaaaa cccttcaaat attcaacata 300
gaaatgaagt caaaaatgaa agcccacacc atgtctgaag acgtaatttt ctggaaatgg 360
atcagcccca atacgttagc gctagtcact gaaacttcag tgtatcattg gtccatggaa 420
ggtgattcaa ttccacagaa aatgtttgac aggcattctt ctcttaacgg ctgccaaatc 480
atcaactacc gaacagatcc caaacaaaac tggctgctac tggtcggtat tagcgctcag 540
caatctcgcg tcgttggtgc tatgcaactg tactcagtag aaagaaaatg ctcgcagcca 600
atcgaaggtc acgccgcttc tttcgcgacc ttcaaaatgg aaggaaaccc tgaaccatcg 660
actctcttct gttttgcagt gaggact 687

<210> SEQ ID NO 382
<211> LENGTH: 693
<212> TYPE: DNA
<213> ORGANISM: Diabrotica virgifera

<400> SEQUENCE: 382
tcgactctct tctgttttgc agtgaggact ttacaaggag gaaagttaca tattatcgag 60
gttggtcaaa gtccagcagg caaccaatcg tttcctaaaa agacagtgga tgttttcttc 120
ccacccgagg cccaaaatga ttttcctgta gctatgcaag tgtccgctaa atacgacgtc 180
atttacctga ttaccaaata cggctatatt catatgtatg acatcgagag cggcacctgt 240
atctacatga acagaatatc tagtgacaca atattcgtaa ccgcaccccca cgaagctacg 300 ggaggaatca ttggtgttaa tagaaagggt caagtcctat ctgtctcggt agatgaggag 360
agcattattc gatacatcaa caccgtctta cacaatgctg acttagcgct gcgtctagct 420
acgagaaaca atctttcagg agccgaagaa ctgtttgtta gtaaattcca gatgttgttc 480
cagaacggac agtacgccga agctgctaaa gtggctgcca acgctccaaa aggaatttta 540
agaaccccag ctacaattca aatgtttcaa caagtcccga ctcaacctgg acaaaacagt 600
ccccttttgc aatatttcgg tatacttcta gaccaagggc aactaaacag atacgaatct 660
ttggaattgt gtaaaccagt tttgttgcaa ggt 693

<210> SEQ ID NO 383
<211> LENGTH: 700
<212> TYPE: DNA
<213> ORGANISM: Diabrotica virgifera

<400> SEQUENCE: 383
gaattgtgta aaccagtttt gttgcaaggt cgcaaacagc ttctagaaaa atggttaaaa 60
gaggaaaaat tagaatgttc cgaagaatta ggagacctag tcaaacaggc agatcctact 120
ctggctttat ctgtgtatct tagagctaat gtacctgcaa aagttatcca aagctttgcc 180
gaaactggcc aattccaaaa gatagtcctc tacgccaaaa aagtgtctta tactcccgac 240
tatgtattcc tgcttcgcca agtcatgcgc accaatcccg accaaggcgc agcatttgca 300
gggatgttgg tagcggacga cgaacctttg gccgatatca accaaatcgt ggacattttc 360
atggagcaaa acatggtgca gcagtgtact gcgttcttgt tggacgcctt aaagaataac 420
aggcctactg aggggcatct acaaactaga ctattagaaa tgaacctgat gtccgcaccg 480
caagtagcag acgccattct cggcaacaac atgttcactc actacgaccg gccccacgta 540
gcccagctct gcgaaaaagc tggtctttta caaagagctc tagaacacta cactgatttg 600
tatgacatca aacgtgctgt ggtacacacc cacttgcttc cagctgattg gttggttaac 660
ttcttcggaa ctctcagcgt ggaagacagt ttggagtgct 700

<210> SEQ ID NO 384
<211> LENGTH: 549
<212> TYPE: DNA
<213> ORGANISM: Diabrotica virgifera

<400> SEQUENCE: 384
tcagcgtgga agacagtttg gagtgcttga gggccatgct gaccgcgaat attcgacaga 60
atttgcagat ttgcgtgcag atcgctacca agtaccacga acaactcacc actaaggctt 120
tgatcgattt gtttgaagga tttaagagct atgagggttt gttctatttc ctcggctcca 180
tcgtcaactt ctcccaagac caagaagtgc acttcaagta catccaagcc gcatgcaaga 240
ctggccaaat caaagaagtc gagcgtatct gtagggaatc aaactgctac aatcccgaaa 300
gagtcaagaa tttcctgaag gaagccaaac ttacagatca gttgccgttg attattgtct 360

```
gtgacagatt tgatttcgtc cacgacttag tgttgtatct atatagaaat tcgctgcaga    420

aatatatcga gatttatgtc cagaaggtca atcccagccg tttaccggtt gtggtaggag    480

gtcttttaga tgtcgactgt tccgaagaca taatcaaaaa cctaattctt gtcgtcagag    540

gccagttct                                                            549


<210> SEQ ID NO 385
<211> LENGTH: 677
<212> TYPE: DNA
<213> ORGANISM: Diabrotica virgifera

<400> SEQUENCE: 385

taatcaaaaa cctaattctt gtcgtcagag gccagttctc cactgacgaa ttagtagaag     60

aagtagaaaa gaggaacaga ttgaaactgt tgttgccctg gttggagagc agagtacacg    120

aaggatgtgt cgagccagct acgcacaatg ctttggccaa gatctacatc gattccaaca    180

acaatgccga aagattcttg aaggaaaatc aatggtacga ttcccgagtt gtgggacgtt    240

attgcgaaaa gcgcgatcca catctggctt gcgttgctta cgaacgaggc caatgcgaca    300

gagaactgat agctgtatgt aacgaaaact ctctatttaa gtctgaagct cgttatttgg    360

tccgtagacg tgacggagaa ttatgggctg aggttttgaa cgagagcaat ccttacagac    420

gtcagttgat agaccaagta gtgcaaacag ctttaagtga aacccaagac cccgaagata    480

tctctgttac cgttaaagca ttcatgacag ctgatttacc aaatgagctc attgaattgt    540

tggaaaagat tgtattggat agttctgtgt tctccgagca tagaaacctt caaaatttgc    600

ttatcctaac agcaatcaaa gccgatgcta caagagttat ggactacatc aaccgcttgg    660

ataactacga tgcccct                                                   677


<210> SEQ ID NO 386
<211> LENGTH: 706
<212> TYPE: DNA
<213> ORGANISM: Diabrotica virgifera

<400> SEQUENCE: 386

aaccgcttgg ataactacga tgcccctgat atcgcgaata tagccatcaa caaccatctc     60

tatgaagaag ctttcgctat tttcaagaaa tttgatgtca acacctcagc tattcaagta    120

ttgatcgaac aagtcaacaa tctggatcgt gcttatgaat tcgcagaacg ttgcaatgaa    180

ccggccgtat ggagtcagct ggccaaagcg caactgaacc aaggcttagt caaggaagca    240

atcgattctt acattaaagc tgatgatcct tcagcttata aggacgtcgt tgagaccgct    300

tcgaaaaata atagctggga ggacttagtg cggtatttgc agatggcaag aaagaaggcc    360

agagagagct acatcgaatc tgaattgatt tattcgtacg cgaagaccgg aagattggct    420

gatttggaag aattcatcag tggacccaac catgctgata tccagaagat tggtgatagg    480

tgctttgatg acaagatgta tgatgctgct aagctactct acaacaatgt atccaacttc    540

gctcgtctcg ctattacttt agtgcatcta aaagaattcc agggagctgt tgacagtgct    600

aggaaggcta atagtaccag aacatggaag gaagtgtgtt ttgcttgcgt cgatgccgaa    660

gaattcagat tggctcagat gtgtggtatg cacatcgtgg tacacg                   706


<210> SEQ ID NO 387
<211> LENGTH: 686
<212> TYPE: DNA
<213> ORGANISM: Diabrotica virgifera

<400> SEQUENCE: 387
```

```
gcacatcgtg gtacacgctg atgagttgca agatttgatt aattattatc aagatagagg     60

atactttgaa gaattaatcg gcctattgga agcagcattg ggcttggaaa gggcacacat    120

gggtatgttc accgaattag caattttgta ttccaaatat aagcccgcca aaatgcgcga    180

acatctggaa ctcttctggt ctcgagtgaa tatccccaaa gttcttaggg cagctgaaca    240

agcacatttg tgggcagagc tagtgttttt gtatgacaaa tatgaagaat atgataacgc    300

tgtgttagcc atgatggctc atcccaccga agcttggcgc gaaggtcatt tcaaggatat    360

tattacaaaa gttgccaata tcgaacttta ttatagagct attcaatttt acttggatta    420

caaaccgctg ttgttaaatg accttttgtt ggtgttggca cccaggatgg atcatactag    480

ggctgtttct ttctttacaa aaacaggaca cttacagttg gttaaatcct atctccggtc    540

tgtgcaaaat ttgaacaaca aagctatcaa cgaggccctc aactctctac ttatcgaaga    600

agaagacttc cagggtctga gaacgtccat cgacgccttc gataacttcg acaacatcgg    660

cttggctcag aaattggaga agcacg                                          686
```

<210> SEQ ID NO 388
<211> LENGTH: 565
<212> TYPE: DNA
<213> ORGANISM: Diabrotica virgifera

<400> SEQUENCE: 388

```
cgacaacatc ggcttggctc agaaattgga gaagcacgaa ctgacggagt tcagacgcat     60

cgccgcctac ttgtacaaag gcaacaaccg gtggaagcag agcgtagaac tgtgcaaaaa    120

ggatagacta tttagagacg ctatggagta cacttctgaa tctagaaatc aagaattggc    180

cgaagagttg ctggcatggt tcttggatag gaaggcctat gattgttttt cggcatgttt    240

gtatcactgc tacgacttgt tacggcccga cgttatcctt gaactagcat ggaaacacaa    300

cattatggac ttcgcaatgc ctttccttat tcaagtaact agagaactga cgacaaaagt    360

agaaaagcta gaacaatcag atgcccaacg acaaagcgag gctgctgaag aaacgaacaa    420

gccaatgatg ataccagaac cccaacttat gctaacggct ggccctggca tgggtattcc    480

accccaacag tatgtacctc cccaaggcta cgcgcagcca ggctacgccc cgcaaatggc    540

ttaccaggga tacccaggca tgtaa                                           565
```

<210> SEQ ID NO 389
<211> LENGTH: 687
<212> TYPE: RNA
<213> ORGANISM: Diabrotica virgifera

<400> SEQUENCE: 389

```
augacgcagc aacuguuacc uaucaaguuc caagaacauu ugcagcuuac caauguuggu     60

auccaugcua ccaacaucac guucgccaau cucaccaugg agagcgacaa guacaucugc    120

gugagagaaa aaguuggaga gacgucccaa guagucauca uagauauggc cgauacggcc    180

aaucccauca gacgaccaau caccgccgaa agugcuauua ugaauccagc auccaaaguc    240

aucgcucuua aagguaaagc aggcguagaa acacaaaaaa cccuucaaau auucaacaua    300

gaaaugaagu caaaaaugaa agcccacacc augucugaag acguaauuuu cuggaaaugg    360

aucagcccca auacguuagc gcuagucacu gaaacuucag uguaucauug guccauggaa    420

ggugauucaa uuccacagaa aauguuugac aggcauucuu cucuuaacgg cugccaaauc    480

aucaacuacc gaacagaucc caaacaaaac uggcugcuac uggucgguau uagcgcucag    540
```

caaucucgcg ucguuggugc uaugcaacug uacucaguag aaagaaaaug cucgcagcca 600
aucgaagguc acgccgcuuc uuucgcgacc uucaaaaugg aaggaaaccc ugaaccaucg 660
acucucuucu guuuugcagu gaggacu 687

<210> SEQ ID NO 390
<211> LENGTH: 693
<212> TYPE: RNA
<213> ORGANISM: Diabrotica virgifera

<400> SEQUENCE: 390
ucgacucucu ucuguuuugc agugaggacu uuacaaggag gaaaguuaca uauuaucgag 60
guuggucaaa guccagcagg caaccaaucg uuuccuaaaa agacagugga uguuuucuuc 120
ccacccgagg cccaaaauga uuuuccugua gcuaugcaag uguccgcuaa auacgacguc 180
auuuaccuga uuaccaaaua cggcuauauu cauauguaug acaucgagag cggcaccugu 240
aucuacauga acagaauauc uagugacaca auauucguaa ccgcacccca cgaagcuacg 300
ggaggaauca uugguguuaa uagaaagggu caaguccuau cugucucggu agaugaggag 360
agcauuauuc gauacaucaa caccgucuua cacaaugcug acuuagcgcu gcgucuagcu 420
acgagaaaca aucuuucagg agccgaagaa cuguuuguua guaaauucca gauguuguuc 480
cagaacggac aguacgccga agcugcuaaa guggcugcca acgcuccaaa aggaauuuua 540
agaaccccag cuacaauuca aauguuucaa caagucccga cucaaccugg acaaaacagu 600
ccccuuuugc aauauuucgg uauacuucua gaccaagggc aacuaaacag auacgaaucu 660
uuggaauugu guaaaccagu uuuguugcaa ggu 693

<210> SEQ ID NO 391
<211> LENGTH: 700
<212> TYPE: RNA
<213> ORGANISM: Diabrotica virgifera

<400> SEQUENCE: 391
gaauugugua aaccaguuuu guugcaaggu cgcaaacagc uucuagaaaa augguuaaaa 60
gaggaaaaau uagaauguuc cgaagaauua ggagaccuag ucaaacaggc agauccuacu 120
cuggcuuuau cuguguaucu uagagcuaau guaccugcaa aaguuaucca aagcuuugcc 180
gaaacuggcc aauuccaaaa gauaguccuc uacgccaaaa aagugucuua uacucccgac 240
uauguauucc ugcuucgcca agucaugcgc accaaucccg accaaggcgc agcauuugca 300
gggauguugg uagcggacga cgaaccuuug gccgauauca accaaaucgu ggacauuuuc 360
auggagcaaa acauggugca gcaguguacu gcguucuugu uggacgccuu aaagaauaac 420
aggccuacug aggggcaucu acaaacuaga cuauuagaaa ugaaccugau guccgcaccg 480
caaguagcag acgccauucu cggcaacaac auguucacuc acuacgaccg gccccacgua 540
gcccagcucu gcgaaaaagc uggucuuuua caaagagcuc uagaacacua cacugauuug 600
uaugacauca aacgugcugu gguacacacc cacuugcuuc cagcugauug guugguuaac 660
uucuucggaa cucucagcgu ggaagacagu uuggagugcu 700

<210> SEQ ID NO 392
<211> LENGTH: 549
<212> TYPE: RNA
<213> ORGANISM: Diabrotica virgifera

<400> SEQUENCE: 392
ucagcgugga agacaguuug gagugcuuga gggccaugcu gaccgcgaau auucgacaga 60
auuugcagau uugcgugcag aucgcuacca aguaccacga acaacucacc acuaaggcuu 120
ugaucgauuu guuugaagga uuuaagagcu augaggguuu guucuauuuc cucggcucca 180
ucgucaacuu cucccaagac caagaagugc acuucaagua cauccaagcc gcaugcaaga 240
cuggccaaau caaagaaguc gagcguaucu guagggaauc aaacugcuac aaucccgaaa 300
gagucaagaa uuuccugaag gaagccaaac uuacagauca guugccguug auuauugucu 360
gugacagauu ugauuucguc cacgacuuag uguuguaucu auauagaaau ucgcugcaga 420
aauauaucga gauuuauguc cagaagguca aucccagccg uuuaccgguu gugguaggag 480
gucuuuuaga ugucgacugu uccgaagaca uaaucaaaaa ccuaauucuu gucgucagag 540
gccaguucu 549

<210> SEQ ID NO 393
<211> LENGTH: 677
<212> TYPE: RNA
<213> ORGANISM: Diabrotica virgifera

<400> SEQUENCE: 393
uaaucaaaaa ccuaauucuu gucgucagag gccaguucuc cacugacgaa uuaguagaag 60
aaguagaaaa gaggaacaga uugaaacugu uguugcccug guuggagagc agaguacacg 120
aaggaugugu cgagccagcu acgcacaaug cuuuggccaa gaucuacauc gauuccaaca 180
acaaugccga aagauucuug aaggaaaauc aaugguacga uucccgaguu gugggacguu 240
auugcgaaaa gcgcgaucca caucuggcuu gcguugcuua cgaacgaggc caaugcgaca 300
gagaacugau agcuguaugu aacgaaaacu cucuauuuaa gucugaagcu cguuauuugg 360
uccguagacg ugacggagaa uuaugggcug agguuuugaa cgagagcaau ccuuacagac 420
gucaguugau agaccaagua gugcaaacag cuuuaaguga aacccaagac cccgaagaua 480
ucucuguuac cguuaaagca uucaugacag cugauuuacc aaaugagcuc auugaauugu 540
uggaaaagau uguauuggau aguucugugu ucuccgagca uagaaaccuu caaaauuugc 600
uuauccuaac agcaaucaaa gccgaugcua caagaguuau ggacuacauc aaccgcuugg 660
auaacuacga ugccccu 677

<210> SEQ ID NO 394
<211> LENGTH: 706
<212> TYPE: RNA
<213> ORGANISM: Diabrotica virgifera

<400> SEQUENCE: 394
aaccgcuugg auaacuacga ugccccugau aucgcgaaua uagccaucaa caaccaucuc 60
uaugaagaag cuuucgcuau uuucaagaaa uuugauguca acaccucagc uauucaagua 120
uugaucgaac aagucaacaa ucuggaucgu gcuuaugaau ucgcagaacg uugcaaugaa 180
ccggccguau ggagucagcu ggccaaagcg caacugaacc aaggcuuagu caaggaagca 240
aucgauucuu acauuaaagc ugaugauccu ucagcuuaua aggacgucgu ugagaccgcu 300
ucgaaaaaua auagcuggga ggacuuagug cgguauuugc agauggcaag aaagaaggcc 360
agagagagcu acaucgaauc ugaauugauu uauucguacg cgaagaccgg aagauuggcu 420
gauuuggaag aauucaucag uggacccaac caugcugaua uccagaagau uggugauagg 480
ugcuuugaug acaagaugua ugaugcugcu aagcuacucu acaacaaugu auccaacuuc 540
gcucgucucg cuauuacuuu agugcaucua aaagaauucc agggagcugu ugacagugcu 600

-continued aggaaggcua auaguaccag aacauggaag gaagugugu uugcuugcgu cgaugccgaa 660
gaauucagau uggcucagau guguggguaug cacaucgugg uacacg 706

<210> SEQ ID NO 395
<211> LENGTH: 686
<212> TYPE: RNA
<213> ORGANISM: Diabrotica virgifera

<400> SEQUENCE: 395
gcacaucgug guacacgcug augaguugca agauuugauu aauuauuauc aagauagagg 60
auacuuugaa gaauuaaucg gccuauugga agcagcauug ggcuuggaaa gggcacacau 120
ggguauguuc accgaauuag caauuuugua uuccaaauau aagcccgcca aaaugcgcga 180
acaucuggaa cucuucuggu cucgagugaa uauccccaaa guucuuaggg cagcugaaca 240
agcacauuug ugggcagagc uaguguuuuu guaugacaaa uaugaagaau augauaacgc 300
uguguuagcc augauggcuc aucccaccga agcuuggcgc gaaggucauu ucaaggauau 360
uauuacaaaa guugccaaua ucgaacuuua uuauagagcu auucaauuuu acuuggauua 420
caaaccgcug uuguuaaaug accuuuuguu gguguuggca cccaggaugg aucauacuag 480
ggcuguuucu uucuuuacaa aaacaggaca cuuacaguug guuaaauccu aucuccgguc 540
ugugcaaaau uugaacaaca aagcuaucaa cgaggcccuc aacucucuac uuaucgaaga 600
agaagacuuc cagggucuga gaacguccau cgacgccuuc gauaacuucg acaacaucgg 660
cuuggcucag aaauuggaga agcacg 686

<210> SEQ ID NO 396
<211> LENGTH: 565
<212> TYPE: RNA
<213> ORGANISM: Diabrotica virgifera

<400> SEQUENCE: 396
cgacaacauc ggcuuggcuc agaaauugga gaagcacgaa cugacggagu ucagacgcau 60
cgccgccuac uuguacaaag gcaacaaccg guggaagcag agcguagaac ugugcaaaaa 120
ggauagacua uuuagagacg cuauggagua cacuucugaa ucuagaaauc aagaauuggc 180
cgaagaguug cuggcauggu ucuuggauag gaaggccuau gauuguuuuu cggcauguuu 240
guaucacugc uacgacuugu uacggcccga cguuauccuu gaacuagcau ggaaacacaa 300
cauuauggac uucgcaaugc cuuuccuuau ucaaguaacu agagaacuga cgacaaaagu 360
agaaaagcua gaacaaucag augcccaacg acaaagcgag gcugcugaag aaacgaacaa 420
gccaaugaug auaccagaac cccaacuuau gcuaacggcu ggcccuggca ugggguauucc 480 accccaacag uauguaccuc cccaaggcua cgcgcagcca ggcuacgccc cgcaaauggc 540
uuaccaggga uacccaggca uguaa 565

<210> SEQ ID NO 397
<211> LENGTH: 20
<212> TYPE: DNA
<213> ORGANISM: Diabrotica virgifera

<400> SEQUENCE: 397
aagaaaaagc aacatgacgc 20

<210> SEQ ID NO 398
<211> LENGTH: 20
<212> TYPE: DNA
<213> ORGANISM: Diabrotica virgifera

<400> SEQUENCE: 398
ggggccttat attacatgcc 20

<210> SEQ ID NO 399
<211> LENGTH: 130
<212> TYPE: DNA
<213> ORGANISM: Diabrotica virgifera

<400> SEQUENCE: 399
gatatcacag acgtattgta gacctagaaa ataagaaatt tgacctcgaa aaagaagtgg 60
aattcagaga ttttcagatc tccgaattga acagccaagt aaacgacctt agaggcaaat 120
tcgtcaaacc 130

<210> SEQ ID NO 400
<211> LENGTH: 119
<212> TYPE: DNA
<213> ORGANISM: Diabrotica virgifera

<400> SEQUENCE: 400
gtaaccaact caaagttgtc aagaagaaag aattcacctt agaagaagaa gacaaagaaa 60
agaaaccaga ctggtcaaag aagggagacg aaaagaaggt acaagaggct gaagcatga 119

<210> SEQ ID NO 401
<211> LENGTH: 130
<212> TYPE: RNA
<213> ORGANISM: Diabrotica virgifera

<400> SEQUENCE: 401
gauaucacag acguauugua gaccuagaaa auaagaaauu ugaccucgaa aaagaagugg 60
aauucagaga uuuucagauc uccgaauuga acagccaagu aaacgaccuu agaggcaaau 120
ucgucaaacc 130

<210> SEQ ID NO 402
<211> LENGTH: 119
<212> TYPE: RNA
<213> ORGANISM: Diabrotica virgifera

<400> SEQUENCE: 402
guaaccaacu caaaguuguc aagaagaaag aauucaccuu agaagaagaa gacaaagaaa 60
agaaaccaga cuggucaaag aagggagacg aaaagaaggu acaagaggcu gaagcauga 119

<210> SEQ ID NO 403
<211> LENGTH: 692
<212> TYPE: DNA
<213> ORGANISM: Artificial Sequence
<220> FEATURE:
<223> OTHER INFORMATION: Diabrotica virgifera, Arabidopsis thaliana

<400> SEQUENCE: 403
gaccttagag gcaaattcgt caaaccaacc ttgaagaagg tatccaaata cgaaaacaaa 60
ttcgccaaac ttcaaaagaa ggcagctgaa tttaacttcc gtaaccaact caaagttgtc 120
aagaagaaag aatggtacca agctgcgaat cttcgttttt ttaaggaatt ctcgatcttt 180
atggtgtata ggctctgggt tttctgtttt ttgtatctct taggattttg taaattccag 240
atctttctat ggccacttag tagtatattt caaaaattct ccaatcgagt tcttcattcg 300
cattttcagt cattttctct tcgacgttgt ttttaagcct gggtattact cctatttagt 360

-continued

```
tgaactctgc agcaatctta gaaaattagg gttttgaggt ttcgatttct ctaggtaacc    420

gatctattgc attcatctga atttctgcat atatgtctta gatttctgat aagcttacga    480

tacgttaggt gtaattgaag tttatttttc aagagtgtta ttttttgttt ctgaattttt    540

cagtcactcc atggcctaga ttctttcttc ttgacaactt tgagttggtt acggaagtta    600

aattcagctg ccttcttttg aagtttggcg aatttgtttt cgtatttgga taccttcttc    660

aaggttggtt tgacgaattt gcctctaagg tc                                  692
```